US012259380B2

(12) United States Patent
Costa et al.

(10) Patent No.: US 12,259,380 B2
(45) Date of Patent: *Mar. 25, 2025

(54) OLIGONUCLEOTIDES FOR INDUCING PATERNAL UBE3A EXPRESSION

(71) Applicant: Hoffmann-La Roche Inc., Little Falls, NJ (US)

(72) Inventors: Veronica Costa, Basel (CH); Maj Hedtjärn, Hørsholm (DK); Marius Hoener, Basel (CH); Ravi Jagasia, Basel (CH); Mads Aaboe Jensen, Hørsholm (DK); Christoph Patsch, Basel (CH); Lykke Pedersen, Hørsholm (DK); Søren Vestergaard Rasmussen, Hørsholm (DK)

(73) Assignee: Hoffmann-La Roche Inc., Little Falls, NJ (US)

( * ) Notice: Subject to any disclaimer, the term of this patent is extended or adjusted under 35 U.S.C. 154(b) by 10 days.

This patent is subject to a terminal disclaimer.

(21) Appl. No.: 18/172,707

(22) Filed: Feb. 22, 2023

(65) Prior Publication Data

US 2023/0296587 A1    Sep. 21, 2023

Related U.S. Application Data

(63) Continuation of application No. 17/581,089, filed on Jan. 21, 2022, now Pat. No. 11,852,627, which is a
(Continued)

(30) Foreign Application Priority Data

| Nov. 12, 2015 | (EP) | ................................... 15194367 |
| Sep. 19, 2016 | (EP) | ................................... 16189502 |

(51) Int. Cl.
*C12N 15/11* (2006.01)
*C12N 5/00* (2006.01)
(Continued)

(52) U.S. Cl.
CPC ....... *G01N 33/5014* (2013.01); *C12N 5/0018* (2013.01); *C12N 5/0619* (2013.01);
(Continued)

(58) Field of Classification Search
CPC ... C12N 15/11; C12N 15/113; C12N 15/1137; C12N 2310/11; C12N 2310/315;
(Continued)

(56) References Cited

U.S. PATENT DOCUMENTS

| 4,373,084 A | 2/1983 | Robinson |
| 6,184,212 B1 | 2/2001 | Miraglia et al. |

(Continued)

FOREIGN PATENT DOCUMENTS

| CL | 2008/000857 A1 | 10/2008 |
| CL | 2020000889 A1 | 8/2020 |

(Continued)

OTHER PUBLICATIONS

Boards of Appeal of the European Patent Office, Datasheet for the decision of Apr. 2, 2020, for European Application No. 06772386.6 (14 pages).

(Continued)

*Primary Examiner* — Terra C Gibbs
(74) *Attorney, Agent, or Firm* — Clark & Elbing LLP; Thomas J. Takara

(57) ABSTRACT

The present invention relates to oligonucleotides that are capable of inducing expression of ubiquitin-protein ligase E3A (UBE3A) from the paternal allele in animal or human neurons. The oligonucleotides target the suppressor of the UBE3A paternal allele by hybridization to SNHG14 long non-coding RNA downstream of SNORD1091B. The present invention further relates to pharmaceutical compositions and methods for treatment of Angelman syndrome.

26 Claims, 2 Drawing Sheets

Specification includes a Sequence Listing.

Related U.S. Application Data continuation of application No. 16/933,445, filed on Jul. 20, 2020, now Pat. No. 11,320,421, which is a continuation of application No. 16/663,024, filed on Oct. 24, 2019, now Pat. No. 10,718,753, which is a continuation of application No. 16/388,714, filed on Apr. 18, 2019, now Pat. No. 10,739,332, which is a continuation of application No. 15/351,113, filed on Nov. 14, 2016, now Pat. No. 10,494,633, which is a continuation of application No. PCT/EP2016/077383, filed on Nov. 11, 2016.

(51) Int. Cl.
| | |
|---|---|
| *C12N 5/074* | (2010.01) |
| *C12N 5/0793* | (2010.01) |
| *C12N 5/0797* | (2010.01) |
| *C12N 15/113* | (2010.01) |
| *G01N 33/50* | (2006.01) |

(52) U.S. Cl.
CPC ......... *C12N 5/0623* (2013.01); *C12N 5/0696* (2013.01); *C12N 15/11* (2013.01); *C12N 15/111* (2013.01); *C12N 15/113* (2013.01); *C12N 15/1137* (2013.01); *G01N 33/5058* (2013.01); *C12N 2310/11* (2013.01); *C12N 2310/20* (2017.05); *C12N 2310/315* (2013.01); *C12N 2310/321* (2013.01); *C12N 2310/322* (2013.01); *C12N 2310/3231* (2013.01); *C12N 2310/33* (2013.01); *C12N 2310/3341* (2013.01); *C12N 2310/341* (2013.01); *C12N 2310/346* (2013.01); *C12N 2310/351* (2013.01); *C12N 2320/34* (2013.01); *C12N 2500/38* (2013.01); *C12N 2500/44* (2013.01); *C12N 2501/01* (2013.01); *C12N 2501/11* (2013.01); *C12N 2501/115* (2013.01); *C12N 2501/119* (2013.01); *C12N 2501/13* (2013.01); *C12N 2501/41* (2013.01); *C12N 2501/60* (2013.01); *C12N 2501/727* (2013.01); *C12N 2501/999* (2013.01); *C12N 2503/02* (2013.01); *C12N 2506/45* (2013.01); *C12N 2533/52* (2013.01)

(58) Field of Classification Search
CPC ........ C12N 2310/321; C12N 2310/341; C12N 2310/351; C12N 2310/3341; C12N 2320/34; A61P 25/28
See application file for complete search history.

(56) References Cited

U.S. PATENT DOCUMENTS

| | | | |
|---|---|---|---|
| 6,300,132 | B1 | 10/2001 | Monia et al. |
| 6,617,162 | B2 | 9/2003 | Dobie et al. |
| 8,067,173 | B2 | 11/2011 | Liew |
| 9,617,539 | B2 * | 4/2017 | Rigo ............... C12N 15/113 |
| 10,494,633 | B2 | 12/2019 | Costa et al. |
| 10,718,753 | B2 | 7/2020 | Costa et al. |
| 10,739,332 | B2 | 8/2020 | Costa et al. |
| 11,320,421 | B2 * | 5/2022 | Costa ............... C12N 15/111 |
| 11,852,627 | B2 * | 12/2023 | Costa ............... A61P 25/14 |
| 2002/0098511 | A1 | 7/2002 | Heichman et al. |
| 2003/0087855 | A1 | 5/2003 | Ward et al. |
| 2005/0124572 | A1 | 6/2005 | Freier et al. |
| 2013/0225659 | A1 | 8/2013 | Bennett |
| 2015/0191723 | A1 | 7/2015 | Rigo et al. |
| 2017/0191064 | A1 | 7/2017 | Costa et al. |
| 2019/0310244 | A1 | 10/2019 | Costa et al. |
| 2020/0057052 | A1 | 2/2020 | Costa et al. |
| 2020/0348286 | A1 | 11/2020 | Costa et al. |
| 2024/0085402 | A1 | 3/2024 | Costa et al. |

FOREIGN PATENT DOCUMENTS

| | | |
|---|---|---|
| CL | 2021002159 A1 | 3/2022 |
| CO | 2020/000679 A2 | 1/2020 |
| EP | 2864479 B1 | 4/2015 |
| EP | 2640853 B1 | 12/2018 |
| EP | 3374509 B1 | 12/2020 |
| JP | 2015-529635 A | 10/2015 |
| WO | WO-93/07883 A1 | 4/1993 |
| WO | WO-98/039352 A1 | 9/1998 |
| WO | WO-99/14226 A2 | 3/1999 |
| WO | WO-00/047599 A1 | 8/2000 |
| WO | WO-00/66604 A2 | 11/2000 |
| WO | WO-01/23613 A1 | 4/2001 |
| WO | WO-2001/092582 A1 | 12/2001 |
| WO | WO-2003/000707 A2 | 1/2003 |
| WO | WO-2004/016754 A2 | 2/2004 |
| WO | WO-2004/028458 A2 | 4/2004 |
| WO | WO-2004/046160 A2 | 6/2004 |
| WO | WO-2007/031091 A2 | 3/2007 |
| WO | WO-2007/087113 A2 | 8/2007 |
| WO | WO-2007/090071 A2 | 8/2007 |
| WO | WO-2007/134181 A2 | 11/2007 |
| WO | WO-2007/146511 A2 | 12/2007 |
| WO | WO-2008/113832 A2 | 9/2008 |
| WO | WO-2008/116860 A2 | 10/2008 |
| WO | WO-2008/150729 A2 | 12/2008 |
| WO | WO-2008/154401 A2 | 12/2008 |
| WO | WO-2009/006478 A2 | 1/2009 |
| WO | WO-2009/067647 A1 | 5/2009 |
| WO | WO-2009/090182 A1 | 7/2009 |
| WO | WO-2009/124238 A1 | 10/2009 |
| WO | WO-2010/036698 A1 | 4/2010 |
| WO | WO-2010/077578 A1 | 7/2010 |
| WO | WO-2011/017521 A2 | 2/2011 |
| WO | WO-2011/079261 A2 | 6/2011 |
| WO | WO-2011/156202 A1 | 12/2011 |
| WO | WO-2012/009402 A2 | 1/2012 |
| WO | WO-2012/012467 A2 | 1/2012 |
| WO | WO-2012/064806 A2 | 5/2012 |
| WO | WO-2012/143379 A1 | 10/2012 |
| WO | WO-2013/033230 A1 | 3/2013 |
| WO | WO-2013/036868 A1 | 3/2013 |
| WO | WO-2013/154798 A1 | 10/2013 |
| WO | WO-2014/004572 A2 | 1/2014 |
| WO | WO-2014/076195 A1 | 5/2014 |
| WO | WO-2014/077693 A1 | 5/2014 |
| WO | WO-2017/081223 A1 | 5/2017 |
| WO | WO-2017/081250 A1 | 5/2017 |
| WO | WO-2017/081254 A1 | 5/2017 |
| WO | WO-2019/006107 A1 | 1/2019 |
| WO | WO-2019/109001 A1 | 6/2019 |
| WO | WO-2019/145384 A1 | 8/2019 |
| WO | WO-2020/205463 A1 | 10/2020 |

OTHER PUBLICATIONS

Hélène C, et al., "Specific regulation of gene expression by antisense, sense and antigene nucleic acids," Biochimica et Biophysica Acta, 1049, pp. 99-125, (1990).

Phillips M., et al., "In vivo applications of antisense oligonucleotides for peptide research," Regulatory Peptides 59 pp. 131-141 (1995).

Yang D. et al., "Gene targets of antisense therapies in breast cancer," Expert Opinion on Therapeutic Targets, 6:3, pp. 375-385, (2005) (12 pages).

European Search Report for European Patent Application No. 23152543, dated Jul. 26, 2023 (7 pages).

"Angelman Syndrome," Cleveland Clinic, <https://my.clevelandclinic.org/health/diseases/17978-angelman-syndrome>, Last reviewed on Dec. 11, 2018, Retrieved on Mar. 31, 2021 (7 pages).

"Angelman Syndrome," Cleveland Clinic. Retrieved from <https://my.clevelandclinic.org/health/diseases/17978-angelman-syndrome/prevention> on Feb. 11, 2019 (1 page).

"Angelman Syndrome," Natural Living Center. Retrieved from <http://www.naturallivingcenter.net/ns/DisplayMonograph.asp?

(56) References Cited

OTHER PUBLICATIONS

StoreID=b571dewxvcs92jj200akhmccqa7w8v75&DocID=condition-angelman#PREVENTION> on Feb. 11, 2019 (1 page).
Abaturov et al., "Angelman Syndrome. part 3, (Differential diagnosis and treatment)," Child's Health, Nov. 2015, 7(67):86-92 (English Abstract).
Bauman, "Uconn Stem Cell Lines Go Global," Health and Wellness Research, dated Feb. 2014 [ retrieved Mar. 31, 2021], retrieved from URL <https://today.uconn.edu/2014/02/uconn-stem-cell-lines-go-global/#>, 6 pages.
Beaudet, "Drugs to awaken a paternal gene," Nature, 2012, 481(7380):150-152.
Bergstrom, "Unnatural Nucleosides with Unusual Base Pairing Properties," Current Protocols in Nucleic Acid Chemistry, Jun. 2009, 1:Unit 1.4-Unit 1.4.32(Supplement 37) 32 pages.
Biological Material transfer agreements relating to the iPSC cells in 029, 8 pages.
Blaydes et al., "Analysis of murine Snrpn and human SNRPN gene imprinting in transgenic mice," Mamm Genome. 10(6):549-55 (1999).
Boissart et al., "Differentiation from human pluripotent stem cells of cortical neurons of the superficial layers amenable to psychiatric disease modeling and high-throughput drug screening," Transl Psychiatry. 3(e294): 11 pages (2013).
Brief Communication for European Patent Application No. 11840796. 4, dated Oct. 18, 2021 (11 pages).
Caruthers et al, "[15] Chemical synthesis of deoxyoligonucleotides by the phosphoramidite method," Methods in Enzymology, 1987, 154:287-313.
Cavaillé et al., "Identification of brain-specific and imprinted small nucleolar RNA genes exhibiting an unusual genomic organization," Proc Natl Acad Sci U S A. 97(26):14311-6 (Dec. 19, 2000).
Cellbank.mcgill.ca, [ online] "The Repository for Mutant Human Cell Strains," available on or before Apr. 2008, Wayback Machine URL <Cellbank.mcgill.ca/?Topic=Order>, 2 pages.
Chamberlain et al., "Angelman Syndrome, A genomic Imprinting Disorder of the Brain," The Journal of Neuroscience, 2010, 30(30):9958-9963.
Chamberlain et al., "Induced pluripotent stem cell models of the genomic imprinting disorders Angelman and Prader-Willi syndromes," Proc Natl Academy Science USA, 2010, 107(41):17668-17673.
Chamberlain, "Declaration of Dr Stormy J. Chamberlain," dated Apr. 8, 2021, 9 pages.
Chung et al., "Prader-Willi syndrome: reflections on seminal studies and future therapies," Open Bioi., 2020, 10(9):2300195 (17 pages).
Colombian Office Action with Colombian Application No. NC20180004550, dated Apr. 14, 2020, 23 pages.
Conference program for Keystone Symposium on MicroRNAs and Huma Disease, Banff, Alberta, Feb. 11-16, 2011, retrieved on Oct. 5, 2019, retrieved from URL <http://www.keystonesymposia.org/11J6>, 7 pages.
Connecticut Stem Cell Research program grant agreement, Dec. 2008, 4 pages.
Crooke, "Basic Principles of Antisense Technology," Antisense Drug Technology: Principles, Strategies and Applications, 2001, 1: 1-18.
CV of Dr Stormy J. Chamberlain, No Date, 9 pages.
Danckwardt et al., "3' end mRNA processing; molecular mechanisms and implications for health and disease," The EMBO Journal, Feb. 6, 2008, 27:482-498.
Declaration of Dr Frank Rigo, Apr. 10, 2019, 21 pages.
Declaration of Lykke Pedersen, Jun. 8, 2020, 24 pages.
Declaration of Professor Claes Wahlestedt, May 10, 2019, 45 pages.
Deleavey et al., "Designing Chemically Modified Oligonucleotides for Targeted Gene Silencing," Chemistry & Biology. 19(8):937-54 (2012).
DeVos et al., "Antisense Oligonucleotides: Treating Neurodegeneration at the Level of RNA," Neurotherapeutics. 10(3):486-97 (2013).
Dunkley et al., "Characterization of a human pluripotent stem cell-derived model of neuronal development using multiplexed targeted proteomics," Proteomics Clin Appl., Aug. 2015, 9(7-8):684-694.
Efthymiou et al., "Functional Screening Assays with Neurons Generated from Pluripotent Stem Cell-Derived Neural Stem Cells," J. Biomol. Screen, 2014, 19(1):32-43.
Entrez gene summary for SNORD109B, dated Mar. 29, 2020, retrieved from URL <https://www.ncbi.nlm.nih.gov/gene?cmd=Retrieve&dopt=full_report&list_uids=338429>, 1 page.
European Grounds of Appeal for European Patent No. 2864479, dated Apr. 29, 2022 (69 pages).
European Opposition in European Patent No. 2864479, dated Jun. 17, 2020, 17 pages.
European Revision of the EPC: Article 54(5), CA/PL4/00, dated Jan. 24, 2000, 4 pages.
European Revision of the European Patent Convention: CA/100/00, dated Aug. 9, 2000, 5 pages.
Extracts of information from US20030087855 Sequence ID No. 87, May 8, 2003, 1 page.
Extracts of information from U.S. Pat. No. 6,184,212 Sequence ID No. 261, Feb. 6, 2001, 2 pages.
Extracts of information from U.S. Pat. No. 6,300,132 Sequence ID No. 71, Oct. 9, 2001, 1 page.
Extracts of information from U.S. Pat. No. 6,617,162 Sequence ID No. 43, Sep. 9, 2003, 1 page.
Extracts of information from WO2004016754 Sequence ID No. 7124, Feb. 26, 2004, 1 page.
Faghihi et al., "Regulatory roles of natural antisense transcripts," Nature Rev Mol Cell Biol., 2009, 10(9):637-643.
Faghihi, "RNAi Screen Indicates Widespread Biological Function for Human Natural Antisense Transcripts," PLoS One, 2010, 5:e13177 10 pages.
Fluiter et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Mol BioSyst. 5(8):838-43 (2009).
Freier et al., "Methods of Selecting Sites in RNA for Antisense Targeting," Antisense Drug Technology: Principles, Strategies and Applications, 2001, 5: 107-119.
Freier et al., "The ups and downs of nucleic acid duplex stability: structure-stability studies on chemically-modified DNA:RNA duplexes," Nucleic Acids Res. 25(22):4429-43 (1997).
GenBank entry NM_130838.1 "*Homo sapiens* ubiquitin protein ligase E3A (UBE3A), Transcript variant 1, mRNA," dated Jul. 2, 2017, 7 pages.
Germain et al., "Antisense oligonucleotides targeting UBE3A-ATS restore expression of UBE3A by relieving transcriptional interference," bioRxiv preprint, https://doi.org/10.1101/2021.07.09.451826, (2021) (33 pages).
Hagedorn et al., "Locked nucleic acid: Modality, diversity, and drug discovery," Drug Discovery Todav, 2018, 23(1):101-114.
Hansen et al., "Entropy titration. A calorimetric method for the determination of deltaG°(K), deltaH° and deltaS°," Chem Comm., 1965, 3:36-38.
Hirao et al., "Natural versus Artificial Creation of Base Pairs in DNA: Origin of Nucleobases from the Perspectives of Unnatural Base Pair Studies," Accounts of Chemical Research, Dec. 18, 2012, 45(12):2055-2065.
Holdgate et al., "Measurements of binding thermodynamics in drug discovery," Drug Discov Today., Nov. 15, 2005, 10(22):1543-1550.
Huang et al., "Topoisomerase inhibitors unsilence the dormant allele of Ube3a in neurons," Nature, 2012, 481(7380):185-189.
Interlocutory decision in Opposition proceedings for European Patent Application No. 11840796.4, dated Jun. 21, 2022 (22 pages).
International Search Report and Written Opinion for International Patent Application No. PCT/EP2016/077383, dated Feb. 23, 2017 (12 pages).
Johnstone et al., "A human imprinting centre demonstrates conserved acquisition but diverged maintenance of imprinting in a mouse model for Angelman syndrome imprinting defects," Human Molecular Genetics. 15(3):393-404 (2006).

(56) References Cited

OTHER PUBLICATIONS

King et al., "Topoisomerases facilitate transcription of long genes linked to autism," Nature, 2013, 501(7456):58-62.
Koch et al., "Quantum Mechanical Studies on DNA and LNA, Nucleic Acid Therapeutics," 2014, 24(2):139-148.
Landers et al., "Regulation of the large (~1000 kb) imprinted murine Ube3a antisense transcript by alternative exons upstream of Snurf/Snrpn," Nucleic Acids Res. 32(11):3480-92 (2004).
Luo et al., "A Ribonucleolytic Rat Torpedoes RNA Polymerase II," Cell, Dec. 29, 2004, 119(7):911-914.
Mangos et al., "Efficient RNase H-Directed Cleavage of RNA Promoted by Antisense DNA or 2'F-ANA Constructs Containing Acyclic Nucleotide Inserts" J Am Chem Soc. 125(3):654-61 (2003).
Manoharan, "Chapter 16: Oligonucleotide Conjugates in Antisense Technology." *Antisense Drug Technology: Principles, Strategies, and Applications.* Marcel Dekker, Inc., 391-469 (2001) (85 pages).
Manoharan, "Oligonucleotide Conjugates as Potential Antisense Drugs with Improved Uptake, Biodistribution, Targeted Delivery, and Mechanism of Action," Antisense and Nucleic Acid Drug Development, Jul. 2004, 12(2):103-128.
McTigue et al., "Sequence-dependent thermodynamic parameters for locked nucleic acid (LNA)-DNA duplex formation," Biochemistry, May 11, 2004, 43(18):5388-5405.
Meng et al., "Ube3a-ATS is an atypical RNA polymerase II transcript that represses the paternal expression of Ube3a," Human Molecular Genetics, 2012, 21(13):3001-3012.
Meng et al., "Towards a therapy for Angelman syndrome by reduction of a long non-coding RNA," Nature. 518(7539):409-12 (Feb. 2015).
Mergny and Lacroix, "Analysis of thermal melting curves," Oligonucleotides, Dec. 2003, 13(6):515-537.
Mitsuoka et al., "A bridged nucleic acid, 2',4'-BNA$^{COC}$: synthesis of fully modified oligonucleotides bearing thymine, 5-methylcytosine, adenine and guanine 2',4'-BNA$^{COC}$ monomers and RNA-selective nucleic-acid recognition," Nucleic Acids Research. 37(4):1225-38 (2009).
Modarresi et al., "Inhibition of natural antisense transcripts in vivo results in gene-specific transcriptional upregulation," Nature Biotechnology, 2012, vol. 30(5):Supporting Online Material: 33 pages.
Modarresi et al., "Inhibition of natural antisense transcripts in vivo results in gene-specific transcriptional upregulation," Nature Biotechnology, Mar. 25, 2012, 30(5):453-459.
Morita et al, "2'-O,4'-C-ethylene-bridged nucleic acids (ENA): highly nuclease-resistant and thermodynamically stable oligonucleotides for antisense drug," Bioorganic & Med Chem Lett., Jan. 7, 2002, 12(1):73-76.
Morris et al., "Bidirectional Transcription Directs Both Transcriptional Gene Activation and Suppression in Human Cells," PLoS Genetics, Nov. 2008, 4(11):e1000258 9 pages.
NCBI.nlm.nih.gov Gene ID: 338429, "SNORD109B small nucleolar RNA, C/D box 109B [*homo sapiens* (human)]," <https://ncbi.nlm.nih.gov/gene/338429>, Last updated on Apr. 8, 2022, Retrieved on Apr. 28, 2022 (5 pages).
NCBI.nlm.nih.gov, "SNORD109A small nucleolar RNA, C/D box 109A [*homo sapiens* (human)]," Mar. 2, 2021, retrieved from URL <https://ncbi.nlm.nih.gov/gene?Dbgene&Cmd=DetailsSearch&Term=338428>, 1 page.
Papargyri et al., "Chemical Diversity of Locked Nucleic Acid-Modified Antisense Oligonucleotides allos Optimization of Pharmaceutical Properties," Molecular Therapy Nucleic Acids., Mar. 2020, (19):706-717.
Petrov, "Chemistry Guide for Schoolchildren," M List, 1998, p. 321.
Philpot et al., "Angelman syndrome: advancing the research frontier of neurodevelopmental disorders," J Neurodevelop Disord, 2011, 3:50-56.
PNAS, "Information for Authors," revised Jan. 2020, 117 :xi-xviii.
Rougelle et al., "The Angelman syndrome candidate gene, UBE3A/E6-AP, is imprinted in brain," Nature Genetics, 1997, 17:14-15.
Rougeulle et al., "An imprinted antisense RNA overlaps UBE3A and a second maternally expressed transcript," Nature Genetics, 1998, 19:15-16.
SantaLucia, John Jr., "A unified view of polymer, dumbbell, and oligonucleotide DNA nearest-neighbor thermodynamics," Proc Natl Acad Sci. 95:1460-5 (1998).
Search overview of documents teaching the targeting of non-overlapping regions, Feb. 17, 2020, 29 pages.
Second Declaration of Claes Wahlestedt, dated Jun. 15, 2020, 50 pages.
Seth at al., "Synthesis and Biophysical Evaluation of 2',4'-Constrained 2'O-Methoxyethyl and 2',4'-Constrained 2'O-Ethyl Nucleic Acid Analogues," J Org Chem., Mar. 5, 2010, 75(5):1569-1581.
Sharma et al., "Antisense oligonucleotides: modifications and clinical trials," MedChemComm. 5(10):1454-1471 (2014).
Shi et al., "In situ entry of oligonucleotides into brain cells can occur through a nucleic acid channel," Oligonucleotides, 2007, 17(1):122-133.
Smith et al., "Transcription is required to establish maternal imprinting at the Prader-Willi syndrome and Angelman syndrome locus," PLoS Genetics, 2011, 7(12):e1002422 10 pages.
Sugimoto et al., "Thermodynamic Parameters To Predict Stability of RNA/DNA Hybrid Duplexes," Biochemistry, Sep. 1995, 34(35): 11211-11216.
Swayze et al., "The Medicinal Chemistry of Oligonucleotides," Antisense Drug Technology, CRC Press, 2nd edition, chapter 6, 23 pages.
UCSC Genome Browser on Human Dec. 2013 (GRCh38/hg38) Assembly, Dec. 2013, 1 page.
Uhlmann, "Recent Advances in the medicinal chemistry of antisense oligonucleotides," Current Opinion in Drug Development, 2000, 3(2):203-213.
U.S. Appl. No. 61/664,083, Rigo et al., filed Jun. 25, 2012, 90 pages.
U.S. Appl. No. 61/738,959, Rigo et al., filed Dec. 18, 2012, 102 pages.
U.S. Appl. No. 61/750,939, Rigo et al., filed Jan. 10, 2013, 105 pages.
U.S. Appl. No. 61/755,617, Rigo et al., filed Jan. 23, 2013, 108 pages.
U.S. Appl. No. 61/772,925, Rigo et al., filed Mar. 5, 2013, 109 pages.
Vester et al., "Chemically modified oligonucleotides with efficient RNase H response," Bioorg Med Chem Lett., Apr. 1, 2008, 18(7):2296-2300.
Wahlestedt, "Natural antisense and noncoding RNA transcripts as potential drug targets," Drug Discovery Today, 2006, 11(11/12):503-508.
Wahlestedt et al., "Presentation: Regulatory Natural Antisense Transcripts," Keystone Symposium on MicroRNAs and Human Disease, Banff, Alberta, Feb. 11-16, 2011, 41 pages.
www.uniprot.org, "UniProtKB—Q05086," Last updated Dec. 11, 2019, retrieved on Feb. 4, 2020, retrieved from URL <httos://www.uniprot.org/uniprot/Q05086>, 23 pages.

\* cited by examiner

OLIGONUCLEOTIDES FOR INDUCING PATERNAL UBE3A EXPRESSION

CROSS-REFERENCE TO RELATED APPLICATIONS

This application is a continuation of application Ser. No. 17/581,089, filed Jan. 21, 2022, which is a continuation of application Ser. No. 16/933,445, filed Jul. 20, 2020, which is a continuation of application Ser. No. 16/663,024, filed Oct. 24, 2019, which is a continuation of application Ser. No. 16/388,714, filed Apr. 18, 2019, which is a continuation of application Ser. No. 15/351,113, filed Nov. 14, 2016, which is a continuation of PCT/EP2016/077383, filed Nov. 11, 2016, which claims priority to EP15194367.7, filed Nov. 12, 2015 and EP16189502.4, filed Sep. 19, 2016, the contents of which are hereby incorporated by reference.

SEQUENCE LISTING

The instant application contains a Sequence Listing which has been submitted electronically in XML format and is hereby incorporated by reference in its entirety. Said XML copy, created on Mar. 29, 2023, is named Sequence_Listing_P118867USBMMM and is 1,508,023 bytes in size.

FIELD OF INVENTION

The present invention relates to oligonucleotides (oligomers) that are complementary to and hybridize to SNHG14 downstream of SNORD109B, leading to induction of paternal expression of Ubiquitin-protein ligase E3A (UBE3A) in an animal or human. The present invention further relates to pharmaceutical compositions and methods for treatment of Angelman syndrome.

BACKGROUND

Angelman syndrome is neuro-genetic disorder caused by deletion or inactivation of the UBE3A genes on the maternally inherited chromosome 15q11.2. The paternal copy of the UBE3A gene is subject to genomic imprinting and silencing in neurons by an endogenous antisense transcript of UBE3A, termed SNHG14 (also known as UBE3A-ATS) (Meng et al. 2012 Hum Mol Genet. Vol. 21 pp. 3001-12). Other cell types than neurons seem to express the UBE3A gene from both the maternal and paternal allele.

Angelman syndrome is characterized by severe intellectual and developmental disability, sleep disturbance, seizures, jerky movements, EEG abnormalities, frequent laughter or smiling, and profound language impairments.

WO 2012/064806 discloses a method of inducing UBE3A expression in a cell by using a topoisomerase inhibitor. The method can be used to treat Angelman syndrome. There is no disclosure of antisense oligonucleotides.

WO 2014/004572 discloses oligonucleotides with 2'-O-methoxyethyl-RNA (MOE) modifications targeting mouse UBE3A-ATS. The oligonucleotides are only tested in mice related assays. In the region downstream of MBII-52 snoRNA (also known as SNORD115) and upstream of the UBE3A pre-mRNA there is no conservation between mouse and human. Oligonucleotides targeting mouse UBE3A-ATS can therefore not be translated into oligonucleotides that will function in a human. There is no disclosure of oligonucleotides targeting human UBE3A-ATS.

OBJECTIVE OF THE INVENTION

The present invention identifies novel oligonucleotides which induce human paternal UBE3A expression in neuronal without affection expression of the paternal SNORD115, SNORD116 and SNRPN transcripts significantly.

SUMMARY OF INVENTION

The present invention relates to oligonucleotides targeting a nucleic acid capable of suppressing the expression of UBE3A and to treat or prevent diseases related to decreased activity of UBE3A, in particular in neuronal cells.

Accordingly, in a first aspect the invention provides oligonucleotides which comprise a contiguous nucleotide sequence of 10 to 30 nucleotides in length with at least 98% complementarity to the part of human SNHG14 long non-coding RNA corresponding to position 25278410 to 25419462 on human chromosome 15 version GRCh38.p2. This region is also resembled by SEQ ID NO: 1. The oligonucleotide can be an antisense oligonucleotide, preferably with a gapmer design. Preferably, the oligonucleotide is capable of inducing the expression of UBE3A, in particular paternal UBE3A expression in a neuron, by degradation, reduction or removal of the UBE3A suppressor, in particular by reduction of the SNHG14 long non-coding RNA transcript downstream of SNORD109B. The UBE3A re-expression is achieved, without significantly affecting the expression of SNORD115. The degradation of the target nucleic acid is preferably achieved via nuclease recruitment.

In a further aspect, the invention provides pharmaceutical compositions comprising the oligonucleotides of the invention and pharmaceutically acceptable diluents, carriers, salts and/or adjuvants.

In a further aspect, the invention provides methods for in vivo or in vitro induction of UBE3A expression in a target cell where expression of paternal UBE3A is suppressed, by administering an oligonucleotide or composition of the invention in an effective amount to said cell.

In a further aspect the invention provides methods for treating or preventing a disease, disorder or dysfunction associated with in vivo activity of UBE3A comprising administering a therapeutically or prophylactically effective amount of the oligonucleotide of the invention to a subject suffering from or susceptible to the disease, disorder or dysfunction.

In a further aspect the oligonucleotide or composition of the invention is used for the treatment or prevention of Angelman syndrome.

DEFINITIONS

Oligonucleotide

Figure 1:
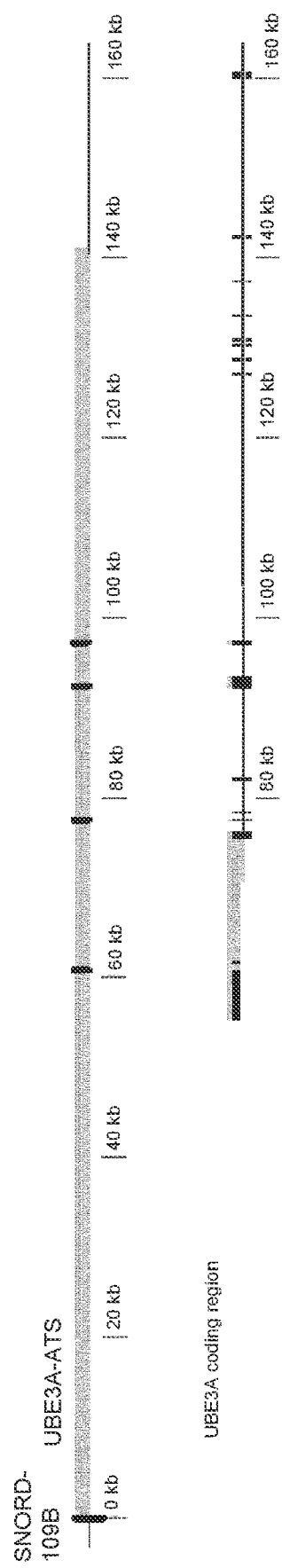
FIG. 1: The upper strand illustrates the region of the SNHG14 transcript downstream of SNORD109B (UBE3A-ATS) where the black boxes indicate the location of the tested mouse oligonucleotides. The lower strand illustrates the UBE3A coding region, where the black boxes indicate exons. Exon 1 is located around 160 kb. The oligonucleotides are placed in the antisense region of Exon 9 (positioned at ~97 kb), Exon 10 (positioned at ~92 kb), Exon 13 (positioned at ~77 kb) and the 5' end of Exon 16 (positioned at ~60 kb).

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs. Preferably, the antisense oligonucleotides of the present invention are single stranded.

Contiguous Nucleotide Sequence

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleotides of the oligonucleotide are present in the contiguous nucleotide sequence. In some embodiments the oligonucleotide comprises the contiguous nucleotide sequence and may, optionally comprise further nucleotide(s), for example a nucleotide linker region which may be used to attach a functional group to the contiguous nucleotide sequence. The nucleotide linker region may or may not be complementary to the target nucleic acid.

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprises a modified sugar moiety. The term modified nucleoside may also be used herein interchangeably with the term "nucleoside analogue" or modified "units" or modified "monomers".

Modified Internucleoside Linkage

The term "modified internucleoside linkage" is defined as generally understood by the skilled person as linkages other than phosphodiester (PO) linkages, that covalently couples two nucleosides together. Nucleotides with modified internucleoside linkage are also termed "modified nucleotides". In some embodiments, the modified internucleoside linkage increases the nuclease resistance of the oligonucleotide compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide of the invention, for example within the gap region of a gapmer oligonucleotide, as well as in regions of modified nucleosides.

In an embodiment, the oligonucleotide comprises one or more internucleoside linkages modified from the natural phosphodiester to a linkage that is for example more resistant to nuclease attack. Nuclease resistance may be determined by incubating the oligonucleotide in blood serum or by using a nuclease resistance assay (e.g. snake venom phosphodiesterase (SVPD)), both are well known in the art. Internucleoside linkages which are capable of enhancing the nuclease resistance of an oligonucleotide are referred to as nuclease resistant internucleoside linkages. In preferred embodiments at least 50% of the internucleoside linkages in the oligonucleotide, or contiguous nucleotide sequence thereof, are modified, such as at least 60%, such as at least 70%, such as at least 80 or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified. It will be recognized that, in some embodiments the nucleosides which link the oligonucleotide of the invention to a non-nucleotide functional group, such as a conjugate, may be phosphodiester. In some embodiments all of the internucleoside linkages of the oligonucleotide, or contiguous nucleotide sequence thereof, are nuclease resistant internucleoside linkages.

Modified internucleoside linkages may be selected from the group comprising phosphorothioate, diphosphorothioate and boranophosphate. In preferred embodiments, the modified internucleoside linkages are compatible with the RNaseH recruitment of the oligonucleotide of the invention, for example phosphorothioate, diphosphorothioate or boranophosphate.

In some embodiments the internucleoside linkage comprises sulphur (S), such as a phosphorothioate internucleoside linkage.

A phosphorothioate internucleoside linkage is particularly useful due to nuclease resistance, beneficial pharmakokinetics and ease of manufacture. In preferred embodiments at least 50% of the internucleoside linkages in the oligonucleotide, or contiguous nucleotide sequence thereof, are phosphorothioate, such as at least 60%, such as at least 70%, such as at least 80 or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

In some embodiments, the oligonucleotide comprises one or more neutral internucleoside linkage, particularly a internucleoside linkage selected from phosphotriester, methylphosphonate, MMI, amide-3, formacetal or thioformacetal.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, —NR$^H$—CO—NR$^H$—, and/or the internucleoside linker may be selected form the group consisting of: —O—CO—O—, —O—CO—NR$^H$—, —NR$^H$—CO—CH$_2$—, —O—CH$_2$—CO—NR$^H$—, —O—CH$_2$—CH$_2$—NR$^H$—, —CO—NR$^H$—CH$_2$—, —CH$_2$—NR$^H$CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is selected from hydrogen and C1-4-alkyl.

Nuclease resistant linkages, such as phosphothioate linkages, are particularly useful in oligonucleotide regions capable of recruiting nuclease when forming a duplex with the target nucleic acid, such as region G for gapmers, or the non-modified nucleoside region of headmers and tailmers. Phosphorothioate linkages may, however, also be useful in non-nuclease recruiting regions and/or affinity enhancing regions such as regions F and F' for gapmers, or the modified nucleoside region of headmers and tailmers.

Each of the design regions may however comprise internucleoside linkages other than phosphorothioate, such as phosphodiester linkages, in particularly in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide—see WO2008/113832, incorporated herein by reference.

In an embodiment all the internucleoside linkages in the oligonucleotide are phosphorothioate and/or boranophosphate linkages. Preferably, all the internucleoside linkages in the oligonucleotide are phosphorothioate linkages.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

Complementarity

The term complementarity describes the capacity for Watson-Crick base-pairing of nucleosides/nucleotides. Watson-Crick base pairs are guanine (G)-cytosine (C) and adenine (A) -thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the number of nucleotides in percent of a contiguous nucleotide sequence in a nucleic acid molecule (e.g. oligonucleotide) which, at a given position, are complementary to (i.e. form Watson Crick base pairs with) a contiguous nucleotide sequence, at a given position of a separate nucleic acid molecule (e.g. the target nucleic acid). The percentage is calculated by counting the number of aligned bases that form pairs between the two sequences, dividing by the total number of nucleotides in the oligonucleotide and multiplying by 100. In such a comparison a nucleobase/nucleotide which does not align (form a base pair) is termed a mismatch.

The term "fully complementary", refers to 100% complementarity.

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, *Oligonucleotides* 13:515-537).

The standard state Gibbs free energy ΔG° is a more accurate representation of binding affinity and is related to the dissociation constant ($K_d$) of the reaction by ΔG°=−RTln($K_d$), where R is the gas constant and T is the absolute temperature. Therefore, a very low ΔG° of the reaction between an oligonucleotide and the target nucleic acid reflects a strong hybridization between the oligonucleotide and target nucleic acid. ΔG° is the energy associated with a reaction where aqueous concentrations are 1 M, the pH is 7, and the temperature is 37° C. The hybridization of oligonucleotides to a target nucleic acid is a spontaneous reaction and for spontaneous reactions ΔG° is less than zero. ΔG° can be measured experimentally, for example, by use of the isothermal titration calorimetry (ITC) method as described in Hansen et al., 1965, Chem. Comm. 36-38 and Holdgate et al., 2005, Drug Discov Today. The skilled person will know that commercial equipment is available for ΔG° measurements. ΔG° can also be estimated numerically by using the nearest neighbor model as described by SantaLucia, 1998, *Proc Natl Acad Sci USA*. 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated ΔG° values below −10 kcal for oligonucleotides that are 10-30 nucleotides in length. In some embodiments the degree or strength of hybridization is measured by the standard state Gibbs free energy ΔG°. The oligonucleotides may hybridize to a target nucleic acid with estimated ΔG° values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

The Target

The target refers to the protein which it is desired to modulate.

Target Nucleic Acid

A target nucleic acid is the intended target which the oligonucleotide of the invention hybridizes to, and may for example be a gene, a RNA, a non-coding RNA, a long non-coding RNA, a mRNA, and pre-mRNA, a mature mRNA or a cDNA sequence. In some embodiments the target nucleic acid is a non-coding RNA or a long non-coding RNA, or a subsequence thereof. For in vivo or in vitro application, the oligonucleotide of the invention is capable of decreasing the level of the SNHG14 transcript downstream of SNORD109B of and thereby relieving the suppression of the paternal UBE3A transcript in the intended target cell. The contiguous sequence of nucleobases of the oligonucleotide of the invention is complementary to the target nucleic acid, as measured across the length of the oligonucleotide, optionally with the exception of one or two mismatches, and optionally excluding nucleotide based linker regions which may link the oligonucleotide to an optional functional group such as a conjugate.

Target Sequence

The oligonucleotide comprises a contiguous nucleotide sequence which is complementary to or hybridizes to a sub-sequence of the target nucleic acid molecule. The term "target sequence" as used herein refers to a sequence of nucleotides present in the target nucleic acid which comprises the nucleobase sequence which is complementary to the oligonucleotide of the invention. In some embodiments, the target sequence consists of a region on the target nucleic acid which is complementary to the contiguous nucleotide sequence of the oligonucleotide of the invention. In some embodiments the target sequence is longer than the complementary sequence of a single oligonucleotide, and may, for example represent a preferred region of the target nucleic acid which may be targeted by several oligonucleotides of the invention.

The oligonucleotide of the invention comprises a contiguous nucleotide sequence which is complementary to the target nucleic acid, such as a target sequence.

The oligonucleotide comprises a contiguous nucleotide sequence of at least 8 nucleotides which is complementary to or hybridizes to a target sequence present in the target nucleic acid molecule. The contiguous nucleotide sequence (and therefore the target sequence) comprises of at least 8 contiguous nucleotides, such as 9, 10, 11, 12, 13, 14, 15, 16, 17, 18, 19, 20, 21, 22, 23, 24, 25, 26, 27, 28, 29 or 30 contiguous nucleotides, such as from 12-25, such as from 14-18 contiguous nucleotides.

Target Cell

The term a target cell as used herein refers to a cell which is expressing the target nucleic acid. In some embodiments the target cell may be in vivo or in vitro. In some embodiments the target cell is a mammalian cell such as a rodent cell, such as a mouse cell or a rat cell, or a primate cell such as a monkey cell or a human cell. In preferred embodiments the target cell is a neuronal cell.

Naturally Occurring Variant

The term "naturally occurring variant" refers to variants of SNHG14 transcript downstream of SNORD109B gene or transcripts which originate from the same genetic loci as the target nucleic acid, but may differ for example, by virtue of degeneracy of the genetic code causing a multiplicity of codons in the long non-coding RNA. The oligonucleotide of the invention may therefore be designed to target the target nucleic acid and naturally occurring variants thereof.

Modulation of Expression

The term "modulation of expression" as used herein is to be understood as an overall term for an oligonucleotide's ability to alter the amount of UBE3A protein when compared to the amount of UBE3A before administration of the oligonucleotide. Alternatively modulation of expression may be determined by reference to a control experiment where the oligonucleotide of the invention is not administered. The modulation effected by the oligonucleotide is related to it's ability to reduce, remove, prevent, lessen, lower or terminate the suppression of the paternal UBE3A transcript, e.g. by degradation or removal of the non-coding SNHG14 transcript downstream of SNORD109B or by blockage or prevention of polymerase activity associated with the SNHG14 transcript downstream of SNORD109B. The modulation can also be viewed as the oligonucleotide's ability to restore, increase or enhance expression of paternal UBE3A, e.g. by removal or blockage of inhibitory mechanisms affected by the non-coding SNHG14 transcript downstream of SNORD109B.

High Affinity Modified Nucleosides

A high affinity modified nucleoside is a modified nucleotide which, when incorporated into the oligonucleotide enhances the affinity of the oligonucleotide for its complementary target, for example as measured by the melting temperature ($T_m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclo-hexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'—OH group naturally found in DNA and RNA nucleosides. Substituents may, for example be introduced at the 2', 3', 4' or 5' positions. Nucleosides with modified sugar moieties also include 2' modified nucleosides, such as 2' substituted nucleosides. Indeed, much focus has been spent on developing 2' substituted nucleosides, and numerous 2' substituted nucleosides have been found to have beneficial properties when incorporated into oligonucleotides, such as enhanced nucleoside resistance and enhanced affinity.

2' Modified Nucleosides.

A 2' sugar modified nucleoside is a nucleoside which has a substituent other than H or —OH at the 2' position (2' substituted nucleoside) or comprises a 2' linked biradicle, and includes 2' substituted nucleosides and LNA (2'-4' biradicle bridged) nucleosides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-fluoro-ANA (F-ANA). For further examples, please see e.g. Freier & Altmann; Nucl. Acid Res., 1997, 25, 4429-4443 and Uhlmann; Curr. Opinion in Drug Development, 2000, 3(2), 293-213; and Deleavey and Damha, Chemistry and Biology 2012, 19, 937. Below are illustrations of some 2' substituted modified nucleosides.

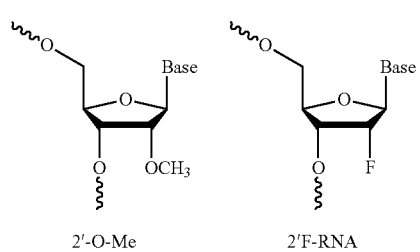

2'-O-Me         2'F-RNA

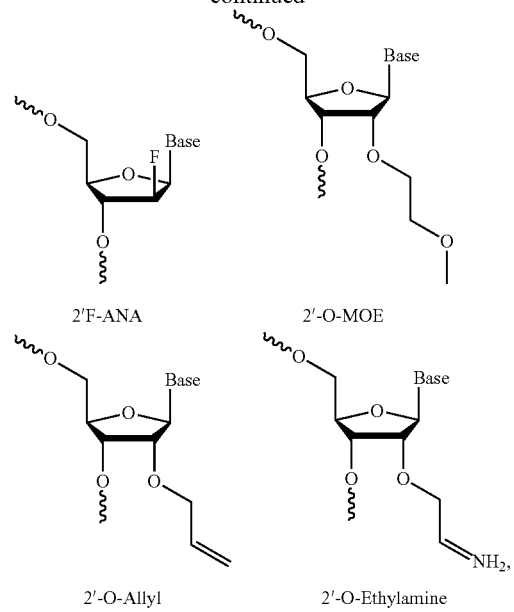

2'F-ANA         2'-O-MOE

2'-O-Allyl      2'-O-Ethylamine

Locked Nucleic Acid Nucleosides (LNA).

LNA nucleosides are modified nucleosides which comprise a linker group (referred to as a biradicle or a bridge) between C2' and C4' of the ribose sugar ring of a nucleotide. These nucleosides are also termed bridged nucleic acid or bicyclic nucleic acid (BNA) in the literature.

In some embodiments, the modified nucleoside or the LNA nucleosides of the oligomer of the invention has a general structure of the formula I or II:

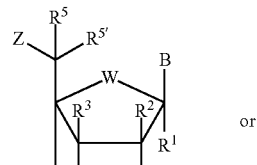

Formula I

β-D

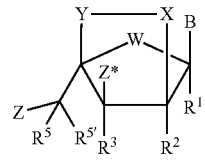

Formula II

α-L wherein W is selected from —O—, —S—, —N($R^a$)—, —C($R^a R^b$)—, such as, in some embodiments —O—;

B designates a nucleobase or modified nucleobase moiety;

Z designates an internucleoside linkage to an adjacent nucleoside, or a 5'-terminal group;

Z* designates an internucleoside linkage to an adjacent nucleoside, or a 3-terminal group;

X designates a group selected from the list consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, X is selected from the group consisting of: —O—, —S—, NH—, $NR^a R^b$, —CH$_2$—, $CR^a R^b$, —C(=CH$_2$)—, and —C(=$CR^a R^b$)—

In some embodiments, X is —O—

Y designates a group selected from the group consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, Y is selected from the group consisting of: —CH$_2$—, —C($R^a R^b$)—, —CH$_2$CH$_2$—, —C($R^a R^b$)—C($R^a R^b$)—, —CH$_2$CH$_2$CH$_2$—, —C($R^a R^b$)C($R^a R^b$)C($R^a R^b$)—, —C($R^a$)=C($R^b$)—, and —C($R^a$)=N—

In some embodiments, Y is selected from the group consisting of: —CH$_2$—, —CHR$^a$—, —CHCH$_3$—, $CR^a R^b$— or —X—Y— together designate a bivalent linker group (also referred to as a radicle) together designate a bivalent linker group consisting of 1, 2, 3 or 4 groups/atoms selected from the group consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z, In some embodiments, —X—Y— designates a biradicle selected from the groups consisting of: —X—CH$_2$—, —X—$CR^a R^b$—, —X—CHR$^a$—, —X—C(HCH$_3$)—, —O—Y—, —O—CH$_2$—, —S—CH$_2$—, —NH—CH$_2$—, —O—CHCH$_3$—, —CH$_2$—O—CH$_2$, —O—CH(CH$_3$CH$_3$)—, —O—CH$_2$—CH$_2$—, OCH$_2$—CH$_2$—CH$_2$—, —O—CH$_2$OCH$_2$—, —O—NCH$_2$—, —C(=CH$_2$)—CH$_2$—, —NR$^a$—CH$_2$—, N—O—CH$_2$, —S—$CR^a R^b$— and —S—CHR$^a$—.

In some embodiments —X—Y— designates —O—CH$_2$— or —O—CH(CH$_3$)—.

wherein Z is selected from —O—, —S—, and —N($R^a$)—, and R$^a$ and, when present R$^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl) amino, carbamoyl, mono- and di(C$_{1-6}$-alkyl)-aminocarbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted and where two geminal substituents R$^a$ and R$^b$ together may designate optionally substituted methylene (=CH$_2$), wherein for all chiral centers, asymmetric groups may be found in either R or S orientation, wherein R$^1$, R$^2$, R$^3$, R$^5$ and R$^{5*}$ are independently selected from the group consisting of: hydrogen, optionally substituted C$_{1-6}$-alkyl, optionally substituted C$_{2-6}$-alkenyl, optionally substituted C$_{2-6}$-alkynyl, hydroxy, C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl) amino, carbamoyl, mono- and di(C$_{1-6}$-alkyl)-aminocarbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted, and where two geminal substituents together may designate oxo, thioxo, imino, or optionally substituted methylene.

In some embodiments R$^1$, R$^2$, R$^3$, R$^5$ and R$^{5*}$ are independently selected from C$_{1-6}$ alkyl, such as methyl, and hydrogen.

In some embodiments R$^1$, R$^2$, R$^3$, R$^5$ and R$^{5*}$ are all hydrogen.

In some embodiments R$^1$, R$^2$, R$^3$, are all hydrogen, and either R$^5$ and R$^{5*}$ is also hydrogen and the other of R$^5$ and R$^{5*}$ is other than hydrogen, such as C$_{1-6}$ alkyl such as methyl.

In some embodiments, R$^a$ is either hydrogen or methyl. In some embodiments, when present, R$^b$ is either hydrogen or methyl.

In some embodiments, one or both of R$^a$ and R$^b$ is hydrogen

In some embodiments, one of R$^a$ and R$^b$ is hydrogen and the other is other than hydrogen In some embodiments, one of R$^a$ and R$^b$ is methyl and the other is hydrogen In some embodiments, both of R$^a$ and R$^b$ are methyl.

In some embodiments, the biradicle —X—Y— is —O—CH$_2$—, W is O, and all of R$^1$, R$^2$, R$^3$, R$^5$ and R$^{5*}$ are all hydrogen. Such LNA nucleosides are disclosed in WO99/014226, WO00/66604, WO98/039352 and WO2004/046160 which are all hereby incorporated by reference, and include what are commonly known as beta-D-oxy LNA and alpha-L-oxy LNA nucleosides.

In some embodiments, the biradicle —X—Y— is —S—CH$_2$—, W is O, and all of R$^1$, R$^2$, R$^3$, R$^5$ and R$^{5*}$ are all hydrogen. Such thio LNA nucleosides are disclosed in WO99/014226 and WO2004/046160 which are hereby incorporated by reference.

In some embodiments, the biradicle —X—Y— is —NH—CH$_2$—, W is O, and all of R$^1$, R$^2$, R$^3$, R$^5$ and R$^{5*}$ are all hydrogen. Such amino LNA nucleosides are disclosed in WO99/014226 and WO2004/046160 which are hereby incorporated by reference.

In some embodiments, the biradicle —X—Y— is —O—CH$_2$—CH$_2$— or —O—CH$_2$—CH$_2$—CH$_2$—, W is O, and all of R$^1$, R$^2$, R$^3$, R$^5$ and R$^{5*}$ are all hydrogen. Such LNA nucleosides are disclosed in WO00/047599 and Morita et al, Bioorganic & Med. Chem. Lett. 12 73-76, which are hereby incorporated by reference, and include what are commonly known as 2'-O-4'C-ethylene bridged nucleic acids (ENA).

In some embodiments, the biradicle —X—Y— is —O—CH$_2$—, W is O, and all of R$^1$, R$^2$, R$^3$, and one of R$^5$ and R$^{5*}$ are hydrogen, and the other of R$^5$ and R$^{5*}$ is other than hydrogen such as C$_{1-6}$ alkyl, such as methyl. Such 5' substituted LNA nucleosides are disclosed in WO2007/134181 which is hereby incorporated by reference.

In some embodiments, the biradicle —X—Y— is —O—$CR^a R^b$—, wherein one or both of R$^a$ and R$^b$ are other than hydrogen, such as methyl, W is O, and all of R$^1$, R$^2$, R$^3$, and one of R$^5$ and R$^{5*}$ are hydrogen, and the other of R$^5$ and R$^{5*}$ is other than hydrogen such as $C_{1-6}$ alkyl, such as methyl. Such bis modified LNA nucleosides are disclosed in WO2010/077578 which is hereby incorporated by reference.

In some embodiments, the biradicle —X—Y— designate the bivalent linker group —O—CH(CH$_2$OCH$_3$)—(2' O-methoxyethyl bicyclic nucleic acid—Seth at al., 2010, J. Org. Chem. Vol 75(5) pp. 1569-81). In some embodiments, the biradicle —X—Y— designate the bivalent linker group —O—CH(CH$_2$CH$_3$)—(2'O-ethyl bicyclic nucleic acid—Seth at al., 2010, J. Org. Chem. Vol 75(5) pp. 1569-81). In some embodiments, the biradicle —X—Y— is —O—CHR$^a$—, W is O, and all of $R^1$, $R^2$, $R^3$, $R^5$ and $R^{5*}$ are all hydrogen. Such 6' substituted LNA nucleosides are disclosed in WO10036698 and WO07090071 which are both hereby incorporated by reference.

In some embodiments, the biradicle —X—Y— is —O—CH(CH$_2$OCH$_3$)—, W is O, and all of $R^1$, $R^2$, $R^3$, $R^5$ and $R^{5*}$ are all hydrogen. Such LNA nucleosides are also known as cyclic MOEs in the art (cMOE) and are disclosed in WO07090071.

In some embodiments, the biradicle —X—Y— designate the bivalent linker group —O—CH(CH$_3$)—.—in either the R- or S-configuration. In some embodiments, the biradicle —X—Y— together designate the bivalent linker group —O—CH$_2$—O—CH$_2$—(Seth at al., 2010, J. Org. Chem). In some embodiments, the biradicle —X—Y— is —O—CH(CH$_3$)—, W is O, and all of $R^1$, $R^2$, $R^3$, $R^5$ and $R^{5*}$ are all hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L) which are both hereby incorporated by reference).

In some embodiments, the biradicle —X—Y— is —O—CR$^a$R$^b$—, wherein in neither R$^a$ or R$^b$ is hydrogen, W is O, and all of $R^1$, $R^2$, $R^3$, $R^5$ and $R^{5*}$ are all hydrogen. In some embodiments, R$^a$ and R$^b$ are both methyl. Such 6' di-substituted LNA nucleosides are disclosed in WO 2009006478 which is hereby incorporated by reference.

In some embodiments, the biradicle —X—Y— is —S—CHR$^a$—, W is O, and all of $R^1$, $R^2$, $R^3$, $R^5$ and $R^{5*}$ are all hydrogen. Such 6' substituted thio LNA nucleosides are disclosed in WO11156202 which is hereby incorporated by reference. In some 6' substituted thio LNA embodiments R$^a$ is methyl.

In some embodiments, the biradicle —X—Y— is —C(=CH$_2$)—C(R$^a$R$^b$)—, such as —C(=CH$_2$)—CH$_2$—, or —C(=CH$_2$)—CH(CH$_3$)—W is O, and all of $R^1$, $R^2$, $R^3$, $R^5$ and $R^{5*}$ are all hydrogen. Such vinyl carbo LNA nucleosides are disclosed in WO08154401 and WO09067647 which are both hereby incorporated by reference.

In some embodiments the biradicle —X—Y— is —N(—OR$^a$)—, W is O, and all of $R^1$, $R^2$, $R^3$, $R^5$ and $R^{5*}$ are all hydrogen. In some embodiments R$^a$ is $C_{1-6}$ alkyl such as methyl. Such LNA nucleosides are also known as N substituted LNAs and are disclosed in WO2008/150729 which is hereby incorporated by reference. In some embodiments, the biradicle —X—Y— together designate the bivalent linker group —O—NR$^a$—CH$_3$-(Seth at al., 2010, J. Org. Chem). In some embodiments the biradicle —X—Y— is —N(R$^a$)—, W is O, and all of $R^1$, $R^2$, $R^3$, $R^5$ and $R^{5*}$ are all hydrogen. In some embodiments R$^a$ is $C_{1-6}$ alkyl such as methyl.

In some embodiments, one or both of $R^5$ and $R^{5*}$ is hydrogen and, when substituted the other of $R^5$ and $R^{5*}$ is $C_{1-6}$ alkyl such as methyl. In such an embodiment, $R^1$, $R^2$, $R^3$, may all be hydrogen, and the biradicle —X—Y— may be selected from —O—CH$_2$— or —O—C(HCR$^a$)—, such as —O—C(HCH$_3$)—.

In some embodiments, the biradicle is —CR$^a$R$^b$—O—CR$^a$R$^b$—, such as CH$_2$—O—CH$_2$—, W is O and all of $R^1$, $R^2$, $R^3$, $R^5$ and $R^{5*}$ are all hydrogen. In some embodiments R$^a$ is $C_{1-6}$ alkyl such as methyl. Such LNA nucleosides are also known as conformationally restricted nucleotides (CRNs) and are disclosed in WO2013036868 which is hereby incorporated by reference.

In some embodiments, the biradicle is —O—CR$^a$R$^b$—O—CR$^a$R$^b$—, such as O—CH$_2$—O—CH$_2$—, W is O and all of $R^1$, $R^2$, $R^3$, $R^5$ and $R^{5*}$ are all hydrogen. In some embodiments R$^a$ is $C_{1-6}$ alkyl such as methyl. Such LNA nucleosides are also known as COC nucleotides and are disclosed in Mitsuoka et al., Nucleic Acids Research 2009 37(4), 1225-1238, which is hereby incorporated by reference.

It will be recognized than, unless specified, the LNA nucleosides may be in the beta-D or alpha-L stereoisoform.

Certain examples of LNA nucleosides are presented in Scheme 1.

Scheme 1

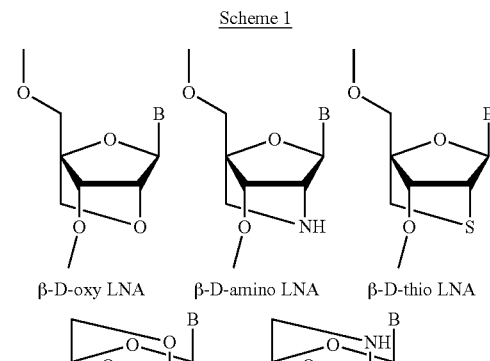

β-D-oxy LNA    β-D-amino LNA    β-D-thio LNA

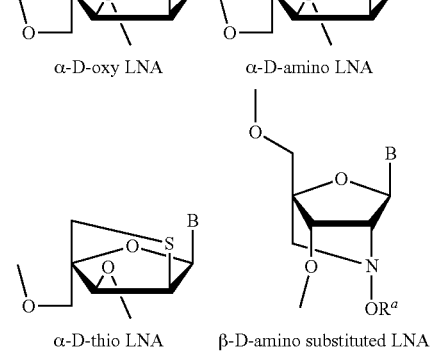

α-D-oxy LNA    α-D-amino LNA

α-D-thio LNA    β-D-amino substituted LNA

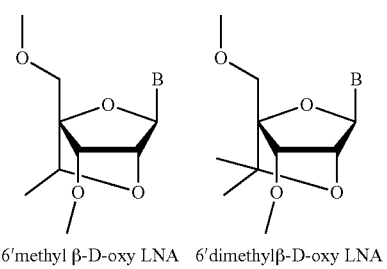

6'methyl β-D-oxy LNA    6'dimethylβ-D-oxy LNA

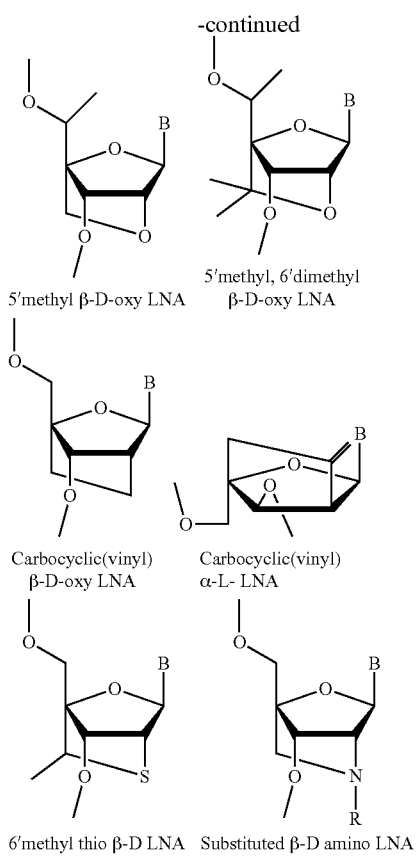

As illustrated in the examples, in preferred embodiments of the invention the LNA nucleosides in the oligonucleotides are beta-D-oxy-LNA nucleosides.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 DNA nucleosides and are flanked on one side or both sides by affinity enhancing nucleosides, for example gapmers, headmers and tailmers.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 10% or more than 20% of the of the initial rate determined when using a oligonucleotide having the same base sequence as the modified oligonucleotide being tested, but containing only DNA monomers, with phosphorothioate linkages between all monomers in the oligonucleotide, and using the methodology provided by Example 91-95 of WO01/23613 (hereby incorporated by reference).

Gapmer

The term gapmer as used herein refers to an antisense oligonucleotide which comprises a region of RNase H recruiting oligonucleotides (gap) which is flanked 5' and 3' by one or more affinity enhancing modified nucleosides (flanks). Various gapmer designs are described herein. Headmers and tailmers are oligonucleotides capable of recruiting RNase H where one of the flanks is missing, i.e. only one of the ends of the oligonucleotide comprises affinity enhancing modified nucleosides. For headmers the 3' flank is missing (i.e. the 5' flanc comprise affinity enhancing modified nucleosides) and for tailmers the 5' flank is missing (i.e. the 3' flank comprises affinity enhancing modified nucleosides).

LNA Gapmer

The term LNA gapmer is a gapmer oligonucleotide wherein at least one of the affinity enhancing modified nucleosides is an LNA nucleoside.

Mixed Wing Gapmer

The term mixed wing gapmer refers to a LNA gapmer wherein the flank regions comprise at least one LNA nucleoside and at least one non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside(s). In some embodiments the mixed wing gapmer has one flank which comprises LNA nucleosides (e.g. 5' or 3') and the other flank (3' or 5' respectfully) comprises 2' substituted modified nucleoside(s).

Conjugate

The term conjugate as used herein refers to an oligonucleotide which is covalently linked to a non-nucleotide moiety (conjugate moiety or region C or third region).

Conjugation of the oligonucleotide of the invention to one or more non-nucleotide moieties may improve the pharmacology of the oligonucleotide, e.g. by affecting the activity, cellular distribution, cellular uptake or stability of the oligonucleotide. In some embodiments the conjugate moiety modify or enhance the pharmacokinetic properties of the oligonucleotide by improving cellular distribution, bioavailability, metabolism, excretion, permeability, and/or cellular uptake of the oligonucleotide. In particular the conjugate may target the oligonucleotide to a specific organ, tissue or cell type and thereby enhance the effectiveness of the oligonucleotide in that organ, tissue or cell type. A the same time the conjugate may serve to reduce activity of the oligonucleotide in non-target cell types, tissues or organs, e.g. off target activity or activity in non-target cell types, tissues or organs. WO 93/07883 and WO 2013/033230 provides suitable conjugate moieties, which are hereby incorporated by reference. WO 2012/143379 provides a method of delivering a drug across the blood-brain-barrier by conjugation to an antibody fragment with affinity to the transferrin receptor, which are hereby incorporated by reference.

Oligonucleotide conjugates and their synthesis has also been reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103, each of which is incorporated herein by reference in its entirety.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids) or combinations thereof. In some embodiments the non-nucleotide moiety an antibody or antibody fragment, such as an antibody or antibody fragment that facilitates delivery across the blood-brain-barrier, in particular an antibody or antibody fragment targeting the transferrin receptor.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety (Region C), to a first region, e.g. an oligonucleotide (region A).

In some embodiments of the invention the conjugate or oligonucleotide conjugate of the invention may optionally, comprise a linker region (second region or region B and/or region Y) which is positioned between the oligonucleotide (region A or first region) and the conjugate moiety (region C or third region).

Region B refers to biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In a preferred embodiment the nuclease susceptible linker comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides comprising at least two consecutive phosphodiester linkages, such as at least 3 or 4 or 5 consecutive phosphodiester linkages. Preferably the nucleosides are DNA or RNA. Phosphodiester containing biocleavable linkers are described in more detail in WO 2014/076195 (hereby incorporated by reference).

Region Y refers to linkers that are not necessarily biocleavable but primarily serve to covalently connect a conjugate moiety (region C or third region), to an oligonucleotide (region A or first region). The region Y linkers may comprise a chain structure or an oligomer of repeating units such as ethylene glycol, amino acid units or amino alkyl groups The oligonucleotide conjugates of the present invention can be constructed of the following regional elements A-C, A-B-C, A-B-Y-C, A-Y-B-C or A-Y-C. In some embodiments the linker (region Y) is an amino alkyl, such as a C2-C36 amino alkyl group, including, for example C6 to C12 amino alkyl groups. In a preferred embodiment the linker (region Y) is a C6 amino alkyl group.

Control

By the term "control" when used in relation to measurements of the effect of an oligonucleotide it is generally understood that the control is an untreated individual or target cell or a individual or target cell treated with a non-targeting oligonucleotide (mock). It may however also be an individual treated with the standard of care.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic.

DETAILED DESCRIPTION OF THE INVENTION

The Target

An aspect of the invention is to modulate the level of pig, primate or human UBE3A protein expression, in particular to increase the expression of paternal UBE3A expression in neuronal cells, in particular in human neuronal cells. The human UBE3A protein exists in several isoforms which are listed under Uniprot nr. Q05086. Several mutations in the maternal UBE3A gene can results in Angelman syndrome.

The target nucleic acid for the oligonucleotides of the invention is RNA, in particular a long non-coding RNA. The long non-coding RNA which is targeted by the oligonucleotides of the present invention is human SNHG14 (also known as UBE3A-ATS with Ensembl entry number ENSG00000224078, version GRCh38.p2). In particular the target nucleic acid is the region downstream of SNORD109B corresponding to position 25278410 to 25419462 on chromosome 15 (SEQ ID NO: 1). In Rhesus monkey (*Macaca mulatta*) the UBE3A supressor is defined as region downstream of SNORD109A corresponding to position 4222848 to U.S. Pat. No. 4,373,084 (forward strand) on chromosome 7 using the Ensembl assembly MMUL 1.0 (SEQ ID NO: 2).

In some embodiments, the target nucleic acid is SEQ ID NO: 1, or naturally occurring variants thereof.

In certain embodiments the target nucleic acid correspond to regions which are conserved between human (SEQ ID NO: 1) and Rhesus monkey (SEQ ID NO: 2). In certain embodiments target nucleic acid correspond to regions which are conserved between human (SEQ ID NO:1), Rhesus monkey (SEQ ID NO: 2) and mouse (SEQ ID NO: 3).

In certain embodiments the target nucleic acid is the region that is antisense to the UBE3A pre-mRNA, this region corresponds to position 55319 to 141053 of SEQ ID NO: 1.

In certain embodiments the target nucleic acid is the region that is downstream of SNORD109B and upstream of the region that is antisense to the UBE3A pre-mRNA, this region corresponds to position 1 to 55319 of SEQ ID NO: 1.

In some embodiments, the target nucleic acid is present in a cell, such as a mammalian cell in particular a human cell in vitro or in vivo (the target cell). In certain embodiments the target cell is a neuron, preferably a human neuronal cell.

The target sequence may be a sub-sequence of the target nucleic acid. In some embodiments the oligonucleotide targets sub-sequence selected from the group consisting of the antisense region of exon 9, exon10, exon13, exon14, intron 14, exon 15, intron15 and exon 16 of UBE3A. In some embodiments the oligonucleotide or contiguous nucleotide sequence hybridize or is complementary to a single stranded nucleic acid molecule selected from the group consisting of positions: 55319-76274, 77483-77573, 92157-93403 and 97056-97354 of SEQ ID NO: 1. In some embodiments the oligonucleotide or contiguous nucleotide sequence hybridize or is complementary to a single stranded nucleic acid molecule selected from the group consisting of positions: 60821-60849, 77567-77583, 92323-92339 and 97156-97172 of SEQ ID NO: 1.

In some embodiments the target nucleic acid is a region corresponding to positions 9200-9250 of SEQ ID NO: 1.

In some embodiments the target nucleic acid is a region corresponding to positions 11505-11555 of SEQ ID NO: 1.

In some embodiments the target nucleic acid is a region corresponding to positions 15100-15150 of SEQ ID NO: 1.

In some embodiments the target nucleic acid is a region corresponding to positions 30590-30740 of SEQ ID NO: 1.

In some embodiments the target nucleic acid is a region corresponding to positions 46380-46430 of SEQ ID NO: 1.

The Oligonucleotides of the Invention

The invention relates to oligonucleotides capable of modulating expression of paternal UBE3A, in particular induction or up-regulation of paternally expressed UBE3A in neuronal cells. The modulation is achieved by hybridizing to a target nucleic acid located on the long non-coding RNA SNHG14 transcript downstream of SNORD109B. In certain embodiments the oligonucleotide of the invention hybridizes to a sub-sequence of the target nucleic acid of SEQ ID NO: 1 with a $\Delta G°$ below −10 kcal, such as with a $\Delta G°$ between −10 to −60 kcal, such as −12 to −40, such as from −15 to −30 kcal or −16 to −27 kcal such as −18 to −25 kcal.

The oligonucleotide of the invention is an antisense oligonucleotide which targets the pig, rhesus monkey and/or human SNHG14 transcript downstream of SNORD109B.

In some embodiments the antisense oligonucleotide of the invention is capable of modulating the expression of the target by removing, interfering with or decreasing the suppressor of the target. Preferably, the oligonucleotides of the invention induce UBE3A expression in a cell, in particular paternal UBE3A expression in a neuron, by degradation or removal of the SNHG14 transcript downstream of SNORD109B. In some embodiments the oligonucleotides of the invention are capable of increasing the expression of UBE3A by least 20% compared to the expression level of UBE3A in a neuronal cell treated with saline or a non-targeting oligonucleotide, more preferably by at least 30%, 35%, 40%, 45%, 50%, 55%, 60%, 80%, 100%, 120%, 150%, 160%, 170%, 180%, 190%, 200%, 210%, 220%, 230%, 240% or 250% compared to the expression level of UBE3A in a neuronal cell treated with saline or a non-targeting oligonucleotide. In additional embodiments the oligonucleotides of the invention are capable of decreasing the level of the SNHG14 transcript downstream of SNORD109B (in particular the part of the transcript that is antisense to the UBE3A pre-mRNA region) by at least 20% compared to the level of the SNHG14 transcript downstream of SNORD109B in a neuronal cell treated with saline or a non-targeting oligonucleotide, more preferably by at least 30%, 40%, 50%, 60%, 70%, 80%, 90% or 95% compared to the level of the SNHG14 transcript downstream of SNORD109B in a neuronal cell treated with saline or a non-targeting oligonucleotide, without reducing SNORD115 levels by more than 0%, 1%, 2%, 3%, 4%, 5%, 6%, 7%, 8%, 9%, 10%, 12%, 14%, 16%, 18%, 20%, 25% or 30% compared to the level of SNORD115 in a cell treated with saline or a non-targeting oligonucleotide. SNRPN and SNORD116 transcripts are located upstream from the SNORD115 transcript consequently if the SNORD115 transcript is not reduced by the oligonucleotide it is highly likely that the SNRPN and SNORD116 transcripts are also not reduced. In a further embodiment SNRPN and SNORD116 transcripts levels are not reduced by more than 0%, 1%, 2%, 3%, 4%, 5%, 6%, 7%, 8%, 9%, 10%, 12%, 14%, 16%, 18%, 20%, 25% or 30% compared to the level of SNRPN and SNORD116 in a cell treated with saline or a non-targeting oligonucleotide.

The target modulation is triggered by the hybridization between a contiguous nucleotide sequence of the oligonucleotide and the target nucleic acid. In some embodiments the oligonucleotide of the invention comprises mismatches between the oligonucleotide and the target nucleic acid. Despite mismatches hybridization to the target nucleic acid may still be sufficient to show a desired modulation of UBE3A expression. Reduced binding affinity resulting from mismatches may advantageously be compensated by increased number of nucleotides in the oligonucleotide and/or an increased number of modified nucleosides capable of increasing the binding affinity to the target, such as 2' modified nucleosides, including LNA, present within the oligonucleotide sequence.

An aspect of the present invention relates to an antisense oligonucleotide which comprises a contiguous nucleotide sequence of 10 to 30 nucleotides in length with at least 90%, such as 95%, such as 98% such as 100% complementarity to position 25278410 to 25419462 on human chromosome 15.

In some embodiments, the oligonucleotide comprises a contiguous sequence which is at least 90% complementary, such as at least 91%, such as at least 92%, such as at least 93%, such as at least 94%, such as at least 95%, such as at least 96%, such as at least 97%, such as at least 98%, or 100% complementary with a region of the target nucleic acid shown as SEQ ID NO: 1, 2 or 3.

In a preferred embodiment the oligonucleotide of the invention, or contiguous nucleotide sequence thereof is fully complementary (100% complementary) to a region of the target nucleic acid shown as SEQ ID NO: 1, or in some embodiments may comprise one or two mismatches between the oligonucleotide and the target nucleic acid.

In some embodiments the oligonucleotide sequence is 100% complementary to a corresponding target nucleic acid region present in SEQ ID NO: 1 and SEQ ID NO: 2. In some embodiments the oligonucleotide sequence is 100% complementary to a corresponding target nucleic acid region present SEQ ID NO: 1, 2 and 3.

In some embodiments, the oligonucleotide comprises a contiguous nucleotide sequence of 10 to 30 nucleotides in length with at least 90% complementary, such as 100% complementarity, to a corresponding target nucleic acid region present in SEQ ID NO: 1, wherein the target nucleic acid region is selected from the group consisting of region A1 to A3649 in table 1

TABLE 1

Regions of SEQ ID NO 1 which may be targeted using oligonucleotide of the invention

| Reg. | Position in SEQ ID NO 1 | | |
|---|---|---|---|
| A | from | to | Length |
| 1 | 10 | 75 | 66 |
| 2 | 77 | 91 | 15 |
| 3 | 93 | 108 | 16 |
| 4 | 168 | 213 | 46 |
| 5 | 217 | 282 | 66 |
| 6 | 284 | 299 | 16 |
| 7 | 301 | 328 | 28 |
| 8 | 330 | 344 | 15 |

TABLE 1-continued

Regions of SEQ ID NO 1 which may be targeted using oligonucleotide of the invention

| Reg. A | Position in SEQ ID NO 1 from | to | Length |
|---|---|---|---|
| 9 | 361 | 400 | 40 |
| 10 | 415 | 447 | 33 |
| 11 | 449 | 470 | 22 |
| 12 | 472 | 487 | 16 |
| 13 | 489 | 521 | 33 |
| 14 | 523 | 540 | 18 |
| 15 | 551 | 570 | 20 |
| 16 | 590 | 638 | 49 |
| 17 | 652 | 670 | 19 |
| 18 | 672 | 733 | 62 |
| 19 | 735 | 756 | 22 |
| 20 | 758 | 773 | 16 |
| 21 | 781 | 829 | 49 |
| 22 | 831 | 870 | 40 |
| 23 | 882 | 903 | 22 |
| 24 | 918 | 949 | 32 |
| 25 | 961 | 990 | 30 |
| 26 | 1007 | 1021 | 15 |
| 27 | 1019 | 1050 | 32 |
| 28 | 1052 | 1090 | 39 |
| 29 | 1092 | 1139 | 48 |
| 30 | 1147 | 1179 | 33 |
| 31 | 1175 | 1212 | 38 |
| 32 | 1220 | 1242 | 23 |
| 33 | 1245 | 1259 | 15 |
| 34 | 1265 | 1278 | 14 |
| 35 | 1285 | 1323 | 39 |
| 36 | 1317 | 1330 | 14 |
| 37 | 1337 | 1355 | 19 |
| 38 | 1357 | 1403 | 47 |
| 39 | 1405 | 1421 | 17 |
| 40 | 1423 | 1481 | 59 |
| 41 | 1486 | 1515 | 30 |
| 42 | 1521 | 1581 | 61 |
| 43 | 1611 | 1633 | 23 |
| 44 | 1631 | 1644 | 14 |
| 45 | 1635 | 1663 | 29 |
| 46 | 1669 | 1684 | 16 |
| 47 | 1685 | 1709 | 25 |
| 48 | 1711 | 1724 | 14 |
| 49 | 1726 | 1746 | 21 |
| 50 | 1754 | 1808 | 55 |
| 51 | 1819 | 1860 | 42 |
| 52 | 1862 | 1878 | 17 |
| 53 | 1896 | 1910 | 15 |
| 54 | 1923 | 1944 | 22 |
| 55 | 1946 | 1987 | 42 |
| 56 | 1985 | 2051 | 67 |
| 57 | 2053 | 2082 | 30 |
| 58 | 2088 | 2104 | 17 |
| 59 | 2106 | 2125 | 20 |
| 60 | 2132 | 2207 | 76 |
| 61 | 2209 | 2234 | 26 |
| 62 | 2247 | 2261 | 15 |
| 63 | 2263 | 2286 | 24 |
| 64 | 2290 | 2306 | 17 |
| 65 | 2308 | 2329 | 22 |
| 66 | 2347 | 2391 | 45 |
| 67 | 2398 | 2431 | 34 |
| 68 | 2447 | 2468 | 22 |
| 69 | 2470 | 2555 | 86 |
| 70 | 2565 | 2579 | 15 |
| 71 | 2579 | 2592 | 14 |
| 72 | 2589 | 2605 | 17 |
| 73 | 2594 | 2657 | 64 |
| 74 | 2672 | 2687 | 16 |
| 75 | 2692 | 2705 | 14 |
| 76 | 2703 | 2721 | 19 |
| 77 | 2770 | 2824 | 55 |
| 78 | 2826 | 2841 | 16 |
| 79 | 2838 | 2851 | 14 |
| 80 | 2843 | 2889 | 47 |
| 81 | 2896 | 2930 | 35 |
| 82 | 2930 | 2967 | 38 |
| 83 | 2965 | 2988 | 24 |
| 84 | 2984 | 3028 | 45 |
| 85 | 3024 | 3080 | 57 |
| 86 | 3081 | 3135 | 55 |
| 87 | 3140 | 3176 | 37 |
| 88 | 3168 | 3189 | 22 |
| 89 | 3197 | 3222 | 26 |
| 90 | 3212 | 3226 | 15 |
| 91 | 3221 | 3248 | 28 |
| 92 | 3243 | 3256 | 14 |
| 93 | 3250 | 3264 | 15 |
| 94 | 3266 | 3292 | 27 |
| 95 | 3326 | 3343 | 18 |
| 96 | 3345 | 3391 | 47 |
| 97 | 3400 | 3422 | 23 |
| 98 | 3424 | 3441 | 18 |
| 99 | 3434 | 3447 | 14 |
| 100 | 3443 | 3503 | 61 |
| 101 | 3495 | 3508 | 14 |
| 102 | 3505 | 3558 | 54 |
| 103 | 3589 | 3609 | 21 |
| 104 | 3611 | 3641 | 31 |
| 105 | 3662 | 3696 | 35 |
| 106 | 3698 | 3719 | 22 |
| 107 | 3723 | 3790 | 68 |
| 108 | 3810 | 3854 | 45 |
| 109 | 3858 | 3873 | 16 |
| 110 | 3902 | 3968 | 67 |
| 111 | 3971 | 4009 | 39 |
| 112 | 4005 | 4018 | 14 |
| 113 | 4011 | 4030 | 20 |
| 114 | 4032 | 4077 | 46 |
| 115 | 4082 | 4114 | 33 |
| 116 | 4123 | 4140 | 18 |
| 117 | 4150 | 4164 | 15 |
| 118 | 4166 | 4183 | 18 |
| 119 | 4185 | 4243 | 59 |
| 120 | 4248 | 4268 | 21 |
| 121 | 4284 | 4313 | 30 |
| 122 | 4317 | 4348 | 32 |
| 123 | 4364 | 4471 | 108 |
| 124 | 4473 | 4491 | 19 |
| 125 | 4494 | 4519 | 26 |
| 126 | 4521 | 4535 | 15 |
| 127 | 4545 | 4560 | 16 |
| 128 | 4567 | 4606 | 40 |
| 129 | 4616 | 4714 | 99 |
| 130 | 4725 | 4755 | 31 |
| 131 | 4757 | 4786 | 30 |
| 132 | 4788 | 4852 | 65 |
| 133 | 4856 | 4910 | 55 |
| 134 | 4912 | 4935 | 24 |
| 135 | 4937 | 4970 | 34 |
| 136 | 4972 | 5010 | 39 |
| 137 | 5058 | 5078 | 21 |
| 138 | 5080 | 5116 | 37 |
| 139 | 5110 | 5124 | 15 |
| 140 | 5135 | 5166 | 32 |
| 141 | 5168 | 5201 | 34 |
| 142 | 5203 | 5247 | 45 |
| 143 | 5261 | 5276 | 16 |
| 144 | 5278 | 5293 | 16 |
| 145 | 5314 | 5330 | 17 |
| 146 | 5332 | 5382 | 51 |
| 147 | 5398 | 5414 | 17 |
| 148 | 5427 | 5456 | 30 |
| 149 | 5458 | 5471 | 14 |
| 150 | 5487 | 5500 | 14 |

TABLE 1-continued

Regions of SEQ ID NO 1 which may be targeted using oligonucleotide of the invention

| Reg. A | Position in SEQ ID NO 1 from | to | Length |
|---|---|---|---|
| 151 | 5506 | 5545 | 40 |
| 152 | 5561 | 5577 | 17 |
| 153 | 5580 | 5617 | 38 |
| 154 | 5607 | 5620 | 14 |
| 155 | 5619 | 5642 | 24 |
| 156 | 5644 | 5683 | 40 |
| 157 | 5685 | 5698 | 14 |
| 158 | 5713 | 5759 | 47 |
| 159 | 5756 | 5769 | 14 |
| 160 | 5784 | 5803 | 20 |
| 161 | 5801 | 5865 | 65 |
| 162 | 5873 | 5905 | 33 |
| 163 | 5907 | 5937 | 31 |
| 164 | 5939 | 5985 | 47 |
| 165 | 5987 | 6017 | 31 |
| 166 | 6016 | 6039 | 24 |
| 167 | 6028 | 6092 | 65 |
| 168 | 6102 | 6127 | 26 |
| 169 | 6127 | 6152 | 26 |
| 170 | 6151 | 6171 | 21 |
| 171 | 6178 | 6206 | 29 |
| 172 | 6217 | 6234 | 18 |
| 173 | 6224 | 6270 | 47 |
| 174 | 6272 | 6289 | 18 |
| 175 | 6291 | 6310 | 20 |
| 176 | 6312 | 6357 | 46 |
| 177 | 6367 | 6389 | 23 |
| 178 | 6396 | 6422 | 27 |
| 179 | 6440 | 6454 | 15 |
| 180 | 6456 | 6482 | 27 |
| 181 | 6484 | 6513 | 30 |
| 182 | 6505 | 6519 | 15 |
| 183 | 6518 | 6553 | 36 |
| 184 | 6552 | 6565 | 14 |
| 185 | 6557 | 6590 | 34 |
| 186 | 6596 | 6628 | 33 |
| 187 | 6640 | 6675 | 36 |
| 188 | 6686 | 6711 | 26 |
| 189 | 6714 | 6746 | 33 |
| 190 | 6781 | 6818 | 38 |
| 191 | 6832 | 6885 | 54 |
| 192 | 6889 | 6912 | 24 |
| 193 | 6920 | 6938 | 19 |
| 194 | 6940 | 6960 | 21 |
| 195 | 6954 | 6976 | 23 |
| 196 | 6998 | 7033 | 36 |
| 197 | 7035 | 7061 | 27 |
| 198 | 7071 | 7143 | 73 |
| 199 | 7159 | 7214 | 56 |
| 200 | 7253 | 7266 | 14 |
| 201 | 7268 | 7281 | 14 |
| 202 | 7283 | 7328 | 46 |
| 203 | 7329 | 7343 | 15 |
| 204 | 7338 | 7355 | 18 |
| 205 | 7345 | 7374 | 30 |
| 206 | 7374 | 7387 | 14 |
| 207 | 7383 | 7396 | 14 |
| 208 | 7389 | 7405 | 17 |
| 209 | 7399 | 7413 | 15 |
| 210 | 7420 | 7437 | 18 |
| 211 | 7427 | 7448 | 22 |
| 212 | 7450 | 7503 | 54 |
| 213 | 7495 | 7565 | 71 |
| 214 | 7561 | 7616 | 56 |
| 215 | 7618 | 7703 | 86 |
| 216 | 7717 | 7772 | 56 |
| 217 | 7776 | 7838 | 63 |
| 218 | 7852 | 7869 | 18 |
| 219 | 7882 | 7910 | 29 |
| 220 | 7919 | 7942 | 24 |
| 221 | 7944 | 7957 | 14 |
| 222 | 7959 | 7977 | 19 |
| 223 | 7979 | 7996 | 18 |
| 224 | 7998 | 8014 | 17 |
| 225 | 8030 | 8046 | 17 |
| 226 | 8059 | 8092 | 34 |
| 227 | 8100 | 8113 | 14 |
| 228 | 8115 | 8141 | 27 |
| 229 | 8143 | 8175 | 33 |
| 230 | 8179 | 8192 | 14 |
| 231 | 8187 | 8208 | 22 |
| 232 | 8205 | 8219 | 15 |
| 233 | 8210 | 8229 | 20 |
| 234 | 8231 | 8252 | 22 |
| 235 | 8254 | 8298 | 45 |
| 236 | 8302 | 8316 | 15 |
| 237 | 8306 | 8329 | 24 |
| 238 | 8331 | 8357 | 27 |
| 239 | 8400 | 8443 | 44 |
| 240 | 8443 | 8456 | 14 |
| 241 | 8445 | 8460 | 16 |
| 242 | 8472 | 8505 | 34 |
| 243 | 8494 | 8507 | 14 |
| 244 | 8554 | 8569 | 16 |
| 245 | 8571 | 8653 | 83 |
| 246 | 8659 | 8673 | 15 |
| 247 | 8675 | 8694 | 20 |
| 248 | 8696 | 8713 | 18 |
| 249 | 8736 | 8844 | 109 |
| 250 | 8847 | 8909 | 63 |
| 251 | 8915 | 8959 | 45 |
| 252 | 8961 | 8975 | 15 |
| 253 | 8993 | 9009 | 17 |
| 254 | 9024 | 9048 | 25 |
| 255 | 9050 | 9063 | 14 |
| 256 | 9089 | 9120 | 32 |
| 257 | 9127 | 9166 | 40 |
| 258 | 9191 | 9249 | 59 |
| 259 | 9257 | 9285 | 29 |
| 260 | 9288 | 9302 | 15 |
| 261 | 9331 | 9397 | 67 |
| 262 | 9399 | 9438 | 40 |
| 263 | 9437 | 9455 | 19 |
| 264 | 9483 | 9505 | 23 |
| 265 | 9507 | 9526 | 20 |
| 266 | 9583 | 9598 | 16 |
| 267 | 9600 | 9613 | 14 |
| 268 | 9628 | 9641 | 14 |
| 269 | 9653 | 9674 | 22 |
| 270 | 9676 | 9690 | 15 |
| 271 | 9745 | 9758 | 14 |
| 272 | 9752 | 9780 | 29 |
| 273 | 9796 | 9809 | 14 |
| 274 | 9811 | 9825 | 15 |
| 275 | 9832 | 9853 | 22 |
| 276 | 9877 | 9899 | 23 |
| 277 | 9901 | 9932 | 32 |
| 278 | 10000 | 10016 | 17 |
| 279 | 10029 | 10049 | 21 |
| 280 | 10051 | 10071 | 21 |
| 281 | 10089 | 10120 | 32 |
| 282 | 10111 | 10127 | 17 |
| 283 | 10122 | 10203 | 82 |
| 284 | 10211 | 10237 | 27 |
| 285 | 10239 | 10256 | 18 |
| 286 | 10258 | 10285 | 28 |
| 287 | 10287 | 10304 | 18 |
| 288 | 10306 | 10350 | 45 |
| 289 | 10352 | 10375 | 24 |
| 290 | 10381 | 10402 | 22 |
| 291 | 10412 | 10470 | 59 |
| 292 | 10474 | 10488 | 15 |

TABLE 1-continued

Regions of SEQ ID NO 1 which may be targeted using oligonucleotide of the invention

| Reg. A | Position in SEQ ID NO 1 from | to | Length |
|---|---|---|---|
| 293 | 10508 | 10557 | 50 |
| 294 | 10565 | 10630 | 66 |
| 295 | 10632 | 10674 | 43 |
| 296 | 10698 | 10711 | 14 |
| 297 | 10701 | 10714 | 14 |
| 298 | 10704 | 10718 | 15 |
| 299 | 10720 | 10740 | 21 |
| 300 | 10742 | 10785 | 44 |
| 301 | 10786 | 10809 | 24 |
| 302 | 10811 | 10829 | 19 |
| 303 | 10832 | 10867 | 36 |
| 304 | 10869 | 10930 | 62 |
| 305 | 10932 | 10950 | 19 |
| 306 | 10959 | 10996 | 38 |
| 307 | 10998 | 11028 | 31 |
| 308 | 11037 | 11077 | 41 |
| 309 | 11079 | 11105 | 27 |
| 310 | 11115 | 11132 | 18 |
| 311 | 11134 | 11154 | 21 |
| 312 | 11156 | 11196 | 41 |
| 313 | 11206 | 11239 | 34 |
| 314 | 11241 | 11255 | 15 |
| 315 | 11266 | 11287 | 22 |
| 316 | 11299 | 11329 | 31 |
| 317 | 11331 | 11352 | 22 |
| 318 | 11358 | 11403 | 46 |
| 319 | 11405 | 11432 | 28 |
| 320 | 11434 | 11480 | 47 |
| 321 | 11482 | 11535 | 54 |
| 322 | 11539 | 11573 | 35 |
| 323 | 11584 | 11732 | 149 |
| 324 | 11731 | 11763 | 33 |
| 325 | 11765 | 11782 | 18 |
| 326 | 11784 | 11813 | 30 |
| 327 | 11815 | 11829 | 15 |
| 328 | 11831 | 11852 | 22 |
| 329 | 11854 | 11871 | 18 |
| 330 | 11866 | 11895 | 30 |
| 331 | 11930 | 11943 | 14 |
| 332 | 11975 | 12007 | 33 |
| 333 | 11996 | 12012 | 17 |
| 334 | 12017 | 12040 | 24 |
| 335 | 12050 | 12083 | 34 |
| 336 | 12088 | 12111 | 24 |
| 337 | 12133 | 12151 | 19 |
| 338 | 12161 | 12174 | 14 |
| 339 | 12179 | 12225 | 47 |
| 340 | 12238 | 12256 | 19 |
| 341 | 12265 | 12278 | 14 |
| 342 | 12296 | 12360 | 65 |
| 343 | 12362 | 12381 | 20 |
| 344 | 12384 | 12399 | 16 |
| 345 | 12400 | 12475 | 76 |
| 346 | 12487 | 12502 | 16 |
| 347 | 12504 | 12531 | 28 |
| 348 | 12533 | 12562 | 30 |
| 349 | 12564 | 12602 | 39 |
| 350 | 12627 | 12646 | 20 |
| 351 | 12655 | 12679 | 25 |
| 352 | 12681 | 12698 | 18 |
| 353 | 12700 | 12812 | 113 |
| 354 | 12828 | 12876 | 49 |
| 355 | 12877 | 12913 | 37 |
| 356 | 12932 | 12945 | 14 |
| 357 | 12936 | 12967 | 32 |
| 358 | 12988 | 13002 | 15 |
| 359 | 12996 | 13009 | 14 |
| 360 | 13018 | 13035 | 18 |
| 361 | 13031 | 13049 | 19 |
| 362 | 13056 | 13093 | 38 |
| 363 | 13096 | 13126 | 31 |
| 364 | 13128 | 13142 | 15 |
| 365 | 13144 | 13193 | 50 |
| 366 | 13201 | 13221 | 21 |
| 367 | 13223 | 13280 | 58 |
| 368 | 13282 | 13298 | 17 |
| 369 | 13300 | 13315 | 16 |
| 370 | 13307 | 13320 | 14 |
| 371 | 13315 | 13331 | 17 |
| 372 | 13351 | 13411 | 61 |
| 373 | 13422 | 13437 | 16 |
| 374 | 13439 | 13456 | 18 |
| 375 | 13461 | 13483 | 23 |
| 376 | 13485 | 13541 | 57 |
| 377 | 13543 | 13560 | 18 |
| 378 | 13574 | 13606 | 33 |
| 379 | 13618 | 13646 | 29 |
| 380 | 13778 | 13801 | 24 |
| 381 | 13994 | 14009 | 16 |
| 382 | 14508 | 14521 | 14 |
| 383 | 15049 | 15067 | 19 |
| 384 | 15069 | 15090 | 22 |
| 385 | 15102 | 15139 | 38 |
| 386 | 15142 | 15180 | 39 |
| 387 | 15182 | 15205 | 24 |
| 388 | 15238 | 15252 | 15 |
| 389 | 15254 | 15277 | 24 |
| 390 | 15292 | 15320 | 29 |
| 391 | 15322 | 15348 | 27 |
| 392 | 15343 | 15358 | 16 |
| 393 | 15362 | 15387 | 26 |
| 394 | 15399 | 15414 | 16 |
| 395 | 15416 | 15445 | 30 |
| 396 | 15459 | 15528 | 70 |
| 397 | 15537 | 15592 | 56 |
| 398 | 15610 | 15638 | 29 |
| 399 | 15640 | 15653 | 14 |
| 400 | 15655 | 15717 | 63 |
| 401 | 15719 | 15738 | 20 |
| 402 | 15757 | 15778 | 22 |
| 403 | 15783 | 15801 | 19 |
| 404 | 15818 | 15838 | 21 |
| 405 | 15835 | 15849 | 15 |
| 406 | 15840 | 15857 | 18 |
| 407 | 15856 | 15898 | 43 |
| 408 | 15900 | 15916 | 17 |
| 409 | 15931 | 15972 | 42 |
| 410 | 15988 | 16028 | 41 |
| 411 | 16030 | 16075 | 46 |
| 412 | 16103 | 16164 | 62 |
| 413 | 16207 | 16243 | 37 |
| 414 | 16233 | 16246 | 14 |
| 415 | 16255 | 16329 | 75 |
| 416 | 16349 | 16376 | 28 |
| 417 | 16378 | 16404 | 27 |
| 418 | 16399 | 16419 | 21 |
| 419 | 16421 | 16461 | 41 |
| 420 | 16463 | 16479 | 17 |
| 421 | 16481 | 16503 | 23 |
| 422 | 16506 | 16579 | 74 |
| 423 | 16582 | 16620 | 39 |
| 424 | 16622 | 16698 | 77 |
| 425 | 16700 | 16716 | 17 |
| 426 | 16723 | 16771 | 49 |
| 427 | 16786 | 16816 | 31 |
| 428 | 16835 | 16864 | 30 |
| 429 | 16865 | 16878 | 14 |
| 430 | 16872 | 16888 | 17 |
| 431 | 16890 | 16906 | 17 |
| 432 | 16904 | 16938 | 35 |
| 433 | 16965 | 17052 | 88 |
| 434 | 17054 | 17069 | 16 |

TABLE 1-continued

Regions of SEQ ID NO 1 which may be targeted using oligonucleotide of the invention

| Reg. A | Position in SEQ ID NO 1 from | to | Length |
|---|---|---|---|
| 435 | 17071 | 17085 | 15 |
| 436 | 17083 | 17098 | 16 |
| 437 | 17088 | 17111 | 24 |
| 438 | 17124 | 17138 | 15 |
| 439 | 17140 | 17159 | 20 |
| 440 | 17181 | 17202 | 22 |
| 441 | 17202 | 17218 | 17 |
| 442 | 17229 | 17248 | 20 |
| 443 | 17250 | 17268 | 19 |
| 444 | 17332 | 17349 | 18 |
| 445 | 17363 | 17387 | 25 |
| 446 | 17389 | 17429 | 41 |
| 447 | 17450 | 17464 | 15 |
| 448 | 17482 | 17497 | 16 |
| 449 | 18104 | 18117 | 14 |
| 450 | 18418 | 18431 | 14 |
| 451 | 18613 | 18626 | 14 |
| 452 | 18620 | 18634 | 15 |
| 453 | 18707 | 18721 | 15 |
| 454 | 18841 | 18855 | 15 |
| 455 | 18875 | 18889 | 15 |
| 456 | 19282 | 19295 | 14 |
| 457 | 19310 | 19323 | 14 |
| 458 | 19454 | 19467 | 14 |
| 459 | 19774 | 19792 | 19 |
| 460 | 19794 | 19864 | 71 |
| 461 | 19862 | 19890 | 29 |
| 462 | 19892 | 19918 | 27 |
| 463 | 19907 | 19931 | 25 |
| 464 | 19927 | 19942 | 16 |
| 465 | 19932 | 19971 | 40 |
| 466 | 19973 | 20011 | 39 |
| 467 | 20022 | 20063 | 42 |
| 468 | 20080 | 20093 | 14 |
| 469 | 20131 | 20144 | 14 |
| 470 | 20240 | 20253 | 14 |
| 471 | 20448 | 20463 | 16 |
| 472 | 20495 | 20508 | 14 |
| 473 | 20532 | 20545 | 14 |
| 474 | 20600 | 20613 | 14 |
| 475 | 20617 | 20630 | 14 |
| 476 | 20960 | 20977 | 18 |
| 477 | 21412 | 21428 | 17 |
| 478 | 21465 | 21479 | 15 |
| 479 | 21489 | 21508 | 20 |
| 480 | 21797 | 21812 | 16 |
| 481 | 22015 | 22030 | 16 |
| 482 | 22144 | 22157 | 14 |
| 483 | 22153 | 22167 | 15 |
| 484 | 22265 | 22278 | 14 |
| 485 | 23110 | 23123 | 14 |
| 486 | 23114 | 23133 | 20 |
| 487 | 23286 | 23303 | 18 |
| 488 | 23364 | 23379 | 16 |
| 489 | 23478 | 23498 | 21 |
| 490 | 23544 | 23587 | 44 |
| 491 | 23589 | 23630 | 42 |
| 492 | 23658 | 23676 | 19 |
| 493 | 23678 | 23702 | 25 |
| 494 | 23704 | 23729 | 26 |
| 495 | 23731 | 23748 | 18 |
| 496 | 23740 | 23755 | 16 |
| 497 | 23744 | 23757 | 14 |
| 498 | 23750 | 23764 | 15 |
| 499 | 23767 | 23795 | 29 |
| 500 | 23802 | 23816 | 15 |
| 501 | 23818 | 23831 | 14 |
| 502 | 23855 | 23869 | 15 |
| 503 | 23906 | 23926 | 21 |
| 504 | 23928 | 23942 | 15 |
| 505 | 23994 | 24007 | 14 |
| 506 | 24005 | 24018 | 14 |
| 507 | 24023 | 24056 | 34 |
| 508 | 24074 | 24088 | 15 |
| 509 | 24088 | 24104 | 17 |
| 510 | 24112 | 24163 | 52 |
| 511 | 24199 | 24212 | 14 |
| 512 | 24231 | 24244 | 14 |
| 513 | 24237 | 24252 | 16 |
| 514 | 24254 | 24267 | 14 |
| 515 | 24281 | 24325 | 45 |
| 516 | 24327 | 24353 | 27 |
| 517 | 24355 | 24374 | 20 |
| 518 | 24376 | 24399 | 24 |
| 519 | 24401 | 24416 | 16 |
| 520 | 24442 | 24489 | 48 |
| 521 | 24492 | 24506 | 15 |
| 522 | 24498 | 24511 | 14 |
| 523 | 24538 | 24556 | 19 |
| 524 | 24546 | 24562 | 17 |
| 525 | 24591 | 24618 | 28 |
| 526 | 24620 | 24633 | 14 |
| 527 | 24635 | 24650 | 16 |
| 528 | 24665 | 24681 | 17 |
| 529 | 24687 | 24706 | 20 |
| 530 | 24709 | 24729 | 21 |
| 531 | 24731 | 24752 | 22 |
| 532 | 24756 | 24771 | 16 |
| 533 | 24773 | 24788 | 16 |
| 534 | 24793 | 24821 | 29 |
| 535 | 24823 | 24854 | 32 |
| 536 | 24856 | 24870 | 15 |
| 537 | 24873 | 24922 | 50 |
| 538 | 24933 | 24954 | 22 |
| 539 | 24965 | 24984 | 20 |
| 540 | 25019 | 25052 | 34 |
| 541 | 25054 | 25099 | 46 |
| 542 | 25112 | 25125 | 14 |
| 543 | 25133 | 25169 | 37 |
| 544 | 25171 | 25184 | 14 |
| 545 | 25186 | 25221 | 36 |
| 546 | 25236 | 25253 | 18 |
| 547 | 25246 | 25296 | 51 |
| 548 | 25298 | 25336 | 39 |
| 549 | 25332 | 25348 | 17 |
| 550 | 25349 | 25363 | 15 |
| 551 | 25388 | 25432 | 45 |
| 552 | 25439 | 25462 | 24 |
| 553 | 25509 | 25523 | 15 |
| 554 | 25525 | 25547 | 23 |
| 555 | 25578 | 25593 | 16 |
| 556 | 25587 | 25601 | 15 |
| 557 | 25604 | 25617 | 14 |
| 558 | 25633 | 25655 | 23 |
| 559 | 25672 | 25716 | 45 |
| 560 | 25725 | 25738 | 14 |
| 561 | 25764 | 25800 | 37 |
| 562 | 25802 | 25828 | 27 |
| 563 | 25831 | 25846 | 16 |
| 564 | 25851 | 25872 | 22 |
| 565 | 25877 | 25904 | 28 |
| 566 | 25921 | 25946 | 26 |
| 567 | 25943 | 25970 | 28 |
| 568 | 25972 | 25986 | 15 |
| 569 | 26051 | 26064 | 14 |
| 570 | 26068 | 26086 | 19 |
| 571 | 26113 | 26137 | 25 |
| 572 | 26139 | 26159 | 21 |
| 573 | 26182 | 26197 | 16 |
| 574 | 26243 | 26296 | 54 |
| 575 | 26298 | 26313 | 16 |
| 576 | 26327 | 26350 | 24 |

TABLE 1-continued

Regions of SEQ ID NO 1 which may be targeted using oligonucleotide of the invention

| Reg. A | Position in SEQ ID NO 1 from | to | Length |
|---|---|---|---|
| 577 | 26366 | 26385 | 20 |
| 578 | 26387 | 26404 | 18 |
| 579 | 26397 | 26415 | 19 |
| 580 | 26416 | 26453 | 38 |
| 581 | 26447 | 26461 | 15 |
| 582 | 26457 | 26471 | 15 |
| 583 | 26481 | 26498 | 18 |
| 584 | 26502 | 26525 | 24 |
| 585 | 26528 | 26562 | 35 |
| 586 | 26564 | 26590 | 27 |
| 587 | 26590 | 26622 | 33 |
| 588 | 26624 | 26638 | 15 |
| 589 | 26687 | 26702 | 16 |
| 590 | 26706 | 26719 | 14 |
| 591 | 26717 | 26730 | 14 |
| 592 | 26729 | 26743 | 15 |
| 593 | 26767 | 26797 | 31 |
| 594 | 26796 | 26816 | 21 |
| 595 | 26831 | 26847 | 17 |
| 596 | 26837 | 26850 | 14 |
| 597 | 26877 | 26890 | 14 |
| 598 | 26900 | 26922 | 23 |
| 599 | 26911 | 26933 | 23 |
| 600 | 26933 | 26946 | 14 |
| 601 | 26938 | 26977 | 40 |
| 602 | 26979 | 26992 | 14 |
| 603 | 26981 | 27017 | 37 |
| 604 | 27023 | 27041 | 19 |
| 605 | 27039 | 27055 | 17 |
| 606 | 27075 | 27121 | 47 |
| 607 | 27138 | 27153 | 16 |
| 608 | 27163 | 27266 | 104 |
| 609 | 27270 | 27293 | 24 |
| 610 | 27325 | 27358 | 34 |
| 611 | 27363 | 27408 | 46 |
| 612 | 27419 | 27448 | 30 |
| 613 | 27450 | 27469 | 20 |
| 614 | 27471 | 27498 | 28 |
| 615 | 27510 | 27523 | 14 |
| 616 | 27535 | 27562 | 28 |
| 617 | 28098 | 28119 | 22 |
| 618 | 28136 | 28155 | 20 |
| 619 | 28169 | 28197 | 29 |
| 620 | 28199 | 28212 | 14 |
| 621 | 28221 | 28244 | 24 |
| 622 | 28271 | 28285 | 15 |
| 623 | 28400 | 28414 | 15 |
| 624 | 28441 | 28476 | 36 |
| 625 | 28490 | 28533 | 44 |
| 626 | 28535 | 28562 | 28 |
| 627 | 28575 | 28600 | 26 |
| 628 | 28621 | 28634 | 14 |
| 629 | 28650 | 28663 | 14 |
| 630 | 28674 | 28687 | 14 |
| 631 | 28681 | 28699 | 19 |
| 632 | 28713 | 28730 | 18 |
| 633 | 28736 | 28761 | 26 |
| 634 | 28763 | 28811 | 49 |
| 635 | 28821 | 28854 | 34 |
| 636 | 28856 | 28881 | 26 |
| 637 | 28883 | 28920 | 38 |
| 638 | 28922 | 28947 | 26 |
| 639 | 28979 | 29006 | 28 |
| 640 | 29008 | 29056 | 49 |
| 641 | 29078 | 29095 | 18 |
| 642 | 29098 | 29129 | 32 |
| 643 | 29122 | 29135 | 14 |
| 644 | 29131 | 29144 | 14 |
| 645 | 29144 | 29158 | 15 |
| 646 | 29160 | 29207 | 48 |
| 647 | 29209 | 29230 | 22 |
| 648 | 29234 | 29266 | 33 |
| 649 | 29268 | 29286 | 19 |
| 650 | 29301 | 29315 | 15 |
| 651 | 29304 | 29323 | 20 |
| 652 | 29330 | 29352 | 23 |
| 653 | 29344 | 29358 | 15 |
| 654 | 29347 | 29365 | 19 |
| 655 | 29377 | 29402 | 26 |
| 656 | 29402 | 29422 | 21 |
| 657 | 29424 | 29445 | 22 |
| 658 | 29443 | 29457 | 15 |
| 659 | 29447 | 29460 | 14 |
| 660 | 29462 | 29475 | 14 |
| 661 | 29491 | 29512 | 22 |
| 662 | 29514 | 29551 | 38 |
| 663 | 29547 | 29560 | 14 |
| 664 | 29553 | 29620 | 68 |
| 665 | 29625 | 29700 | 76 |
| 666 | 29714 | 29745 | 32 |
| 667 | 29774 | 29805 | 32 |
| 668 | 29816 | 29847 | 32 |
| 669 | 29875 | 29892 | 18 |
| 670 | 29894 | 29908 | 15 |
| 671 | 29897 | 29910 | 14 |
| 672 | 29917 | 29938 | 22 |
| 673 | 29939 | 29952 | 14 |
| 674 | 29961 | 29976 | 16 |
| 675 | 29974 | 29987 | 14 |
| 676 | 29978 | 30001 | 24 |
| 677 | 30006 | 30023 | 18 |
| 678 | 30025 | 30039 | 15 |
| 679 | 30043 | 30107 | 65 |
| 680 | 30145 | 30158 | 14 |
| 681 | 30149 | 30166 | 18 |
| 682 | 30173 | 30228 | 56 |
| 683 | 30230 | 30250 | 21 |
| 684 | 30251 | 30309 | 59 |
| 685 | 30321 | 30358 | 38 |
| 686 | 30359 | 30380 | 22 |
| 687 | 30382 | 30422 | 41 |
| 688 | 30428 | 30442 | 15 |
| 689 | 30455 | 30482 | 28 |
| 690 | 30484 | 30498 | 15 |
| 691 | 30516 | 30531 | 16 |
| 692 | 30533 | 30646 | 114 |
| 693 | 30654 | 30745 | 92 |
| 694 | 30745 | 30760 | 16 |
| 695 | 30752 | 30766 | 15 |
| 696 | 30788 | 30843 | 56 |
| 697 | 30845 | 30867 | 23 |
| 698 | 30869 | 30912 | 44 |
| 699 | 30906 | 30920 | 15 |
| 700 | 30934 | 30951 | 18 |
| 701 | 30962 | 30984 | 23 |
| 702 | 30989 | 31002 | 14 |
| 703 | 31010 | 31033 | 24 |
| 704 | 31036 | 31062 | 27 |
| 705 | 31092 | 31106 | 15 |
| 706 | 31128 | 31166 | 39 |
| 707 | 31168 | 31182 | 15 |
| 708 | 31189 | 31203 | 15 |
| 709 | 31205 | 31218 | 14 |
| 710 | 31224 | 31253 | 30 |
| 711 | 31256 | 31272 | 17 |
| 712 | 31274 | 31292 | 19 |
| 713 | 31294 | 31322 | 29 |
| 714 | 31324 | 31353 | 30 |
| 715 | 31357 | 31370 | 14 |
| 716 | 31373 | 31399 | 27 |
| 717 | 31403 | 31426 | 24 |
| 718 | 31445 | 31460 | 16 |

TABLE 1-continued

Regions of SEQ ID NO 1 which may be targeted using oligonucleotide of the invention

| Reg. A | Position in SEQ ID NO 1 from | to | Length |
|---|---|---|---|
| 719 | 31463 | 31483 | 21 |
| 720 | 31485 | 31501 | 17 |
| 721 | 31494 | 31508 | 15 |
| 722 | 31507 | 31529 | 23 |
| 723 | 31531 | 31565 | 35 |
| 724 | 31567 | 31615 | 49 |
| 725 | 31630 | 31665 | 36 |
| 726 | 31675 | 31691 | 17 |
| 727 | 31703 | 31721 | 19 |
| 728 | 31729 | 31769 | 41 |
| 729 | 31770 | 31790 | 21 |
| 730 | 31795 | 31813 | 19 |
| 731 | 31815 | 31835 | 21 |
| 732 | 31837 | 31865 | 29 |
| 733 | 31876 | 31889 | 14 |
| 734 | 31920 | 31945 | 26 |
| 735 | 31962 | 31978 | 17 |
| 736 | 31983 | 32014 | 32 |
| 737 | 32029 | 32050 | 22 |
| 738 | 32058 | 32110 | 53 |
| 739 | 32129 | 32147 | 19 |
| 740 | 32166 | 32242 | 77 |
| 741 | 32244 | 32279 | 36 |
| 742 | 32296 | 32315 | 20 |
| 743 | 32334 | 32396 | 63 |
| 744 | 32398 | 32425 | 28 |
| 745 | 32427 | 32453 | 27 |
| 746 | 32459 | 32481 | 23 |
| 747 | 32475 | 32498 | 24 |
| 748 | 32490 | 32523 | 34 |
| 749 | 32519 | 32534 | 16 |
| 750 | 32525 | 32547 | 23 |
| 751 | 32542 | 32555 | 14 |
| 752 | 32559 | 32572 | 14 |
| 753 | 32574 | 32587 | 14 |
| 754 | 32595 | 32618 | 24 |
| 755 | 32613 | 32626 | 14 |
| 756 | 32627 | 32649 | 23 |
| 757 | 32651 | 32664 | 14 |
| 758 | 32655 | 32689 | 35 |
| 759 | 32693 | 32719 | 27 |
| 760 | 32721 | 32750 | 30 |
| 761 | 32752 | 32778 | 27 |
| 762 | 32780 | 32795 | 16 |
| 763 | 32797 | 32847 | 51 |
| 764 | 32881 | 32894 | 14 |
| 765 | 32891 | 32904 | 14 |
| 766 | 32896 | 32911 | 16 |
| 767 | 32927 | 32972 | 46 |
| 768 | 32986 | 33017 | 32 |
| 769 | 33019 | 33036 | 18 |
| 770 | 33038 | 33096 | 59 |
| 771 | 33102 | 33123 | 22 |
| 772 | 33132 | 33145 | 14 |
| 773 | 33150 | 33163 | 14 |
| 774 | 33166 | 33199 | 34 |
| 775 | 33214 | 33260 | 47 |
| 776 | 33262 | 33292 | 31 |
| 777 | 33294 | 33307 | 14 |
| 778 | 33316 | 33351 | 36 |
| 779 | 33360 | 33402 | 43 |
| 780 | 33412 | 33425 | 14 |
| 781 | 33427 | 33442 | 16 |
| 782 | 33439 | 33452 | 14 |
| 783 | 33443 | 33456 | 14 |
| 784 | 33460 | 33501 | 42 |
| 785 | 33503 | 33535 | 33 |
| 786 | 33542 | 33557 | 16 |
| 787 | 34168 | 34181 | 14 |
| 788 | 34370 | 34385 | 16 |
| 789 | 35422 | 35435 | 14 |

TABLE 1-continued

Regions of SEQ ID NO 1 which may be targeted using oligonucleotide of the invention

| Reg. A | Position in SEQ ID NO 1 from | to | Length |
|---|---|---|---|
| 790 | 35627 | 35641 | 15 |
| 791 | 35685 | 35700 | 16 |
| 792 | 35837 | 35851 | 15 |
| 793 | 35849 | 35864 | 16 |
| 794 | 35866 | 35879 | 14 |
| 795 | 35974 | 35987 | 14 |
| 796 | 36009 | 36042 | 34 |
| 797 | 36044 | 36079 | 36 |
| 798 | 36081 | 36097 | 17 |
| 799 | 36099 | 36120 | 22 |
| 800 | 36119 | 36133 | 15 |
| 801 | 36147 | 36163 | 17 |
| 802 | 36171 | 36200 | 30 |
| 803 | 36216 | 36241 | 26 |
| 804 | 36245 | 36274 | 30 |
| 805 | 36265 | 36283 | 19 |
| 806 | 36295 | 36348 | 54 |
| 807 | 36352 | 36389 | 38 |
| 808 | 36383 | 36400 | 18 |
| 809 | 36402 | 36419 | 18 |
| 810 | 36475 | 36520 | 46 |
| 811 | 36522 | 36539 | 18 |
| 812 | 36541 | 36626 | 86 |
| 813 | 36652 | 36672 | 21 |
| 814 | 36675 | 36705 | 31 |
| 815 | 36707 | 36746 | 40 |
| 816 | 36780 | 36808 | 29 |
| 817 | 36810 | 36823 | 14 |
| 818 | 36825 | 36901 | 77 |
| 819 | 36903 | 36922 | 20 |
| 820 | 36924 | 36982 | 59 |
| 821 | 36999 | 37030 | 32 |
| 822 | 37056 | 37083 | 28 |
| 823 | 37091 | 37135 | 45 |
| 824 | 37194 | 37221 | 28 |
| 825 | 37238 | 37277 | 40 |
| 826 | 37280 | 37294 | 15 |
| 827 | 37298 | 37315 | 18 |
| 828 | 37325 | 37350 | 26 |
| 829 | 37363 | 37383 | 21 |
| 830 | 37377 | 37394 | 18 |
| 831 | 37384 | 37397 | 14 |
| 832 | 37390 | 37438 | 49 |
| 833 | 37456 | 37481 | 26 |
| 834 | 37478 | 37491 | 14 |
| 835 | 37481 | 37503 | 23 |
| 836 | 37506 | 37524 | 19 |
| 837 | 37526 | 37545 | 20 |
| 838 | 37540 | 37572 | 33 |
| 839 | 37574 | 37590 | 17 |
| 840 | 37601 | 37616 | 16 |
| 841 | 37621 | 37658 | 38 |
| 842 | 37673 | 37690 | 18 |
| 843 | 37703 | 37738 | 36 |
| 844 | 37740 | 37753 | 14 |
| 845 | 37764 | 37790 | 27 |
| 846 | 37800 | 37818 | 19 |
| 847 | 37820 | 37850 | 31 |
| 848 | 37888 | 37909 | 22 |
| 849 | 37911 | 37972 | 62 |
| 850 | 37986 | 38014 | 29 |
| 851 | 38016 | 38032 | 17 |
| 852 | 38034 | 38053 | 20 |
| 853 | 38055 | 38073 | 19 |
| 854 | 38075 | 38090 | 16 |
| 855 | 38092 | 38128 | 37 |
| 856 | 38141 | 38167 | 27 |
| 857 | 38171 | 38194 | 24 |
| 858 | 38213 | 38240 | 28 |
| 859 | 38264 | 38286 | 23 |
| 860 | 38288 | 38370 | 83 |

TABLE 1-continued

Regions of SEQ ID NO 1 which may be targeted using oligonucleotide of the invention

| Reg. A | Position in SEQ ID NO 1 from | to | Length |
|---|---|---|---|
| 861 | 38394 | 38420 | 27 |
| 862 | 38452 | 38467 | 16 |
| 863 | 38471 | 38487 | 17 |
| 864 | 38477 | 38490 | 14 |
| 865 | 38494 | 38507 | 14 |
| 866 | 38536 | 38556 | 21 |
| 867 | 38580 | 38593 | 14 |
| 868 | 38602 | 38618 | 17 |
| 869 | 38628 | 38654 | 27 |
| 870 | 38693 | 38709 | 17 |
| 871 | 38709 | 38722 | 14 |
| 872 | 38711 | 38725 | 15 |
| 873 | 38740 | 38756 | 17 |
| 874 | 38749 | 38769 | 21 |
| 875 | 38772 | 38797 | 26 |
| 876 | 38827 | 38846 | 20 |
| 877 | 38860 | 38883 | 24 |
| 878 | 38885 | 38905 | 21 |
| 879 | 38911 | 38931 | 21 |
| 880 | 38933 | 38949 | 17 |
| 881 | 38962 | 39032 | 71 |
| 882 | 39034 | 39047 | 14 |
| 883 | 39049 | 39070 | 22 |
| 884 | 39075 | 39115 | 41 |
| 885 | 39127 | 39143 | 17 |
| 886 | 39148 | 39162 | 15 |
| 887 | 39164 | 39222 | 59 |
| 888 | 39218 | 39231 | 14 |
| 889 | 39224 | 39256 | 33 |
| 890 | 39265 | 39306 | 42 |
| 891 | 39297 | 39311 | 15 |
| 892 | 39308 | 39343 | 36 |
| 893 | 39345 | 39359 | 15 |
| 894 | 39361 | 39381 | 21 |
| 895 | 39370 | 39383 | 14 |
| 896 | 39383 | 39399 | 17 |
| 897 | 39417 | 39469 | 53 |
| 898 | 39490 | 39503 | 14 |
| 899 | 39500 | 39522 | 23 |
| 900 | 39535 | 39549 | 15 |
| 901 | 39551 | 39611 | 61 |
| 902 | 39628 | 39647 | 20 |
| 903 | 39649 | 39690 | 42 |
| 904 | 39707 | 39759 | 53 |
| 905 | 39773 | 39797 | 25 |
| 906 | 39799 | 39858 | 60 |
| 907 | 39872 | 39928 | 57 |
| 908 | 39930 | 39969 | 40 |
| 909 | 39973 | 39997 | 25 |
| 910 | 39998 | 40013 | 16 |
| 911 | 40015 | 40064 | 50 |
| 912 | 40067 | 40108 | 42 |
| 913 | 40110 | 40140 | 31 |
| 914 | 40147 | 40163 | 17 |
| 915 | 40154 | 40179 | 26 |
| 916 | 40181 | 40196 | 16 |
| 917 | 40232 | 40282 | 51 |
| 918 | 40284 | 40307 | 24 |
| 919 | 40309 | 40368 | 60 |
| 920 | 40381 | 40399 | 19 |
| 921 | 40431 | 40471 | 41 |
| 922 | 40479 | 40493 | 15 |
| 923 | 40484 | 40522 | 39 |
| 924 | 40524 | 40544 | 21 |
| 925 | 40547 | 40561 | 15 |
| 926 | 40577 | 40594 | 18 |
| 927 | 40586 | 40599 | 14 |
| 928 | 40616 | 40631 | 16 |
| 929 | 40634 | 40647 | 14 |
| 930 | 40674 | 40727 | 54 |
| 931 | 40738 | 40755 | 18 |
| 932 | 40749 | 40771 | 23 |
| 933 | 40780 | 40802 | 23 |
| 934 | 40811 | 40834 | 24 |
| 935 | 40847 | 40865 | 19 |
| 936 | 40861 | 40875 | 15 |
| 937 | 40869 | 40897 | 29 |
| 938 | 40899 | 40919 | 21 |
| 939 | 40921 | 40939 | 19 |
| 940 | 40942 | 40962 | 21 |
| 941 | 40967 | 40980 | 14 |
| 942 | 41008 | 41097 | 90 |
| 943 | 41099 | 41131 | 33 |
| 944 | 41133 | 41200 | 68 |
| 945 | 41202 | 41223 | 22 |
| 946 | 41225 | 41242 | 18 |
| 947 | 41266 | 41279 | 14 |
| 948 | 41275 | 41298 | 24 |
| 949 | 41300 | 41321 | 22 |
| 950 | 41325 | 41360 | 36 |
| 951 | 41367 | 41388 | 22 |
| 952 | 41403 | 41421 | 19 |
| 953 | 41439 | 41462 | 24 |
| 954 | 41481 | 41496 | 16 |
| 955 | 41508 | 41523 | 16 |
| 956 | 41531 | 41550 | 20 |
| 957 | 41552 | 41590 | 39 |
| 958 | 41590 | 41603 | 14 |
| 959 | 41612 | 41662 | 51 |
| 960 | 41664 | 41688 | 25 |
| 961 | 41685 | 41698 | 14 |
| 962 | 41691 | 41716 | 26 |
| 963 | 41718 | 41764 | 47 |
| 964 | 41761 | 41776 | 16 |
| 965 | 41778 | 41809 | 32 |
| 966 | 41798 | 41811 | 14 |
| 967 | 41838 | 41866 | 29 |
| 968 | 41872 | 41893 | 22 |
| 969 | 41885 | 41898 | 14 |
| 970 | 41912 | 41925 | 14 |
| 971 | 41914 | 41930 | 17 |
| 972 | 41923 | 41942 | 20 |
| 973 | 41933 | 41956 | 24 |
| 974 | 41962 | 41978 | 17 |
| 975 | 41997 | 42012 | 16 |
| 976 | 42026 | 42042 | 17 |
| 977 | 42035 | 42048 | 14 |
| 978 | 42037 | 42050 | 14 |
| 979 | 42048 | 42064 | 17 |
| 980 | 42056 | 42079 | 24 |
| 981 | 42081 | 42095 | 15 |
| 982 | 42096 | 42139 | 44 |
| 983 | 42141 | 42187 | 47 |
| 984 | 42190 | 42226 | 37 |
| 985 | 42232 | 42253 | 22 |
| 986 | 42255 | 42305 | 51 |
| 987 | 42307 | 42320 | 14 |
| 988 | 42347 | 42375 | 29 |
| 989 | 42389 | 42425 | 37 |
| 990 | 42427 | 42442 | 16 |
| 991 | 42452 | 42474 | 23 |
| 992 | 42482 | 42496 | 15 |
| 993 | 42495 | 42509 | 15 |
| 994 | 42536 | 42550 | 15 |
| 995 | 42566 | 42580 | 15 |
| 996 | 42590 | 42612 | 23 |
| 997 | 42646 | 42678 | 33 |
| 998 | 42683 | 42723 | 41 |
| 999 | 42735 | 42750 | 16 |
| 1000 | 42752 | 42817 | 66 |
| 1001 | 42843 | 42873 | 31 |
| 1002 | 42890 | 42939 | 50 |

TABLE 1-continued

Regions of SEQ ID NO 1 which may be targeted using oligonucleotide of the invention

| Reg. A | Position in SEQ ID NO 1 from | to | Length |
|---|---|---|---|
| 1003 | 42938 | 42989 | 52 |
| 1004 | 42991 | 43005 | 15 |
| 1005 | 43007 | 43020 | 14 |
| 1006 | 43036 | 43055 | 20 |
| 1007 | 43057 | 43102 | 46 |
| 1008 | 43113 | 43145 | 33 |
| 1009 | 43147 | 43180 | 34 |
| 1010 | 43204 | 43221 | 18 |
| 1011 | 43221 | 43265 | 45 |
| 1012 | 43267 | 43296 | 30 |
| 1013 | 43311 | 43334 | 24 |
| 1014 | 43336 | 43361 | 26 |
| 1015 | 43371 | 43395 | 25 |
| 1016 | 43399 | 43423 | 25 |
| 1017 | 43425 | 43453 | 29 |
| 1018 | 43452 | 43468 | 17 |
| 1019 | 43470 | 43488 | 19 |
| 1020 | 43495 | 43522 | 28 |
| 1021 | 43525 | 43559 | 35 |
| 1022 | 43561 | 43584 | 24 |
| 1023 | 43590 | 43611 | 22 |
| 1024 | 43618 | 43650 | 33 |
| 1025 | 43670 | 43685 | 16 |
| 1026 | 43722 | 43774 | 53 |
| 1027 | 43776 | 43791 | 16 |
| 1028 | 43808 | 43835 | 28 |
| 1029 | 43835 | 43851 | 17 |
| 1030 | 43853 | 43868 | 16 |
| 1031 | 43923 | 43937 | 15 |
| 1032 | 43952 | 43987 | 36 |
| 1033 | 44011 | 44029 | 19 |
| 1034 | 44028 | 44070 | 43 |
| 1035 | 44072 | 44094 | 23 |
| 1036 | 44101 | 44130 | 30 |
| 1037 | 44137 | 44205 | 69 |
| 1038 | 44224 | 44244 | 21 |
| 1039 | 44246 | 44265 | 20 |
| 1040 | 44267 | 44318 | 52 |
| 1041 | 44316 | 44336 | 21 |
| 1042 | 44338 | 44359 | 22 |
| 1043 | 44361 | 44424 | 64 |
| 1044 | 44439 | 44474 | 36 |
| 1045 | 44476 | 44500 | 25 |
| 1046 | 44502 | 44519 | 18 |
| 1047 | 44539 | 44553 | 15 |
| 1048 | 44563 | 44578 | 16 |
| 1049 | 44585 | 44599 | 15 |
| 1050 | 44601 | 44617 | 17 |
| 1051 | 44640 | 44701 | 62 |
| 1052 | 44704 | 44723 | 20 |
| 1053 | 44741 | 44763 | 23 |
| 1054 | 44766 | 44846 | 81 |
| 1055 | 44870 | 44889 | 20 |
| 1056 | 44887 | 44905 | 19 |
| 1057 | 44920 | 44947 | 28 |
| 1058 | 44949 | 44966 | 18 |
| 1059 | 44994 | 45022 | 29 |
| 1060 | 45042 | 45059 | 18 |
| 1061 | 45061 | 45087 | 27 |
| 1062 | 45116 | 45154 | 39 |
| 1063 | 45156 | 45182 | 27 |
| 1064 | 45183 | 45198 | 16 |
| 1065 | 45210 | 45243 | 34 |
| 1066 | 45245 | 45320 | 76 |
| 1067 | 45331 | 45367 | 37 |
| 1068 | 45380 | 45399 | 20 |
| 1069 | 45415 | 45428 | 14 |
| 1070 | 45421 | 45486 | 66 |
| 1071 | 45488 | 45545 | 58 |
| 1072 | 45556 | 45576 | 21 |
| 1073 | 45578 | 45597 | 20 |
| 1074 | 45603 | 45650 | 48 |
| 1075 | 45652 | 45665 | 14 |
| 1076 | 45675 | 45715 | 41 |
| 1077 | 45749 | 45763 | 15 |
| 1078 | 45804 | 45826 | 23 |
| 1079 | 45839 | 45861 | 23 |
| 1080 | 45878 | 45910 | 33 |
| 1081 | 45926 | 45954 | 29 |
| 1082 | 45956 | 45975 | 20 |
| 1083 | 45977 | 45997 | 21 |
| 1084 | 45999 | 46020 | 22 |
| 1085 | 46046 | 46063 | 18 |
| 1086 | 46065 | 46088 | 24 |
| 1087 | 46097 | 46118 | 22 |
| 1088 | 46120 | 46142 | 23 |
| 1089 | 46144 | 46160 | 17 |
| 1090 | 46162 | 46185 | 24 |
| 1091 | 46204 | 46280 | 77 |
| 1092 | 46302 | 46326 | 25 |
| 1093 | 46328 | 46355 | 28 |
| 1094 | 46358 | 46377 | 20 |
| 1095 | 46379 | 46436 | 58 |
| 1096 | 46457 | 46471 | 15 |
| 1097 | 46473 | 46492 | 20 |
| 1098 | 46501 | 46541 | 41 |
| 1099 | 46543 | 46572 | 30 |
| 1100 | 46584 | 46626 | 43 |
| 1101 | 46655 | 46683 | 29 |
| 1102 | 46685 | 46702 | 18 |
| 1103 | 46704 | 46722 | 19 |
| 1104 | 46724 | 46763 | 40 |
| 1105 | 46784 | 46800 | 17 |
| 1106 | 46802 | 46827 | 26 |
| 1107 | 46830 | 46867 | 38 |
| 1108 | 46869 | 46887 | 19 |
| 1109 | 46889 | 46920 | 32 |
| 1110 | 46922 | 46947 | 26 |
| 1111 | 46976 | 47009 | 34 |
| 1112 | 47011 | 47030 | 20 |
| 1113 | 47032 | 47064 | 33 |
| 1114 | 47066 | 47092 | 27 |
| 1115 | 47108 | 47130 | 23 |
| 1116 | 47132 | 47168 | 37 |
| 1117 | 47170 | 47199 | 30 |
| 1118 | 47201 | 47222 | 22 |
| 1119 | 47238 | 47277 | 40 |
| 1120 | 47296 | 47350 | 55 |
| 1121 | 47352 | 47391 | 40 |
| 1122 | 47416 | 47440 | 25 |
| 1123 | 47452 | 47466 | 15 |
| 1124 | 47468 | 47523 | 56 |
| 1125 | 47522 | 47546 | 25 |
| 1126 | 47548 | 47567 | 20 |
| 1127 | 47569 | 47595 | 27 |
| 1128 | 47597 | 47634 | 38 |
| 1129 | 47657 | 47693 | 37 |
| 1130 | 47712 | 47731 | 20 |
| 1131 | 47749 | 47762 | 14 |
| 1132 | 47771 | 47825 | 55 |
| 1133 | 47827 | 47846 | 20 |
| 1134 | 47848 | 47872 | 25 |
| 1135 | 47874 | 47888 | 15 |
| 1136 | 47890 | 47909 | 20 |
| 1137 | 47911 | 47925 | 15 |
| 1138 | 47927 | 47952 | 26 |
| 1139 | 47961 | 47993 | 33 |
| 1140 | 48001 | 48016 | 16 |
| 1141 | 48051 | 48083 | 33 |
| 1142 | 48096 | 48158 | 63 |
| 1143 | 48158 | 48176 | 19 |
| 1144 | 48186 | 48201 | 16 |

TABLE 1-continued

Regions of SEQ ID NO 1 which may be targeted using oligonucleotide of the invention

| Reg. A | Position in SEQ ID NO 1 from | to | Length |
|---|---|---|---|
| 1145 | 48213 | 48239 | 27 |
| 1146 | 48241 | 48256 | 16 |
| 1147 | 48258 | 48278 | 21 |
| 1148 | 48280 | 48339 | 60 |
| 1149 | 48341 | 48357 | 17 |
| 1150 | 48359 | 48377 | 19 |
| 1151 | 48379 | 48393 | 15 |
| 1152 | 48395 | 48488 | 94 |
| 1153 | 48492 | 48510 | 19 |
| 1154 | 48528 | 48549 | 22 |
| 1155 | 48550 | 48589 | 40 |
| 1156 | 48636 | 48658 | 23 |
| 1157 | 48683 | 48697 | 15 |
| 1158 | 48699 | 48762 | 64 |
| 1159 | 48762 | 48775 | 14 |
| 1160 | 48773 | 48832 | 60 |
| 1161 | 48873 | 48886 | 14 |
| 1162 | 48888 | 48914 | 27 |
| 1163 | 48916 | 48944 | 29 |
| 1164 | 48969 | 49008 | 40 |
| 1165 | 49010 | 49024 | 15 |
| 1166 | 49051 | 49110 | 60 |
| 1167 | 49116 | 49150 | 35 |
| 1168 | 49151 | 49184 | 34 |
| 1169 | 49187 | 49200 | 14 |
| 1170 | 49213 | 49230 | 18 |
| 1171 | 49233 | 49247 | 15 |
| 1172 | 49267 | 49284 | 18 |
| 1173 | 49297 | 49310 | 14 |
| 1174 | 49317 | 49369 | 53 |
| 1175 | 49371 | 49435 | 65 |
| 1176 | 49444 | 49458 | 15 |
| 1177 | 49467 | 49500 | 34 |
| 1178 | 49510 | 49538 | 29 |
| 1179 | 49540 | 49559 | 20 |
| 1180 | 49561 | 49584 | 24 |
| 1181 | 49591 | 49626 | 36 |
| 1182 | 49628 | 49646 | 19 |
| 1183 | 49653 | 49737 | 85 |
| 1184 | 49787 | 49802 | 16 |
| 1185 | 49817 | 49835 | 19 |
| 1186 | 49841 | 49860 | 20 |
| 1187 | 49862 | 49883 | 22 |
| 1188 | 49885 | 49905 | 21 |
| 1189 | 49921 | 49950 | 30 |
| 1190 | 49961 | 49979 | 19 |
| 1191 | 49995 | 50051 | 57 |
| 1192 | 50053 | 50071 | 19 |
| 1193 | 50073 | 50088 | 16 |
| 1194 | 50132 | 50158 | 27 |
| 1195 | 50167 | 50183 | 17 |
| 1196 | 50201 | 50226 | 26 |
| 1197 | 50226 | 50239 | 14 |
| 1198 | 50259 | 50313 | 55 |
| 1199 | 50323 | 50341 | 19 |
| 1200 | 50343 | 50396 | 54 |
| 1201 | 50390 | 50403 | 14 |
| 1202 | 50398 | 50448 | 51 |
| 1203 | 50451 | 50483 | 33 |
| 1204 | 50489 | 50507 | 19 |
| 1205 | 50526 | 50548 | 23 |
| 1206 | 50550 | 50569 | 20 |
| 1207 | 50575 | 50602 | 28 |
| 1208 | 50606 | 50621 | 16 |
| 1209 | 50617 | 50630 | 14 |
| 1210 | 50623 | 50641 | 19 |
| 1211 | 50634 | 50647 | 14 |
| 1212 | 50644 | 50663 | 20 |
| 1213 | 50665 | 50684 | 20 |
| 1214 | 50705 | 50730 | 26 |
| 1215 | 50732 | 50763 | 32 |
| 1216 | 50766 | 50799 | 34 |
| 1217 | 50797 | 50823 | 27 |
| 1218 | 50838 | 50864 | 27 |
| 1219 | 50870 | 50884 | 15 |
| 1220 | 50885 | 50911 | 27 |
| 1221 | 50924 | 50937 | 14 |
| 1222 | 50939 | 50974 | 36 |
| 1223 | 50980 | 51008 | 29 |
| 1224 | 51015 | 51030 | 16 |
| 1225 | 51034 | 51047 | 14 |
| 1226 | 51075 | 51089 | 15 |
| 1227 | 51109 | 51123 | 15 |
| 1228 | 51135 | 51172 | 38 |
| 1229 | 51189 | 51216 | 28 |
| 1230 | 51241 | 51260 | 20 |
| 1231 | 51273 | 51294 | 22 |
| 1232 | 51296 | 51312 | 17 |
| 1233 | 51337 | 51357 | 21 |
| 1234 | 51356 | 51381 | 26 |
| 1235 | 51393 | 51465 | 73 |
| 1236 | 51476 | 51494 | 19 |
| 1237 | 51496 | 51515 | 20 |
| 1238 | 51530 | 51544 | 15 |
| 1239 | 51546 | 51572 | 27 |
| 1240 | 51586 | 51600 | 15 |
| 1241 | 51602 | 51617 | 16 |
| 1242 | 51619 | 51677 | 59 |
| 1243 | 51679 | 51700 | 22 |
| 1244 | 51727 | 51741 | 15 |
| 1245 | 51743 | 51821 | 79 |
| 1246 | 51826 | 51859 | 34 |
| 1247 | 51884 | 51912 | 29 |
| 1248 | 51918 | 51936 | 19 |
| 1249 | 51947 | 51979 | 33 |
| 1250 | 52004 | 52017 | 14 |
| 1251 | 52023 | 52048 | 26 |
| 1252 | 52141 | 52167 | 27 |
| 1253 | 52169 | 52188 | 20 |
| 1254 | 52204 | 52225 | 22 |
| 1255 | 52246 | 52262 | 17 |
| 1256 | 52289 | 52306 | 18 |
| 1257 | 52321 | 52339 | 19 |
| 1258 | 52341 | 52360 | 20 |
| 1259 | 52360 | 52428 | 69 |
| 1260 | 52430 | 52504 | 75 |
| 1261 | 52506 | 52567 | 62 |
| 1262 | 52579 | 52594 | 16 |
| 1263 | 52591 | 52610 | 20 |
| 1264 | 52612 | 52642 | 31 |
| 1265 | 52644 | 52667 | 24 |
| 1266 | 52672 | 52686 | 15 |
| 1267 | 52688 | 52702 | 15 |
| 1268 | 52715 | 52753 | 39 |
| 1269 | 52770 | 52783 | 14 |
| 1270 | 52779 | 52792 | 14 |
| 1271 | 52814 | 52845 | 32 |
| 1272 | 52834 | 52857 | 24 |
| 1273 | 52858 | 52885 | 28 |
| 1274 | 52887 | 52943 | 57 |
| 1275 | 52945 | 52962 | 18 |
| 1276 | 52971 | 53019 | 49 |
| 1277 | 53011 | 53036 | 26 |
| 1278 | 53053 | 53066 | 14 |
| 1279 | 53092 | 53112 | 21 |
| 1280 | 53124 | 53151 | 28 |
| 1281 | 53161 | 53175 | 15 |
| 1282 | 53184 | 53220 | 37 |
| 1283 | 53222 | 53243 | 22 |
| 1284 | 53245 | 53260 | 16 |
| 1285 | 53278 | 53304 | 27 |
| 1286 | 53311 | 53346 | 36 |

TABLE 1-continued

Regions of SEQ ID NO 1 which may be targeted using oligonucleotide of the invention

| Reg. A | Position in SEQ ID NO 1 from | to | Length |
|---|---|---|---|
| 1287 | 53364 | 53386 | 23 |
| 1288 | 53388 | 53404 | 17 |
| 1289 | 53417 | 53431 | 15 |
| 1290 | 53449 | 53463 | 15 |
| 1291 | 53465 | 53484 | 20 |
| 1292 | 53514 | 53527 | 14 |
| 1293 | 53552 | 53567 | 16 |
| 1294 | 53570 | 53591 | 22 |
| 1295 | 53618 | 53644 | 27 |
| 1296 | 53645 | 53667 | 23 |
| 1297 | 53669 | 53684 | 16 |
| 1298 | 53714 | 53742 | 29 |
| 1299 | 53744 | 53764 | 21 |
| 1300 | 53818 | 53843 | 26 |
| 1301 | 53845 | 53860 | 16 |
| 1302 | 53875 | 53889 | 15 |
| 1303 | 53961 | 53991 | 31 |
| 1304 | 53991 | 54013 | 23 |
| 1305 | 54015 | 54055 | 41 |
| 1306 | 54057 | 54081 | 25 |
| 1307 | 54114 | 54135 | 22 |
| 1308 | 54163 | 54178 | 16 |
| 1309 | 54180 | 54193 | 14 |
| 1310 | 54195 | 54254 | 60 |
| 1311 | 54261 | 54290 | 30 |
| 1312 | 54292 | 54307 | 16 |
| 1313 | 54309 | 54327 | 19 |
| 1314 | 54357 | 54372 | 16 |
| 1315 | 54404 | 54420 | 17 |
| 1316 | 54418 | 54439 | 22 |
| 1317 | 54441 | 54466 | 26 |
| 1318 | 54468 | 54512 | 45 |
| 1319 | 54519 | 54532 | 14 |
| 1320 | 54555 | 54572 | 18 |
| 1321 | 54588 | 54601 | 14 |
| 1322 | 54609 | 54633 | 25 |
| 1323 | 54644 | 54688 | 45 |
| 1324 | 54690 | 54721 | 32 |
| 1325 | 54723 | 54761 | 39 |
| 1326 | 54786 | 54802 | 17 |
| 1327 | 54819 | 54835 | 17 |
| 1328 | 54837 | 54912 | 76 |
| 1329 | 54924 | 54941 | 18 |
| 1330 | 54999 | 55017 | 19 |
| 1331 | 55019 | 55035 | 17 |
| 1332 | 55060 | 55073 | 14 |
| 1333 | 55075 | 55100 | 26 |
| 1334 | 55129 | 55171 | 43 |
| 1335 | 55173 | 55188 | 16 |
| 1336 | 55190 | 55203 | 14 |
| 1337 | 55210 | 55230 | 21 |
| 1338 | 55233 | 55281 | 49 |
| 1339 | 55276 | 55289 | 14 |
| 1340 | 55283 | 55320 | 38 |
| 1341 | 55330 | 55379 | 50 |
| 1342 | 55381 | 55423 | 43 |
| 1343 | 55420 | 55441 | 22 |
| 1344 | 55486 | 55502 | 17 |
| 1345 | 55515 | 55533 | 19 |
| 1346 | 55535 | 55553 | 19 |
| 1347 | 55555 | 55569 | 15 |
| 1348 | 55569 | 55588 | 20 |
| 1349 | 55590 | 55611 | 22 |
| 1350 | 55615 | 55663 | 49 |
| 1351 | 55665 | 55678 | 14 |
| 1352 | 55696 | 55713 | 18 |
| 1353 | 55715 | 55738 | 24 |
| 1354 | 55744 | 55774 | 31 |
| 1355 | 55776 | 55794 | 19 |
| 1356 | 55801 | 55823 | 23 |
| 1357 | 55862 | 55906 | 45 |
| 1358 | 55920 | 55933 | 14 |
| 1359 | 55922 | 55947 | 26 |
| 1360 | 55974 | 55993 | 20 |
| 1361 | 55990 | 56031 | 42 |
| 1362 | 56045 | 56073 | 29 |
| 1363 | 56082 | 56114 | 33 |
| 1364 | 56117 | 56140 | 24 |
| 1365 | 56183 | 56214 | 32 |
| 1366 | 56218 | 56236 | 19 |
| 1367 | 56261 | 56282 | 22 |
| 1368 | 56311 | 56336 | 26 |
| 1369 | 56331 | 56345 | 15 |
| 1370 | 56338 | 56358 | 21 |
| 1371 | 56369 | 56390 | 22 |
| 1372 | 56391 | 56431 | 41 |
| 1373 | 56433 | 56451 | 19 |
| 1374 | 56453 | 56473 | 21 |
| 1375 | 56475 | 56498 | 24 |
| 1376 | 56500 | 56546 | 47 |
| 1377 | 56558 | 56581 | 24 |
| 1378 | 56584 | 56597 | 14 |
| 1379 | 56611 | 56647 | 37 |
| 1380 | 56643 | 56657 | 15 |
| 1381 | 56667 | 56691 | 25 |
| 1382 | 56732 | 56759 | 28 |
| 1383 | 56788 | 56805 | 18 |
| 1384 | 56821 | 56845 | 25 |
| 1385 | 56850 | 56882 | 33 |
| 1386 | 56885 | 56906 | 22 |
| 1387 | 56928 | 56942 | 15 |
| 1388 | 56944 | 56959 | 16 |
| 1389 | 56961 | 56975 | 15 |
| 1390 | 56984 | 57002 | 19 |
| 1391 | 57004 | 57041 | 38 |
| 1392 | 57057 | 57082 | 26 |
| 1393 | 57084 | 57122 | 39 |
| 1394 | 57162 | 57222 | 61 |
| 1395 | 57224 | 57246 | 23 |
| 1396 | 57259 | 57284 | 26 |
| 1397 | 57317 | 57332 | 16 |
| 1398 | 57346 | 57369 | 24 |
| 1399 | 57388 | 57423 | 36 |
| 1400 | 57425 | 57440 | 16 |
| 1401 | 57442 | 57455 | 14 |
| 1402 | 57475 | 57492 | 18 |
| 1403 | 57508 | 57522 | 15 |
| 1404 | 57522 | 57546 | 25 |
| 1405 | 57548 | 57576 | 29 |
| 1406 | 57593 | 57634 | 42 |
| 1407 | 57658 | 57675 | 18 |
| 1408 | 57687 | 57771 | 85 |
| 1409 | 57786 | 57803 | 18 |
| 1410 | 57801 | 57819 | 19 |
| 1411 | 57830 | 57858 | 29 |
| 1412 | 57889 | 57911 | 23 |
| 1413 | 57926 | 57945 | 20 |
| 1414 | 57947 | 57972 | 26 |
| 1415 | 58009 | 58028 | 20 |
| 1416 | 58030 | 58060 | 31 |
| 1417 | 58063 | 58091 | 29 |
| 1418 | 58124 | 58146 | 23 |
| 1419 | 58147 | 58162 | 16 |
| 1420 | 58163 | 58198 | 36 |
| 1421 | 58214 | 58292 | 79 |
| 1422 | 58292 | 58309 | 18 |
| 1423 | 58336 | 58429 | 94 |
| 1424 | 58436 | 58457 | 22 |
| 1425 | 58453 | 58501 | 49 |
| 1426 | 58525 | 58553 | 29 |
| 1427 | 58566 | 58579 | 14 |
| 1428 | 58571 | 58584 | 14 |

TABLE 1-continued

Regions of SEQ ID NO 1 which may be targeted using oligonucleotide of the invention

| Reg. A | Position in SEQ ID NO 1 from | to | Length |
|---|---|---|---|
| 1429 | 58586 | 58601 | 16 |
| 1430 | 58604 | 58630 | 27 |
| 1431 | 58656 | 58682 | 27 |
| 1432 | 58696 | 58713 | 18 |
| 1433 | 58722 | 58744 | 23 |
| 1434 | 58757 | 58771 | 15 |
| 1435 | 58805 | 58979 | 175 |
| 1436 | 58987 | 59073 | 87 |
| 1437 | 59072 | 59123 | 52 |
| 1438 | 59124 | 59150 | 27 |
| 1439 | 59154 | 59234 | 81 |
| 1440 | 59231 | 59276 | 46 |
| 1441 | 59291 | 59413 | 123 |
| 1442 | 59413 | 59458 | 46 |
| 1443 | 59466 | 59511 | 46 |
| 1444 | 59513 | 59533 | 21 |
| 1445 | 59549 | 59764 | 216 |
| 1446 | 59762 | 59825 | 64 |
| 1447 | 59824 | 59907 | 84 |
| 1448 | 59916 | 60004 | 89 |
| 1449 | 60006 | 60030 | 25 |
| 1450 | 60027 | 60040 | 14 |
| 1451 | 60032 | 60100 | 69 |
| 1452 | 60119 | 60188 | 70 |
| 1453 | 60191 | 60227 | 37 |
| 1454 | 60220 | 60287 | 68 |
| 1455 | 60289 | 60314 | 26 |
| 1456 | 60316 | 60554 | 239 |
| 1457 | 60556 | 60575 | 20 |
| 1458 | 60579 | 60593 | 15 |
| 1459 | 60595 | 60638 | 44 |
| 1460 | 60651 | 60690 | 40 |
| 1461 | 60692 | 60724 | 33 |
| 1462 | 60716 | 60799 | 84 |
| 1463 | 60801 | 60872 | 72 |
| 1464 | 60868 | 60881 | 14 |
| 1465 | 60885 | 60912 | 28 |
| 1466 | 60961 | 61009 | 49 |
| 1467 | 61014 | 61042 | 29 |
| 1468 | 61046 | 61059 | 14 |
| 1469 | 61053 | 61066 | 14 |
| 1470 | 61061 | 61084 | 24 |
| 1471 | 61134 | 61164 | 31 |
| 1472 | 61178 | 61199 | 22 |
| 1473 | 61201 | 61229 | 29 |
| 1474 | 61258 | 61284 | 27 |
| 1475 | 61286 | 61304 | 19 |
| 1476 | 61316 | 61332 | 17 |
| 1477 | 61341 | 61354 | 14 |
| 1478 | 61356 | 61383 | 28 |
| 1479 | 61407 | 61440 | 34 |
| 1480 | $1451 | 61468 | 18 |
| 1481 | 61470 | 61497 | 28 |
| 1482 | 61493 | 61506 | 14 |
| 1483 | 61499 | 61529 | 31 |
| 1484 | 61531 | 61558 | 28 |
| 1485 | 61590 | 61615 | 26 |
| 1486 | 61623 | 61640 | 18 |
| 1487 | 61673 | 61877 | 205 |
| 1488 | 61879 | 61898 | 20 |
| 1489 | 61900 | 61941 | 42 |
| 1490 | 61943 | 61962 | 20 |
| 1491 | 61964 | 61983 | 20 |
| 1492 | 62003 | 62017 | 15 |
| 1493 | 62015 | 62080 | 66 |
| 1494 | 62100 | 62124 | 25 |
| 1495 | 62133 | 62146 | 14 |
| 1496 | 62139 | 62175 | 37 |
| 1497 | 62191 | 62237 | 47 |
| 1498 | 62250 | 62270 | 21 |
| 1499 | 62283 | 62316 | 34 |
| 1500 | 62310 | 62358 | 49 |
| 1501 | 62357 | 62397 | 41 |
| 1502 | 62399 | 62413 | 15 |
| 1503 | 62415 | 62470 | 56 |
| 1504 | 62472 | 62501 | 30 |
| 1505 | 62503 | 62541 | 39 |
| 1506 | 62553 | 62609 | 57 |
| 1507 | 62611 | 62656 | 46 |
| 1508 | 62663 | 62690 | 28 |
| 1509 | 62703 | 62735 | 33 |
| 1510 | 62737 | 62759 | 23 |
| 1511 | 62765 | 62789 | 25 |
| 1512 | 62802 | 62816 | 15 |
| 1513 | 62810 | 62824 | 15 |
| 1514 | 62853 | 62868 | 16 |
| 1515 | 62864 | 62878 | 15 |
| 1516 | 62878 | 62907 | 30 |
| 1517 | 62905 | 62937 | 33 |
| 1518 | 62937 | 62951 | 15 |
| 1519 | 62943 | 62956 | 14 |
| 1520 | 62946 | 62960 | 15 |
| 1521 | 62961 | 62988 | 28 |
| 1522 | 62993 | 63006 | 14 |
| 1523 | 63005 | 63019 | 15 |
| 1524 | 63030 | 63049 | 20 |
| 1525 | 63057 | 63076 | 20 |
| 1526 | 63073 | 63088 | 16 |
| 1527 | 63078 | 63125 | 48 |
| 1528 | 63128 | 63152 | 25 |
| 1529 | 63154 | 63170 | 17 |
| 1530 | 63172 | 63196 | 25 |
| 1531 | 63185 | 63223 | 39 |
| 1532 | 63225 | 63245 | 21 |
| 1533 | 63236 | 63254 | 19 |
| 1534 | 63245 | 63261 | 17 |
| 1535 | 63263 | 63276 | 14 |
| 1536 | 63280 | 63295 | 16 |
| 1537 | 63292 | 63336 | 45 |
| 1538 | 63344 | 63368 | 25 |
| 1539 | 63369 | 63396 | 28 |
| 1540 | 63385 | 63398 | 14 |
| 1541 | 63395 | 63417 | 23 |
| 1542 | 63433 | 63451 | 19 |
| 1543 | 63440 | 63453 | 14 |
| 1544 | 63454 | 63470 | 17 |
| 1545 | 63472 | 63511 | 40 |
| 1546 | 63513 | 63539 | 27 |
| 1547 | 63547 | 63603 | 57 |
| 1548 | 63625 | 63651 | 27 |
| 1549 | 63676 | 63692 | 17 |
| 1550 | 63730 | 63746 | 17 |
| 1551 | 63759 | 63775 | 17 |
| 1552 | 63779 | 63833 | 55 |
| 1553 | 63844 | 63883 | 40 |
| 1554 | 63889 | 63907 | 19 |
| 1555 | 63910 | 63938 | 29 |
| 1556 | 63943 | 63962 | 20 |
| 1557 | 64004 | 64033 | 30 |
| 1558 | 64056 | 64087 | 32 |
| 1559 | 64112 | 64132 | 21 |
| 1560 | 64142 | 64158 | 17 |
| 1561 | 64160 | 64191 | 32 |
| 1562 | 64193 | 64209 | 17 |
| 1563 | 64214 | 64227 | 14 |
| 1564 | 64228 | 64241 | 14 |
| 1565 | 64254 | 64278 | 25 |
| 1566 | 64280 | 64298 | 19 |
| 1567 | 64300 | 64338 | 39 |
| 1568 | 64340 | 64355 | 16 |
| 1569 | 64357 | 64380 | 24 |
| 1570 | 64412 | 64434 | 23 |

TABLE 1-continued

Regions of SEQ ID NO 1 which may be targeted using oligonucleotide of the invention

| Reg. A | Position in SEQ ID NO 1 from | to | Length |
|---|---|---|---|
| 1571 | 64438 | 64456 | 19 |
| 1572 | 64458 | 64488 | 31 |
| 1573 | 64490 | 64517 | 28 |
| 1574 | 64519 | 64538 | 20 |
| 1575 | 64552 | 64572 | 21 |
| 1576 | 64585 | 64608 | 24 |
| 1577 | 64625 | 64642 | 18 |
| 1578 | 64631 | 64644 | 14 |
| 1579 | 64644 | 64683 | 40 |
| 1580 | 64703 | 64716 | 14 |
| 1581 | 64736 | 64751 | 16 |
| 1582 | 64759 | 64773 | 15 |
| 1583 | 64775 | 64806 | 32 |
| 1584 | 64815 | 64831 | 17 |
| 1585 | 64845 | 64878 | 34 |
| 1586 | 64880 | 64904 | 25 |
| 1587 | 64915 | 64937 | 23 |
| 1588 | 64948 | 64971 | 24 |
| 1589 | 64973 | 64994 | 22 |
| 1590 | 64996 | 65017 | 22 |
| 1591 | 65019 | 65055 | 37 |
| 1592 | 65062 | 65109 | 48 |
| 1593 | 65111 | 65138 | 28 |
| 1594 | 65140 | 65179 | 40 |
| 1595 | 65181 | 65195 | 15 |
| 1596 | 65210 | 65230 | 21 |
| 1597 | 65232 | 65248 | 17 |
| 1598 | 65271 | 65296 | 26 |
| 1599 | 65298 | 65319 | 22 |
| 1600 | 65321 | 65371 | 51 |
| 1601 | 65391 | 65413 | 23 |
| 1602 | 65415 | 65436 | 22 |
| 1603 | 65436 | 65454 | 19 |
| 1604 | 65477 | 65490 | 14 |
| 1605 | 65492 | 65520 | 29 |
| 1606 | 65522 | 65552 | 31 |
| 1607 | 65554 | 65579 | 26 |
| 1608 | 65581 | 65594 | 14 |
| 1609 | 65591 | 65606 | 16 |
| 1610 | 65595 | 65616 | 22 |
| 1611 | 65618 | 65632 | 15 |
| 1612 | 65634 | 65657 | 24 |
| 1613 | 65661 | 65716 | 56 |
| 1614 | 65730 | 65747 | 18 |
| 1615 | 65748 | 65807 | 60 |
| 1616 | 65809 | 65829 | 21 |
| 1617 | 65831 | 65844 | 14 |
| 1618 | 65846 | 65859 | 14 |
| 1619 | 65861 | 65891 | 31 |
| 1620 | 65898 | 65920 | 23 |
| 1621 | 65930 | 65963 | 34 |
| 1622 | 65980 | 66060 | 81 |
| 1623 | 66069 | 66085 | 17 |
| 1624 | 66095 | 66108 | 14 |
| 1625 | 66110 | 66126 | 17 |
| 1626 | 66139 | 66173 | 35 |
| 1627 | 66175 | 66191 | 17 |
| 1628 | 66204 | 66226 | 23 |
| 1629 | 66224 | 66263 | 40 |
| 1630 | 66265 | 66278 | 14 |
| 1631 | 66280 | 66320 | 41 |
| 1632 | 66322 | 66345 | 24 |
| 1633 | 66355 | 66371 | 17 |
| 1634 | 66375 | 66407 | 33 |
| 1635 | 66411 | 66424 | 14 |
| 1636 | 66421 | 66441 | 21 |
| 1637 | 66440 | 66460 | 21 |
| 1638 | 66463 | 66482 | 20 |
| 1639 | 66484 | 66501 | 18 |
| 1640 | 66509 | 66527 | 19 |
| 1641 | 66534 | 66548 | 15 |
| 1642 | 66556 | 66569 | 14 |
| 1643 | 66562 | 66593 | 32 |
| 1644 | 66606 | 66637 | 32 |
| 1645 | 66639 | 66665 | 27 |
| 1646 | 66674 | 66690 | 17 |
| 1647 | 66692 | 66720 | 29 |
| 1648 | 66722 | 66742 | 21 |
| 1649 | 66758 | 66786 | 29 |
| 1650 | 66787 | 66802 | 16 |
| 1651 | 66812 | 66862 | 51 |
| 1652 | 66864 | 66885 | 22 |
| 1653 | 66940 | 66953 | 14 |
| 1654 | 66982 | 66997 | 16 |
| 1655 | 67024 | 67084 | 61 |
| 1656 | 67103 | 67118 | 16 |
| 1657 | 67156 | 67185 | 30 |
| 1658 | 67181 | 67195 | 15 |
| 1659 | 67193 | 67206 | 14 |
| 1660 | 67215 | 67229 | 15 |
| 1661 | 67231 | 67271 | 41 |
| 1662 | 67288 | 67301 | 14 |
| 1663 | 67294 | 67345 | 52 |
| 1664 | 67362 | 67379 | 18 |
| 1665 | 67381 | 67397 | 17 |
| 1666 | 67409 | 67448 | 40 |
| 1667 | 67468 | 67481 | 14 |
| 1668 | 67483 | 67510 | 28 |
| 1669 | 67540 | 67561 | 22 |
| 1670 | 67620 | 67640 | 21 |
| 1671 | 67656 | 67672 | 17 |
| 1672 | 67674 | 67749 | 76 |
| 1673 | 67751 | 67764 | 14 |
| 1674 | 67783 | 67801 | 19 |
| 1675 | 67803 | 67828 | 26 |
| 1676 | 67830 | 67848 | 19 |
| 1677 | 67850 | 67868 | 19 |
| 1678 | 67877 | 67918 | 42 |
| 1679 | 67933 | 67961 | 29 |
| 1680 | 67963 | 67978 | 16 |
| 1681 | 67998 | 68026 | 29 |
| 1682 | 68028 | 68046 | 19 |
| 1683 | 68048 | 68082 | 35 |
| 1684 | 68084 | 68112 | 29 |
| 1685 | 68114 | 68130 | 17 |
| 1686 | 68129 | 68155 | 27 |
| 1687 | 68170 | 68192 | 23 |
| 1688 | 68194 | 68237 | 44 |
| 1689 | 68239 | 68261 | 23 |
| 1690 | 68272 | 68286 | 15 |
| 1691 | 68290 | 68373 | 84 |
| 1692 | 68375 | 68419 | 45 |
| 1693 | 68442 | 68487 | 46 |
| 1694 | 68489 | 68547 | 59 |
| 1695 | 68549 | 68592 | 44 |
| 1696 | 68599 | 68614 | 16 |
| 1697 | 68617 | 68657 | 41 |
| 1698 | 68659 | 68686 | 28 |
| 1699 | 68688 | 68735 | 48 |
| 1700 | 68732 | 68747 | 16 |
| 1701 | 68749 | 68786 | 38 |
| 1702 | 68788 | 68830 | 43 |
| 1703 | 68837 | 68879 | 43 |
| 1704 | 68882 | 68899 | 18 |
| 1705 | 68918 | 68942 | 25 |
| 1706 | 68944 | 68968 | 25 |
| 1707 | 68983 | 69007 | 25 |
| 1708 | 69012 | 69027 | 16 |
| 1709 | 69020 | 69064 | 45 |
| 1710 | 69064 | 69077 | 14 |
| 1711 | 69079 | 69114 | 36 |
| 1712 | 69116 | 69196 | 81 |

TABLE 1-continued

Regions of SEQ ID NO 1 which may be targeted using oligonucleotide of the invention

| Reg. A | Position in SEQ ID NO 1 from | to | Length |
|---|---|---|---|
| 1713 | 69185 | 69198 | 14 |
| 1714 | 69202 | 69219 | 18 |
| 1715 | 69228 | 69246 | 19 |
| 1716 | 69240 | 69282 | 43 |
| 1717 | 69294 | 69317 | 24 |
| 1718 | 69306 | 69324 | 19 |
| 1719 | 69333 | 69346 | 14 |
| 1720 | 69352 | 69366 | 15 |
| 1721 | 69387 | 69431 | 45 |
| 1722 | 69433 | 69447 | 15 |
| 1723 | 69452 | 69480 | 29 |
| 1724 | 69482 | 69497 | 16 |
| 1725 | 69491 | 69504 | 14 |
| 1726 | 69511 | 69564 | 54 |
| 1727 | 69566 | 69628 | 63 |
| 1728 | 69628 | 69642 | 15 |
| 1729 | 69659 | 69681 | 23 |
| 1730 | 69684 | 69697 | 14 |
| 1731 | 69719 | 69744 | 26 |
| 1732 | 69746 | 69763 | 18 |
| 1733 | 69765 | 69792 | 28 |
| 1734 | 69801 | 69828 | 28 |
| 1735 | 69853 | 69901 | 49 |
| 1736 | 69933 | 69949 | 17 |
| 1737 | 69951 | 69966 | 16 |
| 1738 | 69968 | 69983 | 16 |
| 1739 | 69988 | 70061 | 74 |
| 1740 | 70083 | 70100 | 18 |
| 1741 | 70110 | 70154 | 45 |
| 1742 | 70161 | 70199 | 39 |
| 1743 | 70202 | 70225 | 24 |
| 1744 | 70231 | 70246 | 16 |
| 1745 | 70269 | 70295 | 27 |
| 1746 | 70292 | 70327 | 36 |
| 1747 | 70331 | 70349 | 19 |
| 1748 | 70351 | 70371 | 21 |
| 1749 | 70381 | 70403 | 23 |
| 1750 | 70405 | 70420 | 16 |
| 1751 | 70422 | 70483 | 62 |
| 1752 | 70496 | 70533 | 38 |
| 1753 | 70535 | 70578 | 44 |
| 1754 | 70577 | 70639 | 63 |
| 1755 | 70653 | 70667 | 15 |
| 1756 | 70661 | 70674 | 14 |
| 1757 | 70669 | 70695 | 27 |
| 1758 | 70687 | 70705 | 19 |
| 1759 | 70708 | 70744 | 37 |
| 1760 | 70746 | 70764 | 19 |
| 1761 | 70766 | 70779 | 14 |
| 1762 | 70781 | 70832 | 52 |
| 1763 | 70834 | 70851 | 18 |
| 1764 | 70858 | 70887 | 30 |
| 1765 | 70889 | 70902 | 14 |
| 1766 | 70920 | 70933 | 14 |
| 1767 | 70935 | 70964 | 30 |
| 1768 | 70974 | 70987 | 14 |
| 1769 | 71008 | 71028 | 21 |
| 1770 | 71030 | 71046 | 17 |
| 1771 | 71048 | 71073 | 26 |
| 1772 | 71075 | 71106 | 32 |
| 1773 | 71108 | 71133 | 26 |
| 1774 | 71137 | 71152 | 16 |
| 1775 | 71153 | 71170 | 18 |
| 1776 | 71179 | 71192 | 14 |
| 1777 | 71197 | 71224 | 28 |
| 1778 | 71235 | 71251 | 17 |
| 1779 | 71253 | 71311 | 59 |
| 1780 | 71310 | 71329 | 20 |
| 1781 | 71330 | 71364 | 35 |
| 1782 | 71366 | 71386 | 21 |
| 1783 | 71388 | 71410 | 23 |
| 1784 | 71412 | 71433 | 22 |
| 1785 | 71448 | 71472 | 25 |
| 1786 | 71475 | 71491 | 17 |
| 1787 | 71491 | 71553 | 63 |
| 1788 | 71555 | 71581 | 27 |
| 1789 | 71583 | 71624 | 42 |
| 1790 | 71634 | 71700 | 67 |
| 1791 | 71706 | 71725 | 20 |
| 1792 | 71732 | 71747 | 16 |
| 1793 | 71789 | 71804 | 16 |
| 1794 | 71810 | 71824 | 15 |
| 1795 | 71819 | 71834 | 16 |
| 1796 | 71839 | 71872 | 34 |
| 1797 | 71876 | 71889 | 14 |
| 1798 | 71886 | 71908 | 23 |
| 1799 | 71910 | 71924 | 15 |
| 1800 | 71985 | 71999 | 15 |
| 1801 | 72000 | 72021 | 22 |
| 1802 | 72023 | 72047 | 25 |
| 1803 | 72071 | 72158 | 88 |
| 1804 | 72165 | 72192 | 28 |
| 1805 | 72194 | 72234 | 41 |
| 1806 | 72236 | 72255 | 20 |
| 1807 | 72257 | 72281 | 25 |
| 1808 | 72283 | 72299 | 17 |
| 1809 | 72312 | 72329 | 18 |
| 1810 | 72323 | 72336 | 14 |
| 1811 | 72348 | 72395 | 48 |
| 1812 | 72398 | 72411 | 14 |
| 1813 | 72413 | 72455 | 43 |
| 1814 | 72470 | 72503 | 34 |
| 1815 | 72506 | 72541 | 36 |
| 1816 | 72545 | 72558 | 14 |
| 1817 | 72560 | 72586 | 27 |
| 1818 | 72583 | 72597 | 15 |
| 1819 | 72588 | 72602 | 15 |
| 1820 | 72611 | 72636 | 26 |
| 1821 | 72638 | 72688 | 51 |
| 1822 | 72696 | 72736 | 41 |
| 1823 | 72738 | 72761 | 24 |
| 1824 | 72774 | 72799 | 26 |
| 1825 | 72801 | 72886 | 86 |
| 1826 | 72888 | 72903 | 16 |
| 1827 | 72928 | 72958 | 31 |
| 1828 | 72962 | 72990 | 29 |
| 1829 | 73001 | 73014 | 14 |
| 1830 | 73017 | 73053 | 37 |
| 1831 | 73055 | 73078 | 24 |
| 1832 | 73077 | 73090 | 14 |
| 1833 | 73088 | 73121 | 34 |
| 1834 | 73124 | 73153 | 30 |
| 1835 | 73147 | 73172 | 26 |
| 1836 | 73164 | 73203 | 40 |
| 1837 | 73218 | 73257 | 40 |
| 1838 | 73260 | 73273 | 14 |
| 1839 | 73268 | 73281 | 14 |
| 1840 | 73278 | 73291 | 14 |
| 1841 | 73298 | 73313 | 16 |
| 1842 | 73451 | 73465 | 15 |
| 1843 | 73459 | 73472 | 14 |
| 1844 | 73512 | 73567 | 56 |
| 1845 | 73569 | 73611 | 43 |
| 1846 | 73614 | 73645 | 32 |
| 1847 | 73661 | 73713 | 53 |
| 1848 | 73712 | 73727 | 16 |
| 1849 | 73716 | 73731 | 16 |
| 1850 | 73735 | 73748 | 14 |
| 1851 | 73741 | 73760 | 20 |
| 1852 | 73764 | 73782 | 19 |
| 1853 | 73783 | 73801 | 19 |
| 1854 | 73795 | 73829 | 35 |

TABLE 1-continued

Regions of SEQ ID NO 1 which may be targeted using oligonucleotide of the invention

| Reg. A | Position in SEQ ID NO 1 from | to | Length |
|---|---|---|---|
| 1855 | 73860 | 73873 | 14 |
| 1856 | 73885 | 73904 | 20 |
| 1857 | 73906 | 73919 | 14 |
| 1858 | 73916 | 73945 | 30 |
| 1859 | 73947 | 73961 | 15 |
| 1860 | 73978 | 74018 | 41 |
| 1861 | 74020 | 74046 | 27 |
| 1862 | 74061 | 74082 | 22 |
| 1863 | 74092 | 74158 | 67 |
| 1864 | 74160 | 74177 | 18 |
| 1865 | 74179 | 74209 | 31 |
| 1866 | 74216 | 74245 | 30 |
| 1867 | 74270 | 74287 | 18 |
| 1868 | 74289 | 74305 | 17 |
| 1869 | 74307 | 74368 | 62 |
| 1870 | 74369 | 74411 | 43 |
| 1871 | 74416 | 74461 | 46 |
| 1872 | 74463 | 74479 | 17 |
| 1873 | 74506 | 74541 | 36 |
| 1874 | 74543 | 74636 | 94 |
| 1875 | 74647 | 74704 | 58 |
| 1876 | 74745 | 74770 | 26 |
| 1877 | 74789 | 74813 | 25 |
| 1878 | 74815 | 74838 | 24 |
| 1879 | 74850 | 74877 | 28 |
| 1880 | 74891 | 74923 | 33 |
| 1881 | 74925 | 74940 | 16 |
| 1882 | 74952 | 74969 | 18 |
| 1883 | 74979 | 75001 | 23 |
| 1884 | 75037 | 75066 | 30 |
| 1885 | 75068 | 75088 | 21 |
| 1886 | 75097 | 75123 | 27 |
| 1887 | 75131 | 75149 | 19 |
| 1888 | 75152 | 75189 | 38 |
| 1889 | 75210 | 75252 | 43 |
| 1890 | 75254 | 75276 | 23 |
| 1891 | 75288 | 75310 | 23 |
| 1892 | 75338 | 75357 | 20 |
| 1893 | 75359 | 75372 | 14 |
| 1894 | 75376 | 75397 | 22 |
| 1895 | 75405 | 75432 | 28 |
| 1896 | 75440 | 75470 | 31 |
| 1897 | 75482 | 75501 | 20 |
| 1898 | 75503 | 75540 | 38 |
| 1899 | 75544 | 75560 | 17 |
| 1900 | 75562 | 75576 | 15 |
| 1901 | 75589 | 75610 | 22 |
| 1902 | 75633 | 75646 | 14 |
| 1903 | 75648 | 75679 | 32 |
| 1904 | 75691 | 75709 | 19 |
| 1905 | 75711 | 75724 | 14 |
| 1906 | 75740 | 75764 | 25 |
| 1907 | 75763 | 75776 | 14 |
| 1908 | 75767 | 75790 | 24 |
| 1909 | 75780 | 75794 | 15 |
| 1910 | 75792 | 75808 | 17 |
| 1911 | 75810 | 75829 | 20 |
| 1912 | 75831 | 75863 | 33 |
| 1913 | 75865 | 75880 | 16 |
| 1914 | 75882 | 75922 | 41 |
| 1915 | 75932 | 75998 | 67 |
| 1916 | 76000 | 76026 | 27 |
| 1917 | 76028 | 76045 | 18 |
| 1918 | 76046 | 76082 | 37 |
| 1919 | 76098 | 76413 | 316 |
| 1920 | 76420 | 76442 | 23 |
| 1921 | 76456 | 76477 | 22 |
| 1922 | 76484 | 76558 | 75 |
| 1923 | 76573 | 76592 | 20 |
| 1924 | 76608 | 76622 | 15 |
| 1925 | 76627 | 76663 | 37 |
| 1926 | 76665 | 76683 | 19 |
| 1927 | 76685 | 76698 | 14 |
| 1928 | 76702 | 76716 | 15 |
| 1929 | 76725 | 76744 | 20 |
| 1930 | 76745 | 76761 | 17 |
| 1931 | 76780 | 76796 | 17 |
| 1932 | 76798 | 76812 | 15 |
| 1933 | 76814 | 76832 | 19 |
| 1934 | 76834 | 76859 | 26 |
| 1935 | 76871 | 76934 | 64 |
| 1936 | 77012 | 77034 | 23 |
| 1937 | 77039 | 77055 | 17 |
| 1938 | 77081 | 77094 | 14 |
| 1939 | 77121 | 77184 | 64 |
| 1940 | 77186 | 77200 | 15 |
| 1941 | 77202 | 77225 | 24 |
| 1942 | 77227 | 77247 | 21 |
| 1943 | 77261 | 77317 | 57 |
| 1944 | 77327 | 77340 | 14 |
| 1945 | 77342 | 77366 | 25 |
| 1946 | 77377 | 77394 | 18 |
| 1947 | 77396 | 77439 | 44 |
| 1948 | 77453 | 77468 | 16 |
| 1949 | 77462 | 77593 | 132 |
| 1950 | 77586 | 77599 | 14 |
| 1951 | 77595 | 77641 | 47 |
| 1952 | 77643 | 77728 | 86 |
| 1953 | 77730 | 77768 | 39 |
| 1954 | 77778 | 77816 | 39 |
| 1955 | 77818 | 77835 | 18 |
| 1956 | 77837 | 77855 | 19 |
| 1957 | 77861 | 77876 | 16 |
| 1958 | 77882 | 77898 | 17 |
| 1959 | 77900 | 77924 | 25 |
| 1960 | 77923 | 77936 | 14 |
| 1961 | 77957 | 77970 | 14 |
| 1962 | 77962 | 77985 | 24 |
| 1963 | 77994 | 78022 | 29 |
| 1964 | 78024 | 78056 | 33 |
| 1965 | 78079 | 78128 | 50 |
| 1966 | 78132 | 78158 | 27 |
| 1967 | 78173 | 78213 | 41 |
| 1968 | 78224 | 78265 | 42 |
| 1969 | 78275 | 78332 | 58 |
| 1970 | 78334 | 78440 | 107 |
| 1971 | 78442 | 78489 | 48 |
| 1972 | 78491 | 78505 | 15 |
| 1973 | 78501 | 78514 | 14 |
| 1974 | 78507 | 78537 | 31 |
| 1975 | 78557 | 78570 | 14 |
| 1976 | 78562 | 78623 | 62 |
| 1977 | 78625 | 78665 | 41 |
| 1978 | 78668 | 78684 | 17 |
| 1979 | 78686 | 78759 | 74 |
| 1980 | 78761 | 78787 | 27 |
| 1981 | 78793 | 78814 | 22 |
| 1982 | 78816 | 78854 | 39 |
| 1983 | 78847 | 78860 | 14 |
| 1984 | 78874 | 78909 | 36 |
| 1985 | 78917 | 78944 | 28 |
| 1986 | 78956 | 78978 | 23 |
| 1987 | 78991 | 79008 | 18 |
| 1988 | 79003 | 79032 | 30 |
| 1989 | 79026 | 79040 | 15 |
| 1990 | 79044 | 79072 | 29 |
| 1991 | 79098 | 79158 | 61 |
| 1992 | 79162 | 79182 | 21 |
| 1993 | 79184 | 79228 | 45 |
| 1994 | 79221 | 79235 | 15 |
| 1995 | 79230 | 79262 | 33 |
| 1996 | 79287 | 79333 | 47 |

TABLE 1-continued

Regions of SEQ ID NO 1 which may be targeted using oligonucleotide of the invention

| Reg. A | Position in SEQ ID NO 1 from | to | Length |
|---|---|---|---|
| 1997 | 79356 | 79392 | 37 |
| 1998 | 79441 | 79476 | 36 |
| 1999 | 79488 | 79522 | 35 |
| 2000 | 79522 | 79539 | 18 |
| 2001 | 79568 | 79583 | 16 |
| 2002 | 79574 | 79601 | 28 |
| 2003 | 79603 | 79618 | 16 |
| 2004 | 79617 | 79639 | 23 |
| 2005 | 79651 | 79683 | 33 |
| 2006 | 79685 | 79724 | 40 |
| 2007 | 79721 | 79736 | 16 |
| 2008 | 79727 | 79782 | 56 |
| 2009 | 79784 | 79812 | 29 |
| 2010 | 79809 | 79834 | 26 |
| 2011 | 79841 | 79861 | 21 |
| 2012 | 79873 | 79923 | 51 |
| 2013 | 79928 | 79948 | 21 |
| 2014 | 79950 | 79986 | 37 |
| 2015 | 79993 | 80019 | 27 |
| 2016 | 80019 | 80063 | 45 |
| 2017 | 80071 | 80088 | 18 |
| 2018 | 80114 | 80160 | 47 |
| 2019 | 80154 | 80183 | 30 |
| 2020 | 80185 | 80212 | 28 |
| 2021 | 80214 | 80232 | 19 |
| 2022 | 80240 | 80266 | 27 |
| 2023 | 80293 | 80312 | 20 |
| 2024 | 80344 | 80380 | 37 |
| 2025 | 80382 | 80420 | 39 |
| 2026 | 80410 | 80423 | 14 |
| 2027 | 80417 | 80438 | 22 |
| 2028 | 80440 | 80456 | 17 |
| 2029 | 80467 | 80499 | 33 |
| 2030 | 80501 | 80527 | 27 |
| 2031 | 80532 | 80561 | 30 |
| 2032 | 80563 | 80599 | 37 |
| 2033 | 80604 | 80692 | 89 |
| 2034 | 80702 | 80737 | 36 |
| 2035 | 80739 | 80795 | 57 |
| 2036 | 80796 | 80871 | 76 |
| 2037 | 80873 | 80891 | 19 |
| 2038 | 80925 | 80961 | 37 |
| 2039 | 80963 | 80992 | 30 |
| 2040 | 81009 | 81068 | 60 |
| 2041 | 81070 | 81150 | 81 |
| 2042 | 81156 | 81199 | 44 |
| 2043 | 81201 | 81225 | 25 |
| 2044 | 81237 | 81253 | 17 |
| 2045 | 81255 | 81271 | 17 |
| 2046 | 81292 | 81351 | 60 |
| 2047 | 81353 | 81371 | 19 |
| 2048 | 81392 | 81422 | 31 |
| 2049 | 81438 | 81483 | 46 |
| 2050 | 81485 | 81503 | 19 |
| 2051 | 81512 | 81526 | 15 |
| 2052 | 81532 | 81554 | 23 |
| 2053 | 81556 | 81593 | 38 |
| 2054 | 81606 | 81664 | 59 |
| 2055 | 81666 | 81698 | 33 |
| 2056 | 81701 | 81720 | 20 |
| 2057 | 81728 | 81776 | 49 |
| 2058 | 81781 | 81810 | 30 |
| 2059 | 81812 | 81847 | 36 |
| 2060 | 81849 | 81893 | 45 |
| 2061 | 81908 | 81934 | 27 |
| 2062 | 81943 | 81964 | 22 |
| 2063 | 81967 | 82034 | 68 |
| 2064 | 82036 | 82134 | 99 |
| 2065 | 82136 | 82154 | 19 |
| 2066 | 82176 | 82197 | 22 |
| 2067 | 82199 | 82250 | 52 |
| 2068 | 82252 | 82269 | 18 |
| 2069 | 82271 | 82293 | 23 |
| 2070 | 82300 | 82314 | 15 |
| 2071 | 82329 | 82343 | 15 |
| 2072 | 82344 | 82357 | 14 |
| 2073 | 82378 | 82407 | 30 |
| 2074 | 82406 | 82422 | 17 |
| 2075 | 82421 | 82443 | 23 |
| 2076 | 82446 | 82469 | 24 |
| 2077 | 82490 | 82507 | 18 |
| 2078 | 82502 | 82523 | 22 |
| 2079 | 82547 | 82576 | 30 |
| 2080 | 82590 | 82603 | 14 |
| 2081 | 82628 | 82647 | 20 |
| 2082 | 82650 | 82666 | 17 |
| 2083 | 82669 | 82683 | 15 |
| 2084 | 82685 | 82716 | 32 |
| 2085 | 82715 | 82736 | 22 |
| 2086 | 82760 | 82785 | 26 |
| 2087 | 82778 | 82791 | 14 |
| 2088 | 82780 | 82818 | 39 |
| 2089 | 82811 | 82825 | 15 |
| 2090 | 82821 | 82864 | 44 |
| 2091 | 82883 | 82915 | 33 |
| 2092 | 82919 | 82935 | 17 |
| 2093 | 82930 | 82946 | 17 |
| 2094 | 82937 | 82957 | 21 |
| 2095 | 82959 | 82972 | 14 |
| 2096 | 82974 | 83000 | 27 |
| 2097 | 83020 | 83036 | 17 |
| 2098 | 83038 | 83088 | 51 |
| 2099 | 83090 | 83115 | 26 |
| 2100 | 83120 | 83140 | 21 |
| 2101 | 83142 | 83155 | 14 |
| 2102 | 83160 | 83186 | 27 |
| 2103 | 83198 | 83215 | 18 |
| 2104 | 83227 | 83246 | 20 |
| 2105 | 83273 | 83339 | 67 |
| 2106 | 83341 | 83385 | 45 |
| 2107 | 83387 | 83400 | 14 |
| 2108 | 83413 | 83426 | 14 |
| 2109 | 83417 | 83449 | 33 |
| 2110 | 83486 | 83520 | 35 |
| 2111 | 83522 | 83565 | 44 |
| 2112 | 83567 | 83581 | 15 |
| 2113 | 83576 | 83670 | 95 |
| 2114 | 83681 | 83701 | 21 |
| 2115 | 83703 | 83716 | 14 |
| 2116 | 83733 | 83817 | 85 |
| 2117 | 83817 | 83830 | 14 |
| 2118 | 83832 | 83853 | 22 |
| 2119 | 83855 | 83871 | 17 |
| 2120 | 83886 | 83926 | 41 |
| 2121 | 83958 | 83974 | 17 |
| 2122 | 83976 | 83991 | 16 |
| 2123 | 83993 | 84031 | 39 |
| 2124 | 84033 | 84067 | 35 |
| 2125 | 84069 | 84102 | 34 |
| 2126 | 84104 | 84121 | 18 |
| 2127 | 84143 | 84233 | 91 |
| 2128 | 84249 | 84281 | 33 |
| 2129 | 84283 | 84403 | 121 |
| 2130 | 84404 | 84432 | 29 |
| 2131 | 84431 | 84444 | 14 |
| 2132 | 84434 | 84490 | 57 |
| 2133 | 84503 | 84520 | 18 |
| 2134 | 84522 | 84555 | 34 |
| 2135 | 84557 | 84572 | 16 |
| 2136 | 84574 | 84597 | 24 |
| 2137 | 84607 | 84626 | 20 |
| 2138 | 84650 | 84675 | 26 |

TABLE 1-continued

Regions of SEQ ID NO 1 which may be targeted using oligonucleotide of the invention

| Reg. A | Position in SEQ ID NO 1 from | to | Length |
|---|---|---|---|
| 2139 | 84677 | 84700 | 24 |
| 2140 | 84721 | 84753 | 33 |
| 2141 | 84755 | 84807 | 53 |
| 2142 | 84809 | 84826 | 18 |
| 2143 | 84831 | 84849 | 19 |
| 2144 | 84879 | 84893 | 15 |
| 2145 | 84895 | 84915 | 21 |
| 2146 | 84917 | 84961 | 45 |
| 2147 | 85234 | 85247 | 14 |
| 2148 | 85253 | 85267 | 15 |
| 2149 | 85256 | 85351 | 96 |
| 2150 | 85359 | 85374 | 16 |
| 2151 | 85363 | 85376 | 14 |
| 2152 | 85365 | 85381 | 17 |
| 2153 | 85380 | 85414 | 35 |
| 2154 | 85416 | 85454 | 39 |
| 2155 | 85456 | 85484 | 29 |
| 2156 | 85509 | 85545 | 37 |
| 2157 | 85535 | 85550 | 16 |
| 2158 | 85566 | 85584 | 19 |
| 2159 | 85586 | 85610 | 25 |
| 2160 | 85604 | 85627 | 24 |
| 2161 | 85628 | 85665 | 38 |
| 2162 | 85698 | 85723 | 26 |
| 2163 | 85713 | 85728 | 16 |
| 2164 | 85722 | 85735 | 14 |
| 2165 | 85770 | 85785 | 16 |
| 2166 | 85800 | 85813 | 14 |
| 2167 | 85875 | 85888 | 14 |
| 2168 | 85950 | 85963 | 14 |
| 2169 | 86097 | 86125 | 29 |
| 2170 | 86127 | 86142 | 16 |
| 2171 | 86175 | 86198 | 24 |
| 2172 | 86226 | 86242 | 17 |
| 2173 | 86237 | 86302 | 66 |
| 2174 | 86308 | 86327 | 20 |
| 2175 | 86321 | 86334 | 14 |
| 2176 | 86329 | 86382 | 54 |
| 2177 | 86384 | 86400 | 17 |
| 2178 | 86403 | 86417 | 15 |
| 2179 | 86414 | 86437 | 24 |
| 2180 | 86439 | 86455 | 17 |
| 2181 | 86461 | 86478 | 18 |
| 2182 | 86473 | 86487 | 15 |
| 2183 | 86480 | 86517 | 38 |
| 2184 | 86517 | 86531 | 15 |
| 2185 | 86565 | 86583 | 19 |
| 2186 | 86600 | 86632 | 33 |
| 2187 | 86634 | 86651 | 18 |
| 2188 | 86653 | 86678 | 26 |
| 2189 | 86697 | 86756 | 60 |
| 2190 | 86782 | 86796 | 15 |
| 2191 | 86786 | 86809 | 24 |
| 2192 | 86811 | 86855 | 45 |
| 2193 | 86857 | 86891 | 35 |
| 2194 | 86894 | 86908 | 15 |
| 2195 | 86916 | 86933 | 18 |
| 2196 | 86945 | 86959 | 15 |
| 2197 | 86951 | 86965 | 15 |
| 2198 | 86969 | 86990 | 22 |
| 2199 | 87017 | 87057 | 41 |
| 2200 | 87059 | 87073 | 15 |
| 2201 | 87062 | 87076 | 15 |
| 2202 | 87066 | 87089 | 24 |
| 2203 | 87097 | 87121 | 25 |
| 2204 | 87110 | 87134 | 25 |
| 2205 | 87130 | 87155 | 26 |
| 2206 | 87160 | 87194 | 35 |
| 2207 | 87185 | 87198 | 14 |
| 2208 | 87209 | 87260 | 52 |
| 2209 | 87257 | 87270 | 14 |
| 2210 | 87274 | 87287 | 14 |
| 2211 | 87276 | 87294 | 19 |
| 2212 | 87294 | 87328 | 35 |
| 2213 | 87317 | 87333 | 17 |
| 2214 | 87336 | 87360 | 25 |
| 2215 | 87368 | 87418 | 51 |
| 2216 | 87441 | 87460 | 20 |
| 2217 | 87462 | 87487 | 26 |
| 2218 | 87489 | 87518 | 30 |
| 2219 | 87520 | 87539 | 20 |
| 2220 | 87542 | 87570 | 29 |
| 2221 | 87572 | 87601 | 30 |
| 2222 | 87603 | 87644 | 42 |
| 2223 | 87642 | 87750 | 109 |
| 2224 | 87756 | 87776 | 21 |
| 2225 | 87778 | 87803 | 26 |
| 2226 | 87803 | 87837 | 35 |
| 2227 | 87872 | 87888 | 17 |
| 2228 | 87890 | 87917 | 28 |
| 2229 | 87949 | 87964 | 16 |
| 2230 | 87963 | 88008 | 46 |
| 2231 | 88010 | 88027 | 18 |
| 2232 | 88029 | 88046 | 18 |
| 2233 | 88048 | 88089 | 42 |
| 2234 | 88091 | 88108 | 18 |
| 2235 | 88110 | 88177 | 68 |
| 2236 | 88179 | 88192 | 14 |
| 2237 | 88194 | 88229 | 36 |
| 2238 | 88234 | 88259 | 26 |
| 2239 | 88261 | 88291 | 31 |
| 2240 | 88303 | 88328 | 26 |
| 2241 | 88328 | 88341 | 14 |
| 2242 | 88340 | 88354 | 15 |
| 2243 | 88356 | 88372 | 17 |
| 2244 | 88411 | 88446 | 36 |
| 2245 | 88448 | 88465 | 18 |
| 2246 | 88469 | 88511 | 43 |
| 2247 | 88518 | 88533 | 16 |
| 2248 | 88531 | 88557 | 27 |
| 2249 | 88547 | 88560 | 14 |
| 2250 | 88573 | 88593 | 21 |
| 2251 | 88597 | 88618 | 22 |
| 2252 | 88620 | 88690 | 71 |
| 2253 | 88692 | 88745 | 54 |
| 2254 | 88954 | 88973 | 20 |
| 2255 | 88988 | 89047 | 60 |
| 2256 | 89066 | 89091 | 26 |
| 2257 | 89098 | 89119 | 22 |
| 2258 | 89135 | 89149 | 15 |
| 2259 | 89151 | 89181 | 31 |
| 2260 | 89177 | 89193 | 17 |
| 2261 | 89223 | 89273 | 51 |
| 2262 | 89285 | 89300 | 16 |
| 2263 | 89315 | 89383 | 69 |
| 2264 | 89404 | 89442 | 39 |
| 2265 | 89444 | 89541 | 98 |
| 2266 | 89579 | 89639 | 61 |
| 2267 | 89660 | 89692 | 33 |
| 2268 | 89694 | 89741 | 48 |
| 2269 | 89773 | 89787 | 15 |
| 2270 | 89789 | 89817 | 29 |
| 2271 | 89826 | 89888 | 63 |
| 2272 | 89904 | 89922 | 19 |
| 2273 | 89937 | 89950 | 14 |
| 2274 | 89945 | 89958 | 14 |
| 2275 | 89956 | 89974 | 19 |
| 2276 | 89971 | 89985 | 15 |
| 2277 | 89979 | 89992 | 14 |
| 2278 | 89984 | 90000 | 17 |
| 2279 | 89999 | 90014 | 16 |
| 2280 | 90017 | 90041 | 25 |

TABLE 1-continued

Regions of SEQ ID NO 1 which may be targeted using oligonucleotide of the invention

| Reg. A | Position in SEQ ID NO 1 from | to | Length |
|---|---|---|---|
| 2281 | 90036 | 90049 | 14 |
| 2282 | 90077 | 90093 | 17 |
| 2283 | 90099 | 90128 | 30 |
| 2284 | 90130 | 90155 | 26 |
| 2285 | 90157 | 90200 | 44 |
| 2286 | 90225 | 90256 | 32 |
| 2287 | 90258 | 90293 | 36 |
| 2288 | 90305 | 90318 | 14 |
| 2289 | 90320 | 90352 | 33 |
| 2290 | 90356 | 90370 | 15 |
| 2291 | 90400 | 90421 | 22 |
| 2292 | 90423 | 90461 | 39 |
| 2293 | 90464 | 90507 | 44 |
| 2294 | 90509 | 90530 | 22 |
| 2295 | 90529 | 90542 | 14 |
| 2296 | 90531 | 90567 | 37 |
| 2297 | 90569 | 90612 | 44 |
| 2298 | 90614 | 90730 | 117 |
| 2299 | 90732 | 90758 | 27 |
| 2300 | 90760 | 90885 | 126 |
| 2301 | 90887 | 90918 | 32 |
| 2302 | 90920 | 90946 | 27 |
| 2303 | 90938 | 90955 | 18 |
| 2304 | 90960 | 90973 | 14 |
| 2305 | 90965 | 90981 | 17 |
| 2306 | 90973 | 91000 | 28 |
| 2307 | 90997 | 91011 | 15 |
| 2308 | 91002 | 91019 | 18 |
| 2309 | 91059 | 91140 | 82 |
| 2310 | 91142 | 91157 | 16 |
| 2311 | 91157 | 91194 | 38 |
| 2312 | 91196 | 91231 | 36 |
| 2313 | 91233 | 91251 | 19 |
| 2314 | 91253 | 91274 | 22 |
| 2315 | 91296 | 91310 | 15 |
| 2316 | 91335 | 91367 | 33 |
| 2317 | 91406 | 91442 | 37 |
| 2318 | 91447 | 91477 | 31 |
| 2319 | 91489 | 91509 | 21 |
| 2320 | 91520 | 91621 | 102 |
| 2321 | 91623 | 91674 | 52 |
| 2322 | 91680 | 91703 | 24 |
| 2323 | 91715 | 91731 | 17 |
| 2324 | 91733 | 91771 | 39 |
| 2325 | 91773 | 91788 | 16 |
| 2326 | 91790 | 91805 | 16 |
| 2327 | 91807 | 91823 | 17 |
| 2328 | 91825 | 91859 | 35 |
| 2329 | 91861 | 91900 | 40 |
| 2330 | 91907 | 91926 | 20 |
| 2331 | 91928 | 91943 | 16 |
| 2332 | 91950 | 91980 | 31 |
| 2333 | 91982 | 91996 | 15 |
| 2334 | 91998 | 92011 | 14 |
| 2335 | 92010 | 92027 | 18 |
| 2336 | 92027 | 92067 | 41 |
| 2337 | 92069 | 92126 | 58 |
| 2338 | 92128 | 92321 | 194 |
| 2339 | 92323 | 92540 | 218 |
| 2340 | 92542 | 92558 | 17 |
| 2341 | 92566 | 92684 | 119 |
| 2342 | 92686 | 92726 | 41 |
| 2343 | 92728 | 92837 | 110 |
| 2344 | 92839 | 93032 | 194 |
| 2345 | 93034 | 93094 | 61 |
| 2346 | 93100 | 93209 | 110 |
| 2347 | 93211 | 93254 | 44 |
| 2348 | 93256 | 93323 | 68 |
| 2349 | 93325 | 93448 | 124 |
| 2350 | 93459 | 93477 | 19 |
| 2351 | 93475 | 93497 | 23 |
| 2352 | 93509 | 93530 | 22 |
| 2353 | 93532 | 93566 | 35 |
| 2354 | 93568 | 93601 | 34 |
| 2355 | 93606 | 93646 | 41 |
| 2356 | 93668 | 93716 | 49 |
| 2357 | 93718 | 93742 | 25 |
| 2358 | 93744 | 93788 | 45 |
| 2359 | 93790 | 93808 | 19 |
| 2360 | 93811 | 93832 | 22 |
| 2361 | 93874 | 93901 | 28 |
| 2362 | 93904 | 93986 | 83 |
| 2363 | 94021 | 94036 | 16 |
| 2364 | 94038 | 94079 | 42 |
| 2365 | 94073 | 94086 | 14 |
| 2366 | 94097 | 94116 | 20 |
| 2367 | 94118 | 94141 | 24 |
| 2368 | 94140 | 94219 | 80 |
| 2369 | 94242 | 94257 | 16 |
| 2370 | 94264 | 94335 | 72 |
| 2371 | 94337 | 94356 | 20 |
| 2372 | 94358 | 94378 | 21 |
| 2373 | 94373 | 94386 | 14 |
| 2374 | 94384 | 94403 | 20 |
| 2375 | 94405 | 94422 | 18 |
| 2376 | 94453 | 94497 | 45 |
| 2377 | 94497 | 94558 | 62 |
| 2378 | 94560 | 94605 | 46 |
| 2379 | 94630 | 94724 | 95 |
| 2380 | 94739 | 94752 | 14 |
| 2381 | 94755 | 94786 | 32 |
| 2382 | 94800 | 94815 | 16 |
| 2383 | 94872 | 94901 | 30 |
| 2384 | 94903 | 94953 | 51 |
| 2385 | 94955 | 95060 | 106 |
| 2386 | 95070 | 95085 | 16 |
| 2387 | 95093 | 95110 | 18 |
| 2388 | 95135 | 95149 | 15 |
| 2389 | 95154 | 95168 | 15 |
| 2390 | 95170 | 95210 | 41 |
| 2391 | 95227 | 95257 | 31 |
| 2392 | 95302 | 95318 | 17 |
| 2393 | 95311 | 95356 | 46 |
| 2394 | 95359 | 95401 | 43 |
| 2395 | 95403 | 95453 | 51 |
| 2396 | 95450 | 95463 | 14 |
| 2397 | 95475 | 95491 | 17 |
| 2398 | 95503 | 95553 | 51 |
| 2399 | 95555 | 95569 | 15 |
| 2400 | 95583 | 95609 | 27 |
| 2401 | 95634 | 95668 | 35 |
| 2402 | 95718 | 95738 | 21 |
| 2403 | 95727 | 95740 | 14 |
| 2404 | 95836 | 95849 | 14 |
| 2405 | 95851 | 95872 | 22 |
| 2406 | 95874 | 95888 | 15 |
| 2407 | 95890 | 95910 | 21 |
| 2408 | 95912 | 95925 | 14 |
| 2409 | 95938 | 95969 | 32 |
| 2410 | 95973 | 95990 | 18 |
| 2411 | 95992 | 96066 | 75 |
| 2412 | 96073 | 96087 | 15 |
| 2413 | 96103 | 96120 | 18 |
| 2414 | 96122 | 96167 | 46 |
| 2415 | 96169 | 96182 | 14 |
| 2416 | 96183 | 96211 | 29 |
| 2417 | 96213 | 96234 | 22 |
| 2418 | 96246 | 96279 | 34 |
| 2419 | 96300 | 96334 | 35 |
| 2420 | 96358 | 96375 | 18 |
| 2421 | 96377 | 96398 | 22 |
| 2422 | 96424 | 96467 | 44 |

TABLE 1-continued

Regions of SEQ ID NO 1 which may be targeted using oligonucleotide of the invention

| Reg. A | Position in SEQ ID NO 1 from | to | Length |
|---|---|---|---|
| 2423 | 96496 | 96518 | 23 |
| 2424 | 96520 | 96535 | 16 |
| 2425 | 96540 | 96566 | 27 |
| 2426 | 96572 | 96592 | 21 |
| 2427 | 96604 | 96646 | 43 |
| 2428 | 96642 | 96655 | 14 |
| 2429 | 96648 | 96667 | 20 |
| 2430 | 96681 | 96728 | 48 |
| 2431 | 96730 | 96781 | 52 |
| 2432 | 96804 | 96829 | 26 |
| 2433 | 96831 | 96879 | 49 |
| 2434 | 96887 | 96916 | 30 |
| 2435 | 96928 | 96944 | 17 |
| 2436 | 96946 | 96959 | 14 |
| 2437 | 96970 | 96990 | 21 |
| 2438 | 96992 | 97021 | 30 |
| 2439 | 97023 | 97037 | 15 |
| 2440 | 97039 | 97073 | 35 |
| 2441 | 97075 | 97366 | 292 |
| 2442 | 97368 | 97393 | 26 |
| 2443 | 97420 | 97466 | 47 |
| 2444 | 97469 | 97507 | 39 |
| 2445 | 97513 | 97529 | 17 |
| 2446 | 97531 | 97583 | 53 |
| 2447 | 97585 | 97600 | 16 |
| 2448 | 97602 | 97631 | 30 |
| 2449 | 97633 | 97683 | 51 |
| 2450 | 97685 | 97703 | 19 |
| 2451 | 97705 | 97742 | 38 |
| 2452 | 97787 | 97803 | 17 |
| 2453 | 97805 | 97822 | 18 |
| 2454 | 97824 | 97876 | 53 |
| 2455 | 97878 | 97921 | 44 |
| 2456 | 97923 | 97943 | 21 |
| 2457 | 97945 | 97963 | 19 |
| 2458 | 97965 | 97994 | 30 |
| 2459 | 97995 | 98011 | 17 |
| 2460 | 98014 | 98044 | 31 |
| 2461 | 98039 | 98061 | 23 |
| 2462 | 98055 | 98076 | 22 |
| 2463 | 98077 | 98090 | 14 |
| 2464 | 98079 | 98092 | 14 |
| 2465 | 98085 | 98098 | 14 |
| 2466 | 98100 | 98115 | 16 |
| 2467 | 98113 | 98145 | 33 |
| 2468 | 98142 | 98160 | 19 |
| 2469 | 98162 | 98180 | 19 |
| 2470 | 98188 | 98219 | 32 |
| 2471 | 98215 | 98237 | 23 |
| 2472 | 98227 | 98240 | 14 |
| 2473 | 98232 | 98255 | 24 |
| 2474 | 98255 | 98268 | 14 |
| 2475 | 98264 | 98287 | 24 |
| 2476 | 98292 | 98326 | 35 |
| 2477 | 98373 | 98397 | 25 |
| 2478 | 98399 | 98428 | 30 |
| 2479 | 98442 | 98461 | 20 |
| 2480 | 98480 | 98501 | 22 |
| 2481 | 98499 | 98520 | 22 |
| 2482 | 98524 | 98538 | 15 |
| 2483 | 98537 | 98550 | 14 |
| 2484 | 98545 | 98585 | 41 |
| 2485 | 98595 | 98610 | 16 |
| 2486 | 98599 | 98624 | 26 |
| 2487 | 98644 | 98668 | 25 |
| 2488 | 98678 | 98704 | 27 |
| 2489 | 98703 | 98718 | 16 |
| 2490 | 98736 | 98754 | 19 |
| 2491 | 98778 | 98794 | 17 |
| 2492 | 98802 | 98821 | 20 |
| 2493 | 98845 | 98876 | 32 |
| 2494 | 98878 | 98900 | 23 |
| 2495 | 98900 | 98972 | 73 |
| 2496 | 98961 | 98976 | 16 |
| 2497 | 98974 | 98998 | 25 |
| 2498 | 99011 | 99029 | 19 |
| 2499 | 99033 | 99065 | 33 |
| 2500 | 99067 | 99107 | 41 |
| 2501 | 99151 | 99186 | 36 |
| 2502 | 99188 | 99219 | 32 |
| 2503 | 99222 | 99245 | 24 |
| 2504 | 99254 | 99276 | 23 |
| 2505 | 99288 | 99312 | 25 |
| 2506 | 99314 | 99338 | 25 |
| 2507 | 99367 | 99430 | 64 |
| 2508 | 99444 | 99491 | 48 |
| 2509 | 99496 | 99554 | 59 |
| 2510 | 99570 | 99585 | 16 |
| 2511 | 99587 | 99618 | 32 |
| 2512 | 99620 | 99669 | 50 |
| 2513 | 99679 | 99710 | 32 |
| 2514 | 99720 | 99748 | 29 |
| 2515 | 99750 | 99763 | 14 |
| 2516 | 99768 | 99805 | 38 |
| 2517 | 99818 | 99841 | 24 |
| 2518 | 99855 | 99879 | 25 |
| 2519 | 99881 | 99900 | 20 |
| 2520 | 99902 | 99932 | 31 |
| 2521 | 99934 | 99954 | 21 |
| 2522 | 99959 | 100011 | 53 |
| 2523 | 100011 | 100037 | 27 |
| 2524 | 100057 | 100071 | 15 |
| 2525 | 100073 | 100102 | 30 |
| 2526 | 100104 | 100118 | 15 |
| 2527 | 100131 | 100186 | 56 |
| 2528 | 100188 | 100201 | 14 |
| 2529 | 100194 | 100212 | 19 |
| 2530 | 100214 | 100277 | 64 |
| 2531 | 100279 | 100303 | 25 |
| 2532 | 100309 | 100355 | 47 |
| 2533 | 100349 | 100386 | 38 |
| 2534 | 100379 | 100393 | 15 |
| 2535 | 100388 | 100401 | 14 |
| 2536 | 100403 | 100423 | 21 |
| 2537 | 100452 | 100473 | 22 |
| 2538 | 100508 | 100542 | 35 |
| 2539 | 100548 | 100580 | 33 |
| 2540 | 100582 | 100612 | 31 |
| 2541 | 100614 | 100652 | 39 |
| 2542 | 100695 | 100714 | 20 |
| 2543 | 100736 | 100749 | 14 |
| 2544 | 100751 | 100790 | 40 |
| 2545 | 100808 | 100842 | 35 |
| 2546 | 100844 | 100860 | 17 |
| 2547 | 100862 | 100930 | 69 |
| 2548 | 100939 | 100953 | 15 |
| 2549 | 100955 | 100971 | 17 |
| 2550 | 100973 | 101003 | 31 |
| 2551 | 101021 | 101048 | 28 |
| 2552 | 101057 | 101093 | 37 |
| 2553 | 101109 | 101148 | 40 |
| 2554 | 101145 | 101189 | 45 |
| 2555 | 101194 | 101208 | 15 |
| 2556 | 101210 | 101244 | 35 |
| 2557 | 101256 | 101271 | 16 |
| 2558 | 101277 | 101300 | 24 |
| 2559 | 101310 | 101327 | 18 |
| 2560 | 101329 | 101345 | 17 |
| 2561 | 101374 | 101397 | 24 |
| 2562 | 101409 | 101426 | 18 |
| 2563 | 101453 | 101466 | 14 |
| 2564 | 101474 | 101487 | 14 |

TABLE 1-continued

Regions of SEQ ID NO 1 which may be targeted using oligonucleotide of the invention

| Reg. A | Position in SEQ ID NO 1 from | to | Length |
|---|---|---|---|
| 2565 | 101481 | 101515 | 35 |
| 2566 | 101518 | 101541 | 24 |
| 2567 | 101542 | 101560 | 19 |
| 2568 | 101554 | 101591 | 38 |
| 2569 | 101593 | 101609 | 17 |
| 2570 | 101635 | 101695 | 61 |
| 2571 | 101707 | 101746 | 40 |
| 2572 | 101748 | 101763 | 16 |
| 2573 | 101774 | 101810 | 37 |
| 2574 | 101812 | 101828 | 17 |
| 2575 | 101819 | 101835 | 17 |
| 2576 | 101829 | 101842 | 14 |
| 2577 | 101842 | 101855 | 14 |
| 2578 | 101857 | 101878 | 22 |
| 2579 | 101880 | 101943 | 64 |
| 2580 | 101947 | 101981 | 35 |
| 2581 | 101988 | 102009 | 22 |
| 2582 | 102022 | 102066 | 45 |
| 2583 | 102068 | 102084 | 17 |
| 2584 | 102100 | 102113 | 14 |
| 2585 | 102115 | 102130 | 16 |
| 2586 | 102132 | 102145 | 14 |
| 2587 | 102192 | 102241 | 50 |
| 2588 | 102269 | 102285 | 17 |
| 2589 | 102312 | 102327 | 16 |
| 2590 | 102357 | 102392 | 36 |
| 2591 | 102407 | 102428 | 22 |
| 2592 | 102430 | 102444 | 15 |
| 2593 | 102460 | 102485 | 26 |
| 2594 | 102487 | 102508 | 22 |
| 2595 | 102532 | 102573 | 42 |
| 2596 | 102595 | 102642 | 48 |
| 2597 | 102653 | 102694 | 42 |
| 2598 | 102701 | 102718 | 18 |
| 2599 | 102720 | 102734 | 15 |
| 2600 | 102736 | 102757 | 22 |
| 2601 | 102799 | 102836 | 38 |
| 2602 | 102847 | 102882 | 36 |
| 2603 | 102890 | 102927 | 38 |
| 2604 | 102938 | 102971 | 34 |
| 2605 | 102982 | 103019 | 38 |
| 2606 | 103014 | 103027 | 14 |
| 2607 | 103027 | 103054 | 28 |
| 2608 | 103065 | 103088 | 24 |
| 2609 | 103090 | 103108 | 19 |
| 2610 | 103098 | 103112 | 15 |
| 2611 | 103117 | 103138 | 22 |
| 2612 | 103152 | 103170 | 19 |
| 2613 | 103174 | 103204 | 31 |
| 2614 | 103206 | 103234 | 29 |
| 2615 | 103240 | 103268 | 29 |
| 2616 | 103286 | 103325 | 40 |
| 2617 | 103327 | 103347 | 21 |
| 2618 | 103349 | 103384 | 36 |
| 2619 | 103386 | 103405 | 20 |
| 2620 | 103422 | 103449 | 28 |
| 2621 | 103451 | 103493 | 43 |
| 2622 | 103495 | 103509 | 15 |
| 2623 | 103511 | 103560 | 50 |
| 2624 | 103565 | 103582 | 18 |
| 2625 | 103585 | 103607 | 23 |
| 2626 | 103631 | 103645 | 15 |
| 2627 | 103653 | 103684 | 32 |
| 2628 | 103683 | 103696 | 14 |
| 2629 | 103691 | 103733 | 43 |
| 2630 | 103738 | 103762 | 25 |
| 2631 | 103752 | 103765 | 14 |
| 2632 | 103755 | 103768 | 14 |
| 2633 | 103758 | 103771 | 14 |
| 2634 | 103790 | 103814 | 25 |
| 2635 | 103803 | 103816 | 14 |
| 2636 | 103830 | 103865 | 36 |
| 2637 | 103900 | 103923 | 24 |
| 2638 | 103912 | 103933 | 22 |
| 2639 | 103945 | 103964 | 20 |
| 2640 | 103990 | 104005 | 16 |
| 2641 | 104024 | 104055 | 32 |
| 2642 | 104058 | 104077 | 20 |
| 2643 | 104086 | 104099 | 14 |
| 2644 | 104095 | 104122 | 28 |
| 2645 | 104124 | 104146 | 23 |
| 2646 | 104148 | 104168 | 21 |
| 2647 | 104162 | 104176 | 15 |
| 2648 | 104173 | 104187 | 15 |
| 2649 | 104201 | 104241 | 41 |
| 2650 | 104234 | 104266 | 33 |
| 2651 | 104268 | 104286 | 19 |
| 2652 | 104288 | 104302 | 15 |
| 2653 | 104304 | 104335 | 32 |
| 2654 | 104340 | 104354 | 15 |
| 2655 | 104356 | 104373 | 18 |
| 2656 | 104375 | 104391 | 17 |
| 2657 | 104393 | 104417 | 25 |
| 2658 | 104426 | 104439 | 14 |
| 2659 | 104448 | 104478 | 31 |
| 2660 | 104480 | 104504 | 25 |
| 2661 | 104519 | 104546 | 28 |
| 2662 | 104549 | 104580 | 32 |
| 2663 | 104604 | 104620 | 17 |
| 2664 | 104620 | 104646 | 27 |
| 2665 | 104654 | 104673 | 20 |
| 2666 | 104675 | 104691 | 17 |
| 2667 | 104689 | 104776 | 88 |
| 2668 | 104829 | 104842 | 14 |
| 2669 | 104838 | 104852 | 15 |
| 2670 | 104934 | 104952 | 19 |
| 2671 | 104956 | 104987 | 32 |
| 2672 | 104993 | 105045 | 53 |
| 2673 | 105041 | 105055 | 15 |
| 2674 | 105047 | 105078 | 32 |
| 2675 | 105090 | 105107 | 18 |
| 2676 | 105101 | 105115 | 15 |
| 2677 | 105109 | 105137 | 29 |
| 2678 | 105149 | 105167 | 19 |
| 2679 | 105163 | 105176 | 14 |
| 2680 | 105185 | 105237 | 53 |
| 2681 | 105230 | 105243 | 14 |
| 2682 | 105233 | 105250 | 18 |
| 2683 | 105260 | 105286 | 27 |
| 2684 | 105288 | 105340 | 53 |
| 2685 | 105345 | 105370 | 26 |
| 2686 | 105372 | 105402 | 31 |
| 2687 | 105441 | 105458 | 18 |
| 2688 | 105460 | 105521 | 62 |
| 2689 | 105526 | 105541 | 16 |
| 2690 | 105543 | 105560 | 18 |
| 2691 | 105562 | 105575 | 14 |
| 2692 | 105582 | 105606 | 25 |
| 2693 | 105616 | 105671 | 56 |
| 2694 | 105677 | 105704 | 28 |
| 2695 | 105703 | 105725 | 23 |
| 2696 | 105746 | 105759 | 14 |
| 2697 | 105750 | 105765 | 16 |
| 2698 | 105776 | 105796 | 21 |
| 2699 | 105798 | 105824 | 27 |
| 2700 | 105827 | 105907 | 81 |
| 2701 | 105924 | 105939 | 16 |
| 2702 | 105941 | 105963 | 23 |
| 2703 | 105990 | 106014 | 25 |
| 2704 | 106017 | 106048 | 32 |
| 2705 | 106039 | 106072 | 34 |
| 2706 | 106061 | 106074 | 14 |

TABLE 1-continued

Regions of SEQ ID NO 1 which may be targeted using oligonucleotide of the invention

| Reg. A | Position in SEQ ID NO 1 from | to | Length |
|---|---|---|---|
| 2707 | 106073 | 106102 | 30 |
| 2708 | 106092 | 106107 | 16 |
| 2709 | 106114 | 106159 | 46 |
| 2710 | 106161 | 106180 | 20 |
| 2711 | 106197 | 106243 | 47 |
| 2712 | 106237 | 106250 | 14 |
| 2713 | 106243 | 106256 | 14 |
| 2714 | 106247 | 106267 | 21 |
| 2715 | 106273 | 106333 | 61 |
| 2716 | 106335 | 106367 | 33 |
| 2717 | 106369 | 106417 | 49 |
| 2718 | 106419 | 106471 | 53 |
| 2719 | 106486 | 106523 | 38 |
| 2720 | 106525 | 106538 | 14 |
| 2721 | 106552 | 106572 | 21 |
| 2722 | 106584 | 106598 | 15 |
| 2723 | 106609 | 106696 | 88 |
| 2724 | 106698 | 106723 | 26 |
| 2725 | 106725 | 106740 | 16 |
| 2726 | 106743 | 106781 | 39 |
| 2727 | 106783 | 106811 | 29 |
| 2728 | 106826 | 106866 | 41 |
| 2729 | 106875 | 106902 | 28 |
| 2730 | 106916 | 106935 | 20 |
| 2731 | 106942 | 106960 | 19 |
| 2732 | 106991 | 107010 | 20 |
| 2733 | 107019 | 107038 | 20 |
| 2734 | 107040 | 107072 | 33 |
| 2735 | 107079 | 107094 | 16 |
| 2736 | 107087 | 107101 | 15 |
| 2737 | 107090 | 107109 | 20 |
| 2738 | 107113 | 107127 | 15 |
| 2739 | 107129 | 107143 | 15 |
| 2740 | 107154 | 107172 | 19 |
| 2741 | 107174 | 107198 | 25 |
| 2742 | 107210 | 107226 | 17 |
| 2743 | 107226 | 107239 | 14 |
| 2744 | 107237 | 107274 | 38 |
| 2745 | 107296 | 107356 | 61 |
| 2746 | 107358 | 107381 | 24 |
| 2747 | 107383 | 107415 | 33 |
| 2748 | 107417 | 107433 | 17 |
| 2749 | 107435 | 107455 | 21 |
| 2750 | 107457 | 107508 | 52 |
| 2751 | 107510 | 107525 | 16 |
| 2752 | 107527 | 107546 | 20 |
| 2753 | 107559 | 107573 | 15 |
| 2754 | 107586 | 107617 | 32 |
| 2755 | 107643 | 107689 | 47 |
| 2756 | 107694 | 107716 | 23 |
| 2757 | 107744 | 107792 | 49 |
| 2758 | 107790 | 107832 | 43 |
| 2759 | 107834 | 107860 | 27 |
| 2760 | 107864 | 107896 | 33 |
| 2761 | 107898 | 107912 | 15 |
| 2762 | 107914 | 107953 | 40 |
| 2763 | 107967 | 107992 | 26 |
| 2764 | 107994 | 108008 | 15 |
| 2765 | 108010 | 108038 | 29 |
| 2766 | 108065 | 108084 | 20 |
| 2767 | 108113 | 108215 | 103 |
| 2768 | 108220 | 108249 | 30 |
| 2769 | 108253 | 108281 | 29 |
| 2770 | 108283 | 108304 | 22 |
| 2771 | 108317 | 108359 | 43 |
| 2772 | 108361 | 108375 | 15 |
| 2773 | 108386 | 108402 | 17 |
| 2774 | 108421 | 108440 | 20 |
| 2775 | 108538 | 108551 | 14 |
| 2776 | 108561 | 108575 | 15 |
| 2777 | 108577 | 108616 | 40 |
| 2778 | 108618 | 108665 | 48 |
| 2779 | 108677 | 108707 | 31 |
| 2780 | 108735 | 108768 | 34 |
| 2781 | 108762 | 108777 | 16 |
| 2782 | 108780 | 108824 | 45 |
| 2783 | 108842 | 108885 | 44 |
| 2784 | 108907 | 108970 | 64 |
| 2785 | 108983 | 109019 | 37 |
| 2786 | 109021 | 109053 | 33 |
| 2787 | 109055 | 109068 | 14 |
| 2788 | 109070 | 109099 | 30 |
| 2789 | 109097 | 109122 | 26 |
| 2790 | 109113 | 109132 | 20 |
| 2791 | 109125 | 109165 | 41 |
| 2792 | 109167 | 109181 | 15 |
| 2793 | 109183 | 109200 | 18 |
| 2794 | 109214 | 109248 | 35 |
| 2795 | 109256 | 109277 | 22 |
| 2796 | 109281 | 109298 | 18 |
| 2797 | 109298 | 109311 | 14 |
| 2798 | 109300 | 109318 | 19 |
| 2799 | 109324 | 109374 | 51 |
| 2800 | 109377 | 109397 | 21 |
| 2801 | 109399 | 109437 | 39 |
| 2802 | 109446 | 109461 | 16 |
| 2803 | 109463 | 109476 | 14 |
| 2804 | 109472 | 109485 | 14 |
| 2805 | 109478 | 109514 | 37 |
| 2806 | 109516 | 109540 | 25 |
| 2807 | 109556 | 109588 | 33 |
| 2808 | 109601 | 109644 | 44 |
| 2809 | 109661 | 109681 | 21 |
| 2810 | 109683 | 109709 | 27 |
| 2811 | 109707 | 109737 | 31 |
| 2812 | 109739 | 109754 | 16 |
| 2813 | 109754 | 109768 | 15 |
| 2814 | 109770 | 109798 | 29 |
| 2815 | 109810 | 109829 | 20 |
| 2816 | 109859 | 109877 | 19 |
| 2817 | 109879 | 109934 | 56 |
| 2818 | 109955 | 109975 | 21 |
| 2819 | 109975 | 109988 | 14 |
| 2820 | 109994 | 110096 | 103 |
| 2821 | 110103 | 110129 | 27 |
| 2822 | 110131 | 110152 | 22 |
| 2823 | 110153 | 110173 | 21 |
| 2824 | 110175 | 110195 | 21 |
| 2825 | 110192 | 110226 | 35 |
| 2826 | 110297 | 110312 | 16 |
| 2827 | 110301 | 110314 | 14 |
| 2828 | 110308 | 110333 | 26 |
| 2829 | 110335 | 110351 | 17 |
| 2830 | 110353 | 110368 | 16 |
| 2831 | 110376 | 110401 | 26 |
| 2832 | 110418 | 110462 | 45 |
| 2833 | 110464 | 110481 | 18 |
| 2834 | 110531 | 110558 | 28 |
| 2835 | 110571 | 110590 | 20 |
| 2836 | 110599 | 110639 | 41 |
| 2837 | 110630 | 110643 | 14 |
| 2838 | 110641 | 110661 | 21 |
| 2839 | 110668 | 110681 | 14 |
| 2840 | 110683 | 110709 | 27 |
| 2841 | 110717 | 110798 | 82 |
| 2842 | 110804 | 110849 | 46 |
| 2843 | 110853 | 110890 | 38 |
| 2844 | 110928 | 110966 | 39 |
| 2845 | 110971 | 111003 | 33 |
| 2846 | 111000 | 111013 | 14 |
| 2847 | 111015 | 111033 | 19 |
| 2848 | 111035 | 111050 | 16 |

TABLE 1-continued

Regions of SEQ ID NO 1 which may be targeted using oligonucleotide of the invention

| Reg. A | Position in SEQ ID NO 1 from | to | Length |
|---|---|---|---|
| 2849 | 111062 | 111094 | 33 |
| 2850 | 111092 | 111105 | 14 |
| 2851 | 111107 | 111140 | 34 |
| 2852 | 111161 | 111203 | 43 |
| 2853 | 111209 | 111223 | 15 |
| 2854 | 111224 | 111280 | 57 |
| 2855 | 111275 | 111290 | 16 |
| 2856 | 111283 | 111303 | 21 |
| 2857 | 111305 | 111320 | 16 |
| 2858 | 111311 | 111347 | 37 |
| 2859 | 111355 | 111368 | 14 |
| 2860 | 111357 | 111371 | 15 |
| 2861 | 111360 | 111381 | 22 |
| 2862 | 111373 | 111421 | 49 |
| 2863 | 111412 | 111426 | 15 |
| 2864 | 111451 | 111468 | 18 |
| 2865 | 111467 | 111480 | 14 |
| 2866 | 111482 | 111496 | 15 |
| 2867 | 111486 | 111500 | 15 |
| 2868 | 111497 | 111510 | 14 |
| 2869 | 111531 | 111564 | 34 |
| 2870 | 111580 | 111606 | 27 |
| 2871 | 111616 | 111637 | 22 |
| 2872 | 111658 | 111671 | 14 |
| 2873 | 111674 | 111688 | 15 |
| 2874 | 111692 | 111710 | 19 |
| 2875 | 111712 | 111725 | 14 |
| 2876 | 111727 | 111761 | 35 |
| 2877 | 111781 | 111804 | 24 |
| 2878 | 111811 | 111828 | 18 |
| 2879 | 111831 | 111849 | 19 |
| 2880 | 111856 | 111871 | 16 |
| 2881 | 111901 | 111917 | 17 |
| 2882 | 111919 | 111940 | 22 |
| 2883 | 111942 | 111987 | 46 |
| 2884 | 111984 | 112002 | 19 |
| 2885 | 112004 | 112069 | 66 |
| 2886 | 112070 | 112091 | 22 |
| 2887 | 112093 | 112116 | 24 |
| 2888 | 112118 | 112132 | 15 |
| 2889 | 112139 | 112170 | 32 |
| 2890 | 112180 | 112196 | 17 |
| 2891 | 112204 | 112223 | 20 |
| 2892 | 112236 | 112283 | 48 |
| 2893 | 112329 | 112343 | 15 |
| 2894 | 112345 | 112383 | 39 |
| 2895 | 112385 | 112401 | 17 |
| 2896 | 112404 | 112423 | 20 |
| 2897 | 112463 | 112477 | 15 |
| 2898 | 112485 | 112547 | 63 |
| 2899 | 112563 | 112581 | 19 |
| 2900 | 112583 | 112597 | 15 |
| 2901 | 112607 | 112638 | 32 |
| 2902 | 112640 | 112664 | 25 |
| 2903 | 112683 | 112721 | 39 |
| 2904 | 112730 | 112759 | 30 |
| 2905 | 112773 | 112811 | 39 |
| 2906 | 112811 | 112825 | 15 |
| 2907 | 112828 | 112862 | 35 |
| 2908 | 112882 | 112912 | 31 |
| 2909 | 112914 | 112967 | 54 |
| 2910 | 112968 | 112982 | 15 |
| 2911 | 112984 | 113016 | 33 |
| 2912 | 113044 | 113064 | 21 |
| 2913 | 113074 | 113097 | 24 |
| 2914 | 113111 | 113153 | 43 |
| 2915 | 113169 | 113194 | 26 |
| 2916 | 113198 | 113212 | 15 |
| 2917 | 113214 | 113230 | 17 |
| 2918 | 113232 | 113263 | 32 |
| 2919 | 113265 | 113284 | 20 |
| 2920 | 113306 | 113328 | 23 |
| 2921 | 113330 | 113355 | 26 |
| 2922 | 113357 | 113371 | 15 |
| 2923 | 113404 | 113422 | 19 |
| 2924 | 113421 | 113489 | 69 |
| 2925 | 113533 | 113559 | 27 |
| 2926 | 113561 | 113574 | 14 |
| 2927 | 113595 | 113616 | 22 |
| 2928 | 113648 | 113700 | 53 |
| 2929 | 113702 | 113739 | 38 |
| 2930 | 113762 | 113823 | 62 |
| 2931 | 113825 | 113960 | 136 |
| 2932 | 113962 | 114015 | 54 |
| 2933 | 114017 | 114048 | 32 |
| 2934 | 114045 | 114124 | 80 |
| 2935 | 114151 | 114170 | 20 |
| 2936 | 114182 | 114218 | 37 |
| 2937 | 114230 | 114270 | 41 |
| 2938 | 114272 | 114292 | 21 |
| 2939 | 114296 | 114339 | 44 |
| 2940 | 114354 | 114433 | 80 |
| 2941 | 114440 | 114457 | 18 |
| 2942 | 114459 | 114484 | 26 |
| 2943 | 114478 | 114536 | 59 |
| 2944 | 114538 | 114559 | 22 |
| 2945 | 114567 | 114592 | 26 |
| 2946 | 114594 | 114610 | 17 |
| 2947 | 114612 | 114652 | 41 |
| 2948 | 114681 | 114752 | 72 |
| 2949 | 114775 | 114805 | 31 |
| 2950 | 114803 | 114816 | 14 |
| 2951 | 114807 | 114821 | 15 |
| 2952 | 114823 | 114847 | 25 |
| 2953 | 114868 | 114912 | 45 |
| 2954 | 114947 | 114961 | 15 |
| 2955 | 114974 | 114997 | 24 |
| 2956 | 115001 | 115015 | 15 |
| 2957 | 115004 | 115017 | 14 |
| 2958 | 115019 | 115069 | 51 |
| 2959 | 115060 | 115073 | 14 |
| 2960 | 115072 | 115085 | 14 |
| 2961 | 115087 | 115100 | 14 |
| 2962 | 115102 | 115124 | 23 |
| 2963 | 115132 | 115151 | 20 |
| 2964 | 115154 | 115168 | 15 |
| 2965 | 115188 | 115208 | 21 |
| 2966 | 115219 | 115256 | 38 |
| 2967 | 115258 | 115283 | 26 |
| 2968 | 115285 | 115300 | 16 |
| 2969 | 115331 | 115353 | 23 |
| 2970 | 115355 | 115372 | 18 |
| 2971 | 115380 | 115397 | 18 |
| 2972 | 115399 | 115412 | 14 |
| 2973 | 115426 | 115475 | 50 |
| 2974 | 115496 | 115510 | 15 |
| 2975 | 115521 | 115545 | 25 |
| 2976 | 115555 | 115580 | 26 |
| 2977 | 115582 | 115600 | 19 |
| 2978 | 115602 | 115621 | 20 |
| 2979 | 115653 | 115677 | 25 |
| 2980 | 115692 | 115720 | 29 |
| 2981 | 115722 | 115738 | 17 |
| 2982 | 115769 | 115783 | 15 |
| 2983 | 115792 | 115808 | 17 |
| 2984 | 115819 | 115837 | 19 |
| 2985 | 115846 | 115878 | 33 |
| 2986 | 115888 | 115901 | 14 |
| 2987 | 115916 | 115932 | 17 |
| 2988 | 115943 | 115956 | 14 |
| 2989 | 115967 | 115993 | 27 |
| 2990 | 115996 | 116014 | 19 |

TABLE 1-continued

Regions of SEQ ID NO 1 which may be targeted using oligonucleotide of the invention

| Reg. A | Position in SEQ ID NO 1 from | to | Length |
|---|---|---|---|
| 2991 | 116027 | 116045 | 19 |
| 2992 | 116105 | 116127 | 23 |
| 2993 | 116126 | 116139 | 14 |
| 2994 | 116141 | 116158 | 18 |
| 2995 | 116171 | 116186 | 16 |
| 2996 | 116194 | 116208 | 15 |
| 2997 | 116257 | 116279 | 23 |
| 2998 | 116318 | 116373 | 56 |
| 2999 | 116375 | 116437 | 63 |
| 3000 | 116439 | 116454 | 16 |
| 3001 | 116456 | 116496 | 41 |
| 3002 | 116500 | 116532 | 33 |
| 3003 | 116534 | 116554 | 21 |
| 3004 | 116556 | 116573 | 18 |
| 3005 | 116575 | 116592 | 18 |
| 3006 | 116596 | 116615 | 20 |
| 3007 | 116617 | 116650 | 34 |
| 3008 | 116650 | 116664 | 15 |
| 3009 | 116666 | 116694 | 29 |
| 3010 | 116775 | 116792 | 18 |
| 3011 | 116794 | 116811 | 18 |
| 3012 | 116813 | 116838 | 26 |
| 3013 | 116840 | 116872 | 33 |
| 3014 | 116890 | 116911 | 22 |
| 3015 | 116921 | 116948 | 28 |
| 3016 | 116952 | 116988 | 37 |
| 3017 | 116990 | 117006 | 17 |
| 3018 | 117008 | 117036 | 29 |
| 3019 | 117059 | 117133 | 75 |
| 3020 | 117187 | 117207 | 21 |
| 3021 | 117204 | 117217 | 14 |
| 3022 | 117209 | 117237 | 29 |
| 3023 | 117239 | 117252 | 14 |
| 3024 | 117255 | 117275 | 21 |
| 3025 | 117277 | 117300 | 24 |
| 3026 | 117337 | 117371 | 35 |
| 3027 | 117373 | 117416 | 44 |
| 3028 | 117418 | 117450 | 33 |
| 3029 | 117456 | 117507 | 52 |
| 3030 | 117518 | 117532 | 15 |
| 3031 | 117534 | 117590 | 57 |
| 3032 | 117582 | 117604 | 23 |
| 3033 | 117593 | 117617 | 25 |
| 3034 | 117621 | 117648 | 28 |
| 3035 | 117640 | 117662 | 23 |
| 3036 | 117664 | 117688 | 25 |
| 3037 | 117690 | 117711 | 22 |
| 3038 | 117728 | 117743 | 16 |
| 3039 | 117747 | 117781 | 35 |
| 3040 | 117784 | 117801 | 18 |
| 3041 | 117792 | 117822 | 31 |
| 3042 | 117824 | 117842 | 19 |
| 3043 | 117850 | 117869 | 20 |
| 3044 | 117890 | 117940 | 51 |
| 3045 | 117936 | 117968 | 33 |
| 3046 | 117970 | 117990 | 21 |
| 3047 | 117989 | 118034 | 46 |
| 3048 | 118034 | 118057 | 24 |
| 3049 | 118061 | 118083 | 23 |
| 3050 | 118086 | 118122 | 37 |
| 3051 | 118122 | 118182 | 61 |
| 3052 | 118172 | 118186 | 15 |
| 3053 | 118197 | 118211 | 15 |
| 3054 | 118216 | 118275 | 60 |
| 3055 | 118291 | 118316 | 26 |
| 3056 | 118318 | 118354 | 37 |
| 3057 | 118373 | 118388 | 16 |
| 3058 | 118391 | 118405 | 15 |
| 3059 | 118407 | 118423 | 17 |
| 3060 | 118425 | 118456 | 32 |
| 3061 | 118465 | 118492 | 28 |
| 3062 | 118498 | 118521 | 24 |
| 3063 | 118533 | 118551 | 19 |
| 3064 | 118553 | 118581 | 29 |
| 3065 | 118587 | 118617 | 31 |
| 3066 | 118620 | 118679 | 60 |
| 3067 | 118687 | 118716 | 30 |
| 3068 | 118731 | 118771 | 41 |
| 3069 | 118779 | 118805 | 27 |
| 3070 | 118816 | 118830 | 15 |
| 3071 | 118832 | 118895 | 64 |
| 3072 | 118910 | 119065 | 156 |
| 3073 | 119067 | 119081 | 15 |
| 3074 | 119095 | 119140 | 46 |
| 3075 | 119170 | 119205 | 36 |
| 3076 | 119210 | 119232 | 23 |
| 3077 | 119230 | 119246 | 17 |
| 3078 | 119236 | 119252 | 17 |
| 3079 | 119255 | 119274 | 20 |
| 3080 | 119271 | 119284 | 14 |
| 3081 | 119290 | 119307 | 18 |
| 3082 | 119320 | 119335 | 16 |
| 3083 | 119357 | 119463 | 107 |
| 3084 | 119465 | 119483 | 19 |
| 3085 | 119485 | 119535 | 51 |
| 3086 | 119550 | 119571 | 22 |
| 3087 | 119577 | 119608 | 32 |
| 3088 | 119610 | 119646 | 37 |
| 3089 | 119648 | 119688 | 41 |
| 3090 | 119713 | 119752 | 40 |
| 3091 | 119743 | 119784 | 42 |
| 3092 | 119786 | 119800 | 15 |
| 3093 | 119822 | 119836 | 15 |
| 3094 | 119830 | 119847 | 18 |
| 3095 | 119849 | 119900 | 52 |
| 3096 | 119912 | 119925 | 14 |
| 3097 | 119960 | 119982 | 23 |
| 3098 | 119984 | 120013 | 30 |
| 3099 | 120038 | 120054 | 17 |
| 3100 | 120057 | 120090 | 34 |
| 3101 | 120092 | 120134 | 43 |
| 3102 | 120138 | 120154 | 17 |
| 3103 | 120157 | 120189 | 33 |
| 3104 | 120187 | 120200 | 14 |
| 3105 | 120191 | 120211 | 21 |
| 3106 | 120225 | 120239 | 15 |
| 3107 | 120242 | 120267 | 26 |
| 3108 | 120271 | 120301 | 31 |
| 3109 | 120320 | 120340 | 21 |
| 3110 | 120363 | 120406 | 44 |
| 3111 | 120406 | 120421 | 16 |
| 3112 | 120414 | 120468 | 55 |
| 3113 | 120457 | 120470 | 14 |
| 3114 | 120487 | 120518 | 32 |
| 3115 | 120545 | 120563 | 19 |
| 3116 | 120567 | 120587 | 21 |
| 3117 | 120589 | 120625 | 37 |
| 3118 | 120619 | 120633 | 15 |
| 3119 | 120650 | 120663 | 14 |
| 3120 | 120676 | 120694 | 19 |
| 3121 | 120703 | 120717 | 15 |
| 3122 | 120721 | 120737 | 17 |
| 3123 | 120755 | 120812 | 58 |
| 3124 | 120816 | 120838 | 23 |
| 3125 | 120843 | 120871 | 29 |
| 3126 | 120873 | 120899 | 27 |
| 3127 | 120903 | 120922 | 20 |
| 3128 | 120933 | 120946 | 14 |
| 3129 | 120936 | 120981 | 46 |
| 3130 | 120983 | 121004 | 22 |
| 3131 | 121006 | 121021 | 16 |
| 3132 | 121023 | 121036 | 14 |

TABLE 1-continued

Regions of SEQ ID NO 1 which may be targeted using oligonucleotide of the invention

| Reg. A | Position in SEQ ID NO 1 from | to | Length |
|---|---|---|---|
| 3133 | 121035 | 121061 | 27 |
| 3134 | 121063 | 121079 | 17 |
| 3135 | 121081 | 121097 | 17 |
| 3136 | 121105 | 121134 | 30 |
| 3137 | 121138 | 121156 | 19 |
| 3138 | 121155 | 121168 | 14 |
| 3139 | 121158 | 121174 | 17 |
| 3140 | 121166 | 121189 | 24 |
| 3141 | 121194 | 121208 | 15 |
| 3142 | 121201 | 121218 | 18 |
| 3143 | 121213 | 121237 | 25 |
| 3144 | 121246 | 121271 | 26 |
| 3145 | 121298 | 121314 | 17 |
| 3146 | 121311 | 121324 | 14 |
| 3147 | 121327 | 121351 | 25 |
| 3148 | 121359 | 121388 | 30 |
| 3149 | 121390 | 121419 | 30 |
| 3150 | 121446 | 121462 | 17 |
| 3151 | 121468 | 121487 | 20 |
| 3152 | 121499 | 121515 | 17 |
| 3153 | 121517 | 121543 | 27 |
| 3154 | 121545 | 121564 | 20 |
| 3155 | 121575 | 121597 | 23 |
| 3156 | 121599 | 121617 | 19 |
| 3157 | 121619 | 121662 | 44 |
| 3158 | 121664 | 121681 | 18 |
| 3159 | 121683 | 121700 | 18 |
| 3160 | 121702 | 121751 | 50 |
| 3161 | 121773 | 121788 | 16 |
| 3162 | 121790 | 121805 | 16 |
| 3163 | 121807 | 121834 | 28 |
| 3164 | 121836 | 121857 | 22 |
| 3165 | 121859 | 121874 | 16 |
| 3166 | 121877 | 121925 | 49 |
| 3167 | 121923 | 121936 | 14 |
| 3168 | 121928 | 121943 | 16 |
| 3169 | 121962 | 121976 | 15 |
| 3170 | 121978 | 121992 | 15 |
| 3171 | 122004 | 122028 | 25 |
| 3172 | 122030 | 122056 | 27 |
| 3173 | 122046 | 122059 | 14 |
| 3174 | 122052 | 122072 | 21 |
| 3175 | 122080 | 122095 | 16 |
| 3176 | 122099 | 122122 | 24 |
| 3177 | 122143 | 122163 | 21 |
| 3178 | 122169 | 122189 | 21 |
| 3179 | 122258 | 122274 | 17 |
| 3180 | 122289 | 122309 | 21 |
| 3181 | 122311 | 122346 | 36 |
| 3182 | 122357 | 122395 | 39 |
| 3183 | 122446 | 122468 | 23 |
| 3184 | 122471 | 122489 | 19 |
| 3185 | 122491 | 122512 | 22 |
| 3186 | 122526 | 122541 | 16 |
| 3187 | 122543 | 122557 | 15 |
| 3188 | 122579 | 122592 | 14 |
| 3189 | 122606 | 122653 | 48 |
| 3190 | 122663 | 122690 | 28 |
| 3191 | 122728 | 122742 | 15 |
| 3192 | 122757 | 122770 | 14 |
| 3193 | 122779 | 122840 | 62 |
| 3194 | 122842 | 122857 | 16 |
| 3195 | 122900 | 122923 | 24 |
| 3196 | 122933 | 122955 | 23 |
| 3197 | 122968 | 123042 | 75 |
| 3198 | 123055 | 123076 | 22 |
| 3199 | 123094 | 123108 | 15 |
| 3200 | 123114 | 123134 | 21 |
| 3201 | 123143 | 123160 | 18 |
| 3202 | 123162 | 123180 | 19 |
| 3203 | 123184 | 123198 | 15 |
| 3204 | 123200 | 123235 | 36 |
| 3205 | 123237 | 123321 | 85 |
| 3206 | 123314 | 123329 | 16 |
| 3207 | 123342 | 123360 | 19 |
| 3208 | 123356 | 123389 | 34 |
| 3209 | 123391 | 123410 | 20 |
| 3210 | 123412 | 123453 | 42 |
| 3211 | 123455 | 123485 | 31 |
| 3212 | 123488 | 123503 | 16 |
| 3213 | 123506 | 123524 | 19 |
| 3214 | 123526 | 123543 | 18 |
| 3215 | 123545 | 123578 | 34 |
| 3216 | 123598 | 123634 | 37 |
| 3217 | 123654 | 123683 | 30 |
| 3218 | 123685 | 123706 | 22 |
| 3219 | 123710 | 123774 | 65 |
| 3220 | 123803 | 123816 | 14 |
| 3221 | 123818 | 123831 | 14 |
| 3222 | 123896 | 123939 | 44 |
| 3223 | 123941 | 123974 | 34 |
| 3224 | 123976 | 124021 | 46 |
| 3225 | 124026 | 124040 | 15 |
| 3226 | 124042 | 124079 | 38 |
| 3227 | 124091 | 124109 | 19 |
| 3228 | 124158 | 124185 | 28 |
| 3229 | 124238 | 124274 | 37 |
| 3230 | 124319 | 124332 | 14 |
| 3231 | 124335 | 124373 | 39 |
| 3232 | 124394 | 124412 | 19 |
| 3233 | 124419 | 124445 | 27 |
| 3234 | 124450 | 124470 | 21 |
| 3235 | 124472 | 124493 | 22 |
| 3236 | 124499 | 124520 | 22 |
| 3237 | 124522 | 124561 | 40 |
| 3238 | 124564 | 124595 | 32 |
| 3239 | 124607 | 124649 | 43 |
| 3240 | 124662 | 124729 | 68 |
| 3241 | 124750 | 124767 | 18 |
| 3242 | 124769 | 124793 | 25 |
| 3243 | 124812 | 124828 | 17 |
| 3244 | 124853 | 124906 | 54 |
| 3245 | 124923 | 124948 | 26 |
| 3246 | 124958 | 124986 | 29 |
| 3247 | 125023 | 125042 | 20 |
| 3248 | 125032 | 125046 | 15 |
| 3249 | 125065 | 125083 | 19 |
| 3250 | 125073 | 125091 | 19 |
| 3251 | 125093 | 125107 | 15 |
| 3252 | 125132 | 125149 | 18 |
| 3253 | 125139 | 125154 | 16 |
| 3254 | 125151 | 125200 | 50 |
| 3255 | 125201 | 125274 | 74 |
| 3256 | 125314 | 125329 | 16 |
| 3257 | 125331 | 125370 | 40 |
| 3258 | 125372 | 125386 | 15 |
| 3259 | 125411 | 125431 | 21 |
| 3260 | 125433 | 125462 | 30 |
| 3261 | 125475 | 125562 | 88 |
| 3262 | 125564 | 125589 | 26 |
| 3263 | 125605 | 125639 | 35 |
| 3264 | 125641 | 125699 | 59 |
| 3265 | 125719 | 125732 | 14 |
| 3266 | 125737 | 125769 | 33 |
| 3267 | 125815 | 125829 | 15 |
| 3268 | 125834 | 125848 | 15 |
| 3269 | 125850 | 125884 | 35 |
| 3270 | 125899 | 125966 | 68 |
| 3271 | 125967 | 125999 | 33 |
| 3272 | 126026 | 126080 | 55 |
| 3273 | 126097 | 126115 | 19 |
| 3274 | 126130 | 126149 | 20 |

TABLE 1-continued

Regions of SEQ ID NO 1 which may be targeted using oligonucleotide of the invention

| Reg. A | Position in SEQ ID NO 1 from | to | Length |
|---|---|---|---|
| 3275 | 126151 | 126179 | 29 |
| 3276 | 126186 | 126238 | 53 |
| 3277 | 126241 | 126279 | 39 |
| 3278 | 126275 | 126295 | 21 |
| 3279 | 126297 | 126312 | 16 |
| 3280 | 126320 | 126363 | 44 |
| 3281 | 126376 | 126395 | 20 |
| 3282 | 126406 | 126419 | 14 |
| 3283 | 126420 | 126442 | 23 |
| 3284 | 126467 | 126501 | 35 |
| 3285 | 126503 | 126538 | 36 |
| 3286 | 126566 | 126580 | 15 |
| 3287 | 126584 | 126597 | 14 |
| 3288 | 126620 | 126653 | 34 |
| 3289 | 126654 | 126694 | 41 |
| 3290 | 126697 | 126715 | 19 |
| 3291 | 126764 | 126777 | 14 |
| 3292 | 126792 | 126828 | 37 |
| 3293 | 126842 | 126862 | 21 |
| 3294 | 126866 | 126879 | 14 |
| 3295 | 126881 | 126897 | 17 |
| 3296 | 126906 | 126925 | 20 |
| 3297 | 126956 | 126987 | 32 |
| 3298 | 126989 | 127023 | 35 |
| 3299 | 127026 | 127135 | 110 |
| 3300 | 127142 | 127174 | 33 |
| 3301 | 127176 | 127191 | 16 |
| 3302 | 127193 | 127217 | 25 |
| 3303 | 127229 | 127253 | 25 |
| 3304 | 127255 | 127280 | 26 |
| 3305 | 127294 | 127394 | 101 |
| 3306 | 127396 | 127415 | 20 |
| 3307 | 127417 | 127478 | 62 |
| 3308 | 127491 | 127504 | 14 |
| 3309 | 127506 | 127530 | 25 |
| 3310 | 127542 | 127566 | 25 |
| 3311 | 127582 | 127628 | 47 |
| 3312 | 127654 | 127675 | 22 |
| 3313 | 127681 | 127706 | 26 |
| 3314 | 127706 | 127739 | 34 |
| 3315 | 127769 | 127792 | 24 |
| 3316 | 127808 | 127829 | 22 |
| 3317 | 127839 | 127888 | 50 |
| 3318 | 127900 | 127932 | 33 |
| 3319 | 127943 | 127975 | 33 |
| 3320 | 127988 | 128046 | 59 |
| 3321 | 128048 | 128069 | 22 |
| 3322 | 128068 | 128106 | 39 |
| 3323 | 128105 | 128118 | 14 |
| 3324 | 128121 | 128157 | 37 |
| 3325 | 128159 | 128188 | 30 |
| 3326 | 128190 | 128268 | 79 |
| 3327 | 128279 | 128317 | 39 |
| 3328 | 128321 | 128335 | 15 |
| 3329 | 128342 | 128368 | 27 |
| 3330 | 128374 | 128446 | 73 |
| 3331 | 128444 | 128540 | 97 |
| 3332 | 128546 | 128586 | 41 |
| 3333 | 128588 | 128640 | 53 |
| 3334 | 128642 | 128674 | 33 |
| 3335 | 128675 | 128879 | 205 |
| 3336 | 128881 | 128936 | 56 |
| 3337 | 128934 | 129000 | 67 |
| 3338 | 129002 | 129060 | 59 |
| 3339 | 129074 | 129100 | 27 |
| 3340 | 129107 | 129123 | 17 |
| 3341 | 129125 | 129163 | 39 |
| 3342 | 129168 | 129230 | 63 |
| 3343 | 129264 | 129277 | 14 |
| 3344 | 129284 | 129318 | 35 |
| 3345 | 129320 | 129346 | 27 |
| 3346 | 129357 | 129391 | 35 |
| 3347 | 129393 | 129420 | 28 |
| 3348 | 129447 | 129485 | 39 |
| 3349 | 129489 | 129504 | 16 |
| 3350 | 129514 | 129540 | 27 |
| 3351 | 129550 | 129563 | 14 |
| 3352 | 129559 | 129595 | 37 |
| 3353 | 129606 | 129627 | 22 |
| 3354 | 129633 | 129681 | 49 |
| 3355 | 129683 | 129697 | 15 |
| 3356 | 129699 | 129716 | 18 |
| 3357 | 129706 | 129738 | 33 |
| 3358 | 129757 | 129790 | 34 |
| 3359 | 129792 | 129820 | 29 |
| 3360 | 129812 | 129846 | 35 |
| 3361 | 129851 | 129867 | 17 |
| 3362 | 129869 | 129883 | 15 |
| 3363 | 129885 | 129915 | 31 |
| 3364 | 129917 | 129955 | 39 |
| 3365 | 129957 | 130046 | 90 |
| 3366 | 130042 | 130070 | 29 |
| 3367 | 130110 | 130156 | 47 |
| 3368 | 130158 | 130309 | 152 |
| 3369 | 130311 | 130373 | 63 |
| 3370 | 130375 | 130391 | 17 |
| 3371 | 130407 | 130429 | 23 |
| 3372 | 130439 | 130461 | 23 |
| 3373 | 130475 | 130507 | 33 |
| 3374 | 130512 | 130550 | 39 |
| 3375 | 130552 | 130582 | 31 |
| 3376 | 130584 | 130614 | 31 |
| 3377 | 130616 | 130764 | 149 |
| 3378 | 130766 | 130869 | 104 |
| 3379 | 130871 | 131021 | 151 |
| 3380 | 131033 | 131051 | 19 |
| 3381 | 131092 | 131105 | 14 |
| 3382 | 131112 | 131188 | 77 |
| 3383 | 131194 | 131237 | 44 |
| 3384 | 131233 | 131247 | 15 |
| 3385 | 131236 | 131287 | 52 |
| 3386 | 131292 | 131307 | 16 |
| 3387 | 131314 | 131333 | 20 |
| 3388 | 131373 | 131386 | 14 |
| 3389 | 131396 | 131417 | 22 |
| 3390 | 131419 | 131439 | 21 |
| 3391 | 131429 | 131458 | 30 |
| 3392 | 131481 | 131499 | 19 |
| 3393 | 131676 | 131689 | 14 |
| 3394 | 131729 | 131743 | 15 |
| 3395 | 131745 | 131764 | 20 |
| 3396 | 131785 | 131807 | 23 |
| 3397 | 131809 | 131875 | 67 |
| 3398 | 131877 | 131953 | 77 |
| 3399 | 131955 | 131980 | 26 |
| 3400 | 132020 | 132068 | 49 |
| 3401 | 132086 | 132108 | 23 |
| 3402 | 132118 | 132138 | 21 |
| 3403 | 132152 | 132183 | 32 |
| 3404 | 132185 | 132205 | 21 |
| 3405 | 132219 | 132232 | 14 |
| 3406 | 132234 | 132252 | 19 |
| 3407 | 132261 | 132291 | 31 |
| 3408 | 132319 | 132337 | 19 |
| 3409 | 132345 | 132363 | 19 |
| 3410 | 132365 | 132378 | 14 |
| 3411 | 132414 | 132483 | 70 |
| 3412 | 132504 | 132547 | 44 |
| 3413 | 132549 | 132582 | 34 |
| 3414 | 132584 | 132602 | 19 |
| 3415 | 132616 | 132642 | 27 |
| 3416 | 132643 | 132681 | 39 |

TABLE 1-continued

Regions of SEQ ID NO 1 which may be targeted using oligonucleotide of the invention

| Reg. A | Position in SEQ ID NO 1 from | to | Length |
|---|---|---|---|
| 3417 | 132685 | 132714 | 30 |
| 3418 | 132736 | 132769 | 34 |
| 3419 | 132771 | 132793 | 23 |
| 3420 | 132809 | 132825 | 17 |
| 3421 | 132827 | 132841 | 15 |
| 3422 | 132861 | 132884 | 24 |
| 3423 | 132882 | 132900 | 19 |
| 3424 | 132899 | 132915 | 17 |
| 3425 | 132917 | 132951 | 35 |
| 3426 | 132940 | 132954 | 15 |
| 3427 | 132958 | 132983 | 26 |
| 3428 | 132985 | 133031 | 47 |
| 3429 | 133032 | 133051 | 20 |
| 3430 | 133042 | 133060 | 19 |
| 3431 | 133051 | 133071 | 21 |
| 3432 | 133073 | 133087 | 15 |
| 3433 | 133083 | 133104 | 22 |
| 3434 | 133097 | 133110 | 14 |
| 3435 | 133131 | 133199 | 69 |
| 3436 | 133198 | 133222 | 25 |
| 3437 | 133233 | 133249 | 17 |
| 3438 | 133251 | 133284 | 34 |
| 3439 | 133327 | 133429 | 103 |
| 3440 | 133431 | 133596 | 166 |
| 3441 | 133588 | 133602 | 15 |
| 3442 | 133598 | 133611 | 14 |
| 3443 | 133613 | 133628 | 16 |
| 3444 | 133628 | 133646 | 19 |
| 3445 | 133651 | 133670 | 20 |
| 3446 | 133666 | 133707 | 42 |
| 3447 | 133718 | 133742 | 25 |
| 3448 | 133743 | 133777 | 35 |
| 3449 | 133779 | 133794 | 16 |
| 3450 | 133821 | 133851 | 31 |
| 3451 | 133859 | 133880 | 22 |
| 3452 | 133890 | 133921 | 32 |
| 3453 | 133923 | 133974 | 52 |
| 3454 | 133982 | 133998 | 17 |
| 3455 | 134000 | 134036 | 37 |
| 3456 | 134065 | 134107 | 43 |
| 3457 | 134120 | 134173 | 54 |
| 3458 | 134165 | 134179 | 15 |
| 3459 | 134187 | 134200 | 14 |
| 3460 | 134207 | 134242 | 36 |
| 3461 | 134244 | 134258 | 15 |
| 3462 | 134260 | 134273 | 14 |
| 3463 | 134275 | 134299 | 25 |
| 3464 | 134314 | 134346 | 33 |
| 3465 | 134356 | 134371 | 16 |
| 3466 | 134365 | 134380 | 16 |
| 3467 | 134374 | 134420 | 47 |
| 3468 | 134445 | 134477 | 33 |
| 3469 | 134508 | 134523 | 16 |
| 3470 | 134531 | 134548 | 18 |
| 3471 | 134542 | 134555 | 14 |
| 3472 | 134568 | 134621 | 54 |
| 3473 | 134647 | 134667 | 21 |
| 3474 | 134679 | 134719 | 41 |
| 3475 | 134721 | 134824 | 104 |
| 3476 | 134826 | 134849 | 24 |
| 3477 | 134856 | 134869 | 14 |
| 3478 | 134877 | 134910 | 34 |
| 3479 | 134912 | 134966 | 55 |
| 3480 | 134960 | 134980 | 21 |
| 3481 | 134989 | 135012 | 24 |
| 3482 | 135014 | 135066 | 53 |
| 3483 | 135074 | 135093 | 20 |
| 3484 | 135108 | 135125 | 18 |
| 3485 | 135151 | 135260 | 110 |
| 3486 | 135264 | 135277 | 14 |
| 3487 | 135273 | 135310 | 38 |
| 3488 | 135321 | 135337 | 17 |
| 3489 | 135340 | 135365 | 26 |
| 3490 | 135360 | 135374 | 15 |
| 3491 | 135364 | 135386 | 23 |
| 3492 | 135388 | 135430 | 43 |
| 3493 | 135432 | 135447 | 16 |
| 3494 | 135498 | 135521 | 24 |
| 3495 | 135519 | 135545 | 27 |
| 3496 | 135559 | 135622 | 64 |
| 3497 | 135624 | 135647 | 24 |
| 3498 | 135656 | 135673 | 18 |
| 3499 | 135675 | 135704 | 30 |
| 3500 | 135721 | 135742 | 22 |
| 3501 | 135753 | 135796 | 44 |
| 3502 | 135815 | 135858 | 44 |
| 3503 | 135860 | 135880 | 21 |
| 3504 | 135883 | 135915 | 33 |
| 3505 | 135922 | 135965 | 44 |
| 3506 | 135979 | 135993 | 15 |
| 3507 | 135995 | 136036 | 42 |
| 3508 | 136051 | 136065 | 15 |
| 3509 | 136108 | 136165 | 58 |
| 3510 | 136173 | 136190 | 18 |
| 3511 | 136192 | 136287 | 96 |
| 3512 | 136289 | 136303 | 15 |
| 3513 | 136317 | 136346 | 30 |
| 3514 | 136375 | 136415 | 41 |
| 3515 | 136429 | 136470 | 42 |
| 3516 | 136472 | 136496 | 25 |
| 3517 | 136498 | 136532 | 35 |
| 3518 | 136542 | 136565 | 24 |
| 3519 | 136643 | 136657 | 15 |
| 3520 | 136674 | 136701 | 28 |
| 3521 | 136704 | 136719 | 16 |
| 3522 | 136715 | 136728 | 14 |
| 3523 | 136721 | 136737 | 17 |
| 3524 | 136737 | 136750 | 14 |
| 3525 | 136783 | 136810 | 28 |
| 3526 | 136824 | 136849 | 26 |
| 3527 | 136859 | 136896 | 38 |
| 3528 | 136898 | 136927 | 30 |
| 3529 | 136949 | 136983 | 35 |
| 3530 | 136985 | 137000 | 16 |
| 3531 | 137053 | 137071 | 19 |
| 3532 | 137077 | 137097 | 21 |
| 3533 | 137108 | 137164 | 57 |
| 3534 | 137166 | 137196 | 31 |
| 3535 | 137198 | 137221 | 24 |
| 3536 | 137223 | 137267 | 45 |
| 3537 | 137276 | 137359 | 84 |
| 3538 | 137360 | 137385 | 26 |
| 3539 | 137393 | 137440 | 48 |
| 3540 | 137438 | 137496 | 59 |
| 3541 | 137498 | 137518 | 21 |
| 3542 | 137523 | 137536 | 14 |
| 3543 | 137539 | 137572 | 34 |
| 3544 | 137584 | 137612 | 29 |
| 3545 | 137614 | 137628 | 15 |
| 3546 | 137630 | 137644 | 15 |
| 3547 | 137646 | 137669 | 24 |
| 3548 | 137702 | 137727 | 26 |
| 3549 | 137731 | 137745 | 15 |
| 3550 | 137759 | 137772 | 14 |
| 3551 | 137784 | 137819 | 36 |
| 3552 | 137832 | 137858 | 27 |
| 3553 | 137861 | 137876 | 16 |
| 3554 | 137878 | 137900 | 23 |
| 3555 | 137909 | 137925 | 17 |
| 3556 | 137924 | 137961 | 38 |
| 3557 | 137968 | 137981 | 14 |
| 3558 | 138011 | 138033 | 23 |

TABLE 1-continued

Regions of SEQ ID NO 1 which may be targeted using oligonucleotide of the invention

| Reg. A | Position in SEQ ID NO 1 from | to | Length |
|---|---|---|---|
| 3559 | 138035 | 138077 | 43 |
| 3560 | 138079 | 138097 | 19 |
| 3561 | 138224 | 138238 | 15 |
| 3562 | 138232 | 138252 | 21 |
| 3563 | 138242 | 138256 | 15 |
| 3564 | 138255 | 138284 | 30 |
| 3565 | 138295 | 138326 | 32 |
| 3566 | 138328 | 138357 | 30 |
| 3567 | 138359 | 138389 | 31 |
| 3568 | 138403 | 138449 | 47 |
| 3569 | 138451 | 138492 | 42 |
| 3570 | 138500 | 138515 | 16 |
| 3571 | 138524 | 138548 | 25 |
| 3572 | 138555 | 138568 | 14 |
| 3573 | 138571 | 138589 | 19 |
| 3574 | 138589 | 138629 | 41 |
| 3575 | 138644 | 138680 | 37 |
| 3576 | 138697 | 138710 | 14 |
| 3577 | 138712 | 138729 | 18 |
| 3578 | 138744 | 138761 | 18 |
| 3579 | 138776 | 138801 | 26 |
| 3580 | 138860 | 138896 | 37 |
| 3581 | 138898 | 138923 | 26 |
| 3582 | 138925 | 138965 | 41 |
| 3583 | 138967 | 139008 | 42 |
| 3584 | 139010 | 139031 | 22 |
| 3585 | 139029 | 139043 | 15 |
| 3586 | 139034 | 139048 | 15 |
| 3587 | 139041 | 139056 | 16 |
| 3588 | 139055 | 139074 | 20 |
| 3589 | 139078 | 139094 | 17 |
| 3590 | 139084 | 139098 | 15 |
| 3591 | 139092 | 139116 | 25 |
| 3592 | 139133 | 139147 | 15 |
| 3593 | 139154 | 139173 | 20 |
| 3594 | 139175 | 139192 | 18 |
| 3595 | 139204 | 139229 | 26 |
| 3596 | 139231 | 139255 | 25 |
| 3597 | 139257 | 139270 | 14 |
| 3598 | 139272 | 139303 | 32 |
| 3599 | 139315 | 139335 | 21 |
| 3600 | 139337 | 139372 | 36 |
| 3601 | 139383 | 139397 | 15 |
| 3602 | 139399 | 139419 | 21 |
| 3603 | 139423 | 139437 | 15 |
| 3604 | 139435 | 139492 | 58 |
| 3605 | 139501 | 139518 | 18 |
| 3606 | 139508 | 139521 | 14 |
| 3607 | 139571 | 139586 | 16 |
| 3608 | 139588 | 139622 | 35 |
| 3609 | 139636 | 139655 | 20 |
| 3610 | 139657 | 139673 | 17 |
| 3611 | 139685 | 139699 | 15 |
| 3612 | 139724 | 139795 | 72 |
| 3613 | 139796 | 139811 | 16 |
| 3614 | 139818 | 139834 | 17 |
| 3615 | 139836 | 139857 | 22 |
| 3616 | 139856 | 139869 | 14 |
| 3617 | 139859 | 139882 | 24 |
| 3618 | 139891 | 139920 | 30 |
| 3619 | 139930 | 139952 | 23 |
| 3620 | 139965 | 139980 | 16 |
| 3621 | 139982 | 140011 | 30 |
| 3622 | 140013 | 140031 | 19 |
| 3623 | 140047 | 140072 | 26 |
| 3624 | 140074 | 140099 | 26 |
| 3625 | 140101 | 140119 | 19 |
| 3626 | 140121 | 140135 | 15 |
| 3627 | 140144 | 140158 | 15 |
| 3628 | 140157 | 140183 | 27 |
| 3629 | 140185 | 140210 | 26 |
| 3630 | 140231 | 140262 | 32 |
| 3631 | 140258 | 140272 | 15 |
| 3632 | 140264 | 140288 | 25 |
| 3633 | 140290 | 140325 | 36 |
| 3634 | 140339 | 140364 | 26 |
| 3635 | 140369 | 140402 | 34 |
| 3636 | 140428 | 140451 | 24 |
| 3637 | 140453 | 140510 | 58 |
| 3638 | 140512 | 140541 | 30 |
| 3639 | 140556 | 140621 | 66 |
| 3640 | 140626 | 140651 | 26 |
| 3641 | 140653 | 140724 | 72 |
| 3642 | 140726 | 140789 | 64 |
| 3643 | 140802 | 140825 | 24 |
| 3644 | 140837 | 140861 | 25 |
| 3645 | 140863 | 140896 | 34 |
| 3646 | 140903 | 140927 | 25 |
| 3647 | 140958 | 140993 | 36 |
| 3648 | 141001 | 141014 | 14 |
| 3649 | 141022 | 141053 | 32 |

In some embodiments, the oligonucleotide comprises a contiguous nucleotide sequence of 10 to 30 nucleotides in length with at least 90% complementary, such as 100% complementarity, to a corresponding target nucleic acid region present in SEQ ID NO: 1, wherein the target nucleic acid region is selected from the group consisting of region 1B1 to B400 in table 2

TABLE 2

Regions of SEQ ID NO 1 which may be targeted using oligonucleotide of the invention

| Reg. | Position in SEQ ID NO 1 To | From | Length |
|---|---|---|---|
| B1 | 225 | 238 | 14 |
| B2 | 1163 | 1178 | 16 |
| B3 | 2526 | 2539 | 14 |
| B4 | 2805 | 2820 | 16 |
| B5 | 3027 | 3040 | 14 |
| B6 | 3208 | 3222 | 15 |
| B7 | 3212 | 3225 | 14 |
| B8 | 3228 | 3241 | 14 |
| B9 | 3243 | 3256 | 14 |
| B10 | 3810 | 3854 | 45 |
| B11 | 4664 | 4680 | 17 |
| B12 | 5516 | 5529 | 14 |
| B13 | 5657 | 5671 | 15 |
| B14 | 5661 | 5676 | 16 |
| B15 | 5964 | 5977 | 14 |
| B16 | 6217 | 6234 | 18 |
| B17 | 6224 | 6237 | 14 |
| B18 | 6408 | 6422 | 15 |
| B19 | 7300 | 7313 | 14 |
| B20 | 7399 | 7412 | 14 |
| B21 | 7541 | 7564 | 24 |
| B22 | 7626 | 7640 | 15 |
| B23 | 7662 | 7694 | 33 |
| B24 | 7791 | 7806 | 16 |
| B25 | 7853 | 7868 | 16 |
| B26 | 8206 | 8219 | 14 |
| B27 | 8443 | 8456 | 14 |
| B28 | 8739 | 8752 | 14 |
| B29 | 9197 | 9212 | 16 |
| B30 | 10189 | 10203 | 15 |

TABLE 2-continued

Regions of SEQ ID NO 1 which may be targeted using oligonucleotide of the invention Position in SEQ ID NO 1

| Reg. | To | From | Length |
|---|---|---|---|
| B31 | 10754 | 10768 | 15 |
| B32 | 10758 | 10771 | 14 |
| B33 | 11790 | 11803 | 14 |
| B34 | 11870 | 11883 | 14 |
| B35 | 11993 | 12007 | 15 |
| B36 | B11996 | 12011 | 16 |
| B37 | 12017 | 12040 | 24 |
| B38 | 12095 | 12108 | 14 |
| B39 | 12345 | 12358 | 14 |
| B40 | 12721 | 12734 | 14 |
| B41 | 13372 | 13386 | 15 |
| B42 | 13489 | 13505 | 17 |
| B43 | 15576 | 15590 | 15 |
| B44 | 15617 | 15632 | 16 |
| B45 | 15840 | 15853 | 14 |
| B46 | 16041 | 16054 | 14 |
| B47 | 16207 | 16222 | 16 |
| B48 | 16308 | 16321 | 14 |
| B49 | 16349 | 16362 | 14 |
| B50 | 16463 | 16479 | 17 |
| B51 | 16528 | 16542 | 15 |
| B52 | 16543 | 16556 | 14 |
| B53 | 20495 | 20508 | 14 |
| B54 | 20617 | 20630 | 14 |
| B55 | 20960 | 20977 | 18 |
| B56 | 21465 | 21479 | 15 |
| B57 | 21491 | 21508 | 18 |
| B58 | 23479 | 23496 | 18 |
| B59 | 23741 | 23755 | 15 |
| B60 | 25236 | 25249 | 14 |
| B61 | 25323 | 25336 | 14 |
| B62 | 25447 | 25462 | 16 |
| B63 | 25588 | 25601 | 14 |
| B64 | 25853 | 25867 | 15 |
| B65 | 25885 | 25898 | 14 |
| B66 | 26280 | 26293 | 14 |
| B67 | 26388 | 26404 | 17 |
| B68 | 26416 | 26450 | 35 |
| B69 | 26687 | 26702 | 16 |
| B70 | 26706 | 26719 | 14 |
| B71 | 26783 | 26796 | 14 |
| B72 | 27039 | 27052 | 14 |
| B73 | 27251 | 27265 | 15 |
| B74 | 28683 | 28698 | 16 |
| B75 | 29302 | 29315 | 14 |
| B76 | 29304 | 29317 | 14 |
| B77 | 29308 | 29321 | 14 |
| B78 | 29532 | 29545 | 14 |
| B79 | 29974 | 29987 | 14 |
| B80 | 30054 | 30068 | 15 |
| B81 | 30267 | 30281 | 15 |
| B82 | 30623 | 30638 | 16 |
| B83 | 30628 | 30641 | 14 |
| B84 | 30814 | 30827 | 14 |
| B85 | 30881 | 30894 | 14 |
| B86 | 32459 | 32478 | 20 |
| B87 | 37299 | 37315 | 17 |
| B88 | 39083 | 39096 | 14 |
| B89 | 39370 | 39383 | 14 |
| B90 | 39659 | 39672 | 14 |
| B91 | 40814 | 40831 | 18 |
| B92 | 40851 | 40864 | 14 |
| B93 | 41782 | 41795 | 14 |
| B94 | 41873 | 41886 | 14 |
| B95 | 42037 | 42050 | 14 |
| B96 | 42048 | 42063 | 16 |
| B97 | 42096 | 42116 | 21 |
| B98 | 42959 | 42973 | 15 |
| B99 | 43165 | 43178 | 14 |
| B100 | 45926 | 45939 | 14 |
| B101 | 48163 | 48176 | 14 |
| B102 | 52732 | 52745 | 14 |
| B103 | 52984 | 53015 | 32 |
| B104 | 54404 | 54420 | 17 |
| B105 | 55294 | 55320 | 27 |
| B106 | 55337 | 55350 | 14 |
| B107 | 55420 | 55434 | 15 |
| B108 | 55487 | 55501 | 15 |
| B109 | 55623 | 55638 | 16 |
| B110 | 56195 | 56214 | 20 |
| B111 | 56584 | 56597 | 14 |
| B112 | 57267 | 57282 | 16 |
| B113 | 58126 | 58139 | 14 |
| B114 | 58170 | 58183 | 14 |
| B115 | 58295 | 58309 | 15 |
| B116 | 58658 | 58671 | 14 |
| B117 | 58906 | 58921 | 16 |
| B118 | 58988 | 59005 | 18 |
| B119 | 59024 | 59045 | 22 |
| B120 | 59191 | 59207 | 17 |
| B121 | 59236 | 59251 | 16 |
| B122 | 59298 | 59312 | 15 |
| B123 | 59358 | 59378 | 21 |
| B124 | 59400 | 59413 | 14 |
| B125 | 59434 | 59447 | 14 |
| B126 | 59589 | 59602 | 14 |
| B127 | 59620 | 59642 | 23 |
| B128 | 59718 | 59743 | 26 |
| B129 | 59826 | 59841 | 16 |
| B130 | 59843 | 59864 | 22 |
| B131 | 59882 | 59906 | 25 |
| B132 | 59930 | 59958 | 29 |
| B133 | 59959 | 60004 | 46 |
| B134 | 60006 | 60029 | 24 |
| B135 | 60033 | 60071 | 39 |
| B136 | 60139 | 60171 | 33 |
| B137 | 60193 | 60215 | 23 |
| B138 | 60212 | 60225 | 14 |
| B139 | 60231 | 60244 | 14 |
| B140 | 60246 | 60265 | 20 |
| B141 | 60267 | 60282 | 16 |
| B142 | 60292 | 60309 | 18 |
| B143 | 60348 | 60361 | 14 |
| B144 | 60358 | 60429 | 72 |
| B145 | 60427 | 60517 | 91 |
| B146 | 60519 | 60545 | 27 |
| B147 | 60557 | 60575 | 19 |
| B148 | 60580 | 60593 | 14 |
| B149 | 60595 | 60622 | 28 |
| B150 | 60675 | 60690 | 16 |
| B151 | 60697 | 60713 | 17 |
| B152 | 60727 | 60754 | 28 |
| B153 | 60756 | 60799 | 44 |
| B154 | 60801 | 60817 | 17 |
| B155 | 60819 | 60855 | 37 |
| B156 | 61423 | 61436 | 14 |
| B157 | 61592 | 61605 | 14 |
| B158 | 61624 | 61637 | 14 |
| B159 | 61673 | 61713 | 41 |
| B160 | 61715 | 61731 | 17 |
| B161 | 61733 | 61752 | 20 |
| B162 | 61769 | 61794 | 26 |
| B163 | 61805 | 61825 | 21 |
| B164 | 62101 | 62114 | 14 |
| B165 | 62302 | 62315 | 14 |
| B166 | 62436 | 62449 | 14 |
| B167 | 62664 | 62679 | 16 |
| B168 | 62993 | 63006 | 14 |
| B169 | 63098 | 63111 | 14 |
| B170 | 63347 | 63367 | 21 |
| B171 | 63371 | 63396 | 26 |
| B172 | 63385 | 63398 | 14 |
| B173 | 63526 | 63539 | 14 |
| B174 | 65032 | 65045 | 14 |
| B175 | 66556 | 66569 | 14 |
| B176 | 67158 | 67183 | 26 |

TABLE 2-continued

Regions of SEQ ID NO 1 which may be targeted using oligonucleotide of the invention Position in SEQ ID NO 1

| Reg. | To | From | Length |
|---|---|---|---|
| B177 | 67181 | 67194 | 14 |
| B178 | 68007 | 68021 | 15 |
| B179 | 68644 | 68657 | 14 |
| B180 | 69294 | 69317 | 24 |
| B181 | 69306 | 69323 | 18 |
| B182 | 69353 | 69366 | 14 |
| B183 | 70497 | 70511 | 15 |
| B184 | 71600 | 71613 | 14 |
| B185 | 71887 | 71905 | 19 |
| B186 | 72259 | 72272 | 14 |
| B187 | 72589 | 72602 | 14 |
| B188 | 72783 | 72796 | 14 |
| B189 | 73528 | 73541 | 14 |
| B190 | 73783 | 73800 | 18 |
| B191 | 74907 | 74920 | 14 |
| B192 | 75965 | 75981 | 17 |
| B193 | 75983 | 75998 | 16 |
| B194 | 76004 | 76020 | 17 |
| B195 | 76110 | 76166 | 57 |
| B196 | 76186 | 76205 | 20 |
| B197 | 76234 | 76253 | 20 |
| B198 | 76261 | 76280 | 20 |
| B199 | 76369 | 76382 | 14 |
| B200 | 77139 | 77152 | 14 |
| B201 | 77409 | 77422 | 14 |
| B202 | 77478 | 77524 | 47 |
| B203 | 77526 | 77590 | 65 |
| B204 | 77628 | 77641 | 14 |
| B205 | 77688 | 77701 | 14 |
| B206 | 78275 | 78308 | 34 |
| B207 | 78310 | 78332 | 23 |
| B208 | 78340 | 78356 | 17 |
| B209 | 78358 | 78371 | 14 |
| B210 | 78373 | 78395 | 23 |
| B211 | 78397 | 78440 | 44 |
| B212 | 78442 | 78455 | 14 |
| B213 | 78475 | 78489 | 15 |
| B214 | 78696 | 78709 | 14 |
| B215 | 78847 | 78860 | 14 |
| B216 | 79493 | 79516 | 24 |
| B217 | 79705 | 79718 | 14 |
| B218 | 81009 | 81054 | 46 |
| B219 | 81353 | 81367 | 15 |
| B220 | 81970 | 81986 | 17 |
| B221 | 81991 | 82006 | 16 |
| B222 | 82042 | 82106 | 65 |
| B223 | 82278 | 82291 | 14 |
| B224 | 82716 | 82735 | 20 |
| B225 | 84314 | 84328 | 15 |
| B226 | 85628 | 85665 | 38 |
| B227 | 86226 | 86239 | 14 |
| B228 | 86237 | 86253 | 17 |
| B229 | 86566 | 86579 | 14 |
| B230 | 86945 | 86959 | 15 |
| B231 | 87337 | 87358 | 22 |
| B232 | 87662 | 87675 | 14 |
| B233 | 89424 | 89439 | 16 |
| B234 | 89972 | 89985 | 14 |
| B235 | 90782 | 90795 | 14 |
| B236 | 90939 | 90953 | 15 |
| B237 | 90942 | 90955 | 14 |
| B238 | 90965 | 90981 | 17 |
| B239 | 91101 | 91115 | 15 |
| B240 | 92083 | 92096 | 14 |
| B241 | 92164 | 92177 | 14 |
| B242 | 92179 | 92192 | 14 |
| B243 | 92194 | 92210 | 17 |
| B244 | 92212 | 92236 | 25 |
| B245 | 92245 | 92260 | 16 |
| B246 | 92262 | 92302 | 41 |
| B247 | 92304 | 92321 | 18 |
| B248 | 92323 | 92366 | 44 |
| B249 | 92375 | 92389 | 15 |
| B250 | 92392 | 92405 | 14 |
| B251 | 92407 | 92426 | 20 |
| B252 | 92442 | 92459 | 18 |
| B253 | 92497 | 92516 | 20 |
| B254 | 92578 | 92591 | 14 |
| B255 | 92599 | 92612 | 14 |
| B256 | 92614 | 92651 | 38 |
| B257 | 92659 | 92684 | 26 |
| B258 | 92686 | 92699 | 14 |
| B259 | 92704 | 92726 | 23 |
| B260 | 92731 | 92750 | 20 |
| B261 | 92752 | 92774 | 23 |
| B262 | 92780 | 92795 | 16 |
| B263 | 92800 | 92813 | 14 |
| B264 | 92839 | 92858 | 20 |
| B265 | 92860 | 92891 | 32 |
| B266 | 92893 | 92906 | 14 |
| B267 | 92908 | 92921 | 14 |
| B268 | 92923 | 92941 | 19 |
| B269 | 92965 | 92986 | 22 |
| B270 | 92988 | 93002 | 15 |
| B271 | 93044 | 93059 | 16 |
| B272 | 93061 | 93076 | 16 |
| B273 | 93105 | 93122 | 18 |
| B274 | 93142 | 93209 | 68 |
| B275 | 93227 | 93241 | 15 |
| B276 | 93288 | 93305 | 18 |
| B277 | 93325 | 93344 | 20 |
| B278 | 93398 | 93412 | 15 |
| B279 | 93572 | 93586 | 15 |
| B280 | 94509 | 94522 | 14 |
| B281 | 95720 | 95738 | 19 |
| B282 | 97050 | 97065 | 16 |
| B283 | 97079 | 97098 | 20 |
| B284 | 97127 | 97194 | 68 |
| B285 | 97208 | 97230 | 23 |
| B286 | 97232 | 97284 | 53 |
| B287 | 97286 | 97311 | 26 |
| B288 | 97313 | 97362 | 50 |
| B289 | 97368 | 97383 | 16 |
| B290 | 97426 | 97439 | 14 |
| B291 | 98077 | 98090 | 14 |
| B292 | 98227 | 98240 | 14 |
| B293 | 98232 | 98255 | 24 |
| B294 | 99151 | 99164 | 14 |
| B295 | 99405 | 99418 | 14 |
| B296 | 99570 | 99583 | 14 |
| B297 | 99733 | 99748 | 16 |
| B298 | 101829 | 101842 | 14 |
| B299 | 101882 | 101895 | 14 |
| B300 | 101955 | 101968 | 14 |
| B301 | 102202 | 102215 | 14 |
| B302 | 103310 | 103325 | 16 |
| B303 | 103653 | 103666 | 14 |
| B304 | 103908 | 103923 | 16 |
| B305 | 103912 | 103928 | 17 |
| B306 | 103917 | 103933 | 17 |
| B307 | 104971 | 104984 | 14 |
| B308 | 105217 | 105230 | 14 |
| B309 | 105233 | 105250 | 18 |
| B310 | 105443 | 105457 | 15 |
| B311 | 105544 | 105559 | 16 |
| B312 | 106047 | 106071 | 25 |
| B313 | 106061 | 106074 | 14 |
| B314 | 106093 | 106107 | 15 |
| B315 | 106114 | 106130 | 17 |
| B316 | 106243 | 106256 | 14 |
| B317 | 106251 | 106264 | 14 |
| B318 | 106840 | 106855 | 16 |
| B319 | 108113 | 108130 | 18 |
| B320 | 108325 | 108338 | 14 |
| B321 | 108856 | 108869 | 14 |
| B322 | 109109 | 109122 | 14 |

TABLE 2-continued

Regions of SEQ ID NO 1 which may be targeted using oligonucleotide of the invention Position in SEQ ID NO 1

| Reg. | To | From | Length |
|---|---|---|---|
| B323 | 109113 | 109127 | 15 |
| B324 | 109116 | 109132 | 17 |
| B325 | 110301 | 110314 | 14 |
| B326 | 110315 | 110328 | 14 |
| B327 | 110317 | 110330 | 14 |
| B328 | 112528 | 112546 | 19 |
| B329 | 112607 | 112620 | 14 |
| B330 | 114775 | 114788 | 14 |
| B331 | 116322 | 116335 | 14 |
| B332 | 116968 | 116981 | 14 |
| B333 | 117788 | 117801 | 14 |
| B334 | 118034 | 118057 | 24 |
| B335 | 118230 | 118246 | 17 |
| B336 | 118235 | 118248 | 14 |
| B337 | 118870 | 118883 | 14 |
| B338 | 119755 | 119784 | 30 |
| B339 | 119786 | 119800 | 15 |
| B340 | 120363 | 120406 | 44 |
| B341 | 120504 | 120517 | 14 |
| B342 | 121161 | 121174 | 14 |
| B343 | 121330 | 121347 | 18 |
| B344 | 121338 | 121351 | 14 |
| B345 | 123417 | 123430 | 14 |
| B346 | 123464 | 123481 | 18 |
| B347 | 125026 | 125042 | 17 |
| B348 | 127046 | 127071 | 26 |
| B349 | 127090 | 127103 | 14 |
| B350 | 127311 | 127324 | 14 |
| B351 | 127354 | 127367 | 14 |
| B352 | 127363 | 127379 | 17 |
| B353 | 127399 | 127412 | 14 |
| B354 | 127863 | 127876 | 14 |
| B355 | 128134 | 128148 | 15 |
| B356 | 128280 | 128310 | 31 |
| B357 | 128343 | 128368 | 26 |
| B358 | 128444 | 128457 | 14 |
| B359 | 128446 | 128469 | 24 |
| B360 | 128498 | 128511 | 14 |
| B361 | 128511 | 128524 | 14 |
| B362 | 129892 | 129905 | 14 |
| B363 | 130261 | 130283 | 23 |
| B364 | 130375 | 130388 | 14 |
| B365 | 130415 | 130428 | 14 |
| B366 | 130634 | 130650 | 17 |
| B367 | 130667 | 130717 | 51 |
| B368 | 130719 | 130764 | 46 |
| B369 | 130783 | 130796 | 14 |
| B370 | 130798 | 130820 | 23 |
| B371 | 130840 | 130861 | 22 |
| B372 | 130975 | 130994 | 20 |
| B373 | 131112 | 131132 | 21 |
| B374 | 131142 | 131161 | 20 |
| B375 | 131233 | 131246 | 14 |
| B376 | 131729 | 131743 | 15 |
| B377 | 132754 | 132767 | 14 |
| B378 | 132924 | 132937 | 14 |
| B379 | 133174 | 133190 | 17 |
| B380 | 133198 | 133212 | 15 |
| B381 | 133207 | 133222 | 16 |
| B382 | 133476 | 133489 | 14 |
| B383 | 133479 | 133492 | 14 |
| B384 | 133491 | 133531 | 41 |
| B385 | 133533 | 133550 | 18 |
| B386 | 133555 | 133594 | 40 |
| B387 | 134160 | 134173 | 14 |
| B388 | 134165 | 134178 | 14 |
| B389 | 134533 | 134546 | 14 |
| B390 | 136724 | 136737 | 14 |
| B391 | 137438 | 137463 | 26 |
| B392 | 137878 | 137891 | 14 |
| B393 | 138082 | 138097 | 16 |
| B394 | 138233 | 138252 | 20 |
| B395 | 138930 | 138943 | 14 |
| B396 | 138947 | 138960 | 14 |
| B397 | 138950 | 138963 | 14 |
| B398 | 139502 | 139518 | 17 |
| B399 | 139508 | 139521 | 14 |
| B400 | 140978 | 140991 | 14 |

In certain embodiments the oligonucleotide or contiguous nucleotide sequence is complementary to a region (or sub-sequence)(or sub-sequence) of the target nucleic acid, wherein the target nucleic acid region is selected from the group consisting of position 1589-10889, 46089-53989 and 60789-62489 of SEQ ID NO: 1.

In one embodiment the oligonucleotide comprises a contiguous nucleotide sequence of 10 to 30 nucleotides in length with at least 90%, such as 100% complementary to a target nucleic acid sequence of position 55319 to 141053 of SEQ ID NO: 1.

In one embodiment the oligonucleotide comprises a contiguous nucleotide sequence of 10 to 30 nucleotides in length with at least 90%, such as 100% complementary to a target nucleic acid sequence of position 1 to 55318 of SEQ ID NO: 1.

In some embodiments, the oligonucleotide comprises a contiguous nucleotide sequence of 10 to 30 nucleotides in length with at least 90% complementary to a sub-sequence of the target nucleic acid selected from the group corresponding to positions: 55319-76274, 77483-77573, 92157-93403 and 97056-97354 of SEQ ID NO: 1.

In some embodiments the oligonucleotide a contiguous nucleotide sequence of 10 to 30 nucleotides in length with at least 90% complementary to a sub-sequence of the target nucleic acid selected from the group corresponding to positions: 60821-60849, 77567-77583, 92323-92339 and 97156-97172 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions: 5218-5240 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions: 5782-5803 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions: 8113-8139 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions: 9200-9250 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions: 11505-11555 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions: 13223-13242 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions 15100-15150 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions 15113-15180 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions 29635-29705 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions 30590-30740 of SEQ ID NO: 1.

In some embodiments the oligonucleotide a contiguous nucleotide sequence of 10 to 30 nucleotides in length with at least 90% complementary to a sub-sequence of the target nucleic acid corresponding to positions 39800-39855 of SEQ ID NO: 1.

In some embodiments the oligonucleotide a contiguous nucleotide sequence of 10 to 30 nucleotides in length with at least 90% complementary to a sub-sequence of the target nucleic acid to positions 44435-44460 of SEQ ID NO: 1.

In some embodiments the oligonucleotide a contiguous nucleotide sequence of 10 to 30 nucleotides in length with at least 90% complementary to a sub-sequence of the target nucleic acid to positions 45245-45270 of SEQ ID NO: 1.

In some embodiments the oligonucleotide a contiguous nucleotide sequence of 10 to 30 nucleotides in length with at least 90% complementary to a sub-sequence of the target nucleic acid to positions 46380-46430 of SEQ ID NO: 1.

In some embodiments the oligonucleotide a contiguous nucleotide sequence of 10 to 30 nucleotides in length with at least 90% complementary to a sub-sequence of the target nucleic acid to positions 68915-68940 of SEQ ID NO: 1.

In some embodiments, the oligonucleotide comprises or consists of 8 to 35 nucleotides in length, such as from 10 to 30, such as 11 to 22, such as from 12 to 18, such as from 13 to 17 or 14 to 16 contiguous nucleotides in length. In a preferred embodiment, the oligonucleotide comprises or consists of 15 to 20 nucleotides in length.

In some embodiments, the oligonucleotide or contiguous nucleotide sequence thereof comprises or consists of 22 or less nucleotides, such as 20 or less nucleotides, such as 18 or less nucleotides, such as 14, 15, 16 or 17 nucleotides. It is to be understood that any range given herein includes the range endpoints. Accordingly, if an oligonucleotide is said to include from 10 to 30 nucleotides, both 10 and 30 nucleotides are included.

In some embodiments, the contiguous nucleotide sequence comprises or consists of 8, 9, 10, 11, 12, 13, 14, 15, 16, 17, 18, 19, 20, 21, 22, 23, 24, 25, 26, 27, 28, 29 or 30 contiguous nucleotides in length. In a preferred embodiment, the oligonucleotide comprises or consists of 16, 17, 18 or 19 nucleotides in length.

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 4 to 150 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 4 to 818 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 4 to 678 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 166, 167, 167 or 169 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 570, 571, 572, 679, 680, 681, 682 and 683 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 34, 186, 187, 188, 573, 574, 575, 576, 572, 684, 685, 686, 687, 688, 689, 690, 691, 692, 963, 964, 965 and 696 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 35, 199, 200, 201, 202, 203, 204, 205, 206, 207, 209 and 210 or SEQ ID NO: 582, 583 and 584 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 221, 222, 223, 224, 225, 585, 586, 587, 588, 589, 698, 699, 700, 701, 702, 703, 704, 705, 706, 707, 708, 709, 710, 711, 712, 713, 714, 715, 716, 717 and 718 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 236, 237, 238, 239, 240 and 590.

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 241, 591 and 719 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 46, 47, 48, 285, 286, 287, 288, 289, 290, 291, 292, 293, 294, 295, 296, 297, 298, 299, 300, 301, 302, 303, 304, 305, 613, 614, 615, 616, 617, 618, 619, 620, 621, 622, 623, 624, 625, 626, 627, 628, 629, 630, 631, 632, 721, 722, 723, 724, 725, 726, 727, 728, 729, 730, 731, 732, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 800, 800, 800, 800, 801, 801, 802, 803, 804, 805, 806 and 807 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 331, 332, 638, 639, 640, 808, 809, 810, 811, 812, 813, 814 and 815 (see motif sequences listed in table 3 in the Examples section).

In some embodiments, the antisense oligonucleotide or contiguous nucleotide sequence comprises or consists of of 10 to 30 nucleotides in length with at least 90% identity, preferably 100% identity to a sequence selected from the group consisting of SEQ ID NO: 409, 410, 411, 642, 643, 644, 645, 646, 816, 818 and 818 (see motif sequences listed in table 3 in the Examples section).

It is understood that the contiguous nucleobase sequences (motif sequence) can be modified to for example increase nuclease resistance and/or binding affinity to the target nucleic acid. Modifications are described in the definitions and in the "Oligonucleotide design" section. Table 3 lists preferred designs of each motif sequence.

Oligonucleotide Design

Oligonucleotide design refers to the pattern of nucleoside sugar modifications in the oligonucleotide sequence. The oligonucleotides of the invention comprise sugar-modified nucleosides and may also comprise DNA or RNA nucleosides. In some embodiments, the oligonucleotide comprises sugar-modified nucleosides and DNA nucleosides. Incorporation of modified nucleosides into the oligonucleotide of the invention may enhance the affinity of the oligonucleotide for the target nucleic acid. In that case, the modified nucleosides can be referred to as affinity enhancing modified nucleotides.

In an embodiment, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In an embodiment the oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides. In some embodiments, at least 1 of the modified nucleosides is a locked nucleic acid (LNA), such as at least 2, such as at least 3, at least 4, at least 5, at least 6, at least 7, or at least 8 of the modified nucleosides are LNA. In a still further embodiment all the modified nucleosides are LNA.

In an embodiment, the oligonucleotide of the invention may comprise modifications, which are independently selected from these three types of modifications (modified sugar, modified nucleobase and modified internucleoside linkage) or a combination thereof. Preferably the oligonucleotide comprises one or more sugar modified nucleosides, such as 2' sugar modified nucleosides. Preferably the oligonucleotide of the invention comprise the one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. Even more preferably the the one or more modified nucleoside is LNA.

In a further embodiment the oligonucleotide comprises at least one modified internucleoside linkage. In a preferred embodiment the the internucleoside linkages within the contiguous nucleotide sequence are phosphorothioate or boranophosphate internucleoside linkages.

In some embodiments, the oligonucleotide of the invention comprise at least one modified nucleoside which is a 2'-MOE-RNA, such as 2, 3, 4, 5, 6, 7, 8, 9 or 10 2'-MOE-RNA nucleoside units. In some embodiments, at least one of said modified nucleoside is 2'-fluoro DNA, such as 2, 3, 4, 5, 6, 7, 8, 9 or 10 2'-fluoro-DNA nucleoside units.

In some embodiments, the oligonucleotide of the invention comprises at least one LNA unit, such as 1, 2, 3, 4, 5, 6, 7, or 8 LNA units, such as from 2 to 6 LNA units, such as from 3 to 7 LNA units, 4 to 8 LNA units or 3, 4, 5, 6 or 7 LNA units. In some embodiments, all the modified nucleosides are LNA nucleosides. In a further embodiment, the oligonucleotide may comprise both beta-D-oxy-LNA, and one or more of the following LNA units: thio-LNA, amino-LNA, oxy-LNA, and/or ENA in either the beta-D or alpha-L configurations or combinations thereof. In a further embodiment, all LNA cytosine units are 5-methyl-cytosine. In a preferred embodiment the oligonucleotide or contiguous nucleotide sequence has at least 1 LNA unit at the 5' end and at least 2 LNA units at the 3' end of the nucleotide sequence.

In some embodiments, the oligonucleotide of the invention comprises at least one LNA unit and at least one 2' substituted modified nucleoside.

In some embodiments of the invention, the oligonucleotide comprise both 2' sugar modified nucleosides and DNA units. Preferably the oligonucleotide comprise both LNA and DNA units. Preferably, the combined total of LNA and DNA units is 8-30, such as 10-25, preferably 12-22, such as 12-18, even more preferably 11-16. In some embodiments of the invention, the nucleotide sequence of the oligonucleotide, such as the contiguous nucleotide sequence consists of at least one or two LNA units and the remaining nucleotide units are DNA units. In some embodiments the oligonucleotide comprises only LNA nucleosides and naturally occurring nucleosides (such as RNA or DNA, most preferably DNA nucleosides), optionally with modified internucleoside linkages such as phosphorothioate.

In an embodiment of the invention the oligonucleotide of the invention is capable of recruiting RNase H.

Gapmer Design

In a preferred embodiment the oligonucleotide of the invention has a gapmer design or structure also referred herein merely as "Gapmer". In a gapmer structure the oligonucleotide comprises at least three distinct structural regions a 5'-flank, a gap and a 3'-flank, F-G-F' in '5->3' orientation. In this design, flanking regions F and F' (also termed wing regions) comprise a contiguous stretch of modified nucleosides, which are complementary to the UBE3A target nucleic acid, while the gap region, G, comprises a contiguous stretch of nucleotides which are capable of recruiting a nuclease, preferably an endonuclease such as RNase, for example RNase H, when the oligonucleotide is in duplex with the target nucleic acid. Nucleosides which are capable of recruiting a nuclease, in particular RNase H, can be selected from the group consisting of DNA, alpha-L-oxy-LNA, 2'-Flouro-ANA and UNA. Regions F and F', flanking the 5' and 3' ends of region G, preferably comprise non-nuclease recruiting nucleosides (nucleosides with a 3' endo structure), more preferably one or more affinity enhancing modified nucleosides. In some embodiments, the 3' flank comprises at least one LNA nucleoside, preferably at least 2 LNA nucleosides. In some embodiments, the 5' flank comprises at least one LNA nucleoside. In some embodiments both the 5' and 3' flanking regions comprise a LNA nucleoside. In some embodiments all the nucleosides in the flanking regions are LNA nucleosides. In other embodiments, the flanking regions may comprise both LNA nucleosides and other nucleosides (mixed flanks), such as DNA nucleosides and/or non-LNA modified nucleosides, such as 2' substituted nucleosides. In this case the gap is defined as a contiguous sequence of at least 5 RNase H recruiting nucleosides (nucleosides with a 2' endo structure, preferably DNA) flanked at the 5' and 3' end by an affinity enhancing modified nucleoside, preferably LNA, such as beta-D-oxy-LNA. Consequently, the nucleosides of the 5' flanking region and the 3' flanking region which are adjacent to the gap region are modified nucleosides, preferably non-nuclease recruiting nucleosides. In oligonucleotides with mixed flanks where the flanks comprise DNA the 5' and 3' nucleosides are modified nucleosides.

Region F

Region F (5' flank or 5' wing) attached to the '5 end of region G comprises, contains or consists of at least one modified nucleoside such as at least 2, at least 3, at least 4, at least 5, at least 6, at least 7 modified nucleosides. In an embodiment region F comprises or consists of from 1 to 7 modified nucleosides, such as from 2 to 6 modified nucleosides, such as from 2 to 5 modified nucleosides, such as from 2 to 4 modified nucleosides, such as from 1 to 3 modified nucleosides, such as 1, 2, 3 or 4 modified nucleosides. In a further embodiment further additional nucleosides may be attached to the '5 end of region F, representing a region D preferably comprising 1, 2 or 3 nucleoside units, such as DNA nucleosides. Region D can take the function of a biocleavable (B) linker described in the definition of "Linkers".

In some embodiments, the modified nucleosides in region F have a 3' endo structure.

In an embodiment, one or more of the modified nucleosides in region F are 2' modified nucleosides.

In a further embodiment one or more of the 2' modified nucleosides in region F are selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In one embodiment of the invention all the modified nucleosides in region F are LNA nucleosides. In a further embodiment the LNA nucleosides in region F are independently selected from the group consisting of oxy-LNA, thio-LNA, amino-LNA, cET, and/or ENA, in either the beta-D or alpha-L configurations or combinations thereof. In a preferred embodiment region F has at least 1 beta-D-oxy LNA unit, at the 5' end of the contiguous sequence.

Region G

Region G (gap region) preferably comprise, contain or consist of at least 4, such as at least 5, such as at least 6, at least 7, at least 8, at least 9, at least 10, at least 11, at least 12, at least 13, at least 14, at least 15 or at least 16 consecutive nucleosides capable of recruiting the aforementioned nuclease, in particular RNaseH. In a further embodiment region G comprise, contain or consist of from 5 to 12, or from 6 to 10 or from 7 to 9, such as 8 consecutive nucleotide units capable of recruiting aforementioned nuclease.

The nucleoside units in region G, which are capable of recruiting nuclease are in an embodiment selected from the group consisting of DNA, alpha-L-LNA, C4' alkylated DNA (as described in PCT/EP2009/050349 and Vester et al., Bioorg. Med. Chem. Lett. 18 (2008) 2296-2300, both incorporated herein by reference), arabinose derived nucleosides like ANA and 2'F-ANA (Mangos et al. 2003 J. AM. CHEM. SOC. 125, 654-661), UNA (unlocked nucleic acid) (as described in Fluiter et al., Mol. Biosyst., 2009, 10, 1039 incorporated herein by reference). UNA is unlocked nucleic acid, typically where the bond between C2 and C3 of the ribose has been removed, forming an unlocked "sugar" residue.

In a still further embodiment at least one nucleoside unit in region G is a DNA nucleoside unit, such as from 1 to 16 DNA units, such as 2, 3, 4, 5, 6, 7, 8, 9, 10, 11, 12, 13, 14 or 15 DNA units, preferably from 2 to 13 DNA units, such as from 4 to 12 DNA units, more preferably from 5 to 11, or from 10 to 16, 11 to 15 or 12 to 14 DNA units. In some embodiments, region G consists of 100% DNA units. In a preferred embodiment G consists of, most preferably 10, 11, 12, 13, 14 or 15 DNA units.

In further embodiments the region G may consist of a mixture of DNA and other nucleosides capable of mediating RNase H cleavage. Region G may consist of at least 50% DNA, more preferably 60%, 70% or 80% DNA, and even more preferred 90% or 95% DNA.

In a still further embodiment at least one nucleoside unit in region G is an alpha-L-LNA nucleoside unit, such as at least one alpha-L-LNA unit, such as 2, 3, 4, 5, 6, 7, 8 or 9 alpha-L-LNA units. In a further embodiment, region G comprises the least one alpha-L-LNA is alpha-L-oxy-LNA unit. In a further embodiment region G comprises a combination of DNA and alpha-L-LNA nucleoside units.

In some embodiments the size of the contiguous sequence in region G may be longer, such as 15, 16, 17, 18, 19 or 20 nucleoside units.

In some embodiments, nucleosides in region G have a 2' endo structure.

Region F'

Region F' (3' flank or 3' wing) attached to the '3 end of region G comprises, contains or consists of at least one modified nucleoside such as at least 2, at least 3, at least 4, at least 5, at least 6, at least 7 modified nucleosides. In an embodiment region F' comprise or consist of from 1 to 7 modified nucleosides, such as from 2 to 6 modified nucleoside, such as from 2 to 4 modified nucleosides, such as from 1 to 3 modified nucleosides, such as 1, 2, 3 or 4 modified nucleosides. In a further embodiment further additional nucleosides attached to the '3 end of region F', representing a region D', preferably comprising 1, 2 or 3 nucleoside units, such as DNA nucleosides. Region D' can take the function of a biocleavable (B) linker described, in the section "Linkers".

In some embodiments, the modified nucleosides in region F' have a 3' endo structure.

In a preferred embodiment, modified nucleosides in region F' is LNA.

In a further embodiment modified nucleosides in region F' are selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In one embodiment of the invention all the modified nucleosides in region F' are LNA nucleosides. In a further embodiment the LNA nucleosides in region F' are independently selected from the group consisting of oxy-LNA, thio-LNA, amino-LNA, cET and/or ENA, in either the beta-D or alpha-L configurations or combinations thereof. In a preferred embodiment region F' has at least 2 beta-D-oxy LNA unit, at the 3' end of the contiguous sequence.

Region D and D'

Region D and D' can be attached to the 5' end of region F or the 3' end of region F', respectively.

Region D or D' may independently comprise 1, 2, 3, 4 or 5 additional nucleotides, which may be complementary or non-complementary to the target nucleic acid. In this respect the oligonucleotide of the invention, may in some embodiments comprise a contiguous nucleotide sequence capable of modulating the target which is flanked at the 5' and/or 3' end by additional nucleotides. Such additional nucleotides may serve as a nuclease susceptible biocleavable linker (see definition of linkers). In some embodiments the additional 5' and/or 3' end nucleotides are linked with phosphodiester linkages, and may be DNA or RNA. In another embodiment, the additional 5' and/or 3' end nucleotides are modified nucleotides which may for example be included to enhance nuclease stability or for ease of synthesis. In an embodiment of the oligonucleotide of the invention, comprises a region D and/or D' in addition to the contiguous nucleotide sequence.

The gapmer oligonucleotide of the present invention can be represented by the following formulae:

F-G-F'; in particular $F_{1-7}$-$G_{4-12}$-$F'_{1-7}$

D-F-G-F', in particular $D_{1-3}$-$F_{1-7}$-$G_{4-12}$-$F'_{1-7}$

F-G-F'-D', in particular $F_{1-7}$-$G_{4-12}$-$F'_{1-7}$-$D'_{1-3}$

D-F-G-F'-D', in particular $D_{1-3}$-$F_{1-7}$-$G_{4-12}$-$F'_{1-7}$-$D'_{1-3}$

The preferred number and types of nucleosides in regions F, G and F', D and D' have been described above. The design of the individual oligonucleotide may also have profound impact on the properties of the oligonucleotide in its use for modulating expression of UBE3A.

In some embodiments the oligonucleotide is a gapmer consisting of 14, 15, 16, 17, 18, 19 or 20 nucleotides in length, wherein each of regions F and F' independently consists of 2, 3 or 4 modified nucleoside units complementary to a part of the human SNHG14 long non-coding RNA which is antisense to the UBE3A pre-mRNA (the target nucleic acid) and region G consists of 10, 11, 12, 13, 14 or 15 nucleoside units, capable of recruiting nuclease when in duplex with the target nucleic acid.

In a further embodiments, the oligonucleotide is a gapmer wherein each of regions F and F' independently consists of 2, 3, 4 or 5 modified nucleoside units, such as nucleoside units containing a 2'-O-methoxyethyl-ribose sugar (2'-MOE) or nucleoside units containing a 2'-fluoro-deoxyribose sugar and/or LNA units, and region G consists of 9, 10, 11, 12, 13, 14 or 15 nucleoside units, such as DNA units or other nuclease recruiting nucleosides such as alpha-L-LNA or a mixture of DNA and nuclease recruiting nucleosides.

In a further specific embodiment, the oligonucleotide is a gapmer wherein each of regions F and F' region consists of two LNA units each, and region G consists of 10, 11, 12, 13, 14 or 15 nucleoside units, preferably DNA units. Specific gapmer designs of this nature include 2-10-2, 2-11-2, 2-12-2, 2-13-2, 2-14-2 and 2-15-2.

In a further specific embodiment, the oligonucleotide is a gapmer wherein each of regions F and F' independently consists of three LNA units, and region G consists of 10, 11, 12, 13, 14 or 15 nucleoside units, preferably DNA units. Specific gapmer designs of this nature include 3-10-3, 3-11-3, 3-12-3, 3-13-3, 3-14-3 and 3-15-3.

In a further specific embodiment, the oligonucleotide is a gapmer wherein each of regions F and F' consists of four LNA units each, and region G consists of 10, 11, 12, 13, 14 or 15 nucleoside units, preferably DNA units. Specific gapmer designs of this nature include 4-10-4, 4-11-4, 4-12-4, 4-13-4, 4-14-4 and 4-15-4.

Specific gapmer designs of this nature include F-G-F' designs selected from a group consisting of a gap with 10 nucleosides and independently 1 to 4 modified nucleosides in the wings including 1-10-1, 2-10-1, 1-10-2, 1-10-3, 3-10-1, 1-10-4, 4-10-1, 2-10-2, 2-10-3, 3-10-2, 2-10-4, 4-10-2, 3-10-3, 3-10-4, 4-10-3 and 4-10-4 gapmers.

Specific gapmer designs of this nature include F-G-F' designs selected from a group consisting of a gap with 11 nucleosides and independently 1 to 4 modified nucleosides in the wings including, 1-11-1, 2-11-1, 1-11-2, 1-11-3, 3-11-1, 1-11-4, 4-11-1, 2-11-2, 2-11-3, 3-11-2, 2-11-4, 4-11-2, 3-11-3, 3-11-4, 4-11-3 and 4-11-4 gapmers.

Specific gapmer designs of this nature include F-G-F' designs selected from a group consisting of a gap with 12 nucleosides including, 1-12-1, 2-12-1, 1-12-2, 1-12-3, 3-12-1, 1-12-4, 4-12-1, 2-12-2, 2-12-3, 3-12-2, 2-12-4, 4-12-2, 3-12-3, 3-12-4, 4-12-3 and 4-12-4 gapmers. Specific gapmer designs of this nature include F-G-F' designs selected from a group consisting of a gap with 13 nucleosides and independently 1 to 4 modified nucleosides in the wings including 1-13-1, 1-13-2, 1-13-3, 3-13-1, 1-13-4, 4-13-1, 2-13-1, 2-13-2, 2-13-3, 3-13-2, 2-13-4, 4-13-2, 3-13-3, 3-13-4, 4-13-3, and 4-13-4 gapmers.

Specific gapmer designs of this nature include F-G-F' designs selected from a group consisting of a gap with 14 nucleosides and independently 1 to 4 modified nucleosides in the wings including 1-14-1, 1-14-2, 2-14-1, 1-14-3, 3-14-1, 1-14-4, 4-14-1, 2-14-2, 2-14-3, 3-14-2 2-14-4, 4-14-2, 3-14-3, 3-14-4 and 4-14-3 gapmers.

Specific gapmer designs of this nature include F-G-F' designs selected from a group consisting of a gap with 15 nucleosides and independently 1 to 4 modified nucleosides in the wings including 1-15-1, 1-15-2, 2-15-1, 1-15-3, 3-15-1, 1-15-4, 4-15-1, 2-15-2, 2-15-3, 3-15-2 2-15-4, 4-15-2, 3-15-3, 3-15-4 and 4-15-3 gapmers.

Specific gapmer designs of this nature include F-G-F' designs selected from a group consisting of a gap with 16 nucleosides and independently 1 to 4 modified nucleosides in the wings including 1-16-1, 1-16-2, 2-16-1, 1-15-3, 3-16-1, 1-16-4, 4-16-1, 2-16-2, 2-16-3, 3-16-2 2-16-4, 4-16-2, 3-16-3, 3-16-4 and 4-16-3 gapmers.

In some embodiments the F-G-F' design is selected from 2-10-4, 3-10-3 and 4-10-2.

In some embodiments the F-G-F' design is selected from 2-11-4, 3-11-2, 3-11-3 and 4-11-2.

In some embodiments the F-G-F' design is selected from 2-12-2, 2-12-3, 2-12-4, 3-12-2, 3-12-3, and 4-12-2.

In some embodiments the F-G-F' design is selected from 2-13-2, 2-13-3, 2-13-4, 3-13-3 and 4-13-2.

In some embodiments the F-G-F' design is selected from 2-14-2, 2-14-4, 3-14-3 and 4-14-2.

In some embodiments the F-G-F' design is selected from 2-15-2 and 2-16-2.

In some embodiments the F-G-F' design is selected from the designs indicated in table 3.

In all instances the F-G-F' design may further include region D and/or D', which may have 1, 2 or 3 nucleoside units, such as DNA units. Preferably, the nucleosides in region F and F' are modified nucleosides, while nucleotides in region G are preferably unmodified nucleosides.

In each design, the preferred modified nucleoside is LNA.

In another embodiment all the internucleoside linkages in the gap in a gapmer are phosphorothioate and/or boranophosphate linkages. In another embodiment all the internucleoside linkages in the flanks (F and F' region) in a gapmer are phosphorothioate and/or boranophosphate linkages. In another preferred embodiment all the internucleoside linkages in the D and D' region in a gapmer are phosphodiester linkages.

For specific gapmers as disclosed herein, when the cytosine (C) residues are annotated as 5-methyl-cytosine, in various embodiments, one or more of the C's present in the oligonucleotide may be unmodified C residues.

Further gapmer designs are disclosed in WO2004/046160, WO2007/146511 and incorporated by reference.

For certain embodiments of the invention, the oligonucleotide is selected from the group of oligonucleotide compounds in table 3.

For certain embodiments of the invention, the oligonucleotide is selected from the group of oligonucleotide compounds with CMP-ID-NO: 4_1 to 150_2.

For certain embodiments of the invention, the oligonucleotide is selected from the group of oligonucleotide compounds with CMP-ID-NO: 4_1 to 678_1.

For certain embodiments of the invention, the oligonucleotide is selected from the group of oligonucleotide compounds with CMP-ID-NO: 4_1 to 818_1 (see oligonucleotide sequences listed in table 3 in the Examples section).

For certain embodiments of the invention, the oligonucleotide is an oligonucleotide compound with CMP-ID-NO: 155_1 or 165_1.

For certain embodiments of the invention, the oligonucleotide is selected from the group of oligonucleotide compounds with CMP-ID-NO: 169_52, 169_50 or 169_56.

For certain embodiments of the invention, the oligonucleotide is selected from the group of oligonucleotide compounds with CMP-ID-NO: 172_1, 272_1, 5727, 572_6 or 572_5.

For certain embodiments of the invention, the oligonucleotide is an oligonucleotide compound with CMP-ID-NO: 175_1.

For certain embodiments of the invention, the oligonucleotide is an oligonucleotide compound with CMP-ID-NO: 178_1.

For certain embodiments of the invention, the oligonucleotide is selected from the group of oligonucleotide compounds with CMP-ID-NO: 573_8, 186_1 or 187_1.

For certain embodiments of the invention, the oligonucleotide is an oligonucleotide compound with CMP-ID-NO: 186_1.

For certain embodiments of the invention, the oligonucleotide is selected from the group of oligonucleotide compounds with CMP-ID-NO: 200_1, 204_1, 206_1, 35_2 or 209_1.

For certain embodiments of the invention, the oligonucleotide is selected from the group of oligonucleotide compounds with CMP-ID-NO: 585_1, 585_8, 586_9, 586_5, 586_8, 586_4 or 586_6.

For certain embodiments of the invention, the oligonucleotide is an oligonucleotide compound with CMP-ID-NO: 233_1.

For certain embodiments of the invention, the oligonucleotide is an oligonucleotide compound with CMP-ID-NO: 237_8 or 590_13.

For certain embodiments of the invention, the oligonucleotide is an oligonucleotide compound with CMP-ID-NO: 220_1.

For certain embodiments of the invention, the oligonucleotide is selected from the group of oligonucleotide compounds with CMP-ID-NO: 591_1, 592_2, 592_4 or 241_9.

For certain embodiments of the invention, the oligonucleotide is selected from the group of oligonucleotide compounds with CMP-ID-NO: 597_4, 598_4, 39_1 or 602_1.

For certain embodiments of the invention, the oligonucleotide is an oligonucleotide compound with CMP-ID-NO: 39_1.

For certain embodiments of the invention, the oligonucleotide is an oligonucleotide compound with CMP-ID-NO: 611_7.

For certain embodiments of the invention, the oligonucleotide is an oligonucleotide compound with CMP-ID-NO: 271_1 or 278_1.

For certain embodiments of the invention, the oligonucleotide is selected from the group of oligonucleotide compounds with CMP-ID-NO: 616_4, 621_2, 621_1, 622_3, 622_5, 622_4, 624_3, 624_5, 287_1, 625_6, 626_7, 626_8, 626_9, 48_1, 631_6, 631_1, 303_1, 304_6 or 304_10.

For certain embodiments of the invention, the oligonucleotide is an oligonucleotide compound with CMP-ID-NO: 636_8.

For certain embodiments of the invention, the oligonucleotide is selected from the group of oligonucleotide compounds with CMP-ID-NO: 638_8, 639_5, 331_1 or 640_4.

For certain embodiments of the invention, the oligonucleotide is selected from the group of oligonucleotide compounds with CMP-ID-NO: 359_1, 361_1, 361_5, 362_1 or 641_5.

For certain embodiments of the invention, the oligonucleotide is selected from the group of oligonucleotide compounds with CMP-ID-NO: 378_1, 379_1, 399_1.

For certain embodiments of the invention, the oligonucleotide is selected from the group of oligonucleotide compounds with CMP-ID-NO: 403_1, 405_1, 642_12, 642_13, 644_3 or 646_16.

For certain embodiments of the invention, the oligonucleotide is an oligonucleotide compound with CMP-ID-NO: 85_1 or 425_5.

For certain embodiments of the invention, the oligonucleotide is an oligonucleotide compound with CMP-ID-NO: 116_1.

For certain embodiments of the invention, the oligonucleotide is an oligonucleotide compound with CMP-ID-NO: 123_1 or 124_1.

For certain embodiments of the invention, the oligonucleotide is an oligonucleotide compound with CMP-ID-NO: 126_2.

Method of Manufacture

In a further aspect, the invention provides methods for manufacturing the oligonucleotides of the invention comprising reacting nucleotide units and thereby forming covalently linked contiguous nucleotide units comprised in the oligonucleotide. Preferably, the method uses phophoramidite chemistry (see for example Caruthers et al, 1987, Methods in Enzymology vol. 154, pages 287-313). In a further embodiment the method further comprises reacting the contiguous nucleotide sequence with a conjugating moiety (ligand). In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Composition

In a further aspect, the invention provides pharmaceutical compositions comprising any of the aforementioned oligonucleotides and/or oligonucleotide conjugates and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium and potassium salts.

WO 2007/031091 provides suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

Oligonucleotides or oligonucleotide conjugates of the invention may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

In some embodiments, the oligonucleotide or oligonucleotide conjugate of the invention is a prodrug. In particular with respect to oligonucleotide conjugates the conjugate moiety is cleaved of the oligonucleotide once the prodrug is delivered to the site of action, e.g. the target cell.

Applications

The oligonucleotides of the invention may be utilized as research reagents for, for example, therapeutics and prophylaxis.

In research, such oligonucleotides may be used to specifically modulate the synthesis of UBE3A protein in cells (e.g. in vitro cell cultures) and experimental animals thereby facilitating functional analysis of the target or an appraisal of its usefulness as a target for therapeutic intervention. The target modulation is achieved by degrading or inhibiting a modulator of the gene or mRNA producing the protein.

For therapeutics, an animal or a human, suspected of having a disease or disorder, which can be treated by modulating the expression of UBE3A.

The invention provides methods for treating or preventing a disease, comprising administering a therapeutically or prophylactically effective amount of an oligonucleotide, an oligonucleotide conjugate or a pharmaceutical composition of the invention to a subject suffering from or susceptible to the disease.

The invention also relates to an oligonucleotide, a composition or a conjugate as defined herein for use as a medicament.

The oligonucleotide, oligonucleotide conjugate or a pharmaceutical composition according to the invention is typically administered in an effective amount.

The invention also provides for the use of the oligonucleotide or oligonucleotide conjugate of the invention as described for the manufacture of a medicament for the treatment of a disorder as referred to herein, or for a method of the treatment of as a disorder as referred to herein.

The disease or disorder, as referred to herein, is associated with expression of UBE3A. In some embodiments the disease or disorder may be associated with a mutation in the maternal UBE3A gene. In some embodiments, the target nucleic acid is a regulator of the paternal UBE3A gene.

The methods of the invention are preferably employed for treatment or prophylaxis against diseases caused by abnormal levels and/or activity of UBE3A. The disease may in particular be caused by reduced levels and/or activity of UBE3A protein.

The invention further relates to use of an oligonucleotide, oligonucleotide conjugate or a pharmaceutical composition as defined herein for the manufacture of a medicament for the treatment of abnormal levels and/or activity of UBE3A, in particular low levels and/or activity of UBE3A.

In one embodiment, the invention relates to oligonucleotides, oligonucleotide conjugates or pharmaceutical compositions for use in the treatment of Angelman syndrome.

Administration

The oligonucleotides or pharmaceutical compositions of the present invention may be administered topical (such as, to the skin, inhalation, ophthalmic or otic) or enteral (such as, orally or through the gastrointestinal tract) or parenteral (such as, intravenous, subcutaneous, intra-muscular, intracerebral, intracerebroventricular or intrathecal).

In a preferred embodiment the oligonucleotide or pharmaceutical compositions of the present invention are administered by a parenteral route including intravenous, intraarterial, subcutaneous, intraperitoneal or intramuscular injection or infusion, intrathecal or intracranial, e.g., intracerebral or intraventricular, administration. In one embodiment the active oligonucleotide or oligonucleotide conjugate is administered intracerebral or intracerebroventricular. In another embodiment the active oligonucleotide or oligonucleotide conjugate is administered intrathecal.

The invention also provides for the use of the oligonucleotide or oligonucleotide conjugate of the invention as described for the manufacture of a medicament wherein the medicament is in a dosage form for intrathecal administration.

The invention also provides for the use of the oligonucleotide or oligonucleotide conjugate of the invention as described for the manufacture of a medicament wherein the medicament is in a dosage form for intracerebral or intraventricular administration.

The invention also provides for the use of the oligonucleotide or oligonucleotide conjugate of the invention as described for the manufacture of a medicament wherein the medicament is in a dosage form for intracerebroventricular administration.

Combination Therapies

In some embodiments the oligonucleotide, oligonucleotide conjugate or pharmaceutical composition of the invention is for use in a combination treatment with another therapeutic agent. The therapeutic agent can for example be anticonvulsant medication.

EMBODIMENTS

The following embodiments of the present invention may be used in combination with any other embodiments described herein.

1. An antisense oligonucleotide which comprises or consists of a contiguous nucleotide sequence of 10 to 30 nucleotides in length capable of inducing human paternal UBE3A expression, in particular in a neuronal cell.

2. The oligonucleotide of embodiment 1, wherein the contiguous nucleotide sequence is at least 95% complementarity to the part of human SNHG14 long non-coding RNA which is downstream of SNORD109B corresponding to position 25278410 to 25419462 on chromosome 15.

3. The oligonucleotide of embodiment 1 or 2, wherein the oligonucleotide is capable of hybridizing to a target nucleic acid of SEQ ID NO: 1 with a ΔG° below −10 kcal.

4. The oligonucleotide of embodiment 1-3, wherein the contiguous nucleotide sequence is at least 95%, such as 98%, such as 100% complementarity to region of the target nucleic acid of SEQ ID NO: 1 and/or 2.

5. The oligonucleotide of embodiment 1-3, wherein the contiguous nucleotide sequence is 100% complementary to a region of the target nucleic acid of position 1 to 55318 of SEQ ID NO: 1.

6. The oligonucleotide of embodiment 1-4, wherein the contiguous nucleotide sequence is complementary to a sub-sequence of the target nucleic acid, wherein the subsequence is selected from the group consisting of the regions indicated in table 1 or 2.

7. The oligonucleotide of embodiment 1-4, wherein the contiguous nucleotide sequence is at least 98% complementarity to the part of human SNHG14 long non-coding RNA which is antisense to the UBE3A pre-mRNA.

8. The oligonucleotide of embodiments 1-4 or 7, wherein the oligonucleotide is capable of hybridizing to a target nucleic acid corresponding to position 55319 to 141053 of SEQ ID NO: 1, with a ΔG° below −10 kcal.

9. The oligonucleotide of embodiments 1-4 or 7-8, wherein the contiguous nucleotide sequence is 100% complementary to a target nucleic acid of position 55319 to 141053 of SEQ ID NO: 1.

10. The oligonucleotide of embodiment 1-8, wherein the target nucleic acid is RNA.

11. The oligonucleotide of embodiment 10, wherein the RNA is a long non-coding RNA.

12. The oligonucleotide of embodiment 1-11, wherein the contiguous nucleotide sequence comprises or consists of at least 10 contiguous nucleotides, particularly 11, 12, 13, 14, 15, 16, 17, 18, 19, 20, 21, 22, 23, 24, 25, 26, 27, 28, or 29 contiguous nucleotides.

13. The oligonucleotide of embodiment 1-12, wherein the contiguous nucleotide sequence comprises or consists of from 12 to 22 nucleotides.

14. The oligonucleotide of embodiment 13, wherein the contiguous nucleotide sequence comprises or consists of from 15-20 nucleotides.

15. The oligonucleotide of embodiment 1-14, wherein the oligonucleotide comprises or consists of 10 to 35 nucleotides in length.

16. The oligonucleotide of embodiment 15, wherein the oligonucleotide comprises or consists of 15 to 24 nucleotides in length.

17. The oligonucleotide of embodiment 15 or 17, wherein the oligonucleotide comprises or consists of 17 to 22 nucleotides in length.

18. The oligonucleotide of embodiment 1-17, wherein the oligonucleotide or contiguous nucleotide sequence is single stranded.

19. The oligonucleotide of embodiment 1-18, wherein the contiguous nucleotide sequence is complementary to a sub-sequence of the target nucleic acid, selected from the group consisting of the regions indicated in table 1 or 2.

20. The oligonucleotide of embodiment 1-18, wherein the contiguous nucleotide sequence is complementary to a sub-sequence of the target nucleic acid selected from the group consisting of position 1589-10889, 46089-53989 and 60789-62489 of SEQ ID NO: 1.

21. The oligonucleotide of embodiment 1-18, wherein the contiguous nucleotide sequence is complementary to a sub-sequence of the target nucleic acid corresponding to positions 5218-5240 of SEQ ID NO: 1.

22. The oligonucleotide of embodiment 1-18, wherein the contiguous nucleotide sequence is complementary to a sub-sequence of the target nucleic acid corresponding to positions 5782-5803 of SEQ ID NO: 1.

23. The oligonucleotide of embodiment 1-18, wherein the contiguous nucleotide sequence is complementary to a sub-sequence of the target nucleic acid corresponding to positions 8113-8139 of SEQ ID NO: 1.

24. The oligonucleotide of embodiment 1-18, wherein the contiguous nucleotide sequence is complementary to a sub-sequence of the target nucleic acid corresponding to positions: 9200-9250 of SEQ ID NO: 1.

25. The oligonucleotide of embodiment 1-18, wherein the contiguous nucleotide sequence is complementary to a sub-sequence of the target nucleic acid corresponding to positions: 11505-11555 of SEQ ID NO: 1.

26. The oligonucleotide of embodiment 1-18, wherein the contiguous nucleotide sequence is complementary to a sub-sequence of the target nucleic acid corresponding to positions 13223-13242 of SEQ ID NO: 1.

27. The oligonucleotide of embodiment 1-18, wherein the contiguous nucleotide sequence is complementary to a sub-sequence of the target nucleic acid corresponding to positions 15100-15150 of SEQ ID NO: 1.

28. The oligonucleotide of embodiment 1-18, wherein the contiguous nucleotide sequence is complementary to a sub-sequence of the target nucleic acid corresponding to positions 15113-15180 of SEQ ID NO: 1.

29. The oligonucleotide of embodiment 1-18, wherein the contiguous nucleotide sequence is complementary to a sub-sequence of the target nucleic acid corresponding to positions 29635-29705 of SEQ ID NO: 1.

30. The oligonucleotide of embodiment 1-18, wherein the contiguous nucleotide sequence is complementary to a sub-sequence of the target nucleic acid corresponding to positions 30590-30740 of SEQ ID NO: 1.

31. The oligonucleotide of embodiment 1-18, wherein the contiguous nucleotide sequence is complementary to a sub-sequence of the target nucleic acid corresponding to positions 39800-39855 of SEQ ID NO: 1.

32. The oligonucleotide of embodiment 1-18, wherein the contiguous nucleotide sequence is complementary to a sub-sequence of the target nucleic acid corresponding to positions 44435-44460 of SEQ ID NO: 1.

33. The oligonucleotide of embodiment 1-18, wherein the contiguous nucleotide sequence is complementary to a sub-sequence of the target nucleic acid corresponding to positions 45245-45270 of SEQ ID NO: 1

34. The oligonucleotide of embodiment 1-18, wherein the contiguous nucleotide sequence is complementary to a sub-sequence of the target nucleic acid to positions 46380-46430 of SEQ ID NO: 1.

35. The oligonucleotide of embodiment 1-18, wherein the contiguous nucleotide sequence is complementary to a sub-sequence of the target nucleic acid corresponding to positions 68915-68940 of SEQ ID NO: 1.

36. The oligonucleotide of embodiment 1-35, wherein the oligonucleotide is neither siRNA nor self-complementary.

37. The oligonucleotide of embodiment 1-36, wherein the contiguous nucleotide sequence comprises or consists of a sequence selected from the group consisting of SEQ ID NO: 4, 5, 6, 7, 8, 9, 10, 11, 12, 13, 14, 15, 16, 17, 1819, 20, 21, 22, 23, 23, 24, 25, 26, 26, 27, 28, 29, 30, 31, 31, 32, 33, 34, 35, 36, 37, 38, 39, 40, 41, 42, 43, 44, 44, 45, 45, 46, 47, 48, 49, 50, 51, 52, 53, 53, 54, 54, 55, 56, 57, 58, 59, 60, 61, 62, 63, 64, 64, 65, 66, 67, 68, 69, 70, 71, 72, 73, 74, 75, 76, 77, 78, 79, 79, 80, 81, 8283, 84, 85, 86, 87, 88, 89, 90, 91, 92, 93, 94, 95, 95, 96, 96, 96, 97, 98, 99, 100, 101, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 702, 703, 704, 705, 706, 707, 708, 709, 710, 711, 712, 713, 714, 715, 716, 717, 718, 719, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 754, 755, 756, 757, 758, 759, 760, 761, 762, 763, 764, 765, 766, 767, 768, 769, 770, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817 and 818.

38. The oligonucleotide of embodiment 1-36, wherein the contiguous nucleotide sequence comprises or consists of a sequence selected from the group consisting of SEQ ID NO: 166, 167, 167 or 169 (see motif sequences listed in table 3 in the Examples section).

39. The oligonucleotide of embodiment 1-36, wherein the contiguous nucleotide sequence comprises or consists of a sequence selected from the group consisting of SEQ ID NO: 570, 571, 572, 679, 680, 681, 682 and 683 (see motif sequences listed in table 3 in the Examples section).

40. The oligonucleotide of embodiment 1-36, wherein the contiguous nucleotide sequence comprises or consists of a sequence selected from the group consisting of SEQ ID NO: 570, 571, 572, 679, 680, 681, 682 and 683 (see motif sequences listed in table 3 in the Examples section).

41. The oligonucleotide of embodiment 1-36, wherein the contiguous nucleotide sequence comprises or consists of a sequence selected from the group consisting of SEQ ID NO: 35, 199 to 210 or SEQ ID NO: 582 to 584 (see motif sequences listed in table 3 in the Examples section).

42. The oligonucleotide of embodiment 1-36, wherein the contiguous nucleotide sequence comprises or consists of a sequence selected from the group consisting of SEQ ID NO: 236, 237, 238, 239, 240 and 590 (see motif sequences listed in table 3 in the Examples section).

43. The oligonucleotide of embodiment 1-36, wherein the contiguous nucleotide sequence comprises or consists of a sequence selected from the group consisting of SEQ ID NO: 221 to 225 or SEQ ID NO: 585 to 589 (see motif sequences listed in table 3 in the Examples section).

44. The oligonucleotide of embodiment 1-36, wherein the contiguous nucleotide sequence comprises or consists of a sequence selected from the group consisting of SEQ ID NO: 241 or 591 (see motif sequences listed in table 3 in the Examples section).

45. The oligonucleotide of embodiment 1-36, wherein the contiguous nucleotide sequence comprises or consists of a sequence selected from the group consisting of SEQ ID NO: 46-48, 285 to 305 or SEQ ID NO: 613 to 632 or SEQ ID NO: 721 to 807 (see motif sequences listed in table 3 in the Examples section).

46. The oligonucleotide of embodiment 1-36, wherein the contiguous nucleotide sequence comprises or consists of a sequence selected from the group consisting of of SEQ ID NO: 331, 332, 638, 639, 640, 808, 809, 810, 811, 812, 813, 814 and 815 (see motif sequences listed in table 3 in the Examples section).

47. The oligonucleotide of embodiment 1-36, wherein the contiguous nucleotide sequence comprises or consists of a sequence selected from the group consisting of SEQ ID NO: 409 to 411 or SEQ ID NO: 642 to 646 or SEQ ID NO: 816 to 818 (see motif sequences listed in table 3 in the Examples section).
48. The oligonucleotide of embodiment 1-47, wherein the contiguous nucleotide sequence has zero to three mismatches compared to the target nucleic acid it is complementary to.
49. The oligonucleotide of embodiment 48, wherein the contiguous nucleotide sequence has one mismatch compared to the target nucleic acid.
50. The oligonucleotide of embodiment 48, wherein the contiguous nucleotide sequence has two mismatches compared to the target nucleic acid.
51. The oligonucleotide of embodiment 48, wherein the contiguous nucleotide sequence is fully complementary to the target nucleic acid sequence.
52. The oligonucleotide of embodiment 1-51, comprising one or more modified nucleosides.
53. The oligonucleotide of embodiment 52, wherein the one or more modified nucleoside is a high-affinity modified nucleosides.
54. The oligonucleotide of embodiment 52 or 53, wherein the one or more modified nucleoside is a 2' sugar modified nucleoside.
55. The oligonucleotide of embodiment 54, wherein the one or more 2' sugar modified nucleoside is independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, 2'-fluoro-ANA and LNA nucleosides.
56. The oligonucleotide of embodiment 54, wherein the one or more modified nucleoside is a LNA nucleoside.
57. The oligonucleotide of embodiment 56, wherein the modified LNA nucleoside is oxy-LNA.
58. The oligonucleotide of embodiment 57, wherein the modified nucleoside is beta-D-oxy-LNA.
59. The oligonucleotide of embodiment 57, wherein the modified nucleoside is alpha-L-oxy-LNA
60. The oligonucleotide of embodiment 56, wherein the modified nucleoside is thio-LNA.
61. The oligonucleotide of embodiment 56, wherein the modified nucleoside is amino-LNA.
62. The oligonucleotide of embodiment 56, wherein the modified nucleoside is cET.
63. The oligonucleotide of embodiment 56, wherein the modified nucleoside is ENA.
64. The oligonucleotide of embodiment 56, wherein the modified LNA nucleoside is selected from beta-D-oxy-LNA, alpha-L-oxy-LNA, beta-D-amino-LNA, alpha-L-amino-LNA, beta-D-thio-LNA, alpha-L-thio-LNA, (S)cET, (R)cET beta-D-ENA and alpha-L-ENA.
65. The oligonucleotide of any one of embodiments 1-64, wherein the oligonucleotide comprises at least one modified internucleoside linkage.
66. The oligonucleotide of embodiment 65, wherein the modified internucleoside linkage is nuclease resistant.
67. The oligonucleotide of embodiment 65 or 66, wherein at least 50% of the internucleoside linkages within the contiguous nucleotide sequence are phosphorothioate internucleoside linkages or boranophosphate internucleoside linkages.
68. The oligonucleotide of embodiment 65 or 66, wherein all the internucleoside linkages within the contiguous nucleotide sequence are phosphorothioate internucleoside linkages.
69. The oligonucleotide of embodiment 1-68, wherein the oligonucleotide is capable of recruiting RNase H.
70. The oligonucleotide of embodiment 69, wherein the oligonucleotide is a gapmer.
71. The oligonucleotide of embodiment 69 or 70, wherein the oligonucleotide is a gapmer of formula 5'-F-G-F'-3', where region F and F' independently comprise or consist of 1-7 modified nucleosides and G is a region between 6 and 16 nucleosides which are capable of recruiting RNaseH.
72. The oligonucleotide of embodiment 71, wherein the modified nucleoside is a 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.
73. The oligonucleotide of embodiment 71 or 72, wherein one or more of the modified nucleosides in region F and F' is a LNA nucleoside.
74. The oligonucleotide of embodiment 73, wherein all the modified nucleosides in region F and F' are LNA nucleosides.
75. The oligonucleotide of embodiment 74, wherein region F and F' consist of LNA nucleosides.
76. The oligonucleotide of embodiment 73-75, wherein all the modified nucleosides in region F and F' are oxy-LNA nucleosides.
77. The oligonucleotide of embodiment 73, wherein at least one of region F or F' further comprises at least one 2' substituted modified nucleoside independently selected from the group consisting of 2'-O-alkyl-RNA, 2'-O-methyl-RNA, 2'-alkoxy-RNA, 2'-O-methoxyethyl-RNA, 2'-amino-DNA and 2'-fluoro-DNA.
78. The oligonucleotide of embodiment 73-77, wherein the RNaseH recruiting nucleosides in region G are independently selected from DNA, alpha-L-LNA, C4' alkylated DNA, ANA and 2'F-ANA and UNA.
79. The oligonucleotide of embodiment 78, wherein the nucleosides in region G is DNA and/or alpha-L-LNA nucleosides.
80. The oligonucleotide of embodiment 78 or 79, wherein region G consists of at least 75% DNA nucleosides.
81. The oligonucleotide of embodiment 1-80, wherein the oligonucleotide is capable of increasing the expression of UBE3A by at least 30% compared to a control.
82. The oligonucleotide of embodiment 1-81, wherein the level of the SNHG14 transcript downstream of SNORD109B is reduced by at least 20% compared to a control.
83. The oligonucleotide of embodiment 1-82, wherein the expression of SNORD115 is not significantly affected compared to a control.
84. The oligonucleotide of embodiment 1-83, wherein the oligonucleotide is selected from CMP ID NO: 4_1 to 678_1.
85. The oligonucleotide of embodiment 1-83, wherein the oligonucleotide is selected from the group consisting of CMP ID NO: 4_1, 4_2, 5_1, 5_2, 6_1, 6_2, 7_1, 7_2, 8_1, 9_1, 101, 111, 11_2, 121, 12_2, 13_1, 13_2, 14_1, 15_1, 16_1, 17_1, 17_2, 18_1, 18_2, 19_1, 19_2, 20_1, 21_1, 22_1, 23_1, 23_2, 24_1, 25_1, 26_1, 26_2, 27_1, 28_1, 28_2, 29_1, 29_2, 30_1, 31_1, 31_2, 32_1, 33_1, 34_1, 34_2, 34_3, 34_4, 34_5, 34_6, 34_7, 35_1, 35_2, 36_1, 37_1, 38_1, 38_2, 38_3, 38_4, 38_5, 38_6, 39_1, 39_2, 39_3, 39_4, 39_5, 40_1, 40_2, 40_3, 40_4, 40_5, 40_6, 40_7, 40_8, 41_1, 42_1, 43_1, 44_1, 44_2, 45_1, 4_2, 46_1, 47_1, 48_1, 48_2, 48_3, 48_4, 48_5, 48_6, 48_7, 49_1, 50_1, 51_1, 52_1, 53_1, 53_2, 54_1, 54_2, 54_3, 55_1, 55_2, 56_1, 57_1, 58_1, 58_2, 58_3, 59_1, 59_2, 60_1, 60_2, 60_3, 61_1, 62_1, 63_1, 64_1, 64_2, 65_1, 66_1, 67_1, 68_1, 69_1, 69_2, 69_3, 70_1, 70_2, 70_3, 71_1, 72_1, 72_2, 73_1, 73_2, 73_3, 74_1, 74_2, 75_1, 75_2, 76_1, 77_1, 77_2, 77_3, 78_1, 79_1, 79_2, 79_3, 80_1, 80_2, 80_3, 81_1, 82_1, 82_2, 83_1, 83_2, 84_1, 84_2, 85_1, 85_2, 86_1, 87_1, 88_1, 88_2, 89_1, 90_1, 91_1, 92_1, 93_1, 94_1, 95_1, 95_2, 961, 96_2, 96_3, 97_1, 97_2, 97_3, 97_4, 98_1, 98_2, 98_3, 99_1, 99_2, 99_3, 99_4, 100_1, 100_2, 100_3, 101_1, 101_2, 101_3, 101_4, 102_1, 102_2, 102_3, 102_4, 103_1, 103_2, 103_3, 103_4, 104_1, 104_2, 104_3, 105_1, 105_2, 105_3, 105_4, 106_1, 106_2, 106_3, 106_4, 107_1, 107_2, 107_3, 107_4, 108_1, 108_2, 108_3, 108_4, 109_1, 109_2, 109_3, 109_4, 110_1, 110_2, 111_1, 111_2, 111_3, 112_1, 112_2, 113_1, 114_1, 115_1, 116_1, 117_1, 118_1, 119_1, 120_1, 120_2, 121_1, 122_1, 123_1, 124_1, 125_1, 126_1, 126_2, 127_1, 128_1, 128_2, 128_3, 128_4, 129_1, 129_2, 130_1, 131_1, 132_1, 132_2, 132_3, 133_1, 133_2, 133_3, 133_4, 134_1, 134_2, 135_1, 135_2, 136_1, 137_1, 138_1, 139_1, 140_1, 141_1, 142_1, 143_1, 144_1, 145_1, 145_2, 146_1, 146_2, 147_1, 148_1, 149_1, 150_1, 150_2, 151_1, 152_1, 153_1, 154_1, 155_1, 156_1, 157_1, 158_1, 159_1, 160_1, 161_1, 162_1, 163_1, 164_1, 165_1, 166_1, 167_1, 168_1, 169_1, 169_10, 169_11, 169_12, 169_13, 169_14, 169_15, 169_16, 169_17, 169_18, 169_19, 169_2, 169_20, 169_21, 169_22, 169_23, 169_24, 169_25, 169_26, 169_27, 169_28, 169_29, 169_3, 169_30, 169_31, 169_32, 169_33, 169_34, 169_35, 169_36, 169_37, 169_38, 169_39, 169_4, 169_40, 169_41, 169_42, 169_43, 169_44, 169_45, 169_46, 169_47, 169_48, 169_49, 169_5, 169_50, 169_51, 169_52, 169_53, 169_54, 169_55, 169_56, 169_57, 169_6, 169_7, 169_8, 169_9, 169_58, 169_59, 169_60, 169_61, 169_62, 170_1, 171_1, 172_1, 173_1, 174_1, 175_1, 176_1, 177_1, 178_1, 179_1, 180_1, 181_1, 182_1, 183_1, 184_1, 185_1, 186_1, 187_1, 188_1, 189_1, 190_1, 191_1, 192_1, 193_1, 194_1, 195_1, 196_1, 197_1, 198_1, 199_1, 200_1, 201_1, 202_1, 203_1, 204_1, 205_1, 206_1, 207_1, 208_1, 208_2, 208_3, 208_4, 208_5, 208_6, 208_7, 209_1, 209_10, 209_2, 209_3, 209_4, 209_5, 209_6, 209_7, 209_8, 209_9, 210_1, 211_1, 212_1, 213_1, 214_1, 215_1, 216_1, 217_1, 218_1, 219_1, 220_1, 221_1, 222_1, 223_1, 224_1, 225_1, 226_1, 227_1, 228_1, 229_1, 230_1, 231_1, 232_1, 233_1, 234_1, 235_1, 236_1, 236_10, 236_11, 236_12, 236_13, 236_14, 236_15, 236_16, 236_2, 236_3, 236_4, 236_5, 236_6, 236_7, 236_8, 236_9, 236_17, 236_18, 236_19, 236_20, 236_21, 237_1, 237_10, 237_11, 237_12, 237_13, 237_14, 237_15, 237_16, 237_2, 237_3, 237_4, 237_5, 237_6, 237_7, 237_8, 237_9, 237_17, 237_18, 237_19, 237_20, 237_21, 238_1, 239_1, 239_10, 239_11, 239_12, 239_13, 239_14, 239_15, 239_16, 239_2, 239_3, 239_4, 239_5, 239_6, 239_7, 239_8, 239_9, 239_17, 239_18, 239_19, 239_20, 239_21, 240_1, 241_1, 241_10, 241_2, 241_3, 241_4, 241_5, 241_6, 241_7, 241_8, 241_9, 241_11, 241_12, 241_13, 241_14, 241_15, 242_1, 243_1, 244_1, 244_2, 244_3, 244_4, 244_5, 245_1, 246_1, 247_1, 248_1, 249_1, 250_1, 251_1, 252_1, 253_1, 254_1, 255_1, 256_1, 257_1, 258_1, 259_1, 260_1, 261_1, 262_1, 263_1, 264_1, 265_1, 266_1, 267_1, 268_1, 269_1, 270_1, 271_1, 272_1, 273_1, 274_1, 275_1, 276_1, 277_1, 278_1, 279_1, 280_1, 281_1, 282_1, 283_1, 284_1, 285_1, 285_2, 285_3, 285_4, 285_5, 285_6, 285_7, 285_8, 285_9, 285_10, 285_11, 286_1, 287_1, 288_1, 289_1, 290_1, 291_1, 292_1, 293_1, 294_1, 295_1, 296_1, 297_1, 298_1, 299_1, 300_1, 301_1, 302_1, 303_1, 304_1, 304_10, 304_2, 304_3, 304_4, 304_5, 304_6, 304_7, 304_8, 304_9, 304_11, 304_12, 304_13, 304_14, 304_15, 305_1, 306_1, 307_1, 308_1, 309_1, 310_1, 311_1, 312_1, 313_1, 314_1, 315_1, 316_1, 317_1, 318_1, 319_1, 320_1, 321_1, 322_1, 323_1, 324_1, 325_1, 326_1, 327_1, 328_1, 329_1, 330_1, 331_1, 332_1, 333_1, 334_1, 335_1, 336_1, 337_1, 338_1, 339_1, 340_1, 341_1, 342_1, 343_1, 344_1, 345_1, 346_1, 347_1, 348_1, 349_1, 350_1, 351_1, 352_1, 353_1, 354_1, 355_1, 356_1, 357_1, 358_1, 359_1, 360_1, 361_1, 361_10, 361_2, 361_3, 361_4, 361_5, 361_6, 361_7, 361_8, 361_9, 362_1, 362_10, 362_2, 362_3, 362_4, 362_5, 362_6, 362_7, 362_8, 362_9, 363_1, 364_1, 365_1, 366_1, 367_1, 368_1, 369_1, 370_1, 371_1, 372_1, 373_1, 374_1, 375_1, 376_1, 377_1, 378_1, 379_1, 380_1, 381_1, 382_1, 383_1, 384_1, 385_1, 386_1, 387_1, 388_1, 389_1, 390_1, 391_1, 392_1, 393_1, 394_1, 395_1, 396_1, 397_1, 398_1, 399_1, 400_1, 401_1, 402_1, 403_1, 404_1, 405_1, 406_1, 407_1, 408_1, 409_1, 410_1, 411_1, 412_1, 413_1, 414_1, 415_1, 416_1, 417_1, 418_1, 419_1, 420_1, 421_1, 422_1, 423_1, 424_1, 425_1, 425_10, 425_2, 425_3, 425_4, 425_5425_6425__7425_8425_942614271428_1, 429_1, 430_1, 431_1, 432_1, 433_1, 434_1, 435_1, 436_1, 437_1, 438_1, 439_1, 440_1, 441_1, 442_1, 443_1, 444_1, 445_1, 446_1, 447_1, 448_1, 449_1, 450_1, 451_1, 452_1, 453_1, 454_1, 455_1, 456_1, 457_1, 458_1, 459_1, 460_1, 461_1, 462_1, 463_1, 464_1, 465_1, 466_1, 467_1, 468_1, 469_1, 470_1, 471_1, 472_1, 473_1, 474_1, 475_1, 476_1, 477_1, 478_1, 479_1, 480_1, 481_1, 482_1, 483_1, 484_1, 485_1, 486_1, 487_1, 488_1, 489_1, 490_1, 491_1, 492_1, 493_1, 494_1, 495_1, 496_1, 497_1, 498_1, 499_1, 500_1, 501_1, 502_1, 503_1, 504_1, 505_1, 506_1, 507_1, 508_1, 509_1, 510_1, 511_1, 512_1, 513_1, 514_1, 515_1, 516_1, 517_1, 518_1, 519_1, 520_1, 521_1, 522_1, 523_1, 524_1, 525_1, 526_1, 527_1, 528_1, 529_1, 530_1, 531_1, 532_1, 533_1, 534_1, 535_1, 536_1, 537_1, 538_1, 539_1, 540_1, 541_1, 542_1, 543_1, 544_1, 545_1, 546_1, 547_1, 548_1, 549_1, 550_1, 551_1, 552_1, 553_1, 554_1, 555_1, 556_1, 557_1, 558_1, 559_1, 560_1, 561_1, 562_1, 563_1, 564_1, 565_1, 566_1, 567_1, 568_1, 569_1, 570_1, 570_2, 570_3, 570_4, 570_5, 570_6, 570_7, 570_8, 570_9, 570_10, 570_11, 570_12, 570_13, 570_14, 571_1, 571_2, 571_3, 571_4, 571_5, 571_6, 571_7, 571_8, 571_9, 571_10, 571_11, 571_12, 571_13, 571_14, 572_1, 572_2, 572_3, 572_4, 572_5, 572_6, 572_7, 572_8, 572_9, 572_10, 572_11, 572_12, 572_13, 572_14, 573_1, 573_2, 573_3, 573_4, 573_5, 573_6, 573_7, 573_8, 573_9, 573_10, 573_11, 573_12, 573_13, 573_14, 574_1, 574_2, 574_3, 574_4, 574_5, 574_6, 574_7, 574_8, 574_9, 574_10, 574_11, 574_12, 574_13, 574_14, 575_1, 575_2, 575_3, 575_4, 575_5, 575_6, 575_7, 575_8, 575_9, 575_10, 575_11, 575_12, 575_13, 575_14, 576_1, 576_2, 576_3, 576_4, 576_5, 576_6, 576_7, 576_8, 576_9, 576_10, 576_11, 576_12, 576_13, 576_14, 577_1, 577_2, 577_3, 577_4, 577_5, 577_6, 577_7, 577_8, 577_9, 577_10, 577_11, 577_12, 577_13, 577_14, 578_1, 578_2, 578_3, 578_4, 578_5, 578_6, 578_7, 578_8, 578_9, 579_1, 579_2, 579_3, 579_4, 579_5, 579_6, 579_7, 579_8, 579_9, 580_1, 580_2, 580_3, 580_4, 580_5, 580_6, 580_7, 580_8, 580_9, 581_1, 581_2, 581_3, 581_4, 581_5, 581_6, 581_7, 581_8, 581_9, 582_1, 582_2, 582_3, 582_4, 582_5, 582_6, 582_7, 582_8, 582_9, 583_1, 583_2, 583_3, 583_4, 583_5, 583_6, 583_7, 583_8, 583_9, 584_1, 584_2, 584_3, 584_4, 584_5, 584_6, 584_7, 584_8, 585_1, 585_2, 585_3, 585_4, 585_5, 585_6, 585_7, 585_8, 585_9, 585_10, 585_11, 585_12, 585_13, 585_14, 586_1, 586_2, 586_3, 586_4, 586_5, 586_6, 586_7, 586_8, 586_9, 586_10, 586_11, 586_12, 586_13, 586_14, 587_1, 587_2, 587_3, 587_4, 587_5, 587_6, 587_7, 587_8, 587_9, 587_10, 587_11, 587_12, 587_13, 587_14, 588_1, 588_2, 588_3, 588_4, 588_5, 588_6, 588_7, 588_8, 588_9, 588_10, 588_11, 588_12, 588_13, 588_14, 589_1, 589_2, 589_3, 589_4, 589_5, 589_6, 589_7, 589_8, 589_9, 589_10, 589_11, 589_12, 589_13, 589_14, 590_1, 590_10, 590_11, 590_12, 590_13, 590_14, 590_15, 590_2, 590_3, 590_4, 590_5, 590_6, 590_7, 590_8, 590_9, 590_16, 590_17, 590_18, 590_19, 590_20, 591_1, 591_2, 592_1, 592_2, 592_3, 592_4, 592_5, 592_6, 592_7, 592_8, 592_9, 592_10, 592_11, 592_12, 592_13, 592_14, 593_1, 593_2, 593_3, 593_4, 594_1, 594_2, 594_3, 594_4, 595_1, 595_2, 595_3, 595_4, 596_1, 596_2, 596_3, 596_4, 597_1, 597_2, 597_3, 597_4, 598_1, 598_2, 598_3, 598_4, 599_1, 599_2, 599_3, 599_4, 600_1, 600_2, 600_3, 600_4, 601_1, 601_2, 601_3, 601_4, 602_1, 602_2, 602_3, 602_4, 603_1, 603_2, 603_3, 603_4, 604_1, 604_2, 604_3, 604_4, 605_1, 605_2, 605_3, 605_4, 606_1, 606_2, 606_3, 606_4, 607_1, 607_2, 607_3, 607_4, 608_1, 608_2, 608_3, 608_4, 608_5, 608_6, 608_7, 608_8, 608_9, 609_1, 609_2, 609_3, 609_4, 609_5, 609_6, 609_7, 609_8, 609_9, 610_1, 610_2, 610_3, 610_4, 610_5, 610_6, 610_7, 610_8, 610_9, 611_1, 611_2, 611_3, 611_4, 611_5, 611_6, 611_7, 611_8, 611_9, 612_1, 612_2, 612_3, 612_4, 612_5, 612_6, 612_7, 612_8, 612_9, 613_1, 613_2, 613_3, 613_4, 613_5, 613_6, 613_7, 613_8, 613_9, 613_10, 614_1, 614_2, 614_3, 614_4, 614_5, 614_6, 614_7, 614_8, 614_9, 614_10, 615_1, 615_2, 615_3, 615_4, 615_5, 615_6, 615_7, 615_8, 615_9, 615_10, 616_1, 616_2, 616_3, 616_4, 616_5, 616_6, 616_7, 616_8, 616_9, 616_10, 617_1, 617_2, 617_3, 617_4, 617_5, 617_6, 617_7, 617_8, 617_9, 617_10, 618_1, 618_2, 618_3, 618_4, 618_5, 618_6, 618_7, 618_8, 618_9, 618_10, 619_1, 619_2, 619_3, 619_4, 619_5, 619_6, 619_7, 619_8, 619_9, 619_10, 620_1, 620_2, 620_3, 620_4, 620_5, 620_6, 620_7, 620_8, 620_9, 620_10, 621_1, 621_2, 621_3, 621_4, 621_5, 621_6, 621_7, 621_8, 621_9, 621_10, 621_11, 622_1, 622_2, 622_3, 622_4, 622_5, 622_6, 622_7, 622_8, 622_9, 622_10, 623_1, 623_2, 623_3, 623_4, 623_5, 623_6, 623_7, 623_8, 623_9, 623_10, 624_1, 624_2, 624_3, 624_4, 624_5, 624_6, 624_7, 624_8, 624_9, 624_10, 625_1, 625_2, 625_3, 625_4, 625_5, 625_6, 625_7, 625_8, 625_9, 625_10, 625_11, 625_12, 625_13, 625_14, 626_1, 626_2, 626_3, 626_4, 626_5, 626_6, 626_7, 626_8, 626_9, 626_10, 626_11, 626_12, 626_13, 626_14, 627_1, 627_2, 627_3, 627_4, 627_5, 627_6, 627_7, 627_8, 627_9, 627_10, 627_11, 627_12, 627_13, 627_14, 628_1, 628_2, 628_3, 628_4, 628_5, 628_6, 628_7, 628_8, 628_9, 628_10, 628_11, 628_12, 628_13, 628_14, 629_1, 629_10, 629_11, 629_2, 629_3, 629_4, 629_5, 629_6, 629_7, 629_8, 629_9, 629_12, 629_13, 629_14, 629_15, 629_16, 630_1, 630_2, 630_3, 631_1, 631_10, 631_2, 631_3, 631_4, 631_5, 631_6, 631_7, 631_8, 631_9, 631_11, 631_12, 631_13, 631_14, 631_15, 632_1, 632_2, 632_3, 632_4, 632_5, 632_6, 632_7, 632_8, 632_9, 632_10, 632_11, 632_12, 632_13, 632_14, 633_1, 633_2, 633_3, 633_4, 633_5, 633_6, 633_7, 633_8, 633_9, 634_1, 634_2, 634_3, 634_4, 634_5, 634_6, 634_7, 634_8, 634_9, 635_1, 635_2, 635_3, 635_4, 635_5, 635_6, 635_7, 635_8, 635_9, 636_1, 636_2, 636_3, 636_4, 636_5, 636_6, 636_7, 636_8, 636_9, 637_1, 637_2, 637_3, 637_4, 637_5, 637_6, 637_7, 637_8, 637_9, 638_1, 638_2, 638_3, 638_4, 638_5, 638_6, 638_7, 638_8, 638_9, 638_10, 638_11, 638_12, 638_13, 638_14, 639_1, 639_2, 639_3, 639_4, 639_5, 639_6, 639_7, 639_8, 639_9, 639_10, 639_11, 639_12, 639_13, 639_14, 640_1, 640_2, 640_3, 640_4, 640_5, 640_6, 640_7, 640_8, 640_9, 640_10, 640_11, 640_12, 640_13, 640_14, 641_1, 641_2, 641_3, 641_4, 641_5, 641_6, 641_7, 641_8, 641_9, 642_1, 642_10, 642_11, 642_12, 642_13, 642_14, 642_15, 642_16, 642_17, 642_2, 642_3, 642_4, 642_5, 642_6, 642_7, 642_8, 642_9, 642_18, 642_19, 642_20, 642_21, 642_22, 643_1, 644_1, 644_2, 644_3, 644_4, 644_5, 644_6, 645_1, 645_2, 645_3, 645_4, 645_5, 645_6, 645_7, 645_8, 645_9, 645_10, 646_1, 646_10, 646_11, 646_12, 646_13, 646_14, 646_15, 646_16, 646_17, 646_18, 646_19, 646_2, 646_3, 646_4, 646_5, 646_6, 646_7, 646_8, 646_9, 646_20, 646_21, 646_22, 646_23, 646_24, 647_1, 648_1, 649_1, 650_1, 651_1, 652_1, 653_1, 654_1, 655_1, 656_1, 657_1, 658_1, 659_1, 660_1, 661_1, 662_1, 663_1, 664_1, 665_1, 666_1, 667_1, 668_1, 669_1, 670_1, 671_1, 672_1, 673_1, 674_1, 675_1, 676_1, 677_1, 678_1, 679_1, 679_2, 679_3, 679_4, 679_5, 680_1, 680_2, 680_3, 680_4, 680_5, 681_1, 681_2, 681_3, 681_4, 681_5, 682_1, 682_2, 682_3, 682_4, 682_5, 683_1, 683_2, 683_3, 683_4, 683_5, 684_1, 684_2, 684_3, 684_4, 684_5, 685_1, 685_2, 685_3, 685_4, 685_5, 686_1, 686_2, 686_3, 686_4, 686_5, 687_1, 687_2, 687_3, 687_4, 687_5, 688_1, 688_2, 688_3, 688_4, 688_5, 689_1, 689_2, 689_3, 689_4, 689_5, 690_1, 690_2, 690_3, 690_4, 690_5, 691_1, 691_2, 692_1, 692_2, 692_3, 692_4, 692_5, 693_1, 693_2, 693_3, 693_4, 693_5, 694_1, 694_2, 694_3, 694_4, 694_5, 695_1, 695_2, 695_3, 695_4, 695_5, 696_1, 696_2, 696_3, 696_4, 696_5, 697_1, 697_2, 697_3, 697_4, 697_5, 698_1, 698_2, 698_3, 698_4, 698_5, 699_1, 699_2, 699_3, 699_4, 699_5, 700_1, 700_2, 700_3, 700_4, 700_5, 701_1, 701_2, 701_3, 701_4, 701_5, 702_1, 702_2, 702_3, 702_4, 702_5, 703_1, 703_2, 703_3, 703_4, 703_5, 704_1, 704_2, 704_3, 704_4, 704_5, 705_1, 705_2, 705_3, 705_4, 705_5, 706_1, 706_2, 706_3, 706_4, 706_5, 707_1, 707_2, 707_3, 707_4, 707_5, 708_1, 708_2, 708_3, 708_4, 708_5, 709_1, 709_2, 709_3, 709_4, 709_5, 710_1, 710_2, 710_3, 710_4, 710_5, 711_1, 711_2, 711_3, 711_4, 711_5, 712_1, 712_2, 712_3, 712_4, 712_5, 713_1, 713_2, 713_3, 713_4, 713_5, 714_1, 714_2, 714_3, 714_4, 714_5, 715_1, 715_2, 715_3, 715_4, 715_5, 716_1, 716_2, 716_3, 716_4, 716_5, 717_1, 717_2, 717_3, 717_4, 717_5, 718_1, 718_2, 719_1, 719_2, 719_3, 719_4, 719_5, 720_1, 720_2, 720_3, 720_4, 720_5, 721_1, 721_2, 721_3, 721_4, 721_5, 722_1, 722_2, 722_3, 722_4, 722_5, 723_1, 723_2, 723_3, 723_4, 723_5, 724_1, 724_2, 724_3, 724_4, 724_5, 725_1, 725_2, 725_3, 725_4, 725_5, 726_1, 726_2, 726_3, 726_4, 726_5, 727_1, 727_2, 727_3, 727_4, 727_5, 728_1, 728_2, 728_3, 728_4, 728_5, 729_1, 729_2, 729_3, 729_4, 729_5, 730_1, 730_2, 730_3, 730_4, 730_5, 731_1, 731_2, 731_3, 731_4, 731_5, 732_1, 732_2, 732_3, 732_4, 732_5, 733_1, 733_2, 733_3, 733_4, 733_5, 734_1, 734_2, 373_4, 34_4, 734_5, 735_1, 735_2, 735_3, 735_4, 735_5, 736_1, 736_2, 736_3, 736_4, 736_5, 737_1, 737_2, 737_3, 737_4, 737_5, 738_1, 738_2, 738_3, 738_4, 738_5, 738_6, 739_1, 739_2, 739_3, 739_4, 739_5, 740_1, 740_2, 740_3, 740_4, 740_5, 741_1, 741_2, 741_3, 741_4, 741_5, 742_1, 742_2, 742_3, 743_1, 743_2, 743_3, 743_4, 743_5, 744_1, 744_2, 744_3, 744_4, 744_5, 745_1, 745_2, 745_3, 745_4, 745_5, 746_1, 746_2, 746_3, 747_1, 747_2, 747_3, 747_4, 747_5, 748_1, 748_2, 748_3, 748_4, 748_5, 749_1, 749_2, 749_3, 749_4, 749_5, 750_1, 750_2, 750_3, 750_4, 7_1, 751_2, 751_3, 751_4, 751_5, 752_1, 752_2, 752_3, 752_4, 752_5, 753_1, 753_2, 753_3, 753_4, 753_5, 754_1, 754_2, 754_3, 754_4, 754_5, 755_1, 755_2, 755_3, 755_4, 755_5, 756_1, 756_2, 756_3, 756_4, 756_5, 757_1, 757_2, 757_3, 757_4, 757_5, 758_1, 758_2, 758_3, 758_4, 758_5, 759_1, 759_2, 759_3, 759_4, 759_5, 760_1, 760_2, 760_3, 760_4, 760_5, 761_1, 761_2, 761_3, 761_4, 761_5, 762_1, 762_2, 762_3, 762_4, 762_5, 763_1, 763_2, 763_3, 763_4, 763_5, 764_1, 764_2, 764_3, 764_4, 764_5, 765_1, 765_2, 765_3, 765_4, 765_5, 766_1, 766_2, 766_3, 766_4, 766_5, 767_1, 767_2, 767_3, 767_4, 767_5, 768_1, 768_2, 768_3, 768_4, 768_5, 769_1, 769_2, 769_3, 769_4, 769_5, 770_1, 770_2, 770_3, 770_4, 770_5, 771_1, 771_2, 771_3, 771_4, 771_5, 772_1, 772_2, 772_3, 772_4, 772_5, 773_1, 773_2, 773_3, 773_4, 773_5, 774_1, 774_2, 774_3, 774_4, 774_5, 775_1, 775_2, 775_3, 775_4, 775_5, 776_1, 776_2, 776_3, 776_4, 776_5, 777_1, 777_2, 777_3, 777_4, 777_5, 778_1, 778_2, 778_3, 778_4, 778_5, 779_1, 779_2, 779_3, 779_4, 779_5, 780_1, 780_2, 780_3, 780_4, 780_5, 781_1, 782_1, 782_2, 782_3, 782_4, 782_5, 783_1, 783_2, 783_3, 783_5, 784_1, 784_2, 784_3, 784_4, 784_5, 785_1, 786_1, 786_2, 786_3, 786_4, 786_5, 787_1, 787_2, 787_3, 787_4, 787_5, 788_1, 788_2, 788_3, 788_4, 788_5, 789_1, 789_2, 789_3, 789_4, 789_5, 790_1, 790_2, 790_3, 790_4, 790_5, 791_1, 791_2, 791_3, 791_4, 791_5, 792_1, 792_2, 792_3, 792_4, 792_5, 793_1, 793_2, 793_3, 793_4, 793_5, 794_1, 794_2, 794_3, 4, 7_4, 794_5, 795_1, 795_2, 795_3, 795_4, 795_5, 796_1, 796_2, 796_3, 796_4, 796_5, 797_1, 797_2, 797_3, 797_4, 797_5, 798_1, 798_2, 798_3, 798_4, 798_5, 799_1, 799_2, 799_3, 799_4, 799_5, 800_1, 800_2, 800_3, 800_4, 800_5, 801_1, 801_2, 801_3, 801_4, 801_5, 802_1, 802_2, 802_3, 802_4, 802_5, 803_1, 803_2, 803_3, 803_4, 803_5, 804_1, 804_2, 804_3, 804_4, 804_5, 805_1, 805_2, 805_3, 805_4, 805_5, 806_1, 806_2, 806_3, 806_4, 806_5, 807_1, 807_2, 807_3, 807_4, 807_5, 808_1, 808_2, 808_3, 808_4, 808_5, 809_1, 809_2, 809_3, 809_4, 809_5, 810_1, 810_2, 810_3, 810_4, 810_5, 811_1, 811_2, 811_3, 811_4, 811_5, 812_1, 812_2, 812_3, 812_4, 812_5, 813_1, 813_2, 813_3, 813_4, 813_5, 814_1, 814_2, 814_3, 814_4, 814_5, 815_1, 815_2, 815_3, 15_4, 815_5, 816_1, 816_2, 816_3, 816_4, 816_5, 816_6, 817_1 and 818_1.

86. The oligonucleotide of embodiment 85, wherein the oligonucleotide is selected from CMP-ID-NO: 155_1 or 165_1.
87. The oligonucleotide of embodiment 85, wherein the oligonucleotide is selected from the group consisting of CMP-ID-NO 169_52, 169_50 or 169_56.
88. The oligonucleotide of embodiment 85, wherein the oligonucleotide is selected from the group consisting of CMP-ID-NO: 172_1, 272_1, 572_7, 572_6 or 572_5.
89. The oligonucleotide of embodiment 85, wherein the oligonucleotide is selected from CMP-ID-NO: 175_1.
90. The oligonucleotide of embodiment 85, wherein the oligonucleotide is selected from CMP-ID-NO: 178_1.
91. The oligonucleotide of embodiment 85, wherein the oligonucleotide is selected from CMP-ID-NO: 573_8, 186_1 or 187_1.
92. The oligonucleotide of embodiment 85, wherein the oligonucleotide is selected from CMP-ID-NO: 186_1.
93. The oligonucleotide of embodiment 85, wherein the oligonucleotide is selected from the group consisting of CMP-ID-NO: 200_1, 204_1, 206_1, 35_2 or 209_1.
94. The oligonucleotide of embodiment 85, wherein the oligonucleotide is selected from the group consisting of CMP-ID-NO: 585_1, 585_8, 586_9, 586_5, 586_8, 586_4 or 586_6.
95. The oligonucleotide of embodiment 85, wherein the oligonucleotide is selected from CMP-ID-NO: 233_1.
96. The oligonucleotide of embodiment 85, wherein the oligonucleotide is selected from CMP-ID-NO: 237_8 or 590_13.
97. The oligonucleotide of embodiment 85, wherein the oligonucleotide is selected from CMP-ID-NO: 220_1.
98. The oligonucleotide of embodiment 85, wherein the oligonucleotide is selected from the group consisting of CMP-ID-NO: 591_1, 592_2, 592_4 or 241_9.
99. The oligonucleotide of embodiment 85, wherein the oligonucleotide is selected from the group consisting of CMP-ID-NO: 597_4, 598_4, 39_1 or 602_1.
100. The oligonucleotide of embodiment 85, wherein the oligonucleotide is selected from CMP-ID-NO: 39_1.
101. The oligonucleotide of embodiment 85, wherein the oligonucleotide is selected from CMP-ID-NO: 611_7.
102. The oligonucleotide of embodiment 85, wherein the oligonucleotide is selected from the group consisting of CMP-ID-NO: 271_1 or 278_1.
103. The oligonucleotide of embodiment 85, wherein the oligonucleotide is selected from the group consisting of CMP-ID-NO: 616_4, 621_2, 621_1, 622_3, 622_5, 622_4, 624_3, 624_5, 287_1, 625_6, 626_7, 626_8, 626_9, 48_1, 631_6, 631_1, 303_1, 304_6 or 304_10.
104. The oligonucleotide of embodiment 85, wherein the oligonucleotide is selected from CMP-ID-NO: 636_8.
105. The oligonucleotide of embodiment 85, wherein the oligonucleotide is selected from the group consisting of CMP-ID-NO: 638_8, 639_5, 331_1 or 640_4.
106. The oligonucleotide of embodiment 85, wherein the oligonucleotide is selected from the group consisting of CMP-ID-NO: 359_1, 361_1, 361_5, 362_1 or 641_5.
107. The oligonucleotide of embodiment 85, wherein the oligonucleotide is selected from the group consisting of CMP-ID-NO: 378_1, 379_1 or 399_1.
108. The oligonucleotide of embodiment 85, wherein the oligonucleotide is selected from the group consisting of CMP-ID-NO: 403_1, 405_1, 642_12, 642_13, 644_3 or 646_16.

109. The oligonucleotide of embodiment 85, wherein the oligonucleotide is selected from CMP-ID-NO: 85_1 or 425_5.
110. The oligonucleotide of embodiment 85, wherein the oligonucleotide is selected from CMP-ID-NO: 116_1.
111. The oligonucleotide of embodiment 85, wherein the oligonucleotide is selected from CMP-ID-NO: 123_1 or 124_1.
112. The oligonucleotide of embodiment 85, wherein the oligonucleotide is selected from CMP-ID-NO: 126_2.
113. A conjugate comprising the oligonucleotide according to any one of claims 1-112, and at least one conjugate moiety covalently attached to said oligonucleotide.
114. The oligonucleotide conjugate of embodiment 113, wherein the conjugate moiety is selected from carbohydrates, cell surface receptor ligands, drug substances, hormones, lipophilic substances, polymers, proteins, peptides, toxins, vitamins, viral proteins or combinations thereof.
115. The oligonucleotide conjugate of embodiment 113 or 114, wherein the conjugate moiety is an antibody or antibody fragment.
116. The oligonucleotide conjugate of embodiment 115, wherein the antibody or antibody fragment has affinity to the transferrin receptor.
117. The oligonucleotide conjugate of embodiment 113-115, comprising a linker which is positioned between the oligonucleotide and the conjugate moiety.
118. The oligonucleotide conjugate of embodiment 117, wherein the linker is a physiologically labile linker.
119. The oligonucleotide conjugate of embodiment 118, wherein the physiologically labile linker is nuclease susceptible linker.
120. The oligonucleotide conjugate of embodiment 118 or 119, wherein the oligonucleotide has the formula D-F-G-F' or F-G-F'-D', wherein F, F' and G are as defined in embodiments 73-80 and D or D' comprises 1, 2 or 3 DNA nucleosides with phosphorothioate internucleoside linkages.
121. The oligonucleotide conjugate of embodiment 113-120, which display improved uptake into the brain of the conjugate oligonucleotide as compared to an unconjugated oligonucleotide.
122. A pharmaceutical composition comprising the oligonucleotide of embodiment 1-112 or a conjugate of embodiment 113-121 and a pharmaceutically acceptable diluent, carrier, salt and/or adjuvant.
123. A method for manufacturing the oligonucleotide of embodiment 1-112, comprising reacting nucleotide units thereby forming covalently linked contiguous nucleotide units comprised in the oligonucleotide.
124. The method of embodiment 123, further comprising reacting the contiguous nucleotide sequence with a non-nucleotide conjugation moiety.
125. A method for manufacturing the composition of embodiment 122, comprising mixing the oligonucleotide with a pharmaceutically acceptable diluent, carrier, salt and/or adjuvant.
126. An in vivo or in vitro method for inducing UBE3A expression in a target cell where expression of paternal UBE3A is suppressed, said method comprising administering an oligonucleotide of any one of embodiments 1-112 or a conjugate of embodiment 113-121 or the pharmaceutical composition of embodiment 122 in an effective amount to said cell.
127. The method of embodiment 126, wherein the expression of UBE3A is increased by at least 40% compared to a control.
128. The method of embodiment 126 or 127, wherein the level of the SNHG14 transcript downstream of SNORD109B is reduced by at least 30% compared to a control.
129. The method of embodiment 126-128, wherein the target cell is a neuronal cell.
130. The method of embodiment 126-129, wherein the expression of SNORD115 is not significantly affected compared to a control.
131. A method for treating or preventing a disease comprising administering a therapeutically or prophylactically effective amount of an oligonucleotide of embodiment 1-112 or a conjugate of embodiment 113-121 or the pharmaceutical composition of embodiment 122 to a subject suffering from or susceptible to the disease.
132. The oligonucleotide of embodiment 1-112 or a conjugate of embodiment 113-121 or the pharmaceutical composition of embodiment 122, for use as a medicament for treatment or prevention of a disease in a subject.
133. Use of the oligonucleotide of oligonucleotide of embodiment 1-112 or a conjugate of embodiment 113-121 for the preparation of a medicament for treatment or prevention of a disease in a subject.
134. The method, the oligonucleotide or the use of embodiments 131-133, wherein the disease is associated with in vivo activity of UBE3A.
135. The method, the oligonucleotide or the use of embodiments 131-134, wherein the disease is associated with reduced expression of UBE3A and/or reduced activity of UBE3A in neuronal cells.
136. The method, the oligonucleotide or the use of embodiment 135, wherein the reduced expression of UBE3A and/or reduced activity of UBE3A is due to mutations in the maternal allele of the UBE3A gene.
137. The method, the oligonucleotide or the use of embodiments 134-136, wherein the UBE3A expression is increased by at least 30%, or at least 50%, or at least 70%, or at least 90%, or at least 100%, or at least 150% or at least 200%, compared to the expression without the oligonucleotide of embodiment 1-112 or a conjugate of embodiment 113-121 or the pharmaceutical composition of embodiment 122.
138. The method, the oligonucleotide or the use of embodiments 131-137, wherein the disease is Angelman syndrome.
139. The method, the oligonucleotide or the use of embodiments 131-138, wherein the subject is a mammal.
140. The method, the oligonucleotide or the use of embodiment 139, wherein the mammal is human.
141. The method, the oligonucleotide or the use of embodiment 139 or 140, wherein the subject is an infant or a juvenile.

EXAMPLES

Materials and Methods

TABLE_3

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Mctif | Design | Compound | CMP ID_NO | ΔG° | Start SEQ_ID NO |
|---|---|---|---|---|---|---|
| 4 | AACTTCATCAATATTTCCC | 3-13-3 | AACttcatcaatatttCCC | 4_1 | -23.36 | 1677 |
| 4 | AACTTCATCAATATTTCCC | 2-15-2 | AActtcatcaatatttcCC | 4_2 | -19.60 | 1677 |
| 5 | ACTTCATCAATATTTCCC | 3-12-3 | ACTtcatcaatatttCCC | 5_1 | -23.80 | 1677 |
| 5 | ACTTCATCAATATTTCCC | 2-14-2 | ACttcatcaatatttcCC | 5_2 | -20.24 | 1677 |
| 6 | CAACTTCATCAATATTTCCC | 2-14-4 | CAacttcatcaatattTCCC | 6_1 | -25.64 | 1677 |
| 6 | CAACTTCATCAATATTTCCC | 2-16-2 | CAacttcatcaatatttcCC | 6_2 | -22.28 | 1677 |
| 7 | CAACTTCATCAATATTTCC | 4-13-2 | CAACttcatcaatatttCC | 7_1 | -21.47 | 1678 |
| 7 | CAACTTCATCAATATTTCC | 2-15-2 | CAacttcatcaatatttCC | 7_2 | -19.46 | 1678 |
| 8 | CCAACTTCATCAATATTTCC | 3-14-3 | CCAacttcatcaatattTCC | 8_1 | -25.64 | 1678 |
| 9 | CCCAACTTCATCAATATTTC | 4-14-2 | CCCAacttcatcaatattTC | 9_1 | -25.64 | 1679 |
| 10 | ACCCAACTTCATCAATATTT | 2-16-2 | ACccaacttcatcaatatTT | 10_1 | -20.05 | 1680 |
| 11 | CCCAACTTCATCAATATTT | 4-13-2 | CCCAacttcatcaatatTT | 11_1 | -23.96 | 1680 |
| 11 | CCCAACTTCATCAATATTT | 2-15-2 | CCcaacttcatcaatatTT | 11_2 | -20.28 | 1680 |
| 12 | ACCCAACTTCATCAATATT | 4-13-2 | ACCCaacttcatcaataTT | 12_1 | -23.64 | 1681 |
| 12 | ACCCAACTTCATCAATATT | 2-15-2 | ACccaacttcatcaataTT | 12_2 | -19.18 | 1681 |
| 13 | CCCAACTTCATCAATATT | 4-12-2 | CCCAacttcatcaataTT | 13_1 | -23.09 | 1681 |
| 13 | CCCAACTTCATCAATATT | 2-14-2 | CCcaacttcatcaataTT | 13_2 | -19.41 | 1681 |
| 14 | TACCCAACTTCATCAATAT | 2-15-2 | TAcccaacttcatcaatAT | 14_1 | -19.31 | 1682 |
| 15 | TACCCAACTTCATCAATA | 2-14-2 | TAcccaacttcatcaaTA | 15_1 | -19.14 | 1683 |
| 16 | TTACCCAACTTCATCAATA | 2-15-2 | TTacccaacttcatcaaTA | 16_1 | -19.74 | 1683 |
| 17 | TTTACCCAACTTCATCAAT | 4-13-2 | TTTAcccaacttcatcaAT | 17_1 | -21.68 | 1684 |
| 17 | TTTACCCAACTTCATCAAT | 2-15-2 | TTtacccaacttcatcaAT | 17_2 | -19.22 | 1684 |
| 18 | ATACTTTACCCAACTTCAT | 3-13-3 | ATActtttacccaacttCAT | 18_1 | -23.44 | 1688 |
| 18 | ATACTTTACCCAACTTCAT | 2-15-2 | ATactttacccaacttcAT | 18_2 | -20.13 | 1688 |
| 19 | TACTTTACCCAACTTCAT | 3-12-3 | TACtttacccaacttCAT | 19_1 | -22.78 | 1688 |
| 19 | TACTTTACCCAACTTCAT | 2-14-2 | TActtttacccaacttcAT | 19_2 | -19.30 | 1688 |
| 20 | TTATACTTTACCCAACTTCA | 2-16-2 | TTatactttacccaacttCA | 20_1 | -21.40 | 1689 |
| 21 | TCACTGTTCTGACTTT | 3-10-3 | TCActgttctgacTTT | 21_1 | -19.11 | 1712 |
| 22 | TTCAATCTCTATCTCATCAT | 2-16-2 | TTcaatctctatctcatcAT | 22_1 | -19.42 | 4169 |
| 23 | CTTCAATCTCTATCTCATCA | 4-14-2 | CTTCaatctctatctcatCA | 23_1 | -24.21 | 4170 |
| 23 | CTTCAATCTCTATCTCATCA | 2-16-2 | CTtcaatctctatctcatCA | 23_2 | -22.04 | 4170 |
| 24 | TTCAATCTCTATCTCATCA | 2-15-2 | TTcaatctctatctcatCA | 24_1 | -19.44 | 4170 |
| 25 | CTTCAATCTCTATCTCATC | 2-15-2 | CTtcaatctctatctcaTC | 25_1 | -19.87 | 4171 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 26 | ACTTCAATCTCTATCTCAT | 3-13-3 | ACTtcaatctctatctCAT | 26_1 | -22.36 | 4172 |
| 26 | ACTTCAATCTCTATCTCAT | 2-15-2 | ACttcaatctctatctcAT | 26_2 | -19.08 | 4172 |
| 27 | CACTTCAATCTCTATCTCAT | 2-16-2 | CActtcaatctctatctcAT | 27_1 | -20.98 | 4172 |
| 28 | ACTTCAATCTCTATCTCA | 2-12-4 | ACttcaatctctatCTCA | 28_1 | -21.96 | 4173 |
| 28 | ACTTCAATCTCTATCTCA | 2-14-2 | ACttcaatctctatctCA | 28_2 | -19.10 | 4173 |
| 29 | CACTTCAATCTCTATCTCA | 2-13-4 | CActtcaatctctatCTCA | 29_1 | -23.86 | 4173 |
| 29 | CACTTCAATCTCTATCTCA | 2-15-2 | CActtcaatctctatctCA | 29_2 | -21.00 | 4173 |
| 30 | ACACTTCAATCTCTATCTC | 2-15-2 | ACacttcaatctctatcTC | 30_1 | -19.38 | 4174 |
| 31 | TACACTTCAATCTCTATCTC | 2-14-4 | TAcacttcaatctctaTCTC | 31_1 | -23.31 | 4174 |
| 31 | TACACTTCAATCTCTATCTC | 2-16-2 | TAcacttcaatctctatcTC | 31_2 | -20.53 | 4174 |
| 32 | TACACTTCAATCTCTATCT | 4-13-2 | TACActtcaatctctatCT | 32_1 | -22.34 | 4175 |
| 33 | CTTTGTCTCTCTTTACT | 2-13-2 | CTttgtctctctttaCT | 33_1 | -19.36 | 4374 |
| 34 | TATACCTTTCTTTAACCC | 3-12-3 | TATaccttctttaaCCC | 34_1 | -24.89 | 8118 |
| 34 | TATACCTTTCTTTAACCC | 2-14-2 | TAtaccttctttaacCC | 34_2 | -20.83 | 8118 |
| 34 | TATACCTTTCTTTAACCC | 1-3-1-7-1-1-1-1-2 | TataCctttcttTaAcCC | 34_3 | -21.63 | 8116 |
| 34 | TATACCTTTCTTTAACCC | 1-4-1-6-1-3-2 | TatacCtttcttTaacCC | 34_4 | -21.31 | 8116 |
| 34 | TATACCTTTCTTTAACCC | 1-2-1-1-1-7-2-1-2 | TatAcCtttctttAAcCC | 34_5 | -21.51 | 8116 |
| 34 | TATACCTTTCTTTAACCC | 2-3-1-7-1-2-2 | TAtacCtttctttAacCC | 34_6 | -21.84 | 8116 |
| 34 | TATACCTTTCTTTAACCC | 2-13-3 | TAtaccttctttaaCCC | 34_7 | -23.21 | 8116 |
| 35 | TGTTTATACCCTTTCC | 2-12-2 | TGtttatacccttCC | 35_1 | -20.33 | 9212 |
| 35 | TGTTTATACCCTTTCC | 4-10-2 | TGTTtatacccttCC | 35_2 | -22.69 | 9212 |
| 36 | TCTCCTTTATGACTCC | 2-10-4 | TCtcctttatgaCTCC | 36_1 | -23.29 | 10839 |
| 37 | CTTCTCCTTTATGACTC | 2-13-2 | CTtctcctttatgacTC | 37_1 | -19.26 | 10840 |
| 38 | CCATTTATTTCCATTTATT | 4-13-2 | CCATttatttccatttaTT | 38_1 | -22.32 | 15567 |
| 38 | CCATTTATTTCCATTTATT | 2-15-2 | CCatttatttccatttaTT | 38_2 | -19.61 | 15567 |
| 38 | CCATTTATTTCCATTTATT | 1-2-1-9-2-1-3 | CcaTttatttccaTTtATT | 38_3 | -20.02 | 15567 |
| 38 | CCATTTATTTCCATTTATT | 1-1-1-1-8-1-1-1-1-2 | CcAtTtatttccaTtTaTT | 38_4 | -18.95 | 15567 |
| 38 | CCATTTATTTCCATTTATT | 2-2-1-8-1-3-2 | CCatTtatttcca_TttaTT | 38_5 | -20.35 | 15567 |
| 38 | CCATTTATTTCCATTTATT | 1-2-3-6-1-3-3 | CcaTTtatttccAtttATT | 38_6 | -20.87 | 15567 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 39 | CTTTCCATTTATTTCCATTT | 2-14-4 | CTttccatttatttccATTT | 39_1 | -23.14 | 15570 |
| 39 | CTTTCCATTTATTTCCATTT | 1-13-1-1-1-1-2 | CtttccatttatttCcAtTT | 39_2 | -20.96 | 15570 |
| 39 | CTTTCCATTTATTTCCATTT | 1-13-1-3-2 | CtttccatttatttCcatTT | 39_3 | -20.91 | 15570 |
| 39 | CTTTCCATTTATTTCCATTT | 1-3-1-1-1-11-2 | CtttCcAtttatttccatTT | 39_4 | -20.96 | 15570 |
| 39 | CTTTCCATTTATTTCCATTT | 1-1-1-3-1-9-1-1-2 | CtTtccAtttatttccAtTT | 39_5 | -20.54 | 15570 |
| 40 | TCTTTCCATTTATTTCCATT | 2-14-4 | TCtttccatttatttcCATT | 40_1 | -24.62 | 15571 |
| 40 | TCTTTCCATTTATTTCCATT | 2-13-1-1-3 | TCtttccatttatttCcATT | 40_2 | -23.39 | 15571 |
| 40 | TCTTTCCATTTATTTCCATT | 2-13-1-2-2 | TCtttccatttatttCcaTT | 40_3 | -22.53 | 15571 |
| 40 | TCTTTCCATTTATTTCCATT | 2-14-1-1-2 | TCtttccatttatttcCaTT | 40_4 | -22.34 | 15571 |
| 40 | TCTTTCCATTTATTTCCATT | 2-3-1-11-3 | TCtttCcatttatttccATT | 40_5 | -23.39 | 15571 |
| 40 | TCTTTCCATTTATTTCCATT | 2-4-1-10-3 | TCtttcCatttatttccATT | 40_6 | -23.20 | 15571 |
| 40 | TCTTTCCATTTATTTCCATT | 2-3-1-12-2 | TCtttCcatttatttccaTT | 40_7 | -22.53 | 15571 |
| 40 | TCTTTCCATTTATTTCCATT | 2-4-1-11-2 | TCtttcCatttatttccaTT | 40_8 | -22.34 | 15571 |
| 41 | ATTACCCATCCGTTCT | 2-12-2 | ATtacccatccgttCT | 41_1 | -21.15 | 21965 |
| 42 | GCATTAGGCACATTACAT | 3-12-3 | GCAttaggcacattaCAT | 42_1 | -23.96 | 22211 |
| 43 | ATTATTATTTAACCTTCCTA | 2-16-2 | ATtattatttaaccttccTA | 43_1 | -19.28 | 30451 |
| 44 | ACATTATTATTTAACCTTCC | 4-14-2 | ACATtattatttaaccttCC | 44_1 | -22.84 | 30453 |
| 44 | ACATTATTATTTAACCTTCC | 2-16-2 | ACattattatttaaccttCC | 44_2 | -20.13 | 30453 |
| 45 | CATTATTATTTAACCTTCC | 4-13-2 | CATTattatttaaccttCC | 45_1 | -22.04 | 30453 |
| 45 | CATTATTATTTAACCTTCC | 2-15-2 | CAttattatttaaccttCC | 45_2 | -19.55 | 30453 |
| 46 | CCTCTGCTTATAACTTT | 2-13-2 | CCtctgcttataactTT | 46_1 | -19.15 | 30699 |
| 47 | CTACTATACTTTCCTCT | 2-11-4 | CTactatactttcCTCT | 47_1 | -22.32 | 30711 |
| 48 | GTTCTACTATACTTTCC | 4-11-2 | GTTCtactatactttCC | 48_1 | -21.69 | 30714 |
| 48 | GTTCTACTATACTTTCC | 2-13-2 | GTtctactatactttCC | 48_2 | -19.21 | 30714 |
| 48 | GTTCTACTATACTTTCC | 1-2-1-7-2-2-2 | GttCtactataCTttCC | 48_3 | -20.83 | 30712 |
| 48 | GTTCTACTATACTTTCC | 2-9-1-3-2 | GTtctactataCtttCC | 48_4 | -20.20 | 30712 |
| 48 | GTTCTACTATACTTTCC | 1-2-1-9-1-1-2 | GttCtactatactTtCC | 48_5 | -18.95 | 30712 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 48 | GTTCTACTATACTTTCC | 2-1-1-10-3 | GTtCtactatactttTCC | 48_6 | −21.18 | 30712 |
| 48 | GTTCTACTATACTTTCC | 1-3-1-10-2 | GttcTactatactttCC | 48_7 | −18.61 | 30712 |
| 49 | CACCTGATAACAGACCCT | 3-12-3 | CACctgataacagacCCT | 49_1 | −26.38 | 36068 |
| 50 | CACCTGATAACAGACC | 3-10-3 | CACctgataacagACC | 50_1 | −21.10 | 36070 |
| 51 | CCCACCAAAGGATATATT | 3-12-3 | CCCaccaaaggatatATT | 51_1 | −23.47 | 37208 |
| 52 | ACCAGCTACAGGAACCTC | 3-12-3 | ACCagctacaggaacCTC | 52_1 | −26.57 | 46132 |
| 53 | CTATATCTCACTCCTATTT | 4-13-2 | CTATatctcactcctatTT | 53_1 | −23.07 | 48143 |
| 53 | CTATATCTCACTCCTATTT | 2-13-4 | CTatatctcactcctATTT | 53_2 | −22.12 | 48143 |
| 54 | CTATATCTCACTCCTATT | 2-14-2 | CTatatctcactcctaTT | 54_1 | −19.40 | 48144 |
| 54 | CTATATCTCACTCCTATT | 2-12-4 | CTatatctcactccTATT | 54_2 | −22.28 | 48144 |
| 54 | CTATATCTCACTCCTATT | 3-12-3 | CTAtatctcactcctATT | 54_3 | −21.44 | 48144 |
| 55 | CTACTATATCTCACTCCTAT | 2-16-2 | CTactatatctcactcctAT | 55_1 | −22.00 | 48145 |
| 55 | CTACTATATCTCACTCCTAT | 2-14-4 | CTactatatctcactcCTAT | 55_2 | −25.54 | 48145 |
| 56 | TACTATATCTCACTCCTAT | 2-13-4 | TActatatctcactcCTAT | 56_1 | −23.29 | 48145 |
| 57 | CTACTATATCTCACTCCTA | 2-15-2 | CTactatatctcactccTA | 57_1 | −21.91 | 48146 |
| 58 | TACTATATCTCACTCCTA | 2-14-2 | TActatatctcactccTA | 58_1 | −19.66 | 48146 |
| 58 | TACTATATCTCACTCCTA | 2-12-4 | TActatatctcactCCTA | 58_2 | −23.59 | 48146 |
| 58 | TACTATATCTCACTCCTA | 3-12-3 | TACtatatctcactcCTA | 58_3 | −22.62 | 48146 |
| 59 | CTACTATATCTCACTCCT | 2-14-2 | CTactatatctcactcCT | 59_1 | −21.25 | 48147 |
| 59 | CTACTATATCTCACTCCT | 4-12-2 | CTACtatatctcactcCT | 59_2 | −23.87 | 48147 |
| 60 | CTACTATATCTCACTCC | 2-13-2 | CTactatatctcactCC | 60_1 | −20.13 | 48148 |
| 60 | CTACTATATCTCACTCC | 2-11-4 | CTactatatctcaCTCC | 60_2 | −23.00 | 48148 |
| 60 | CTACTATATCTCACTCC | 3-11-3 | CTActatatctcacTCC | 60_3 | −22.56 | 48148 |
| 61 | CCTACTATATCTCACTC | 2-11-4 | CCtactatatctcACTC | 61_1 | −21.93 | 48149 |
| 62 | CTCCTACTATATCTCACTC | 4-13-2 | CTCCtactatatctcacTC | 62_1 | −25.69 | 48149 |
| 63 | TCCTACTATATCTCACTC | 3-12-3 | TCCtactatatctcaCTC | 63_1 | −23.88 | 48149 |
| 64 | CTCCTACTATATCTCACT | 4-12-2 | CTCCtactatatctcaCT | 64_1 | −24.87 | 48150 |
| 64 | CTCCTACTATATCTCACT | 3-12-3 | CTCctactatatctcACT | 64_2 | −22.93 | 48150 |
| 65 | TTTCCTCTCCTACTATATC | 2-15-2 | TTtcctctcctactataTC | 65_1 | −21.23 | 48155 |
| 66 | ATCCATATCCTTTCCT | 3-10-3 | ATCcatatcctttCCT | 66_1 | −24.02 | 48168 |
| 67 | CATCCATATCCTTTCCT | 4-11-2 | CATCcatatcctttcCT | 67_1 | −24.94 | 48168 |
| 68 | ATCATCCATATCCTTTCC | 4-12-2 | ATCAtccatatcctttCC | 68_1 | −25.69 | 48169 |
| 69 | CATCATCCATATCCTTTC | 4-12-2 | CATCatccatatccttTC | 69_1 | −23.32 | 48170 |
| 69 | CATCATCCATATCCTTTC | 2-14-2 | CAtcatccatatccttTC | 69_2 | −20.72 | 48170 |
| 69 | CATCATCCATATCCTTTC | 2-12-4 | CAtcatccatatccTTTC | 69_3 | −22.56 | 48170 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 70 | TACATCATCCATATCCTTTC | 2-16-2 | TAcatcatccatatccttTC | 70_1 | -22.45 | 48170 |
| 70 | TACATCATCCATATCCTTTC | 4-14-2 | TACAtcatccatatccttTC | 70_2 | -25.00 | 48170 |
| 70 | TACATCATCCATATCCTTTC | 2-14-4 | TAcatcatccatatccTTTC | 70_3 | -24.29 | 48170 |
| 71 | ACATCATCCATATCCTTT | 3-12-3 | ACAtcatccatatccTTT | 71_1 | -22.11 | 48171 |
| 72 | CATCATCCATATCCTTT | 2-13-2 | CAtcatccatatcctTT | 72_1 | -19.04 | 48171 |
| 72 | CATCATCCATATCCTTT | 4-11-2 | CATCatccatatcctTT | 72_2 | -21.64 | 48171 |
| 73 | TACATCATCCATATCCTTT | 2-15-2 | TAcatcatccatatcctTT | 73_1 | -20.76 | 48171 |
| 73 | TACATCATCCATATCCTTT | 2-13-4 | TAcatcatccatatcCTTT | 73_2 | -23.36 | 48171 |
| 73 | TACATCATCCATATCCTTT | 3-13-3 | TACatcatccatatccTTT | 73_3 | -22.88 | 48171 |
| 74 | ATACATCATCCATATCCTT | 2-15-2 | ATacatcatccatatccTT | 74_1 | -20.80 | 48172 |
| 74 | ATACATCATCCATATCCTT | 4-13-2 | ATACatcatccatatccTT | 74_2 | -23.12 | 48172 |
| 75 | TACATCATCCATATCCTT | 2-14-2 | TAcatcatccatatccTT | 75_1 | -19.97 | 48172 |
| 75 | TACATCATCCATATCCTT | 4-12-2 | TACAtcatccatatccTT | 75_2 | -22.52 | 48172 |
| 76 | TATACATCATCCATATCCTT | 2-16-2 | TAtacatcatccatatccTT | 76_1 | -21.36 | 48172 |
| 77 | ATACATCATCCATATCCT | 3-12-3 | ATAcatcatccatatCCT | 77_1 | -24.15 | 48173 |
| 77 | ATACATCATCCATATCCT | 2-14-2 | ATacatcatccatatcCT | 77_2 | -20.55 | 48173 |
| 77 | ATACATCATCCATATCCT | 2-13-3 | ATacatcatccatatCCT | 77_3 | -22.92 | 48173 |
| 78 | ATATACATCATCCATATCCT | 2-16-2 | ATatacatcatccatatcCT | 78_1 | -22.04 | 48173 |
| 79 | TACATCATCCATATCCT | 2-11-4 | TAcatcatccataTCCT | 79_1 | -23.21 | 48173 |
| 79 | TACATCATCCATATCCT | 2-13-2 | TAcatcatccatatcCT | 79_2 | -19.71 | 48173 |
| 79 | TACATCATCCATATCCT | 4-11-2 | TACAtcatccatatcCT | 79_3 | -22.27 | 48173 |
| 80 | TATACATCATCCATATCCT | 2-15-2 | TAtacatcatccatatcCT | 80_1 | -21.11 | 48173 |
| 80 | TATACATCATCCATATCCT | 3-13-3 | TATacatcatccatatCCT | 80_2 | -25.15 | 48173 |
| 80 | TATACATCATCCATATCCT | 4-13-2 | TATAcatcatccatatcCT | 80_3 | -24.01 | 48173 |
| 81 | ATACATCATCCATATCC | 3-11-3 | ATAcatcatccataTCC | 81_1 | -21.79 | 48174 |
| 82 | ATATACATCATCCATATCC | 4-13-2 | ATATacatcatccatatCC | 82_1 | -23.73 | 48174 |
| 82 | ATATACATCATCCATATCC | 2-15-2 | ATatacatcatccatatCC | 82_2 | -20.93 | 48174 |
| 83 | TATACATCATCCATATCC | 2-14-2 | TAtacatcatccatatCC | 83_1 | -20.00 | 48174 |
| 83 | TATACATCATCCATATCC | 4-12-2 | TATAcatcatccatatCC | 83_2 | -22.90 | 48174 |
| 84 | TATATACATCATCCATATCC | 2-16-2 | TAtatacatcatccatatCC | 84_1 | -21.49 | 48174 |
| 84 | TATATACATCATCCATATCC | 4-14-2 | TATAtacatcatccatatCC | 84_2 | -24.29 | 48174 |
| 85 | GCTTCATATTTCTCCA | 2-12-2 | GCttcatatttctcCA | 85_1 | -20.44 | 49345 |
| 85 | GCTTCATATTTCTCCA | 2-11-3 | GCttcatatttctCCA | 85_2 | -22.81 | 49345 |
| 86 | CATCTTGTTCTTTACCT | 2-13-2 | CAtcttgttctttacCT | 86_1 | -19.67 | 49581 |
| 87 | TATATTCACCATTGCC | 2-10-4 | TAtattcaccatTGCC | 87_1 | -22.70 | 49724 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 88 | CCTTATATTCACCATTG | 2-13-2 | CCttatattcaccatTG | 88_1 | -19.44 | 49726 |
| 88 | CCTTATATTCACCATTG | 2-11-4 | CCttatattcaccATTG | 88_2 | -21.25 | 49726 |
| 89 | CCTCCTTATATTCACC | 4-10-2 | CCTCcttatattcaCC | 89_1 | -24.64 | 49730 |
| 90 | CCCTTCCTTTATTCAA | 3-10-3 | CCCttcctttattCAA | 90_1 | -23.86 | 50189 |
| 91 | CCTTACTGTTAAATCCT | 2-13-2 | CCttactgttaaatcCT | 91_1 | -19.81 | 50475 |
| 92 | CAGGCAGATAACCTCCAA | 3-12-3 | CAGgcagataacctcCAA | 92_1 | -25.31 | 52419 |
| 93 | CAGCAGGCAGATAACCTC | 3-12-3 | CAGcaggcagataacCTC | 93_1 | -25.88 | 52422 |
| 94 | CGAATCTTGACATACAGG | 3-12-3 | CGAatcttgacatacAGG | 94_1 | -21.47 | 53955 |
| 95 | CTCATACTTGCTTTAAT | 4-11-2 | CTCAtacttgctttaAT | 95_1 | -19.10 | 60821 |
| 95 | CTCATACTTGCTTTAAT | 2-13-2 | CTcatacttgctttaAT | 95_2 | -16.35 | 60821 |
| 96 | ACATCTCATACTTGCTT | 2-11-4 | ACatctcatacttGCTT | 96_1 | -21.31 | 60825 |
| 96 | ACATCTCATACTTGCTT | 2-13-2 | ACatctcatacttgcTT | 96_2 | -17.66 | 60825 |
| 96 | ACATCTCATACTTGCTT | 2-12-3 | ACatctcatacttgCTT | 96_3 | -19.52 | 60825 |
| 97 | ACATCTCATACTTGCT | 2-10-4 | ACatctcatactTGCT | 97_1 | -21.18 | 60826 |
| 97 | ACATCTCATACTTGCT | 2-12-2 | ACatctcatacttgCT | 97_2 | -17.70 | 60826 |
| 97 | ACATCTCATACTTGCT | 2-11-3 | ACatctcatacttGCT | 97_3 | -19.49 | 60826 |
| 97 | ACATCTCATACTTGCT | 4-10-2 | ACATctcatacttgCT | 97_4 | -20.48 | 60826 |
| 98 | TACATCTCATACTTGCT | 2-11-4 | TAcatctcatactTGCT | 98_1 | -22.33 | 60826 |
| 98 | TACATCTCATACTTGCT | 2-13-2 | TAcatctcatacttgCT | 98_2 | -18.85 | 60826 |
| 98 | TACATCTCATACTTGCT | 4-11-2 | TACAtctcatacttgCT | 98_3 | -21.40 | 60826 |
| 99 | CCTACATCTCATACTTGC | 3-12-3 | CCTacatctcatactTGC | 99_1 | -26.29 | 60827 |
| 99 | CCTACATCTCATACTTGC | 2-14-2 | CCtacatctcatacttGC | 99_2 | -22.98 | 60827 |
| 99 | CCTACATCTCATACTTGC | 2-13-3 | CCtacatctcatactTGC | 99_3 | -24.67 | 60827 |
| 99 | CCTACATCTCATACTTGC | 2-12-4 | CCtacatctcatacTTGC | 99_4 | -25.70 | 60827 |
| 100 | CTACATCTCATACTTGC | 3-11-3 | CTAcatctcatactTGC | 100_1 | -22.33 | 60827 |
| 100 | CTACATCTCATACTTGC | 2-13-2 | CTacatctcatacttGC | 100_2 | -19.41 | 60827 |
| 100 | CTACATCTCATACTTGC | 2-12-3 | CTacatctcatactTGC | 100_3 | -21.10 | 60827 |
| 101 | TACATCTCATACTTGC | 3-10-3 | TACatctcatactTGC | 101_1 | -19.94 | 60827 |
| 101 | TACATCTCATACTTGC | 2-12-2 | TAcatctcatacttGC | 101_2 | -17.15 | 60827 |
| 101 | TACATCTCATACTTGC | 2-11-3 | TAcatctcatactTGC | 101_3 | -18.85 | 60827 |
| 101 | TACATCTCATACTTGC | 4-10-2 | TACatctcatacttGC | 101_4 | -19.71 | 60827 |
| 102 | CCTACATCTCATACTTG | 4-11-2 | CCTAcatctcatactTG | 102_1 | -22.52 | 60828 |
| 102 | CCTACATCTCATACTTG | 2-13-2 | CCtacatctcatactTG | 102_2 | -19.67 | 60828 |
| 102 | CCTACATCTCATACTTG | 3-12-2 | CCTacatctcatactTG | 102_3 | -21.29 | 60828 |
| 102 | CCTACATCTCATACTTG | 3-11-3 | CCTacatctcatacTTG | 102_4 | -22.31 | 60828 |
| 103 | ACCTACATCTCATACTT | 3-11-3 | ACCtacatctcataCTT | 103_1 | -21.93 | 60829 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 103 | ACCTACATCTCATACTT | 2-13-2 | ACctacatctcatacTT | 103_2 | -17.76 | 60829 |
| 103 | ACCTACATCTCATACTT | 2-11-4 | ACctacatctcatACTT | 103_3 | -20.03 | 60829 |
| 103 | ACCTACATCTCATACTT | 3-12-2 | ACCtacatctcatacTT | 103_4 | -20.26 | 60829 |
| 104 | CCTACATCTCATACTT | 3-10-3 | CCTacatctcataCTT | 104_1 | -21.50 | 60829 |
| 104 | CCTACATCTCATACTT | 2-12-2 | CCtacatctcatacTT | 104_2 | -18.21 | 60829 |
| 104 | CCTACATCTCATACTT | 2-10-4 | CCtacatctcatACTT | 104_3 | -20.48 | 60829 |
| 105 | TACCTACATCTCATACTT | 4-12-2 | TACCtacatctcatacTT | 105_1 | -22.49 | 60829 |
| 105 | TACCTACATCTCATACTT | 2-14-2 | TActacatctcatacTT | 105_2 | -18.81 | 60829 |
| 105 | TACCTACATCTCATACTT | 2-13-3 | TActacatctcataCTT | 105_3 | -20.48 | 60829 |
| 105 | TACCTACATCTCATACTT | 2-12-4 | TActacatctcatACTT | 105_4 | -21.08 | 60829 |
| 106 | TTACCTACATCTCATACTT | 3-13-3 | TTActacatctcataCTT | 106_1 | -22.30 | 60829 |
| 106 | TTACCTACATCTCATACTT | 2-15-2 | TTacctacatctcatacTT | 106_2 | -19.40 | 60829 |
| 106 | TTACCTACATCTCATACTT | 2-14-3 | TTacctacatctcataCTT | 106_3 | -21.08 | 60829 |
| 106 | TTACCTACATCTCATACTT | 2-13-4 | TTacctacatctcatACTT | 106_4 | -21.67 | 60829 |
| 107 | ACCTACATCTCATACT | 4-10-2 | ACCTacatctcataCT | 107_1 | -21.72 | 60830 |
| 107 | ACCTACATCTCATACT | 2-12-2 | ACctacatctcataCT | 107_2 | -17.61 | 60830 |
| 107 | ACCTACATCTCATACT | 3-11-2 | ACCtacatctcataCT | 107_3 | -20.10 | 60830 |
| 107 | ACCTACATCTCATACT | 2-10-4 | ACctacatctcaTACT | 107_4 | -20.11 | 60830 |
| 108 | TACCTACATCTCATACT | 4-11-2 | TACCtacatctcataCT | 108_1 | -22.34 | 60830 |
| 108 | TACCTACATCTCATACT | 2-13-2 | TActacatctcataCT | 108_2 | -18.66 | 60830 |
| 108 | TACCTACATCTCATACT | 3-12-2 | TACctacatctcataCT | 108_3 | -19.85 | 60830 |
| 108 | TACCTACATCTCATACT | 3-11-3 | TACctacatctcatACT | 108_4 | -20.44 | 60830 |
| 109 | TTACCTACATCTCATACT | 2-12-4 | TTacctacatctcaTACT | 109_1 | -21.75 | 60830 |
| 109 | TTACCTACATCTCATACT | 2-14-2 | TTacctacatctcataCT | 109_2 | -19.25 | 60830 |
| 109 | TTACCTACATCTCATACT | 3-13-2 | TTActacatctcataCT | 109_3 | -20.48 | 60830 |
| 109 | TTACCTACATCTCATACT | 3-12-3 | TTAcctacatctcatACT | 109_4 | -21.08 | 60830 |
| 110 | TTACCTACATCTCATAC | 3-11-3 | TTAcctacatctcaTAC | 110_1 | -19.50 | 60831 |
| 110 | TTACCTACATCTCATAC | 2-13-2 | TTacctacatctcatAC | 110_2 | -16.37 | 60831 |
| 111 | GTTACCTACATCTCATA | 2-11-4 | GTtacctacatctCATA | 111_1 | -21.69 | 60832 |
| 111 | GTTACCTACATCTCATA | 2-13-2 | GTtacctacatctcaTA | 111_2 | -18.74 | 60832 |
| 111 | GTTACCTACATCTCATA | 3-12-2 | GTTacctacatctcaTA | 111_3 | -19.98 | 60832 |
| 112 | GTTACCTACATCTCAT | 3-10-3 | GTTacctacatctCAT | 112_1 | -20.69 | 60833 |
| 112 | GTTACCTACATCTCAT | 2-12-2 | GTtacctacatctcAT | 112_2 | -17.37 | 60833 |
| 113 | ATATACCCAAAGGCACCT | 3-12-3 | ATAtacccaaaggcaCCT | 113_1 | -25.99 | 62200 |
| 114 | TCTACTCATCCTTTAACTCA | 2-14-4 | TCtactcatcctttaaCTCA | 114_1 | -25.63 | 62251 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 115 | CCTTAATCTGTATCACT | 2-13-2 | CCttaatctgtatcaCT | 115_1 | -19.58 | 62286 |
| 116 | CCATACACAGCACATA | 2-12-2 | CCatacacagcacaTA | 116_1 | -19.04 | 62424 |
| 117 | CTCCATACACAGCACAT | 2-13-2 | CTccatacacagcacAT | 117_1 | -20.08 | 62425 |
| 118 | CAGAATAATTCTCCTCC | 2-13-2 | CAgaataattctcctCC | 118_1 | -19.86 | 62441 |
| 119 | GTCCTACATATATACC | 4-10-2 | GTCCtacatatataCC | 119_1 | -22.09 | 66380 |
| 120 | TGCTTCCTTACTAACC | 4-10-2 | TGCTtccttactaaCC | 120_1 | -23.93 | 66701 |
| 120 | TGCTTCCTTACTAACC | 2-12-2 | TGcttccttactaaCC | 120_2 | -20.10 | 66701 |
| 121 | CCCTTTGTAATCATCT | 4-10-2 | CCCTttgtaatcatCT | 121_1 | -23.44 | 66838 |
| 122 | TCCCTTTGTAATCATCT | 2-13-2 | TCcctttgtaatcatCT | 122_1 | -19.97 | 66838 |
| 123 | CTGCCATCAATACCAT | 2-12-2 | CTgccatcaataccAT | 123_1 | -19.14 | 68918 |
| 124 | TCACTGCCATCAATACC | 2-13-2 | TCactgccatcaataCC | 124_1 | -21.35 | 68920 |
| 125 | ATTCTTACTTTATTCCTCA | 2-15-2 | ATtcttactttattcctCA | 125_1 | -20.16 | 70033 |
| 126 | TCACTTTCCAGATATCA | 4-11-2 | TCACtttccagatatCA | 126_1 | -21.61 | 77567 |
| 126 | TCACTTTCCAGATATCA | 2-13-2 | TCactttccagatatCA | 126_2 | -18.65 | 77567 |
| 127 | TCCTTCAAATTCCACATAC | 3-13-3 | TCCttcaaattccacaTAC | 127_1 | -24.09 | 82053 |
| 128 | ACATGTCCCTTTATATT | 4-11-2 | ACATgtccctttataTT | 128_1 | -20.87 | 92323 |
| 128 | ACATGTCCCTTTATATT | 2-13-2 | ACatgtccctttataTT | 128_2 | -17.66 | 92323 |
| 128 | ACATGTCCCTTTATATT | 3-12-2 | ACAtgtccctttataTT | 128_3 | -19.13 | 92323 |
| 128 | ACATGTCCCTTTATATT | 3-11-3 | ACAtgtccctttatATT | 128_4 | -20.03 | 92323 |
| 129 | ACATGTCCCTTTATAT | 3-10-3 | ACAtgtcccttttaTAT | 129_1 | -20.11 | 92324 |
| 129 | ACATGTCCCTTTATAT | 2-12-2 | ACatgtcccttttatAT | 129_2 | -16.74 | 92324 |
| 130 | CCAAGAAAGGAGCAAGCT | 3-12-3 | CCAagaaaggagcaaGCT | 130_1 | -25.26 | 97146 |
| 131 | TCCAAGAAAGGAGCAAGC | 3-12-3 | TCCaagaaaggagcaAGC | 131_1 | -24.12 | 97147 |
| 132 | CTCATCCCTCCAAGAAA | 4-11-2 | CTCatccctccaagaAA | 132_1 | -22.58 | 97156 |
| 132 | CTCATCCCTCCAAGAAA | 2-13-2 | CTcatccctccaagaAA | 132_2 | -19.83 | 97156 |
| 132 | CTCATCCCTCCAAGAAA | 3-12-2 | CTCatccctccaagaAA | 132_3 | -21.11 | 97156 |
| 133 | TCATCCCTCCAAGAAA | 4-10-2 | TCATccctccaagaAA | 133_1 | -20.41 | 97156 |
| 133 | TCATCCCTCCAAGAAA | 2-12-2 | TCatccctccaagaAA | 133_2 | -17.63 | 97156 |
| 133 | TCATCCCTCCAAGAAA | 3-11-2 | TCAtccctccaagaAA | 133_3 | -19.09 | 97156 |
| 133 | TCATCCCTCCAAGAAA | 3-10-3 | TCAtccctccaagAAA | 133_4 | -19.81 | 97156 |
| 134 | CACCTCCCTATTACATAAA | 4-13-2 | CACCtccctattacataAA | 134_1 | -24.18 | 100018 |
| 134 | CACCTCCCTATTACATAAA | 2-15-2 | CAcctccctattacataAA | 134_2 | -20.51 | 100018 |
| 135 | CACCTCCCTATTACATAA | 4-12-2 | CACCtccctattacatAA | 135_1 | -23.75 | 100019 |
| 135 | CACCTCCCTATTACATAA | 2-14-2 | CAcctccctattacatAA | 135_2 | -20.07 | 100019 |
| 136 | CCTCCCTATTACATAA | 2-12-2 | CCtccctattacatAA | 136_1 | -18.40 | 100019 |
| 137 | CTAAATCTTCCAATTCATA | 2-15-2 | CTaaatcttccaattcaTA | 137_1 | -18.12 | 106139 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 138 | TATCCCTTGATTATCCT | 2-13-2 | TAtcccttgattatcCT | 138_1 | -20.68 | 109406 |
| 139 | CCTCTTTGTCAAATACT | 2-13-2 | CCtctttgtcaaataCT | 139_1 | -19.30 | 110768 |
| 140 | CAGCTTATTTACCTCTT | 2-13-2 | CAgcttatttacctcTT | 140_1 | -19.30 | 114828 |
| 141 | ACTCTTTACCTCTAACACT | 4-13-2 | ACTCtttacctctaacaCT | 141_1 | -24.26 | 117468 |
| 142 | TTACTCTTTACCTCTAACAC | 3-14-3 | TTActctttacctctaaCAC | 142_1 | -23.23 | 117469 |
| 143 | CCAACCTAATACCTTAATA | 2-15-2 | CCaacctaataccttaaTA | 143_1 | -20.27 | 118639 |
| 144 | TACCAACCTAATACCTTAA | 2-15-2 | TAccaacctaataccttAA | 144_1 | -18.32 | 118641 |
| 145 | CCAATACCCACAAACC | 3-10-3 | CCAatacccacaaACC | 145_1 | -23.17 | 124162 |
| 145 | CCAATACCCACAAACC | 2-12-2 | CCaatacccacaaACC | 145_2 | -20.85 | 124162 |
| 146 | CCATTATTCTACTTTGT | 3-11-3 | CCAttattctactttTGT | 146_1 | -21.79 | 125501 |
| 146 | CCATTATTCTACTTTGT | 2-13-2 | CCattattctactttGT | 146_2 | -18.63 | 125501 |
| 147 | CATTTCCTTATCTTCACA | 2-14-2 | CAtttccttatcttcaCA | 147_1 | -20.39 | 125529 |
| 148 | TCATTTCCTTATCTTCACA | 4-13-2 | TCATttccttatcttcaCA | 148_1 | -24.13 | 125529 |
| 149 | AATAATTCCTCATTTCCT | 2-14-2 | AAtaattcctcatttcCT | 149_1 | -18.01 | 125539 |
| 150 | ACAATAATTCCTCATTTCC | 3-13-3 | ACAataattcctcattTCC | 150_1 | -22.71 | 125540 |
| 150 | ACAATAATTCCTCATTTCC | 2-15-2 | ACaataattcctcatttCC | 150_2 | -20.23 | 125540 |
| 151 | TATTGAACCAATTCTA | 3-10-3 | TATgaaccaattCTA | 151_1 | -16.93 | 4806 |
| 152 | CATATTGAACCAATTC | 4-10-2 | CATAttgaaccaatTC | 152_1 | -16.32 | 4808 |
| 153 | TCATATTGAACCAATT | 4-10-2 | TCATattgaaccaaTT | 153_1 | -16.14 | 4809 |
| 154 | CATCATATTGAACCAA | 2-10-4 | CAtcatattgaaCCAA | 154_1 | -17.65 | 4811 |
| 155 | TCATCATATTGAACCA | 3-10-3 | TCAtcatattgaaCCA | 155_1 | -19.40 | 4812 |
| 156 | CACAATCAACAACAAATA | 4-12-2 | CACAatcaacaacaaaTA | 156_1 | -16.16 | 4972 |
| 157 | TACACAATCAACAACAAAT | 4-13-2 | TACAcaatcaacaacaaAT | 157_1 | -16.76 | 4973 |
| 158 | CTGTACACAATCAACA | 4-10-2 | CTGTacacaatcaaCA | 158_1 | -19.05 | 4979 |
| 159 | CACTAATAATTCACTTT | 4-11-2 | CACTaataattcactTT | 159_1 | -16.39 | 5058 |
| 160 | CAACATTATTGACACT | 2-10-4 | CAacattattgaCACT | 160_1 | -17.17 | 5071 |
| 161 | AAACTTTCCCAACATTAT | 2-12-4 | AAactttcccaacaTTAT | 161_1 | -18.69 | 5078 |
| 162 | TCCTATATTCTCTTAAA | 4-11-2 | TCCTatattctcttaAA | 162_1 | -18.58 | 5094 |
| 163 | TTTCCTATATTCTCTTA | 4-11-2 | TTTCctatattctctTA | 163_1 | -18.69 | 5096 |
| 164 | CAAGTTTCCTATATTCT | 4-11-2 | CAAGtttcctatattCT | 164_1 | -19.97 | 5100 |
| 165 | CAAGTTTCCTATATTC | 4-10-2 | CAAGtttcctatatTC | 165_1 | -17.47 | 5101 |
| 166 | CATTCTATCTGCCAAA | 2-10-4 | CAttctatctgcCAAA | 166_1 | -18.36 | 5218 |
| 167 | CCATTCTATCTGCCAAA | 2-11-4 | CCattctatctgcCAAA | 167_1 | -22.08 | 5218 |
| 168 | TATAGCCATTCTATCT | 4-10-2 | TATAgccattctatCT | 168_1 | -20.63 | 5224 |
| 169 | TTATAGCCATTCTATCT | 4-11-2 | TTATagccattctatCT | 169_1 | -20.82 | 5224 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 169 | TTATAGCCATTCTATCT | 1-10-3-1-2 | TtatagccattCTAtCT | 169_2 | -20.51 | 5224 |
| 169 | TTATAGCCATTCTATCT | 2-9-1-2-3 | TTatagccattCtaTCT | 169_3 | -20.12 | 5224 |
| 169 | TTATAGCCATTCTATCT | 1-1-1-8-2-1-3 | TtAtagccattCTaTCT | 169_4 | -20.59 | 5224 |
| 169 | TTATAGCCATTCTATCT | 1-3-1-6-2-2-2 | TtatAgccattCTatCT | 169_5 | -19.97 | 5224 |
| 169 | TTATAGCCATTCTATCT | 3-8-1-3-2 | TTAtagccattCtatCT | 169_6 | -20.13 | 5224 |
| 169 | TTATAGCCATTCTATCT | 1-10-2-2-2 | TtatagccattCTatCT | 169_7 | -19.37 | 5224 |
| 169 | TTATAGCCATTCTATCT | 2-9-1-1-4 | TTatagccattCtATCT | 169_8 | -21.02 | 5224 |
| 169 | TTATAGCCATTCTATCT | 1-1-1-8-1-1-4 | TtAtagccattCtATCT | 169_9 | -19.88 | 5224 |
| 169 | TTATAGCCATTCTATCT | 1-2-1-7-1-1-4 | TtaTagccattCtATCT | 169_10 | -20.65 | 5224 |
| 169 | TTATAGCCATTCTATCT | 1-3-1-6-1-1-4 | TtatAgccattCtATCT | 169_11 | -20.38 | 5224 |
| 169 | TTATAGCCATTCTATCT | 1-10-1-1-4 | TtatagccattCtATCT | 169_12 | -19.78 | 5224 |
| 169 | TTATAGCCATTCTATCT | 3-8-1-1-1-2 | TTAtagccattCtAtCT | 169_13 | -20.22 | 5224 |
| 169 | TTATAGCCATTCTATCT | 2-1-1-7-1-1-1-2 | TTaTagccattCtAtCT | 169_14 | -19.96 | 5224 |
| 169 | TTATAGCCATTCTATCT | 2-2-1-6-1-1-1-2 | TTatAgccattCtAtCT | 169_15 | -19.69 | 5224 |
| 169 | TTATAGCCATTCTATCT | 2-9-1-1-1-2 | TTatagccattCtAtCT | 169_16 | -19.09 | 5224 |
| 169 | TTATAGCCATTCTATCT | 1-2-2-6-1-1-1-2 | TtaTagccattCtAtCT | 169_17 | -20.35 | 5224 |
| 169 | TTATAGCCATTCTATCT | 1-2-1-7-1-1-1-2 | TtaTagccattCtAtCT | 169_18 | -18.72 | 5224 |
| 169 | TTATAGCCATTCTATCT | 1-3-1-6-1-1-1-2 | TtatAgccattCtAtCT | 169_19 | -18.45 | 5224 |
| 169 | TTATAGCCATTCTATCT | 2-2-1-6-1-2-3 | TTatAgccattCtaTCT | 169_20 | -20.71 | 5224 |
| 169 | TTATAGCCATTCTATCT | 1-1-2-7-1-2-3 | TtATagccattCtaTCT | 169_21 | -20.65 | 5224 |
| 169 | TTATAGCCATTCTATCT | 1-1-1-1-6-1-2-3 | TtATagccattCtaTCT | 169_22 | -19.57 | 5224 |
| 169 | TTATAGCCATTCTATCT | 1-1-1-8-1-2-3 | TtAtagccattCtaTCT | 169_23 | -18.98 | 5224 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 169 | TTATAGCCATTCTATCT | 4-7-1-3-2 | TTATagccattCtatCT | 169_24 | -21.80 | 5224 |
| 169 | TTATAGCCATTCTATCT | 3-1-1-6-1-3-2 | TTAtAgccattCtatCT | 169_25 | -20.72 | 5224 |
| 169 | TTATAGCCATTCTATCT | 2-1-1-7-1-3-2 | TTaTagccattCtatCT | 169_26 | -19.86 | 5224 |
| 169 | TTATAGCCATTCTATCT | 2-2-1-6-1-3-2 | TTatAgccattCtatCT | 169_27 | -19.59 | 5224 |
| 169 | TTATAGCCATTCTATCT | 2-9-1-3-2 | TTatagccattCtatCT | 169_28 | -18.99 | 5224 |
| 169 | TTATAGCCATTCTATCT | 1-1-3-6-1-3-2 | TtATAgccattCtatCT | 169_29 | -21.16 | 5224 |
| 169 | TTATAGCCATTCTATCT | 1-1-2-7-1-3-2 | TtATagccattCtatCT | 169_30 | -19.53 | 5224 |
| 169 | TTATAGCCATTCTATCT | 1-1-1-1-1-6-1-3-2 | TtAtAgccattCtatCT | 169_31 | -18.45 | 5224 |
| 169 | TTATAGCCATTCTATCT | 1-2-2-6-1-3-2 | TtaTAgccattCtatCT | 169_32 | -20.25 | 5224 |
| 169 | TTATAGCCATTCTATCT | 1-2-1-7-1-3-2 | TtaTagccattCtatCT | 169_33 | -18.62 | 5224 |
| 169 | TTATAGCCATTCTATCT | 1-3-1-6-1-3-2 | TtatAgccattCtatCT | 169_34 | -18.35 | 5224 |
| 169 | TTATAGCCATTCTATCT | 1-1-1-9-5 | TtAtagccattcTATCT | 169_35 | -20.88 | 5224 |
| 169 | TTATAGCCATTCTATCT | 2-10-2-1-2 | TTatagccattcTAtCT | 169_36 | -20.09 | 5224 |
| 169 | TTATAGCCATTCTATCT | 1-1-1-9-2-1-2 | TtAtagccattcTAtCT | 169_37 | -18.95 | 5224 |
| 169 | TTATAGCCATTCTATCT | 1-2-1-8-2-1-2 | Tta_TagccattcTAtCT | 169_38 | -19.72 | 5224 |
| 169 | TTATAGCCATTCTATCT | 1-3-1-7-2-1-2 | TtatAgccattcTAtCT | 169_39 | -19.44 | 5224 |
| 169 | TTATAGCCATTCTATCT | 1-11-2-1-2 | TtatagccattcTAtCT | 169_40 | -18.85 | 5224 |
| 169 | TTATAGCCATTCTATCT | 3-9-1-1-3 | TTAtagccattcTaTCT | 169_41 | -21.21 | 5224 |
| 169 | TTATAGCCATTCTATCT | 1-1-1-9-1-1-3 | TtAtagccattcTaTCT | 169_42 | -18.94 | 5224 |
| 169 | TTATAGCCATTCTATCT | 3-9-1-2-2 | TTAtagccattcTatCT | 169_43 | -20.09 | 5224 |
| 169 | TTATAGCCATTCTATCT | 1-2-1-8-1-2-2 | TtaTagccattcTatCT | 169_44 | -18.58 | 5224 |
| 169 | TTATAGCCATTCTATCT | 1-3-1-7-1-2-2 | TtatAgccattcTatCT | 169_45 | -18.31 | 5224 |
| 169 | TTATAGCCATTCTATCT | 1-1-1-10-4 | TtAtagccattctATCT | 169_46 | -18.90 | 5224 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 169 | TTATAGCCATTCTATCT | 3-10-1-1-2 | TTAtagccattctAtCT | 169_47 | -19.24 | 5224 |
| 169 | TTATAGCCATTCTATCT | 2-11-1-1-2 | TTatagccattctAtCT | 169_48 | -18.11 | 5224 |
| 169 | TTATAGCCATTCTATCT | 1-2-2-8-1-1-2 | TtaTAgccattctAtCT | 169_49 | -19.37 | 5224 |
| 169 | TTATAGCCATTCTATCT | 3-1-1-10-2 | TTAtAgccattctatCT | 169_50 | -19.74 | 5224 |
| 169 | TTATAGCCATTCTATCT | 3-12-2 | TTAtagccattctatCT | 169_51 | -19.15 | 5224 |
| 169 | TTATAGCCATTCTATCT | 2-1-2-10-2 | TTaTAgccattctatCT | 169_52 | -20.51 | 5224 |
| 169 | TTATAGCCATTCTATCT | 2-1-1-11-2 | TTaTagccattctatCT | 169_53 | -18.88 | 5224 |
| 169 | TTATAGCCATTCTATCT | 2-2-1-10-2 | TTatAgccattctatCT | 169_54 | -18.61 | 5224 |
| 169 | TTATAGCCATTCTATCT | 2-13-2 | TTatagccattctatCT | 169_55 | -18.02 | 5224 |
| 169 | TTATAGCCATTCTATCT | 1-1-3-10-2 | TtATAgccattctatCT | 169_56 | -20.18 | 5224 |
| 169 | TTATAGCCATTCTATCT | 1-1-2-11-2 | TtATagccattctatCT | 169_57 | -18.55 | 5224 |
| 169 | TTATAGCCATTCTATCT | 2-9-3-1-2 | TTatagccattCTAtCT | 169_58 | -21.75 | 5224 |
| 169 | TTATAGCCATTCTATCT | 1-1-1-8-2-2-2 | TtAtagccattCTatCT | 169_59 | -19.47 | 5224 |
| 169 | TTATAGCCATTCTATCT | 1-2-2-6-2-2-2 | TtaTAgccattCTatCT | 169_60 | -21.87 | 5224 |
| 169 | TTATAGCCATTCTATCT | 1-1-3-6-1-1-1-1-2 | TtATAgccattCtAtCT | 169_61 | -21.25 | 5224 |
| 169 | TTATAGCCATTCTATCT | 3-8-1-2-3 | TTAtagccattCtaTCT | 169_62 | -21.25 | 5224 |
| 170 | ATTTAAATTTCCAAACATT | 2-13-4 | ATttaaatttccaaaCATT | 170_1 | -16.82 | 5427 |
| 171 | GCTAATTTAAATTTCC | 4-10-2 | GCTAatttaaatttCC | 171_1 | -18.50 | 5434 |
| 172 | ATCAATATCTTCTCAC | 3-10-3 | ATCaatatcttctCAC | 172_1 | -17.10 | 5785 |
| 173 | TATCAATATCTTCTCA | 2-10-4 | TAtcaatatcttCTCA | 173_1 | -17.55 | 5786 |
| 174 | CTACAAATTCAATTTACT | 2-12-4 | CTacaaattcaattTACT | 174_1 | -17.38 | 6341 |
| 175 | TCTTACTCTGACTTTCCA | 2-14-2 | TCttactctgactttcCA | 175_1 | -21.47 | 6694 |
| 176 | TCTTACTCTGACTTTCC | 2-12-3 | TCttactctgactttCC | 176_1 | -21.53 | 6695 |
| 177 | AAATTTCCAAACCTTTC | 2-11-4 | AAatttccaaaccTTTC | 177_1 | -16.30 | 6958 |
| 178 | CTTCTTGTTTATCCCAA | 2-11-4 | CTtcttgtttatcCCAA | 178_1 | -22.77 | 7159 |
| 179 | TTCTTGTTTATCCCAA | 2-10-4 | TTcttgtttatcCCAA | 179_1 | -20.17 | 7159 |
| 180 | ATGCTTCTAACTAACA | 4-10-2 | ATGCttctaactaaCA | 180_1 | -19.21 | 7720 |
| 181 | CTTTAATGCTTCTAACT | 4-11-2 | CTTTaatgcttctaaCT | 181_1 | -18.49 | 7724 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 182 | CCTTTAATGCTTCTAAC | 2-11-4 | CCtttaatgcttcTAAC | 182_1 | -20.06 | 7725 |
| 183 | CTTTAATGCTTCTAAC | 2-10-4 | CTttaatgcttcTAAC | 183_1 | -16.07 | 7725 |
| 184 | TTCCTTTAATGCTTCTA | 4-11-2 | TTCCtttaatgcttcTA | 184_1 | -21.59 | 7727 |
| 185 | TATACCTTTCTTTAACCCT | 2-15-2 | TAtacctttctttaaccCT | 185_1 | -22.03 | 8117 |
| 186 | ATACCTTTCTTTAACCC | 4-11-2 | ATACctttctttaacCC | 186_1 | -22.68 | 8118 |
| 187 | TTATACCTTTCTTTAACC | 4-12-2 | TTATacctttctttaaCC | 187_1 | -21.52 | 8119 |
| 188 | TTTATACCTTTCTTTAAC | 2-12-4 | TTtatacctttcttTAAC | 188_1 | -17.01 | 8120 |
| 189 | TCAAGAATTCTCTCCTT | 2-11-4 | TCaagaattctctCCTT | 189_1 | -21.29 | 8571 |
| 190 | TTCAAGAATTCTCTCC | 2-10-4 | TTcaagaattctCTCC | 190_1 | -19.38 | 8573 |
| 191 | CTTCAAGAATTCTCTC | 2-10-4 | CTtcaagaattcTCTC | 191_1 | -18.00 | 8574 |
| 192 | TCTTCAAGAATTCTCT | 2-10-4 | TCttcaagaattCTCT | 192_1 | -18.46 | 8575 |
| 193 | ATCTTCAAGAATTCTC | 3-10-3 | ATCttcaagaattCTC | 193_1 | -17.04 | 8576 |
| 194 | TTTCTTACTATCTTCA | 4-10-2 | TTTCttactatcttCA | 194_1 | -17.47 | 8585 |
| 195 | CCTTTAGCATTTCTATT | 2-11-4 | CCtttagcatttcTATT | 195_1 | -21.72 | 8819 |
| 196 | TCCTTTAGCATTTCTAT | 3-11-3 | TCCtttagcatttcTAT | 196_1 | -22.39 | 8820 |
| 197 | GTTCTCTTTATTTCTTCT | 2-12-4 | GTtctctttatttcTTCT | 197_1 | -21.76 | 8887 |
| 198 | TTTACTGTCAACTCCT | 2-10-4 | TTtactgtcaacTCCT | 198_1 | -20.83 | 9150 |
| 199 | TTTCCAATGAATCTAT | 2-10-4 | TTtccaatgaatCTAT | 199_1 | -16.61 | 9201 |
| 200 | CCTTTCCAATGAATCTA | 2-11-4 | CCtttccaatgaaTCTA | 200_1 | -22.34 | 9202 |
| 201 | CTTTCCAATGAATCTA | 2-10-4 | CTttccaatgaaTCTA | 201_1 | -18.34 | 9202 |
| 202 | CCTTTCCAATGAATCT | 3-10-3 | CCTttccaatgaaTCT | 202_1 | -21.30 | 9203 |
| 203 | TTATACCCTTTCCAAT | 2-10-4 | TTataccctttcCAAT | 203_1 | -19.61 | 9209 |
| 204 | GTTTATACCCTTTCCAA | 3-11-3 | GTTtatacccttcCAA | 204_1 | -21.88 | 9210 |
| 205 | TTTATACCCTTTCCAA | 2-10-4 | TTtatacccttCCAA | 205_1 | -20.50 | 9210 |
| 206 | GTTTATACCCTTTCCA | 2-11-3 | GTttatacccttCCA | 206_1 | -22.69 | 9211 |
| 207 | TGTTTATACCCTTTCCA | 3-12-2 | TGTttatacccttcCA | 207_1 | -22.80 | 9211 |
| 208 | ACTGTTTATACCCTTTCC | 2-14-2 | ACtgtttatacccttCC | 208_1 | -22.96 | 9212 |
| 208 | ACTGTTTATACCCTTTCC | 1-11-1-3-2 | Actgtttataccctttcc | 208_2 | -22.45 | 9212 |
| 208 | ACTGTTTATACCCTTTCC | 1-2-1-10-1-1-2 | ActGtttataccctTtCC | 208_3 | -22.17 | 9212 |
| 208 | ACTGTTTATACCCTTTCC | 1-2-1-1-1-10-2 | ActGtTtatacccttCC | 208_4 | -22.17 | 9212 |
| 208 | ACTGTTTATACCCTTTCC | 1-2-1-12-2 | ActGtttatacccttCC | 208_5 | -21.87 | 9212 |
| 208 | ACTGTTTATACCCTTTCC | 1-3-1-11-2 | ActgTttatacccttCC | 208_6 | -22.22 | 9212 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 208 | ACTGTTTATACCCTTTCC | 1-15-2 | ActgtttatacccttttCC | 208_7 | -21.56 | 9212 |
| 209 | ACTGTTTATACCCTTTC | 4-11-2 | ACTGtttatacccttTC | 209_1 | -21.65 | 9213 |
| 209 | ACTGTTTATACCCTTTC | 1-11-1-2-2 | ActgtttataccCttTC | 209_2 | -18.25 | 9213 |
| 209 | ACTGTTTATACCCTTTC | 1-1-1-8-1-1-1-1-2 | AcTgtttatacCcTtTC | 209_3 | -19.56 | 9213 |
| 209 | ACTGTTTATACCCTTTC | 1-2-1-9-4 | ActGtttatacccTTTC | 209_4 | -19.51 | 9213 |
| 209 | ACTGTTTATACCCTTTC | 1-3-1-6-1-2-3 | ActgTttatacCctTTC | 209_5 | -19.51 | 9213 |
| 209 | ACTGTTTATACCCTTTC | 2-9-1-3-2 | ActgtttatacCcttTC | 209_6 | -19.43 | 9213 |
| 209 | ACTGTTTATACCCTTTC | 1-2-1-7-1-3-2 | ActGtttatacCcttTC | 209_7 | -18.35 | 9213 |
| 209 | ACTGTTTATACCCTTTC | 1-3-1-8-1-1-2 | ActgTttatacccTtTC | 209_8 | -18.53 | 9213 |
| 209 | ACTGTTTATACCCTTTC | 1-11-1-1-3 | ActgtttataccCtTTC | 209_9 | -19.06 | 9213 |
| 209 | ACTGTTTATACCCTTTC | 2-10-1-2-2 | ACtgtttataccCttTC | 209_10 | -19.64 | 9213 |
| 210 | AACTGTTTATACCCTTT | 4-11-2 | AACTgtttatacccttTT | 210_1 | -19.51 | 9214 |
| 211 | TATGACTCCAATAATC | 3-10-3 | TATgactccaataATC | 211_1 | -16.57 | 10832 |
| 212 | CTCCTTTATGACTCCAA | 4-11-2 | CTCCtttatgactccAA | 212_1 | -22.74 | 10837 |
| 213 | CTCCTTTATGACTCCA | 3-11-2 | CTCctttatgactcCA | 213_1 | -21.50 | 10838 |
| 214 | CCATTATTTCTTAAATA | 4-11-2 | CCATtatttcttaaaTA | 214_1 | -17.56 | 10877 |
| 215 | ATTTCATATTACTAACTA | 2-12-4 | ATttcatattactaACTA | 215_1 | -16.64 | 11434 |
| 216 | CATTTCATATTACTAACT | 3-12-3 | CATttcatattactaACT | 216_1 | -17.70 | 11435 |
| 217 | TCATTTCATATTACTAAC | 4-12-2 | TCATttcatattactaAC | 217_1 | -16.72 | 11436 |
| 218 | ATCATTTCATATTACTA | 3-11-3 | ATCatttcatattaCTA | 218_1 | -17.23 | 11438 |
| 219 | TTATCATTTCATATTACT | 4-12-2 | TTATcatttcatattaCT | 219_1 | -17.77 | 11439 |
| 220 | TGTACTTTCCTTTACCA | 2-13-2 | TGtactttcctttacCA | 220_1 | -20.37 | 11464 |
| 221 | TATACACCATCATTATA | 4-11-2 | TATAcaccatcattaTA | 221_1 | -18.48 | 11507 |
| 222 | TTATACACCATCATTAT | 3-11-3 | TTAtacaccatcatTAT | 222_1 | -17.83 | 11508 |
| 223 | TATTTATACACCATCAT | 3-11-3 | TATttatacaccatCAT | 223_1 | -18.54 | 11511 |
| 224 | TTATTTATACACCATC | 2-10-4 | TTatttatacacCATC | 224_1 | -16.60 | 11513 |
| 225 | AATTATTTATACACCAT | 2-11-4 | AAttatttatacaCCAT | 225_1 | -16.82 | 11514 |
| 226 | CATGACACTTACATAA | 3-10-3 | CATgacacttacaTAA | 226_1 | -16.26 | 11736 |
| 227 | AGTTCACTACTATTAC | 3-10-3 | AGTtcactactatTAC | 227_1 | -17.55 | 12361 |
| 228 | ATAAGCTTACCTCATA | 2-10-4 | ATaagcttacctCATA | 228_1 | -19.32 | 12794 |
| 229 | TATAAGCTTACCTCAT | 3-10-3 | TATaagcttacctCAT | 229_1 | -19.32 | 12795 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 230 | ATATAAGCTTACCTCA | 4-10-2 | ATATaagcttacctCA | 230_1 | -19.32 | 12796 |
| 231 | CTTCCCTTTGATAACAT | 3-11-3 | CTTccctttgataaCAT | 231_1 | -21.19 | 12894 |
| 232 | TTCCCTTTGATAACAT | 4-10-2 | TTCCctttgataacAT | 232_1 | -19.27 | 12894 |
| 233 | CCTTCCCTTTGATAACA | 2-12-3 | CCttcccttkgataACA | 233_1 | -23.06 | 12895 |
| 234 | CTTCCCTTTGATAACA | 4-10-2 | CTTccctttgataACA | 234_1 | -20.51 | 12895 |
| 235 | CCTTCCCTTTGATAAC | 3-11-2 | CCTtcccttkgataAC | 235_1 | -20.96 | 12896 |
| 236 | TTGATTCAATTCCCTTA | 2-11-4 | TTgattcaattccCTTA | 236_1 | -20.48 | 13223 |
| 236 | TTGATTCAATTCCCTTA | 2-9-1-1-1-1-2 | TTgattcaattCcCtTA | 236_2 | -19.54 | 13223 |
| 236 | TTGATTCAATTCCCTTA | 2-10-1-1-3 | TTgattcaattcCcTTA | 236_3 | -19.59 | 13223 |
| 236 | TTGATTCAATTCCCTTA | 2-1-1-8-1-2-2 | TTgAttcaattcCctTA | 236_4 | -19.06 | 13223 |
| 236 | TTGATTCAATTCCCTTA | 2-2-1-7-1-2-2 | TTgaTtcaattcCctTA | 236_5 | -19.00 | 13223 |
| 236 | TTGATTCAATTCCCTTA | 2-9-1-3-2 | TTgattcaattCcctTA | 236_6 | -18.65 | 13223 |
| 236 | TTGATTCAATTCCCTTA | 1-2-2-6-2-2-2 | TtgATtcaattCCctTA | 236_7 | -21.37 | 13223 |
| 236 | TTGATTCAATTCCCTTA | 2-1-1-7-1-1-1-2 | TTgAttcaattcCtCtTA | 236_8 | -20.04 | 13223 |
| 236 | TTGATTCAATTCCCTTA | 1-1-2-7-1-1-1-2 | TtGAttcaattcCtCtTA | 236_9 | -20.10 | 13223 |
| 236 | TTGATTCAATTCCCTTA | 1-2-1-9-4 | TtgAttcaattccCTTA | 236_10 | -19.67 | 13223 |
| 236 | TTGATTCAATTCCCTTA | 1-3-1-6-1-1-1-2 | TtgaTtcaattcCtCtTA | 236_11 | -18.67 | 13223 |
| 236 | TTGATTCAATTCCCTTA | 2-10-1-2-2 | TTgattcaattcCctTA | 236_12 | -18.56 | 13223 |
| 236 | TTGATTCAATTCCCTTA | 1-2-2-7-2-1-2 | TtgATtcaattcCCtTA | 236_13 | -21.49 | 13223 |
| 236 | TTGATTCAATTCCCTTA | 1-1-2-8-1-2-2 | TtGAttcaattcCctTA | 236_14 | -19.13 | 13223 |
| 236 | TTGATTCAATTCCCTTA | 2-11-1-1-2 | TTgattcaattccCtTA | 236_15 | -18.77 | 13223 |
| 236 | TTGATTCAATTCCCTTA | 1-1-1-1-1-8-1-1-2 | TtGaTtcaattccCtTA | 236_16 | -18.07 | 13223 |
| 236 | TTGATTCAATTCCCTTA | 1-1-2-7-2-2-2 | TtGAttcaattcCCtTA | 236_17 | -21.50 | 13223 |
| 236 | TTGATTCAATTCCCTTA | 1-2-1-7-1-1-4 | TtgAttcaattcCCTTA | 236_18 | -20.44 | 13223 |
| 236 | TTGATTCAATTCCCTTA | 3-8-1-1-1-1-2 | TTGattcaattcCtCtTA | 236_19 | -20.60 | 13223 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Mctif | Design | Compound | CMP ID_NO | ΔG° | Start SEQ_ID NO |
|---|---|---|---|---|---|---|
| 236 | TTGATTCAATTCCCTTA | 2-2-1-6-1-3-2 | TTgaTtcaattCcctTA | 236_20 | -19.09 | 13223 |
| 236 | TTGATTCAATTCCCTTA | 2-2-1-7-2-1-2 | TTgaTtcaattcCCtTA | 236_21 | -21.49 | 13223 |
| 237 | ATTGATTCAATTCCCTT | 2-11-4 | ATtgattcaattcCCTT | 237_1 | -21.28 | 13224 |
| 237 | ATTGATTCAATTCCCTT | 3-8-3-1-2 | ATTgattcaatTCCcTT | 237_2 | -22.78 | 13224 |
| 237 | ATTGATTCAATTCCCTT | 1-1-1-8-3-1-2 | AtTgattcaatTCCcTT | 237_3 | -21.02 | 13224 |
| 237 | ATTGATTCAATTCCCTT | 1-2-1-8-2-1-2 | AttGattcaattCCcTT | 237_4 | -19.40 | 13224 |
| 237 | ATTGATTCAATTCCCTT | 1-3-1-7-2-1-2 | AttgAttcaattCCcTT | 237_5 | -19.74 | 13224 |
| 237 | ATTGATTCAATTCCCTT | 1-2-1-7-2-1-3 | AttGattcaatTCcCTT | 237_6 | -19.67 | 13224 |
| 237 | ATTGATTCAATTCCCTT | 2-2-1-7-1-1-3 | ATtgAttcaattCcCTT | 237_7 | -20.27 | 13224 |
| 237 | ATTGATTCAATTCCCTT | 1-1-1-9-1-1-3 | AtTgattcaattCcCTT | 237_8 | -19.32 | 13224 |
| 237 | ATTGATTCAATTCCCTT | 1-3-1-7-1-1-3 | AttgAttcaattCCcTT | 237_9 | -19.02 | 13224 |
| 237 | ATTGATTCAATTCCCTT | 1-1-1-1-1-7-2-1-2 | AtTgAttcaattCCcTT | 237_10 | -20.53 | 13224 |
| 237 | ATTGATTCAATTCCCTT | 1-2-2-7-2-1-2 | AttGAttcaattCCcTT | 237_11 | -21.11 | 13224 |
| 237 | ATTGATTCAATTCCCTT | 1-2-1-8-1-1-3 | AttGattcaattCcCTT | 237_12 | -18.68 | 13224 |
| 237 | ATTGATTCAATTCCCTT | 1-1-2-8-1-2-2 | AtTGattcaattCccTT | 237_13 | -18.81 | 13224 |
| 237 | ATTGATTCAATTCCCTT | 3-10-1-1-2 | ATTgattcaattcCcTT | 237_14 | -19.42 | 13224 |
| 237 | ATTGATTCAATTCCCTT | 1-1-2-9-4 | AtTGattcaattcCCTT | 237_15 | -21.89 | 13224 |
| 237 | ATTGATTCAATTCCCTT | 2-2-1-8-1-1-2 | ATtgAttcaattcCcTT | 237_16 | -18.61 | 13224 |
| 237 | ATTGATTCAATTCCCTT | 1-2-2-6-3-1-2 | AttGAttcaatTCCcTT | 237_17 | -22.09 | 13224 |
| 237 | ATTGATTCAATTCCCTT | 1-1-1-8-2-1-3 | AtTgattcaatTCcCTT | 237_18 | -20.30 | 13224 |
| 237 | ATTGATTCAATTCCCTT | 1-1-1-9-2-1-2 | AtTgattcaattCCcTT | 237_19 | -20.03 | 13224 |
| 237 | ATTGATTCAATTCCCTT | 1-1-1-1-1-7-1-3 | AtTgAttcaattCcCTT | 237_20 | -19.82 | 13224 |
| 237 | ATTGATTCAATTCCCTT | 3-1-1-8-1-1-2 | ATTgAttcaattcCcTT | 237_21 | -19.92 | 13224 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 238 | TTGATTCAATTCCCTT | 2-10-4 | TTgattcaattcCCTT | 238_1 | -20.52 | 13224 |
| 239 | TATTGATTCAATTCCCT | 2-11-4 | TAttgattcaattCCCT | 239_1 | -22.82 | 13225 |
| 239 | TATTGATTCAATTCCCT | 3-9-2-1-2 | TATtgattcaatTCcCT | 239_2 | -21.17 | 13225 |
| 239 | TATTGATTCAATTCCCT | 2-9-1-1-1-1-2 | TAttgattcaaTtCcCT | 239_3 | -19.37 | 13225 |
| 239 | TATTGATTCAATTCCCT | 1-1-2-7-3-1-2 | TaTTgattcaaTTCcCT | 239_4 | -21.49 | 13225 |
| 239 | TATTGATTCAATTCCCT | 1-3-1-6-3-1-2 | TattGattcaaTTCcCT | 239_5 | -19.90 | 13225 |
| 239 | TATTGATTCAATTCCCT | 2-9-1-2-3 | TAttgattcaaTtcCCT | 239_6 | -20.89 | 13225 |
| 239 | TATTGATTCAATTCCCT | 1-10-1-2-3 | TattgattcaaTtcCCT | 239_7 | -19.76 | 13225 |
| 239 | TATTGATTCAATTCCCT | 1-1-1-1-1-8-1-1-2 | TaTtGattcaattCcCT | 239_8 | -18.41 | 13225 |
| 239 | TATTGATTCAATTCCCT | 1-2-2-8-1-1-2 | TatTGattcaattCcCT | 239_9 | -19.66 | 13225 |
| 239 | TATTGATTCAATTCCCT | 1-2-1-9-1-1-2 | TatTgattcaattCcCT | 239_10 | -18.60 | 13225 |
| 239 | TATTGATTCAATTCCCT | 2-2-1-10-2 | TAttGattcaattccCT | 239_11 | -18.33 | 13225 |
| 239 | TATTGATTCAATTCCCT | 1-12-4 | TattgattcaattCCCT | 239_12 | -21.69 | 13225 |
| 239 | TATTGATTCAATTCCCT | 2-1-1-9-1-1-2 | TAtTgattcaattCcCT | 239_13 | -19.73 | 13225 |
| 239 | TATTGATTCAATTCCCT | 2-12-3 | TAttgattcaattcCCT | 239_14 | -20.45 | 13225 |
| 239 | TATTGATTCAATTCCCT | 1-2-1-10-3 | TatTgattcaattcCCT | 239_15 | -20.11 | 13225 |
| 239 | TATTGATTCAATTCCCT | 1-1-3-10-2 | TaTTgattcaattccCT | 239_16 | -19.84 | 13225 |
| 239 | TATTGATTCAATTCCCT | 1-1-1-1-1-6-3-1-2 | TaTtGattcaaTTCcCT | 239_17 | -20.34 | 13225 |
| 239 | TATTGATTCAATTCCCT | 2-2-1-6-1-1-1-1-2 | TAttGattcaaTtCcCT | 239_18 | -19.54 | 13225 |
| 239 | TATTGATTCAATTCCCT | 2-1-1-8-2-1-2 | TAtTgattcaatTCcCT | 239_19 | -20.72 | 13225 |
| 239 | TATTGATTCAATTCCCT | 1-1-2-9-1-1-2 | TaTTgattcaattCcCT | 239_20 | -19.55 | 13225 |
| 239 | TATTGATTCAATTCCCT | 2-1-1-10-3 | TAtTgattcaattcCCT | 239_21 | -21.24 | 13225 |
| 240 | TATTGATTCAATTCCC | 3-10-3 | TATtgattcaattCCC | 240_1 | -20.58 | 13226 |
| 241 | GCACATTCTTTCTATAC | 3-11-3 | GCAcattctttctaTAC | 241_1 | -21.17 | 15115 |
| 241 | GCACATTCTTTCTATAC | 1-1-3-6-2-2-2 | GcACattctttCTatAC | 241_2 | -20.68 | 15115 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 241 | GCACATTCTTTCTATAC | 1-1-1-1-1-6-1-2-3 | GcAcAttctttCtaTAC | 241_3 | -18.46 | 15115 |
| 241 | GCACATTCTTTCTATAC | 1-1-2-7-1-2-3 | GcACattctttCtaTAC | 241_4 | -19.49 | 15115 |
| 241 | GCACATTCTTTCTATAC | 2-9-1-3-2 | GCacattctttCtatAC | 241_5 | -18.68 | 15115 |
| 241 | GCACATTCTTTCTATAC | 1-1-3-8-4 | GcACAttctttctATAC | 241_6 | -20.89 | 15115 |
| 241 | GCACATTCTTTCTATAC | 2-2-1-9-3 | GCacAttctttctaTAC | 241_7 | -19.66 | 15115 |
| 241 | GCACATTCTTTCTATAC | 2-1-1-11-2 | GCaCattctttctatAC | 241_8 | -18.39 | 15115 |
| 241 | GCACATTCTTTCTATAC | 1-1-3-9-3 | GcACAttctttctaTAC | 241_9 | -19.98 | 15115 |
| 241 | GCACATTCTTTCTATAC | 3-12-2 | GCAcattctttctatAC | 241_10 | -19.27 | 15115 |
| 241 | GCACATTCTTTCTATAC | 1-1-1-1-1-6-1-1-4 | GcAcAttctttCtATAC | 241_11 | -19.36 | 15115 |
| 241 | GCACATTCTTTCTATAC | 3-8-1-1-1-1-2 | GCAcattctttCtAtAC | 241_12 | -20.34 | 15115 |
| 241 | GCACATTCTTTCTATAC | 2-1-1-7-1-2-3 | GCaCattctttCtaTAC | 241_13 | -21.27 | 15115 |
| 241 | GCACATTCTTTCTATAC | 1-2-2-8-4 | GcaCAttctttctATAC | 241_14 | -20.33 | 15115 |
| 241 | GCACATTCTTTCTATAC | 1-1-3-10-2 | GcACAttctttctatAC | 241_15 | -18.08 | 15115 |
| 242 | GAATTTCAACTACTAT | 2-10-4 | GAatttcaactaCTAT | 242_1 | -16.13 | 15258 |
| 243 | CCATTTATTTCCATTTAT | 3-12-3 | CCAtttatttccattTAT | 243_1 | -21.92 | 15568 |
| 244 | TTTCCATTTATTTCCATTT | 4-13-2 | TTTCcatttatttccatTT | 244_1 | -20.93 | 15570 |
| 244 | TTTCCATTTATTTCCATTT | 1-4-1-7-1-1-4 | TttccAtttatttCcATTT | 244_2 | -20.48 | 15570 |
| 244 | TTTCCATTTATTTCCATTT | 2-1-1-10-2-1-2 | TTtCcatttatttcCAtTT | 244_3 | -21.47 | 15570 |
| 244 | TTTCCATTTATTTCCATTT | 1-2-1-1-1-7-1-3-2 | TttCcAtttatttCcatTT | 244_4 | -19.43 | 15570 |
| 244 | TTTCCATTTATTTCCATTT | 2-2-2-11-2 | TTtcCAtttatttccatTT | 244_5 | -20.70 | 15570 |
| 245 | CTTTCCATTTATTTCCAT | 3-12-3 | CTTtccatttatttcCAT | 245_1 | -22.31 | 15572 |
| 246 | TCTTTCCATTTATTTCCA | 4-12-2 | TCTTtccatttatttcCA | 246_1 | -22.74 | 15573 |
| 247 | ATCTTTCCATTTATTTCC | 3-12-3 | ATCtttccatttattTCC | 247_1 | -22.85 | 15574 |
| 248 | TTCCATGCAAACTTTA | 4-10-2 | TTCCatgcaaacttTA | 248_1 | -19.01 | 15722 |
| 249 | CAGTTTAAATTCACAC | 3-10-3 | CAGtttaaattcaCAC | 249_1 | -16.68 | 16597 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 250 | CTATTCCAGTTTAAAT | 4-10-2 | CTATtccagtttaaAT | 250_1 | -16.86 | 16603 |
| 251 | TGCAAATACCTCTTCA | 4-10-2 | TGCAaatacctcttCA | 251_1 | -21.49 | 16730 |
| 252 | CTAAATAGATTCCACT | 2-10-4 | CTaaatagattcCACT | 252_1 | -17.95 | 16849 |
| 253 | TATTGATATTTACTCT | 2-10-4 | TAttgatatttaCTCT | 253_1 | -16.32 | 17089 |
| 254 | CCTTAGTATTACAATT | 4-10-2 | CCTTagtattacaaTT | 254_1 | -17.43 | 17401 |
| 255 | CTATTCAATAAACTAAACA | 4-13-2 | CTATtcaataaactaaaCA | 255_1 | -16.45 | 24290 |
| 256 | CAGCTATTCAATAAAC | 4-10-2 | CAGCtattcaataaAC | 256_1 | -16.94 | 24296 |
| 257 | TATAGACCCAAACTAT | 3-10-3 | TATagacccaaacTAT | 257_1 | -18.15 | 24811 |
| 258 | TAATCCCATACATCTAT | 2-11-4 | TAatcccatacatCTAT | 258_1 | -20.45 | 25032 |
| 259 | ATAATCCCATACATCTA | 3-11-3 | ATAatcccatacatCTA | 259_1 | -20.45 | 25033 |
| 260 | ATCTCAACTACCATTT | 4-10-2 | ATCTcaactaccatTT | 260_1 | -18.14 | 25250 |
| 261 | AATCTCAACTACCATT | 4-10-2 | AATCtcaactaccaTT | 261_1 | -16.76 | 25251 |
| 262 | ACAACTTCTATCATAC | 3-10-3 | ACAacttctatcaTAC | 262_1 | -16.33 | 25718 |
| 263 | GAACAACTTCTATCAT | 2-10-4 | GAacaacttctaTCAT | 263_1 | -16.94 | 25720 |
| 264 | TGAACAACTTCTATCA | 3-10-3 | TGAacaacttctaTCA | 264_1 | -17.36 | 25721 |
| 265 | TACACAAATACTTAAATCA | 4-13-2 | TACAcaaatacttaaatCA | 265_1 | -16.93 | 26331 |
| 266 | TTAAGCTTTCACCTAT | 2-10-4 | TTaagctttcacCTAT | 266_1 | -19.36 | 27165 |
| 267 | AAACTCTTGCATCTACT | 2-13-2 | AAactcttgcatctaCT | 267_1 | -16.65 | 27248 |
| 268 | AAATTTCTCAACCTAAATTT | 2-14-4 | AAatttctcaacctaaATTT | 268_1 | -16.78 | 29330 |
| 269 | CCAACATAGATCCTCT | 2-10-4 | CCaacatagatcCTCT | 269_1 | -22.49 | 29635 |
| 270 | TCCAACATAGATCCTCT | 2-11-4 | TCcaacatagatcCTCT | 270_1 | -22.81 | 29635 |
| 271 | CTCCAACATAGATCCTC | 3-11-3 | CTCcaacatagatcCTC | 271_1 | -22.81 | 29636 |
| 272 | TCCAACATAGATCCTC | 2-10-4 | TCcaacatagatCCTC | 272_1 | -21.69 | 29636 |
| 273 | CTCCAACATAGATCCT | 3-10-3 | CTCcaacatagatCCT | 273_1 | -22.68 | 29637 |
| 274 | TCTCCAACATAGATCCT | 4-11-2 | TCTCcaacatagatcCT | 274_1 | -22.81 | 29637 |
| 275 | ATTCTCAATTGCACTT | 4-10-2 | ATTCtcaattgcacTT | 275_1 | -17.90 | 29661 |
| 276 | TATTCTCAATTGCACTT | 4-11-2 | TATTctcaattgcacTT | 276_1 | -18.54 | 29661 |
| 277 | TCACCTAATAGCACCA | 2-10-4 | TCacctaatagcACCA | 277_1 | -21.99 | 29684 |
| 278 | TTCACCTAATAGCACCA | 2-11-4 | TTcacctaatagcACCA | 278_1 | -22.53 | 29684 |
| 279 | CATTATTATTTAACCTT | 2-11-4 | CAttattatttaaCCTT | 279_1 | -17.83 | 30455 |
| 280 | ACATTATTATTTAACCT | 3-11-3 | ACAttattatttaaCCT | 280_1 | -18.05 | 30456 |
| 281 | TACATTATTATTTAACC | 4-11-2 | TACattattatttaaCC | 281_1 | -16.80 | 30457 |
| 282 | CATTTACATTATTATTTAAC | 2-14-4 | CAtttacattattattTAAC | 282_1 | -16.44 | 30458 |
| 283 | CTCATTTACATTATTATT | 4-12-2 | CTCatttacattattaTT | 283_1 | -17.33 | 30462 |
| 284 | TATCTCATTTACATTATT | 4-12-2 | TATCtcatttacattaTT | 284_1 | -17.62 | 30465 |
| 285 | ATCATTCTCAACAATTA | 4-11-2 | ATCAttctcaacaatTA | 285_1 | -17.04 | 30601 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 285 | ATCATTCTCAACAATTA | 4-7-6 | ATCAttctcaaCAATTA | 285_2 | -21.48 | 30601 |
| 285 | ATCATTCTCAACAATTA | 1-1-3-6-6 | AtCATtctcaaCAATTA | 285_3 | -20.80 | 30601 |
| 285 | ATCATTCTCAACAATTA | 5-6-2-2-2 | ATCATtctcaaCAatTA | 285_4 | -20.46 | 30601 |
| 285 | ATCATTCTCAACAATTA | 4-7-1-1-4 | ATCAttctcaaCaATTA | 285_5 | -19.80 | 30601 |
| 285 | ATCATTCTCAACAATTA | 5-7-1-1-3 | ATCATtctcaacAaTTA | 285_6 | -19.31 | 30601 |
| 285 | ATCATTCTCAACAATTA | 5-6-3-1-2 | ATCATtctcaaCAAtTA | 285_7 | -20.97 | 30601 |
| 285 | ATCATTCTCAACAATTA | 4-7-2-1-3 | ATCAttctcaaCAaTTA | 285_8 | -20.16 | 30601 |
| 285 | ATCATTCTCAACAATTA | 5-6-1-1-4 | ATCATtctcaaCaATTA | 285_9 | -21.05 | 30601 |
| 285 | ATCATTCTCAACAATTA | 5-6-1-1-1-2 | ATCATtctcaaCaAtTA | 285_10 | -19.29 | 30601 |
| 285 | ATCATTCTCAACAATTA | 1-1-3-7-5 | AtCATtctcaacAATTA | 285_11 | -18.70 | 30601 |
| 286 | AAGATCATTCTCAACA | 4-10-2 | AAGAtcattctcaaCA | 286_1 | -17.15 | 30605 |
| 287 | TCTCAAAGATCATTCTC | 3-11-3 | TCTcaaagatcattCTC | 287_1 | -19.02 | 30609 |
| 288 | TCTCAAAGATCATTCT | 4-10-2 | TCTCaaagatcattCT | 288_1 | -17.81 | 30610 |
| 289 | ACTTAATTATACTTCC | 4-10-2 | ACTTaattatacttCC | 289_1 | -17.28 | 30667 |
| 290 | TACACTTAATTATACTTC | 2-12-4 | TAcacttaattataCTTC | 290_1 | -16.87 | 30668 |
| 291 | TTACACTTAATTATACTT | 3-12-3 | TTAcacttaattataCTT | 291_1 | -16.20 | 30669 |
| 292 | TTTACACTTAATTATACT | 2-12-4 | TTtacacttaattaTACT | 292_1 | -16.23 | 30670 |
| 293 | CTATTTAATTTACACTT | 3-11-3 | CTAtttaatttacaCTT | 293_1 | -16.26 | 30679 |
| 294 | TATCTATTTAATTTACAC | 3-12-3 | TATctatttaatttaCAC | 294_1 | -16.06 | 30681 |
| 295 | TTTATCTATTTAATTTACA | 4-13-2 | TTTAtctatttaatttaCA | 295_1 | -16.34 | 30682 |
| 296 | CTCTGCTTATAACTTT | 4-10-2 | CTCTgcttataactTT | 296_1 | -18.51 | 30699 |
| 297 | CCTCTGCTTATAACTT | 3-10-3 | CCTctgcttataaCTT | 297_1 | -21.29 | 30700 |
| 298 | TCCTCTGCTTATAACTT | 3-12-2 | TCCtctgcttataacTT | 298_1 | -20.86 | 30700 |
| 299 | TCCTCTGCTTATAACT | 3-11-2 | TCCtctgcttataaCT | 299_1 | -20.70 | 30701 |
| 300 | TTCCTCTGCTTATAACT | 3-12-2 | TTCctctgcttataaCT | 300_1 | -20.03 | 30701 |
| 301 | TTTCCTCTGCTTATAAC | 4-11-2 | TTTCctctgcttataAC | 301_1 | -19.20 | 30702 |
| 302 | TACTATACTTTCCTCT | 2-10-4 | TActatactttcCTCT | 302_1 | -20.07 | 30711 |
| 303 | TTCTACTATACTTTCC | 4-10-2 | TTCTactatactttCC | 303_1 | -19.55 | 30714 |
| 304 | AGTTCTACTATACTTTC | 4-11-2 | AGTTctactatactttC | 304_1 | -18.49 | 30715 |
| 304 | AGTTCTACTATACTTTC | 1-10-6 | AgttctactatACTTTC | 304_2 | -18.76 | 30715 |
| 304 | AGTTCTACTATACTTTC | 1-1-2-7-1-1-4 | AgTTctactatAcTTTC | 304_3 | -18.23 | 30715 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 304 | AGTTCTACTATACTTTC | 3-8-2-2-2 | AGTtctactatACttTC | 304_4 | -19.19 | 30715 |
| 304 | AGTTCTACTATACTTTC | 2-2-1-6-1-1-4 | AGttCtactatAcTTTC | 304_5 | -19.07 | 30715 |
| 304 | AGTTCTACTATACTTTC | 1-2-2-8-4 | AgtTCtactatacTTTC | 304_6 | -18.46 | 30715 |
| 304 | AGTTCTACTATACTTTC | 3-10-1-1-2 | AGTtctactatacTtTC | 304_7 | -18.12 | 30715 |
| 304 | AGTTCTACTATACTTTC | 3-11-3 | AGTtctactatactTTC | 304_8 | -18.42 | 30715 |
| 304 | AGTTCTACTATACTTTC | 3-1-1-10-2 | AGTtCtactatactTTC | 304_9 | -18.58 | 30715 |
| 304 | AGTTCTACTATACTTTC | 2-1-2-10-2 | AGtTCtactatactTTC | 304_10 | -18.02 | 30715 |
| 304 | AGTTCTACTATACTTTC | 1-2-2-6-2-1-3 | AgtTCtactatACtTTC | 304_11 | -19.02 | 30715 |
| 304 | AGTTCTACTATACTTTC | 2-1-2-6-1-3-2 | AGtTCtactatActtTC | 304_12 | -18.22 | 30715 |
| 304 | AGTTCTACTATACTTTC | 2-2-1-7-2-1-2 | AGttCtactataCTtTC | 304_13 | -19.22 | 30715 |
| 304 | AGTTCTACTATACTTTC | 3-1-1-7-1-1-3 | AGTtCtactataCtTTC | 304_14 | -20.39 | 30715 |
| 304 | AGTTCTACTATACTTTC | 1-1-1-1-1-8-4 | AgTtCtactatacTTTC | 304_15 | -18.13 | 30715 |
| 305 | GTTCTACTATACTTTC | 4-10-2 | GTTCtactatactTTC | 305_1 | -17.48 | 30715 |
| 306 | CATTATATTTAAACTATCA | 4-13-2 | CATTatatttaaactatCA | 306_1 | -16.93 | 31630 |
| 307 | CACATTATATTTAAACTAT | 2-13-4 | CAcattatatttaaaCTAT | 307_1 | -17.11 | 31632 |
| 308 | ACACATTATATTTAAACTA | 3-13-3 | ACAcattatatttaaaCTA | 308_1 | -17.09 | 31633 |
| 309 | ACCACCTAAGACCTCAA | 2-11-4 | ACcacctaagaccTCAA | 309_1 | -22.49 | 32755 |
| 310 | CCACCTAAGACCTCAA | 2-10-4 | CCcacctaagaccTCAA | 310_1 | -22.63 | 32755 |
| 311 | ACCACCTAAGACCTCA | 2-11-3 | ACcacctaagaccTCA | 311_1 | -21.74 | 32756 |
| 312 | ACCTTAAGTAACATTT | 4-10-2 | ACCTtaagtaacatTT | 312_1 | -16.82 | 33366 |
| 313 | CACCTTAAGTAACATT | 4-10-2 | CACCttaagtaacaTT | 313_1 | -18.05 | 33367 |
| 314 | CCACCTTAAGTAACAT | 3-10-3 | CCAccttaagtaaCAT | 314_1 | -20.70 | 33368 |
| 315 | ACCACCTTAAGTAACA | 4-10-2 | ACCAccttaagtaaCA | 315_1 | -20.68 | 33369 |
| 316 | TTATTAACCACCTTAA | 3-10-3 | TTAttaaccacctTAA | 316_1 | -16.19 | 33375 |
| 317 | CATTATTAACCACCTT | 2-10-4 | CAttattaaccaCCTT | 317_1 | -19.92 | 33377 |
| 318 | ACATTATTAACCACCT | 3-10-3 | ACAttattaaccaCCT | 318_1 | -20.14 | 33378 |
| 319 | ACCAATTATACTTACAA | 3-11-3 | ACCaattatacttaCAA | 319_1 | -17.16 | 36606 |
| 320 | AACCAATTATACTTACA | 4-11-2 | AACCaattatacttaCA | 320_1 | -17.16 | 36607 |
| 321 | CAAATACAGATTATCC | 2-10-4 | CAaatacagattATCC | 321_1 | -16.44 | 38092 |
| 322 | TTTACATTCCCATCATC | 2-11-4 | TTtacattcccatCATC | 322_1 | -21.08 | 38297 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 323 | CACACCTATTATATAAT | 4-11-2 | CACacctattatataAT | 323_1 | -17.02 | 39173 |
| 324 | TCACACCTATTATATAA | 3-11-3 | TCAcacctattataTAA | 324_1 | -17.02 | 39174 |
| 325 | CTTCACACCTATTATATA | 2-12-4 | CTtcacacctattaTATA | 325_1 | -20.65 | 39175 |
| 326 | ACTTCACACCTATTATAT | 3-12-3 | ACTtcacacctattaTAT | 326_1 | -20.46 | 39176 |
| 327 | GCTCACACTAATTATT | 2-10-4 | GCtcacactaatTATT | 327_1 | -18.72 | 39228 |
| 328 | ATGCTCACACTAATTA | 4-10-2 | ATGCtcacactaatTA | 328_1 | -19.38 | 39230 |
| 329 | AATGCTCACACTAATT | 4-10-2 | AATGctcacactaaTT | 329_1 | -16.21 | 39231 |
| 330 | AAACTGTACACCTACT | 2-10-4 | AAactgtacaccTACT | 330_1 | -17.99 | 39563 |
| 331 | GTTTCCATCTACTATTA | 2-11-4 | GTttccatctactATTA | 331_1 | -19.78 | 39808 |
| 332 | TTTCCATCTACTATTA | 4-10-2 | TTTCcatctactatTA | 332_1 | -17.25 | 39808 |
| 333 | TGACATAACCATATAC | 3-10-3 | TGAcataaccataTAC | 333_1 | -16.63 | 39931 |
| 334 | GCTCCCAAACAACTAA | 2-12-2 | GCtcccaaacaactAA | 334_1 | -17.55 | 41114 |
| 335 | CCTCAATACTCTACTT | 4-10-2 | CCTCaatactctacTT | 335_1 | -20.30 | 41444 |
| 336 | GACCTCAATACTCTACT | 3-11-3 | GACctcaatactctACT | 336_1 | -21.01 | 41445 |
| 337 | GACCTCAATACTCTAC | 4-10-2 | GACCtcaatactctAC | 337_1 | -20.02 | 41446 |
| 338 | TACTAAACATACACATA | 4-11-2 | TACTaaacatacacaTA | 338_1 | -16.12 | 41725 |
| 339 | CTACTAAACATACACAT | 3-11-3 | CTActaaacatacaCAT | 339_1 | -17.31 | 41726 |
| 340 | TTCTACTAAACATACAC | 3-11-3 | TTCtactaaacataCAC | 340_1 | -16.07 | 41728 |
| 341 | TACCAATAGTTACCTT | 2-10-4 | TAccaatagttaCCTT | 341_1 | -20.03 | 42167 |
| 342 | CTTACCAATAGTTACCT | 3-11-3 | CTTaccaatagttaCCT | 342_1 | -22.29 | 42168 |
| 343 | TTACCAATAGTTACCT | 3-10-3 | TTAccaatagttaCCT | 343_1 | -20.03 | 42168 |
| 344 | CTTACCAATAGTTACC | 4-10-2 | CTTAccaatagttaCC | 344_1 | -20.03 | 42169 |
| 345 | TCTTACCAATAGTTACC | 4-11-2 | TCTTaccaatagttaCC | 345_1 | -21.30 | 42169 |
| 346 | TCAAAGCACACCACCAC | 2-12-3 | TCaaagcacaccacCAC | 346_1 | -21.69 | 42287 |
| 347 | ATTCAAAGCACACCACC | 2-12-3 | ATtcaaagcacaccACC | 347_1 | -21.00 | 42289 |
| 348 | AGACTAATCCTCTTAA | 3-10-3 | AGActaatcctctTAA | 348_1 | -17.72 | 43452 |
| 349 | TAGACTAATCCTCTTA | 4-10-2 | TAGActaatcctctTA | 349_1 | -19.20 | 43453 |
| 350 | CCCATTTCTAACATTTAC | 3-12-3 | CCCatttctaacattTAC | 350_1 | -22.93 | 43562 |
| 351 | ACCCATTTCTAACATT | 4-10-2 | ACCCatttctaacaTT | 351_1 | -20.64 | 43565 |
| 352 | AACCCATTTCTAACAT | 4-10-2 | AACCcatttctaacAT | 352_1 | -18.25 | 43566 |
| 353 | CCTCAACTTCACCAAT | 2-10-4 | CCtcaacttcacCAAT | 353_1 | -21.73 | 43634 |
| 354 | ACTGATTTCCTTAAAC | 4-10-2 | ACTGatttccttaaAC | 354_1 | -16.67 | 44180 |
| 355 | CACTGATTTCCTTAAAC | 4-11-2 | CACTgatttccttaaAC | 355_1 | -18.91 | 44180 |
| 356 | CCACTGATTTCCTTAAA | 4-11-2 | CCACtgatttccttaAA | 356_1 | -20.91 | 44181 |
| 357 | ACCACTGATTTCCTTA | 2-10-4 | ACcactgatttcCTTA | 357_1 | -20.98 | 44183 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 358 | CACCACTGATTTCCTT | 3-10-3 | CACcactgatttcCTT | 358_1 | -22.04 | 44184 |
| 359 | CTCTGCAATACACCAA | 2-10-4 | CTctgcaatacaCCAA | 359_1 | -20.90 | 44439 |
| 360 | ACTCTGCAATACACCA | 3-10-3 | ACTctgcaatacaCCA | 360_1 | -22.19 | 44440 |
| 361 | TACTCTGCAATACACCA | 2-11-4 | TActctgcaatacACCA | 361_1 | -22.32 | 44440 |
| 361 | TACTCTGCAATACACCA | 1-1-1-10-1-1-2 | TaCtctgcaatacAcCA | 361_2 | -19.29 | 44440 |
| 361 | TACTCTGCAATACACCA | 1-3-1-8-1-1-2 | TactCtgcaatacAcCA | 361_3 | -19.28 | 44440 |
| 361 | TACTCTGCAATACACCA | 1-10-1-3-2 | TactctgcaatAcacCA | 361_4 | -18.35 | 44440 |
| 361 | TACTCTGCAATACACCA | 2-10-2-1-2 | TActctgcaataCACCA | 361_5 | -21.63 | 44440 |
| 361 | TACTCTGCAATACACCA | 1-13-3 | TactctgcaatacaCCA | 361_6 | -20.54 | 44440 |
| 361 | TACTCTGCAATACACCA | 2-10-1-2-2 | TActctgcaataCacCA | 361_7 | -20.06 | 44440 |
| 361 | TACTCTGCAATACACCA | 1-1-1-12-2 | TaCtctgcaatacacCA | 361_8 | -19.14 | 44440 |
| 361 | TACTCTGCAATACACCA | 1-2-2-10-2 | TacTCtgcaatacacCA | 361_9 | -20.33 | 44440 |
| 361 | TACTCTGCAATACACCA | 1-3-1-10-2 | TactCtgcaatacacCA | 361_10 | -19.13 | 44440 |
| 362 | TACTCTGCAATACACC | 2-10-4 | TActctgcaataCACC | 362_1 | -21.12 | 44441 |
| 362 | TACTCTGCAATACACC | 1-1-1-11-2 | TaCtctgcaatacaCC | 362_2 | -18.23 | 44441 |
| 362 | TACTCTGCAATACACC | 1-1-1-10-3 | TaCtctgcaatacACC | 362_3 | -18.78 | 44441 |
| 362 | TACTCTGCAATACACC | 1-3-1-7-4 | TactCtgcaataCACC | 362_4 | -20.87 | 44441 |
| 362 | TACTCTGCAATACACC | 3-11-2 | TACtctgcaatacaCC | 362_5 | -19.86 | 44441 |
| 362 | TACTCTGCAATACACC | 2-2-1-9-2 | TActCtgcaatacaCC | 362_6 | -19.44 | 44441 |
| 362 | TACTCTGCAATACACC | 2-12-2 | TActctgcaatacaCC | 362_7 | -18.47 | 44441 |
| 362 | TACTCTGCAATACACC | 1-2-2-9-2 | TacTCtgcaatacaCC | 362_8 | -19.42 | 44441 |
| 362 | TACTCTGCAATACACC | 2-1-2-9-2 | TACTctgcaatacaCC | 362_9 | -20.64 | 44441 |
| 362 | TACTCTGCAATACACC | 1-3-1-9-2 | TactCtgcaatacaCC | 362_10 | -18.22 | 44441 |
| 363 | TTACTCTGCAATACACC | 2-11-4 | TTactctgcaataCACC | 363_1 | -21.71 | 44441 |
| 364 | TTACTCTGCAATACAC | 3-10-3 | TTActctgcaataCAC | 364_1 | -17.75 | 44442 |
| 365 | TTTACTCTGCAATACAC | 3-11-3 | TTTactctgcaataCAC | 365_1 | -18.34 | 44442 |
| 366 | CTTTACTCTGCAATACA | 2-11-4 | CTttactctgcaaTACA | 366_1 | -20.23 | 44443 |
| 367 | TTTACTCTGCAATACA | 2-10-4 | TTtactctgcaaTACA | 367_1 | -17.56 | 44443 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 368 | GACCACACTTTCTACCA | 2-13-2 | GAccacactttctacCA | 368_1 | -21.72 | 44477 |
| 369 | GACCACACTTTCTACC | 2-12-2 | GAccacactttctaCC | 369_1 | -20.81 | 44478 |
| 370 | AAGAAACACCCTTCCA | 2-10-4 | AAgaaacaccctTCCA | 370_1 | -21.48 | 44776 |
| 371 | ATCTGCTACATATTCTT | 4-11-2 | ATCTgctacatattcTT | 371_1 | -19.88 | 45216 |
| 372 | ATCTGCTACATATTCT | 4-10-2 | ATCTgctacatattCT | 372_1 | -19.71 | 45217 |
| 373 | CATCTGCTACATATTCT | 4-11-2 | CATCtgctacatattCT | 373_1 | -21.32 | 45217 |
| 374 | CATCTGCTACATATTC | 4-10-2 | CATCtgctacatatTC | 374_1 | -18.82 | 45218 |
| 375 | TTCAACCCTAATCACT | 4-10-2 | TTCAaccctaatcaCT | 375_1 | -19.99 | 45246 |
| 376 | ATTCAACCCTAATCAC | 2-10-4 | ATtcaaccctaaTCAC | 376_1 | -18.67 | 45247 |
| 377 | CATTCAACCCTAATCA | 3-10-3 | CATtcaaccctaaTCA | 377_1 | -19.93 | 45248 |
| 378 | GCATTCAACCCTAATCA | 3-12-2 | GCAttcaaccctaatCA | 378_1 | -22.56 | 45248 |
| 379 | AGCATTCAACCCTAATC | 4-11-2 | AGCAttcaaccctaaTC | 379_1 | -22.98 | 45249 |
| 380 | GCATTCAACCCTAATC | 4-10-2 | GCATtcaaccctaaTC | 380_1 | -21.63 | 45249 |
| 381 | AGCATTCAACCCTAAT | 4-10-2 | AGCAttcaaccctaAT | 381_1 | -21.62 | 45250 |
| 382 | CAGCATTCAACCCTAAT | 3-12-2 | CAGcattcaaccctaAT | 382_1 | -21.12 | 45250 |
| 383 | TTAAATCCAGCATTCA | 3-10-3 | TTAaatccagcatTCA | 383_1 | -18.08 | 45258 |
| 384 | CTCCATATTTAAATCC | 4-10-2 | CTCCatatttaaatCC | 384_1 | -20.02 | 45266 |
| 385 | GCTCCATATTTAAATCC | 4-11-2 | GCTCcatatttaaatCC | 385_1 | -22.84 | 45266 |
| 386 | GCTCCATATTTAAATC | 4-10-2 | GCTCcatatttaaaTC | 386_1 | -18.78 | 45267 |
| 387 | AGCTCCATATTTAAAT | 4-10-2 | AGCTccatatttaaAT | 387_1 | -18.62 | 45268 |
| 388 | TAAGCTCCATATTTAA | 3-10-3 | TAAgctccatatttTAA | 388_1 | -16.08 | 45270 |
| 389 | CCTAAGCTCCATATTTA | 3-11-3 | CCTaagctccatatTTA | 389_1 | -22.65 | 45271 |
| 390 | CTAAGCTCCATATTTA | 4-10-2 | CTAAgctccatattTA | 390_1 | -18.81 | 45271 |
| 391 | CCTAAGCTCCATATTT | 4-10-2 | CCTAagctccatatTT | 391_1 | -21.57 | 45272 |
| 392 | TCTACCCTAAATTCCC | 2-11-3 | TCtaccctaaattCCC | 392_1 | -23.00 | 45560 |
| 393 | CACATCTTGTATACAA | 3-10-3 | CACatcttgtataCAA | 393_1 | -16.65 | 45627 |
| 394 | ACACATCTTGTATACA | 4-10-2 | ACACatcttgtataCA | 394_1 | -17.95 | 45628 |
| 395 | CTACACATCTTGTATAC | 3-11-3 | CTAcacatcttgtaTAC | 395_1 | -19.13 | 45629 |
| 396 | TACACATCTTGTATAC | 3-10-3 | TACacatcttgtaTAC | 396_1 | -16.73 | 45629 |
| 397 | CTTGACTACACATCTT | 3-10-3 | CTTgactacacatCTT | 397_1 | -18.89 | 45635 |
| 398 | CTCTACAACAGTCCCA | 3-11-2 | CTCtacaacagtccCA | 398_1 | -22.06 | 45709 |
| 399 | TCTCTACAACAGTCCCA | 2-13-2 | TCtctacaacagtccCA | 399_1 | -21.70 | 45709 |
| 400 | ATAACATTACTCTTAACA | 3-12-3 | ATAacattactcttaACA | 400_1 | -17.03 | 46215 |
| 401 | TTTGACATTCCATCTCC | 2-12-3 | TTtgacattccatcTCC | 401_1 | -21.62 | 46256 |
| 402 | CTTTGACATTCCATCTC | 2-11-4 | CTttgacattccaTCTC | 402_1 | -21.88 | 46257 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 403 | TCTTTGACATTCCATCTC | 4-12-2 | TCTTtgacattccatcTC | 403_1 | -22.41 | 46257 |
| 404 | TTTGACATTCCATCTC | 3-10-3 | TTTgacattccatCTC | 404_1 | -19.40 | 46257 |
| 405 | ATCTTTGACATTCCATC | 2-11-4 | ATctttgacattcCATC | 405_1 | -20.53 | 46259 |
| 406 | TATCTTTGACATTCCAT | 2-11-4 | TAtctttgacattCCAT | 406_1 | -21.32 | 46260 |
| 407 | TACTATCTTTGACATTC | 4-11-2 | TACTatctttgacatTC | 407_1 | -18.39 | 46263 |
| 408 | TACTATCTTTGACATT | 4-10-2 | TACTatctttgacaTT | 408_1 | -16.84 | 46264 |
| 409 | CTGTATACACCATCCC | 2-12-2 | CTgtatacaccatcCC | 409_1 | -21.84 | 46392 |
| 410 | TCTGTATACACCATCC | 4-10-2 | TCTGtatacaccatCC | 410_1 | -22.73 | 46393 |
| 411 | TTTCTGACTCCCTATCC | 2-13-2 | TTtctgactccctatCC | 411_1 | -22.48 | 46420 |
| 412 | CCTATGTTAATACTTTC | 4-11-2 | CCTAtgttaatactTTC | 412_1 | -19.53 | 46505 |
| 413 | CTATGTTAATACTTTC | 4-10-2 | CTATgttaatactTTC | 413_1 | -16.09 | 46505 |
| 414 | CCTATGTTAATACTTT | 4-10-2 | CCTAtgttaatactTT | 414_1 | -17.85 | 46506 |
| 415 | TCCTATGTTAATACTT | 3-10-3 | TCCtatgttaataCTT | 415_1 | -18.47 | 46507 |
| 416 | ATCCTATGTTAATACT | 4-10-2 | ATCCtatgttaataCT | 416_1 | -18.71 | 46508 |
| 417 | ATTTCATTAAGTCACCC | 3-11-3 | ATTtcattaagtcaCCC | 417_1 | -22.16 | 47364 |
| 418 | ATTTCATTAAGTCACC | 2-10-4 | ATtttcattaagtCACC | 418_1 | -18.79 | 47365 |
| 419 | CTCTCCTCAAGATCAAC | 3-11-3 | CTCtcctcaagatcAAC | 419_1 | -20.29 | 48110 |
| 420 | CTCTCCTCAAGATCAA | 3-10-3 | CTCtcctcaagatCAA | 420_1 | -20.33 | 48111 |
| 421 | CCATACAGTATATACA | 4-10-2 | CCATacagtatataCA | 421_1 | -19.53 | 48186 |
| 422 | CAACTATTATCTTCTT | 2-10-4 | CAactattatctTCTT | 422_1 | -16.38 | 48221 |
| 423 | ACAACTATTATCTTCT | 3-10-3 | ACAactattatctTCT | 423_1 | -16.60 | 48222 |
| 424 | TTGCTTCCAATTTATTT | 4-11-2 | TTGCttccaatttatTT | 424_1 | -19.93 | 50282 |
| 425 | ATCTCATGACCACCTAA | 3-11-3 | ATCtcatgaccaccTAA | 425_1 | -21.74 | 51241 |
| 425 | ATCTCATGACCACCTAA | 1-1-1-9-2-1-2 | AtCtcatgaccaCCtAA | 425_2 | -21.11 | 51241 |
| 425 | ATCTCATGACCACCTAA | 1-1-1-8-1-2-3 | AtCtcatgaccAccTAA | 425_3 | -19.96 | 51241 |
| 425 | ATCTCATGACCACCTAA | 1-12-4 | AtctcatgaccacCTAA | 425_4 | -20.40 | 51241 |
| 425 | ATCTCATGACCACCTAA | 3-10-1-1-2 | ATCtcatgaccacCtAA | 425_5 | -20.66 | 51241 |
| 425 | ATCTCATGACCACCTAA | 1-1-1-10-1-1-2 | AtCtcatgaccacCtAA | 425_6 | -18.72 | 51241 |
| 425 | ATCTCATGACCACCTAA | 1-1-1-9-1-1-3 | AtCtcatgaccaCcTAA | 425_7 | -20.59 | 51241 |
| 425 | ATCTCATGACCACCTAA | 1-2-2-7-1-1-3 | AtcTCatgaccaCcTAA | 425_8 | -21.48 | 51241 |
| 425 | ATCTCATGACCACCTAA | 1-3-1-8-4 | AtctCatgaccacCTAA | 425_9 | -21.07 | 51241 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 425 | ATCTCATGACCACCTAA | 1-1-3-8-1-1-2 | AtCTCatgaccacCtAA | 425_10 | -21.27 | 51241 |
| 426 | TCTCATGACCACCTAA | 2-10-4 | TCtcatgaccacCTAA | 426_1 | -21.25 | 51241 |
| 427 | ATCTCATGACCACCTA | 3-10-3 | ATCtcatgaccacCTA | 427_1 | -22.56 | 51242 |
| 428 | TATCTCATGACCACCTA | 2-12-3 | TAtctcatgaccacCTA | 428_1 | -21.88 | 51242 |
| 429 | TTTATCTCATGACCACC | 2-11-4 | TTtatctcatgacCACC | 429_1 | -22.37 | 51244 |
| 430 | TTTATCTCATGACCAC | 2-10-4 | TTtatctcatgaCCAC | 430_1 | -19.56 | 51245 |
| 431 | ATTCTTACCGTCTTTA | 4-10-2 | ATTCttaccgtcttTA | 431_1 | -19.52 | 51358 |
| 432 | TATTCTTACCGTCTTTA | 3-11-3 | TATtcttaccgtctTTA | 432_1 | -20.10 | 51358 |
| 433 | TATTCTTACCGTCTTT | 2-10-4 | TAttcttaccgtCTTT | 433_1 | -19.30 | 51359 |
| 434 | TTATTCTTACCGTCTTT | 2-11-4 | TTattcttaccgtCTTT | 434_1 | -19.99 | 51359 |
| 435 | ATCTGATCTCACACAT | 3-10-3 | ATCtgatctcacaCAT | 435_1 | -19.62 | 51438 |
| 436 | CATCTGATCTCACACAT | 4-11-2 | CATCtgatctcacacAT | 436_1 | -20.82 | 51438 |
| 437 | ACTTCCAGATTTCTACA | 2-11-4 | ACttccagatttcTACA | 437_1 | -21.44 | 51953 |
| 438 | TTTATGTTTACTTCAT | 3-10-3 | TTTatgtttacttCAT | 438_1 | -16.05 | 52150 |
| 439 | TAAAGATCCCATCACTC | 3-11-3 | TAAagatcccatcaCTC | 439_1 | -20.31 | 52549 |
| 440 | TAAAGATCCCATCACT | 4-10-2 | TAAAgatcccatcaCT | 440_1 | -18.82 | 52550 |
| 441 | CCTAAAGATCCCATCAC | 2-12-3 | CCtaaagatcccatCAC | 441_1 | -22.32 | 52551 |
| 442 | ATCATCAGTTACATCA | 4-10-2 | ATCAtcagttacatCA | 442_1 | -18.64 | 52579 |
| 443 | ACTCTCACTGTAACTTT | 4-11-2 | ACTCtcactgtaactTT | 443_ | -19.76 | 53012 |
| 444 | AACTCTCACTGTAACTT | 3-11-3 | AACtctcactgtaaCTT | 444_1 | -18.53 | 53013 |
| 445 | ACTCTCACTGTAACTT | 3-10-3 | ACTctcactgtaaCTT | 445_1 | -19.04 | 53013 |
| 446 | AACTCTCACTGTAACT | 4-10-2 | AACTctcactgtaaCT | 446_1 | -17.97 | 53014 |
| 447 | CAACTCTCACTGTAACT | 4-11-2 | CAACtctcactgtaaCT | 447_1 | -20.01 | 53014 |
| 448 | CCTTTCATTAACATTTA | 3-11-3 | CCTttcattaacatTTA | 448_1 | -19.03 | 54198 |
| 449 | TTCCTTTCATTAACATTT | 4-12-2 | TTCCtttcattaacatTT | 449_1 | -19.92 | 54199 |
| 450 | TAATCCTATTCCAACT | 3-10-3 | TAAtcctattccaACT | 450_1 | -18.05 | 54232 |
| 451 | CTAATCCTATTCCAAC | 2-10-4 | CTaatcctattcCAAC | 451_1 | -18.65 | 54233 |
| 452 | CTCTAATCCTATTCCA | 3-10-3 | CTCtaatcctattCCA | 452_1 | -22.58 | 54235 |
| 453 | TCTCTAATCCTATTCC | 4-10-2 | TCTCtaatcctattCC | 453_1 | -21.78 | 54236 |
| 454 | TTGTCTCTAATCCTATT | 2-11-4 | TTgtctctaatccTATT | 454_1 | -19.70 | 54238 |
| 455 | TTGTCTCTAATCCTAT | 2-10-4 | TTgtctctaatcCTAT | 455_1 | -19.45 | 54239 |
| 456 | TCTTTAAGCTTCCCAC | 2-10-4 | TCttttaagcttcCCAC | 456_1 | -22.96 | 54609 |
| 457 | AAACTACCCTGCACAA | 3-10-3 | AAActaccctgcaCAA | 457_1 | -18.41 | 54924 |
| 458 | CCATGCTACATAAACC | 4-10-2 | CCATgctacataaaCC | 458_1 | -22.25 | 55337 |
| 459 | TCCATGCTACATAAAC | 4-10-2 | TCCAtgctacataaAC | 459_1 | -18.64 | 55338 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 460 | ACTCCTAAGAATTACA | 4-10-2 | ACTCctaagaattaCA | 460_1 | -17.62 | 59565 |
| 461 | GAAACTATTACTCCTA | 2-10-4 | GAaactattactCCTA | 461_1 | -19.06 | 59574 |
| 462 | TGAAACTATTACTCCT | 3-10-3 | TGAaactattactCCT | 462_1 | -19.30 | 59575 |
| 463 | ATGAAACTATTACTCC | 2-10-4 | ATgaaactattaCTCC | 463_1 | -17.96 | 59576 |
| 464 | AACAACTCATGCCACA | 2-10-4 | AAcaactcatgcCACA | 464_1 | -19.72 | 60012 |
| 465 | AAATATTGCCACCATT | 2-10-4 | AAatattgccacCATT | 465_1 | -17.78 | 60298 |
| 466 | GTTACATATTCTTTCAC | 3-11-3 | GTTacatattctttCAC | 466_1 | -18.76 | 60448 |
| 467 | TCATACTTGCTTTAAT | 4-10-2 | TCATacttgctttaAT | 467_1 | -17.29 | 60821 |
| 468 | ATCCTGATAATTAACT | 4-10-2 | ATCCtgataattaaCT | 468_1 | -17.73 | 61925 |
| 469 | CCTTAATCTGTATCAC | 3-10-3 | CCTtaatctgtatCAC | 469_1 | -19.92 | 62287 |
| 470 | ATACACAGCACATATT | 2-10-4 | ATacacagcacaTATT | 470_1 | -17.58 | 62422 |
| 471 | TCAGAATAATTCTCCT | 3-10-3 | TCAgaataattctCCT | 471_1 | -19.81 | 62443 |
| 472 | TCTTCAGCTTTCTAAAT | 4-11-2 | TCTTcagctttctaaAT | 472_1 | -18.58 | 64113 |
| 473 | AGTCCTTCCTTTAACCA | 2-13-2 | AGtccttcctttaacCA | 473_1 | -22.20 | 64461 |
| 474 | TAGTCCTTCCTTTAACC | 2-13-2 | TAgtccttcctttaaCC | 474_1 | -22.12 | 64462 |
| 475 | TTTAACCTTGCTTATA | 2-10-4 | TTtaaccttgctTATA | 475_1 | -17.50 | 65272 |
| 476 | ATCCCTTTGTAATCAT | 4-10-2 | ATCCctttgtaatcAT | 476_1 | -20.31 | 66840 |
| 477 | CTTGCATTTCTAATTAC | 3-11-3 | CTTgcatttctaatTAC | 477_1 | -18.09 | 67426 |
| 478 | CTTGTCAAATCATTTCT | 4-11-2 | CTTGtcaaatcatttCT | 478_1 | -19.10 | 68194 |
| 479 | CCATCTAATGATTATT | 4-10-2 | CCATctaatgattaTT | 479_1 | -17.28 | 68328 |
| 480 | TATCAGTTATCCAATA | 4-10-2 | TATCagttatccaaTA | 480_1 | -17.39 | 68805 |
| 481 | TCACTGCCATCAATAC | 4-10-2 | TCACtgccatcaatAC | 481_1 | -19.71 | 68921 |
| 482 | TGTCATCTACAAATCA | 4-10-2 | TGTCatctacaaatCA | 482_1 | -18.01 | 70133 |
| 483 | CTCTTTAGATTCATCC | 4-10-2 | CTCTttagattcatCC | 483_1 | -20.94 | 72377 |
| 484 | ACTCTTTAGATTCATC | 2-10-4 | ACtctttagattCATC | 484_1 | -17.81 | 72378 |
| 485 | CAACTCTATGACTACC | 2-10-4 | CAactctatgacTACC | 485_1 | -20.07 | 72826 |
| 486 | ACCTGTAATACTTCTT | 4-10-2 | ACCTgtaatacttcTT | 486_1 | -19.67 | 72861 |
| 487 | GAATTCTTTATTCCTCC | 2-11-4 | GAattctttattcCTCC | 487_1 | -22.53 | 72887 |
| 488 | ATCTGAATCAAACCTT | 2-10-4 | ATctgaatcaaaCCTT | 488_1 | -17.97 | 73474 |
| 489 | ACTTACTGCCATAATC | 3-11-3 | ACTttactgccataATC | 489_1 | -19.60 | 73992 |
| 490 | TTACTCTTAGCAACCT | 4-10-2 | TTACtcttagcaacCT | 490_1 | -20.19 | 74791 |
| 491 | CACCAGTATTTCTTCTT | 4-11-2 | CACCagtatttcttcTT | 491_1 | -22.15 | 74851 |
| 492 | TTCACCAGTATTTCTTC | 4-11-2 | TTCAccagtatttctTC | 492_1 | -20.43 | 74853 |
| 493 | CCAAATAAGCAAACTC | 3-10-3 | CCAaataagcaaaCTC | 493_1 | -17.54 | 75840 |
| 494 | CCCAAATAAGCAAACT | 4-10-2 | CCCAaataagcaaaCT | 494_1 | -20.23 | 75841 |
| 495 | GACTACATTCTCAATA | 3-10-3 | GACtacattctcaATA | 495_1 | -17.49 | 76238 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 496 | TTGTCAATCTTTATTCT | 4-11-2 | TTGTcaatctttattCT | 496_1 | -18.85 | 76254 |
| 497 | AGCTTACCAAATATTC | 4-10-2 | AGCTtaccaaatatTC | 497_1 | -18.68 | 76811 |
| 498 | TTACACATGTATATCC | 3-10-3 | TTAcacatgtataTCC | 498_1 | -18.23 | 77114 |
| 499 | ATCCTGTTAATACCAT | 2-10-4 | ATcctgttaataCCAT | 499_1 | -20.41 | 80468 |
| 500 | TTCTTAGTCACACACA | 4-10-2 | TTCTtagtcacacaCA | 500_1 | -19.37 | 81047 |
| 501 | TTCTGTTTCCATTTACA | 4-11-2 | TTCTgtttccatttaCA | 501_1 | -21.31 | 82233 |
| 502 | TCTATATCAAGTTCCTT | 2-11-4 | TCtatatcaagttCCTT | 502_1 | -20.95 | 84166 |
| 503 | ATTCAGTTACCAACTA | 3-10-3 | ATTcagttaccaaCTA | 503_1 | -18.37 | 85392 |
| 504 | GCTTCTACTTAAATAT | 3-10-3 | GCTtctacttaaaTAT | 504_1 | -17.58 | 86974 |
| 505 | CCCTCAAAGTAATTTC | 4-10-2 | CCCTcaaagtaattTC | 505_1 | -20.53 | 87728 |
| 506 | AACATGTAATTTCCAT | 2-10-4 | AAcatgtaattCCAT | 506_1 | -17.21 | 87810 |
| 507 | CCAGACTCCAATATTT | 4-10-2 | CCAGactccaatatTT | 507_1 | -20.78 | 88417 |
| 508 | CTTAGACTTCACCTTTC | 2-11-4 | CTtagacttcaccTTTC | 508_1 | -20.56 | 88991 |
| 509 | CTGCTTAATTATATCA | 4-10-2 | CTGCttaattatatCA | 509_1 | -18.85 | 90228 |
| 510 | AAATTGTCTACCTTCCT | 2-12-3 | AAattgtctaccttCCT | 510_1 | -20.62 | 90474 |
| 511 | CACTTAGAATATCCCT | 2-10-4 | CActtagaatatCCCT | 511_1 | -22.28 | 91625 |
| 512 | ATCCAAAGTTTCTTTC | 4-10-2 | ATCCaaagtttctTC | 512_1 | -18.64 | 91885 |
| 513 | ATATTTGTCACCTAAC | 4-10-2 | ATATttgtcacctaAC | 513_1 | -17.12 | 92976 |
| 514 | CTATTCTCAGTATTAT | 3-10-3 | CTAttctcagtatTAT | 514_1 | -17.42 | 94304 |
| 515 | CCATTCAATGATCACT | 2-10-4 | CCattcaatgatCACT | 515_1 | -20.55 | 94528 |
| 516 | CACTAGTACTCTTATT | 4-10-2 | CACTagtactcttaTT | 516_1 | -18.01 | 95653 |
| 517 | GCCACAACATCTATTT | 4-10-2 | GCCAcaacatctatTT | 517_1 | -21.53 | 96751 |
| 518 | AGCACATATACCATCA | 4-10-2 | AGCAcatataccatCA | 518_1 | -21.98 | 97636 |
| 519 | GTCATCTAACTTCTTAC | 3-11-3 | GTCatctaacttctTAC | 519_1 | -19.25 | 98480 |
| 520 | TGTCATCTAACTTCTTA | 4-11-2 | TGTCatctaacttctTA | 520_1 | -19.69 | 98481 |
| 521 | CCCTTATAGTTATTAA | 3-10-3 | CCCttatagttatTAA | 521_1 | -19.32 | 99646 |
| 522 | TCCATAGAATTCTTCA | 4-10-2 | TCCAtagaattcttCA | 522_1 | -19.92 | 100334 |
| 523 | TTGATTCCACCATTAA | 3-10-3 | TTGattccaccatTAA | 523_1 | -18.05 | 101110 |
| 524 | CAGCCATAAACTATAT | 4-10-2 | CAGCcataaactatAT | 524_1 | -18.60 | 101898 |
| 525 | TATGACTTATTCCATA | 2-10-4 | TAtgacttattcCATA | 525_1 | -17.88 | 102558 |
| 526 | GTTAACCTATATTTCA | 4-10-2 | GTTAacctatatttCA | 526_1 | -17.69 | 103589 |
| 527 | TGTCTATTCTCTTCATT | 4-11-2 | TGTCtattctcttcaTT | 527_1 | -20.62 | 104309 |
| 528 | TTACTCTTTGATTTCAT | 3-11-3 | TTActctttgatttCAT | 528_1 | -18.39 | 105686 |
| 529 | GATAATTCCAAATCCC | 2-10-4 | GAtaattccaaaTCCC | 529_1 | -20.99 | 107972 |
| 530 | TCTTATCCTTGAATTTC | 4-11-2 | TCTTatccttgaattTC | 530_1 | -18.85 | 108257 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 531 | ATATCCCTTGATTATCC | 3-11-3 | ATAtcccttgattaTCC | 531_1 | -22.75 | 109407 |
| 532 | TTAGTATACCCTTTAT | 3-10-3 | TTAgtatacccttTAT | 532_1 | -18.67 | 110210 |
| 533 | CTCTTTGTCAAATACT | 4-10-2 | CTCTttgtcaaataCT | 533_1 | -18.16 | 110768 |
| 534 | CCAAACTGTCTTCTAAT | 2-11-4 | CCaaactgtcttcTAAT | 534_1 | -19.87 | 111811 |
| 535 | TCCAAACTGTCTTCTAA | 3-12-2 | TCCaaactgtcttctAA | 535_1 | -18.33 | 111812 |
| 536 | CCAGCATATTATATAC | 3-10-3 | CCAgcatattataTAC | 536_1 | -18.96 | 112149 |
| 537 | TCCAGCATATTATATA | 4-10-2 | TCCAgcatattataTA | 537_1 | -19.41 | 112150 |
| 538 | TCATTGAACAACTCTTC | 4-11-2 | TCATtgaacaactctTC | 538_1 | -18.01 | 112945 |
| 539 | CTGCCATCTTTATTTAT | 4-11-2 | CTGCcatctttattTAT | 539_1 | -21.89 | 113533 |
| 540 | TGAAACATTCTTCCCAC | 2-12-3 | TGaaacattcttccCAC | 540_1 | -19.76 | 114274 |
| 541 | TTTATTAGATTACTCC | 2-10-4 | TTtattagattaCTCC | 541_1 | -17.38 | 114495 |
| 542 | TTCCAGCTTATTTACCT | 3-12-2 | TTCcagcttatttacCT | 542_1 | -21.28 | 114831 |
| 543 | AGCATCATATAAACCT | 3-10-3 | AGCatcatataaaCCT | 543_1 | -20.62 | 115355 |
| 544 | GTACTTACACATCTAT | 2-10-4 | GTacttacacatCTAT | 544_1 | -18.96 | 116105 |
| 545 | TGTACTTACACATCTA | 3-10-3 | TGTacttacacatCTA | 545_1 | -19.38 | 116106 |
| 546 | ATTTCTCTATGTCACAT | 3-11-3 | ATTtctctatgtcaCAT | 546_1 | -19.28 | 117096 |
| 547 | CAAACCTACGTCTCTC | 2-10-4 | CAaacctacgtcTCTC | 547_1 | -20.87 | 117189 |
| 548 | GTATTTACTCTTTACCT | 3-11-3 | GTAtttactctttaCCT | 548_1 | -22.15 | 117476 |
| 549 | CTAATGCAATAACCCA | 2-10-4 | CTaatgcaataaCCCA | 549_1 | -21.79 | 118293 |
| 550 | ACTAATGCAATAACCC | 3-10-3 | ACTaatgcaataaCCC | 550_1 | -20.53 | 118294 |
| 551 | AGCTCTAAACCTTCAA | 3-10-3 | AGCtctaaaccttCAA | 551_1 | -20.51 | 118756 |
| 552 | TATTTGTCACCAAACC | 3-10-3 | TATttgtcaccaaACC | 552_1 | -19.63 | 119621 |
| 553 | CTCAGACATCTCAATA | 4-10-2 | CTCAgacatctcaaTA | 553_1 | -19.25 | 120655 |
| 554 | TCTCAGCTTCTTCAAAT | 2-12-3 | TCtcagcttcttcaAAT | 554_1 | -18.33 | 123733 |
| 555 | GCCAATACCCACAAAC | 3-10-3 | GCCaatacccacaAAC | 555_1 | -22.03 | 124163 |
| 556 | CCTCTGACAACCATTA | 4-10-2 | CCTCtgacaaccatTA | 556_1 | -22.57 | 125512 |
| 557 | CAGATAACTCTAAACC | 4-10-2 | CAGAtaactctaaaCC | 557_1 | -18.43 | 126882 |
| 558 | CTAACTGTTTCTCAATT | 3-11-3 | CTAactgtttctcaATT | 558_1 | -18.10 | 127105 |
| 559 | CCAAGATAATCATCAT | 3-10-3 | CCAagataatcatCAT | 559_1 | -18.37 | 127809 |
| 560 | TACATATTGTACTTCT | 4-10-2 | TACAtattgtacttCT | 560_1 | -17.48 | 129020 |
| 561 | TAGCCTACTTTAATAT | 4-10-2 | TAGCctactttaatAT | 561_1 | -18.67 | 129205 |
| 562 | CATTTACAAGCACATA | 2-10-4 | CAtttacaagcaCATA | 562_1 | -17.81 | 129928 |
| 563 | TTATTCTGACACACTT | 3-10-3 | TTAttctgacacaCTT | 563_1 | -17.49 | 130020 |
| 564 | TACATTGACACCTAAT | 4-10-2 | TACAttgacacctaAT | 564_1 | -17.37 | 130884 |
| 565 | TTTACATTGACACCTA | 2-10-4 | TTtacattgacaCCTA | 565_1 | -19.42 | 130886 |
| 566 | TGTATATAACTATTCC | 4-10-2 | TGTAtataactattCC | 566_1 | -17.79 | 131404 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 567 | GAATCTTCTAATTCCAC | 2-11-4 | GAatcttctaattCCAC | 567_1 | -20.40 | 132514 |
| 568 | TGCTCACTAACTACAC | 3-10-3 | TGCtcactaactaCAC | 568_1 | -20.66 | 133367 |
| 569 | TGCTACCATCATTACCT | 2-13-2 | TGctaccatcattacCT | 569_1 | -21.32 | 136198 |
| 570 | TTTATCAATATCTTCTCACT | 1-13-1-1-1-1-2 | TttatcaatatcttCtCaCT | 570_1 | -19.69 | 5784 |
| 570 | TTTATCAATATCTTCTCACT | 1-2-1-10-1-2-3 | TttAtcaatatcttCtcACT | 570_2 | -19.67 | 5784 |
| 570 | TTTATCAATATCTTCTCACT | 1-5-1-7-1-2-3 | TttatcAatatcttCtcACT | 570_3 | -19.65 | 5784 |
| 570 | TTTATCAATATCTTCTCACT | 1-1-1-11-1-3-2 | TtTatcaatatcttCtcaCT | 570_4 | -19.75 | 5784 |
| 570 | TTTATCAATATCTTCTCACT | 1-2-1-2-1-11-2 | TttAtcAatatcttctcaCT | 570_5 | -18.21 | 5784 |
| 570 | TTTATCAATATCTTCTCACT | 1-4-1-8-1-3-2 | TttatCaatatcttCtcaCT | 570_6 | -19.69 | 5784 |
| 570 | TTTATCAATATCTTCTCACT | 1-2-1-2-1-9-1-1-2 | TttAtcAatatcttctCaCT | 570_7 | -18.88 | 5784 |
| 570 | TTTATCAATATCTTCTCACT | 1-2-1-1-1-11-3 | TttAtCaatatcttctcACT | 570_8 | -19.36 | 5784 |
| 570 | TTTATCAATATCTTCTCACT | 1-4-1-10-1-1-2 | TttatCaatatcttctCaCT | 570_9 | -19.38 | 5784 |
| 570 | TTTATCAATATCTTCTCACT | 2-1-1-10-1-1-1-1-2 | TTtAtcaatatcttCtCaCT | 570_10 | -20.60 | 5784 |
| 570 | TTTATCAATATCTTCTCACT | 1-4-1-8-1-1-1-1-2 | TttatCaatatcttCtCaCT | 570_11 | -20.36 | 5784 |
| 570 | TTTATCAATATCTTCTCACT | 1-2-1-1-1-8-1-2-3 | TttAtCaatatcttCtcACT | 570_12 | -20.34 | 5784 |
| 570 | TTTATCAATATCTTCTCACT | 1-2-1-2-1-7-1-3-2 | TttAtcAatatcttCtcaCT | 570_13 | -19.19 | 5784 |
| 570 | TTTATCAATATCTTCTCACT | 1-1-2-1-1-10-1-1-2 | TtTAtCaatatcttctCaCT | 570_14 | -21.24 | 5784 |
| 571 | TTTATCAATATCTTCTCAC | 1-12-2-1-3 | TttatcaatatctTCtCAC | 571_1 | -19.16 | 5785 |
| 571 | TTTATCAATATCTTCTCAC | 2-1-1-1-1-6-2-2-3 | TTtAtCaatatcTTctCAC | 571_2 | -20.17 | 5785 |
| 571 | TTTATCAATATCTTCTCAC | 3-2-1-7-2-2-2 | TTTatCaatatctTCtcAC | 571_3 | -19.79 | 5785 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 571 | TTTATCAATATCTTCTCAC | 1-2-3-8-1-2-2 | TttATCaatatcttCtcAC | 571_4 | -18.78 | 5785 |
| 571 | TTTATCAATATCTTCTCAC | 1-4-1-9-4 | TttatCaatatcttcTCAC | 571_5 | -19.06 | 5785 |
| 571 | TTTATCAATATCTTCTCAC | 2-1-1-1-1-8-1-1-3 | TTtAtCaatatcttCtCAC | 571_6 | -19.75 | 5785 |
| 571 | TTTATCAATATCTTCTCAC | 1-1-1-2-1-6-1-3-3 | TtTatCaatatcTtctCAC | 571_7 | -19.11 | 5785 |
| 571 | TTTATCAATATCTTCTCAC | 2-1-3-6-1-4-2 | TTtATCaatatcTtctcAC | 571_8 | -19.13 | 5785 |
| 571 | TTTATCAATATCTTCTCAC | 4-12-3 | TTTAtcaatatcttctCAC | 571_9 | -20.38 | 5785 |
| 571 | TTTATCAATATCTTCTCAC | 1-1-2-1-1-6-1-3-3 | TtTAtcaatatcTtctCAC | 571_10 | -20.24 | 5785 |
| 571 | TTTATCAATATCTTCTCAC | 2-1-1-1-1-7-2-2-2 | TTtAtCaatatctTCtcAC | 571_11 | -18.65 | 5785 |
| 571 | TTTATCAATATCTTCTCAC | 3-2-1-8-1-1-3 | TTTatCaatatcttCtCAC | 571_12 | -20.89 | 5785 |
| 571 | TTTATCAATATCTTCTCAC | 1-3-2-8-1-1-3 | TttaTCaatatcttCtCAC | 571_13 | -19.96 | 5785 |
| 571 | TTTATCAATATCTTCTCAC | 1-2-1-1-1-9-4 | TttAtCaatatcttcTCAC | 571_14 | -19.16 | 5785 |
| 572 | TTTATCAATATCTTCTCA | 2-1-1-1-1-7-2-1-2 | TTtAtCaatatctTCtCA | 572_1 | -18.69 | 5786 |
| 572 | TTTATCAATATCTTCTCA | 3-2-1-6-1-1-1-1-2 | TTTatCaatatcTtCtCA | 572_2 | -19.36 | 5786 |
| 572 | TTTATCAATATCTTCTCA | 1-4-1-6-1-1-4 | TttatCaatatcTtCTCA | 572_3 | -19.19 | 5786 |
| 572 | TTTATCAATATCTTCTCA | 1-2-3-6-1-2-3 | TttATCaatatcTtcTCA | 572_4 | -19.56 | 5786 |
| 572 | TTTATCAATATCTTCTCA | 4-1-1-7-1-2-2 | TTTAtCaatatctTctCA | 572_5 | -19.37 | 5786 |
| 572 | TTTATCAATATCTTCTCA | 1-2-3-8-1-1-2 | TttATCaatatcttCtCA | 572_6 | -18.83 | 5786 |
| 572 | TTTATCAATATCTTCTCA | 3-2-1-9-3 | TTTatCaatatcttcTCA | 572_7 | -19.07 | 5786 |
| 572 | TTTATCAATATCTTCTCA | 1-2-1-10-4 | TttAtcaatatcttCTCA | 572_8 | -18.10 | 5786 |
| 572 | TTTATCAATATCTTCTCA | 4-10-1-1-2 | TTTAtcaatatcttCtCA | 572_9 | -19.31 | 5786 |
| 572 | TTTATCAATATCTTCTCA | 2-1-3-6-1-1-1-1-2 | TTtATCaatatcTtCtCA | 572_10 | -20.15 | 5786 |
| 572 | TTTATCAATATCTTCTCA | 3-2-1-6-1-2-3 | TTTatCaatatcTtcTCA | 572_11 | -19.59 | 5786 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 572 | TTTATCAATATCTTCTCA | 1-1-2-1-1-7-2-1-2 | TtTAtCaatatctTCtCA | 572_12 | -19.64 | 5786 |
| 572 | TTTATCAATATCTTCTCA | 4-9-1-1-3 | TTTAtcaatatctTcTCA | 572_13 | -19.90 | 5786 |
| 572 | TTTATCAATATCTTCTCA | 1-3-2-8-4 | TttaTCaatatcttCTCA | 572_14 | -19.80 | 5786 |
| 573 | TATACCTTTCTTTAACCCTT | 1-4-1-10-1-1-2 | TatacCtttctttaacCcTT | 573_1 | -22.72 | 8116 |
| 573 | TATACCTTTCTTTAACCCTT | 2-4-1-11-2 | TAtaccTttctttaacccTT | 573_2 | -22.80 | 8116 |
| 573 | TATACCTTTCTTTAACCCTT | 1-3-1-10-1-2-2 | TataCctttctttaaCccTT | 573_3 | -22.72 | 8116 |
| 573 | TATACCTTTCTTTAACCCTT | 1-4-1-9-1-2-2 | TatacCtttctttaaCccTT | 573_4 | -22.82 | 8116 |
| 573 | TATACCTTTCTTTAACCCTT | 1-5-1-9-1-1-2 | TataccTttctttaacCcTT | 573_5 | -22.35 | 8116 |
| 573 | TATACCTTTCTTTAACCCTT | 1-15-1-1-2 | TataccttctttaacCcTT | 573_6 | -21.83 | 8116 |
| 573 | TATACCTTTCTTTAACCCTT | 1-2-1-1-1-10-1-1-2 | TatAcCtttctttaacCcTT | 573_7 | -22.91 | 8116 |
| 573 | TATACCTTTCTTTAACCCTT | 2-2-1-1-1-11-2 | TAtaCcTttctttaacccTT | 573_8 | -23.58 | 8116 |
| 573 | TATACCTTTCTTTAACCCTT | 2-3-1-12-2 | TAtacCtttctttaacccTT | 573_9 | -23.17 | 8116 |
| 573 | TATACCTTTCTTTAACCCTT | 1-3-1-8-2-1-1-2 | TataCctttctttAAcCcTT | 573_10 | -23.35 | 8116 |
| 573 | TATACCTTTCTTTAACCCTT | 2-2-1-1-1-7-1-1-1-1-2 | TAtaCcTttctttaAcCcTT | 573_11 | -24.68 | 8116 |
| 573 | TATACCTTTCTTTAACCCTT | 2-4-1-8-2-1-2 | TAtaccTttctttaaCCcTT | 573_12 | -25.86 | 8116 |
| 573 | TATACCTTTCTTTAACCCTT | 2-3-1-9-1-2-2 | TAtacCtttctttaaCccTT | 573_13 | -23.96 | 8116 |
| 573 | TATACCTTTCTTTAACCCTT | 2-3-1-10-1-1-2 | TAtacCtttctttaacCcTT | 573_14 | -23.85 | 8116 |
| 574 | TTATACCTTTCTTTAACCCT | 1-1-1-10-1-4-2 | TtAtacctttcttTaaccCT | 574_1 | -22.31 | 8117 |
| 574 | TTATACCTTTCTTTAACCCT | 1-13-1-1-1-1-2 | TtataccttctttAaCcCT | 574_2 | -22.38 | 8117 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 574 | TTATACCTTTCTTTAACCCT | 1-1-1-3-1-11-2 | TtAtacCtttctttaaccCT | 574_3 | -22.47 | 8117 |
| 574 | TTATACCTTTCTTTAACCCT | 1-3-1-1-1-7-1-3-2 | TtatAcCtttctttAaccCT | 574_4 | -22.68 | 8117 |
| 574 | TTATACCTTTCTTTAACCCT | 1-4-1-8-1-3-2 | TtataCctttctttAaccCT | 574_5 | -22.38 | 8117 |
| 574 | TTATACCTTTCTTTAACCCT | 1-1-1-13-1-1-2 | TtAtacctttctttaaCcCT | 574_6 | -22.36 | 8117 |
| 574 | TTATACCTTTCTTTAACCCT | 1-3-1-11-1-1-2 | TtatAcctttctttaaCcCT | 574_7 | -22.46 | 8117 |
| 574 | TTATACCTTTCTTTAACCCT | 1-1-1-2-1-12-2 | TtAtaCctttctttaaccCT | 574_8 | -22.36 | 8117 |
| 574 | TTATACCTTTCTTTAACCCT | 1-5-1-11-2 | TtatacCtttctttaaccCT | 574_9 | -22.37 | 8117 |
| 574 | TTATACCTTTCTTTAACCCT | 1-1-1-2-1-10-1-1-2 | TtAtaCctttctttaaCcCT | 574_10 | -23.14 | 8117 |
| 574 | TTATACCTTTCTTTAACCCT | 1-1-1-3-1-9-1-1-2 | TtAtacCtttctttaaCcCT | 574_11 | -23.25 | 8117 |
| 574 | TTATACCTTTCTTTAACCCT | 1-1-1-3-1-10-3 | TtAtacCtttctttaacCCT | 574_12 | -24.75 | 8117 |
| 574 | TTATACCTTTCTTTAACCCT | 1-1-1-2-2-11-2 | TtAtaCCtttctttaaccCT | 574_13 | -24.85 | 8117 |
| 574 | TTATACCTTTCTTTAACCCT | 1-3-1-1-1-11-2 | TtatAcCtttctttaaccCT | 574_14 | -22.56 | 8117 |
| 575 | TTTATACCTTTCTTTAACCC | 1-2-1-9-1-4-2 | TttAtacctttctTtaacCC | 575_1 | -21.69 | 8118 |
| 575 | TTTATACCTTTCTTTAACCC | 1-12-1-4-2 | TttatacctttctTtaacCC | 575_2 | -21.59 | 8118 |
| 575 | TTTATACCTTTCTTTAACCC | 1-12-1-1-1-2-2 | TttatacctttctTtAacCC | 575_3 | -21.71 | 8118 |
| 575 | TTTATACCTTTCTTTAACCC | 1-4-1-10-1-1-2 | TttatAcctttctttaAcCC | 575_4 | -21.90 | 8118 |
| 575 | TTTATACCTTTCTTTAACCC | 1-13-1-3-2 | TttatacctttcttTaacCC | 575_5 | -22.01 | 8118 |
| 575 | TTTATACCTTTCTTTAACCC | 2-1-1-14-2 | TTtAtacctttctttaacCC | 575_6 | -22.20 | 8118 |
| 575 | TTTATACCTTTCTTTAACCC | 1-14-2-1-2 | TttatacctttctttAAcCC | 575_7 | -22.02 | 8118 |
| 575 | TTTATACCTTTCTTTAACCC | 1-14-1-2-2 | TttatacctttctttAacCC | 575_8 | -21.41 | 8118 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Mctif | Design | Compound | CMP ID_NO | ΔG° | Start SEQ_ID NO |
|---|---|---|---|---|---|---|
| 575 | TTTATACCTTTCTTTAACCC | 1-15-1-1-2 | TttataccttcttaAcCC | 575_9 | -21.71 | 8118 |
| 575 | TTTATACCTTTCTTTAACCC | 2-1-1-9-1-4-2 | TTtAtacctttctTtaacCC | 575_10 | -22.50 | 8118 |
| 575 | TTTATACCTTTCTTTAACCC | 1-2-1-10-1-3-2 | TttAtacctttcttTaacCC | 575_11 | -22.11 | 8118 |
| 575 | TTTATACCTTTCTTTAACCC | 1-4-2-8-2-1-2 | TttatACcttctttAAcCC | 575_12 | -23.40 | 8118 |
| 575 | TTTATACCTTTCTTTAACCC | 1-2-1-2-1-9-1-1-2 | TttAtaCcttctttaAcCC | 575_13 | -22.59 | 8118 |
| 575 | TTTATACCTTTCTTTAACCC | 1-1-2-14-2 | TtTatacctttctttaacCC | 575_14 | -23.15 | 8118 |
| 576 | TTTTATACCTTTCTTTAACC | 1-1-1-10-2-3-2 | TtTtataccttcTTtaaCC | 576_1 | -21.12 | 8119 |
| 576 | TTTTATACCTTTCTTTAACC | 1-3-1-8-1-4-2 | TtttAtacctttcTttaaCC | 576_2 | -20.10 | 8119 |
| 576 | TTTTATACCTTTCTTTAACC | 1-1-1-10-1-2-4 | TtTtataccttcTttAACC | 576_3 | -21.45 | 8119 |
| 576 | TTTTATACCTTTCTTTAACC | 3-11-1-1-1-1-2 | TTTtataccttctTtAaCC | 576_4 | -21.54 | 8119 |
| 576 | TTTTATACCTTTCTTTAACC | 2-4-1-7-1-3-2 | TTttatAcctttctTtaaCC | 576_5 | -20.80 | 8119 |
| 576 | TTTTATACCTTTCTTTAACC | 1-14-1-2-2 | TtttataccttctTaaCC | 576_6 | -20.22 | 8119 |
| 576 | TTTTATACCTTTCTTTAACC | 1-15-1-1-2 | TtttataccttcttAaCC | 576_7 | -19.61 | 8119 |
| 576 | TTTTATACCTTTCTTTAACC | 1-5-1-10-3 | TtttatAcctttctttaACC | 576_8 | -20.51 | 8119 |
| 576 | TTTTATACCTTTCTTTAACC | 1-1-2-14-2 | TtTTatacctttctttaaCC | 576_9 | -21.03 | 8119 |
| 576 | TTTTATACCTTTCTTTAACC | 1-1-2-10-1-1-1-1-2 | TtTTatacctttctTtAaCC | 576_10 | -21.46 | 8119 |
| 576 | TTTTATACCTTTCTTTAACC | 2-2-1-9-1-3-2 | TTttAtacctttctTtaaCC | 576_11 | -20.70 | 8119 |
| 576 | TTTTATACCTTTCTTTAACC | 1-5-1-7-1-3-2 | TttatAcctttctTtaaCC | 576_12 | -19.99 | 8119 |
| 576 | TTTTATACCTTTCTTTAACC | 1-1-1-12-2-1-2 | TtTtataccttctttTAaCC | 576_13 | -21.68 | 8119 |
| 576 | TTTTATACCTTTCTTTAACC | 1-1-1-1-1-13-2 | TtTtAtacctttctttaaCC | 576_14 | -19.89 | 8119 |
| 577 | TTTTTATACCTTTCTTTAAC | 1-12-1-2-4 | TttttataccttCttTAAC | 577_1 | -19.19 | 8120 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 577 | TTTTTATACCTTTCTTTAAC | 1-2-1-9-1-1-2-1-2 | TttTtataccttCtTTaAC | 577_2 | -18.96 | 8120 |
| 577 | TTTTTATACCTTTCTTTAAC | 2-12-3-1-2 | TTtttataccttcTTTaAC | 577_3 | -19.52 | 8120 |
| 577 | TTTTTATACCTTTCTTTAAC | 1-1-1-2-1-7-2-3-2 | TtTttAtaccttCTttaAC | 577_4 | -18.71 | 8120 |
| 577 | TTTTTATACCTTTCTTTAAC | 4-9-1-1-1-2-2 | TTTTtataccttCtTtaAC | 577_5 | -19.85 | 8120 |
| 577 | TTTTTATACCTTTCTTTAAC | 3-1-1-8-1-1-1-1-3 | TTTtTataccttCtTtAAC | 577_6 | -20.08 | 8120 |
| 577 | TTTTTATACCTTTCTTTAAC | 2-1-2-8-2-2-3 | TTtTTataccttCTttAAC | 577_7 | -20.97 | 8120 |
| 577 | TTTTTATACCTTTCTTTAAC | 1-1-2-10-2-1-3 | TtTtataccttcTTtAAC | 577_8 | -18.89 | 8120 |
| 577 | TTTTTATACCTTTCTTTAAC | 1-3-2-7-1-4-2 | TtttTAtaccttCtttaAC | 577_9 | -18.97 | 8120 |
| 577 | TTTTTATACCTTTCTTTAAC | 1-2-1-9-2-1-1-1-2 | TttTtataccttCTtTaAC | 577_10 | -19.34 | 8120 |
| 577 | TTTTTATACCTTTCTTTAAC | 2-3-1-7-2-2-3 | TTtttAtaccttCTttAAC | 577_11 | -19.53 | 8120 |
| 577 | TTTTTATACCTTTCTTTAAC | 1-1-2-9-1-1-1-1-3 | TtTTtataccttCtTtAAC | 577_12 | -18.84 | 8120 |
| 577 | TTTTTATACCTTTCTTTAAC | 1-3-2-7-1-1-1-2-2 | TtttTAtaccttCtTaAC | 577_13 | -19.27 | 8120 |
| 577 | TTTTTATACCTTTCTTTAAC | 3-1-1-8-1-2-1-1-2 | TTTtTataccttCttTaAC | 577_14 | -20.20 | 8120 |
| 578 | TTTTTTCTTACTATCTTCAA | 1-5-1-7-2-2-2 | TtttttCttactatCTtcAA | 578_1 | -19.02 | 8584 |
| 578 | TTTTTTCTTACTATCTTCAA | 2-2-1-1-1-7-1-1-1-1-2 | TTttTtCttactatCtTcAA | 578_2 | -19.31 | 8584 |
| 578 | TTTTTTCTTACTATCTTCAA | 1-2-2-9-1-2-3 | TttTTtcttactatCttCAA | 578_3 | -20.05 | 8584 |
| 578 | TTTTTTCTTACTATCTTCAA | 1-1-1-1-1-1-1-7-1-3-2 | TtTtTtCttactatCttcAA | 578_4 | -18.43 | 8584 |
| 578 | TTTTTTCTTACTATCTTCAA | 3-3-1-8-1-2-2 | TTTtttCttactatcTtcAA | 578_5 | -18.99 | 8584 |
| 578 | TTTTTTCTTACTATCTTCAA | 2-1-2-1-1-8-1-2-2 | TTtTTtCttactatcTtcAA | 578_6 | -19.29 | 8584 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 578 | TTTTTTCTTACTATCTTCAA | 1-1-3-1-1-9-1-1-2 | TtTTTtCttactatctTcAA | 578_7 | -19.15 | 8584 |
| 578 | TTTTTTCTTACTATCTTCAA | 2-1-1-11-1-1-3 | TTtTttcttactatcTtCAA | 578_8 | -19.58 | 8584 |
| 578 | TTTTTTCTTACTATCTTCAA | 1-4-1-10-4 | TttttTcttactatctTCAA | 578_9 | -19.31 | 8584 |
| 579 | TTTTTTTCTTACTATCTTCA | 1-12-1-1-1-2-2 | TttttttcttactAtCttCA | 579_1 | -19.29 | 8585 |
| 579 | TTTTTTTCTTACTATCTTCA | 2-1-1-9-1-4-2 | TTtTtttcttactAtcttCA | 579_2 | -19.42 | 8585 |
| 579 | TTTTTTTCTTACTATCTTCA | 1-1-1-2-1-7-1-4-2 | TtTttTcttactAtcttCA | 579_3 | -18.91 | 8585 |
| 579 | TTTTTTTCTTACTATCTTCA | 1-1-2-9-1-2-1-1-2 | TtTTttcttactAtcTtCA | 579_4 | -19.94 | 8585 |
| 579 | TTTTTTTCTTACTATCTTCA | 1-3-2-10-1-1-2 | TttttTtcttactatcTtCA | 579_5 | -19.84 | 8585 |
| 579 | TTTTTTTCTTACTATCTTCA | 2-3-1-12-2 | TTtttTtcttactatcttCA | 579_6 | -19.33 | 8585 |
| 579 | TTTTTTTCTTACTATCTTCA | 3-15-2 | TTTttttcttactatcttCA | 579_7 | -19.84 | 8585 |
| 579 | TTTTTTTCTTACTATCTTCA | 1-2-2-13-2 | TttTTtcttactatcttCA | 579_8 | -19.33 | 8585 |
| 579 | TTTTTTTCTTACTATCTTCA | 1-14-1-2-2 | TttttttcttactatCttCA | 579_9 | -19.19 | 8585 |
| 580 | ATTTTTTTCTTACTATCTTC | 1-4-1-8-1-1-1-1-2 | AttttTttcttactAtCtTC | 580_1 | -18.09 | 8586 |
| 580 | ATTTTTTTCTTACTATCTTC | 2-1-1-10-1-2-3 | ATtTttttcttactAtcTTC | 580_2 | -19.39 | 8586 |
| 580 | ATTTTTTTCTTACTATCTTC | 1-3-2-8-1-2-3 | AtttTTttcttactAtcTTC | 580_3 | -18.95 | 8586 |
| 580 | ATTTTTTTCTTACTATCTTC | 1-5-1-6-1-3-3 | AtttttTtcttacTatcTTC | 580_4 | -18.98 | 8586 |
| 580 | ATTTTTTTCTTACTATCTTC | 2-2-1-1-1-7-1-3-2 | ATttTtTcttactAtctTC | 580_5 | -18.66 | 8586 |
| 580 | ATTTTTTTCTTACTATCTTC | 1-3-8-1-4-2 | AtTTTttcttacTatctTC | 580_6 | -19.58 | 8586 |
| 580 | ATTTTTTTCTTACTATCTTC | 2-1-1-12-1-1-2 | ATtTttttcttactatCtTC | 580_7 | -19.24 | 8586 |
| 580 | ATTTTTTTCTTACTATCTTC | 1-1-1-2-1-11-3 | AtTttTttcttactatcTTC | 580_8 | -18.34 | 8586 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 580 | ATTTTTTTCTTACTATCTTC | 1-1-2-1-2-11-2 | AtTTtTTtcttactatctTC | 580_9 | -18.94 | 8586 |
| 581 | AATTTTTTTCTTACTATCTT | 1-4-1-7-1-1-1-1-3 | AatttTtttcttaCtAtCTT | 581_1 | -18.53 | 8587 |
| 581 | AATTTTTTTCTTACTATCTT | 1-3-1-1-1-6-2-3-2 | AattTtTttcttaCTatcTT | 581_2 | -18.69 | 8587 |
| 581 | AATTTTTTTCTTACTATCTT | 1-1-2-10-2-2-2 | AaTTtttttcttacTAtcTT | 581_3 | -18.80 | 8587 |
| 581 | AATTTTTTTCTTACTATCTT | 2-1-1-1-1-8-1-2-3 | AAtTtTtttcttacTatCTT | 581_4 | -19.20 | 8587 |
| 581 | AATTTTTTTCTTACTATCTT | 4-2-1-7-1-3-2 | AATTttTtttcttacTatcTT | 581_5 | -19.30 | 8587 |
| 581 | AATTTTTTTCTTACTATCTT | 2-2-2-7-1-1-2-1-2 | AAttTTttttcttaCtATcTT | 581_6 | -19.52 | 8587 |
| 581 | AATTTTTTTCTTACTATCTT | 1-12-1-2-4 | AattttttttcttaCtaTCTT | 581_7 | -19.25 | 8587 |
| 581 | AATTTTTTTCTTACTATCTT | 1-1-4-7-1-4-2 | AaTTTTttttcttaCtatcTT | 581_8 | -19.35 | 8587 |
| 581 | AATTTTTTTCTTACTATCTT | 2-1-3-9-1-1-3 | AAtTTTttttcttactAtCTT | 581_9 | -19.68 | 8587 |
| 582 | GTTTATACCCTTTCCAAT | 1-1-1-1-1-7-2-2-2 | GtTtAtaccctttTCcaAT | 582_1 | -21.48 | 9209 |
| 582 | GTTTATACCCTTTCCAAT | 1-12-2-1-2 | GtttatacccctttCCaAT | 582_2 | -22.28 | 9209 |
| 582 | GTTTATACCCTTTCCAAT | 1-3-1-8-1-1-3 | GtttAtaccctttCcAAT | 582_3 | -20.46 | 9209 |
| 582 | GTTTATACCCTTTCCAAT | 1-1-1-1-1-9-1-1-2 | GtTtAtaccctttcCaAT | 582_4 | -20.30 | 9209 |
| 582 | GTTTATACCCTTTCCAAT | 2-11-1-2-2 | GTttataccctttCcaAT | 582_5 | -21.64 | 9209 |
| 582 | GTTTATACCCTTTCCAAT | 1-1-2-9-1-1-3 | GtTTatacccctttCcAAT | 582_6 | -21.90 | 9209 |
| 582 | GTTTATACCCTTTCCAAT | 1-1-1-13-2 | GtTtataccctttccaAT | 582_7 | -19.63 | 9209 |
| 582 | GTTTATACCCTTTCCAAT | 1-2-1-12-2 | GttTataccctttccaAT | 582_8 | -20.05 | 9209 |
| 582 | GTTTATACCCTTTCCAAT | 1-13-4 | GtttataccctttcCAAT | 582_9 | -21.59 | 9209 |
| 583 | TGTTTATACCCTTTCCAA | 2-1-1-10-1-1-2 | TGtTtatacccctttCcAA | 583_1 | -21.08 | 9210 |
| 583 | TGTTTATACCCTTTCCAA | 1-4-1-6-1-1-1-1-2 | TgtttAtaccctTtCcAA | 583_2 | -19.97 | 9210 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 583 | TGTTTATACCCTTTCCAA | 1-3-1-9-1-1-2 | TgttTatacccttCcAA | 583_3 | -20.30 | 9210 |
| 583 | TGTTTATACCCTTTCCAA | 2-1-1-1-1-6-1-3-2 | TGtTtAtaccctTtccAA | 583_4 | -20.71 | 9210 |
| 583 | TGTTTATACCCTTTCCAA | 1-2-1-8-1-2-3 | TgtTtatacccTTtcCAA | 583_5 | -21.40 | 9210 |
| 583 | TGTTTATACCCTTTCCAA | 1-4-1-9-3 | TgtttAtaccctttcCAA | 583_6 | -20.89 | 9210 |
| 583 | TGTTTATACCCTTTCCAA | 1-1-2-12-2 | TgTTtacccttttccAA | 583_7 | -20.27 | 9210 |
| 583 | TGTTTATACCCTTTCCAA | 1-12-2-1-2 | TgtttataccctttTCcAA | 583_8 | -20.56 | 9210 |
| 583 | TGTTTATACCCTTTCCAA | 2-2-1-11-2 | TGttTatacccttccAA | 583_9 | -20.74 | 9210 |
| 584 | CTGTTTATACCCTTTCCA | 1-1-1-10-1-2-2 | CtGtttatacccTTtcCA | 584_1 | -22.45 | 9211 |
| 584 | CTGTTTATACCCTTTCCA | 1-12-1-2-2 | CtgtttatacccTTtcCA | 584_2 | -22.14 | 9211 |
| 584 | CTGTTTATACCCTTTCCA | 1-1-1-1-1-11-2 | CtGtTtataccctttcCA | 584_3 | -22.45 | 9211 |
| 584 | CTGTTTATACCCTTTCCA | 1-1-1-13-2 | CtGtttataccctttcCA | 584_4 | -22.15 | 9211 |
| 584 | CTGTTTATACCCTTTCCA | 1-2-1-12-2 | CtgTttataccctttcCA | 584_5 | -22.50 | 9211 |
| 584 | CTGTTTATACCCTTTCCA | 1-3-1-11-2 | CtgtTtataccctttcCA | 584_6 | -22.14 | 9211 |
| 584 | CTGTTTATACCCTTTCCA | 1-4-1-10-2 | CtgttTataccctttcCA | 584_7 | -22.57 | 9211 |
| 584 | CTGTTTATACCCTTTCCA | 1-15-2 | CtgtttataccctttcCA | 584_8 | -21.84 | 9211 |
| 585 | AATTATTTATACACCATCAT | 2-1-1-1-1-8-3-1-2 | AAtTaTttatacacCATCAT | 585_1 | -20.76 | 11511 |
| 585 | AATTATTTATACACCATCAT | 3-2-2-6-1-1-2-1-2 | AATtaTTtatacaCcATcAT | 585_2 | -20.88 | 11511 |
| 585 | AATTATTTATACACCATCAT | 1-4-1-7-2-1-1-1-2 | AattaTttatacaCCaTcAT | 585_3 | -19.62 | 11511 |
| 585 | AATTATTTATACACCATCAT | 1-3-1-1-1-6-1-3-3 | AattAtTtatacaCcatCAT | 585_4 | -18.98 | 11511 |
| 585 | AATTATTTATACACCATCAT | 1-2-3-7-1-1-1-2-2 | AatTATttatacaCcAtcAT | 585_5 | -19.65 | 11511 |
| 585 | AATTATTTATACACCATCAT | 1-1-2-11-1-1-3 | AaTTatttatacaccAtCAT | 585_6 | -19.53 | 11511 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 585 | AATTATTTATACACCATCAT | 2-2-1-9-1-1-4 | AAttAtttatacacCaTCAT | 585_7 | -20.11 | 11511 |
| 585 | AATTATTTATACACCATCAT | 3-1-2-8-1-2-3 | AATtAtttatacacCatCAT | 585_8 | -21.48 | 11511 |
| 585 | AATTATTTATACACCATCAT | 4-2-1-7-1-3-2 | AATTatTtatacacCatcAT | 585_9 | -19.60 | 11511 |
| 585 | AATTATTTATACACCATCAT | 2-1-1-2-1-6-3-2-2 | AAtAtTtatacaCCAtcAT | 585_10 | -21.69 | 11511 |
| 585 | AATTATTTATACACCATCAT | 1-3-2-7-1-1-1-1-3 | AattATttatacaCcAtCAT | 585_11 | -19.97 | 11511 |
| 585 | AATTATTTATACACCATCAT | 2-1-3-8-1-1-1-1-2 | AAtTATttatacacCaTcAT | 585_12 | -20.42 | 11511 |
| 585 | AATTATTTATACACCATCAT | 1-1-2-1-1-8-1-2-3 | AaTTAtttatacacCatCAT | 585_13 | -20.49 | 11511 |
| 585 | AATTATTTATACACCATCAT | 2-1-1-2-1-9-4 | AAtTatTtatacaccaTCAT | 585_14 | -20.47 | 11511 |
| 586 | AAATTATTTATACACCATCA | 1-12-3-1-3 | AaattatttatacACCaTCA | 586_1 | -20.58 | 11512 |
| 586 | AAATTATTTATACACCATCA | 1-1-1-2-1-7-1-1-2-1-2 | AaAttAtttatacAcCAtCA | 586_2 | -18.56 | 11512 |
| 586 | AAATTATTTATACACCATCA | 3-2-2-6-2-3-2 | AAAttATttatacACcatCA | 586_3 | -19.68 | 11512 |
| 586 | AAATTATTTATACACCATCA | 4-10-1-2-3 | AAAATtatttatacaCcaTCA | 586_4 | -20.15 | 11512 |
| 586 | AAATTATTTATACACCATCA | 1-1-4-8-1-1-1-1-2 | AaATTAtttatacaCcAtCA | 586_5 | -20.72 | 11512 |
| 586 | AAATTATTTATACACCATCA | 2-1-2-1-1-7-1-3-2 | AAaTTaTttatacaCcatCA | 586_6 | -19.39 | 11512 |
| 586 | AAATTATTTATACACCATCA | 1-3-2-7-1-1-1-1-3 | AaatTAtttatacAcCaTCA | 586_7 | -19.65 | 11512 |
| 586 | AAATTATTTATACACCATCA | 1-1-3-8-1-2-4 | AaATTatttatacAccATCA | 586_8 | -20.88 | 11512 |
| 586 | AAATTATTTATACACCATCA | 2-2-1-1-1-9-4 | AAatTaTttatacaccATCA | 586_9 | -19.63 | 11512 |
| 586 | AAATTATTTATACACCATCA | 1-1-1-1-1-1-1-6-3-2-2 | AaAtTaTttatacACCatCA | 586_10 | -20.95 | 11512 |
| 586 | AAATTATTTATACACCATCA | 1-3-2-7-1-1-2-1-2 | AaatTAtttatacAcCAtCA | 586_11 | -20.00 | 11512 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 586 | AAATTATTTATACACCATCA | 2-1-2-1-1-7-1-1-1-1-2 | AAaTTaTtttatacaCcAtCA | 586_12 | -19.44 | 11512 |
| 586 | AAATTATTTATACACCATCA | 3-2-1-8-1-2-3 | AAAttAtttatacaCcaTCA | 586_13 | -19.00 | 11512 |
| 586 | AAATTATTTATACACCATCA | 1-1-4-9-1-1-3 | AaATTAtttatacacCaTCA | 586_14 | -21.59 | 11512 |
| 587 | AAAATTATTTATACACCATC | 2-3-1-7-1-1-5 | AAaatTatttataCaCCATC | 587_1 | -21.17 | 11513 |
| 587 | AAAATTATTTATACACCATC | 1-2-2-9-6 | AaaATtatttatacACCATC | 587_2 | -21.34 | 11513 |
| 587 | AAAATTATTTATACACCATC | 2-3-2-6-3-1-3 | AAaatTAtttataCACcATC | 587_3 | -20.67 | 11513 |
| 587 | AAAATTATTTATACACCATC | 3-1-1-1-1-7-3-1-2 | AAAaTtAtttatacACCaTC | 587_4 | -19.11 | 11513 |
| 587 | AAAATTATTTATACACCATC | 7-6-1-1-1-2-2 | AAAATTAtttataCaCcaTC | 587_5 | -20.66 | 11513 |
| 587 | AAAATTATTTATACACCATC | 1-1-1-1-2-8-2-1-3 | AaAaTTatttatacACcATC | 587_6 | -18.20 | 11513 |
| 587 | AAAATTATTTATACACCATC | 1-1-5-6-2-3-2 | AaAATTatttataCAccaTC | 587_7 | -20.71 | 11513 |
| 587 | AAAATTATTTATACACCATC | 2-1-3-7-1-2-4 | AAaATTatttataCacCATC | 587_8 | -20.87 | 11513 |
| 587 | AAAATTATTTATACACCATC | 4-1-1-8-1-1-4 | AAAAtTatttatacAcCATC | 587_9 | -19.30 | 11513 |
| 587 | AAAATTATTTATACACCATC | 1-1-2-1-2-6-3-2-2 | AaAAtTAtttataCACcaTC | 587_10 | -20.13 | 11513 |
| 587 | AAAATTATTTATACACCATC | 1-2-3-7-1-1-2-1-2 | AaaATTatttataCaCCaTC | 587_11 | -20.44 | 11513 |
| 587 | AAAATTATTTATACACCATC | 3-1-2-7-1-2-4 | AAAaTTatttataCacCATC | 587_12 | -20.27 | 11513 |
| 587 | AAAATTATTTATACACCATC | 3-2-1-8-3-1-2 | AAAatTatttatacACCaTC | 587_13 | -19.30 | 11513 |
| 587 | AAAATTATTTATACACCATC | 2-1-3-8-2-1-3 | AAaATTatttatacACcATC | 587_14 | -19.52 | 11513 |
| 588 | TAAAATTATTTATACACCAT | 2-3-1-7-1-1-5 | TAaaaTtatttatAcACCAT | 588_1 | -20.14 | 11514 |
| 588 | TAAAATTATTTATACACCAT | 1-2-1-2-1-6-2-1-4 | TaaAatTatttatAcaCCAT | 588_2 | -20.15 | 11514 |
| 588 | TAAAATTATTTATACACCAT | 1-1-1-1-2-8-1-1-4 | TaAaATtatttataCaCCAT | 588_3 | -20.40 | 11514 |
| 588 | TAAAATTATTTATACACCAT | 4-1-2-6-4-1-2 | TAAAaTTatttatACACcAT | 588_4 | -21.36 | 11514 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 588 | TAAAATTATTTATACACCAT | 1-3-3-6-3-1-3 | TaaaATTatttatACAcCAT | 588_5 | -21.07 | 11514 |
| 588 | TAAAATTATTTATACACCAT | 2-1-4-7-3-1-2 | TAaAATTatttataCACcAT | 588_6 | -21.36 | 11514 |
| 588 | TAAAATTATTTATACACCAT | 3-1-1-1-1-7-2-1-3 | TAAaAtTatttataCAcCAT | 588_7 | -20.41 | 11514 |
| 588 | TAAAATTATTTATACACCAT | 7-6-1-3-3 | TAAAATTatttatAcacCAT | 588_8 | -20.85 | 11514 |
| 588 | TAAAATTATTTATACACCAT | 2-1-2-11-4 | TAaAAtatttatacaCCAT | 588_9 | -19.82 | 11514 |
| 588 | TAAAATTATTTATACACCAT | 2-2-3-6-4-1-2 | TAaaATTatttatACACcAT | 588_10 | -21.41 | 11514 |
| 588 | TAAAATTATTTATACACCAT | 1-1-1-1-3-6-1-2-4 | TaAaATTatttatAcaCCAT | 588_11 | -21.15 | 11514 |
| 588 | TAAAATTATTTATACACCAT | 2-1-2-1-1-7-2-1-3 | TAaAAtTatttataCAcCAT | 588_12 | -20.41 | 11514 |
| 588 | TAAAATTATTTATACACCAT | 3-2-2-7-1-1-4 | TAAaaTTatttataCaCCAT | 588_13 | -21.86 | 11514 |
| 588 | TAAAATTATTTATACACCAT | 1-1-2-1-1-9-5 | TaAAattatttatacACCAT | 588_14 | -19.68 | 11514 |
| 589 | TAAAATTATTTATACACCA | 1-1-2-1-1-7-6 | TaAAattatttatACACCA | 589_1 | -20.31 | 11515 |
| 589 | TAAAATTATTTATACACCA | 1-2-3-6-1-1-5 | TaaAATtatttaTaCACCA | 589_2 | -21.36 | 11515 |
| 589 | TAAAATTATTTATACACCA | 2-3-1-7-6 | TAaaaTtatttatACACCA | 589_3 | -20.58 | 11515 |
| 589 | TAAAATTATTTATACACCA | 3-1-2-6-4-1-2 | TAAaATtatttaTACAcCA | 589_4 | -21.36 | 11515 |
| 589 | TAAAATTATTTATACACCA | 4-1-1-6-2-2-3 | TAAAaTtatttaTAcaCCA | 589_5 | -20.51 | 11515 |
| 589 | TAAAATTATTTATACACCA | 2-1-2-7-1-1-1-1-3 | TAaAAttatttaTaCaCCA | 589_6 | -19.30 | 11515 |
| 589 | TAAAATTATTTATACACCA | 1-3-2-6-2-2-3 | TaaaATtatttaTAcaCCA | 589_7 | -19.40 | 11515 |
| 589 | TAAAATTATTTATACACCA | 5-8-2-1-3 | TAAAAttatttatACaCCA | 589_8 | -19.77 | 11515 |
| 589 | TAAAATTATTTATACACCA | 3-1-2-9-4 | TAAaATtatttatacACCA | 589_9 | -19.55 | 11515 |
| 589 | TAAAATTATTTATACACCA | 2-1-3-6-4-1-2 | TAaAAtatttaTACAcCA | 589_10 | -21.36 | 11515 |
| 589 | TAAAATTATTTATACACCA | 3-1-2-6-3-1-3 | TAAaATtatttaTACaCCA | 589_11 | -22.18 | 11515 |
| 589 | TAAAATTATTTATACACCA | 1-1-3-7-2-1-4 | TaAAAttatttaTAcACCA | 589_12 | -19.78 | 11515 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Mctif | Design | Compound | CMP ID_NO | ΔG° | Start SEQ_ID NO |
|---|---|---|---|---|---|---|
| 589 | TAAAATTATTTATACACCA | 2-2-1-7-1-1-1-1-3 | TAaaAttatttaTaCaCCA | 589_13 | -18.76 | 11515 |
| 589 | TAAAATTATTTATACACCA | 4-1-1-8-5 | TAAAaTtatttataCACCA | 589_14 | -21.06 | 11515 |
| 590 | ATATTGATTCAATTCCC | 2-9-2-1-3 | ATattgattcaATtCCC | 590_1 | -21.84 | 13226 |
| 590 | ATATTGATTCAATTCCC | 1-2-1-7-6 | AtaTtgattcaATTCCC | 590_2 | -22.10 | 13226 |
| 590 | ATATTGATTCAATTCCC | 2-9-1-1-1-2 | ATattgattcaAtTcCC | 590_3 | -18.59 | 13226 |
| 590 | ATATTGATTCAATTCCC | 1-1-2-8-5 | AtATtgattcaaTTCCC | 590_4 | -21.87 | 13226 |
| 590 | ATATTGATTCAATTCCC | 1-2-2-7-2-1-2 | AtaTTgattcaaTTcCC | 590_5 | -19.29 | 13226 |
| 590 | ATATTGATTCAATTCCC | 1-3-1-6-2-2-2 | AtatTgattcaATtcCC | 590_6 | -18.59 | 13226 |
| 590 | ATATTGATTCAATTCCC | 1-2-2-6-1-2-3 | AtaTTgattcaAttCCC | 590_7 | -20.66 | 13226 |
| 590 | ATATTGATTCAATTCCC | 1-1-1-1-1-7-1-1-3 | AtAtTgattcaaTtCCC | 590_8 | -19.92 | 13226 |
| 590 | ATATTGATTCAATTCCC | 1-1-1-8-1-2-3 | AtAttgattcaAttCCC | 590_9 | -19.01 | 13226 |
| 590 | ATATTGATTCAATTCCC | 4-7-1-3-2 | ATATtgattcaAttcCC | 590_10 | -20.60 | 13226 |
| 590 | ATATTGATTCAATTCCC | 3-1-1-7-1-2-2 | ATAtTgattcaaTtcCC | 590_11 | -20.26 | 13226 |
| 590 | ATATTGATTCAATTCCC | 1-3-1-8-4 | AtatTgattcaatTCCC | 590_12 | -20.37 | 13226 |
| 590 | ATATTGATTCAATTCCC | 2-1-1-10-3 | ATaTtgattcaattCCC | 590_13 | -20.71 | 13226 |
| 590 | ATATTGATTCAATTCCC | 2-2-1-9-3 | ATatTgattcaattCCC | 590_14 | -21.06 | 13226 |
| 590 | ATATTGATTCAATTCCC | 1-1-3-10-2 | AtATTgattcaattcCC | 590_15 | -18.87 | 13226 |
| 590 | ATATTGATTCAATTCCC | 2-2-1-6-2-2-2 | ATatTgattcaATtcCC | 590_16 | -20.26 | 13226 |
| 590 | ATATTGATTCAATTCCC | 3-8-1-1-4 | ATAttgattcaAtTCCC | 590_17 | -22.71 | 13226 |
| 590 | ATATTGATTCAATTCCC | 1-1-3-6-1-2-3 | AtATTgattcaAttCCC | 590_18 | -21.57 | 13226 |
| 590 | ATATTGATTCAATTCCC | 1-1-1-1-1-7-5 | AtAtTgattcaaTTCCC | 590_19 | -21.42 | 13226 |
| 590 | ATATTGATTCAATTCCC | 2-1-1-8-1-1-3 | ATaTtgattcaaTtCCC | 590_20 | -21.15 | 13226 |
| 591 | GCACATTCTTTCTATACCT | 1-1-1-1-1-12-2 | GcAcAttctttctatacCT | 591_1 | -21.27 | 15113 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 591 | GCACATTCTTTCTATACCT | 1-3-1-12-2 | GcacAttctttctatacCT | 591_2 | -21.12 | 15113 |
| 592 | GCACATTCTTTCTATACC | 1-12-1-2-2 | GcacattctttctAtaCC | 592_1 | -20.07 | 15114 |
| 592 | GCACATTCTTTCTATACC | 1-1-1-1-1-11-2 | GcAcAttctttctataCC | 592_2 | -20.17 | 15114 |
| 592 | GCACATTCTTTCTATACC | 1-3-1-11-2 | GcacAttctttctataCC | 592_3 | -20.02 | 15114 |
| 592 | GCACATTCTTTCTATACC | 1-1-2-11-3 | GcACattctttctatACC | 592_4 | -21.80 | 15114 |
| 592 | GCACATTCTTTCTATACC | 1-1-1-1-2-7-1-1-3 | GcAcATtctttctAtACC | 592_5 | -22.11 | 15114 |
| 592 | GCACATTCTTTCTATACC | 1-1-1-1-2-7-1-2-2 | GcAcATtctttctAtaCC | 592_6 | -21.51 | 15114 |
| 592 | GCACATTCTTTCTATACC | 1-15-2 | GcacattctttctataCC | 592_7 | -19.97 | 15114 |
| 592 | GCACATTCTTTCTATACC | 1-4-1-9-3 | GcacaTtctttctatACC | 592_8 | -21.01 | 15114 |
| 592 | GCACATTCTTTCTATACC | 1-4-1-10-2 | GcacaTtctttctataCC | 592_9 | -20.41 | 15114 |
| 592 | GCACATTCTTTCTATACC | 2-11-1-2-2 | GCacattctttctAtaCC | 592_10 | -22.39 | 15114 |
| 592 | GCACATTCTTTCTATACC | 1-1-1-1-8-1-2-2 | GcAcAttctttctAtaCC | 592_11 | -20.27 | 15114 |
| 592 | GCACATTCTTTCTATACC | 1-3-1-9-1-1-2 | GcacAttctttctaTaCC | 592_12 | -20.89 | 15114 |
| 592 | GCACATTCTTTCTATACC | 1-1-1-1-1-10-3 | GcAcAttctttctatACC | 592_13 | -20.77 | 15114 |
| 592 | GCACATTCTTTCTATACC | 1-1-1-2-1-10-2 | GcAcaTtctttctataCC | 592_14 | -20.56 | 15114 |
| 593 | TTATTTCCATTTATTTTCA | 1-1-1-1-1-8-3-1-2 | TtAtTtccatttaTTTtCA | 593_1 | -19.10 | 15563 |
| 593 | TTATTTCCATTTATTTTCA | 1-2-2-7-1-1-1-1-3 | TtaTTccatttAtTtTCA | 593_2 | -19.27 | 15563 |
| 593 | TTATTTCCATTTATTTTCA | 2-2-1-8-1-1-1-2 | TTatTtccatttaTtTtCA | 593_3 | -18.92 | 15563 |
| 593 | TTATTTCCATTTATTTTCA | 1-1-2-9-1-2-3 | TtATttccatttaTttTCA | 593_4 | -19.41 | 15563 |
| 594 | TTTATTTCCATTTATTTTCA | 1-1-1-11-1-2-3 | TtTatttccatttaTttTCA | 594_1 | -19.80 | 15563 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 594 | TTTATTTCCATTTATTTTCA | 1-4-1-7-1-1-1-2-2 | TttatTtccatttAtTttCA | 594_2 | -18.34 | 15563 |
| 594 | TTTATTTCCATTTATTTTCA | 1-3-2-9-2-1-2 | TttaTTtccatttatTTtCA | 594_3 | -20.01 | 15563 |
| 594 | TTTATTTCCATTTATTTTCA | 2-1-1-1-1-8-1-1-1-1-2 | TTtAtTtccatttaTtTtCA | 594_4 | -19.60 | 15563 |
| 595 | ATTTATTTCCATTTATTTTC | 1-1-1-2-1-8-3-1-2 | AtTtaTttccatttATTtTC | 595_1 | -19.05 | 15564 |
| 595 | ATTTATTTCCATTTATTTTC | 1-3-2-7-1-3-3 | AtttATttccattTattTTC | 595_2 | -19.03 | 15564 |
| 595 | ATTTATTTCCATTTATTTTC | 1-1-2-10-1-2-3 | AtTTatttccatttAttTTC | 595_3 | -18.60 | 15564 |
| 595 | ATTTATTTCCATTTATTTTC | 2-1-1-1-1-8-1-1-1-1-2 | ATtTaTttccatttAtTtTC | 595_4 | -18.96 | 15564 |
| 596 | TTTATTTCCATTTATTTTC | 1-1-1-1-1-8-2-1-3 | TtTaTttccatttATtTTC | 596_1 | -18.66 | 15564 |
| 596 | TTTATTTCCATTTATTTTC | 3-2-1-7-3-1-2 | TTTatTttccatttATTtTC | 596_2 | -19.84 | 15564 |
| 596 | TTTATTTCCATTTATTTTC | 2-2-2-7-1-1-4 | TTtaTTtccatttAtTTTC | 596_3 | -19.12 | 15564 |
| 596 | TTTATTTCCATTTATTTTC | 5-7-1-3-3 | TTTATttccattTattTTC | 596_4 | -21.30 | 15564 |
| 597 | CCATTTATTTCCATTTATTT | 1-1-1-11-2-2-2 | CcAtttatttccatTTatTT | 597_1 | -19.89 | 15566 |
| 597 | CCATTTATTTCCATTTATTT | 1-3-1-9-1-1-1-1-2 | CcatTtatttccatTtAtTT | 597_2 | -19.00 | 15566 |
| 597 | CCATTTATTTCCATTTATTT | 1-1-1-2-1-8-1-2-3 | CcAttTatttccatTtaTTT | 597_3 | -20.33 | 15566 |
| 597 | CCATTTATTTCCATTTATTT | 1-2-2-1-1-11-2 | CcaTTtAtttccatttatTT | 597_4 | -19.64 | 15566 |
| 598 | TCCATTTATTTCCATTTATT | 2-11-2-3-2 | TCcatttatttccATttaTT | 598_1 | -21.22 | 15567 |
| 598 | TCCATTTATTTCCATTTATT | 2-2-1-8-1-1-1-2-2 | TCcaTttatttccAtTtaTT | 598_2 | -20.71 | 15567 |
| 598 | TCCATTTATTTCCATTTATT | 1-1-2-9-1-4-2 | TcCAtttatttccAtttaTT | 598_3 | -20.63 | 15567 |
| 598 | TCCATTTATTTCCATTTATT | 2-1-1-1-1-11-3 | TCcAtTtatttccatttATT | 598_4 | -21.18 | 15567 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 599 | TCCATTTATTTCCATTTAT | 2-11-2-2-2 | TCcatttatttccATttAT | 599_1 | -20.30 | 15568 |
| 599 | TCCATTTATTTCCATTTAT | 2-2-1-8-1-1-1-1-2 | TCcaTttatttccAtTtAT | 599_2 | -19.80 | 15568 |
| 599 | TCCATTTATTTCCATTTAT | 1-1-2-9-1-3-2 | TcCatttatttccAtttAT | 599_3 | -19.72 | 15568 |
| 599 | TCCATTTATTTCCATTTAT | 1-1-1-1-2-7-1-3-2 | TcCaTTtatttccAtttAT | 599_4 | -19.50 | 15568 |
| 600 | TTCCATTTATTTCCATTTAT | 1-1-1-2-1-8-1-1-1-2 | TtCcaTttatttccAtTtAT | 600_1 | -20.12 | 15568 |
| 600 | TTCCATTTATTTCCATTTAT | 1-3-1-10-2-1-2 | TtccAtttatttccaTTtAT | 600_2 | -19.86 | 15568 |
| 600 | TTCCATTTATTTCCATTTAT | 1-1-1-3-1-7-1-3-2 | TtCcatTtatttccAtttAT | 600_3 | -19.68 | 15568 |
| 600 | TTCCATTTATTTCCATTTAT | 1-1-1-1-2-8-1-3-2 | TtCcATttatttccAtttAT | 600_4 | -20.68 | 15568 |
| 601 | TTTCCATTTATTTCCATTTA | 1-4-1-7-1-2-1-1-2 | TttccAtttatttCcaTtTA | 601_1 | -20.53 | 15569 |
| 601 | TTTCCATTTATTTCCATTTA | 2-2-1-12-3 | TTtcCatttatttccatTTA | 601_2 | -21.47 | 15569 |
| 601 | TTTCCATTTATTTCCATTTA | 1-2-1-2-1-8-1-2-2 | TttCcaTttatttccAttTA | 601_3 | -20.53 | 15569 |
| 601 | TTTCCATTTATTTCCATTTA | 1-4-1-9-1-2-2 | TttccAtttatttccAttTA | 601_4 | -19.37 | 15569 |
| 602 | CTTTCCATTTATTTCCATT | 1-11-1-1-1-1-3 | CtttccatttatTtCcATT | 602_1 | -21.20 | 15571 |
| 602 | CTTTCCATTTATTTCCATT | 2-2-1-9-1-2-2 | CTttCcatttatttCcaTT | 602_2 | -22.00 | 15571 |
| 602 | CTTTCCATTTATTTCCATT | 1-4-1-9-1-1-2 | CtttcCatttatttcCaTT | 602_3 | -20.42 | 15571 |
| 602 | CTTTCCATTTATTTCCATT | 1-3-1-11-3 | CtttCcatttatttccATT | 602_4 | -20.89 | 15571 |
| 603 | ATCTTTCCATTTATTTCCAT | 1-2-1-12-1-1-2 | AtcTttccatttatttCcAT | 603_1 | -21.24 | 15572 |
| 603 | ATCTTTCCATTTATTTCCAT | 1-3-1-1-1-7-1-3-2 | AtctTtCcatttatTtccAT | 603_2 | -21.33 | 15572 |
| 603 | ATCTTTCCATTTATTTCCAT | 1-5-1-6-1-4-2 | AtctttCcatttaTttccAT | 603_3 | -21.16 | 15572 |
| 603 | ATCTTTCCATTTATTTCCAT | 1-16-3 | AtctttccatttatttcCAT | 603_4 | -21.95 | 15572 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 604 | TCTTTCCATTTATTTCCAT | 2-13-1-1-2 | TCtttccatttatttCcAT | 604_1 | -21.57 | 15572 |
| 604 | TCTTTCCATTTATTTCCAT | 1-2-1-1-1-7-1-1-1-1-2 | TctTtCcatttatTtCcAT | 604_2 | -21.35 | 15572 |
| 604 | TCTTTCCATTTATTTCCAT | 2-14-3 | TCtttccatttatttcCAT | 604_3 | -22.80 | 15572 |
| 604 | TCTTTCCATTTATTTCCAT | 2-3-1-11-2 | TCtttCcatttatttccAT | 604_4 | -21.57 | 15572 |
| 605 | ATCTTTCCATTTATTTCCA | 1-2-1-10-1-2-2 | AtcTttccatttatTtcCA | 605_1 | -20.70 | 15573 |
| 605 | ATCTTTCCATTTATTTCCA | 1-3-1-8-1-3-2 | AtctTtccatttaTttcCA | 605_2 | -20.63 | 15573 |
| 605 | ATCTTTCCATTTATTTCCA | 1-1-1-14-2 | AtCtttccatttatttcCA | 605_3 | -20.86 | 15573 |
| 605 | ATCTTTCCATTTATTTCCA | 1-4-1-9-1-1-2 | AtcttTccatttattTcCA | 605_4 | -20.63 | 15573 |
| 606 | TATCTTTCCATTTATTTCCA | 1-4-1-8-2-2-2 | TatctTtccatttaTTtcCA | 606_1 | -22.54 | 15573 |
| 606 | TATCTTTCCATTTATTTCCA | 2-16-2 | TAtctttccatttatttcCA | 606_2 | -22.12 | 15573 |
| 606 | TATCTTTCCATTTATTTCCA | 1-2-1-14-2 | TatCtttccatttatttcCA | 606_3 | -21.97 | 15573 |
| 606 | TATCTTTCCATTTATTTCCA | 1-17-2 | Tatctttccatttatttcca | 606_4 | -20.99 | 15573 |
| 607 | TATCTTTCCATTTATTTCC | 2-12-1-2-2 | TAtctttccatttaTttCC | 607_1 | -21.63 | 15574 |
| 607 | TATCTTTCCATTTATTTCC | 1-2-1-13-2 | TatCtttccatttatttCC | 607_2 | -21.04 | 15574 |
| 607 | TATCTTTCCATTTATTTCC | 1-2-2-12-2 | TatCTttccatttatttCC | 607_3 | -22.23 | 15574 |
| 607 | TATCTTTCCATTTATTTCC | 1-4-1-9-1-1-2 | TatctTtccatttatTtCC | 607_4 | -20.66 | 15574 |
| 608 | AAATCTCAACTACCATTTTT | 1-1-1-3-1-7-3-1-2 | AaAtctCaactaccATTtTT | 608_1 | -19.53 | 25248 |
| 608 | AAATCTCAACTACCATTTTT | 3-1-1-9-2-1-3 | AAAtCtcaactaccATtTTT | 608_2 | -20.58 | 25248 |
| 608 | AAATCTCAACTACCATTTTT | 1-3-1-8-1-1-5 | AaatCtcaactacCaTTTTT | 608_3 | -20.56 | 25248 |
| 608 | AAATCTCAACTACCATTTTT | 1-1-1-2-1-7-2-2-3 | AaAtCtcaactacCAttTTT | 608_4 | -20.20 | 25248 |
| 608 | AAATCTCAACTACCATTTTT | 1-3-1-1-1-6-1-1-1-2-2 | AaatCtCaactacCaTttTT | 608_5 | -19.10 | 25248 |
| 608 | AAATCTCAACTACCATTTTT | 2-3-2-6-1-2-4 | AAatcTCaactacCatTTTT | 608_6 | -21.04 | 25248 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 608 | AAATCTCAACTACCATTTTT | 2-1-2-1-1-7-1-3-2 | AAaTCtCaactaccAtttTT | 608_7 | -19.79 | 25248 |
| 608 | AAATCTCAACTACCATTTTT | 1-1-3-11-1-1-2 | AaATCtcaactaccatTtTT | 608_8 | -19.97 | 25248 |
| 608 | AAATCTCAACTACCATTTTT | 3-1-1-1-1-10-3 | AAAtCtCaactaccattTTT | 608_9 | -19.95 | 25248 |
| 609 | AAAATCTCAACTACCATTTT | 1-12-4-1-2 | AaaatctcaactaCCAtTT | 609_1 | -21.31 | 25249 |
| 609 | AAAATCTCAACTACCATTTT | 3-11-2-1-3 | AAAatctcaactacCAtTTT | 609_2 | -19.57 | 25249 |
| 609 | AAAATCTCAACTACCATTTT | 2-1-1-1-1-8-2-1-3 | AAaAtCtcaactacCAtTTT | 609_3 | -20.33 | 25249 |
| 609 | AAAATCTCAACTACCATTTT | 1-1-4-9-1-2-2 | AaAATCtcaactaccAttTT | 609_4 | -19.46 | 25249 |
| 609 | AAAATCTCAACTACCATTTT | 1-1-2-2-1-7-2-2-2 | AaAAtcTcaactacCAttTT | 609_5 | -19.13 | 25249 |
| 609 | AAAATCTCAACTACCATTTT | 4-1-1-7-1-2-4 | AAAAtCtcaactaCcaTTTT | 609_6 | -20.75 | 25249 |
| 609 | AAAATCTCAACTACCATTTT | 1-1-1-2-1-8-1-1-4 | AaAatCtcaactacCaTTTT | 609_7 | -19.30 | 25249 |
| 609 | AAAATCTCAACTACCATTTT | 1-2-3-7-1-1-1-1-3 | AaaATCtcaactaCcAtTTT | 609_8 | -20.51 | 25249 |
| 609 | AAAATCTCAACTACCATTTT | 2-2-2-10-1-1-2 | AAaaTCtcaactaccaTtTT | 609_9 | -18.72 | 25249 |
| 610 | AAAATCTCAACTACCATTT | 1-4-1-6-4-1-2 | AaaatCtcaactACCAtTT | 610_1 | -20.63 | 25250 |
| 610 | AAAATCTCAACTACCATTT | 3-10-6 | AAAatctcaactaCCATTT | 610_2 | -21.90 | 25250 |
| 610 | AAAATCTCAACTACCATTT | 6-6-2-2-3 | AAAATCtcaactACcaTTT | 610_3 | -21.46 | 25250 |
| 610 | AAAATCTCAACTACCATTT | 2-2-2-7-2-1-3 | AAaaTCtcaactaCCaTTT | 610_4 | -21.18 | 25250 |
| 610 | AAAATCTCAACTACCATTT | 6-7-2-2-2 | AAAATCtcaactaCCatTT | 610_5 | -22.10 | 25250 |
| 610 | AAAATCTCAACTACCATTT | 2-1-1-1-1-8-5 | AAaAtCtcaactacCATTT | 610_6 | -20.27 | 25250 |
| 610 | AAAATCTCAACTACCATTT | 1-1-1-1-2-8-5 | AaAaTCtcaactacCATTT | 610_7 | -20.88 | 25250 |
| 610 | AAAATCTCAACTACCATTT | 1-1-2-1-1-8-2-1-2 | AaAAtCtcaactacCAtTT | 610_8 | -18.51 | 25250 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 610 | AAAATCTCAACTACCATTT | 6-9-4 | AAAATCtcaactaccATTT | 610_9 | -20.94 | 25250 |
| 611 | GAAAATCTCAACTACCATT | 1-1-3-7-1-2-4 | GaAAAtctcaacTacCATT | 611_1 | -20.48 | 25251 |
| 611 | GAAAATCTCAACTACCATT | 1-1-2-8-1-1-1-1-3 | GaAAatctcaacTaCcATT | 611_2 | -18.75 | 25251 |
| 611 | GAAAATCTCAACTACCATT | 3-1-1-10-4 | GAAaAtctcaactacCATT | 611_3 | -20.73 | 25251 |
| 611 | GAAAATCTCAACTACCATT | 2-1-2-10-4 | GAaAAtctcaactacCATT | 611_4 | -20.73 | 25251 |
| 611 | GAAAATCTCAACTACCATT | 2-2-1-7-1-4-2 | GAaaAtctcaacTaccaTT | 611_5 | -18.28 | 25251 |
| 611 | GAAAATCTCAACTACCATT | 2-12-5 | GAaaatctcaactaCCATT | 611_6 | -22.25 | 25251 |
| 611 | GAAAATCTCAACTACCATT | 4-10-2-1-2 | GAAAatctcaactaCCaTT | 611_7 | -21.06 | 25251 |
| 611 | GAAAATCTCAACTACCATT | 4-10-1-1-3 | GAAAatctcaactaCcATT | 611_8 | -19.73 | 25251 |
| 611 | GAAAATCTCAACTACCATT | 5-12-2 | GAAAAtctcaactaccaTT | 611_9 | -18.61 | 25251 |
| 612 | TGAAAATCTCAACTACCAT | 1-4-1-6-1-1-2-1-2 | TgaaaAtctcaaCtACcAT | 612_1 | -18.43 | 25252 |
| 612 | TGAAAATCTCAACTACCAT | 2-1-2-7-1-2-1-1-2 | TGaAAatctcaaCtaCcAT | 612_2 | -19.46 | 25252 |
| 612 | TGAAAATCTCAACTACCAT | 1-1-2-8-1-2-1-1-2 | TgAAaatctcaaCtaCcAT | 612_3 | -18.58 | 25252 |
| 612 | TGAAAATCTCAACTACCAT | 1-2-1-1-1-6-1-3-3 | TgaAaAtctcaaCtacCAT | 612_4 | -19.40 | 25252 |
| 612 | TGAAAATCTCAACTACCAT | 1-3-2-10-3 | TgaaAAtctcaactacCAT | 612_5 | -18.60 | 25252 |
| 612 | TGAAAATCTCAACTACCAT | 1-11-1-2-4 | TgaaaatctcaaCtaCCAT | 612_6 | -21.11 | 25252 |
| 612 | TGAAAATCTCAACTACCAT | 3-1-2-6-1-4-2 | TGAaAAtctcaaCtaccAT | 612_7 | -20.39 | 25252 |
| 612 | TGAAAATCTCAACTACCAT | 1-1-1-1-1-7-1-3-3 | TgAaAatctcaaCtacCAT | 612_8 | -19.60 | 25252 |
| 612 | TGAAAATCTCAACTACCAT | 4-12-3 | TGAAatctcaactacCAT | 612_9 | -21.07 | 25252 |
| 613 | ATCATTCTCAACAATTAAA | 4-8-7 | ATCAttctcaacAATTAAA | 613_1 | -20.89 | 30599 |
| 613 | ATCATTCTCAACAATTAAA | 1-1-4-6-7 | AtCATTctcaacAATTAAA | 613_2 | -21.09 | 30599 |
| 613 | ATCATTCTCAACAATTAAA | 5-7-2-1-1-2 | ATCATtctcaacAAtTaAA | 613_3 | -19.03 | 30599 |
| 613 | ATCATTCTCAACAATTAAA | 5-8-2-2-2 | ATCATtctcaacaATtaAA | 613_4 | -19.28 | 30599 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 613 | ATCATTCTCAACAATTAAA | 4-1-1-8-5 | ATCAtTctcaacaaTTAAA | 613_5 | -19.86 | 30599 |
| 613 | ATCATTCTCAACAATTAAA | 5-7-4-1-2 | ATCATtctcaacAATTaAA | 613_6 | -20.79 | 30599 |
| 613 | ATCATTCTCAACAATTAAA | 4-8-1-1-5 | ATCAttctcaacAaTTAAA | 613_7 | -19.56 | 30599 |
| 613 | ATCATTCTCAACAATTAAA | 1-1-4-6-1-1-5 | AtCATTctcaacAaTTAAA | 613_8 | -19.76 | 30599 |
| 613 | ATCATTCTCAACAATTAAA | 4-1-1-7-3-1-2 | ATCAtTctcaacaATTaAA | 613_9 | -19.64 | 30599 |
| 613 | ATCATTCTCAACAATTAAA | 5-8-1-1-4 | ATCATtctcaacaAtTAAA | 613_10 | -20.11 | 30599 |
| 614 | ATCATTCTCAACAATTAA | 4-8-6 | ATCAttctcaacAATTAA | 614_1 | -20.14 | 30600 |
| 614 | ATCATTCTCAACAATTAA | 1-1-4-6-6 | AtCATTctcaacAATTAA | 614_2 | -20.34 | 30600 |
| 614 | ATCATTCTCAACAATTAA | 5-8-1-1-3 | ATCATtctcaacaAtTAA | 614_3 | -19.36 | 30600 |
| 614 | ATCATTCTCAACAATTAA | 4-8-1-1-4 | ATCAttctcaacAaTTAA | 614_4 | -18.81 | 30600 |
| 614 | ATCATTCTCAACAATTAA | 5-8-5 | ATCATtctcaacaATTAA | 614_5 | -21.12 | 30600 |
| 614 | ATCATTCTCAACAATTAA | 5-7-1-2-3 | ATCATtctcaacAatTAA | 614_6 | -19.11 | 30600 |
| 614 | ATCATTCTCAACAATTAA | 3-10-5 | ATCattctcaacaATTAA | 614_7 | -18.40 | 30600 |
| 614 | ATCATTCTCAACAATTAA | 4-9-1-1-3 | ATCAttctcaacAAtTAA | 614_8 | -18.11 | 30600 |
| 614 | ATCATTCTCAACAATTAA | 4-1-1-8-4 | ATCAtTctcaacaaTTAA | 614_9 | -19.11 | 30600 |
| 614 | ATCATTCTCAACAATTAA | 1-1-3-9-4 | AtCATtctcaacaaTTAA | 614_10 | -18.05 | 30600 |
| 615 | GATCATTCTCAACAATTAA | 2-3-1-6-2-1-4 | GAtcaTtctcaaCAaTTAA | 615_1 | -20.54 | 30600 |
| 615 | GATCATTCTCAACAATTAA | 1-2-2-7-1-2-4 | GatCAttctcaaCaaTTAA | 615_2 | -19.04 | 30600 |
| 615 | GATCATTCTCAACAATTAA | 2-1-3-6-3-2-2 | GAtCATtctcaaCAAttAA | 615_3 | -21.29 | 30600 |
| 615 | GATCATTCTCAACAATTAA | 2-1-2-8-2-1-3 | GAtCAttctcaacAAtTAA | 615_4 | -19.70 | 30600 |
| 615 | GATCATTCTCAACAATTAA | 5-8-1-1-1-1-2 | GATCAttctcaacAaTtAA | 615_5 | -19.79 | 30600 |
| 615 | GATCATTCTCAACAATTAA | 4-8-3-2-2 | GATCattctcaaCAAttAA | 615_6 | -20.50 | 30600 |
| 615 | GATCATTCTCAACAATTAA | 1-2-3-6-2-2-3 | GatCAttctcaaCAatTAA | 615_7 | -20.82 | 30600 |
| 615 | GATCATTCTCAACAATTAA | 2-2-2-6-1-1-5 | GAtcATtctcaaCaATTAA | 615_8 | -21.04 | 30600 |
| 615 | GATCATTCTCAACAATTAA | 2-1-1-8-1-2-4 | GAtCattctcaaCaaTTAA | 615_9 | -19.28 | 30600 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 615 | GATCATTCTCAACAATTAA | 1-1-3-9-1-1-3 | GaTCAttctcaacaAtTAA | 615_10 | -18.85 | 30600 |
| 616 | AGATCATTCTCAACAATTA | 1-1-1-2-1-7-3-1-2 | AgAtcAttctcaaCAAtTA | 616_1 | -19.10 | 30601 |
| 616 | AGATCATTCTCAACAATTA | 1-3-1-8-2-1-3 | AgatCattctcaaCAaTTA | 616_2 | -19.65 | 30601 |
| 616 | AGATCATTCTCAACAATTA | 1-3-2-6-1-1-1-2-2 | AgatCAttctcaAcAatTA | 616_3 | -18.49 | 30601 |
| 616 | AGATCATTCTCAACAATTA | 1-1-1-1-2-11-2 | AgAtCAttctcaacaatTA | 616_4 | -18.49 | 30601 |
| 616 | AGATCATTCTCAACAATTA | 1-1-1-2-1-9-4 | AgAtcAttctcaacaATTA | 616_5 | -18.49 | 30601 |
| 616 | AGATCATTCTCAACAATTA | 1-3-2-6-1-1-5 | AgatCAttctcaAcAATTA | 616_6 | -20.76 | 30601 |
| 616 | AGATCATTCTCAACAATTA | 2-2-1-8-3-1-2 | AGatCattctcaaCAAtTA | 616_7 | -20.47 | 30601 |
| 616 | AGATCATTCTCAACAATTA | 3-2-1-7-1-2-3 | AGAtcAttctcaaCaaTTA | 616_8 | -20.51 | 30601 |
| 616 | AGATCATTCTCAACAATTA | 1-2-3-7-1-3-2 | AgaTCAttctcaaCaatTA | 616_9 | -19.80 | 30601 |
| 616 | AGATCATTCTCAACAATTA | 1-1-1-1-2-8-2-1-2 | AgAtCAttctcaacAAtTA | 616_10 | -19.08 | 30601 |
| 617 | GATCATTCTCAACAATTA | 2-3-1-6-6 | GAtcaTtctcaaCAATTA | 617_1 | -21.11 | 30601 |
| 617 | GATCATTCTCAACAATTA | 2-1-2-8-5 | GAtCAttctcaacAATTA | 617_2 | -20.71 | 30601 |
| 617 | GATCATTCTCAACAATTA | 2-2-2-6-2-2-2 | GAtcATtctcaaCAatTA | 617_3 | -19.70 | 30601 |
| 617 | GATCATTCTCAACAATTA | 1-1-3-7-1-1-1-1-2 | GaTCAttctcaaCaAtTA | 617_4 | -18.78 | 30601 |
| 617 | GATCATTCTCAACAATTA | 2-1-2-10-3 | GAtCAttctcaacaaTTA | 617_5 | -19.31 | 30601 |
| 617 | GATCATTCTCAACAATTA | 2-1-1-1-1-6-3-1-2 | GAtCaTtctcaaCAAtTA | 617_6 | -20.02 | 30601 |
| 617 | GATCATTCTCAACAATTA | 2-1-2-7-2-2-2 | GAtCAttctcaaCAatTA | 617_7 | -20.53 | 30601 |
| 617 | GATCATTCTCAACAATTA | 2-1-3-6-1-2-3 | GAtCATtctcaaCaaTTA | 617_8 | -21.24 | 30601 |
| 617 | GATCATTCTCAACAATTA | 2-2-1-8-5 | GAtcAttctcaacAATTA | 617_9 | -18.63 | 30601 |
| 617 | GATCATTCTCAACAATTA | 1-1-3-9-1-1-2 | GaTCAttctcaacaAtTA | 617_10 | -18.10 | 30601 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 618 | AGATCATTCTCAACAATT | 1-3-2-6-6 | AgatCAttctcaACAATT | 618_1 | -21.03 | 30602 |
| 618 | AGATCATTCTCAACAATT | 1-1-1-1-2-7-5 | AgAtCAttctcaaCAATT | 618_2 | -20.70 | 30602 |
| 618 | AGATCATTCTCAACAATT | 1-1-4-6-1-3-2 | AgATCAttctcaAcaaTT | 618_3 | -19.56 | 30602 |
| 618 | AGATCATTCTCAACAATT | 3-1-1-9-4 | AGAtCattctcaacAATT | 618_4 | -19.61 | 30602 |
| 618 | AGATCATTCTCAACAATT | 2-1-3-10-2 | AGaTCAttctcaacaaTT | 618_5 | -19.09 | 30602 |
| 618 | AGATCATTCTCAACAATT | 1-2-3-6-1-3-2 | AgaTCAttctcaAcaaTT | 618_6 | -18.25 | 30602 |
| 618 | AGATCATTCTCAACAATT | 2-2-2-7-2-1-2 | AGatCAttctcaaCAaTT | 618_7 | -20.14 | 30602 |
| 618 | AGATCATTCTCAACAATT | 1-1-1-1-2-7-1-1-3 | AgAtCAttctcaaCaATT | 618_8 | -19.02 | 30602 |
| 618 | AGATCATTCTCAACAATT | 1-2-3-8-4 | AgaTCAttctcaacAATT | 618_9 | -19.23 | 30602 |
| 618 | AGATCATTCTCAACAATT | 3-1-1-10-3 | AGAtCattctcaacaATT | 618_10 | -19.34 | 30602 |
| 619 | GATCATTCTCAACAATT | 2-1-2-6-6 | GAtCAttctcaACAATT | 619_1 | -21.40 | 30602 |
| 619 | GATCATTCTCAACAATT | 1-1-3-7-5 | GaTCAttctcaaCAATT | 619_2 | -19.99 | 30602 |
| 619 | GATCATTCTCAACAATT | 5-7-1-2-2 | GATCAttctcaaCaaTT | 619_3 | -19.69 | 30602 |
| 619 | GATCATTCTCAACAATT | 5-6-1-1-4 | GATCAttctcaAcAATT | 619_4 | -20.83 | 30602 |
| 619 | GATCATTCTCAACAATT | 2-1-2-7-5 | GAtCAttctcaaCAATT | 619_5 | -20.57 | 30602 |
| 619 | GATCATTCTCAACAATT | 5-6-1-3-2 | GATCAttctcaAcaaTT | 619_6 | -19.43 | 30602 |
| 619 | GATCATTCTCAACAATT | 4-8-5 | GATCattctcaaCAATT | 619_7 | -21.04 | 30602 |
| 619 | GATCATTCTCAACAATT | 1-1-3-7-2-1-2 | GaTCAttctcaaCAaTT | 619_8 | -18.67 | 30602 |
| 619 | GATCATTCTCAACAATT | 5-7-1-1-3 | GATCAttctcaaCaATT | 619_9 | -20.82 | 30602 |
| 619 | GATCATTCTCAACAATT | 2-1-2-8-4 | GAtCAttctcaacAATT | 619_10 | -18.48 | 30602 |
| 620 | AAGATCATTCTCAACAAT | 4-1-1-6-1-1-4 | AAGAtCattctcAaCAAT | 620_1 | -20.71 | 30603 |
| 620 | AAGATCATTCTCAACAAT | 4-9-5 | AAGAtcattctcaACAAT | 620_2 | -20.79 | 30603 |
| 620 | AAGATCATTCTCAACAAT | 2-2-2-6-6 | AAgaTCattctcAACAAT | 620_3 | -19.88 | 30603 |
| 620 | AAGATCATTCTCAACAAT | 4-1-1-7-2-1-2 | AAGAtCattctcaACaAT | 620_4 | -19.77 | 30603 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 620 | AAGATCATTCTCAACAAT | 2-1-3-8-4 | AAgATCattctcaaCAAT | 620_5 | -20.10 | 30603 |
| 620 | AAGATCATTCTCAACAAT | 4-1-1-6-2-2-2 | AAGAtCattctcAAcaAT | 620_6 | -18.96 | 30603 |
| 620 | AAGATCATTCTCAACAAT | 3-1-2-6-1-1-4 | AAGaTCattctcAaCAAT | 620_7 | -20.12 | 30603 |
| 620 | AAGATCATTCTCAACAAT | 2-1-3-6-1-1-4 | AAgATCattctcAaCAAT | 620_8 | -20.17 | 30603 |
| 620 | AAGATCATTCTCAACAAT | 1-1-1-2-1-7-5 | AaGatCattctcaACAAT | 620_9 | -18.21 | 30603 |
| 620 | AAGATCATTCTCAACAAT | 4-1-1-8-4 | AAGAtCattctcaaCAAT | 620_10 | -20.63 | 30603 |
| 621 | AAAGATCATTCTCAACAA | 1-1-1-9-6 | AaAgatcattctCAACAA | 621_1 | -18.13 | 30604 |
| 621 | AAAGATCATTCTCAACAA | 1-1-3-7-2-1-3 | AaAGAtcattctCAaCAA | 621_2 | -20.08 | 30604 |
| 621 | AAAGATCATTCTCAACAA | 1-3-2-6-2-1-3 | AaagATcattctCAaCAA | 621_3 | -18.11 | 30604 |
| 621 | AAAGATCATTCTCAACAA | 1-2-2-7-1-1-4 | AaaGAtcattctCaACAA | 621_4 | -18.07 | 30604 |
| 621 | AAAGATCATTCTCAACAA | 5-10-3 | AAAGAtcattctcaaCAA | 621_5 | -18.65 | 30604 |
| 621 | AAAGATCATTCTCAACAA | 1-1-3-7-3-1-2 | AaAGAtcattctCAAcAA | 621_6 | -18.59 | 30604 |
| 621 | AAAGATCATTCTCAACAA | 4-8-2-1-3 | AAAGatcattctCAaCAA | 621_7 | -19.10 | 30604 |
| 621 | AAAGATCATTCTCAACAA | 3-1-1-7-2-1-3 | AAAgAtcattctCAaCAA | 621_8 | -18.35 | 30604 |
| 621 | AAAGATCATTCTCAACAA | 1-1-2-8-2-1-3 | AaAGatcattctCAaCAA | 621_9 | -18.37 | 30604 |
| 621 | AAAGATCATTCTCAACAA | 1-2-2-7-2-1-3 | AaaGAtcattctCAaCAA | 621_10 | -18.74 | 30604 |
| 621 | AAAGATCATTCTCAACAA | 5-7-1-2-3 | AAAGAtcattctCaaCAA | 621_11 | -19.32 | 30604 |
| 622 | CAAAGATCATTCTCAACA | 1-1-2-8-6 | CaAAgatcattcTCAACA | 622_1 | -20.93 | 30605 |
| 622 | CAAAGATCATTCTCAACA | 2-1-1-9-5 | CAaAgatcattctCAACA | 622_2 | -20.68 | 30605 |
| 622 | CAAAGATCATTCTCAACA | 1-4-1-7-5 | CaaagAtcattctCAACA | 622_3 | -18.86 | 30605 |
| 622 | CAAAGATCATTCTCAACA | 4-1-1-7-1-2-2 | CAAAgAtcattctCaaCA | 622_4 | -19.40 | 30605 |
| 622 | CAAAGATCATTCTCAACA | 3-1-2-10-2 | CAAaGAtcattctcaaCA | 622_5 | -19.67 | 30605 |
| 622 | CAAAGATCATTCTCAACA | 4-8-2-2-2 | CAAAgatcattcTCaaCA | 622_6 | -20.10 | 30605 |
| 622 | CAAAGATCATTCTCAACA | 1-1-2-1-1-7-5 | CaAAgAtcattctCAACA | 622_7 | -20.23 | 30605 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 622 | CAAAGATCATTCTCAACA | 2-1-1-9-2-1-2 | CAaAgatcattctCAaCA | 622_8 | -19.66 | 30605 |
| 622 | CAAAGATCATTCTCAACA | 3-2-1-7-1-1-3 | CAAagAtcattctCaACA | 622_9 | -19.21 | 30605 |
| 622 | CAAAGATCATTCTCAACA | 1-3-2-7-1-2-2 | CaaaGatcattctCaaCA | 622_10 | -18.30 | 30605 |
| 623 | CAAAGATCATTCTCAAC | 3-8-6 | CAAagatcattCTCAAC | 623_1 | -19.95 | 30606 |
| 623 | CAAAGATCATTCTCAAC | 2-1-1-7-6 | CAaAgatcattCTCAAC | 623_2 | -20.23 | 30606 |
| 623 | CAAAGATCATTCTCAAC | 2-2-1-6-6 | CAaaGatcattCTCAAC | 623_3 | -20.15 | 30606 |
| 623 | CAAAGATCATTCTCAAC | 1-2-2-6-6 | CaaAGatcattCTCAAC | 623_4 | -20.00 | 30606 |
| 623 | CAAAGATCATTCTCAAC | 5-6-1-1-4 | CAAAGatcattCtCAAC | 623_5 | -20.35 | 30606 |
| 623 | CAAAGATCATTCTCAAC | 4-7-3-1-2 | CAAAgatcattCTCaAC | 623_6 | -19.28 | 30606 |
| 623 | CAAAGATCATTCTCAAC | 3-1-1-6-1-1-4 | CAAaGatcattCtCAAC | 623_7 | -18.81 | 30606 |
| 623 | CAAAGATCATTCTCAAC | 2-1-1-7-1-1-4 | CAaAgatcattCtCAAC | 623_8 | -18.36 | 30606 |
| 623 | CAAAGATCATTCTCAAC | 1-2-2-6-1-1-4 | CaaAGatcattCtCAAC | 623_9 | -18.12 | 30606 |
| 623 | CAAAGATCATTCTCAAC | 4-8-5 | CAAAgatcattcTCAAC | 623_10 | -19.31 | 30606 |
| 624 | CTCAAAGATCATTCTCA | 1-2-1-7-6 | CtcAaagatcaTTCTCA | 624_1 | -20.57 | 30608 |
| 624 | CTCAAAGATCATTCTCA | 1-1-1-1-1-7-2-1-2 | CtCaAagatcatTCtCA | 624_2 | -18.69 | 30608 |
| 624 | CTCAAAGATCATTCTCA | 1-1-2-7-1-2-3 | CtCAaagatcaTtcTCA | 624_3 | -19.51 | 30608 |
| 624 | CTCAAAGATCATTCTCA | 3-10-1-1-2 | CTCaaagatcattCtCA | 624_4 | -19.23 | 30608 |
| 624 | CTCAAAGATCATTCTCA | 1-1-3-8-4 | CtCAAagatcattCTCA | 624_5 | -21.26 | 30608 |
| 624 | CTCAAAGATCATTCTCA | 1-1-3-6-1-1-1-1-2 | CtCAAagatcaTtCtCA | 624_6 | -19.82 | 30608 |
| 624 | CTCAAAGATCATTCTCA | 4-7-1-3-2 | CTCAaagatcaTtctCA | 624_7 | -20.18 | 30608 |
| 624 | CTCAAAGATCATTCTCA | 1-2-2-7-5 | CtcAAagatcatTCTCA | 624_8 | -20.16 | 30608 |
| 624 | CTCAAAGATCATTCTCA | 1-1-2-8-2-1-2 | CtCAaagatcatTCtCA | 624_9 | -19.83 | 30608 |
| 624 | CTCAAAGATCATTCTCA | 3-10-4 | CTCaaagatcattCTCA | 624_10 | -21.11 | 30608 |
| 625 | TACACTTAATTATACTTCCA | 1-2-1-1-1-7-2-3-2 | TacAcTtaattatACttcCA | 625_1 | -20.33 | 30666 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 625 | TACACTTAATTATACTTCCA | 1-2-1-2-1-6-1-4-2 | TacActTaattatActtcCA | 625_2 | -19.15 | 30666 |
| 625 | TACACTTAATTATACTTCCA | 1-4-1-7-1-1-1-2-2 | TacacTtaattatAcTtcCA | 625_3 | -19.30 | 30666 |
| 625 | TACACTTAATTATACTTCCA | 1-1-1-2-2-6-1-4-2 | TaCacTTaattatActtcCA | 625_4 | -20.71 | 30666 |
| 625 | TACACTTAATTATACTTCCA | 1-1-1-3-1-8-1-2-2 | TaCactTaattatacTtcCA | 625_5 | -20.00 | 30666 |
| 625 | TACACTTAATTATACTTCCA | 1-2-1-1-2-8-1-2-2 | TacAcTTaattatacTtcCA | 625_6 | -20.50 | 30666 |
| 625 | TACACTTAATTATACTTCCA | 1-2-1-13-3 | TacActtaattatacttCCA | 625_7 | -20.60 | 30666 |
| 625 | TACACTTAATTATACTTCCA | 1-4-1-11-3 | TacacTtaattatacttCCA | 625_8 | -20.96 | 30666 |
| 625 | TACACTTAATTATACTTCCA | 2-1-1-1-1-12-2 | TAcActtaattatacttcCA | 625_9 | -19.97 | 30666 |
| 625 | TACACTTAATTATACTTCCA | 1-1-1-2-1-7-2-3-2 | TaCacTtaattatACttcCA | 625_10 | -20.87 | 30666 |
| 625 | TACACTTAATTATACTTCCA | 1-2-1-1-2-6-1-1-1-2-2 | TacAcTTaattatAcTtcCA | 625_11 | -20.69 | 30666 |
| 625 | TACACTTAATTATACTTCCA | 1-2-1-1-1-9-1-1-3 | TacAcTtaattatacTtCCA | 625_12 | -21.63 | 30666 |
| 625 | TACACTTAATTATACTTCCA | 1-1-1-3-1-10-3 | TaCactTaattatacttCCA | 625_13 | -21.86 | 30666 |
| 625 | TACACTTAATTATACTTCCA | 2-1-2-1-1-11-2 | TAcACtTaattatacttcCA | 625_14 | -21.58 | 30666 |
| 626 | TTACACTTAATTATACTTCC | 1-3-1-1-1-7-2-2-2 | TtacAcTtaattatACttCC | 626_1 | -19.98 | 30667 |
| 626 | TTACACTTAATTATACTTCC | 1-5-1-7-1-1-1-1-2 | TtacacTtaattatAcTtCC | 626_2 | -18.96 | 30667 |
| 626 | TTACACTTAATTATACTTCC | 2-4-1-11-2 | TTacacTtaattatacttCC | 626_3 | -19.49 | 30667 |
| 626 | TTACACTTAATTATACTTCC | 1-5-1-9-4 | TtacacTtaattatacTTCC | 626_4 | -20.26 | 30667 |
| 626 | TTACACTTAATTATACTTCC | 1-1-1-3-1-8-1-2-2 | TtAcacTtaattataCttCC | 626_5 | -19.43 | 30667 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 626 | TTACACTTAATTATACTTCC | 1-1-2-2-1-7-1-3-2 | TtACacTtaattatActtCC | 626_6 | -19.72 | 30667 |
| 626 | TTACACTTAATTATACTTCC | 3-1-1-12-3 | TTAcActtaattatactTCC | 626_7 | -21.33 | 30667 |
| 626 | TTACACTTAATTATACTTCC | 1-1-1-1-1-1-1-9-1-1-2 | TtAcAcTtaattatacTtCC | 626_8 | -19.10 | 30667 |
| 626 | TTACACTTAATTATACTTCC | 1-2-2-1-1-11-2 | TtaCAcTtaattatacttCC | 626_9 | -20.49 | 30667 |
| 626 | TTACACTTAATTATACTTCC | 1-5-1-7-2-1-3 | TtacacTtaattatACtTCC | 626_10 | -20.82 | 30667 |
| 626 | TTACACTTAATTATACTTCC | 4-2-1-7-1-3-2 | TTACacTtaattatActtCC | 626_11 | -21.99 | 30667 |
| 626 | TTACACTTAATTATACTTCC | 1-1-1-1-3-8-1-2-2 | TtAcACTtaattataCttCC | 626_12 | -21.65 | 30667 |
| 626 | TTACACTTAATTATACTTCC | 2-1-2-11-4 | TTaCActtaattatacTTCC | 626_13 | -23.23 | 30667 |
| 626 | TTACACTTAATTATACTTCC | 2-2-1-1-1-9-1-1-2 | TTacAcTtaattatacTtCC | 626_14 | -20.15 | 30667 |
| 627 | TTTACACTTAATTATACTTC | 2-1-2-8-1-1-5 | TTtACacttaattAtACTTC | 627_1 | -20.02 | 30668 |
| 627 | TTTACACTTAATTATACTTC | 2-3-1-7-4-1-2 | TTtacActtaattATACtTC | 627_2 | -19.89 | 30668 |
| 627 | TTTACACTTAATTATACTTC | 1-2-1-1-1-7-2-1-4 | TttAcActtaattATaCTTC | 627_3 | -19.35 | 30668 |
| 627 | TTTACACTTAATTATACTTC | 1-1-3-8-3-2-2 | TtTACacttaattATActTC | 627_4 | -20.58 | 30668 |
| 627 | TTTACACTTAATTATACTTC | 3-2-1-7-3-1-3 | TTTacActtaattATAcTTC | 627_5 | -20.76 | 30668 |
| 627 | TTTACACTTAATTATACTTC | 1-3-2-7-2-2-3 | TttaCActtaattATacTTC | 627_6 | -19.58 | 30668 |
| 627 | TTTACACTTAATTATACTTC | 3-2-1-7-2-1-4 | TTTacActtaattATaCTTC | 627_7 | -21.21 | 30668 |
| 627 | TTTACACTTAATTATACTTC | 3-1-1-8-1-2-4 | TTTaCacttaattAtaCTTC | 627_8 | -20.07 | 30668 |
| 627 | TTTACACTTAATTATACTTC | 6-7-1-4-2 | TTTACActtaattAtactTC | 627_9 | -20.56 | 30668 |
| 627 | TTTACACTTAATTATACTTC | 4-1-1-7-4-1-2 | TTTAcActtaattATACtTC | 627_10 | -22.36 | 30668 |
| 627 | TTTACACTTAATTATACTTC | 3-1-1-1-1-6-3-1-3 | TTTaCaCttaattATAcTTC | 627_11 | -22.29 | 30668 |
| 627 | TTTACACTTAATTATACTTC | 2-1-3-7-3-2-2 | TTtACActtaattATActTC | 627_12 | -21.19 | 30668 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 627 | TTTACACTTAATTATACTTC | 3-1-2-7-2-1-4 | TTTaCActtaattATaCTTC | 627_13 | -23.30 | 30668 |
| 627 | TTTACACTTAATTATACTTC | 1-1-4-7-1-2-4 | TtTACActtaattAtaCTTC | 627_14 | -21.94 | 30668 |
| 628 | ATTTACACTTAATTATACTT | 2-1-1-2-1-6-3-1-3 | ATtTacActtaatTATaCTT | 628_1 | -21.21 | 30669 |
| 628 | ATTTACACTTAATTATACTT | 3-1-1-8-2-1-4 | ATTtAcacttaatTAtACTT | 628_2 | -20.27 | 30669 |
| 628 | ATTTACACTTAATTATACTT | 1-1-2-2-1-6-4-1-2 | AtTTacActtaatTATAcTT | 628_3 | -20.33 | 30669 |
| 628 | ATTTACACTTAATTATACTT | 1-3-1-1-1-7-6 | AtttAcActtaattATACTT | 628_4 | -19.30 | 30669 |
| 628 | ATTTACACTTAATTATACTT | 2-2-2-7-3-2-2 | ATttACacttaatTATacTT | 628_5 | -19.94 | 30669 |
| 628 | ATTTACACTTAATTATACTT | 4-1-2-6-2-3-2 | ATTTaCActtaatTAtacTT | 628_6 | -21.29 | 30669 |
| 628 | ATTTACACTTAATTATACTT | 1-1-4-7-1-1-1-2-2 | AtTTACacttaatTaTacTT | 628_7 | -19.33 | 30669 |
| 628 | ATTTACACTTAATTATACTT | 2-2-3-6-1-2-4 | ATttACActtaatTatACTT | 628_8 | -20.97 | 30669 |
| 628 | ATTTACACTTAATTATACTT | 4-2-1-6-1-3-3 | ATTTacActtaatTataCTT | 628_9 | -19.73 | 30669 |
| 628 | ATTTACACTTAATTATACTT | 1-1-2-1-2-6-4-1-2 | AtTTaCActtaatTATAcTT | 628_10 | -22.43 | 30669 |
| 628 | ATTTACACTTAATTATACTT | 3-2-2-6-2-2-3 | ATTtaCActtaatTAtaCTT | 628_11 | -21.72 | 30669 |
| 628 | ATTTACACTTAATTATACTT | 1-2-4-6-2-2-3 | AttTACActtaatTAtaCTT | 628_12 | -22.02 | 30669 |
| 628 | ATTTACACTTAATTATACTT | 2-1-1-1-2-6-1-1-5 | ATtTaCActtaatTaTACTT | 628_13 | -23.00 | 30669 |
| 628 | ATTTACACTTAATTATACTT | 5-8-1-1-1-1-3 | ATTTAcacttaatTaTaCTT | 628_14 | -21.68 | 30669 |
| 629 | TTCTACTATACTTTCCTCT | 1-3-1-7-1-1-1-2-2 | TtctActatactTtCctCT | 629_1 | -21.04 | 30711 |
| 629 | TTCTACTATACTTTCCTCT | 1-11-1-1-1-2-2 | TtctactatactTtCctCT | 629_2 | -20.85 | 30711 |
| 629 | TTCTACTATACTTTCCTCT | 1-11-1-2-1-1-2 | TtctactatactTtcCtCT | 629_3 | -20.97 | 30711 |
| 629 | TTCTACTATACTTTCCTCT | 1-1-1-9-1-4-2 | TtCtactatactTtcctCT | 629_4 | -21.06 | 30711 |
| 629 | TTCTACTATACTTTCCTCT | 1-1-1-11-1-2-2 | TtCtactatactttCctCT | 629_5 | -21.53 | 30711 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 629 | TTCTACTATACTTTCCTCT | 1-3-1-9-1-2-2 | TtctActatactttCctCT | 629_6 | -20.74 | 30711 |
| 629 | TTCTACTATACTTTCCTCT | 1-4-1-8-1-2-2 | TtctaCtatactttCctCT | 629_7 | -21.54 | 30711 |
| 629 | TTCTACTATACTTTCCTCT | 1-13-1-2-2 | TtctactatactttCctCT | 629_8 | -20.55 | 30711 |
| 629 | TTCTACTATACTTTCCTCT | 1-1-1-12-1-1-2 | TtCtactatactttcCtCT | 629_9 | -21.65 | 30711 |
| 629 | TTCTACTATACTTTCCTCT | 1-3-1-10-1-1-2 | TtctActatactttcCtCT | 629_10 | -20.86 | 30711 |
| 629 | TTCTACTATACTTTCCTCT | 1-14-1-1-2 | TtctactatactttcCtCT | 629_11 | -20.67 | 30711 |
| 629 | TTCTACTATACTTTCCTCT | 1-1-1-1-1-7-1-1-1-2-2 | TtCtActatactTtCctCT | 629_12 | -22.02 | 30711 |
| 629 | TTCTACTATACTTTCCTCT | 1-1-1-2-1-8-1-2-2 | TtCtaCtatactttCctCT | 629_13 | -22.52 | 30711 |
| 629 | TTCTACTATACTTTCCTCT | 1-3-2-8-1-2-2 | TtctACtatactttCctCT | 629_14 | -22.14 | 30711 |
| 629 | TTCTACTATACTTTCCTCT | 1-1-1-1-1-10-1-1-2 | TtCtActatactttcCtCT | 629_15 | -21.84 | 30711 |
| 629 | TTCTACTATACTTTCCTCT | 1-1-1-2-1-9-1-1-2 | TtCtaCtatactttcCtCT | 629_16 | -22.64 | 30711 |
| 630 | GTTCTACTATACTTTCCTC | 1-12-1-1-1-1-2 | GttctactatactTtCcTC | 630_1 | -20.78 | 30712 |
| 630 | GTTCTACTATACTTTCCTC | 1-4-1-9-1-1-2 | GttctActatactttCcTC | 630_2 | -20.67 | 30712 |
| 630 | GTTCTACTATACTTTCCTC | 1-14-1-1-2 | GttctactatactttCcTC | 630_3 | -20.48 | 30712 |
| 631 | GTTCTACTATACTTTCCT | 1-2-1-1-1-7-1-2-2 | GttCtactatactTtcCT | 631_1 | -20.25 | 30713 |
| 631 | GTTCTACTATACTTTCCT | 1-2-1-9-1-2-2 | GttCtactatactTtcCT | 631_2 | -20.06 | 30713 |
| 631 | GTTCTACTATACTTTCCT | 1-2-1-11-3 | GttCtactatactttCCT | 631_3 | -22.13 | 30713 |
| 631 | GTTCTACTATACTTTCCT | 1-4-1-9-3 | GttctActatactttCCT | 631_4 | -21.34 | 30713 |
| 631 | GTTCTACTATACTTTCCT | 1-14-3 | GttctactatactttCCT | 631_5 | -21.15 | 30713 |
| 631 | GTTCTACTATACTTTCCT | 2-1-1-1-1-10-2 | GTtCtActatactttcCT | 631_6 | -21.50 | 30713 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 631 | GTTCTACTATACTTTCCT | 2-1-1-12-2 | GTtCtactatactttcCT | 631_7 | -21.30 | 30713 |
| 631 | GTTCTACTATACTTTCCT | 1-2-1-1-1-10-2 | GttCtActatactttcCT | 631_8 | -19.95 | 30713 |
| 631 | GTTCTACTATACTTTCCT | 1-2-1-12-2 | GttCtactatactttcCT | 631_9 | -19.76 | 30713 |
| 631 | GTTCTACTATACTTTCCT | 1-15-2 | GttctactatactttcCT | 631_10 | -18.78 | 30713 |
| 631 | GTTCTACTATACTTTCCT | 1-2-1-9-1-1-3 | GttCtactatactTtCCT | 631_11 | -22.43 | 30713 |
| 631 | GTTCTACTATACTTTCCT | 2-1-1-1-1-7-1-2-2 | GTtCtActatactTtcCT | 631_12 | -21.80 | 30713 |
| 631 | GTTCTACTATACTTTCCT | 1-2-2-8-1-2-2 | GttCTactatactTtcCT | 631_13 | -21.68 | 30713 |
| 631 | GTTCTACTATACTTTCCT | 1-2-1-1-1-9-3 | GttCtActatactttCCT | 631_14 | -22.32 | 30713 |
| 631 | GTTCTACTATACTTTCCT | 1-2-3-10-2 | GttCTActatactttcCT | 631_15 | -22.60 | 30713 |
| 632 | AGTTCTACTATACTTTCC | 1-12-1-2-2 | AgttctactatacTttCC | 632_1 | -19.37 | 30714 |
| 632 | AGTTCTACTATACTTTCC | 1-13-1-1-2 | AgttctactatactTtCC | 632_2 | -19.16 | 30714 |
| 632 | AGTTCTACTATACTTTCC | 1-1-1-13-2 | AgTtctactatactttCC | 632_3 | -19.51 | 30714 |
| 632 | AGTTCTACTATACTTTCC | 1-15-2 | AgttctactatactttCC | 632_4 | -18.86 | 30714 |
| 632 | AGTTCTACTATACTTTCC | 1-1-1-10-1-2-2 | AgTtctactatacTttCC | 632_5 | -20.03 | 30714 |
| 632 | AGTTCTACTATACTTTCC | 1-4-1-7-1-2-2 | AgttcTactatacTttCC | 632_6 | -20.31 | 30714 |
| 632 | AGTTCTACTATACTTTCC | 2-14-2 | AGttctactatactttCC | 632_7 | -20.26 | 30714 |
| 632 | AGTTCTACTATACTTTCC | 1-2-1-12-2 | AgtTctactatactttCC | 632_8 | -19.23 | 30714 |
| 632 | AGTTCTACTATACTTTCC | 1-4-1-10-2 | AgttcTactatactttCC | 632_9 | -19.80 | 30714 |
| 632 | AGTTCTACTATACTTTCC | 2-10-1-3-2 | AGttctactataCtttCC | 632_10 | -21.25 | 30714 |
| 632 | AGTTCTACTATACTTTCC | 1-4-1-6-1-3-2 | AgttcTactataCtttCC | 632_11 | -20.79 | 30714 |
| 632 | AGTTCTACTATACTTTCC | 1-4-1-7-2-1-2 | AgttcTactatacTTtCC | 632_12 | -21.13 | 30714 |
| 632 | AGTTCTACTATACTTTCC | 1-1-1-11-1-1-2 | AgTtctactatactTtCC | 632_13 | -19.82 | 30714 |
| 632 | AGTTCTACTATACTTTCC | 1-3-1-11-2 | AgttCtactatactttCC | 632_14 | -19.83 | 30714 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 633 | CAACATTATTAACCACCTTA | 1-13-3-1-2 | CaacattattaaccACCtTA | 633_1 | -22.44 | 33376 |
| 633 | CAACATTATTAACCACCTTA | 4-10-1-2-3 | CAACattattaaccAccTTA | 633_2 | -22.98 | 33376 |
| 633 | CAACATTATTAACCACCTTA | 2-2-1-10-1-1-3 | CAacAttattaaccaCcTTA | 633_3 | -21.97 | 33376 |
| 633 | CAACATTATTAACCACCTTA | 1-4-2-8-1-2-2 | CaacaTTattaaccaCctTA | 633_4 | -21.08 | 33376 |
| 633 | CAACATTATTAACCACCTTA | 1-1-2-11-1-2-2 | CaACattattaaccaCctTA | 633_5 | -20.90 | 33376 |
| 633 | CAACATTATTAACCACCTTA | 1-2-2-13-2 | CaaCattattaaccacctTA | 633_6 | -20.76 | 33376 |
| 633 | CAACATTATTAACCACCTTA | 1-1-1-1-1-11-1-1-2 | CaAcAttattaaccacCtTA | 633_7 | -19.97 | 33376 |
| 633 | CAACATTATTAACCACCTTA | 1-15-4 | CaacattattaaccacCTTA | 633_8 | -21.21 | 33376 |
| 633 | CAACATTATTAACCACCTTA | 2-4-1-11-2 | CAacatTattaaccacctTA | 633_9 | -20.83 | 33376 |
| 634 | CAACATTATTAACCACCTT | 2-10-2-3-2 | CAacattattaaCCaccTT | 634_1 | -21.86 | 33377 |
| 634 | CAACATTATTAACCACCTT | 1-14-4 | CaacattattaaccaCCTT | 634_2 | -21.36 | 3337 |
| 634 | CAACATTATTAACCACCTT | 1-1-1-11-1-1-3 | CaAcattattaaccAcCTT | 634_3 | -19.54 | 33377 |
| 634 | CAACATTATTAACCACCTT | 3-1-1-11-3 | CAAcAttattaaccacCTT | 634_4 | -21.13 | 33377 |
| 634 | CAACATTATTAACCACCTT | 3-11-2-1-2 | CAAcattattaaccACcTT | 634_5 | -20.84 | 33377 |
| 634 | CAACATTATTAACCACCTT | 2-1-2-9-1-1-3 | CAaCattattaaccAcCTT | 634_6 | -22.76 | 33377 |
| 634 | CAACATTATTAACCACCTT | 2-1-2-10-1-1-2 | CAaCattattaaccaCcTT | 634_7 | -21.83 | 33377 |
| 634 | CAACATTATTAACCACCTT | 1-1-2-11-1-1-2 | CaACattattaaccaCcTT | 634_8 | -19.70 | 33377 |
| 634 | CAACATTATTAACCACCTT | 1-2-1-12-3 | CaaCattattaaccacCTT | 634_9 | -19.66 | 33377 |
| 635 | GCAACATTATTAACCACCT | 1-1-1-2-1-6-2-3-2 | GcAacAttattaACcacCT | 635_1 | -21.56 | 33378 |
| 635 | GCAACATTATTAACCACCT | 1-1-2-1-1-6-1-2-1-1-2 | GcAAcAttattaAccAcCT | 635_2 | -21.14 | 33378 |
| 635 | GCAACATTATTAACCACCT | 1-11-2-1-1-1-2 | GcaacattattaACcAcCT | 635_3 | -21.59 | 33378 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 635 | GCAACATTATTAACCACCT | 1-4-1-6-1-3-3 | GcaacAttattaAccaCCT | 635_4 | -22.69 | 33378 |
| 635 | GCAACATTATTAACCACCT | 1-1-1-1-1-7-1-4-2 | GcAaCattattaAccacCT | 635_5 | -21.01 | 33378 |
| 635 | GCAACATTATTAACCACCT | 1-11-1-1-1-2-2 | GcaacattattaAcCacCT | 635_6 | -20.83 | 33378 |
| 635 | GCAACATTATTAACCACCT | 2-3-1-6-1-4-2 | GCaacAttattaAccacCT | 635_7 | -22.63 | 33378 |
| 635 | GCAACATTATTAACCACCT | 1-1-1-12-1-1-2 | GcAacattattaaccAcCT | 635_8 | -20.05 | 33378 |
| 635 | GCAACATTATTAACCACCT | 1-2-1-1-1-11-2 | GcaAcAttattaaccacCT | 635_9 | -20.30 | 33378 |
| 636 | AGCAACATTATTAACCACC | 1-2-1-9-2-1-3 | AgcAacattattaACCACC | 636_1 | -22.13 | 33379 |
| 636 | AGCAACATTATTAACCACC | 1-11-1-1-1-2-2 | AgcaacattattAaCcaCC | 636_2 | -20.80 | 33379 |
| 636 | AGCAACATTATTAACCACC | 1-4-1-6-2-3-2 | AgcaaCattattAAccaCC | 636_3 | -21.32 | 33379 |
| 636 | AGCAACATTATTAACCACC | 1-2-2-7-1-2-1-1-2 | AgcAAcattattAacCaCC | 636_4 | -21.29 | 33379 |
| 636 | AGCAACATTATTAACCACC | 2-11-1-3-2 | AGcaacattattaAccaCC | 636_5 | -21.75 | 33379 |
| 636 | AGCAACATTATTAACCACC | 1-1-1-1-1-8-1-2-3 | AgCaAcattattaAccACC | 636_6 | -22.16 | 33379 |
| 636 | AGCAACATTATTAACCACC | 1-2-1-1-1-6-1-3-3 | AgcAaCattattAaccACC | 636_7 | -21.33 | 33379 |
| 636 | AGCAACATTATTAACCACC | 2-1-2-12-2 | AGcAAcattattaaccaCC | 636_8 | -22.02 | 33379 |
| 636 | AGCAACATTATTAACCACC | 1-15-3 | AgcaacattattaaccACC | 636_9 | -20.45 | 33379 |
| 637 | AGCAACATTATTAACCAC | 2-1-1-9-5 | AGcAacattattaACCAC | 637_1 | -21.97 | 33380 |
| 637 | AGCAACATTATTAACCAC | 1-3-1-7-6 | AgcaAcattattAACCAC | 637_2 | -21.20 | 33380 |
| 637 | AGCAACATTATTAACCAC | 2-10-2-1-3 | AGcaacattattAAcCAC | 637_3 | -19.42 | 33380 |
| 637 | AGCAACATTATTAACCAC | 1-2-1-8-1-1-4 | AgcAacattattAaCCAC | 637_4 | -19.84 | 33380 |
| 637 | AGCAACATTATTAACCAC | 3-9-3-1-2 | AGCaacattattAACCAC | 637_5 | -20.94 | 33380 |
| 637 | AGCAACATTATTAACCAC | 1-1-3-7-3-1-2 | AgCAAcattattAAcCAC | 637_6 | -20.15 | 33380 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 637 | AGCAACATTATTAACCAC | 1-1-3-7-2-1-3 | AgCAacattattAAcCAC | 637_7 | -20.96 | 33380 |
| 637 | AGCAACATTATTAACCAC | 5-7-1-3-2 | AGCAacattattAaccAC | 637_8 | -21.24 | 33380 |
| 637 | AGCAACATTATTAACCAC | 3-1-1-8-1-2-2 | AGCaAcattattaAccAC | 637_9 | -19.86 | 33380 |
| 638 | GTTTCCATCTACTATTAAT | 1-3-1-7-1-1-1-1-3 | GtttCcatctacTaTtAAT | 638_1 | -19.59 | 39806 |
| 638 | GTTTCCATCTACTATTAAT | 1-1-1-9-2-3-2 | GtTtccatctacTAttaAT | 638_2 | -19.50 | 39806 |
| 638 | GTTTCCATCTACTATTAAT | 1-4-1-6-2-2-3 | GtttcCatctacTAttAAT | 638_3 | -20.09 | 39806 |
| 638 | GTTTCCATCTACTATTAAT | 1-3-1-8-1-2-3 | GtttCcatctactAttAAT | 638_4 | -18.3 | 39806 |
| 638 | GTTTCCATCTACTATTAAT | 3-1-1-8-1-3-2 | GTTtCcatctactAttaAT | 638_5 | -20.35 | 39806 |
| 638 | GTTTCCATCTACTATTAAT | 1-2-2-12-2 | GttTCcatctactattaAT | 638_6 | -18.88 | 39806 |
| 638 | GTTTCCATCTACTATTAAT | 1-1-1-11-1-1-3 | GtTtccatctactaTtAAT | 638_7 | -18.18 | 39806 |
| 638 | GTTTCCATCTACTATTAAT | 2-2-1-10-1-1-2 | GTttCcatctactatTaAT | 638_8 | -20.16 | 39806 |
| 638 | GTTTCCATCTACTATTAAT | 1_1-1-1-2-10-3 | GtTtCCatctactattAAT | 638_9 | -20.69 | 39806 |
| 638 | GTTTCCATCTACTATTAAT | 2-2-1-7-1-3-3 | GTttCcatctacTattAAT | 638_10 | -20.69 | 39806 |
| 638 | GTTTCCATCTACTATTAAT | 1-1-1-10-2-1-3 | GtTtccatctactATtAAT | 638_11 | -19.08 | 39806 |
| 638 | GTTTCCATCTACTATTAAT | 1-3-1-8-1-1-1-1-2 | GtttCcatctactAtTaAT | 638_12 | -18.72 | 39806 |
| 638 | GTTTCCATCTACTATTAAT | 1-2-3-7-1-2-3 | GttTCcatctactAttAAT | 638_13 | -21.47 | 39806 |
| 638 | GTTTCCATCTACTATTAAT | 1-1-1-1-2-11-2 | GtTtCCatctactattaAT | 638_14 | -20.37 | 39806 |
| 639 | GTTTCCATCTACTATTAA | 1-11-2-1-3 | GtttccatctacTAtTAA | 639_1 | -19.21 | 39807 |
| 639 | GTTTCCATCTACTATTAA | 1-3-1-7-1-1-4 | GtttCcatctacTaTTAA | 639_2 | -19.80 | 39807 |
| 639 | GTTTCCATCTACTATTAA | 3-1-1-7-2-2-2 | GTTtCcatctacTAttAA | 639_3 | -20.57 | 39807 |
| 639 | GTTTCCATCTACTATTAA | 2-2-1-7-1-1-1-1-2 | GTttCcatctacTaTtAA | 639_4 | -19.07 | 39807 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 639 | GTTTCCATCTACTATTAA | 1-3-2-7-2-1-2 | GtttCCatctactATtAA | 639_5 | -19.67 | 39807 |
| 639 | GTTTCCATCTACTATTAA | 3-2-1-6-1-3-2 | GTTtcCatctacTattAA | 639_6 | -19.25 | 39807 |
| 639 | GTTTCCATCTACTATTAA | 1-1-3-8-1-2-2 | GtTTCcatctactAttAA | 639_7 | -18.04 | 39807 |
| 639 | GTTTCCATCTACTATTAA | 1-1-1-1-2-10-2 | GtTtCCatctactattAA | 639_8 | -18.62 | 39807 |
| 639 | GTTTCCATCTACTATTAA | 3-1-1-9-4 | GTTCcatctactaTTAA | 639_9 | -21.21 | 39807 |
| 639 | GTTTCCATCTACTATTAA | 1-3-2-6-2-2-2 | GtttCCatctacTAttAA | 639_10 | -20.39 | 39807 |
| 639 | GTTTCCATCTACTATTAA | 1-1-3-7-1-1-1-1-2 | GtTTCcatctacTaTtAA | 639_11 | -19.32 | 39807 |
| 639 | GTTTCCATCTACTATTAA | 2-2-1-7-1-2-3 | GTttCcatctacTatTAA | 639_12 | -20.39 | 39807 |
| 639 | GTTTCCATCTACTATTAA | 2-2-1-8-2-1-2 | GTttCcatctactATtAA | 639_13 | -19.03 | 39807 |
| 639 | GTTTCCATCTACTATTAA | 1-1-1-1-2-8-4 | GtTtCCatctactaTTAA | 639_14 | -21.34 | 39807 |
| 640 | TGTTTCCATCTACTATTA | 1-1-1-11-1-1-2 | TgTttccatctactAtTA | 640_1 | -18.41 | 39808 |
| 640 | TGTTTCCATCTACTATTA | 1-2-1-9-2-1-2 | TgtTtccatctacTAtTA | 640_2 | -20.03 | 39808 |
| 640 | TGTTTCCATCTACTATTA | 1-4-1-7-1-2-2 | TgtttCcatctacTatTA | 640_3 | -19.37 | 39808 |
| 640 | TGTTTCCATCTACTATTA | 1-4-1-8-4 | TgtttCcatctactATTA | 640_4 | -20.28 | 39808 |
| 640 | TGTTTCCATCTACTATTA | 1-4-1-8-1-1-2 | TgtttCcatctactAtTA | 640_5 | -18.52 | 39808 |
| 640 | TGTTTCCATCTACTATTA | 1-1-2-1-1-10-2 | TgTTtCcatctactatTA | 640_6 | -19.89 | 39808 |
| 640 | TGTTTCCATCTACTATTA | 1-4-1-9-3 | TgtttCcatctactaTTA | 640_7 | -19.37 | 39808 |
| 640 | TGTTTCCATCTACTATTA | 1-2-1-1-1-10-2 | TgtTtccatctactatTA | 640_8 | -18.73 | 39808 |
| 640 | TGTTTCCATCTACTATTA | 1-4-1-10-2 | TgtttCcatctactatTA | 640_9 | -18.42 | 39808 |
| 640 | TGTTTCCATCTACTATTA | 1-4-1-6-1-1-4 | TgtttCcatctaCtATTA | 640_10 | -21.27 | 39808 |
| 640 | TGTTTCCATCTACTATTA | 2-1-1-9-2-1-2 | TGtTtccatctacTAtTA | 640_11 | -21.24 | 39808 |
| 640 | TGTTTCCATCTACTATTA | 1-3-2-8-1-1-2 | TgttTCcatctactAtTA | 640_12 | -19.51 | 39808 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 640 | TGTTTCCATCTACTATTA | 2-1-1-1-1-10-2 | TGtTtCcatctactatTA | 640_13 | -19.94 | 39808 |
| 640 | TGTTTCCATCTACTATTA | 1-1-1-2-1-10-2 | TgTttCcatctactatTA | 640_14 | -19.08 | 39808 |
| 641 | ACTCTGCAATACACCAA | 2-1-1-8-2-1-2 | ACtCtgcaatacACCAA | 641_1 | -19.61 | 44439 |
| 641 | ACTCTGCAATACACCAA | 2-2-1-6-1-1-1-1-2 | ACtcTgcaataCaCcAA | 641_2 | -19.77 | 44439 |
| 641 | ACTCTGCAATACACCAA | 1-2-1-7-1-1-1-1-2 | ActCtgcaataCaCcAA | 641_3 | -18.35 | 44439 |
| 641 | ACTCTGCAATACACCAA | 2-1-2-6-2-2-2 | ACtCTgcaataCAccAA | 641_4 | -22.21 | 44439 |
| 641 | ACTCTGCAATACACCAA | 1-3-1-7-1-1-3 | ActcTgcaataAcCAA | 641_5 | -19.05 | 44439 |
| 641 | ACTCTGCAATACACCAA | 4-8-1-2-2 | ACTCtgcaatacAccAA | 641_6 | -20.30 | 44439 |
| 641 | ACTCTGCAATACACCAA | 2-1-2-9-3 | ACtCTgcaatacacCAA | 641_7 | -21.96 | 44439 |
| 641 | ACTCTGCAATACACCAA | 2-11-4 | ACtctgcaatacaCCAA | 641_8 | -21.68 | 44439 |
| 641 | ACTCTGCAATACACCAA | 1-1-2-10-3 | AcTCtgcaatacacCAA | 641_9 | -20.07 | 44439 |
| 642 | CTGTATACACCATCCCA | 1-10-1-1-1-1-2 | CtgtatacaccAtCcCA | 642_1 | -21.99 | 46391 |
| 642 | CTGTATACACCATCCCA | 1-10-1-3-2 | CtgtatacaccAtccCA | 642_2 | -21.22 | 46391 |
| 642 | CTGTATACACCATCCCA | 1-1-1-8-1-3-2 | CtGtatacaccAtccCA | 642_3 | -21.53 | 46391 |
| 642 | CTGTATACACCATCCCA | 1-2-1-7-1-3-2 | CtgTatacaccAtccCA | 642_4 | -22.31 | 46391 |
| 642 | CTGTATACACCATCCCA | 1-3-1-6-1-3-2 | CtgtAtacaccAtccCA | 642_5 | -21.32 | 46391 |
| 642 | CTGTATACACCATCCCA | 1-11-2-1-2 | CtgtatacaccaTCcCA | 642_6 | -23.06 | 46391 |
| 642 | CTGTATACACCATCCCA | 1-1-1-1-1-8-1-1-2 | CtGtAtacaccatCcCA | 642_7 | -22.35 | 46391 |
| 642 | CTGTATACACCATCCCA | 1-1-1-10-1-1-2 | CtGtatacaccatCcCA | 642_8 | -22.25 | 46391 |
| 642 | CTGTATACACCATCCCA | 1-2-1-9-1-1-2 | CtgTatacaccatCcCA | 642_9 | -23.02 | 46391 |
| 642 | CTGTATACACCATCCCA | 1-3-1-8-1-1-2 | CtgtAtacaccatCcCA | 642_10 | -22.04 | 46391 |
| 642 | CTGTATACACCATCCCA | 1-12-1-1-2 | CtgtatacaccatCcCA | 642_11 | -21.94 | 46391 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 642 | CTGTATACACCATCCCA | 2-2-1-10-2 | CTgtAtacaccatccCA | 642_12 | -22.95 | 46391 |
| 642 | CTGTATACACCATCCCA | 1-1-1-1-1-10-2 | CtGtAtacaccatccCA | 642_13 | -21.58 | 46391 |
| 642 | CTGTATACACCATCCCA | 1-1-1-12-2 | CtGtatacaccatccCA | 642_14 | -21.48 | 46391 |
| 642 | CTGTATACACCATCCCA | 1-2-2-10-2 | CtgTAtacaccatccCA | 642_15 | -23.39 | 46391 |
| 642 | CTGTATACACCATCCCA | 1-3-1-10-2 | CtgtAtacaccatccCA | 642_16 | -21.27 | 46391 |
| 642 | CTGTATACACCATCCCA | 1-14-2 | CtgtatacaccatccCA | 642_17 | -21.17 | 46391 |
| 642 | CTGTATACACCATCCCA | 1-3-1-6-3-1-2 | CtgtAtacaccATCcCA | 642_18 | -24.02 | 46391 |
| 642 | CTGTATACACCATCCCA | 1-1-1-8-1-1-1-1-2 | CtGtatacaccAtCcCA | 642_19 | -22.30 | 46391 |
| 642 | CTGTATACACCATCCCA | 1-1-3-6-1-3-2 | CtGTAtacaccAtccCA | 642_20 | -24.64 | 46391 |
| 642 | CTGTATACACCATCCCA | 2-2-1-8-1-1-2 | CTgtAtacaccatCcCA | 642_21 | -23.72 | 46391 |
| 642 | CTGTATACACCATCCCA | 1-3-1-9-3 | CtgtAtacaccatcCCA | 642_22 | -23.55 | 46391 |
| 643 | TCTGTATACACCATCCCA | 1-4-1-8-1-1-2 | TctgtAtacaccatCcCA | 643_1 | -22.94 | 46391 |
| 644 | TCTGTATACACCATCCC | 2-10-1-2-2 | TCtgtatacaccAtcCC | 644_1 | -22.70 | 46392 |
| 644 | TCTGTATACACCATCCC | 1-11-1-2-2 | TctgtatacaccAtcCC | 644_2 | -21.11 | 46392 |
| 644 | TCTGTATACACCATCCC | 2-1-1-11-2 | TCtGtatacaccatcCC | 644_3 | -22.96 | 46392 |
| 644 | TCTGTATACACCATCCC | 2-13-2 | TCtgtatacaccatcCC | 644_4 | -22.65 | 46392 |
| 644 | TCTGTATACACCATCCC | 3-9-1-2-2 | TCTgtatacaccAtcCC | 644_5 | -24.39 | 46392 |
| 644 | TCTGTATACACCATCCC | 2-1-1-8-1-2-2 | TCtGtatacaccAtcCC | 644_6 | -23.01 | 46392 |
| 645 | TTCTGTATACACCATCCC | 1-11-1-3-2 | TtctgtatacacCatcCC | 645_1 | -22.57 | 46392 |
| 645 | TTCTGTATACACCATCCC | 1-1-1-10-1-2-2 | TtCtgtatacaccAtcCC | 645_2 | -23.02 | 46392 |
| 645 | TTCTGTATACACCATCCC | 1-3-1-8-1-2-2 | TtctGtatacaccAtcCC | 645_3 | -22.36 | 46392 |
| 645 | TTCTGTATACACCATCCC | 1-12-1-2-2 | TtctgtatacaccAtcCC | 645_4 | -22.05 | 46392 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 645 | TTCTGTATACACCATCCC | 1-15-2 | TtctgtatacaccatcCC | 645_5 | -22.00 | 46392 |
| 645 | TTCTGTATACACCATCCC | 1-4-1-6-2-2-2 | TtctgTatacacCAtcCC | 645_6 | -25.12 | 46392 |
| 645 | TTCTGTATACACCATCCC | 1-3-1-8-1-1-3 | TtctGtatacaccAtCCC | 645_7 | -24.73 | 46392 |
| 645 | TTCTGTATACACCATCCC | 3-10-1-2-2 | TTctgtatacaccAtcCC | 645_8 | -24.52 | 46392 |
| 645 | TTCTGTATACACCATCCC | 1-1-2-9-1-2-2 | TtCTgtatacaccAtcCC | 645_9 | -24.71 | 46392 |
| 645 | TTCTGTATACACCATCCC | 1-1-1-1-1-8-1-2-2 | TtCtGtatacaccAtcCC | 645_10 | -23.34 | 46392 |
| 646 | TTCTGTATACACCATCC | 1-10-1-3-2 | TtctgtatacaCcatCC | 646_1 | -19.96 | 46393 |
| 646 | TTCTGTATACACCATCC | 1-12-4 | TtctgtatacaccATCC | 646_2 | -21.16 | 46393 |
| 646 | TTCTGTATACACCATCC | 2-11-1-1-2 | TTctgtatacaccAtCC | 646_3 | -20.11 | 46393 |
| 646 | TTCTGTATACACCATCC | 1-2-1-9-1-1-2 | TtcTgtatacaccAtCC | 646_4 | -20.24 | 46393 |
| 646 | TTCTGTATACACCATCC | 1-3-1-8-1-1-2 | TtctGtatacaccAtCC | 646_5 | -19.54 | 46393 |
| 646 | TTCTGTATACACCATCC | 1-2-1-8-1-2-2 | TtcTgtatacacCatCC | 646_6 | -20.77 | 46393 |
| 646 | TTCTGTATACACCATCC | 1-12-1-1-2 | TtctgtatacaccAtCC | 646_7 | -19.23 | 46393 |
| 646 | TTCTGTATACACCATCC | 1-3-1-7-1-1-3 | TtctGtatacacCaTCC | 646_8 | -21.19 | 46393 |
| 646 | TTCTGTATACACCATCC | 1-1-1-1-1-10-2 | TtCtGtatacaccatCC | 646_9 | -20.47 | 46393 |
| 646 | TTCTGTATACACCATCC | 1-1-1-12-2 | TtCtgtatacaccatCC | 646_10 | -20.16 | 46393 |
| 646 | TTCTGTATACACCATCC | 1-1-1-11-3 | TtCtgtatacaccaTCC | 646_11 | -21.28 | 46393 |
| 646 | TTCTGTATACACCATCC | 1-3-1-9-3 | TtctGtatacaccaTCC | 646_12 | -20.61 | 46393 |
| 646 | TTCTGTATACACCATCC | 1-13-3 | TtctgtatacaccaTCC | 646_13 | -20.30 | 46393 |
| 646 | TTCTGTATACACCATCC | 3-1-1-10-2 | TTCtGtatacaccatCC | 646_14 | -21.96 | 46393 |
| 646 | TTCTGTATACACCATCC | 3-12-2 | TTCtgtatacaccatCC | 646_15 | -21.65 | 46393 |
| 646 | TTCTGTATACACCATCC | 1-1-2-11-2 | TtCTgtatacaccatCC | 646_16 | -21.84 | 46393 |
| 646 | TTCTGTATACACCATCC | 1-2-1-11-2 | TtcTgtatacaccatCC | 646_17 | -20.19 | 46393 |
| 646 | TTCTGTATACACCATCC | 1-3-1-10-2 | TtctGtatacaccatCC | 646_18 | -19.49 | 46393 |
| 646 | TTCTGTATACACCATCC | 1-14-2 | TtctgtatacaccatCC | 646_19 | -19.18 | 46393 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 646 | TTCTGTATACACCATCC | 3-8-1-3-2 | TTCtgtatacaCcatCC | 646_20 | -22.44 | 46393 |
| 646 | TTCTGTATACACCATCC | 1-3-1-6-1-3-2 | TtctGtatacaCcatCC | 646_21 | -20.27 | 46393 |
| 646 | TTCTGTATACACCATCC | 1-3-1-7-2-1-2 | TtctGtatacacCAtCC | 646_22 | -21.53 | 46393 |
| 646 | TTCTGTATACACCATCC | 1-1-1-9-1-2-2 | TtCtgtatacacCatCC | 646_23 | -20.74 | 46393 |
| 646 | TTCTGTATACACCATCC | 1-1-1-10-1-1-2 | TtCtgtatacaccAtCC | 646_24 | -20.21 | 46393 |
| 647 | AGCTTTTAACCAGAGT | 2-10-4 | AGcttttaaccaGAGT | 647_1 | -21.73 | EX-EX |
| 648 | AGCTTTTAACCAGAGTG | 2-11-4 | AGcttttaaccagAGTG | 648_1 | -22.27 | EX-EX |
| 649 | AGCTTTTAACCAGAGTGG | 1-14-3 | AgcttttaaccagagTGG | 649_1 | -21.63 | EX-EX |
| 650 | AGCTTTTAACCAGAGTGGC | 1-16-2 | AgcttttaaccagagtgGC | 650_1 | -23.20 | EX-EX |
| 651 | AGCTTTTAACCAGAGTGGCA | 1-17-2 | AgcttttaaccagagtggCA | 651_1 | -24.11 | EX-EX |
| 652 | CAGCTTTTAACCAGAGT | 2-12-3 | CAgcttttaaccagAGT | 652_1 | -21.65 | EX-EX |
| 653 | CAGCTTTTAACCAGAGTG | 3-13-2 | CAGcttttaaccagagTG | 653_1 | -22.27 | EX-EX |
| 654 | CAGCTTTTAACCAGAGTGG | 1-15-3 | CagcttttaaccagagTGG | 654_1 | -22.97 | EX-EX |
| 655 | CAGCTTTTAACCAGAGTGGC | 1-17-2 | CagcttttaaccagagtgGC | 655_1 | -24.53 | EX-EX |
| 656 | CTTTTAACCAGAGTG | 4-7-4 | CTTTtaaccagAGTG | 656_1 | -20.12 | EX-EX |
| 657 | CTTTTAACCAGAGTGG | 4-9-3 | CTTTtaaccagagTGG | 657_1 | -20.92 | EX-EX |
| 658 | CTTTTAACCAGAGTGGC | 4-11-2 | CTTTtaaccagagtgGC | 658_1 | -22.48 | EX-EX |
| 659 | CTTTTAACCAGAGTGGCA | 1-14-3 | CttttaaccagagtgGCA | 659_1 | -22.96 | EX-EX |
| 660 | CTTTTAACCAGAGTGGCAT | 3-13-3 | CTTtaaccagagtggCAT | 660_1 | -24.65 | EX-EX |
| 661 | CTTTTAACCAGAGTGGCATC | 2-16-2 | CTtttaaccagagtggcaTC | 661_1 | -23.19 | EX-EX |
| 662 | GCTTTTAACCAGAGT | 3-9-3 | GCTtttaaccagAGT | 662_1 | -21.02 | EX-EX |
| 663 | GCTTTTAACCAGAGTG | 4-10-2 | GCTTtttaaccagagTG | 663_1 | -21.02 | EX-EX |
| 664 | GCTTTTAACCAGAGTGG | 1-12-4 | GcttttaaccagaGTGG | 664_1 | -22.24 | EX-EX |
| 665 | GCTTTTAACCAGAGTGGC | 1-14-3 | GcttttaaccagagtGGC | 665_1 | -23.42 | EX-EX |
| 666 | GCTTTTAACCAGAGTGGCA | 1-16-2 | GcttttaaccagagtggCA | 666_1 | -22.94 | EX-EX |
| 667 | GCTTTTAACCAGAGTGGCAT | 1-16-3 | GcttttaaccagagtggCAT | 667_1 | -25.01 | EX-EX |
| 668 | TCAGCTTTTAACCAGAGT | 2-13-3 | TCagcttttaaccagAGT | 668_1 | -22.18 | EX-EX |
| 669 | TCAGCTTTTAACCAGAGTG | 2-14-3 | TCagcttttaaccagaGTG | 669_1 | -23.15 | EX-EX |
| 670 | TCAGCTTTTAACCAGAGTGG | 2-16-2 | TCagcttttaaccagagtGG | 670_1 | -23.41 | EX-EX |
| 671 | TTCAGCTTTTAACCAGAGT | 2-14-3 | TTcagcttttaaccagAGT | 671_1 | -22.72 | EX-EX |
| 672 | TTCAGCTTTTAACCAGAGTG | 2-15-3 | TTcagcttttaaccagaGTG | 672_1 | -23.69 | EX-EX |
| 673 | TTTCAGCTTTTAACCAGAGT | 2-15-3 | TTtcagcttttaaccagAGT | 673_1 | -23.66 | EX-EX |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 674 | TTTTAACCAGAGTGGC | 1-11-4 | TtttaaccagagTGGC | 674_1 | -20.81 | EX-EX |
| 675 | TTTTAACCAGAGTGGCA | 3-11-3 | TTTtaaccagagtgGCA | 675_1 | -22.30 | EX-EX |
| 676 | TTTTAACCAGAGTGGCAT | 4-11-3 | TTTTaaccagagtggCAT | 676_1 | -23.21 | EX-EX |
| 677 | TTTTAACCAGAGTGGCATC | 4-13-2 | TTTTaaccagagtggcaTC | 677_1 | -22.57 | EX-EX |
| 678 | TTTTAACCAGAGTGGCATCC | 2-16-2 | TTttaaccagagtggcatCC | 678_1 | -24.58 | EX-EX |
| 679 | ATCAATATCTTCTCACT | 1-1-2-7-1-1-1-1-2 | AtCAatatcttCtCaCT | 679_1 | -19.16 | 5782 |
| 679 | ATCAATATCTTCTCACT | 5-6-1-2-3 | ATCAatatcttCtcACT | 679_2 | -21.49 | 5782 |
| 679 | ATCAATATCTTCTCACT | 1-1-1-1-1-7-5 | AtCaAtatcttcTCACT | 679_3 | -20.18 | 5782 |
| 679 | ATCAATATCTTCTCACT | 1-1-3-8-4 | AtCAAtatcttctCACT | 679_4 | -20.66 | 5782 |
| 679 | ATCAATATCTTCTCACT | 3-10-1-1-2 | ATCaatatcttctCaCT | 679_5 | -18.62 | 5782 |
| 680 | TATCAATATCTTCTCACT | 2-2-1-7-1-1-1-1-2 | TAtcAatatcttCtCaCT | 680_1 | -19.31 | 5782 |
| 680 | TATCAATATCTTCTCACT | 1-1-2-8-1-1-1-1-2 | TaTCaatatcttCtCaCT | 680_2 | -19.89 | 5782 |
| 680 | TATCAATATCTTCTCACT | 1-2-3-6-1-2-3 | TatCAatatcttCtcACT | 680_3 | -20.66 | 5782 |
| 680 | TATCAATATCTTCTCACT | 1-2-3-7-2-1-2 | TatCAatatcttcTCaCT | 680_4 | -20.99 | 5782 |
| 680 | TATCAATATCTTCTCACT | 2-1-1-10-4 | TAtCaatatcttctCACT | 680_5 | -20.89 | 5782 |
| 681 | TATCAATATCTTCTCAC | 4-7-2-1-3 | TATCaatatctTCtCAC | 681_1 | -21.30 | 5783 |
| 681 | TATCAATATCTTCTCAC | 1-2-2-6-2-1-3 | TatCAatatctTCtCAC | 681_2 | -19.73 | 5783 |
| 681 | TATCAATATCTTCTCAC | 2-1-1-8-5 | TAtCaatatcttCTCAC | 681_3 | -20.26 | 5783 |
| 681 | TATCAATATCTTCTCAC | 1-1-3-7-5 | TaTCAatatcttCTCAC | 681_4 | -21.74 | 5783 |
| 681 | TATCAATATCTTCTCAC | 5-9-3 | TATCAatatcttctCAC | 681_5 | -20.83 | 5783 |
| 682 | TTATCAATATCTTCTCAC | 1-1-1-1-2-6-2-2-2 | TtAtCAatatctTCtcAC | 682_1 | -18.32 | 5783 |
| 682 | TTATCAATATCTTCTCAC | 1-3-1-8-5 | TtatCaatatcttCTCAC | 682_2 | -19.71 | 5783 |
| 682 | TTATCAATATCTTCTCAC | 3-10-1-1-3 | TTAtcaatatcttCtCAC | 682_3 | -19.53 | 5783 |
| 682 | TTATCAATATCTTCTCAC | 2-1-2-8-1-1-3 | TTaTCaatatcttCtCAC | 682_4 | -20.20 | 5783 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 682 | TTATCAATATCTTCTCAC | 1-2-3-9-3 | TtaTCAatatcttctCAC | 682_5 | -19.47 | 5783 |
| 683 | TTATCAATATCTTCTCACT | 1-1-1-1-8-1-1-1-2 | TtAtCaatatcttCtCaCT | 683_1 | -19.45 | 5782 |
| 683 | TTATCAATATCTTCTCACT | 1-3-1-8-1-1-1-1-2 | TtatCaatatcttCtCaCT | 683_2 | -19.35 | 5782 |
| 683 | TTATCAATATCTTCTCACT | 1-1-1-1-8-1-2-3 | TtAtCaatatcttCtcACT | 683_3 | -19.33 | 5782 |
| 683 | TTATCAATATCTTCTCACT | 1-1-1-2-1-7-1-3-2 | TtAtcAatatcttCtcaCT | 683_4 | -18.18 | 5782 |
| 683 | TTATCAATATCTTCTCACT | 1-1-1-2-1-9-4 | TtAtcAatatcttctCACT | 683_5 | -19.84 | 5782 |
| 684 | ACCTTTCTTTAACCCTTT | 2-1-1-8-2-1-3 | ACcTttctttaaCCcTTT | 684_1 | -25.24 | 8113 |
| 684 | ACCTTTCTTTAACCCTTT | 2-10-1-1-1-1-2 | ACctttctttaaCcCtTT | 684_2 | -22.31 | 8113 |
| 684 | ACCTTTCTTTAACCCTTT | 1-1-1-9-1-1-1-1-2 | AcCtttctttaaCcCtTT | 684_3 | -22.01 | 8113 |
| 684 | ACCTTTCTTTAACCCTTT | 1-1-1-1-1-9-1-1-2 | AcCtTtctttaaccCtTT | 684_4 | -21.53 | 8113 |
| 684 | ACCTTTCTTTAACCCTTT | 1-1-1-11-1-1-2 | AcCtttctttaaccCtTT | 684_5 | -21.23 | 8113 |
| 685 | TACCTTTCTTTAACCCTTT | 1-2-1-8-1-1-1-2-2 | TacCtttctttaAcCctTT | 685_1 | -22.44 | 8113 |
| 685 | TACCTTTCTTTAACCCTTT | 1-2-1-1-1-7-1-1-1-2 | TacCtTtctttaaCcCtTT | 685_2 | -23.32 | 8113 |
| 685 | TACCTTTCTTTAACCCTTT | 2-1-1-10-1-1-3 | TAcCtttctttaacCcTTT | 685_3 | -24.28 | 8113 |
| 685 | TACCTTTCTTTAACCCTTT | 1-1-1-12-1-1-2 | TaCctttctttaaccCtTT | 685_4 | -22.13 | 8113 |
| 685 | TACCTTTCTTTAACCCTTT | 1-2-1-11-1-1-2 | TacCtttctttaaccCtTT | 685_5 | -22.23 | 8113 |
| 686 | ATACCTTTCTTTAACCC | 1-2-1-7-1-1-1-1-2 | AtaCctttcttTaAcCC | 686_1 | -20.53 | 8116 |
| 686 | ATACCTTTCTTTAACCC | 1-3-1-6-1-3-2 | AtacCtttcttTaacCC | 686_2 | -20.21 | 8116 |
| 686 | ATACCTTTCTTTAACCC | 2-2-1-7-2-1-2 | ATacCtttctttAAcCC | 686_3 | -21.89 | 8116 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 686 | ATACCTTTCTTTAACCC | 1-1-1-1-1-8-1-1-2 | AtAcCtttctttaAcCC | 686_4 | -20.10 | 8116 |
| 686 | ATACCTTTCTTTAACCC | 1-2-1-10-3 | AtaCctttctttaaCCC | 686_5 | -21.76 | 8116 |
| 687 | ATACCTTTCTTTAACCCTT | 1-3-2-6-1-2-4 | AtacCTttctttAacCCTT | 687_1 | -26.10 | 8114 |
| 687 | ATACCTTTCTTTAACCCTT | 1-1-1-1-1-8-1-1-1-1-2 | AtAcCtttctttaAcCcTT | 687_2 | -22.23 | 8114 |
| 687 | ATACCTTTCTTTAACCCTT | 1-2-1-9-1-1-1-2 | AtaCctttctttaAcCcTT | 687_3 | -21.93 | 8114 |
| 687 | ATACCTTTCTTTAACCCTT | 1-2-1-1-1-8-2-1-2 | AtaCcTttctttaaCCcTT | 687_4 | -24.41 | 8114 |
| 687 | ATACCTTTCTTTAACCCTT | 1-3-1-11-3 | AtacCtttctttaaccCTT | 687_5 | -22.51 | 8114 |
| 688 | ATACCTTTCTTTAACCCTTT | 1-3-1-8-1-1-1-2-2 | AtacCtttctttaAcCctTT | 688_1 | -22.83 | 8113 |
| 688 | ATACCTTTCTTTAACCCTTT | 1-3-1-9-1-1-1-1-2 | AtacCtttctttaaCcCtTT | 688_2 | -23.41 | 8113 |
| 688 | ATACCTTTCTTTAACCCTTT | 1-4-2-7-1-2-3 | AtaccTTtctttaaCccTTT | 688_3 | -23.98 | 8113 |
| 688 | ATACCTTTCTTTAACCCTTT | 1-1-1-1-1-10-1-1-3 | AtAcCtttctttaaccCcTTT | 688_4 | -23.63 | 8113 |
| 688 | ATACCTTTCTTTAACCCTTT | 1-2-1-12-1-1-2 | AtaCctttctttaaccCtTT | 688_5 | -22.52 | 8113 |
| 689 | ATACCTTTCTTTAACCCT | 1-3-2-6-2-2-2 | AtacCTttctttAAccCT | 689_1 | -22.61 | 8115 |
| 689 | ATACCTTTCTTTAACCCT | 1-1-1-1-2-8-1-1-2 | AtAcCTttctttaaCcCT | 689_2 | -22.85 | 8115 |
| 689 | ATACCTTTCTTTAACCCT | 1-2-1-10-1-1-2 | AtaCctttctttaaCcCT | 689_3 | -21.36 | 8115 |
| 689 | ATACCTTTCTTTAACCCT | 1-2-3-10-2 | AtaCCTttctttaaccCT | 689_4 | -24.26 | 8115 |
| 689 | ATACCTTTCTTTAACCCT | 1-3-1-11-2 | AtacCtttctttaaccCT | 689_5 | -20.69 | 8115 |
| 690 | TATACCTTTCTTTAACCCT | 2-2-1-10-1-1-2 | TAtaCctttctttaaCcCT | 690_1 | -23.60 | 8115 |
| 690 | TATACCTTTCTTTAACCCT | 1-4-1-9-1-1-2 | TatacCtttctttaaCcCT | 690_2 | -22.57 | 8115 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 690 | TATACCTTTCTTTAACCCT | 2-3-1-11-2 | TAtacCtttctttaaccCT | 690_3 | -22.92 | 8115 |
| 690 | TATACCTTTCTTTAACCCT | 1-3-1-12-2 | TataCctttctttaaccCT | 690_4 | -21.68 | 8115 |
| 690 | TATACCTTTCTTTAACCCT | 1-4-1-11-2 | TatacCtttctttaaccCT | 690_5 | -21.79 | 8115 |
| 691 | TTATACCTTTCTTTAAC | 4-7-2-2-2 | TTATaccttcTTtaAC | 691_1 | -18.49 | 8118 |
| 691 | TTATACCTTTCTTTAAC | 3-8-1-1-4 | TTAtaccttcTtTAAC | 691_2 | -18.07 | 8118 |
| 692 | TTATACCTTTCTTTAACCC | 2-10-1-1-1-2-2 | TTataccttctTtAacCC | 692_1 | -21.94 | 8116 |
| 692 | TTATACCTTTCTTTAACCC | 1-1-1-9-1-4-2 | TtAtaccttctTtaacCC | 692_2 | -20.68 | 8116 |
| 692 | TTATACCTTTCTTTAACCC | 1-4-1-7-1-3-2 | TtataCcttctttTaacCC | 692_3 | -21.79 | 8116 |
| 692 | TTATACCTTTCTTTAACCC | 1-3-2-8-2-1-2 | TtatACcttctttAAcCC | 692_4 | -22.39 | 8116 |
| 692 | TTATACCTTTCTTTAACCC | 1-1-1-2-1-9-1-1-2 | TtAtaCcttctttaAcCC | 692_5 | -21.58 | 8116 |
| 693 | TTATACCTTTCTTTAACC | 2-3-1-6-1-3-2 | TTataCcttctTtaaCC | 693_1 | -19.80 | 8117 |
| 693 | TTATACCTTTCTTTAACC | 1-1-1-1-2-6-1-3-2 | TtAtACcttctTtaaCC | 693_2 | -19.25 | 8117 |
| 693 | TTATACCTTTCTTTAACC | 1-3-2-7-2-1-2 | TtatACcttctttTAaCC | 693_3 | -20.74 | 8117 |
| 693 | TTATACCTTTCTTTAACC | 1-1-1-2-1-7-1-2-2 | TtAtaCcttctttTaaCC | 693_4 | -19.08 | 8117 |
| 693 | TTATACCTTTCTTTAACC | 1-2-1-1-1-8-4 | TtaTaCcttctctttAACC | 693_5 | -20.26 | 8117 |
| 694 | TTTATACCTTTCTTTAACC | 2-1-1-8-2-3-2 | TTtAtaccttcTTtaaCC | 694_1 | -20.72 | 8117 |
| 694 | TTTATACCTTTCTTTAACC | 1-4-1-6-1-2-4 | TttatAccttcTttAACC | 694_2 | -20.33 | 8117 |
| 694 | TTTATACCTTTCTTTAACC | 2-11-1-1-1-1-2 | TTtataccttctTtAaCC | 694_3 | -19.72 | 8117 |
| 694 | TTTATACCTTTCTTTAACC | 1-1-2-9-1-3-2 | TtTAtaccttctTtaaCC | 694_4 | -20.65 | 8117 |
| 694 | TTTATACCTTTCTTTAACC | 1-3-2-7-1-3-2 | TttaTAccttctTtaaCC | 694_5 | -20.88 | 8117 |
| 695 | TTTATACCTTTCTTTAAC | 3-9-3-1-2 | TTTatacctttcTTTAAC | 695_1 | -18.74 | 8118 |
| 695 | TTTATACCTTTCTTTAAC | 5-7-2-2-2 | TTTTAccttcTTaAC | 695_2 | -20.31 | 8118 |
| 695 | TTTATACCTTTCTTTAAC | 1-1-3-7-2-2-2 | TtTATaccttcTTtaAC | 695_3 | -18.98 | 8118 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 695 | TTTATACCTTTCTTTAAC | 4-8-1-1-4 | TTTAtacctttcTtTAAC | 695_4 | -19.89 | 8118 |
| 695 | TTTATACCTTTCTTTAAC | 2-3-1-7-5 | TTtatAcctttctTTAAC | 695_5 | -18.02 | 8118 |
| 696 | TTTTATACCTTTCTTTAAC | 2-3-1-6-3-2-2 | TTttaTacctttCTTtaAC | 696_1 | -19.79 | 8118 |
| 696 | TTTTATACCTTTCTTTAAC | 1-1-2-8-2-1-1-1-2 | TtTTatacctttCTtTaAC | 696_2 | -19.57 | 8118 |
| 696 | TTTTATACCTTTCTTTAAC | 2-1-2-7-2-2-3 | TTtTAtacctttCTttAAC | 696_3 | -20.28 | 8118 |
| 696 | TTTTATACCTTTCTTTAAC | 3-9-1-1-5 | TTTtatacctttCtTTAAC | 696_4 | -20.62 | 8118 |
| 696 | TTTTATACCTTTCTTTAAC | 1-1-3-7-1-1-1-2-2 | TtTTatacctttCtTtaAC | 696_5 | -19.08 | 8118 |
| 697 | TGTACTTTCCTTTACCA | 2-9-1-3-2 | TGtactttcctTtacCA | 697_1 | -20.68 | 11462 |
| 697 | TGTACTTTCCTTTACCA | 1-2-1-7-1-3-2 | TgtActttcctTtacCA | 697_2 | -19.66 | 11462 |
| 697 | TGTACTTTCCTTTACCA | 1-3-1-6-1-3-2 | TgtaCtttcctTtacCA | 697_3 | -20.46 | 11462 |
| 697 | TGTACTTTCCTTTACCA | 2-2-1-8-1-1-2 | TGtaCtttcctttAcCA | 697_4 | -21.56 | 11462 |
| 697 | TGTACTTTCCTTTACCA | 1-3-1-9-3 | TgtaCtttcctttaCCA | 697_5 | -22.54 | 11462 |
| 698 | TTATACACCATCATTAT | 4-7-3-1-2 | TTATacaccatCATtAT | 698_1 | -21.13 | 11506 |
| 698 | TTATACACCATCATTAT | 4-7-2-1-3 | TTATacaccatCAtTAT | 698_2 | -21.64 | 11506 |
| 698 | TTATACACCATCATTAT | 3-8-1-1-4 | TTAtacaccatCaTTAT | 698_3 | -19.45 | 11506 |
| 698 | TTATACACCATCATTAT | 2-1-2-7-5 | TTaTAcaccatcATTAT | 698_4 | -20.61 | 11506 |
| 698 | TTATACACCATCATTAT | 5-9-3 | TTATAcaccatcatTAT | 698_5 | -20.74 | 11506 |
| 699 | TTATACACCATCATTATA | 3-2-1-6-2-2-2 | TTAtaCaccatcATtaTA | 699_1 | -19.38 | 11505 |
| 699 | TTATACACCATCATTATA | 1-2-3-6-1-1-4 | TtaTAcaccatcAtTATA | 699_2 | -20.93 | 11505 |
| 699 | TTATACACCATCATTATA | 4-1-1-7-2-1-2 | TTATaCaccatcaTTaTA | 699_3 | -21.44 | 11505 |
| 699 | TTATACACCATCATTATA | 2-1-2-8-1-1-3 | TTaTAcaccatcaTtATA | 699_4 | -19.71 | 11505 |
| 699 | TTATACACCATCATTATA | 3-2-1-8-4 | TTAtaCaccatcatTATA | 699_5 | -20.75 | 11505 |
| 700 | TTTATACACCATCATTAT | 2-1-2-7-3-1-2 | TTtATacaccatCATtAT | 700_1 | -20.67 | 11506 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 700 | TTTATACACCATCATTAT | 3-1-1-7-2-1-3 | TTTaTacaccatCAtTAT | 700_2 | -21.52 | 11506 |
| 700 | TTTATACACCATCATTAT | 1-3-2-6-2-1-3 | TttaTAcaccatCAtTAT | 700_3 | -20.70 | 11506 |
| 700 | TTTATACACCATCATTAT | 1-1-3-8-1-1-3 | TtTATacaccatcAtTAT | 700_4 | -20.05 | 11506 |
| 700 | TTTATACACCATCATTAT | 3-1-1-9-4 | TTTaTacaccatcaTTAT | 700_5 | -20.34 | 11506 |
| 701 | TTTATACACCATCATTATA | 4-8-1-1-2-1-2 | TTTAtacaccatCaTTaTA | 701_1 | -21.57 | 11505 |
| 701 | TTTATACACCATCATTATA | 2-2-1-7-1-2-4 | TTtaTacaccatCatTATA | 701_2 | -21.05 | 11505 |
| 701 | TTTATACACCATCATTATA | 1-1-1-1-1-8-2-1-3 | TtTaTacaccatcATtATA | 701_3 | -19.83 | 11505 |
| 701 | TTTATACACCATCATTATA | 2-2-2-7-2-2-2 | TTtaTAcaccatcATtaTA | 701_4 | -20.24 | 11505 |
| 701 | TTTATACACCATCATTATA | 1-1-3-10-1-1-2 | TtTATacaccatcatTaTA | 701_5 | -20.30 | 11505 |
| 702 | ATTTATACACCATCATTAT | 1-1-1-2-1-7-3-1-2 | AtTta_TacaccatCAtTAT | 702_1 | -20.07 | 11506 |
| 702 | ATTTATACACCATCATTAT | 1-1-2-1-1-7-2-2-2 | AtTTaTacaccatCAttAT | 702_2 | -20.07 | 11506 |
| 702 | ATTTATACACCATCATTAT | 2-1-2-8-1-1-1-2 | ATtTAtacaccatCaTtAT | 702_3 | -19.74 | 11506 |
| 702 | ATTTATACACCATCATTAT | 2-3-1-7-1-2-3 | ATttaTacaccatCatTAT | 702_4 | -20.07 | 11506 |
| 702 | ATTTATACACCATCATTAT | 1-1-1-1-1-10-4 | AtTtAtacaccatcaTTAT | 702_5 | -18.64 | 11506 |
| 703 | ATTTATACACCATCATTATA | 1-4-1-7-1-2-4 | AtttaTacaccatCatTATA | 703_1 | -21.05 | 11505 |
| 703 | ATTTATACACCATCATTATA | 2-1-1-2-1-7-2-2-2 | ATtTatAcaccatcATtaTA | 703_2 | -20.32 | 11505 |
| 703 | ATTTATACACCATCATTATA | 1-1-1-2-1-8-1-1-1-2 | AtTtaTacaccatcAtTaTA | 703_3 | -18.80 | 11505 |
| 703 | ATTTATACACCATCATTATA | 1-2-3-8-1-1-1-2 | AttTAtacaccatcAtTaTA | 703_4 | -21.17 | 11505 |
| 703 | ATTTATACACCATCATTATA | 3-1-1-9-1-2-3 | ATTtAtacaccatcAttATA | 703_5 | -19.97 | 11505 |
| 704 | TATTTATACACCATCATTA | 1-2-3-6-2-3-2 | TatTTAtacaccATcatTA | 704_1 | -20.37 | 11507 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 704 | TATTTATACACCATCATTA | 4-8-1-1-2-1-2 | TATTtatacaccAtCAtTA | 704_2 | -21.70 | 11507 |
| 704 | TATTTATACACCATCATTA | 1-1-1-1-1-7-1-1-1-3 | TaTtTatacaccAtCaTTA | 704_3 | -19.16 | 11507 |
| 704 | TATTTATACACCATCATTA | 2-2-1-8-2-2-2 | TAttTatacaccaTCatTA | 704_4 | -19.98 | 11507 |
| 704 | TATTTATACACCATCATTA | 2-2-1-10-4 | TAttTatacaccatcATTA | 704_5 | -19.99 | 11507 |
| 705 | TATTTATACACCATCATTAT | 2-2-1-1-1-7-2-2-2 | TAttTaTacaccatCAttAT | 705_1 | -21.49 | 11506 |
| 705 | TATTTATACACCATCATTAT | 2-1-1-10-1-1-4 | TAtTtatacaccatCaTTAT | 705_2 | -21.44 | 11506 |
| 705 | TATTTATACACCATCATTAT | 1-1-1-2-1-8-1-1-1-1-2 | TaTttAtacaccatCaTtAT | 705_3 | -18.27 | 11506 |
| 705 | TATTTATACACCATCATTAT | 2-1-2-9-1-3-2 | TAtTTatacaccatCattAT | 705_4 | -19.97 | 11506 |
| 705 | TATTTATACACCATCATTAT | 1-2-3-9-1-1-3 | TatTTAtacaccatcAtTAT | 705_5 | -21.11 | 11506 |
| 706 | TTATTTATACACCATCATTA | 2-3-1-7-1-1-1-1-3 | TTattTatacaccAtCaTTA | 706_1 | -20.54 | 11507 |
| 706 | TTATTTATACACCATCATTA | 1-1-2-1-1-7-1-2-4 | TtATtTatacaccAtcATTA | 706_2 | -20.84 | 11507 |
| 706 | TTATTTATACACCATCATTA | 1-1-1-2-1-8-2-2-2 | TtAttTatacaccaTCatTA | 706_3 | -19.52 | 11507 |
| 706 | TTATTTATACACCATCATTA | 1-2-3-8-1-1-1-1-2 | TtaTTTatacaccaTcAtTA | 706_4 | -19.96 | 11507 |
| 706 | TTATTTATACACCATCATTA | 3-1-1-11-1-1-2 | TTAtTtatacaccatcAtTA | 706_5 | -19.63 | 11507 |
| 707 | ATTATTTATACACCATCAT | 2-2-2-6-3-2-2 | ATtaTTtatacaCCAtcAT | 707_1 | -22.41 | 11509 |
| 707 | ATTATTTATACACCATCAT | 2-3-1-6-1-2-4 | ATtatTtatacaCcaTCAT | 707_2 | -21.02 | 11509 |
| 707 | ATTATTTATACACCATCAT | 1-1-1-1-1-8-3-1-2 | AtTaTttatacacCATCAT | 707_3 | -20.01 | 11509 |
| 707 | ATTATTTATACACCATCAT | 1-1-2-1-1-7-1-2-3 | AtTAtTtatacacCatCAT | 707_4 | -20.30 | 11509 |
| 707 | ATTATTTATACACCATCAT | 2-1-2-9-1-1-3 | ATtATttatacaccAtCAT | 707_5 | -20.20 | 11509 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 708 | ATTATTTATACACCATCA | 2-2-2-6-2-2-2 | ATtaTTtatacaCCatCA | 708_1 | -20.96 | 11510 |
| 708 | ATTATTTATACACCATCA | 3-1-1-7-1-1-4 | ATTaTttatacaCcATCA | 708_2 | -21.19 | 11510 |
| 708 | ATTATTTATACACCATCA | 1-1-3-7-1-3-2 | AtTATttatacaCcatCA | 708_3 | -19.39 | 11510 |
| 708 | ATTATTTATACACCATCA | 1-1-1-2-1-7-2-1-2 | AtTatTtacacCAtCA | 708_4 | -18.57 | 11510 |
| 708 | ATTATTTATACACCATCA | 2-1-2-8-1-1-3 | ATtATttatacacCaTCA | 708_5 | -19.79 | 11510 |
| 709 | ATTATTTATACACCATCATT | 1-2-3-7-1-1-2-1-2 | AttATTtatacacCaTCaTT | 709_1 | -20.97 | 11508 |
| 709 | ATTATTTATACACCATCATT | 1-1-1-2-2-6-1-4-2 | AtTatTTatacacCatcaTT | 709_2 | -19.29 | 11508 |
| 709 | ATTATTTATACACCATCATT | 1-1-1-2-1-8-2-1-3 | AtTatTtatacaccATcATT | 709_3 | -19.70 | 11508 |
| 709 | ATTATTTATACACCATCATT | 3-1-1-9-1-1-1-1-2 | ATTaTttatacaccAtCaTT | 709_4 | -20.09 | 11508 |
| 709 | ATTATTTATACACCATCATT | 2-1-2-1-1-7-1-2-3 | ATtATtTatacaccAtcATT | 709_5 | -20.67 | 11508 |
| 710 | ATTATTTATACACCATC | 5-6-3-1-2 | ATTATttatacACCaTC | 710_1 | -21.70 | 11511 |
| 710 | ATTATTTATACACCATC | 5-6-2-1-3 | ATTATttatacACcATC | 710_2 | -20.38 | 11511 |
| 710 | ATTATTTATACACCATC | 2-2-1-7-5 | ATtaTttatacaCCATC | 710_3 | -20.25 | 11511 |
| 710 | ATTATTTATACACCATC | 1-1-2-8-5 | AtTAtttatacaCCATC | 710_4 | -20.42 | 11511 |
| 710 | ATTATTTATACACCATC | 5-8-4 | ATTATttatacacCATC | 710_5 | -21.04 | 11511 |
| 711 | AATTATTTATACACCATC | 2-2-2-6-3-1-2 | AAttATttatacACCaTC | 711_1 | -18.93 | 11511 |
| 711 | AATTATTTATACACCATC | 2-1-3-6-1-1-4 | AAtTATttatacAcCATC | 711_2 | -20.18 | 11511 |
| 711 | AATTATTTATACACCATC | 4-1-1-7-5 | AATTaTttatacaCCATC | 711_3 | -22.24 | 11511 |
| 711 | AATTATTTATACACCATC | 2-1-2-8-5 | AAtTAtttatacaCCATC | 711_4 | -21.17 | 11511 |
| 711 | AATTATTTATACACCATC | 1-1-4-7-2-1-2 | AaTTATttatacaCCaTC | 711_5 | -20.58 | 11511 |
| 712 | AATTATTTATACACCATCA | 1-2-1-1-1-6-3-2-2 | AatTatttatacACCatCA | 712_1 | -20.42 | 11510 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 712 | AATTATTTATACACCATCA | 2-2-1-7-1-1-2-1-2 | AAttAtttatacAcCAtCA | 712_2 | -18.54 | 11510 |
| 712 | AATTATTTATACACCATCA | 1-1-3-7-1-2-4 | AaTTAtttatacAccATCA | 712_3 | -20.67 | 11510 |
| 712 | AATTATTTATACACCATCA | 2-1-2-8-2-1-3 | AAtTAtttatacaCCaTCA | 712_4 | -22.20 | 11510 |
| 712 | AATTATTTATACACCATCA | 3-1-1-8-1-2-3 | AATtAtttatacaCcaTCA | 712_5 | -19.50 | 11510 |
| 713 | AAATTATTTATACACCATC | 3-2-1-6-3-1-3 | AAAttAtttataCACcATC | 713_1 | -19.21 | 11511 |
| 713 | AAATTATTTATACACCATC | 1-2-3-6-3-2-2 | AaaTTAtttataCACcaTC | 713_2 | -20.01 | 11511 |
| 713 | AAATTATTTATACACCATC | 1-1-3-7-2-1-4 | AaATTatttataCAcCATC | 713_3 | -21.68 | 11511 |
| 713 | AAATTATTTATACACCATC | 2-1-2-7-1-1-2-1-2 | AAaTTatttataCaCCaTC | 713_4 | -19.63 | 11511 |
| 713 | AAATTATTTATACACCATC | 1-1-2-1-1-8-5 | AaATtAtttatacaCCATC | 713_5 | -20.67 | 11511 |
| 714 | AAATTATTTATACACCAT | 1-1-4-6-2-1-3 | AaATTAtttataCAcCAT | 714_1 | -20.31 | 11512 |
| 714 | AAATTATTTATACACCAT | 2-2-2-6-1-1-4 | AAatTAtttataCaCCAT | 714_2 | -19.59 | 11512 |
| 714 | AAATTATTTATACACCAT | 1-1-3-7-1-1-4 | AaATTatttataCaCCAT | 714_3 | -20.00 | 11512 |
| 714 | AAATTATTTATACACCAT | 4-9-5 | AAATtatttatacACCAT | 714_4 | -19.36 | 11512 |
| 714 | AAATTATTTATACACCAT | 3-1-2-7-5 | AAAtTAtttatacACCAT | 714_5 | -19.98 | 11512 |
| 715 | AAAATTATTTATACACCAT | 2-1-2-7-3-1-3 | AAaATtatttatACAcCAT | 715_1 | -19.29 | 11512 |
| 715 | AAAATTATTTATACACCAT | 1-3-2-6-2-1-4 | AaaaTTatttatACaCCAT | 715_2 | -19.68 | 11512 |
| 715 | AAAATTATTTATACACCAT | 3-2-1-6-1-1-5 | AAAatTatttatAcACCAT | 715_3 | -19.27 | 11512 |
| 715 | AAAATTATTTATACACCAT | 1-1-4-7-1-1-4 | AaAATTatttataCaCCAT | 715_4 | -20.75 | 11512 |
| 715 | AAAATTATTTATACACCAT | 2-1-2-9-5 | AAaATtatttatacACCAT | 715_5 | -19.38 | 11512 |
| 716 | TAAAATTATTTATACACC | 2-1-3-6-3-1-2 | TAaAATtatttaTACaCC | 716_1 | -18.88 | 11514 |
| 716 | TAAAATTATTTATACACC | 3-1-2-7-5 | TAAaATtatttatACACC | 716_2 | -18.95 | 11514 |
| 716 | TAAAATTATTTATACACC | 1-1-4-7-5 | TaAAATtatttatACACC | 716_3 | -18.33 | 11514 |
| 716 | TAAAATTATTTATACACC | 3-1-2-8-4 | TAAaATtatttataCACC | 716_4 | -18.35 | 11514 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 716 | TAAAATTATTTATACACC | 2-1-3-8-4 | TAaAATtatttataCACC | 716_5 | -18.35 | 11514 |
| 717 | GTAAAATTATTTATACACC | 2-1-3-6-4-1-2 | GTaAAttatttATACaCC | 717_1 | -21.68 | 11514 |
| 717 | GTAAAATTATTTATACACC | 3-2-1-6-2-2-3 | GTAaaAttatttATacACC | 717_2 | -20.00 | 11514 |
| 717 | GTAAAATTATTTATACACC | 3-1-2-7-2-1-3 | GTAaAAttattaTAcACC | 717_3 | -20.86 | 11514 |
| 717 | GTAAAATTATTTATACACC | 2-1-3-7-1-1-4 | GTaAAAttattaTaCACC | 717_4 | -21.11 | 11514 |
| 717 | GTAAAATTATTTATACACC | 4-1-1-8-5 | GTAAaAttatttatACACC | 717_5 | -21.46 | 11514 |
| 718 | GTAAAATTATTTATACAC | 4-1-1-7-5 | GTAAaAttatttaTACAC | 718_1 | -18.17 | 11515 |
| 718 | GTAAAATTATTTATACAC | 3-1-2-7-5 | GTAaAAttatttaTACAC | 718_2 | -18.17 | 11515 |
| 719 | GAGTATATTACCTCCA | 3-10-3 | GAGtatattacctCCA | 719_1 | -22.56 | 15162 |
| 719 | GAGTATATTACCTCCA | 2-1-1-9-3 | GAgTatattacctCCA | 719_2 | -22.24 | 15162 |
| 719 | GAGTATATTACCTCCA | 2-11-3 | GAgtatattacctCCA | 719_3 | -21.15 | 15162 |
| 719 | GAGTATATTACCTCCA | 1-1-3-8-3 | GaGTAtattacctCCA | 719_4 | -22.93 | 15162 |
| 719 | GAGTATATTACCTCCA | 5-9-2 | GAGTAtattacctcCA | 719_5 | -23.29 | 15162 |
| 720 | CTTTTCTATAATCTCAC | 2-2-1-6-3-1-2 | CTttTctataaTCTCAC | 720_1 | -18.54 | 30553 |
| 720 | CTTTTCTATAATCTCAC | 3-8-2-1-3 | CTTttctataaTCtCAC | 720_2 | -19.80 | 30553 |
| 720 | CTTTTCTATAATCTCAC | 1-1-3-6-1-1-4 | CtTTTctataaTcTCAC | 720_3 | -19.40 | 30553 |
| 720 | CTTTTCTATAATCTCAC | 4-8-5 | CTTTtctataatCTCAC | 720_4 | -21.37 | 30553 |
| 720 | CTTTTCTATAATCTCAC | 1-3-1-7-5 | CtttTctataatCTCAC | 720_5 | -18.92 | 30553 |
| 721 | CTTTTCTATAATCTCACA | 2-3-1-6-1-1-1-1-2 | CTtttCtataatCtCaCA | 721_1 | -20.17 | 30552 |
| 721 | CTTTTCTATAATCTCACA | 1-1-1-1-2-6-1-2-3 | CtTtTctataatCtcACA | 721_2 | -20.15 | 30552 |
| 721 | CTTTTCTATAATCTCACA | 1-2-1-1-1-7-2-1-2 | CttTtCtataatcTCaCA | 721_3 | -19.50 | 30552 |
| 721 | CTTTTCTATAATCTCACA | 1-1-3-8-1-1-3 | CtTTTctataatcTcACA | 721_4 | -19.49 | 30552 |
| 721 | CTTTTCTATAATCTCACA | 3-2-1-8-4 | CTTttCtataatctCACA | 721_5 | -21.97 | 30552 |
| 722 | TCTTTTCTATAATCTCACA | 1-1-3-7-1-1-1-1-3 | TcTTTtctataaTcTcACA | 722_1 | -21.04 | 30552 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 722 | TCTTTTCTATAATCTCACA | 1-4-1-6-1-2-1-1-2 | TctttTctataaTctCaCA | 722_2 | -18.81 | 30552 |
| 722 | TCTTTTCTATAATCTCACA | 2-2-1-8-1-2-3 | TCttTtctataatCtcACA | 722_3 | -20.68 | 30552 |
| 722 | TCTTTTCTATAATCTCACA | 2-1-1-9-1-3-2 | TCtTttctataatCtcaCA | 722_4 | -20.13 | 30552 |
| 722 | TCTTTTCTATAATCTCACA | 2-13-1-1-2 | TCttttctataatctCaCA | 722_5 | -19.52 | 30552 |
| 723 | TCTTTTCTATAATCTCAC | 2-1-1-8-2-2-2 | TCtTttctataaTCtcAC | 723_1 | -18.51 | 30553 |
| 723 | TCTTTTCTATAATCTCAC | 3-10-1-1-3 | TCTttctataatCtCAC | 723_2 | -20.36 | 30553 |
| 723 | TCTTTTCTATAATCTCAC | 1-2-3-7-1-1-3 | TctTTTctataatCtCAC | 723_3 | -19.57 | 30553 |
| 723 | TCTTTTCTATAATCTCAC | 2-2-2-8-4 | TCttTTctataatcTCAC | 723_4 | -20.57 | 30553 |
| 723 | TCTTTTCTATAATCTCAC | 1-1-4-8-4 | TcTTTTctataatcTCAC | 723_5 | -20.82 | 30553 |
| 724 | ATCTTTTCTATAATCTCACA | 1-1-1-1-9-1-1-1-1-2 | AtCtTttctataatCtCaCA | 724_1 | -20.93 | 30552 |
| 724 | ATCTTTTCTATAATCTCACA | 1-1-1-11-1-2-3 | AtCttttctataatCtcACA | 724_2 | -20.51 | 30552 |
| 724 | ATCTTTTCTATAATCTCACA | 1-2-1-1-1-8-1-2-3 | AtcTtTtctataatCtcACA | 724_3 | -20.35 | 30552 |
| 724 | ATCTTTTCTATAATCTCACA | 1-3-2-8-1-3-2 | AtctTTtctataatCtcaCA | 724_4 | -20.10 | 30552 |
| 724 | ATCTTTTCTATAATCTCACA | 1-1-1-2-1-10-1-1-2 | AtCttTtctataatctCaCA | 724_5 | -19.95 | 30552 |
| 725 | ATCTTTTCTATAATCTCAC | 1-1-1-9-1-1-1-1-3 | AtCttttctataAtCtCAC | 725_1 | -19.62 | 30553 |
| 725 | ATCTTTTCTATAATCTCAC | 1-2-2-7-1-1-1-1-3 | AtcTTttctataAtCtCAC | 725_2 | -19.97 | 30553 |
| 725 | ATCTTTTCTATAATCTCAC | 1-1-2-1-1-7-2-2-2 | AtCTtTtctataaTCtcAC | 725_3 | -19.83 | 30553 |
| 725 | ATCTTTTCTATAATCTCAC | 1-2-1-1-1-9-4 | AtcTtTtctataatcTCAC | 725_4 | -19.36 | 30553 |
| 725 | ATCTTTTCTATAATCTCAC | 3-13-3 | ATCttttctataatctCAC | 725_5 | -20.25 | 30553 |
| 726 | ATCTTTTCTATAATCTCA | 1-1-2-8-1-1-1-1-2 | AtCTtttctataAtCtCA | 726_1 | -18.77 | 30554 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 726 | ATCTTTTCTATAATCTCA | 3-1-1-7-1-2-3 | ATCtTttctataAtcTCA | 726_2 | -20.03 | 30554 |
| 726 | ATCTTTTCTATAATCTCA | 3-10-2-1-2 | ATCttttctataaTCtCA | 726_3 | -20.31 | 30554 |
| 726 | ATCTTTTCTATAATCTCA | 1-1-1-1-2-7-2-1-2 | AtCtTTtctataaTCtCA | 726_4 | -19.49 | 30554 |
| 726 | ATCTTTTCTATAATCTCA | 1-1-3-9-4 | AtCTTttctataatCTCA | 726_5 | -21.14 | 30554 |
| 727 | CATCTTTTCTATAATCTCAC | 2-11-1-1-1-2-2 | CAtcttttctataAtCtcAC | 727_1 | -19.86 | 30553 |
| 727 | CATCTTTTCTATAATCTCAC | 1-1-2-9-1-1-1-2-2 | CaTCttttctataAtCtcAC | 727_2 | -20.49 | 30553 |
| 727 | CATCTTTTCTATAATCTCAC | 1-3-1-1-1-8-1-1-3 | CatcTtTtctataatCtCAC | 727_3 | -20.97 | 30553 |
| 727 | CATCTTTTCTATAATCTCAC | 1-2-1-1-1-9-1-2-2 | CatCtTttctataatCtcAC | 727_4 | -19.35 | 30553 |
| 727 | CATCTTTTCTATAATCTCAC | 2-1-1-2-1-10-3 | CAtCttTtctataatctCAC | 727_5 | -21.92 | 30553 |
| 728 | CATCTTTTCTATAATCTCA | 1-3-1-7-2-1-1-1-2 | CatcTtttctatAAtCtCA | 728_1 | -19.26 | 30554 |
| 728 | CATCTTTTCTATAATCTCA | 2-3-1-6-2-2-3 | CAtctTttctatAAtcTCA | 728_2 | -20.74 | 30554 |
| 728 | CATCTTTTCTATAATCTCA | 1-2-1-8-1-2-1-1-2 | CatCttttctatAatCtCA | 728_3 | -19.21 | 30554 |
| 728 | CATCTTTTCTATAATCTCA | 2-1-1-1-1-9-1-1-2 | CAtCtTttctataatCtCA | 728_4 | -20.86 | 30554 |
| 728 | CATCTTTTCTATAATCTCA | 1-1-2-13-2 | CaTCttttctataatctCA | 728_5 | -19.23 | 30554 |
| 729 | TCATCTTTTCTATAATCTCA | 1-1-1-2-1-7-2-1-1-1-2 | TcAtcTtttctatAAtCtCA | 729_1 | -20.53 | 30554 |
| 729 | TCATCTTTTCTATAATCTCA | 2-4-1-6-2-3-2 | TCatctTttctatAAtctCA | 729_2 | -20.57 | 30554 |
| 729 | TCATCTTTTCTATAATCTCA | 2-2-1-8-1-2-1-1-2 | TCatCttttctatAatCtCA | 729_3 | -21.70 | 30554 |
| 729 | TCATCTTTTCTATAATCTCA | 3-13-1-1-2 | TCActtttctataatCtCA | 729_4 | -22.07 | 30554 |
| 729 | TCATCTTTTCTATAATCTCA | 3-1-1-13-2 | TCAtCttttctataatctCA | 729_5 | -22.07 | 30554 |
| 730 | TCATCTTTTCTATAATCTC | 3-2-1-7-2-2-2 | TCAtcTttctatAAtcTC | 730_1 | -20.15 | 30555 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 730 | TCATCTTTTCTATAATCTC | 3-1-1-8-1-3-2 | TCAtCttttctatAatcTC | 730_2 | -20.09 | 30555 |
| 730 | TCATCTTTTCTATAATCTC | 2-2-1-9-1-2-2 | TCatCttttctataAtcTC | 730_3 | -18.83 | 30555 |
| 730 | TCATCTTTTCTATAATCTC | 3-13-3 | TCActtttctataatCTC | 730_4 | -20.65 | 30555 |
| 730 | TCATCTTTTCTATAATCTC | 2-2-2-10-3 | TCatCTtttctataatCTC | 730_5 | -21.35 | 30555 |
| 731 | GTCATCTTTTCTATAATC | 1-1-1-2-1-6-3-1-2 | GtCatCttttctATAaTC | 731_1 | -19.76 | 30557 |
| 731 | GTCATCTTTTCTATAATC | 1-1-1-1-2-6-1-2-3 | GtCaTCttttctAtaATC | 731_2 | -19.19 | 30557 |
| 731 | GTCATCTTTTCTATAATC | 4-9-1-2-2 | GTCAtcttttctaTaaTC | 731_3 | -20.42 | 30557 |
| 731 | GTCATCTTTTCTATAATC | 3-2-1-8-4 | GTCatCttttctatAATC | 731_4 | -20.51 | 30557 |
| 731 | GTCATCTTTTCTATAATC | 1-1-4-10-2 | GtCATCttttctataaTC | 731_5 | -20.23 | 30557 |
| 732 | TGTCATCTTTTCTATAAT | 2-1-1-8-2-1-3 | TGtCatcttttcTAtAAT | 732_1 | -19.36 | 30558 |
| 732 | TGTCATCTTTTCTATAAT | 2-1-2-7-2-2-2 | TGtCAtctttttcTAtaAT | 732_2 | -20.51 | 30558 |
| 732 | TGTCATCTTTTCTATAAT | 1-1-3-7-1-3-2 | TgTCAtctttttcTataAT | 732_3 | -19.51 | 30558 |
| 732 | TGTCATCTTTTCTATAAT | 4-10-4 | TGTCatcttttctaTAAT | 732_4 | -21.42 | 30558 |
| 732 | TGTCATCTTTTCTATAAT | 2-2-1-9-4 | TGtcAtctttttctaTAAT | 732_5 | -18.57 | 30558 |
| 733 | ACTTAATTATACTTCCA | 5-6-2-2-2 | ACTTAattataCTtcCA | 733_1 | -21.55 | 30664 |
| 733 | ACTTAATTATACTTCCA | 2-1-2-6-1-2-3 | ACtTAattataCttCCA | 733_2 | -21.02 | 30664 |
| 733 | ACTTAATTATACTTCCA | 1-2-2-7-5 | ActTAattatacTTCCA | 733_3 | -20.65 | 30664 |
| 733 | ACTTAATTATACTTCCA | 4-8-1-1-3 | ACTTaattatacTtCCA | 733_4 | -21.09 | 30664 |
| 733 | ACTTAATTATACTTCCA | 1-1-1-1-1-8-4 | AcTtAattatactTCCA | 733_5 | -18.37 | 30664 |
| 734 | CACTTAATTATACTTCC | 2-1-2-6-2-2-2 | CAcTTaattatACttCC | 734_1 | -20.10 | 30665 |
| 734 | CACTTAATTATACTTCC | 5-6-1-2-3 | CACTTaattatActTCC | 734_2 | -21.76 | 30665 |
| 734 | CACTTAATTATACTTCC | 1-1-1-1-1-7-2-1-2 | CaCtTaattataCTtCC | 734_3 | -19.09 | 30665 |
| 734 | CACTTAATTATACTTCC | 1-1-3-7-1-1-3 | CaCTTaattatactCtCC | 734_4 | -20.59 | 30665 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 734 | CACTTAATTATACTTCC | 2-1-2-8-4 | CAcTTaattatacTTCC | 734_5 | -20.52 | 30665 |
| 735 | CACTTAATTATACTTCCA | 2-2-1-7-2-1-3 | CActTaattataCTtCCA | 735_1 | -22.96 | 30664 |
| 735 | CACTTAATTATACTTCCA | 2-1-1-1-1-6-1-3-2 | CAcTtAattataCttcCA | 735_2 | -19.31 | 30664 |
| 735 | CACTTAATTATACTTCCA | 1-1-3-8-1-1-3 | CaCTTaattatacTtCCA | 735_3 | -22.43 | 30664 |
| 735 | CACTTAATTATACTTCCA | 1-1-1-1-2-7-1-2-2 | CaCtTAattatacTtcCA | 735_4 | -19.51 | 30664 |
| 735 | CACTTAATTATACTTCCA | 2-2-1-9-4 | CActTaattatactTCCA | 735_5 | -21.76 | 30664 |
| 736 | ACACTTAATTATACTTCCA | 1-1-2-1-1-6-2-3-2 | AcACtTaattatACttcCA | 736_1 | -20.93 | 30664 |
| 736 | ACACTTAATTATACTTCCA | 2-2-1-7-1-1-1-2-2 | ACacTtaattatAcTtcCA | 736_2 | -19.38 | 30664 |
| 736 | ACACTTAATTATACTTCCA | 1-1-1-1-1-8-1-2-3 | AcAcTtaattataCttCCA | 736_3 | -21.10 | 30664 |
| 736 | ACACTTAATTATACTTCCA | 1-1-1-2-1-9-4 | AcActTaattatactTCCA | 736_4 | -21.31 | 30664 |
| 736 | ACACTTAATTATACTTCCA | 2-2-2-11-2 | ACacTTaattatacttcCA | 736_5 | -19.91 | 30664 |
| 737 | ACACTTAATTATACTTCC | 1-3-1-7-2-1-3 | AcacTtaattatACtTCC | 737_1 | -19.24 | 30665 |
| 737 | ACACTTAATTATACTTCC | 1-1-1-1-2-6-2-2-2 | AcAcTTaattatACttCC | 737_2 | -19.64 | 30665 |
| 737 | ACACTTAATTATACTTCC | 2-1-2-7-1-1-1-1-2 | ACaCTtaattatAcTtCC | 737_3 | -20.12 | 30665 |
| 737 | ACACTTAATTATACTTCC | 3-2-1-8-4 | ACActTaattatacTTCC | 737_4 | -21.53 | 30665 |
| 737 | ACACTTAATTATACTTCC | 1-1-2-1-1-9-3 | AcACtTaattatactTCC | 737_5 | -19.40 | 30665 |
| 738 | ACACTTAATTATACTTC | 5-7-5 | ACACTtaattatACTTC | 738_1 | -20.47 | 30666 |
| 738 | ACACTTAATTATACTTC | 3-1-1-7-5 | ACAcTtaattatACTTC | 738_2 | -18.40 | 30666 |
| 738 | ACACTTAATTATACTTC | 2-1-2-7-5 | ACaCTtaattatACTTC | 738_3 | -18.51 | 30666 |
| 738 | ACACTTAATTATACTTC | 5-7-2-1-2 | ACACTtaattatACtTC | 738_4 | -18.77 | 30666 |
| 738 | ACACTTAATTATACTTC | 5-7-1-1-3 | ACACTtaattatAcTTC | 738_5 | -18.40 | 30666 |
| 738 | ACACTTAATTATACTTC | 5-8-4 | ACACTtaattataCTTC | 738_6 | -19.88 | 30666 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 739 | TACACTTAATTATACTTCC | 3-2-1-7-2-2-2 | TACacTtaattatACttCC | 739_1 | -21.57 | 30665 |
| 739 | TACACTTAATTATACTTCC | 1-4-1-7-1-1-4 | TacacTtaattatAcTTCC | 739_2 | -19.87 | 30665 |
| 739 | TACACTTAATTATACTTCC | 1-2-3-8-1-2-2 | TacACTtaattataCttCC | 739_3 | -20.88 | 30665 |
| 739 | TACACTTAATTATACTTCC | 4-11-4 | TACActtaattatacTTCC | 739_4 | -23.04 | 30665 |
| 739 | TACACTTAATTATACTTCC | 2-1-1-1-1-10-3 | TAcAcTtaattatactTCC | 739_5 | -20.03 | 30665 |
| 740 | TACACTTAATTATACTTC | 4-1-1-7-5 | TACAcTtaattatACTTC | 740_1 | -20.63 | 30666 |
| 740 | TACACTTAATTATACTTC | 3-1-2-7-5 | TACaCTtaattatACTTC | 740_2 | -20.74 | 30666 |
| 740 | TACACTTAATTATACTTC | 2-1-3-7-5 | TAcACTtaattatACTTC | 740_3 | -20.21 | 30666 |
| 740 | TACACTTAATTATACTTC | 3-1-2-8-4 | TACaCTtaattataCTTC | 740_4 | -20.14 | 30666 |
| 740 | TACACTTAATTATACTTC | 1-1-4-8-4 | TaCACTtaattataCTTC | 740_5 | -20.48 | 30666 |
| 741 | TTACACTTAATTATACTTC | 2-1-2-7-4-1-2 | TTaCActtaattATACtTC | 741_ | -21.41 | 30666 |
| 741 | TTACACTTAATTATACTTC | 5-7-3-1-3 | TTACActtaattATAcTTC | 741_2 | -22.67 | 30666 |
| 741 | TTACACTTAATTATACTTC | 4-1-1-6-2-1-4 | TTACaCttaattATaCTTC | 741_3 | -22.54 | 30666 |
| 741 | TTACACTTAATTATACTTC | 2-1-2-7-2-1-4 | TTaCActtaattATaCTTC | 741_4 | -21.48 | 30666 |
| 741 | TTACACTTAATTATACTTC | 5-7-1-1-5 | TTACActtaattAtACTTC | 741_5 | -22.04 | 30666 |
| 742 | TTACACTTAATTATACTT | 5-7-3-1-2 | TTACActtaattATAcTT | 742_1 | -20.18 | 30667 |
| 742 | TTACACTTAATTATACTT | 5-7-2-1-3 | TTACActtaattATaCTT | 742_2 | -20.62 | 30667 |
| 742 | TTACACTTAATTATACTT | 5-7-1-1-4 | TTACActtaattAtACTT | 742_3 | -19.54 | 30667 |
| 743 | TTTACACTTAATTATACTT | 4-1-1-6-4-1-2 | TTTAcActtaatTATAcTT | 743_1 | -21.26 | 30667 |
| 743 | TTTACACTTAATTATACTT | 3-1-2-6-3-1-3 | TTTaCActtaatTATaCTT | 743_2 | -22.57 | 30667 |
| 743 | TTTACACTTAATTATACTT | 4-8-2-1-4 | TTTAcacttaatTAtACTT | 743_3 | -20.48 | 30667 |
| 743 | TTTACACTTAATTATACTT | 1-1-4-6-2-2-3 | TtTACActtaatTAtaCTT | 743_4 | -21.20 | 30667 |
| 743 | TTTACACTTAATTATACTT | 2-2-2-6-1-1-5 | TTtaCActtaatTaTACTT | 743_5 | -21.02 | 30667 |
| 744 | TTTACACTTAATTATACT | 3-1-2-6-3-1-2 | TTTaCActtaatTATaCT | 744_1 | -20.75 | 30668 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 744 | TTTACACTTAATTATACT | 1-1-4-6-3-1-2 | TtTACActtaatTATaCT | 744_2 | -21.06 | 30668 |
| 744 | TTTACACTTAATTATACT | 2-1-3-6-2-1-3 | TTtACActtaatTAtACT | 744_3 | -19.03 | 30668 |
| 744 | TTTACACTTAATTATACT | 4-8-1-1-4 | TTTAcacttaatTaTACT | 744_4 | -19.42 | 30668 |
| 744 | TTTACACTTAATTATACT | 1-1-1-1-2-6-1-1-4 | TtTaCActtaatTaTACT | 744_5 | -19.12 | 30668 |
| 745 | ATTTACACTTAATTATACT | 4-1-1-6-4-1-2 | ATTTaCacttaaTTATaCT | 745_1 | -22.20 | 30668 |
| 745 | ATTTACACTTAATTATACT | 2-1-3-6-3-1-3 | ATtTACacttaaTTAtACT | 745_2 | -21.43 | 30668 |
| 745 | ATTTACACTTAATTATACT | 5-7-2-1-4 | ATTTAcacttaaTTaTACT | 745_3 | -22.44 | 30668 |
| 745 | ATTTACACTTAATTATACT | 1-2-3-6-2-1-4 | AttTACacttaaTTaTACT | 745_4 | -20.95 | 30668 |
| 745 | ATTTACACTTAATTATACT | 3-1-2-6-1-1-5 | ATTtACacttaaTtATACT | 745_5 | -20.92 | 30668 |
| 746 | ATTTACACTTAATTATAC | 5-8-5 | ATTTAcacttaatTATAC | 746_1 | -19.94 | 30669 |
| 746 | ATTTACACTTAATTATAC | 4-1-1-7-5 | ATTTaCacttaatTATAC | 746_2 | -19.40 | 30669 |
| 746 | ATTTACACTTAATTATAC | 2-1-3-7-5 | ATtTACacttaatTATAC | 746_3 | -19.70 | 30669 |
| 747 | AATTTACACTTAATTATAC | 3-1-2-6-3-1-3 | AATtTAcacttaATTaTAC | 747_1 | -19.51 | 30669 |
| 747 | AATTTACACTTAATTATAC | 1-1-4-6-3-1-3 | AaTTTAcacttaATTaTAC | 747_2 | -19.51 | 30669 |
| 747 | AATTTACACTTAATTATAC | 4-8-2-1-4 | AATTtacacttaATtATAC | 747_3 | -18.04 | 30669 |
| 747 | AATTTACACTTAATTATAC | 5-7-1-1-5 | AATTTacacttaAtTATAC | 747_4 | -19.79 | 30669 |
| 747 | AATTTACACTTAATTATAC | 2-1-3-6-1-1-5 | AAtTTAcacttaAtTATAC | 747_5 | -19.26 | 30669 |
| 748 | AATTTACACTTAATTATACT | 3-2-2-6-4-1-2 | AATttACacttaaTTATaCT | 748_1 | -21.50 | 30668 |
| 748 | AATTTACACTTAATTATACT | 5-1-1-6-3-1-3 | AATTTaCacttaaTTAtACT | 748_2 | -21.87 | 30668 |
| 748 | AATTTACACTTAATTATACT | 3-1-3-6-2-1-4 | AATtTACacttaaTTaTACT | 748_3 | -22.95 | 30668 |
| 748 | AATTTACACTTAATTATACT | 1-1-4-7-2-1-1-2 | AaTTTAcacttaaTTaTaCT | 748_4 | -20.23 | 30668 |
| 748 | AATTTACACTTAATTATACT | 2-1-2-1-6-1-1-5 | AAtTTaCacttaaTtATACT | 748_5 | -20.55 | 30668 |
| 749 | TAATTTACACTTAATTATAC | 2-1-4-6-4-1-2 | TAaTTTAcacttaATTAtAC | 749_1 | -20.98 | 30669 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 749 | TAATTTACACTTAATTATAC | 5-8-3-1-3 | TAATTtacacttaATTaTAC | 749_2 | -20.60 | 30669 |
| 749 | TAATTTACACTTAATTATAC | 2-2-3-6-3-1-3 | TAatTTAcacttaATTaTAC | 749_3 | -20.80 | 30669 |
| 749 | TAATTTACACTTAATTATAC | 4-1-2-6-2-1-4 | TAATtTAcacttaATtATAC | 749_4 | -21.41 | 30669 |
| 749 | TAATTTACACTTAATTATAC | 1-1-1-1-2-7-1-1-5 | TaAtTTacacttaAtTATAC | 749_5 | -18.92 | 30669 |
| 750 | TAATTTACACTTAATTAT | 5-8-5 | TAATTtacacttaATTAT | 750_1 | -18.27 | 30671 |
| 750 | TAATTTACACTTAATTAT | 4-1-1-7-5 | TAATtTacacttaATTAT | 750_2 | -18.18 | 30671 |
| 750 | TAATTTACACTTAATTAT | 2-1-3-7-5 | TAaTTTacacttaATTAT | 750_3 | -18.18 | 30671 |
| 750 | TAATTTACACTTAATTAT | 1-1-4-7-5 | TaATTTacacttaATTAT | 750_4 | -18.16 | 30671 |
| 751 | TAATTTACACTTAATTATA | 5-7-4-1-2 | TAATTtacacttAATTaTA | 751_1 | -18.87 | 30670 |
| 751 | TAATTTACACTTAATTATA | 5-7-2-1-4 | TAATTtacacttAAtTATA | 751_2 | -19.05 | 30670 |
| 751 | TAATTTACACTTAATTATA | 3-1-2-6-2-1-4 | TAAtTTacacttAAtTATA | 751_3 | -18.54 | 30670 |
| 751 | TAATTTACACTTAATTATA | 4-1-1-6-1-1-5 | TAATtTacacttAaTTATA | 751_4 | -19.40 | 30670 |
| 751 | TAATTTACACTTAATTATA | 2-1-3-6-1-1-5 | TAaTTTacacttAaTTATA | 751_5 | -19.41 | 30670 |
| 752 | TTAATTTACACTTAATTATA | 3-1-3-6-4-1-2 | TTAaTTTacacttAATTaTA | 752_1 | -20.61 | 30670 |
| 752 | TTAATTTACACTTAATTATA | 5-1-1-6-3-1-3 | TTAATtTacacttAATtATA | 752_2 | -20.28 | 30670 |
| 752 | TTAATTTACACTTAATTATA | 2-1-4-6-2-1-4 | TTaATTTacacttAAtTATA | 752_3 | -20.77 | 30670 |
| 752 | TTAATTTACACTTAATTATA | 3-2-2-6-1-1-5 | TTAatTTacacttAaTTATA | 752_4 | -20.28 | 30670 |
| 752 | TTAATTTACACTTAATTATA | 4-1-1-8-1-1-4 | TTAAtTtacacttaAtTATA | 752_5 | -18.80 | 30670 |
| 753 | TTAATTTACACTTAATTAT | 4-1-1-6-3-1-3 | TTAAtTtacactTAAtTAT | 753_1 | -18.65 | 30671 |
| 753 | TTAATTTACACTTAATTAT | 3-1-2-6-2-1-4 | TTAaTTtacactTAaTTAT | 753_2 | -19.52 | 30671 |
| 753 | TTAATTTACACTTAATTAT | 2-1-2-7-2-1-4 | TTaATttacactTAaTTAT | 753_3 | -18.68 | 30671 |
| 753 | TTAATTTACACTTAATTAT | 5-7-1-1-5 | TTAATtacactTaATTAT | 753_4 | -20.00 | 30671 |
| 753 | TTAATTTACACTTAATTAT | 2-1-3-6-1-1-5 | TTaATTtacactTaATTAT | 753_5 | -19.47 | 30671 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 754 | TTTAATTTACACTTAATTA | 3-1-2-6-3-1-3 | TTTaATttacacTTaATTA | 754_1 | -19.46 | 30672 |
| 754 | TTTAATTTACACTTAATTA | 5-7-2-1-4 | TTTAAtttacacTTaATTA | 754_2 | -19.54 | 30672 |
| 754 | TTTAATTTACACTTAATTA | 4-1-1-6-2-1-4 | TTTAaTttacacTTaATTA | 754_3 | -19.46 | 30672 |
| 754 | TTTAATTTACACTTAATTA | 1-1-1-1-2-6-2-1-4 | TtTaATttacacTTaATTA | 754_4 | -18.11 | 30672 |
| 754 | TTTAATTTACACTTAATTA | 1-1-4-7-3-1-2 | TtTAATttacactTAAtTA | 754_5 | -18.02 | 30672 |
| 755 | TTTAATTTACACTTAATTAT | 4-1-2-6-3-1-3 | TTTAaTTtacactTAAtTAT | 755_1 | -20.90 | 30671 |
| 755 | TTTAATTTACACTTAATTAT | 3-1-2-7-2-1-4 | TTTaATttacactTAaTTAT | 755_2 | -20.50 | 30671 |
| 755 | TTTAATTTACACTTAATTAT | 1-1-5-6-2-1-4 | TtTAATTtacactTAaTTAT | 755_3 | -21.34 | 30671 |
| 755 | TTTAATTTACACTTAATTAT | 5-8-1-1-5 | TTTAAtttacactTaATTAT | 755_4 | -20.58 | 30671 |
| 755 | TTTAATTTACACTTAATTAT | 2-2-3-6-1-1-5 | TTtaATTtacactTaATTAT | 755_5 | -20.05 | 30671 |
| 756 | ATTTAATTTACACTTAATTA | 5-1-1-6-4-1-2 | ATTTAaTttacacTTAAtTA | 756_1 | -21.11 | 30672 |
| 756 | ATTTAATTTACACTTAATTA | 3-2-2-6-3-1-3 | ATTtaATttacacTTaATTA | 756_2 | -20.29 | 30672 |
| 756 | ATTTAATTTACACTTAATTA | 4-1-2-6-2-1-4 | ATTTaATttacacTTaATTA | 756_3 | -21.50 | 30672 |
| 756 | ATTTAATTTACACTTAATTA | 2-1-4-6-2-2-3 | ATtTAATttacacTTaaTTA | 756_4 | -20.39 | 30672 |
| 756 | ATTTAATTTACACTTAATTA | 2-1-4-8-5 | ATtTAATttacacttAATTA | 756_5 | -20.08 | 30672 |
| 757 | ATTTAATTTACACTTAATT | 5-7-3-1-3 | ATTTAatttacaCTTaATT | 757_1 | -20.52 | 30673 |
| 757 | ATTTAATTTACACTTAATT | 4-1-1-7-2-1-3 | ATTTaAtttacacTTaATT | 757_2 | -18.02 | 30673 |
| 757 | ATTTAATTTACACTTAATT | 2-1-3-7-2-1-3 | ATtTAAtttacacTTaATT | 757_3 | -18.04 | 30673 |
| 757 | ATTTAATTTACACTTAATT | 4-1-1-8-5 | ATTTaAtttacactTAATT | 757_4 | -18.34 | 30673 |
| 757 | ATTTAATTTACACTTAATT | 2-1-3-8-5 | ATtTAAtttacactTAATT | 757_5 | -18.37 | 30673 |
| 758 | TATTTAATTTACACTTAAT | 3-1-2-6-4-1-2 | TATtTAatttacACTTaAT | 758_1 | -20.16 | 30674 |
| 758 | TATTTAATTTACACTTAAT | 2-1-3-6-2-1-4 | TAtTTAatttacACtTAAT | 758_2 | -19.37 | 30674 |
| 758 | TATTTAATTTACACTTAAT | 1-1-4-6-2-1-4 | TaTTTAatttacACtTAAT | 758_3 | -19.19 | 30674 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 758 | TATTTAATTTACACTTAAT | 3-1-2-6-1-1-5 | TATtTAatttacAcTTAAT | 758_4 | -19.44 | 30674 |
| 758 | TATTTAATTTACACTTAAT | 2-1-3-6-1-1-5 | TAtTTAatttacAcTTAAT | 758_5 | -19.00 | 30674 |
| 759 | TATTTAATTTACACTTAATT | 2-1-4-6-4-1-2 | TAtTTAAttacaCTTAaTT | 759_1 | -21.54 | 30673 |
| 759 | TATTTAATTTACACTTAATT | 5-1-1-6-3-1-3 | TATTTaAtttacaCTTaATT | 759_2 | -21.92 | 30673 |
| 759 | TATTTAATTTACACTTAATT | 4-1-2-7-3-1-2 | TATTtAAtttacacTTAaTT | 759_3 | -19.35 | 30673 |
| 759 | TATTTAATTTACACTTAATT | 3-1-3-7-2-1-3 | TATtTAAtttacacTTaATT | 759_4 | -20.28 | 30673 |
| 759 | TATTTAATTTACACTTAATT | 2-1-4-8-5 | TAtTTAAtttacactTAATT | 759_5 | -20.16 | 30673 |
| 760 | CTATTTAATTTACACTT | 5-6-1-1-4 | CTATTtaatttAcACTT | 760_1 | -19.07 | 30677 |
| 760 | CTATTTAATTTACACTT | 5-7-5 | CTATTtaatttaCACTT | 760_2 | -20.97 | 30677 |
| 760 | CTATTTAATTTACACTT | 2-2-1-7-5 | CTatTtaatttaCACTT | 760_3 | -18.08 | 30677 |
| 760 | CTATTTAATTTACACTT | 5-7-2-1-2 | CTATTtaatttaCAcTT | 760_4 | -18.90 | 30677 |
| 760 | CTATTTAATTTACACTT | 5-7-1-1-3 | CTATTtaatttaCaCTT | 760_5 | -19.01 | 30677 |
| 761 | CTATTTAATTTACACTTAA | 2-1-3-6-4-1-2 | CTaTTTaatttaCACTtAA | 761_1 | -20.98 | 30675 |
| 761 | CTATTTAATTTACACTTAA | 3-1-2-6-3-1-3 | CTAtTTaatttaCACtTAA | 761_2 | -21.73 | 30675 |
| 761 | CTATTTAATTTACACTTAA | 4-1-1-6-2-1-4 | CTATtTaatttaCAcTTAA | 761_3 | -21.80 | 30675 |
| 761 | CTATTTAATTTACACTTAA | 5-7-2-2-3 | CTATTtaatttaCActTAA | 761_4 | -20.86 | 30675 |
| 761 | CTATTTAATTTACACTTAA | 2-1-3-6-1-1-5 | CTaTTTaatttaCaCTTAA | 761_5 | -21.29 | 30675 |
| 762 | CTATTTAATTTACACTTA | 5-7-3-1-2 | CTATTtaatttaCACtTA | 762_1 | -21.50 | 30676 |
| 762 | CTATTTAATTTACACTTA | 3-2-1-6-3-1-2 | CTAttTaatttaCACtTA | 762_2 | -20.17 | 30676 |
| 762 | CTATTTAATTTACACTTA | 3-1-1-7-2-1-3 | CTAtTaatttaCAcTTA | 762_3 | -19.37 | 30676 |
| 762 | CTATTTAATTTACACTTA | 2-1-3-6-2-1-3 | CTaTTTaatttaCAcTTA | 762_4 | -20.43 | 30676 |
| 762 | CTATTTAATTTACACTTA | 2-1-3-6-1-1-4 | CTaTTTaatttaCaCTTA | 762_5 | -20.54 | 30676 |
| 763 | CTATTTAATTTACACTTAAT | 2-1-4-6-3-2-2 | CTaTTTAatttacACTtaAT | 763_1 | -21.79 | 30674 |
| 763 | CTATTTAATTTACACTTAAT | 4-1-2-6-2-1-4 | CTATtTAatttacACtTAAT | 763_2 | -23.29 | 30674 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Mctif | Design | Compound | CMP ID_NO | ΔG° | Start SEQ_ID NO |
|---|---|---|---|---|---|---|
| 763 | CTATTTAATTTACACTTAAT | 1-2-4-6-1-1-5 | CtaTTTAatttacAcTTAAT | 763_3 | -20.68 | 30674 |
| 763 | CTATTTAATTTACACTTAAT | 3-1-3-6-1-1-2-1-2 | CTAtTTAatttacAcTTaAT | 763_4 | -21.14 | 30674 |
| 763 | CTATTTAATTTACACTTAAT | 5-1-1-7-3-1-2 | CTATTtAatttacaCTTaAT | 763_5 | -22.14 | 30674 |
| 764 | TCTATTTAATTTACACTTA | 2-1-3-6-4-1-2 | TCtATTtaatttACACtTA | 764_1 | -21.94 | 30676 |
| 764 | TCTATTTAATTTACACTTA | 4-1-1-6-3-1-3 | TCTAtTaatttACAcTTA | 764_2 | -22.47 | 30676 |
| 764 | TCTATTTAATTTACACTTA | 3-1-2-7-2-1-3 | TCTaTTtaatttaCAcTTA | 764_3 | -21.69 | 30676 |
| 764 | TCTATTTAATTTACACTTA | 1-1-4-7-2-2-2 | TcTATTtaatttaCActTA | 764_4 | -20.33 | 30676 |
| 764 | TCTATTTAATTTACACTTA | 3-2-1-7-1-1-4 | TCTatTtaatttaCaCTTA | 764_5 | -20.85 | 30676 |
| 765 | TCTATTTAATTTACACTT | 3-2-1-6-2-1-3 | TCTatTtaatttACaCTT | 765_1 | -19.21 | 30677 |
| 765 | TCTATTTAATTTACACTT | 3-1-2-7-5 | TCTaTTtaatttaCACTT | 765_2 | -21.53 | 30677 |
| 765 | TCTATTTAATTTACACTT | 2-1-3-7-5 | TCtATTtaatttaCACTT | 765_3 | -20.81 | 30677 |
| 765 | TCTATTTAATTTACACTT | 4-1-1-7-2-1-2 | TCTAtTaatttaCAcTT | 765_4 | -19.64 | 30677 |
| 765 | TCTATTTAATTTACACTT | 1-1-4-7-2-1-2 | TcTATTtaatttaCAcTT | 765_5 | -19.12 | 30677 |
| 766 | TCTATTTAATTTACACTTAA | 2-1-2-1-1-6-3-2-2 | TCtATtTaatttaCACttAA | 766_1 | -20.25 | 30675 |
| 766 | TCTATTTAATTTACACTTAA | 4-1-1-7-2-1-4 | TCTAtTaatttaCAcTTAA | 766_2 | -22.62 | 30675 |
| 766 | TCTATTTAATTTACACTTAA | 1-1-1-1-3-6-2-2-3 | TcTaTTTaatttaCActTAA | 766_3 | -20.38 | 30675 |
| 766 | TCTATTTAATTTACACTTAA | 3-1-2-7-1-1-2-1-2 | TCTaTTtaatttaCaCTtAA | 766_4 | -20.27 | 30675 |
| 766 | TCTATTTAATTTACACTTAA | 2-3-2-6-1-1-1-1-3 | TCtatTTaatttaCaCtTAA | 766_5 | -19.51 | 30675 |
| 767 | ATCTATTTAATTTACACTT | 2-1-2-7-4-1-2 | ATcTAtttaattTACAcTT | 767_1 | -21.49 | 30677 |
| 767 | ATCTATTTAATTTACACTT | 1-1-4-6-3-1-3 | AtCTATttaattTACaCTT | 767_2 | -23.18 | 30677 |
| 767 | ATCTATTTAATTTACACTT | 4-1-1-6-2-1-4 | ATCTaTttaattTAcACTT | 767_3 | -22.64 | 30677 |
| 767 | ATCTATTTAATTTACACTT | 5-7-2-2-3 | ATCTAtttaattTAcaCTT | 767_4 | -22.78 | 30677 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 767 | ATCTATTTAATTTACACTT | 1-1-4-6-1-1-5 | AtCTATttaatttTaCACTT | 767_5 | 23.52 | 30677 |
| 768 | ATCTATTTAATTTACACTTA | 1-2-4-6-2-1-1-1-2 | AtcTATTtaatttACaCtTA | 768_1 | -21.10 | 30676 |
| 768 | ATCTATTTAATTTACACTTA | 1-1-3-1-1-6-1-1-5 | AtCTAtTtaatttAcACTTA | 768_2 | -22.17 | 30676 |
| 768 | ATCTATTTAATTTACACTTA | 3-2-2-6-1-1-2-1-2 | ATCtaTTtaatttAcACtTA | 768_3 | -20.60 | 30676 |
| 768 | ATCTATTTAATTTACACTTA | 1-1-2-1-2-7-2-2-2 | AtCTaTTtaatttaCActTA | 768_4 | -20.80 | 30676 |
| 768 | ATCTATTTAATTTACACTTA | 3-1-1-1-1-7-1-2-3 | ATCtAtTtaatttaCacTTA | 768_5 | -19.72 | 30676 |
| 769 | TATCTATTTAATTTACACTT | 1-1-2-1-2-6-4-1-2 | TaTCtATttaattTACAcTT | 769_1 | -22.65 | 30677 |
| 769 | TATCTATTTAATTTACACTT | 2-1-1-1-2-6-2-1-4 | TAtCtATttaattTAcACTT | 769_2 | -22.23 | 30677 |
| 769 | TATCTATTTAATTTACACTT | 2-1-4-6-2-3-2 | TAtCTATttaattTAcacTT | 769_3 | -22.66 | 30677 |
| 769 | TATCTATTTAATTTACACTT | 1-3-3-6-1-1-5 | TatcTATttaattTaCACTT | 769_4 | -22.96 | 30677 |
| 769 | TATCTATTTAATTTACACTT | 1-1-3-1-1-6-1-3-3 | TaTCTaTttaattTacaCTT | 769_5 | -21.15 | 30677 |
| 770 | TATCTATTTAATTTACACT | 2-1-3-6-3-1-3 | TAtCTAtttaatTTAcACT | 770_1 | -22.62 | 30678 |
| 770 | TATCTATTTAATTTACACT | 1-1-4-6-3-1-3 | TaTCTAtttaatTTAcACT | 770_2 | -22.62 | 30678 |
| 770 | TATCTATTTAATTTACACT | 2-2-2-6-2-1-4 | TAtcTAtttaatTTaCACT | 770_3 | -21.84 | 30678 |
| 770 | TATCTATTTAATTTACACT | 1-2-3-6-1-1-5 | TatCTAtttaatTtACACT | 770_4 | -21.72 | 30678 |
| 770 | TATCTATTTAATTTACACT | 4-1-1-7-2-1-3 | TATCtAtttaattTAcACT | 770_5 | -21.09 | 30678 |
| 771 | TTATCTATTTAATTTACACT | 2-4-1-6-4-1-2 | TTatctAtttaatTTACaCT | 771_1 | -20.22 | 30678 |
| 771 | TTATCTATTTAATTTACACT | 2-2-3-6-3-2-2 | TTatCTAtttaatTTAcaCT | 771_2 | -22.76 | 30678 |
| 771 | TTATCTATTTAATTTACACT | 1-1-5-6-2-2-3 | TtATCTAtttaatTTacACT | 771_3 | -22.87 | 30678 |
| 771 | TTATCTATTTAATTTACACT | 2-2-3-6-1-2-4 | TTatCTAtttaatTtaCACT | 771_4 | -22.94 | 30678 |
| 771 | TTATCTATTTAATTTACACT | 5-1-1-7-1-2-3 | TTATCtAtttaattTacACT | 771_5 | -21.68 | 30678 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 772 | TTTATCTATTTAATTTACA | 1-1-3-7-4-1-2 | TtTATctatttaATTTaCA | 772_1 | -19.96 | 30680 |
| 772 | TTTATCTATTTAATTTACA | 4-1-1-6-3-2-2 | TTTAtCtatttaATTtaCA | 772_2 | -19.70 | 30680 |
| 772 | TTTATCTATTTAATTTACA | 3-1-2-6-2-1-4 | TTTaTCtatttaATtTACA | 772_3 | -21.24 | 30680 |
| 772 | TTTATCTATTTAATTTACA | 5-7-2-2-3 | TTTATctatttaATttACA | 772_4 | -19.82 | 30680 |
| 772 | TTTATCTATTTAATTTACA | 1-1-4-6-1-1-5 | TtTATCtatttaAtTTACA | 772_5 | -21.42 | 30680 |
| 773 | TTTTATCTATTTAATTTAC | 2-1-3-6-3-1-3 | TTtTATctatttAATtTAC | 773_1 | -19.10 | 30681 |
| 773 | TTTTATCTATTTAATTTAC | 1-1-4-6-2-1-4 | TtTTATctatttAAtTTAC | 773_2 | -18.66 | 30681 |
| 773 | TTTTATCTATTTAATTTAC | 3-1-2-6-1-1-5 | TTTtATctatttAaTTTAC | 773_3 | -18.15 | 30681 |
| 773 | TTTTATCTATTTAATTTAC | 1-2-3-6-1-1-5 | TttTATctatttAaTTTAC | 773_4 | -18.29 | 30681 |
| 773 | TTTTATCTATTTAATTTAC | 2-1-3-6-1-2-4 | TTtTATctatttAatTTAC | 773_5 | -18.15 | 30681 |
| 774 | TTTTATCTATTTAATTTACA | 1-1-2-1-1-7-4-1-2 | TtTTaTctatttaATTTaCA | 774_1 | -19.84 | 30680 |
| 774 | TTTTATCTATTTAATTTACA | 2-1-1-1-2-6-3-1-3 | TTtTaTCtatttaATTtACA | 774_2 | -20.79 | 30680 |
| 774 | TTTTATCTATTTAATTTACA | 4-2-1-6-2-1-4 | TTTTatCtatttaATtTACA | 774_3 | -21.94 | 30680 |
| 774 | TTTTATCTATTTAATTTACA | 1-1-5-6-2-3-2 | TtTTATCtatttaATttaCA | 774_4 | -21.32 | 30680 |
| 774 | TTTTATCTATTTAATTTACA | 2-2-3-6-1-2-4 | TTttATCtatttaAttTACA | 774_5 | -20.67 | 30680 |
| 775 | CTTTTATCTATTTAATTTA | 5-7-4-1-2 | CTTTTatctattTAATtTA | 775_1 | -21.18 | 30682 |
| 775 | CTTTTATCTATTTAATTTA | 5-7-2-1-4 | CTTTTatctattTAaTTTA | 775_2 | -21.18 | 30682 |
| 775 | CTTTTATCTATTTAATTTA | 5-7-2-2-3 | CTTTTatctattTAatTTA | 775_3 | -20.23 | 30682 |
| 775 | CTTTTATCTATTTAATTTA | 3-1-1-7-1-1-5 | CTTtTatctattTaATTTA | 775_4 | -19.83 | 30682 |
| 775 | CTTTTATCTATTTAATTTA | 2-1-2-7-1-1-1-1-3 | CTtTTatctattTaAtTTA | 775_5 | -18.07 | 30682 |
| 776 | CTTTTATCTATTTAATTTAC | 1-1-5-6-4-1-2 | CtTTTATctatttAATTtAC | 776_1 | -21.25 | 30681 |
| 776 | CTTTTATCTATTTAATTTAC | 3-1-1-8-3-1-3 | CTTtTatctatttAATtTAC | 776_2 | -20.13 | 30681 |
| 776 | CTTTTATCTATTTAATTTAC | 5-8-2-1-4 | CTTTTatctatttAAtTTAC | 776_3 | -21.02 | 30681 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 776 | CTTTTATCTATTTAATTTAC | 1-1-2-1-2-6-2-1-4 | CtTTtATctatttAAtTTAC | 776_4 | -19.49 | 30681 |
| 776 | CTTTTATCTATTTAATTTAC | 2-1-4-6-2-2-3 | CTtTTATctatttAAttTAC | 776_5 | -21.33 | 30681 |
| 777 | ACTTTTATCTATTTAATTT | 4-1-1-6-4-1-2 | ACTTtTatctatTTAAtTT | 777_1 | -20.04 | 30683 |
| 777 | ACTTTTATCTATTTAATTT | 3-1-2-6-3-1-3 | ACTtTTatctatTTAaTTT | 777_2 | -20.48 | 30683 |
| 777 | ACTTTTATCTATTTAATTT | 5-7-2-1-4 | ACTTTtatctatTTaATTT | 777_3 | -20.54 | 30683 |
| 777 | ACTTTTATCTATTTAATTT | 2-2-2-6-2-1-4 | ACttTTatctatTTaATTT | 777_4 | -19.26 | 30683 |
| 777 | ACTTTTATCTATTTAATTT | 4-1-1-6-1-2-4 | ACTTtTatctatTtaATTT | 777_5 | -19.21 | 30683 |
| 778 | ACTTTTATCTATTTAATTTA | 2-3-1-7-4-1-2 | ACtttTatctattTAATtTA | 778_1 | -19.89 | 30682 |
| 778 | ACTTTTATCTATTTAATTTA | 1-1-4-7-2-1-1-1-2 | AcTTTTatctattTAaTtTA | 778_2 | -19.82 | 30682 |
| 778 | ACTTTTATCTATTTAATTTA | 3-2-1-7-2-2-3 | ACTttTatctattTAatTTA | 778_3 | -20.13 | 30682 |
| 778 | ACTTTTATCTATTTAATTTA | 4-9-1-1-5 | ACTTttatctattTaATTTA | 778_4 | -21.14 | 30682 |
| 778 | ACTTTTATCTATTTAATTTA | 2-1-3-7-1-1-5 | ACtTTTatctattTaATTTA | 778_5 | -21.49 | 30682 |
| 779 | ACTTTTATCTATTTAATT | 2-1-3-6-2-1-3 | ACtTTTatctatTTaATT | 779_1 | -18.25 | 30684 |
| 779 | ACTTTTATCTATTTAATT | 4-1-1-7-5 | ACTTtTatctattTAATT | 779_2 | -19.17 | 30684 |
| 779 | ACTTTTATCTATTTAATT | 3-1-2-7-5 | ACTtTTatctattTAATT | 779_3 | -19.17 | 30684 |
| 779 | ACTTTTATCTATTTAATT | 2-1-3-7-5 | ACtTTTatctattTAATT | 779_4 | -18.79 | 30684 |
| 779 | ACTTTTATCTATTTAATT | 1-1-4-7-5 | AcTTTTatctattTAATT | 779_5 | -18.42 | 30684 |
| 780 | AACTTTTATCTATTTAATT | 5-7-3-1-3 | AACTTttatctaTTTaATT | 780_1 | -19.61 | 30684 |
| 780 | AACTTTTATCTATTTAATT | 5-8-3-1-2 | AACTTttatctatTTAaTT | 780_2 | -18.68 | 30684 |
| 780 | AACTTTTATCTATTTAATT | 4-1-1-7-3-1-2 | AACTtTatctatTTAaTT | 780_3 | -18.17 | 30684 |
| 780 | AACTTTTATCTATTTAATT | 1-1-4-7-2-1-3 | AaCTTTtatctatTTaATT | 780_4 | -18.45 | 30684 |
| 780 | AACTTTTATCTATTTAATT | 5-9-5 | AACTTtatctattTAATT | 780_5 | -19.19 | 30684 |
| 781 | AACTTTTATCTATTTAAT | 5-8-5 | AACTTttatctatTTAAT | 781_1 | -18.18 | 30685 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 782 | AACTTTTATCTATTTAATTT | 1-1-1-1-3-6-4-1-2 | AaCtTTTatctatTTAAtTT | 782_1 | -19.40 | 30683 |
| 782 | AACTTTTATCTATTTAATTT | 4-2-1-6-3-1-3 | AACTttTatctatTTAaTTT | 782_2 | -20.41 | 30683 |
| 782 | AACTTTTATCTATTTAATTT | 5-1-1-6-2-1-4 | AACTTtTatctatTTaATTT | 782_3 | -21.20 | 30683 |
| 782 | AACTTTTATCTATTTAATTT | 2-1-4-6-1-2-4 | AAcTTTTatctatTtaATTT | 782_4 | -19.21 | 30683 |
| 782 | AACTTTTATCTATTTAATTT | 1-1-2-1-2-7-2-1-3 | AaCTtTTatctattTAaTTT | 782_5 | -19.40 | 30683 |
| 783 | TAACTTTTATCTATTTAAT | 2-1-3-6-4-1-2 | TAaCTTttatctATTTaAT | 783_1 | -19.91 | 30685 |
| 783 | TAACTTTTATCTATTTAAT | 2-1-3-6-2-1-4 | TAaCTTttatctATtTAAT | 783_2 | -19.93 | 30685 |
| 783 | TAACTTTTATCTATTTAAT | 5-7-2-1-1-1-2 | TAACTtttatctATtTaAT | 783_3 | -18.79 | 30685 |
| 783 | TAACTTTTATCTATTTAAT | 1-1-4-6-1-1-5 | TaACTTttatctAtTTAAT | 783_4 | -19.16 | 30685 |
| 783 | TAACTTTTATCTATTTAAT | 5-9-5 | TAACTtttatctatTTAAT | 783_5 | -19.60 | 30685 |
| 784 | TAACTTTTATCTATTTAATT | 4-1-1-7-1-1-2-1-2 | TAACtTttatctaTtTAaTT | 784_1 | -18.83 | 30684 |
| 784 | TAACTTTTATCTATTTAATT | 2-1-4-7-3-1-2 | TAaCTTTtatctatTTAaTT | 784_2 | -20.71 | 30684 |
| 784 | TAACTTTTATCTATTTAATT | 2-1-3-8-2-1-3 | TAaCTTttatctatTTAaTT | 784_3 | -19.87 | 30684 |
| 784 | TAACTTTTATCTATTTAATT | 1-1-5-7-2-1-3 | TaACTTTtatctatTTaATT | 784_ | -20.35 | 30684 |
| 784 | TAACTTTTATCTATTTAATT | 5-10-5 | TAACTtttatctattTAATT | 784_5 | -20.61 | 30684 |
| 785 | TAACTTTTATCTATTTAA | 5-7-2-1-3 | TAACTtttatctATtTAA | 785_1 | -18.07 | 30686 |
| 786 | ATAACTTTTATCTATTTAA | 3-1-2-6-4-1-2 | ATAaCTtttatcTATTtAA | 786_1 | -20.14 | 30686 |
| 786 | ATAACTTTTATCTATTTAA | 4-1-1-6-3-1-3 | ATAAcTtttatcTATtTAA | 786_2 | -20.03 | 30686 |
| 786 | ATAACTTTTATCTATTTAA | 2-1-3-6-2-1-4 | ATaACTtttatcTAtTTAA | 786_3 | -20.33 | 30686 |
| 786 | ATAACTTTTATCTATTTAA | 3-1-2-6-2-2-3 | ATAaCTtttatcTAttTAA | 786_4 | -19.84 | 30686 |
| 786 | ATAACTTTTATCTATTTAA | 5-7-1-1-5 | ATAACtttatcTaTTTAA | 786_5 | -20.30 | 30686 |
| 787 | ATAACTTTTATCTATTTAAT | 3-1-3-6-3-2-2 | ATAaCTTttatctATTtaAT | 787_1 | -20.73 | 30685 |
| 787 | ATAACTTTTATCTATTTAAT | 2-1-4-6-2-1-4 | ATaACTTttatctATtTAAT | 787_2 | -21.66 | 30685 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 787 | ATAACTTTTATCTATTTAAT | 3-1-2-7-1-2-4 | ATAaCTttTatctAttTAAT | 787_3 | -19.93 | 30685 |
| 787 | ATAACTTTTATCTATTTAAT | 4-2-1-7-3-1-2 | ATAActTttatctaTTTaAT | 787_4 | -18.98 | 30685 |
| 787 | ATAACTTTTATCTATTTAAT | 2-1-4-8-5 | ATaACTTttatctatTTAAT | 787_5 | -21.13 | 30685 |
| 788 | TATAACTTTTATCTATTTA | 1-1-2-1-1-6-4-1-2 | TaTAaCttttatCTAtTTA | 788_1 | -21.10 | 30687 |
| 788 | TATAACTTTTATCTATTTA | 2-2-2-6-3-1-3 | TAtaACttttatCTAtTTA | 788_2 | -20.60 | 30687 |
| 788 | TATAACTTTTATCTATTTA | 3-1-2-6-2-1-4 | TATaACttttatCTaTTTA | 788_3 | -22.09 | 30687 |
| 788 | TATAACTTTTATCTATTTA | 5-7-1-1-5 | TATAActtttatCtATTTA | 788_4 | -21.33 | 30687 |
| 788 | TATAACTTTTATCTATTTA | 4-1-1-7-2-2-2 | TATAaCttttatcTAttTA | 788_5 | -20.13 | 30687 |
| 789 | TATAACTTTTATCTATTTAA | 4-1-1-7-4-1-2 | TATAaCttttatcTATTtAA | 789_1 | -21.18 | 30686 |
| 789 | TATAACTTTTATCTATTTAA | 2-2-3-6-3-1-3 | TAtaACTttTatcTATtTAA | 789_2 | -21.32 | 30686 |
| 789 | TATAACTTTTATCTATTTAA | 1-1-5-6-2-1-4 | TaTAACTttTatcTAtTTAA | 789_3 | -21.97 | 30686 |
| 789 | TATAACTTTTATCTATTTAA | 3-1-2-7-1-1-1-1-3 | TATaACttttatcTaTtTAA | 789_4 | -19.86 | 30686 |
| 789 | TATAACTTTTATCTATTTAA | 4-2-1-6-1-2-4 | TATAacTtttatcTatTTAA | 789_5 | -20.09 | 30686 |
| 790 | TTATAACTTTTATCTATTT | 2-1-3-6-4-1-2 | TTaTAActtttaTCTAtTT | 790_1 | -21.00 | 30688 |
| 790 | TTATAACTTTTATCTATTT | 5-7-2-2-3 | TTATAactttaTCtaTTT | 790_2 | -20.52 | 30688 |
| 790 | TTATAACTTTTATCTATTT | 4-1-1-6-1-1-5 | TTATaActtttaTcTATTT | 790_3 | -21.08 | 30688 |
| 790 | TTATAACTTTTATCTATTT | 4-1-1-7-3-1-2 | TTATaActtttatCTAtTT | 790_4 | -20.46 | 30688 |
| 790 | TTATAACTTTTATCTATTT | 2-1-3-8-5 | TTaTAActtttatcTATTT | 790_5 | -19.98 | 30688 |
| 791 | TTATAACTTTTATCTATT | 5-7-3-1-2 | TTATAactttaTCTaTT | 791_1 | -20.32 | 30689 |
| 791 | TTATAACTTTTATCTATT | 5-7-1-1-4 | TTATAactttaTcTATT | 791_2 | -19.99 | 30689 |
| 791 | TTATAACTTTTATCTATT | 4-1-1-7-5 | TTATaActtttatCTATT | 791_3 | -20.40 | 30689 |
| 791 | TTATAACTTTTATCTATT | 4-9-5 | TTATaacttttatCTATT | 791_4 | -19.98 | 30689 |
| 791 | TTATAACTTTTATCTATT | 2-1-3-7-5 | TTaTAActtttatCTATT | 791_5 | -19.81 | 30689 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 792 | TTATAACTTTTATCTATTTA | 1-2-1-1-2-6-3-2-2 | TtaTaACttttatCTAttTA | 792_1 | −20.10 | 30687 |
| 792 | TTATAACTTTTATCTATTTA | 3-2-1-7-1-1-2-1-2 | TTAtaActtttatCtATtTA | 792_2 | −18.80 | 30687 |
| 792 | TTATAACTTTTATCTATTTA | 4-1-2-6-1-3-3 | TTATaACttttatCtatTTA | 792_3 | −21.34 | 30687 |
| 792 | TTATAACTTTTATCTATTTA | 2-1-2-1-1-7-2-1-3 | TTaTAaCttttatcTAtTTA | 792_4 | −20.83 | 30687 |
| 792 | TTATAACTTTTATCTATTTA | 1-1-4-8-1-1-4 | TtATAActtttatcTaTTTA | 792_5 | −19.94 | 30687 |
| 793 | CTTATAACTTTTATCTATT | 1-1-1-1-2-6-3-2-2 | CtTaTAacttttATCtaTT | 793_1 | −19.45 | 30689 |
| 793 | CTTATAACTTTTATCTATT | 1-2-3-6-1-1-5 | CttATAacttttAtCTATT | 793_2 | −21.25 | 30689 |
| 793 | CTTATAACTTTTATCTATT | 3-2-1-8-5 | CTTatAacttttatCTATT | 793_3 | −20.78 | 30689 |
| 793 | CTTATAACTTTTATCTATT | 1-1-3-9-2-1-2 | CtTATAacttttatCTaTT | 793_4 | −19.82 | 30689 |
| 793 | CTTATAACTTTTATCTATT | 5-9-1-1-3 | CTTATAacttttatCtATT | 793_5 | −20.81 | 30689 |
| 794 | CTTATAACTTTTATCTAT | 5-7-3-1-2 | CTTATAacttttATCtAT | 794_1 | −21.02 | 30690 |
| 794 | CTTATAACTTTTATCTAT | 1-1-3-7-1-1-4 | CtTATAacttttAtCTAT | 794_2 | −20.04 | 30690 |
| 794 | CTTATAACTTTTATCTAT | 2-2-1-8-5 | CTtaTaacttttaTCTAT | 794_3 | −19.59 | 30690 |
| 794 | CTTATAACTTTTATCTAT | 3-1-2-8-4 | CTTATaacttttatCTAT | 794_4 | −20.86 | 30690 |
| 794 | CTTATAACTTTTATCTAT | 5-10-3 | CTTATAacttttatcTAT | 794_5 | −19.99 | 30690 |
| 795 | CTTATAACTTTTATCTATTT | 1-1-1-2-2-6-2-1-1-1-2 | CtTatAActtttaTCtAtTT | 795_1 | −18.22 | 30688 |
| 795 | CTTATAACTTTTATCTATTT | 1-1-1-1-2-8-2-1-3 | CtTaTAacttttatCTaTTT | 795_2 | −20.86 | 30688 |
| 795 | CTTATAACTTTTATCTATTT | 2-1-2-1-1-7-2-2-2 | CTtATAActtttatCTatTT | 795_3 | −20.54 | 30688 |
| 795 | CTTATAACTTTTATCTATTT | 3-2-1-8-1-1-1-1-2 | CTTatAacttttatCtAtTT | 795_4 | −18.19 | 30688 |
| 795 | CTTATAACTTTTATCTATTT | 1-2-2-1-1-9-4 | CttATaActtttatctATTT | 795_5 | −18.61 | 30688 |
| 796 | CTTATAACTTTTATCTA | 5-6-2-1-3 | CTTATAactttTAtCTA | 796_1 | −21.44 | 30691 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 796 | CTTATAACTTTTATCTA | 5-6-1-2-3 | CTTATaactttTatCTA | 796_2 | -20.31 | 30691 |
| 796 | CTTATAACTTTTATCTA | 1-1-3-7-5 | CtTATaacttttATCTA | 796_3 | -19.90 | 30691 |
| 796 | CTTATAACTTTTATCTA | 3-1-1-8-4 | CTTaTaacttttaTCTA | 796_4 | -18.77 | 30691 |
| 796 | CTTATAACTTTTATCTA | 2-1-2-8-4 | CTtATaacttttaTCTA | 796_5 | -18.43 | 30691 |
| 797 | GCTTATAACTTTTATCTA | 2-2-2-6-2-2-2 | GCttATaactttTAtcTA | 797_1 | -21.32 | 30691 |
| 797 | GCTTATAACTTTTATCTA | 4-9-1-1-3 | GCTTataacttttAtCTA | 797_2 | -21.88 | 30691 |
| 797 | GCTTATAACTTTTATCTA | 2-12-4 | GCttataacttttaTCTA | 797_3 | -20.47 | 30691 |
| 797 | GCTTATAACTTTTATCTA | 2-1-1-1-1-9-3 | GCtTaTaacttttatCTA | 797_4 | -20.94 | 30691 |
| 797 | GCTTATAACTTTTATCTA | 1-1-4-10-2 | GcTTATaacttttatcTA | 797_5 | -19.62 | 30691 |
| 798 | GCTTATAACTTTTATCT | 2-9-1-2-3 | GCttataactttTtaTCT | 798_1 | -18.54 | 30692 |
| 798 | GCTTATAACTTTTATCT | 2-10-5 | GCttataactttTATCT | 798_2 | -20.90 | 30692 |
| 798 | GCTTATAACTTTTATCT | 4-8-1-1-3 | GCTTataacttttTaTCT | 798_3 | -21.40 | 30692 |
| 798 | GCTTATAACTTTTATCT | 2-1-2-8-4 | GCtTAtaacttttATCT | 798_4 | -21.00 | 30692 |
| 798 | GCTTATAACTTTTATCT | 5-10-2 | GCTTAtaactttttatCT | 798_5 | -20.68 | 30692 |
| 799 | TGCTTATAACTTTTATC | 3-8-3-1-2 | TGCttataaactTTTaTC | 799_1 | -19.59 | 30693 |
| 799 | TGCTTATAACTTTTATC | 3-8-2-1-3 | TGCttataaactTTtATC | 799_2 | -19.26 | 30693 |
| 799 | TGCTTATAACTTTTATC | 2-10-5 | TGcttataactttTTATC | 799_3 | -18.08 | 30693 |
| 799 | TGCTTATAACTTTTATC | 5-8-4 | TGCTTataactttTATC | 799_4 | -22.34 | 30693 |
| 799 | TGCTTATAACTTTTATC | 3-10-4 | TGCttataaactttTATC | 799_5 | -19.90 | 30693 |
| 800 | TGCTTATAACTTTTATCT | 3-9-3-1-2 | TGCttataaactTTAtCT | 800_1 | -22.27 | 30692 |
| 800 | TGCTTATAACTTTTATCT | 2-2-2-7-5 | TGctTAtaactttTATCT | 800_2 | -22.61 | 30692 |
| 800 | TGCTTATAACTTTTATCT | 3-10-1-1-3 | TGCttataaactttTaTCT | 800_3 | -21.45 | 30692 |
| 800 | TGCTTATAACTTTTATCT | 1-1-1-1-2-8-4 | TgCtTAtaacttttATCT | 800_4 | -20.79 | 30692 |
| 800 | TGCTTATAACTTTTATCT | 4-1-1-10-2 | TGCTtAtaacttttatCT | 800_5 | -20.89 | 30692 |
| 801 | CTGCTTATAACTTTTATC | 2-1-1-8-2-1-3 | CTgCttataactTTtATC | 801_1 | -20.05 | 30693 |
| 801 | CTGCTTATAACTTTTATC | 4-8-1-3-2 | CTGCttataaactTttaTC | 801_2 | -21.02 | 30693 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 801 | CTGCTTATAACTTTTATC | 2-1-1-10-4 | CTgCttataactttTATC | 801_3 | -20.69 | 30693 |
| 801 | CTGCTTATAACTTTTATC | 1-1-2-10-1-1-2 | CtGCttataactttTaTC | 801_4 | -18.86 | 30693 |
| 801 | CTGCTTATAACTTTTATC | 1-1-4-9-3 | CtGCTTataacttttATC | 801_5 | -21.47 | 30693 |
| 802 | CTCTGCTTATAACTTTT | 1-1-1-1-1-6-2-1-3 | CtCtGcttataACtTTT | 802_1 | -18.92 | 30696 |
| 802 | CTCTGCTTATAACTTTT | 1-1-1-1-1-7-2-1-2 | CtCtGcttataaCTtTT | 802_2 | -18.47 | 30696 |
| 802 | CTCTGCTTATAACTTTT | 1-1-2-8-1-1-3 | CtCTgcttataaCtTTT | 802_3 | -19.44 | 30696 |
| 802 | CTCTGCTTATAACTTTT | 1-2-2-7-1-1-3 | CtcTGcttataaCtTTT | 802_4 | -19.02 | 30696 |
| 802 | CTCTGCTTATAACTTTT | 3-1-1-10-2 | CTCtGcttataacttTT | 802_5 | -18.16 | 30696 |
| 803 | CCTCTGCTTATAACTTT | 1-1-2-7-2-1-3 | CcTCtgcttatAAcTTT | 803_1 | -20.60 | 30697 |
| 803 | CCTCTGCTTATAACTTT | 2-9-1-3-2 | CCtctgcttatAactTT | 803_2 | -19.28 | 30697 |
| 803 | CCTCTGCTTATAACTTT | 2-2-1-7-1-2-2 | CCtcTgcttataActTT | 803_3 | -20.58 | 30697 |
| 803 | CCTCTGCTTATAACTTT | 1-2-1-8-1-2-2 | CctCtgcttataActTT | 803_4 | -18.06 | 30697 |
| 803 | CCTCTGCTTATAACTTT | 2-1-1-9-1-1-2 | CCtCtgcttataaCtTT | 803_5 | -21.12 | 30697 |
| 804 | CTACTATACTTTCCTCT | 3-8-2-2-2 | CTActatactTCctCT | 804_1 | -22.54 | 30709 |
| 804 | CTACTATACTTTCCTCT | 1-1-1-9-2-1-2 | CtActatactttCCtCT | 804_2 | -21.39 | 30709 |
| 804 | CTACTATACTTTCCTCT | 1-2-1-8-1-2-2 | CtaCtatactttCctCT | 804_3 | -19.70 | 30709 |
| 804 | CTACTATACTTTCCTCT | 2-11-1-1-2 | CTactatacttTCctCT | 804_4 | -20.45 | 30709 |
| 804 | CTACTATACTTTCCTCT | 1-3-1-8-1-1-2 | CtacTatactttcCtCT | 804_5 | -19.77 | 30709 |
| 805 | TCTACTATACTTTCCTCT | 2-1-1-9-1-2-2 | TCtActatactttCctCT | 805_1 | -21.40 | 30709 |
| 805 | TCTACTATACTTTCCTCT | 2-2-1-8-1-2-2 | TCtaCtatactttCctCT | 805_2 | -22.20 | 30709 |
| 805 | TCTACTATACTTTCCTCT | 2-11-1-2-2 | TCtactatactttCctCT | 805_3 | -21.20 | 30709 |
| 805 | TCTACTATACTTTCCTCT | 2-1-1-10-1-1-2 | TCtActatactttcCtCT | 805_4 | -21.52 | 30709 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 805 | TCTACTATACTTTCCTCT | 2-2-1-9-1-1-2 | TCtaCtatactttcCtCT | 805_5 | -22.32 | 30709 |
| 806 | TTCTACTATACTTTCCT | 1-1-1-8-1-3-2 | TtCtactatacTttcCT | 806_1 | -18.06 | 30711 |
| 806 | TTCTACTATACTTTCCT | 1-2-1-7-1-3-2 | TtcTactatacTttcCT | 806_2 | -18.02 | 30711 |
| 806 | TTCTACTATACTTTCCT | 1-1-1-1-1-7-1-1-3 | TtCtActatactTtCCT | 806_3 | -20.41 | 30711 |
| 806 | TTCTACTATACTTTCCT | 1-1-1-10-4 | TtCtactatacttTCCT | 806_4 | -20.90 | 30711 |
| 806 | TTCTACTATACTTTCCT | 1-1-1-1-1-9-3 | TtCtActatactttCCT | 806_5 | -20.11 | 30711 |
| 807 | TTCTACTATACTTTCCTC | 1-2-1-8-1-1-1-1-2 | TtcTactatactTtCcTC | 807_1 | -19.51 | 30710 |
| 807 | TTCTACTATACTTTCCTC | 1-1-1-2-1-6-1-3-2 | TtCtaCtatactTtccTC | 807_2 | -19.77 | 30710 |
| 807 | TTCTACTATACTTTCCTC | 1-1-1-1-1-9-1-1-2 | TtCtActatactttCcTC | 807_3 | -19.44 | 30710 |
| 807 | TTCTACTATACTTTCCTC | 1-1-1-12-3 | TtCtactatactttcCTC | 807_4 | -20.04 | 30710 |
| 807 | TTCTACTATACTTTCCTC | 1-2-1-1-1-10-2 | TtcTaCtatactttccTC | 807_5 | -19.43 | 30710 |
| 808 | TTTCCATCTACTATTAAT | 1-1-3-7-3-1-2 | TtTCCatctactATTaAT | 808_1 | -21.43 | 39804 |
| 808 | TTTCCATCTACTATTAAT | 2-1-2-7-1-1-1-1-2 | TTtCCatctactAtTaAT | 808_2 | -19.50 | 39804 |
| 808 | TTTCCATCTACTATTAAT | 1-1-4-6-1-2-3 | TtTCCAtctactAttAAT | 808_3 | -20.72 | 39804 |
| 808 | TTTCCATCTACTATTAAT | 2-1-2-8-1-1-3 | TTtCCatctactaTtAAT | 808_4 | -19.43 | 39804 |
| 808 | TTTCCATCTACTATTAAT | 4-1-1-8-4 | TTTCcAtctactatTAAT | 808_5 | -20.12 | 39804 |
| 809 | TTTCCATCTACTATTAA | 5-6-3-1-2 | TTTCCatctacTATtAA | 809_1 | -21.74 | 39805 |
| 809 | TTTCCATCTACTATTAA | 2-1-2-6-2-1-3 | TTtCCatctacTAtTAA | 809_2 | -20.76 | 39805 |
| 809 | TTTCCATCTACTATTAA | 1-1-3-6-1-1-4 | TtTCCatctacTaTTAA | 809_3 | -20.75 | 39805 |
| 809 | TTTCCATCTACTATTAA | 2-1-2-7-5 | TTtCCatctactATTAA | 809_4 | -20.54 | 39805 |
| 809 | TTTCCATCTACTATTAA | 5-9-3 | TTTCCatctactatTAA | 809_5 | -20.18 | 39805 |
| 810 | GTTTCCATCTACTATTA | 3-9-2-1-2 | GTTtccatctacTAtTA | 810_1 | -20.81 | 39806 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 810 | GTTTCCATCTACTATTA | 1-1-1-1-1-7-1-1-3 | GtTtCcatctacTaTTA | 810_2 | -19.35 | 39806 |
| 810 | GTTTCCATCTACTATTA | 2-2-1-7-1-2-2 | GTttCcatctacTatTA | 810_3 | -19.64 | 39806 |
| 810 | GTTTCCATCTACTATTA | 3-1-1-8-4 | GTTtCcatctactATTA | 810_4 | -21.37 | 39806 |
| 810 | GTTTCCATCTACTATTA | 1-2-2-10-2 | GttTCcatctactatTA | 810_5 | -18.14 | 39806 |
| 811 | AATACAAAATCATCTTAC | 3-1-2-6-1-1-4 | AATaCAaaatcaTcTTAC | 811_1 | -18.05 | 39836 |
| 811 | AATACAAAATCATCTTAC | 4-9-5 | AATAcaaaatcatCTTAC | 811_2 | -18.25 | 39836 |
| 811 | AATACAAAATCATCTTAC | 3-1-2-7-5 | AATaCAaaatcatCTTAC | 811_3 | -19.20 | 39836 |
| 811 | AATACAAAATCATCTTAC | 2-1-3-7-5 | AAtACAaaatcatCTTAC | 811_4 | -18.12 | 39836 |
| 811 | AATACAAAATCATCTTAC | 1-1-4-7-5 | AaTACAaaatcatCTTAC | 811_5 | -19.50 | 39836 |
| 812 | AATACAAAATCATCTTACA | 2-2-2-6-4-1-2 | AAtaCAaaatcaTCTTaCA | 812_1 | -20.31 | 39835 |
| 812 | AATACAAAATCATCTTACA | 4-8-3-2-2 | AATAcaaaatcaTCTtaCA | 812_2 | -19.80 | 39835 |
| 812 | AATACAAAATCATCTTACA | 3-1-2-6-2-1-4 | AATaCAaaatcaTCtTACA | 812_3 | -21.91 | 39835 |
| 812 | AATACAAAATCATCTTACA | 1-1-4-7-2-2-2 | AaTACAaaatcatCTtaCA | 812_4 | -19.93 | 39835 |
| 812 | AATACAAAATCATCTTACA | 5-8-1-1-4 | AATACaaaatcatCtTACA | 812_5 | -20.93 | 39835 |
| 813 | TAATACAAAATCATCTTA | 1-1-4-6-3-1-2 | TaATACaaaatcATCtTA | 813_1 | -18.46 | 39837 |
| 813 | TAATACAAAATCATCTTA | 5-8-5 | TAATAcaaaatcaTCTTA | 813_2 | -19.57 | 39837 |
| 813 | TAATACAAAATCATCTTA | 5-9-4 | TAATAcaaaatcatCTTA | 813_3 | -18.44 | 39837 |
| 813 | TAATACAAAATCATCTTA | 2-1-3-8-4 | TAaTACaaaatcatCTTA | 813_4 | -18.20 | 39837 |
| 813 | TAATACAAAATCATCTTA | 1-1-4-8-4 | TaATACaaaatcatCTTA | 813_5 | -18.18 | 39837 |
| 814 | TAATACAAAATCATCTTAC | 2-1-3-6-4-1-2 | TAaTACaaaatcATCTtAC | 814_1 | -19.95 | 39836 |
| 814 | TAATACAAAATCATCTTAC | 4-1-1-6-3-1-3 | TAATaCaaaatcATCtTAC | 814_2 | -20.22 | 39836 |
| 814 | TAATACAAAATCATCTTAC | 1-2-3-6-1-1-5 | TaaTACaaaatcAtCTTAC | 814_3 | -19.14 | 39836 |
| 814 | TAATACAAAATCATCTTAC | 5-8-2-1-3 | TAATAcaaaatcaTCtTAC | 814_4 | -19.90 | 39836 |
| 814 | TAATACAAAATCATCTTAC | 4-1-1-8-5 | TAATaCaaaatcatCTTAC | 814_5 | -19.94 | 39836 |

TABLE_3-continued

List of oligonucleotides or contiguous nucleobase sequences complementary to SEQ ID NO: 1 (motif sequences indicated by SEQ ID NO), oligonucleotide designs made from these, as well as specific oligonucleotide compounds (indicated by CMP ID NO) designed based on the motif sequence.

| Seq ID NO | Motif | Design | Compound | CMP ID_NO | ΔG° | Start SEQ_ID NO |
|---|---|---|---|---|---|---|
| 815 | TAATACAAAATCATCTTACA | 3-2-2-6-2-1-1-1-2 | TAAtaCAaaatcaTCtTaCA | 815_1 | -20.84 | 39835 |
| 815 | TAATACAAAATCATCTTACA | 2-3-1-8-2-1-3 | TAataCaaaatcatCTtACA | 815_2 | -18.77 | 39835 |
| 815 | TAATACAAAATCATCTTACA | 2-1-2-1-1-7-2-2-2 | TAaTAcAaaatcatCTtaCA | 815_3 | -19.66 | 39835 |
| 815 | TAATACAAAATCATCTTACA | 1-1-1-1-2-8-1-1-4 | TaAtACaaaatcatCtTACA | 815_4 | -19.11 | 39835 |
| 815 | TAATACAAAATCATCTTACA | 4-10-1-1-1-1-2 | TAATacaaaatcatCtTaCA | 815_5 | -19.22 | 39835 |
| 816 | TCTGTATACACCATCCCA | 2-10-1-1-1-1-2 | TCtgtatacaccAtCcCA | 816_1 | -24.49 | 46389 |
| 816 | TCTGTATACACCATCCCA | 2-3-1-6-1-3-2 | TCtgtAtacaccAtccCA | 816_2 | -23.81 | 46389 |
| 816 | TCTGTATACACCATCCCA | 2-10-1-3-2 | TCtgtatacaccAtccCA | 816_3 | -23.72 | 46389 |
| 816 | TCTGTATACACCATCCCA | 2-1-1-10-1-1-2 | TCtGtatacaccatCcCA | 816_4 | -24.75 | 46389 |
| 816 | TCTGTATACACCATCCCA | 2-3-1-8-1-1-2 | TCtgtAtacaccatCcCA | 816_5 | -24.53 | 46389 |
| 816 | TCTGTATACACCATCCCA | 2-3-1-10-2 | TCtgtAtacaccatccCA | 816_6 | -23.76 | 46389 |
| 817 | TTCTGACTCCCTATCCA | 1-1-1-12-2 | TtCtgactccctatcCA | 817_1 | -22.56 | 46417 |
| 818 | TTTCTGACTCCCTATCC | 1-2-1-11-2 | TttCtgactccctatCC | 818_1 | -22.64 | 46418 |

Designs refer to the gapmer design, F-G-F', where each number represents the number of consecutive modified nucleosides, e.g 2' modified nucleosides (first number=5' flank), followed by the number of DNA nucleosides (second number=gap region), followed by the number of modified nucleosides, e.g 2' modified nucleosides (third number=3' flank), optionally preceded by or followed by further repeated regions of DNA and LNA, which are not necessarily part of the contiguous sequence that is complementary to the target nucleic acid. For some oligonucleotides in table 3 the flanks are mixed flanks, such flanks start and end with a 2' modified nucleosides, in these cases the gap region is the number above 5 not located at the 5' or 3' terminal in of the design.

For the oligonucleotide compounds capital letters represent beta-D-oxy LNA nucleosides, lowercase letters represent DNA nucleosides, all LNA C are 5-methyl cytosine, and 5-methyl DNA cytosines are presented by "e", all internucleoside linkages are phosphorothioate internucleoside linkages.

Oligonucleotides with an EX-EX indication as Start on SEQ ID NO: 1 are exon-exon spanning oligonucleotides designed to be complementary across exon-exon junctions of SNHG14-023 (ENST00000554726). The oligonucleotides primarily span exon2 and exon3 (i.e. are complementary to a region in exon2 and a region in exon 3)

Oligonucleotide Synthesis

Oligonucleotide synthesis is generally known in the art. Below is a protocol which may be applied. The oligonucleotides of the present invention may have been produced by slightly varying methods in terms of apparatus, support and concentrations used.

Oligonucleotides are synthesized on uridine universal supports using the phosphoramidite approach on a MerMade12 or an Oligomaker DNA/RNA synthesizer at 1-4 μmol scale. At the end of the synthesis, the oligonucleotides are cleaved from the solid support using aqueous ammonia for 5-16 hours at 60° C. The oligonucleotides are purified by reverse phase HPLC (RP-HPLC) or by solid phase extractions and characterized by UPLC, and the molecular mass is further confirmed by ESI-MS.

Elongation of the Oligonucleotide:

The coupling of β-cyanoethyl-phosphoramidites (DNA-A(Bz), DNA-G(ibu), DNA-C(Bz), DNA-T, LNA-5-methyl- C(Bz), LNA-A(Bz), LNA-G(dmf), LNA-T or amino-C6 linker) is performed by using a solution of 0.1 M of the 5'-O-DMT-protected amidite in acetonitrile and DCI (4,5-dicyanoimidazole) in acetonitrile (0.25 M) as activator. For the final cycle a phosphoramidite with desired modifications can be used, e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphordiester linkages can be introduced using 0.02 M iodine in THF/Pyridine/water 7:2:1. The rest of the reagents are the ones typically used for oligonucleotide synthesis.

Purification by RP-HPLC:

The crude compounds are purified by preparative RP-HPLC on a Phenomenex Jupiter C18 10μ 150×10 mm column. 0.1 M ammonium acetate pH 8 and acetonitrile is used as buffers at a flow rate of 5 mL/min. The collected fractions are lyophilized to give the purified compound typically as a white solid.

Abbreviations

DCI: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography $T_m$ Assay Oligonucleotide and RNA target duplexes are diluted to 3 mM in 500 ml RNase-free water and mixed with 500 ml 2×$T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Preparation of Mouse Primary Cortical Neuron Cell Cultures

Primary cortical neuron cultures were prepared from mouse embryo brains of 15 days of age according to standard procedure. In brief, culture plates were coated with Poly-L-Lysine (50 μg/ml Poly-L-Lysine, 10 mM Na-tetraborate, pH 8 buffer) for 2-3 hrs at room temperature. The plates were washed with 1×PBS before use. Harvested mouse embryo brains were dissected and homogenized by a razor blade and submerged into 38 ml dissection medium (HBSS, 0.01 M Hepes, Penicillin/Streptomycin). Then, 2 ml trypsin was added and cells were incubated for 30 min at 37° C. and centrifuged down. The cells were dissolved in 20 ml DMEM (+10% FBS) and passed through a syringe for further homogenization. This was followed by centrifugation at 500 rpm for 15 mins. The cells were dissolved in DMEM (+10% FBS) and seeded in 96 well plates (0.1×10^6 cells/well in 100 μl). The neuronal cell cultures were ready for use directly after seeding.

Screening Oligonucleotides in Mouse Primary Cortical Neuron Cell Cultures

Cells were cultured in growth medium (Gibco Neurobasal medium, B27 supplement, Glutamax, Pencillin-streptomycin) in 96-well plates and incubated with oligonucleotides for 3 days at the desired concentrations. Total RNA was isolated from the cells and the knock-down efficacy was measured by qPCR analysis using the qScript™ XLT One-Step RT-qPCR ToughMix®, Low ROX™ kit from Quanta Bioscience (95134-500). A commercial taqman assays from Thermo Fisher Scientific was used to measure Ube3a_ATS including GAPDH for normalization.

Generation of Human Primary Neuronal Cell Cultures

Any cell lines at any described time point was incubated at 37° C., 5% CO2 concentration and 95% relative humidity.

Human Induced Pluripotent Stem Cells (hiPSC) Culture

Whole human blood samples were obtained from patients diagnosed with Angelman syndrome. The subsequent cultures of primary Peripheral Blood Mononuclear Cells (PMCSs) were enriched for erythroblasts. Patient-specific iPSC lines were generated by reprogramming erythroblast with CytoTune-iPS Sendai Reprogramming Kit (Thermo Fisher Scientific). Derived iPSC lines were maintained in feeder-free conditions using hESC-qualified Matrigel (Corning) in mTESR1 (STEMCELL Technologies) with daily medium replacement. Upon reaching confluence, colonies were dissociated into cell cluster of 50-200 μm in size using Gentle Cell Dissociation Reagent (STEMCELL Technologies) and subcultured at a ratio of 1:10-1:20 in the presence of 10 μM Y-27632 (Calbiochem).

Differentiation into Neural Progenitor Cells (NPC)

Upon induction of neural differentiation iPSC-derived cells were maintained in basal medium composed of equal volumes of DMEM:F12 Glutamax medium and Neurobasal medium (Gibco, Invitrogen), supplemented with 1×B27 (Gibco, Invitrogen), 1×N2 (Gibco, Invitrogen), 0.1 mM beta-mercaptoethanol (Gibco, Invitrogen) and indicated supplements.

Neural progenitor cells (NPCs) were derived from hiPSCs by dual SMAD inhibition and according to published procedures with slight modifications (Chambers et al. 2009 Nat Biotechnol. Vol. 3 pp. 275-80, Boissart et al., 2013 Transl Psychiatry. 3:e294). HiPSCs were dissociated with Accutase (Innovative Cell Technologies Inc.) into a single cell suspension and resuspended in basic medium further supplemented with 10 μM Y-27632 (Calbiochem), 5 ng/ml FGF (Peprotech), 10 μM SB-431542 (Calbiochem) and 100 nM LDN (Calbiochem). Single cell suspension was transferred to AggreWell800 plates (STEMCELL Technologies) enabling the formation of aggregates consisting of 8000 cells. After 5 days neural aggregates were transferred onto plates coated with poly-L-ornithine (Sigma) and laminin (Roche) and allowed to form neural rosettes under continued dual SMAD inhibition (SB-431542 and LDN) in basic medium supplemented with FGF. Neural rosettes were selectively isolated using STEMdiff™ Neural Rosette Selection Reagent (STEMCELL Technologies), replated onto dishes coated with poly-L-ornithine and Laminin521 (Bio-Lamina) and expanded in basic medium supplemented with 10 ng/ml FGF (Peprotech), 10 ng/ml EGF (RnD), and 20 ng/ml BDNF (Peprotech). When reaching confluency, cells were enzymatically dissociated with 0.05% Trypsin/EDTA (Gibco, Invitrogen) and sub-cultured. Continued passaging in basic medium supplemented with FGF, EGF and BDNF leads to a stable neural progenitor cell line (NPC line) within 10 to 20 passages. A stable neural progenitor cell line is defined by its capacity to self-renew and by the expression of the developmental stage-specific markers Sox2 and Nestin. Upon specific stimuli, NPCs differentiate into neuronal (MAP2+, Tau+, HuC/D+) and astroglial (GFAP+) progenies (Dunkley et al., 2015 Proteomics Clin Appl. Vol. 7-8 pp. 684-94).

NPC Culture

Conditions for NPC culture have been described previously and were used with slight modifications (Boissart et al., 2013 Transl Psychiatry. 3:e294). In brief, cells were maintained in dishes coated with Laminin521 (BioLamina) and cultured in basic medium [composed of equal volumes of DMEM:F12 Glutamax medium and Neurobasal medium (Gibco, Invitrogen), supplemented with 1×B27 (Gibco, Invitrogen), 1×N2 (Gibco, Invitrogen), 0.1 mM beta-mercaptoethanol (Gibco, Invitrogen)] and supplemented with 10 ng/ml FGF (Peprotech), 10 ng/ml EGF (RnD), and 20 ng/ml BDNF (Peprotech).

Differentiation into Neuronal Cell Culture

To induce neuronal differentiation of NPC, cells were dissociated with 0.05% Trypsin/EDTA (Gibco, Invitrogen) into single cell suspension and seeded onto Laminin521 (BioLamina) coated dishes at a density of 12.000 cells/cm2 and maintained in basic medium supplemented with 200 ng/ml Shh (Peprotech), 100 ng/ml FGF8 (Peprotech), and 100 µM ascorbic acid phosphate (Sigma) for a period of 7 days. Subsequently, cells were replated in basal medium supplemented with 20 ng/ml BDNF (Peprotech), 10 ng/ml GDNF (Peprotech), 0.5 mM cAMP (BIOLOG Life Science), and 100 µM ascorbic acid phosphate (Sigma) at a density of 45000 cells/cm2 and differentiated for a period of 21 days. At day 21 of differentiation, differentiated neuronal cultures were replated onto the screening-compatible plate format. Replating was performed by dissociating the cultures with Accutase (Innovative Cell Technologies Inc.) into a single cell suspension. Cells were seeded at a density of 200.000 cells/cm2 in presence of 10 µM Y-27632 (a cell-permeable, reversible, inhibitor of Rho kinases from Calbiochem) into the 384 well microtiter plates for final oligonucleotides screening assay. Neuronal cultures were further differentiated for additional 7 days in basal medium supplemented with 20 ng/ml BDNF (Peprotech), 10 ng/ml GDNF (Peprotech), 0.5 mM cAMP (BIOLOG Life Science), and 100 µM ascorbic acid phosphate (Sigma). Differentiation medium was exchanged twice per week. After a total differentiation period of 35 days neuronal cell cultures were ready for oligonucleotide treatment.

Screening Oligonucleotides in Human Neuronal Cell Cultures—384 Well System

For screening, oligonucleotide stocks were pre-diluted to the indicated concentrations with water into 384 well microtiter plates (compound plate). The plate layout served as a treatment template. Two microliter oligonucleotide dilution from each well was transferred from the compound plate to a respective culture plate. All liquid handling was done under sterile conditions in a laminar flow using a semi-automated laboratory robotic system (Beckmancoulter). Neuronal cell cultures were incubated with oligonucleotides for 5 days without media change. Subsequently, neuronal cultures were lysed and processed for qPCR assay with RealTime ready Cell lysis and RNA Virus Master kit (Roche). Liquid handling was performed using a semi-automated laboratory robotic system (Beckmancoulter). Samples were analyzed by a Lightcycler480 real-time PCR system (Roche).

Activity of the oligonucleotides was assessed by qPCR monitoring transcript abundance of UBE3A using the following primers and probes

```
UBE3a-Sense: Forward primer:
                                     (SEQ ID NO: 837)
ATATGTGGAAGCCGGAATCT, Reverse primer:
                                     (SEQ ID NO: 838)
TCCCAGAACTCCCTAATCAGAA, Internal probe labeled with dye FAM:
                                     (SEQ ID NO: 839)
ATGACGGTGGCTATACCAGG
```

The RT-qPCR was multiplexed with PPIA (peptidylprolyl isomerase A) as housekeeping gene for normalization. PPIA primers and probe labeled with the dye VIC were purchased from Thermo Fisher Scientific (assay ID Hs99999904_m1). Each plate includes a non-targeting oligonucleotide (mock) as negative control (TTGaataagtggaTGT (SEQ ID NO: 846)) and a reference oligonucleotide CMP ID NO: 411, resulting in up-regulation of UBE3A mRNA.

Selectivity of oligonucleotides was verified by counter screening for SNORD 115 transcript, which is located upstream of SNORD109B on chromosome 15. Expression of SNORD115 was monitored by qPCR using the following primers and probe

```
Forward primer:
                                     (SEQ ID NO: 840)
GGGTCAATGATGAGAACCTTAT, Reverse primer
                                     (SEQ ID NO: 841)
GGGCCTCAGCGTAATCCTATT, Internal probe labeled with the dye FAM:
                                     (SEQ ID NO: 842)
TTCTGAAGAGAGGTGATGACTTAAAA
```

The RT-qPCR was multiplexed with PPIA (Thermo Fisher Scientific) upon oligonucleotide treatment.

The reduction of the SNHG14 transcript downstream of SNORD109B (also termed the UBE3A suppressor) was measured by RT-qPCR using the following primers and probe

```
Forward primer:
                                     (SEQ ID NO: 843)
ATCCGAGGCATGAATCTCAC, Reverse primer:
                                     (SEQ ID NO: 844)
CAGGCCAAAACCCTTGATAA, Internal probe labeled with dye FAM:
                                     (SEQ ID NO: 845)
TTGCTGAGCATTTTTGCATC
```

The RT-qPCR was multiplexed with PPIA (Thermo Fisher Scientific).

Data are presented as average % expression relative to mock across all plates and normalized to the reference oligonucleotide to account for plate to plate variation.

Screening Oligonucleotides in Human Neuronal Cell Cultures—96 Well System

For screening, oligonucleotide stocks were pre-diluted to the indicated concentrations with water into 96 well microtiter plates (compound plate). The plate layout served as a treatment template. Two microliter oligonucleotide dilution from each well was transferred from the compound plate to a respective culture plate. All liquid handling was done under sterile conditions in a laminar flow using a semi-automated laboratory robotic system (Beckman Coulter). Neuronal cell cultures were incubated with oligonucleotides for 5 days without media change. Subsequently, neuronal cultures were lysed and RNA purified using RNA purification kit Pure Link Pro96 (12173011 A) LifeTechnologies. Liquid handling was performed using a semi-automated laboratory robotic system (Beckmancoulter). qPCR analysis of Ube3a and Ube3a-ATS was carried out on a ViiA™ 7 Real-Time PCR System Thermo Fisher Scientific using the qScript™ XLT 1-Step RT-qPCR ToughMix Low ROX, from Quanta (95134-50).

The following primers and probes were used:

```
qPCR UBE3a-Sense:
Forward primer:
                              (SEQ ID NO: 697)
ATATGTGGAAGCCGGAATCT, Reverse primer:
                              (SEQ ID NO: 698)
TCCCAGAACTCCCTAATCAGAA, Internal probe labeled with dye FAM:
                              (SEQ ID NO: 699)
ATGACGGTGGCTATACCAGG
``` qPCR SNHG14 transcript downstream of SNORD109B (also termed the UBE3A suppressor): Commercially available primer and probe set from ThermoFisher: Hs01372957_m1. These primers amplifies a 87 bp exon-exon spanning sequence in the Genbank transcript AF400500.1

QPCR GAPDH Transcript:

Commercially available primer and probe set from Thermofisher: Gene Symbol: with following assay details: RefSeq: NM_002046.3, Probe Exon Location:3, Amplicon Size: 122 bp. Corresponding TaqMan Assay ID: Hs99999905_m1.

The RT-qPCR for both Ube3a and Ube3a-ATS was multiplexed with GAPDH as housekeeping gene for normalization. Each plate includes a non-targeting oligonucleotide (mock) as negative control (TTGaataagtggaTGT (SEQ ID NO: 846)) and a reference oligonucleotide CMP ID NO: 211, resulting in up-regulation of UBE3A mRNA. Moreover panel of oligos not targeting Ub3a or SNHG14 transcript downstream of SNORD109B (also termed the UBE3A suppressor) were included to monitor the assay noise and risk of detecting false positives. These were randomly distributed over the plates.

Control Oligonucleotides:

```
                              (SEQ ID NO: 819)
CGAaccactgaaCAA (SEQ ID NO: 820)
CGAaccactgaacAAA (SEQ ID NO: 821)
CGAagtgcacaCG (SEQ ID NO: 822)
GCGtaaagagaGGT (SEQ ID NO: 823)
GAGAaggcacagaCGG (SEQ ID NO: 824)
GCGaagtgcacaCGG (SEQ ID NO: 825)
GAGaaggcacagaCGG (SEQ ID NO: 826)
CGAaccactgAACA (SEQ ID NO: 827)
GAAccactgaacAAA (SEQ ID NO: 828)
caGCGtaaagagaGG (SEQ ID NO: 829)
GCgtaaagagAGG (SEQ ID NO: 830)
CGAaccactgaAC (SEQ ID NO: 831)
CGAAccactgaaCAAA (SEQ ID NO: 832)
AGCgaagtgcacaCGG (SEQ ID NO: 833)
AGGtgaagcgaAGTG (SEQ ID NO: 834)
TAGTaaactgagCCA (SEQ ID NO: 835)
AGAaggcacagaCGG (SEQ ID NO: 836)
CCGcagtatggaTCG
```

Example 1—Oligonucleotide Activity in Mouse Primary Neuronal Cell Cultures

Oligonucleotides targeting the part of SNHG14 long non-coding RNA which is antisense to the UBE3A pre-mRNA (position 55319 to 141053 of SEQ ID NO: 1) were tested for their ability to reduce the SNHG14 long non-coding RNA transcript preventing UBE3A expression (also termed UBE3A suppressor or UBE3A-SUP in the data table) and their ability to induce UBE3A mRNA re-expression in mouse primary cortical neuron cell cultures, obtained as described in the "Materials and methods" section above. The oligonucleotide concentration was 5 microM.

The oligonucleotides were screened according to the protocol for screening in mouse cortical neuron cell cultures described in the section "Materials and methods". The results are shown in table 4.

TABLE 4

Oligonucleotide activity in primary mouse neuronal cell cultures.

| CMP ID NO | oligonucleotide | % of Mock UBE3A_SUP | sd | % of Mock UBE3A | sd |
|---|---|---|---|---|---|
| 95_1 | CTCAtacttgctttaAT | 3.6 | 0.1 | 154.1 | 15.1 |
| 95_2 | CTcatacttgctttaAT | 15.9 | 2.6 | 119.8 | 12.4 |

TABLE 4-continued

Oligonucleotide activity in primary mouse neuronal cell cultures.

| CMP ID NO | oligonucleotide | % of Mock UBE3A_SUP | sd | % of Mock UBE3A | sd |
|---|---|---|---|---|---|
| 96_1 | ACatctcatacttGCTT | 4.0 | 0.5 | 149.9 | 11.5 |
| 96_2 | ACatctcatacttgcTT | 9.3 | 3.9 | 139.9 | 36.4 |
| 96_3 | ACatctcatacttgCTT | 3.1 | 0.2 | 143.2 | 3.9 |
| 97_1 | ACatctcatactTGCT | 4.0 | 1.5 | 154.5 | 10.0 |
| 97_2 | ACatctcatacttgCT | 6.1 | 1.7 | 141.1 | 14.1 |
| 97_3 | ACatctcatacttGCT | 3.7 | 0.6 | 162.7 | 15.0 |
| 97_4 | ACATctcatacttgCT | 5.2 | 0.4 | 156.7 | 24.4 |
| 98_1 | TAcatctcatactTGCT | 5.0 | 0.9 | 159.0 | 15.6 |
| 98_2 | TAcatctcatacttgCT | 15.5 | 5.3 | 130.4 | 3.4 |
| 98_3 | TACatctcatacttgCT | 4.7 | 0.4 | 140.3 | 38.2 |
| 101_1 | TACatctcatactTGC | 2.6 | 0.5 | 152.6 | 10.2 |
| 101_2 | TAcatctcatacttGC | 19.2 | 6.0 | 112.0 | 15.0 |
| 101_3 | TAcatctcatactTGC | 3.5 | 0.4 | 117.2 | 13.7 |
| 101_4 | TACatctcatacttGC | 3.0 | 0.7 | 140.5 | 12.4 |
| 100_1 | CTAcatctcatactTGC | 5.4 | 0.8 | 160.4 | 4.1 |
| 100_2 | CTacatctcatacttGC | 9.6 | 3.7 | 159.2 | 14.5 |
| 100_3 | CTacatctcatactTGC | 3.0 | 0.1 | 133.2 | 5.9 |
| 99_2 | CCtacatctcatacttGC | 7.8 | 1.4 | 150.7 | 11.0 |
| 99_3 | CCtacatctcatactTGC | 3.2 | 0.6 | 134.7 | 12.5 |
| 99_4 | CCtacatctcatacTTGC | 2.7 | 0.2 | 145.2 | 4.7 |
| 102_1 | CCTacatctcatactTG | 5.8 | 1.7 | 127.0 | 24.5 |
| 102_2 | CCtacatctcatactTG | 20.2 | 6.6 | 129.7 | 9.2 |
| 102_4 | CCTacatctcatacTTG | 4.0 | 0.6 | 140.2 | 7.2 |
| 102_3 | CCTacatctcatactTG | 3.9 | 1.0 | 133.3 | 10.0 |
| 104_1 | CCTacatctcataCTT | 6.6 | 1.5 | 136.5 | 8.7 |
| 104_3 | CCtacatctcatACTT | 3.5 | 0.4 | 131.4 | 6.0 |
| 103_1 | ACCtacatctcataCTT | 5.8 | 1.4 | 130.8 | 0.7 |
| 103_2 | ACctacatctcatacTT | 11.4 | 2.2 | 123.6 | 12.4 |
| 103_3 | ACctacatctcatACTT | 5.8 | 0.8 | 132.2 | 4.5 |
| 105_1 | TACCtacatctcatacTT | 5.2 | 0.8 | 152.3 | 7.2 |
| 106_1 | TTAcctacatctcataCTT | 13.3 | 3.0 | 140.1 | 17.5 |
| 106_2 | TTacctacatctcatacTT | 21.0 | 1.4 | 116.9 | 15.0 |
| 107_1 | ACCTacatctcataCT | 6.2 | 0.9 | 119.2 | 3.4 |
| 107_2 | ACctacatctcataCT | 14.3 | 7.4 | 142.9 | 13.7 |
| 108_1 | TACCtacatctcataCT | 5.6 | 1.0 | 127.0 | 10.7 |
| 108_2 | TAcctacatctcataCT | 21.4 | 12.5 | 117.1 | 8.5 |
| 109_1 | TTacctacatctcaTACT | 4.4 | 0.4 | 138.9 | 1.2 |

TABLE 4-continued

Oligonucleotide activity in primary mouse neuronal cell cultures.

| CMP ID NO | oligonucleotide | % of Mock UBE3A_SUP | sd | % of Mock UBE3A | sd |
|---|---|---|---|---|---|
| 109_2 | TTacctacatctcataCT | 22.9 | 3.3 | 117.1 | 13.0 |
| 110_1 | TTAcctacatctcaTAC | 8.7 | 2.1 | 133.2 | 5.1 |
| 110_2 | TTacctacatctcatAC | 21.0 | 5.1 | 111.4 | 11.1 |
| 111_1 | GTtacctacatctCATA | 8.0 | 2.4 | 143.8 | 14.8 |
| 111_2 | GTtacctacatctcaTA | 19.0 | 2.3 | 115.4 | 4.1 |
| 112_1 | GTTacctacatctCAT | 6.6 | 1.4 | 145.5 | 16.8 |
| 112_2 | GTtacctacatctcAT | 15.8 | 4.5 | 120.3 | 8.1 |
| 126_1 | TCACtttccagatatCA | 8.0 | 1.9 | 133.8 | 5.4 |
| 126_3 | TCactttccagatatCA | 53.4 | 75.9 | 112.0 | 11.4 |
| 128_1 | ACATgtccctttataTT | 16.3 | 2.5 | 114.7 | 11.1 |
| 128_2 | ACatgtccctttataTT | 14.8 | 1.1 | 136.9 | 6.2 |
| 129_1 | ACAtgtccctttaTAT | 11.8 | 1.9 | 135.0 | 14.3 |
| 132_1 | CTCAtccctccaagaAA | 9.1 | 1.6 | 131.7 | 8.4 |
| 132_2 | CTcatccctccaagaAA | 11.2 | 3.9 | 159.3 | 17.7 |

Example 2—Oligonucleotide activity in human neuronal cell cultures

Oligonucleotides targeting human SNHG14 in the region downstream of SNORD109B corresponding to position 25278410 to 25419462 on chromosome 15 (SEQ ID NO: 1) were tested in patient derived human neuronal cell cultures (see protocol in "Materials and methods" section). The oligonucleotides ability to reduce the SNHG14 transcript in the region downstream of SNORD109B (also termed UBE3A suppressor or UBE3A-SUP in the data table), without affecting expression of SNORD115 was analyzed. Furthermore, the ability to induce UBE3A mRNA re-expression was analyzed.

The oligonucleotides were screened according to the protocol for screening oligonucleotides in human neuronal cell cultures described in the section "Materials and methods" above.

The results are shown in table 5. The expression of UBE3A mRNA has been measured for all compounds, whereas the knock-down of the UBE3A suppressor and the maintenance of SNORD61115 levels have not been analyzed for all compounds.

TABLE 5

Oligonucleotide activity in patient derived human neuronal cell cultures.

| Start SEQ ID NO 1 | CMP ID NO | Target | % of Mock Oligo conc 0.2 µM | sd | % of Mock Oligo conc 1.0 µM | sd | % of Mock Oligo conc 5.0 µM | sd |
|---|---|---|---|---|---|---|---|---|
| 1678 | 10_1 | UBE3A | 107 | 14 | 88 | 10 | 151 | 8 |
| 1679 | 12_2 | UBE3A | 100 | 9 | 87 | 14 | 158 | 16 |
| 1687 | 20_1 | UBE3A | 87 | 7 | 102 | 22 | 213 | 44 |
| 1712 | 21_1 | UBE3A | 127 | 23 | 166 | 6 | 178 | 13 |
| 1712 | 21_1 | UBE3A-SUP | 81 | 3 | 82 | 8 | 72 | 12 |
| 1712 | 21_1 | SNORD115 | 115 | 6 | 142 | 24 | 169 | 26 |
| 4167 | 22_1 | UBE3A | 87 | 5 | 90 | 8 | 146 | 20 |
| 4170 | 27_1 | UBE3A | 94 | 16 | 106 | 11 | 170 | 10 |
| 4171 | 29_2 | UBE3A | 86 | 13 | 100 | 12 | 194 | 35 |
| 4172 | 30_1 | UBE3A | 96 | 6 | 121 | 12 | 209 | 27 |
| 9210 | 35_1 | UBE3A | 88 | 5 | 112 | 23 | 195 | 27 |
| 10838 | 37_1 | UBE3A | 77 | 7 | 85 | 9 | 169 | 24 |
| 15565 | 38_2 | UBE3A | 93 | 11 | 108 | 6 | 167 | 34 |
| 22209 | 42_1 | UBE3A | 125 | 16 | 143 | 14 | 180 | 17 |
| 22209 | 42_1 | UBE3A-SUP | 108 | 14 | 98 | 15 | 85 | 18 |
| 22209 | 42_1 | SNORD115 | 101 | 14 | 93 | 25 | 127 | 21 |
| 30449 | 43_1 | UBE3A | 99 | 5 | 95 | 13 | 115 | 8 |
| 30451 | 44_1 | UBE3A | 99 | 15 | 80 | 20 | 141 | 17 |
| 30451 | 44_2 | UBE3A | 98 | 31 | 104 | 16 | 119 | 7 |

TABLE 5-continued

Oligonucleotide activity in patient derived human neuronal cell cultures.

| Start SEQ ID NO 1 | CMP ID NO | Target | % of Mock Oligo conc 0.2 μM | sd | % of Mock Oligo conc 1.0 μM | sd | % of Mock Oligo conc 5.0 μM | sd |
|---|---|---|---|---|---|---|---|---|
| 30697 | 46_1 | UBE3A | 91 | 8 | 87 | 5 | 167 | 20 |
| 36066 | 49_1 | UBE3A | 95 | 6 | 111 | 10 | 155 | 29 |
| 36066 | 49_1 | UBE3A-SUP | 76 | 7 | 84 | 24 | 110 | 31 |
| 36066 | 49_1 | SNORD115 | 99 | 14 | 111 | 20 | 94 | 6 |
| 36068 | 50_1 | UBE3A | 109 | 15 | 105 | 11 | 92 | 14 |
| 36068 | 50_1 | UBE3A-SUP | 122 | 24 | 93 | 28 | 73 | 7 |
| 36068 | 50_1 | SNORD115 | 120 | 15 | 113 | 12 | 99 | 6 |
| 37206 | 51_1 | UBE3A | 114 | 16 | 101 | 7 | 101 | 3 |
| 37206 | 51_1 | UBE3A-SUP | 128 | 21 | 67 | 9 | 84 | 13 |
| 37206 | 51_1 | SNORD115 | 140 | 26 | 110 | 9 | 100 | 11 |
| 46130 | 52_1 | UBE3A | 139 | 3 | 160 | 1 | 236 | 36 |
| 46130 | 52_1 | UBE3A-SUP | 135 | 16 | 133 | 26 | 160 | 32 |
| 46130 | 52_1 | SNORD115 | 104 | 8 | 119 | 14 | 100 | 8 |
| 48145 | 59_1 | UBE3A | 179 | 3 | 122 | 17 | 115 | NA |
| 48170 | 76_1 | UBE3A | 85 | 16 | 100 | 8 | 155 | 12 |
| 48171 | 80_1 | UBE3A | 120 | 7 | 114 | 10 | 172 | 20 |
| 48171 | 78_1 | UBE3A | 136 | 31 | 103 | 20 | 169 | 11 |
| 48172 | 82_2 | UBE3A | 96 | 11 | 121 | 4 | 186 | 32 |
| 48172 | 84_1 | UBE3A | 95 | 14 | 100 | 8 | 158 | 14 |
| 49343 | 85_1 | UBE3A | 97 | 22 | 121 | 10 | 189 | 17 |
| 49722 | 87_1 | UBE3A | 111 | 9 | 126 | 11 | 177 | 22 |
| 52417 | 92_1 | UBE3A | 133 | 7 | 140 | 30 | 140 | 8 |
| 52417 | 92_1 | UBE3A-SUP | 88 | 14 | 80 | 14 | 82 | 8 |
| 52417 | 92_1 | SNORD115 | 102 | 8 | 114 | 20 | 91 | 9 |
| 52420 | 93_1 | UBE3A | 111 | 14 | 120 | 9 | 126 | 16 |
| 52420 | 93_1 | UBE3A-SUP | 104 | 23 | 82 | 20 | 79 | 8 |
| 52420 | 93_1 | SNORD115 | 110 | 11 | 114 | 17 | 95 | 7 |
| 53953 | 94_1 | UBE3A | 117 | 12 | 147 | 15 | 166 | 15 |
| 53953 | 94_1 | UBE3A-SUP | 92 | 18 | 81 | 5 | 86 | 22 |
| 53953 | 94_1 | SNORD115 | 124 | 33 | 122 | 17 | 106 | 14 |
| 60819 | 95_1 | UBE3A | 103 | 11 | 131 | 14 | 175 | 7 |
| 60819 | 95_1 | UBE3A-SUP | 93 | 13 | 87 | 3 | 74 | 6 |
| 60819 | 95_1 | SNORD115 | 162 | 19 | 158 | 20 | 201 | 11 |
| 60819 | 95_2 | UBE3A | 147 | 10 | 129 | 20 | 117 | 2 |
| 60819 | 95_2 | UBE3A-SUP | 118 | 24 | 87 | 13 | 83 | 8 |
| 60819 | 95_2 | SNORD115 | 104 | 17 | 118 | 10 | 129 | 6 |
| 60823 | 96_1 | UBE3A | 115 | 16 | 135 | 19 | 174 | 17 |
| 60823 | 96_1 | UBE3A-SUP | 104 | 25 | 93 | 32 | 91 | 11 |
| 60823 | 96_2 | UBE3A | 108 | 7 | 114 | 9 | 115 | 13 |
| 60823 | 96_2 | UBE3A-SUP | 99 | 17 | 92 | 19 | 93 | 10 |
| 60824 | 97_1 | UBE3A | 111 | 12 | 134 | 23 | 169 | 14 |
| 60824 | 97_1 | UBE3A-SUP | 110 | 27 | 105 | 33 | 92 | 10 |
| 60824 | 97_2 | UBE3A | 124 | 13 | 126 | 12 | 124 | 11 |
| 60824 | 97_2 | UBE3A-SUP | 113 | 17 | 107 | 33 | 96 | 20 |
| 60824 | 98_1 | UBE3A | 111 | 16 | 119 | 11 | 138 | 14 |
| 60824 | 98_1 | UBE3A-SUP | 118 | 34 | 98 | 23 | 82 | 19 |
| 60824 | 98_1 | SNORD115 | 109 | 11 | 123 | 18 | 114 | 16 |
| 60824 | 98_2 | UBE3A | 128 | 10 | 109 | 7 | 136 | 12 |
| 60824 | 98_2 | UBE3A-SUP | 91 | 15 | 77 | 11 | 110 | 16 |
| 60824 | 98_2 | SNORD115 | 101 | 3 | 110 | 7 | 124 | 11 |
| 60825 | 99_1 | UBE3A | 125 | 6 | 115 | 5 | 131 | 10 |
| 60825 | 99_1 | UBE3A-SUP | 139 | 18 | 121 | 34 | 127 | 45 |
| 60825 | 99_1 | SNORD115 | 110 | 18 | 112 | 12 | 99 | 19 |
| 60825 | 99_2 | UBE3A | 120 | 21 | 111 | 11 | 135 | 22 |
| 60825 | 99_2 | UBE3A-SUP | 96 | 2 | 79 | 15 | 75 | 11 |
| 60825 | 99_2 | SNORD115 | 104 | 34 | 113 | 22 | 131 | 24 |
| 60825 | 100_1 | UBE3A | 123 | 34 | 139 | 34 | 145 | 21 |
| 60825 | 100_1 | UBE3A-SUP | 104 | 37 | 127 | 46 | 99 | 17 |
| 60825 | 100_2 | UBE3A | 124 | 46 | 138 | 37 | 145 | 31 |
| 60825 | 100_2 | UBE3A-SUP | 111 | 36 | 120 | 47 | 92 | 11 |
| 60825 | 101_1 | UBE3A | 112 | 18 | 123 | 15 | 150 | 13 |
| 60825 | 101_1 | UBE3A-SUP | 96 | 18 | 102 | 14 | 88 | 12 |
| 60825 | 101_2 | UBE3A | 118 | 15 | 138 | 24 | 139 | 32 |
| 60825 | 101_2 | UBE3A-SUP | 100 | 29 | 110 | 39 | 92 | 10 |
| 60826 | 102_1 | UBE3A | 132 | 17 | 120 | 7 | 125 | 9 |
| 60826 | 102_1 | UBE3A-SUP | 113 | 16 | 83 | 5 | 88 | 18 |
| 60826 | 102_1 | SNORD115 | 121 | 36 | 131 | 23 | 100 | 9 |
| 60826 | 102_2 | UBE3A | 90 | 6 | 116 | 23 | 103 | 7 |
| 60826 | 102_2 | UBE3A-SUP | 91 | 7 | 90 | 12 | 64 | 18 |
| 60826 | 102_2 | SNORD115 | 116 | 15 | 146 | 27 | 183 | 28 |
| 60827 | 103_1 | UBE3A | 106 | 8 | 112 | 10 | 115 | 9 |
| 60827 | 103_1 | UBE3A-SUP | 99 | 15 | 110 | 28 | 94 | 8 |
| 60827 | 103_2 | UBE3A | 107 | 14 | 120 | 13 | 112 | 14 |
| 60827 | 103_2 | UBE3A-SUP | 97 | 14 | 118 | 38 | 93 | 20 |

TABLE 5-continued

Oligonucleotide activity in patient derived human neuronal cell cultures.

| Start SEQ ID NO 1 | CMP ID NO | Target | % of Mock Oligo conc 0.2 μM | sd | % of Mock Oligo conc 1.0 μM | sd | % of Mock Oligo conc 5.0 μM | sd |
|---|---|---|---|---|---|---|---|---|
| 60827 | 104_1 | UBE3A | 128 | 14 | 111 | 9 | 111 | 6 |
| 60827 | 104_1 | UBE3A-SUP | 111 | 12 | 97 | 9 | 87 | 19 |
| 60827 | 104_1 | SNORD115 | 114 | 10 | 110 | 12 | 109 | 13 |
| 60827 | 104_2 | UBE3A | 108 | 10 | 111 | 16 | 109 | 10 |
| 60827 | 104_2 | UBE3A-SUP | 103 | 13 | 103 | 33 | 89 | 9 |
| 60827 | 105_1 | UBE3A | 122 | 13 | 121 | 12 | 121 | 4 |
| 60827 | 105_1 | UBE3A-SUP | 119 | 7 | 97 | 15 | 93 | 7 |
| 60827 | 105_1 | SNORD115 | 114 | 21 | 128 | 12 | 118 | 9 |
| 60827 | 105_2 | UBE3A | 123 | 5 | 110 | 9 | 114 | 8 |
| 60827 | 105_2 | UBE3A-SUP | 110 | 11 | 89 | 17 | 94 | 21 |
| 60827 | 105_2 | SNORD115 | 102 | 15 | 108 | 16 | 107 | 18 |
| 60827 | 106_1 | UBE3A | 114 | 17 | 133 | 23 | 125 | 9 |
| 60827 | 106_1 | UBE3A-SUP | 112 | 35 | 103 | 15 | 87 | 12 |
| 60827 | 106_2 | UBE3A | 110 | 12 | 130 | 22 | 123 | 14 |
| 60827 | 106_2 | UBE3A-SUP | 105 | 19 | 107 | 27 | 93 | 10 |
| 60828 | 107_1 | UBE3A | 83 | 11 | 117 | 13 | 112 | 6 |
| 60828 | 107_1 | UBE3A-SUP | 86 | 11 | 114 | 16 | 67 | 7 |
| 60828 | 107_1 | SNORD115 | 108 | 17 | 130 | 21 | 137 | 24 |
| 60828 | 107_2 | UBE3A | 143 | 42 | 117 | 10 | 122 | 11 |
| 60828 | 107_2 | UBE3A-SUP | 116 | 12 | 92 | 4 | 100 | 8 |
| 60828 | 107_2 | SNORD115 | 108 | 4 | 127 | 16 | 108 | 14 |
| 60828 | 108_1 | UBE3A | 120 | 7 | 127 | 31 | 132 | 31 |
| 60828 | 108_1 | UBE3A-SUP | 153 | 33 | 118 | 34 | 89 | 17 |
| 60828 | 108_1 | SNORD115 | 114 | 9 | 114 | 9 | 105 | 15 |
| 60828 | 108_2 | UBE3A | 122 | 18 | 133 | 26 | 128 | 9 |
| 60828 | 108_2 | UBE3A-SUP | 101 | 19 | 100 | 28 | 89 | 17 |
| 60828 | 109_1 | UBE3A | 108 | 10 | 129 | 14 | 128 | 5 |
| 60828 | 109_1 | UBE3A-SUP | 106 | 21 | 107 | 24 | 84 | 8 |
| 60828 | 109_2 | UBE3A | 109 | 11 | 110 | 8 | 111 | 13 |
| 60828 | 109_2 | UBE3A-SUP | 95 | 15 | 86 | 14 | 83 | 9 |
| 60829 | 110_1 | UBE3A | 104 | 6 | 83 | 3 | 101 | 15 |
| 60829 | 110_1 | UBE3A-SUP | 100 | 13 | 95 | 12 | 79 | 4 |
| 60829 | 110_1 | SNORD115 | 126 | 21 | 125 | 6 | 182 | 13 |
| 60829 | 110_2 | UBE3A | 92 | 7 | 87 | 8 | 96 | 7 |
| 60829 | 110_2 | UBE3A-SUP | 99 | 7 | 108 | 9 | 81 | 5 |
| 60829 | 110_2 | SNORD115 | 118 | 15 | 139 | 22 | 198 | 39 |
| 60830 | 111_1 | UBE3A | 110 | 6 | 122 | 13 | 124 | 10 |
| 60830 | 111_1 | UBE3A-SUP | 104 | 14 | 90 | 28 | 79 | 11 |
| 60830 | 111_2 | UBE3A | 115 | 10 | 120 | 15 | 121 | 10 |
| 60830 | 111_2 | UBE3A-SUP | 114 | 20 | 89 | 19 | 87 | 9 |
| 60831 | 112_1 | UBE3A | 93 | 8 | 94 | 13 | 106 | 10 |
| 60831 | 112_1 | UBE3A-SUP | 97 | 1 | 68 | 29 | 82 | 7 |
| 60831 | 112_1 | SNORD115 | 116 | 20 | 110 | 13 | 158 | 20 |
| 60831 | 112_2 | UBE3A | 83 | 8 | 78 | 7 | 83 | 6 |
| 60831 | 112_2 | UBE3A-SUP | 106 | 35 | 80 | 23 | 69 | 9 |
| 60831 | 112_2 | SNORD115 | 107 | 6 | 106 | 8 | 159 | 21 |
| 62198 | 113_1 | UBE3A | 110 | 3 | 122 | 6 | 134 | 9 |
| 62198 | 113_1 | UBE3A-SUP | 113 | 20 | 85 | 19 | 79 | 24 |
| 62198 | 113_1 | SNORD115 | 116 | 18 | 123 | 9 | 91 | 9 |
| 62284 | 115_1 | UBE3A | 105 | 14 | 98 | 19 | 141 | 36 |
| 62422 | 116_1 | UBE3A | 130 | 19 | 142 | 29 | 172 | 18 |
| 62423 | 117_1 | UBE3A | 76 | 8 | 93 | 13 | 171 | 17 |
| 62439 | 118_1 | UBE3A | 75 | 7 | 88 | 9 | 150 | 19 |
| 66378 | 119_1 | UBE3A | 96 | 14 | 93 | 5 | 110 | 10 |
| 77565 | 126_1 | UBE3A | 94 | 6 | 113 | 5 | 125 | 14 |
| 77565 | 126_1 | UBE3A-SUP | 83 | 17 | 95 | 33 | 85 | 5 |
| 77565 | 126_1 | SNORD115 | 105 | 11 | 123 | 19 | 152 | 15 |
| 77565 | 126_2 | UBE3A | 95 | 5 | 126 | 9 | 111 | 2 |
| 77565 | 126_2 | UBE3A-SUP | 77 | 27 | 106 | 21 | 83 | 15 |
| 77565 | 126_2 | SNORD115 | 115 | 17 | 157 | 13 | 180 | 15 |
| 92321 | 128_1 | UBE3A | 102 | 7 | 91 | 5 | 111 | 13 |
| 92321 | 128_1 | UBE3A-SUP | 115 | 3 | 104 | 25 | 91 | 13 |
| 92321 | 128_1 | SNORD115 | 135 | 9 | 132 | 12 | 196 | 35 |
| 92321 | 128_2 | UBE3A | 91 | 5 | 96 | 8 | 104 | 8 |
| 92321 | 128_2 | UBE3A-SUP | 112 | 20 | 92 | 20 | 79 | 7 |
| 92321 | 128_2 | SNORD115 | 125 | 7 | 111 | 13 | 169 | 12 |
| 92322 | 129_1 | UBE3A | 101 | 5 | 103 | 2 | 110 | 7 |
| 92322 | 129_1 | UBE3A-SUP | 99 | 39 | 113 | 12 | 94 | 13 |
| 92322 | 129_1 | SNORD115 | 124 | 25 | 114 | 6 | 140 | 13 |
| 92322 | 129_2 | UBE3A | 93 | 2 | 100 | 4 | 113 | 16 |
| 92322 | 129_2 | UBE3A-SUP | 109 | 4 | 102 | 22 | 85 | 7 |
| 92322 | 129_2 | SNORD115 | 103 | 11 | 99 | 9 | 152 | 31 |
| 97154 | 132_1 | UBE3A | 100 | 10 | 128 | 13 | 142 | 13 |
| 97154 | 132_1 | UBE3A-SUP | 103 | 9 | 115 | 8 | 109 | 6 |

TABLE 5-continued

Oligonucleotide activity in patient derived human neuronal cell cultures.

| Start SEQ ID NO 1 | CMP ID NO | Target | % of Mock Oligo conc 0.2 µM | sd | % of Mock Oligo conc 1.0 µM | sd | % of Mock Oligo conc 5.0 µM | sd |
|---|---|---|---|---|---|---|---|---|
| 97154 | 132_1 | SNORD115 | 49 | 7 | 90 | 12 | 143 | 25 |
| 97154 | 132_2 | UBE3A | 111 | 8 | 128 | 17 | 128 | 17 |
| 97154 | 132_2 | UBE3A-SUP | 95 | 7 | 116 | 9 | 105 | 13 |
| 97154 | 133_2 | SNORD115 | 86 | 7 | 106 | 9 | 121 | 9 |
| 97154 | 133_1 | UBE3A | 101 | 3 | 107 | 11 | 124 | 19 |
| 97154 | 133_1 | UBE3A-SUP | 112 | 9 | 117 | 7 | 146 | 25 |
| 97154 | 133_1 | SNORD115 | 60 | 7 | 110 | 15 | 141 | 15 |
| 97154 | 133_2 | UBE3A | 94 | 13 | 116 | 14 | 138 | 12 |
| 97154 | 133_2 | UBE3A-SUP | 116 | 6 | 128 | 13 | 148 | 38 |
| 97154 | 132_2 | SNORD115 | 70 | 5 | 108 | 9 | 160 | 34 |
| 106137 | 137_1 | UBE3A | 83 | 12 | 74 | 11 | 124 | 20 |
| 109404 | 138_1 | UBE3A | 80 | 20 | 92 | 7 | 120 | 21 |
| 110766 | 139_1 | UBE3A | 76 | 5 | 85 | 12 | 121 | 17 |
| 114826 | 140_1 | UBE3A | 87 | 10 | 88 | 11 | 136 | 9 |
| 118637 | 143_1 | UBE3A | 83 | 7 | 104 | 30 | 141 | 28 |
| 118639 | 144_1 | UBE3A | 74 | 17 | 31 | 39 | 106 | 33 |
| 124160 | 145_2 | UBE3A | 89 | 6 | 95 | 10 | 115 | 25 |
| 125499 | 146_1 | UBE3A | 83 | 13 | 76 | 7 | 124 | 16 |
| 125499 | 146_2 | UBE3A | 123 | 30 | 79 | 14 | 102 | 13 |
| 125538 | 150_2 | UBE3A | 82 | 17 | 82 | 7 | 119 | 24 |

Figure 2:
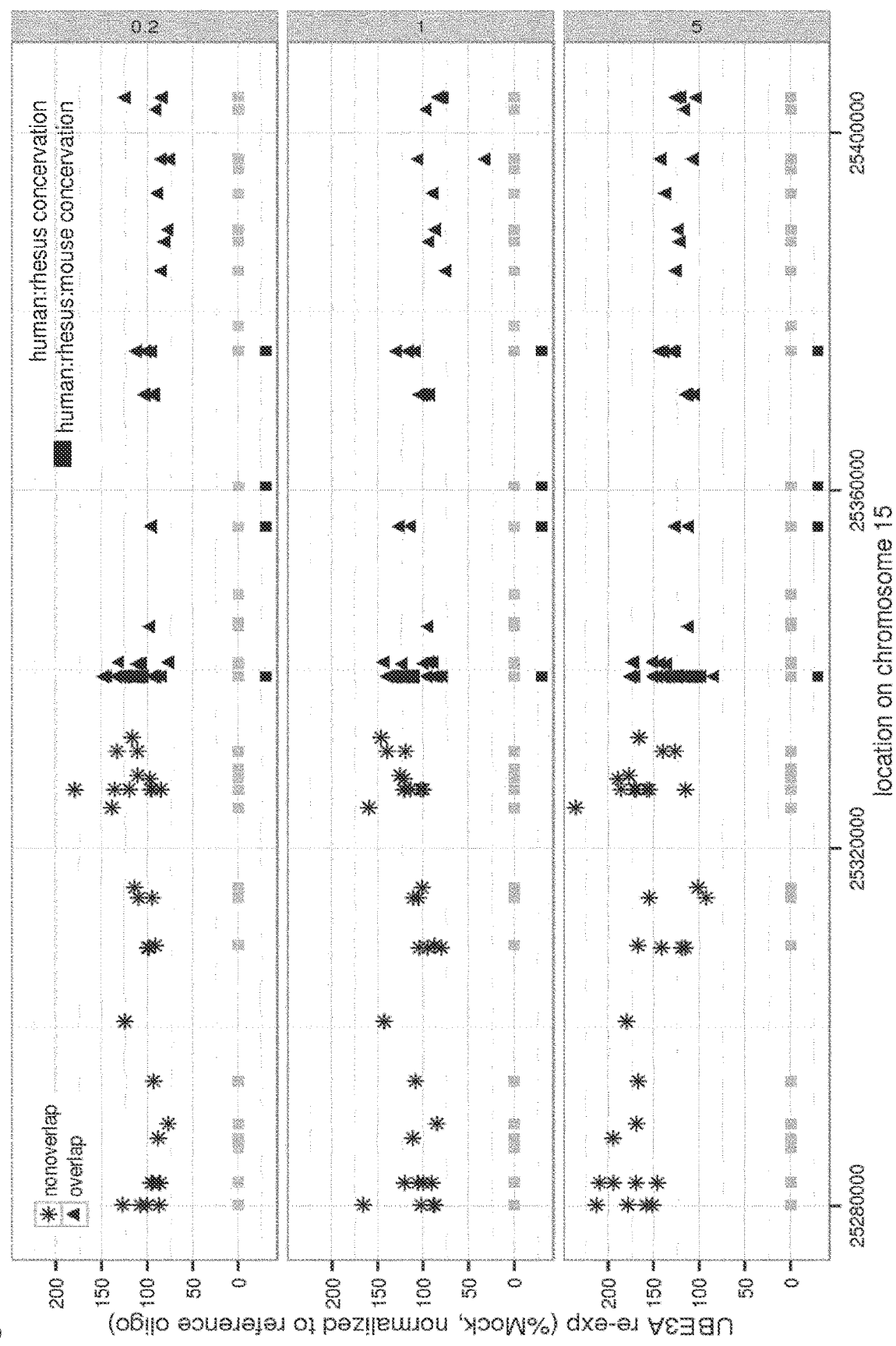
FIG. 2: Representation of the ability of the oligonucleotides, tested in Example 2, to induce re-expression of UBE3A in human neuronal cell cultures. Oligonucleotides complementary to the region of human SNHG14 long non-coding RNA between SNORD109B and the region upstream of the UBE3A coding region (position 1 to 55318 of SEQ ID NO: 1) are indicated with ● nonoverlap. Oligonucleotides complementary to the region of human SNHG14 long non-coding RNA which is antisense to the UBE3A pre-mRNA (position 55319 to 141053 of SEQ ID NO: 1) are indicated with ▲ overlap. Oligonucleotides from Table 3 with conservation to human and rhesus monkey are indicated at the bottom of each plot as ▢. Conservation between human:rhesus:mouse is indicated by ▬. The oligonucleotide concentrations were 0.2, 1 and 5 microM as indicated in the right hand side each plot.

Of the 187 compounds tested approximately 90% showed re-expression of UBE3A when compared to the mock oligonucleotide at the 5 micro Molar concentration. The number of oligonucleotides capable of inducing re-expression of UBE3A is higher in the region between position 1 to 55318 of SEQ ID NO: 1 (non-overlapping region) then in the region complementary to UBE3A coding region (overlapping region. FIG. 2 plots the distribution of the oligonucleotides according to their position on chromosome 15 versus the UBE3A mRNA expression relative to the mock oligonucleotide.

For the oligonucleotides where SNORD115 has been tested there is no significant down regulation when compared to mock at 1 and 5 microM.

Example 3—Activity of Oligonucleotides Targeting the SNHG14 Transcript in the Region Downstream of SNORD109B and Upstream of the Region Antisense to to the UBE3A Pre-mRNA Oligonucleotides targeting position 4806-54939 of SEQ ID NO: 1 were tested in patient derived human neuronal cell cultures (see protocol in "Materials and methods" section). The oligonucleotides ability to reduce the SNHG14 transcript in the region downstream of SNORD109B (also termed UBE3A suppressor or UBE3A-SUP in the data table. Furthermore, the ability to induce UBE3A mRNA re-expression was analyzed.

The oligonucleotides were screened according to the protocol for screening oligonucleotides in human neuronal cell cultures described in the section "Materials and methods"—"Screening oligonucleotides in human neuronal cell cultures—96 well system"

The results are shown in table 6.

TABLE 6

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 4806 | 151_1 | 0.2 | 66 | 2 | 125 | NA |
| 4806 | 151_1 | 1 | 53 | 10 | NA | NA |
| 4808 | 152_1 | 0.2 | 49 | 6 | 167 | NA |
| 4808 | 152_1 | 1 | 33 | 4 | 289 | NA |
| 4809 | 153_1 | 0.2 | 41 | 1 | 208 | NA |
| 4809 | 153_1 | 1 | 29 | 10 | NA | NA |
| 4811 | 154_1 | 0.2 | 48 | 3 | 282 | NA |
| 4811 | 154_1 | 1 | 37 | 5 | 331 | NA |
| 4812 | 155_1 | 0.2 | 35 | 5 | 286 | 64 |
| 4812 | 155_1 | 1 | 32 | 3 | 327 | 21 |
| 4972 | 156_1 | 0.2 | 60 | 6 | 145 | 6 |
| 4972 | 156_1 | 1 | 46 | 14 | 145 | NA |
| 4973 | 157_1 | 0.2 | 75 | 9 | 128 | 6 |
| 4973 | 157_1 | 1 | 59 | NA | 158 | NA |
| 4979 | 158_1 | 0.2 | 46 | 9 | 131 | NA |
| 4979 | 158_1 | 1 | 37 | 5 | 219 | 8 |
| 5058 | 159_1 | 0.2 | 69 | 6 | 133 | 19 |

TABLE 6-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 5058 | 159_1 | 1 | 51 | 14 | NA | NA |
| 5071 | 160_1 | 0.2 | 55 | 8 | 98 | NA |
| 5071 | 160_1 | 1 | 39 | 7 | 136 | 34 |
| 5078 | 161_1 | 0.2 | 65 | 7 | 205 | 18 |
| 5078 | 161_1 | 1 | 51 | 10 | 306 | 31 |
| 5094 | 162_1 | 0.2 | 53 | 5 | 154 | 27 |
| 5094 | 162_1 | 1 | 34 | 8 | 300 | 65 |
| 5096 | 163_1 | 0.2 | 44 | 1 | 206 | 49 |
| 5096 | 163_1 | 1 | 36 | 6 | 316 | NA |
| 5100 | 164_1 | 0.2 | 34 | 3 | 220 | NA |
| 5100 | 164_1 | 1 | 30 | 3 | 227 | 32 |
| 5101 | 165_1 | 0.2 | 38 | 7 | 245 | NA |
| 5101 | 165_1 | 1 | 36 | 4 | 246 | 55 |
| 5218 | 166_1 | 0.2 | 45 | 4 | 240 | NA |
| 5218 | 166_1 | 1 | 36 | 6 | 280 | 44 |
| 5218 | 167_1 | 0.2 | 46 | 2 | 261 | NA |
| 5218 | 167_1 | 1 | 31 | 4 | 346 | 30 |
| 5224 | 168_1 | 0.2 | 39 | 3 | 377 | 40 |
| 5224 | 168_1 | 1 | 33 | 5 | 338 | 65 |
| 5224 | 169_1 | 0.2 | 37 | 4 | 313 | NA |
| 5224 | 169_1 | 1 | 3 | 2 | 308 | 3 |
| 5427 | 170_1 | 0.2 | 89 | 13 | 105 | 26 |
| 5427 | 170_1 | 1 | 117 | 35 | 124 | NA |
| 5434 | 171_1 | 0.2 | 51 | 5 | 164 | 10 |
| 5434 | 171_1 | 1 | 33 | 6 | 213 | 46 |
| 5785 | 172_1 | 0.2 | 46 | 5 | 210 | NA |
| 5785 | 172_1 | 1 | 38 | 4 | 342 | NA |
| 5786 | 173_1 | 0.2 | 54 | 4 | 292 | 61 |
| 5786 | 173_1 | 1 | 3 | 6 | 552 | NA |
| 6341 | 174_1 | 0.2 | 97 | 11 | 126 | 3 |
| 6341 | 174_1 | 1 | 90 | 33 | NA | NA |
| 6694 | 175_1 | 0.2 | 44 | 4 | 226 | NA |
| 6694 | 175_1 | 1 | 35 | 4 | 296 | NA |
| 6695 | 176_1 | 0.2 | 32 | 7 | 297 | 87 |
| 6695 | 176_1 | 1 | 29 | 4 | 263 | 9 |
| 6958 | 177_1 | 0.2 | 58 | 7 | 244 | 76 |
| 6958 | 177_1 | 1 | 47 | NA | NA | NA |
| 7159 | 179_1 | 0.2 | 33 | 4 | 282 | NA |
| 7159 | 179_1 | 1 | 29 | 5 | 289 | 7 |
| 7159 | 178_1 | 0.2 | 43 | 5 | 248 | NA |
| 7159 | 178_1 | 1 | 32 | 4 | 258 | NA |
| 7720 | 180_1 | 0.2 | 75 | 6 | 144 | 36 |
| 7720 | 180_1 | 1 | 54 | 7 | 233 | 26 |
| 7724 | 181_1 | 0.2 | 72 | 6 | 177 | 20 |
| 7724 | 181_1 | 1 | 45 | 19 | 224 | 62 |
| 7725 | 182_1 | 0.2 | 65 | 5 | 139 | 37 |
| 7725 | 182_1 | 1 | 47 | 4 | 208 | 76 |
| 7725 | 183_1 | 0.2 | 103 | 13 | 140 | 2 |
| 7725 | 183_1 | 1 | 74 | 6 | NA | NA |
| 7727 | 184_1 | 0.2 | 45 | 2 | 300 | 107 |
| 7727 | 184_1 | 1 | 35 | 2 | 272 | 16 |
| 8117 | 185_1 | 0.2 | 87 | 17 | 122 | 13 |
| 8117 | 185_1 | 1 | 63 | 17 | 175 | NA |
| 8118 | 186_1 | 0.2 | 40 | 5 | 368 | 105 |
| 8118 | 186_1 | 1 | 33 | 5 | NA | NA |
| 8119 | 187_1 | 0.2 | 62 | 5 | 197 | NA |
| 8119 | 187_1 | 1 | 43 | 13 | 517 | 143 |
| 8120 | 188_1 | 0.2 | 96 | 10 | 136 | 41 |
| 8120 | 188_1 | 1 | 79 | 22 | 146 | 19 |
| 8571 | 189_1 | 0.2 | 53 | 11 | 204 | NA |
| 8571 | 189_1 | 1 | 49 | 24 | 298 | 15 |
| 8573 | 190_1 | 0.2 | 54 | 9 | 140 | 9 |
| 8573 | 190_1 | 1 | 50 | 10 | 267 | 4 |
| 8574 | 191_1 | 0.2 | 56 | 1 | 117 | NA |
| 8574 | 191_1 | 1 | 57 | 13 | 199 | NA |
| 8575 | 192_1 | 0.2 | 56 | 9 | 165 | 10 |
| 8575 | 192_1 | 1 | 54 | 13 | 246 | NA |
| 8576 | 193_1 | 0.2 | 56 | 6 | 185 | 7 |
| 8576 | 193_1 | 1 | 52 | 8 | 330 | 35 |
| 8585 | 194_1 | 0.2 | 47 | 2 | 302 | NA |
| 8585 | 194_1 | 1 | 39 | 7 | NA | NA |
| 8819 | 195_1 | 0.2 | 62 | 10 | 155 | 10 |
| 8819 | 195_1 | 1 | 41 | 3 | 192 | 7 |
| 8820 | 196_1 | 0.2 | 55 | 12 | 237 | 69 |
| 8820 | 196_1 | 1 | 40 | 3 | 278 | 26 |

TABLE 6-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 8887 | 197_1 | 0.2 | 69 | 15 | 301 | 59 |
| 8887 | 197_1 | 1 | 58 | 7 | 383 | 92 |
| 9150 | 198_1 | 0.2 | 49 | 6 | NA | NA |
| 9150 | 198_1 | 1 | 43 | 3 | 365 | 38 |
| 9201 | 199_1 | 0.2 | 79 | 23 | 88 | 42 |
| 9201 | 199_1 | 1 | 64 | 24 | 140 | 22 |
| 9202 | 201_1 | 0.2 | 61 | 10 | NA | NA |
| 9202 | 201_1 | 1 | 45 | 8 | 343 | 27 |
| 9202 | 200_1 | 0.2 | 47 | 3 | 287 | 76 |
| 9202 | 200_1 | 1 | 41 | 4 | 281 | NA |
| 9203 | 202_1 | 0.2 | 55 | 17 | 166 | 92 |
| 9203 | 202_1 | 1 | 40 | 5 | 297 | 54 |
| 9209 | 203_1 | 0.2 | 60 | 1 | 122 | NA |
| 9209 | 203_1 | 1 | 40 | 14 | 204 | 8 |
| 9210 | 204_1 | 0.2 | 43 | 2 | 216 | NA |
| 9210 | 204_1 | 1 | 37 | 3 | 409 | NA |
| 9210 | 205_1 | 0.2 | 45 | 8 | 187 | NA |
| 9210 | 205_1 | 1 | 37 | 22 | 336 | 18 |
| 9211 | 206_1 | 0.2 | 51 | 10 | 384 | 17 |
| 9211 | 206_1 | 1 | 42 | 3 | 381 | 35 |
| 9211 | 207_1 | 0.2 | 65 | 8 | 301 | 28 |
| 9211 | 207_1 | 1 | 50 | 5 | 272 | 53 |
| 9212 | 35_2 | 0.2 | 42 | 11 | 203 | 16 |
| 9212 | 35_2 | 1 | 44 | 18 | 335 | NA |
| 9212 | 208_1 | 0.2 | 64 | 5 | 147 | 58 |
| 9212 | 208_1 | 1 | 50 | 6 | 260 | 73 |
| 9213 | 209_1 | 0.2 | 57 | 7 | NA | NA |
| 9213 | 209_1 | 1 | 49 | 4 | 346 | 31 |
| 9214 | 210_1 | 0.2 | 49 | 7 | 139 | NA |
| 9214 | 210_1 | 1 | 45 | 7 | 223 | 59 |
| 10832 | 211_1 | 0.2 | 70 | 6 | 147 | 10 |
| 10832 | 211_1 | 1 | 56 | 9 | 200 | 38 |
| 10837 | 212_1 | 0.2 | 59 | 9 | 146 | 46 |
| 10837 | 212_1 | 1 | 41 | 6 | 226 | 47 |
| 10838 | 213_1 | 0.2 | 50 | 8 | 247 | 69 |
| 10838 | 213_1 | 1 | 44 | 12 | 307 | NA |
| 10877 | 214_1 | 0.2 | 108 | 21 | 115 | 1 |
| 10877 | 214_1 | 1 | 92 | 37 | 88 | 32 |
| 11434 | 215_1 | 0.2 | 97 | 12 | 8 | 23 |
| 11434 | 215_1 | 1 | 80 | 26 | 111 | 11 |
| 11435 | 216_1 | 0.2 | 90 | 16 | 87 | NA |
| 11435 | 216_1 | 1 | 8 | 29 | 82 | 21 |
| 11436 | 217_1 | 0.2 | 87 | 6 | 83 | 11 |
| 11436 | 217_1 | 1 | 68 | 26 | 123 | NA |
| 11438 | 218_1 | 0.2 | 57 | 5 | 133 | NA |
| 11438 | 218_1 | 1 | 44 | 16 | 188 | NA |
| 11439 | 219_1 | 0.2 | 84 | 1 | 93 | NA |
| 11439 | 219_1 | 1 | 66 | 22 | 113 | 29 |
| 11464 | 220_1 | 0.2 | 67 | 9 | 209 | 51 |
| 11464 | 220_1 | 1 | 41 | 6 | 256 | 33 |
| 11507 | 221_1 | 0.2 | 59 | 6 | 237 | NA |
| 11507 | 221_1 | 1 | 40 | 63 | 320 | NA |
| 11508 | 222_1 | 0.2 | 53 | 7 | 195 | NA |
| 11508 | 222_1 | 1 | 48 | 12 | 302 | NA |
| 11511 | 223_1 | 0.2 | 41 | 3 | 210 | 6 |
| 11511 | 223_1 | 1 | 37 | 9 | 273 | NA |
| 11513 | 224_1 | 0.2 | 22 | 8 | 288 | 91 |
| 11513 | 224_1 | 1 | 26 | 5 | 360 | 46 |
| 11514 | 225_1 | 0.2 | 98 | 17 | 98 | 31 |
| 11514 | 225_1 | 1 | 68 | 16 | 129 | 11 |
| 11736 | 226_1 | 0.2 | 69 | 8 | 197 | 80 |
| 11736 | 226_1 | 1 | 55 | 7 | 329 | 66 |
| 12361 | 227_1 | 0.2 | 48 | 8 | 183 | 56 |
| 12361 | 227_1 | 1 | 37 | 4 | 193 | 46 |
| 12794 | 228_1 | 0.2 | 38 | 9 | 201 | 71 |
| 12794 | 228_1 | 1 | 32 | 2 | 362 | 48 |
| 12795 | 229_1 | 0.2 | 50 | 12 | 161 | 30 |
| 12795 | 229_1 | 1 | 34 | 7 | 301 | 35 |
| 12796 | 230_1 | 0.2 | 44 | 12 | 237 | 86 |
| 12796 | 230_1 | 1 | 32 | 3 | 379 | 106 |
| 12894 | 232_1 | 0.2 | 91 | 17 | 79 | 27 |
| 12894 | 232_1 | 1 | 66 | 10 | 99 | 24 |
| 12894 | 231_1 | 0.2 | 80 | 5 | 89 | NA |
| 12894 | 231_1 | 1 | 57 | 14 | 164 | 31 |
| 12895 | 234_1 | 0.2 | 88 | 11 | 75 | 32 |

TABLE 6-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 12895 | 234_1 | 1 | 68 | 19 | 91 | 24 |
| 12895 | 233_1 | 0.2 | 57 | 5 | 199 | 37 |
| 12895 | 233_1 | 1 | 38 | 7 | 249 | 57 |
| 12896 | 235_1 | 0.2 | 72 | 3 | 176 | 9 |
| 12896 | 235_1 | 1 | 45 | 3 | 251 | 42 |
| 13223 | 236_1 | 0.2 | 40 | 3 | 267 | 66 |
| 13223 | 236_1 | 1 | 31 | 3 | 270 | 23 |
| 13224 | 238_1 | 0.2 | 33 | 3 | 265 | NA |
| 13224 | 238_1 | 1 | 28 | 4 | 265 | 6 |
| 13224 | 237_1 | 0.2 | 38 | 2 | 212 | NA |
| 13224 | 237_1 | 1 | 31 | 1 | 254 | 31 |
| 13225 | 239_1 | 0.2 | 42 | 5 | 317 | 113 |
| 13225 | 239_1 | 1 | 29 | 7 | 215 | 26 |
| 13226 | 240_1 | 0.2 | 38 | 7 | 223 | NA |
| 13226 | 240_1 | 1 | 32 | 5 | 232 | 16 |
| 15115 | 241_1 | 0.2 | 61 | 8 | 377 | 15 |
| 15115 | 241_1 | 1 | 41 | 3 | 377 | 43 |
| 15258 | 242_1 | 0.2 | 66 | 14 | 133 | 35 |
| 15258 | 242_1 | 1 | 55 | 10 | 170 | 17 |
| 15568 | 243_1 | 0.2 | 62 | 13 | 192 | 58 |
| 15568 | 243_1 | 1 | 41 | 11 | 309 | 5 |
| 15570 | 244_1 | 0.2 | 53 | 17 | 252 | 59 |
| 15570 | 244_1 | 1 | 44 | 5 | 332 | 52 |
| 15572 | 245_1 | 0.2 | 57 | 21 | 321 | 122 |
| 15572 | 245_1 | 1 | 4 | 7 | 407 | 77 |
| 15573 | 246_1 | 0.2 | 47 | 16 | 348 | 129 |
| 15573 | 246_1 | 1 | 40 | 7 | 410 | 69 |
| 15574 | 247_1 | 0.2 | 48 | 14 | 326 | 116 |
| 15574 | 247_1 | 1 | 44 | 8 | 411 | 36 |
| 15722 | 248_1 | 0.2 | 51 | 3 | 258 | 17 |
| 15722 | 248_1 | 1 | 36 | 3 | 230 | NA |
| 16597 | 249_1 | 0.2 | 66 | 19 | 111 | 39 |
| 16597 | 249_1 | 1 | 54 | 14 | 174 | 44 |
| 16603 | 250_1 | 0.2 | 67 | 26 | 89 | 31 |
| 16603 | 250_1 | 1 | 56 | 6 | 172 | 32 |
| 16730 | 251_1 | 0.2 | 36 | 5 | 354 | 41 |
| 16730 | 251_1 | 1 | 31 | 2 | 326 | 75 |
| 16849 | 252_1 | 0.2 | 74 | 17 | 188 | 81 |
| 16849 | 252_1 | 1 | 48 | 17 | 282 | 1 |
| 17089 | 253_1 | 0.2 | 70 | 17 | 98 | 37 |
| 17089 | 253_1 | 1 | 62 | 19 | 153 | 13 |
| 17401 | 254_1 | 0.2 | 42 | 6 | 209 | 83 |
| 17401 | 254_1 | 1 | 29 | 3 | 327 | 49 |
| 24290 | 255_1 | 0.2 | 106 | 13 | 105 | 36 |
| 24290 | 255_1 | 1 | 109 | 21 | 136 | NA |
| 24296 | 256_1 | 0.2 | 92 | 20 | 117 | 30 |
| 24296 | 256_1 | 1 | 93 | 15 | 138 | 21 |
| 24811 | 257_1 | 0.2 | 85 | 12 | 126 | 4 |
| 24811 | 257_1 | 1 | 74 | 12 | 137 | 7 |
| 25032 | 258_1 | 0.2 | 50 | 11 | 329 | 131 |
| 25032 | 258_1 | 1 | 39 | 5 | 411 | 53 |
| 25033 | 259_1 | 0.2 | 40 | 10 | 343 | 50 |
| 25033 | 259_1 | 1 | 31 | 3 | 483 | 84 |
| 25250 | 260_1 | 0.2 | 33 | 10 | 279 | 42 |
| 25250 | 260_1 | 1 | 33 | 4 | 338 | 65 |
| 25251 | 261_1 | 0.2 | 40 | 8 | 209 | 97 |
| 25251 | 261_1 | 1 | 34 | 3 | 370 | 57 |
| 25718 | 262_1 | 0.2 | 56 | 20 | 113 | 48 |
| 25718 | 262_1 | 1 | 45 | 8 | 198 | 65 |
| 25720 | 263_1 | 0.2 | 84 | 7 | 121 | 39 |
| 25720 | 263_1 | 1 | 72 | 11 | 88 | 10 |
| 25721 | 264_1 | 0.2 | 83 | 15 | 87 | 40 |
| 25721 | 264_1 | 1 | 84 | 22 | NA | NA |
| 26331 | 265_1 | 0.2 | 93 | 5 | 88 | 38 |
| 26331 | 265_1 | 1 | 81 | 8 | NA | NA |
| 27165 | 266_1 | 0.2 | 63 | 3 | 117 | 39 |
| 27165 | 266_1 | 1 | 46 | 9 | 174 | 15 |
| 27248 | 267_1 | 0.2 | 81 | 10 | 124 | 17 |
| 27248 | 267_1 | 1 | 59 | 10 | 190 | 112 |
| 29330 | 268_1 | 0.2 | 109 | 4 | 124 | 48 |
| 29330 | 268_1 | 1 | 98 | 28 | 114 | 35 |
| 29635 | 269_1 | 0.2 | 45 | 1 | 218 | 50 |
| 29635 | 269_1 | 1 | 33 | 9 | 267 | NA |
| 29635 | 270_1 | 0.2 | 55 | 5 | 225 | 41 |
| 29635 | 270_1 | 1 | 45 | 8 | NA | NA |

TABLE 6-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 29636 | 271_1 | 0.2 | 48 | 2 | 285 | 56 |
| 29636 | 271_1 | 1 | 40 | 7 | 359 | 99 |
| 29636 | 272_1 | 0.2 | 48 | 3 | 166 | 5 |
| 29636 | 272_1 | 1 | 35 | 8 | 293 | 40 |
| 29637 | 273_1 | 0.2 | 56 | 5 | 255 | 47 |
| 29637 | 273_1 | 1 | 46 | 4 | 300 | 105 |
| 29637 | 274_1 | 0.2 | 67 | 7 | 134 | 35 |
| 29637 | 274_1 | 1 | 54 | 7 | 234 | 19 |
| 29661 | 275_1 | 0.2 | 5 | 3 | 167 | 15 |
| 29661 | 275_1 | 1 | 42 | 11 | 251 | NA |
| 29661 | 276_1 | 0.2 | 54 | 5 | 127 | 17 |
| 29661 | 276_1 | 1 | 39 | 8 | 229 | NA |
| 29684 | 277_1 | 0.2 | 40 | 3 | 168 | 73 |
| 29684 | 277_1 | 1 | 31 | 13 | NA | NA |
| 29684 | 278_1 | 0.2 | 46 | 7 | 179 | 2 |
| 29684 | 278_1 | 1 | 36 | 8 | NA | NA |
| 30455 | 279_1 | 0.2 | 102 | 20 | 96 | 34 |
| 30455 | 279_1 | 1 | 86 | 22 | 118 | 23 |
| 30456 | 280_1 | 0.2 | 94 | 23 | 91 | 28 |
| 30456 | 280_1 | 1 | 83 | 18 | 134 | 36 |
| 30457 | 281_1 | 0.2 | 89 | 23 | 97 | 37 |
| 30457 | 281_1 | 1 | 94 | 23 | 106 | 39 |
| 30458 | 282_1 | 0.2 | 99 | 14 | 77 | 27 |
| 30458 | 282_1 | 1 | 103 | 17 | 96 | 20 |
| 30462 | 283_1 | 0.2 | 66 | 26 | 98 | 36 |
| 30462 | 283_1 | 1 | 56 | 14 | 129 | 13 |
| 30465 | 284_1 | 0.2 | 73 | 11 | 114 | 47 |
| 30465 | 284_1 | 1 | 57 | 10 | 197 | 63 |
| 30601 | 285_1 | 0.2 | 41 | 31 | 311 | 29 |
| 30601 | 285_1 | 1 | 30 | 16 | 373 | 40 |
| 30605 | 286_1 | 0.2 | 40 | 2 | 221 | 86 |
| 30605 | 286_1 | 1 | 33 | 6 | 375 | NA |
| 30609 | 287_1 | 0.2 | 43 | 3 | 267 | 65 |
| 30609 | 287_1 | 1 | 37 | 5 | 332 | 27 |
| 30610 | 288_1 | 0.2 | 46 | 6 | 253 | 79 |
| 30610 | 288_1 | 1 | 38 | 3 | 338 | NA |
| 30667 | 289_1 | 0.2 | 38 | 15 | 325 | 144 |
| 30667 | 289_1 | 1 | 36 | 3 | 461 | 68 |
| 30668 | 290_1 | 0.2 | 74 | 19 | 124 | 54 |
| 30668 | 290_1 | 1 | 58 | 14 | 183 | 20 |
| 30669 | 291_1 | 0.2 | 86 | 18 | 98 | 40 |
| 30669 | 291_1 | 1 | 78 | 12 | 133 | 26 |
| 30670 | 292_1 | 0.2 | 93 | 10 | 86 | 31 |
| 30670 | 292_1 | 1 | 94 | 16 | 127 | 22 |
| 30679 | 293_1 | 0.2 | 85 | 19 | 83 | 21 |
| 30679 | 293_1 | 1 | 87 | 21 | 113 | 23 |
| 30681 | 294_1 | 0.2 | 92 | 17 | 78 | 20 |
| 30681 | 294_1 | 1 | 100 | 19 | 86 | 22 |
| 30682 | 295_1 | 0.2 | 93 | 22 | 101 | 40 |
| 30682 | 295_1 | 1 | 94 | 33 | 101 | 8 |
| 30699 | 296_1 | 0.2 | 80 | 24 | 134 | 6 |
| 30699 | 296_1 | 1 | 47 | 21 | 232 | 36 |
| 30700 | 297_1 | 0.2 | 53 | 5 | 146 | 26 |
| 30700 | 297_1 | 1 | 32 | 8 | NA | NA |
| 30700 | 298_1 | 0.2 | 47 | 4 | 221 | NA |
| 30700 | 298_1 | 1 | 38 | 0 | 294 | NA |
| 30701 | 299_1 | 0.2 | 49 | 4 | 140 | NA |
| 30701 | 299_1 | 1 | 23 | NA | NA | NA |
| 30701 | 300_1 | 0.2 | 50 | 9 | 163 | 19 |
| 30701 | 300_1 | 1 | 39 | 11 | 346 | 11 |
| 30702 | 301_1 | 0.2 | 66 | 9 | 116 | 36 |
| 30702 | 301_1 | 1 | 44 | 14 | 230 | 51 |
| 30711 | 302_1 | 0.2 | 41 | 14 | 288 | 120 |
| 30711 | 302_1 | 1 | 40 | 5 | 422 | 132 |
| 30714 | 303_1 | 0.2 | 45 | 9 | 355 | 94 |
| 30714 | 303_1 | 1 | 31 | 5 | 355 | 8 |
| 30715 | 305_1 | 0.2 | 39 | 4 | 292 | 56 |
| 30715 | 305_1 | 1 | 34 | 12 | 253 | 5 |
| 30715 | 304_1 | 0.2 | 50 | 13 | 263 | 87 |
| 30715 | 304_1 | 1 | 43 | 7 | 285 | 12 |
| 31630 | 306_1 | 0.2 | 92 | 32 | 134 | 48 |
| 31630 | 306_1 | 1 | 85 | 25 | 177 | 26 |
| 31632 | 307_1 | 0.2 | 94 | 24 | 92 | 32 |
| 31632 | 307_1 | 1 | 86 | 17 | 109 | 33 |
| 31633 | 308_1 | 0.2 | 92 | 18 | 78 | 13 |

TABLE 6-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 31633 | 308_1 | 1 | 102 | 23 | 98 | 7 |
| 32755 | 310_1 | 0.2 | 47 | 12 | 220 | 40 |
| 32755 | 310_1 | 1 | 40 | 16 | 285 | NA |
| 32755 | 309_1 | 0.2 | 62 | 6 | 167 | NA |
| 32755 | 309_1 | 1 | 40 | 10 | 225 | NA |
| 32756 | 311_1 | 0.2 | 55 | 9 | 128 | 9 |
| 32756 | 311_1 | 1 | 56 | NA | 224 | NA |
| 33366 | 312_1 | 0.2 | 64 | 23 | 121 | 4 |
| 33366 | 312_1 | 1 | 56 | 10 | 137 | 1 |
| 33367 | 313_1 | 0.2 | 81 | 7 | 9 | NA |
| 33367 | 313_1 | 1 | 79 | 22 | 115 | 12 |
| 33368 | 314_1 | 0.2 | 70 | 4 | 103 | NA |
| 33368 | 314_1 | 1 | 57 | 15 | 157 | NA |
| 33369 | 315_1 | 0.2 | 73 | 12 | 87 | 20 |
| 33369 | 315_1 | 1 | 67 | 19 | 155 | NA |
| 33375 | 316_1 | 0.2 | 79 | 18 | 100 | 18 |
| 33375 | 316_1 | 1 | 51 | 14 | 159 | 39 |
| 33377 | 317_1 | 0.2 | 46 | 21 | 248 | 72 |
| 33377 | 317_1 | 1 | 41 | 9 | 313 | NA |
| 33378 | 318_1 | 0.2 | 38 | 17 | 273 | 63 |
| 33378 | 318_1 | 1 | 36 | 7 | 321 | 1 |
| 36606 | 319_1 | 0.2 | 79 | 10 | 154 | 21 |
| 36606 | 319_1 | 1 | 48 | 9 | 233 | 65 |
| 36607 | 320_1 | 0.2 | 60 | 9 | 157 | 18 |
| 36607 | 320_1 | 1 | 49 | 9 | 206 | 25 |
| 38092 | 321_1 | 0.2 | 51 | 10 | 221 | 59 |
| 38092 | 321_1 | 1 | 41 | 5 | 328 | 39 |
| 38297 | 322_1 | 0.2 | 43 | 9 | 298 | 31 |
| 38297 | 322_1 | 1 | 34 | 6 | 365 | 91 |
| 39173 | 323_1 | 0.2 | 98 | 8 | 119 | 27 |
| 39173 | 323_1 | 1 | 82 | 20 | 177 | 21 |
| 39174 | 324_1 | 0.2 | 89 | 8 | 139 | 24 |
| 39174 | 324_1 | 1 | 84 | 23 | 192 | 15 |
| 39175 | 325_1 | 0.2 | 93 | 18 | 167 | 13 |
| 39175 | 325_1 | 1 | 68 | 17 | 203 | 33 |
| 39176 | 326_1 | 0.2 | 79 | 12 | 185 | 83 |
| 39176 | 326_1 | 1 | 55 | 17 | 374 | 107 |
| 39228 | 327_1 | 0.2 | 75 | 12 | 151 | 29 |
| 39228 | 327_1 | 1 | 57 | 8 | 207 | 32 |
| 39230 | 328_1 | 0.2 | 65 | 11 | 176 | 19 |
| 39230 | 328_1 | 1 | 52 | 19 | 357 | NA |
| 39231 | 329_1 | 0.2 | 63 | 19 | 150 | 35 |
| 39231 | 329_1 | 1 | 46 | 6 | 257 | 43 |
| 39563 | 330_1 | 0.2 | 69 | 10 | 116 | 34 |
| 39563 | 330_1 | 1 | 56 | 11 | 196 | NA |
| 39808 | 331_1 | 0.2 | 40 | 8 | 201 | 17 |
| 39808 | 331_1 | 1 | 25 | 5 | 300 | NA |
| 39808 | 332_1 | 0.2 | 40 | 14 | 282 | 109 |
| 39808 | 332_1 | 1 | 33 | 7 | 404 | 81 |
| 39931 | 333_1 | 0.2 | 80 | 11 | 107 | 53 |
| 39931 | 333_1 | 1 | 70 | 16 | 112 | 26 |
| 41114 | 334_1 | 0.2 | 64 | 4 | 113 | NA |
| 41114 | 334_1 | 1 | 28 | NA | 179 | NA |
| 41444 | 335_1 | 0.2 | 57 | 17 | 165 | 39 |
| 41444 | 335_1 | 1 | 46 | 4 | 290 | 40 |
| 41445 | 336_1 | 0.2 | 51 | 2 | 134 | NA |
| 41445 | 336_1 | 1 | 42 | 15 | 238 | NA |
| 41446 | 337_1 | 0.2 | 63 | 1 | 108 | NA |
| 41446 | 337_1 | 1 | 56 | 14 | 151 | 22 |
| 41725 | 338_1 | 0.2 | 91 | 16 | 130 | 50 |
| 41725 | 338_1 | 1 | 75 | 23 | 154 | 27 |
| 41726 | 339_1 | 0.2 | 6 | 20 | 142 | 23 |
| 41726 | 339_1 | 1 | 55 | 14 | 193 | NA |
| 41728 | 340_1 | 0.2 | 60 | 16 | 137 | 23 |
| 41728 | 340_1 | 1 | 51 | 13 | 233 | NA |
| 42167 | 341_1 | 0.2 | 70 | 9 | 138 | 7 |
| 42167 | 341_1 | 1 | 51 | 11 | 182 | 20 |
| 42168 | 343_1 | 0.2 | 67 | 9 | 210 | 92 |
| 42168 | 343_1 | 1 | 52 | 6 | 193 | NA |
| 42168 | 342_1 | 0.2 | 51 | 6 | 183 | NA |
| 42168 | 342_1 | 1 | 46 | 10 | 275 | 14 |
| 42169 | 344_1 | 0.2 | 55 | 1 | 231 | 32 |
| 42169 | 344_1 | 1 | 35 | 3 | NA | NA |
| 42169 | 345_1 | 0.2 | 55 | 7 | 164 | 41 |
| 42169 | 345_1 | 1 | 45 | 5 | 284 | 27 |

TABLE 6-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 42287 | 346_1 | 0.2 | 66 | 7 | 144 | 32 |
| 42287 | 346_1 | 1 | 53 | 5 | 279 | 34 |
| 42289 | 347_1 | 0.2 | 75 | 20 | 125 | 10 |
| 42289 | 347_1 | 1 | 68 | 7 | 241 | 69 |
| 43452 | 348_1 | 0.2 | 62 | 12 | 231 | 92 |
| 43452 | 348_1 | 1 | 48 | 23 | 257 | 72 |
| 43453 | 349_1 | 0.2 | 52 | 11 | 142 | 41 |
| 43453 | 349_1 | 1 | 44 | 23 | 257 | 34 |
| 43562 | 350_1 | 0.2 | 50 | 13 | 148 | 35 |
| 43562 | 350_1 | 1 | 36 | 10 | NA | NA |
| 43565 | 351_1 | 0.2 | 71 | 10 | 116 | 43 |
| 43565 | 351_1 | 1 | 60 | 11 | 154 | 37 |
| 43566 | 352_1 | 0.2 | 65 | 19 | 139 | 14 |
| 43566 | 352_1 | 1 | 44 | 8 | 255 | 23 |
| 43634 | 353_1 | 0.2 | 63 | 25 | 172 | 75 |
| 43634 | 353_1 | 1 | 51 | 22 | 214 | NA |
| 44180 | 355_1 | 0.2 | 60 | 6 | 165 | 8 |
| 44180 | 355_1 | 1 | 57 | 25 | 145 | NA |
| 44180 | 354_1 | 0.2 | 76 | 17 | 149 | 55 |
| 44180 | 354_1 | 1 | 48 | 10 | 240 | 29 |
| 44181 | 356_1 | 0.2 | 60 | 5 | 170 | 27 |
| 44181 | 356_1 | 1 | 43 | 15 | 154 | 55 |
| 44183 | 357_1 | 0.2 | 50 | 15 | 214 | 33 |
| 44183 | 357_1 | 1 | 37 | 17 | 196 | 19 |
| 44184 | 358_1 | 0.2 | 57 | 5 | 155 | 31 |
| 44184 | 358_1 | 1 | 47 | 10 | 257 | 94 |
| 44439 | 359_1 | 0.2 | 46 | 4 | 220 | 53 |
| 44439 | 359_1 | 1 | 45 | 2 | 347 | 52 |
| 44440 | 360_1 | 0.2 | 48 | 9 | 261 | 37 |
| 44440 | 360_1 | 1 | 44 | 6 | NA | NA |
| 44440 | 361_1 | 0.2 | 43 | 5 | 218 | 46 |
| 44440 | 361_1 | 1 | 29 | 3 | 291 | 19 |
| 44441 | 362_1 | 0.2 | 50 | 5 | 192 | 60 |
| 44441 | 362_1 | 1 | 45 | 7 | 290 | 58 |
| 44441 | 363_1 | 0.2 | 45 | 10 | 185 | 51 |
| 44441 | 363_1 | 1 | 43 | 10 | 247 | NA |
| 44442 | 364_1 | 0.2 | 54 | 8 | 124 | 24 |
| 44442 | 364_1 | 1 | 39 | 5 | 271 | 54 |
| 44442 | 365_1 | 0.2 | 59 | 6 | 166 | 9 |
| 44442 | 365_1 | 1 | 44 | 8 | 313 | 47 |
| 44443 | 367_1 | 0.2 | 55 | 10 | 161 | 29 |
| 44443 | 367_1 | 1 | 40 | 7 | 314 | 67 |
| 44443 | 366_1 | 0.2 | 51 | 5 | 202 | 44 |
| 44443 | 366_1 | 1 | 41 | 10 | 300 | 31 |
| 44477 | 368_1 | 0.2 | 73 | 6 | 155 | 58 |
| 44477 | 368_1 | 1 | 52 | 3 | 362 | 141 |
| 44478 | 369_1 | 0.2 | 82 | 18 | 130 | 35 |
| 44478 | 369_1 | 1 | 58 | 11 | 228 | 66 |
| 44776 | 370_1 | 0.2 | 60 | 7 | 128 | 20 |
| 44776 | 370_1 | 1 | 46 | 5 | 274 | NA |
| 45216 | 371_1 | 0.2 | 50 | 10 | 149 | 33 |
| 45216 | 371_1 | 1 | 41 | 8 | 260 | 59 |
| 45217 | 372_1 | 0.2 | 59 | 7 | 132 | 45 |
| 45217 | 372_1 | 1 | 39 | 4 | 270 | 12 |
| 45217 | 373_1 | 0.2 | 47 | 3 | 167 | 52 |
| 45217 | 373_1 | 1 | 38 | 4 | 330 | 62 |
| 45218 | 374_1 | 0.2 | 51 | 9 | 189 | 27 |
| 45218 | 374_1 | 1 | 42 | 9 | 359 | 93 |
| 45246 | 375_1 | 0.2 | 61 | 8 | 175 | 29 |
| 45246 | 375_1 | 1 | 50 | 7 | 257 | NA |
| 45247 | 376_1 | 0.2 | 84 | 4 | 116 | 40 |
| 45247 | 376_1 | 1 | 74 | 10 | 144 | NA |
| 45248 | 378_1 | 0.2 | 61 | 10 | 226 | 2 |
| 45248 | 378_1 | 1 | 50 | 5 | 367 | 141 |
| 45248 | 377_1 | 0.2 | 74 | 11 | 138 | 29 |
| 45248 | 377_1 | 1 | 62 | 4 | 251 | NA |
| 45249 | 379_1 | 0.2 | 48 | 5 | 232 | NA |
| 45249 | 379_1 | 1 | 50 | NA | 312 | NA |
| 45249 | 380_1 | 0.2 | 54 | 4 | 203 | 16 |
| 45249 | 380_1 | 1 | 53 | 1 | 353 | 12 |
| 45250 | 381_1 | 0.2 | 48 | 6 | 230 | 25 |
| 45250 | 381_1 | 1 | 40 | 7 | 387 | 79 |
| 45250 | 382_1 | 0.2 | 60 | 7 | 153 | 30 |
| 45250 | 382_1 | 1 | 46 | 3 | 288 | 43 |
| 45258 | 383_1 | 0.2 | 46 | 4 | 211 | NA |

TABLE 6-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 45258 | 383_1 | 1 | 34 | 6 | 307 | 29 |
| 45266 | 385_1 | 0.2 | 80 | 34 | 85 | 8 |
| 45266 | 385_1 | 1 | 55 | 13 | 128 | 25 |
| 45266 | 384_1 | 0.2 | 92 | 4 | 128 | 50 |
| 45266 | 384_1 | 1 | 79 | 12 | 108 | 23 |
| 45267 | 386_1 | 0.2 | 93 | 23 | 105 | 13 |
| 45267 | 386_1 | 1 | 80 | 23 | 139 | 14 |
| 45268 | 387_1 | 0.2 | 90 | 17 | 111 | 1 |
| 45268 | 387_1 | 1 | 109 | 9 | 122 | 44 |
| 45270 | 388_1 | 0.2 | 97 | 7 | 146 | 47 |
| 45270 | 388_1 | 1 | 88 | 9 | 113 | 22 |
| 45271 | 390_1 | 0.2 | 79 | 12 | 141 | 14 |
| 45271 | 390_1 | 1 | 58 | 14 | 197 | 38 |
| 45271 | 389_1 | 0.2 | 70 | 3 | 97 | 28 |
| 45271 | 389_1 | 1 | 53 | 6 | 150 | 26 |
| 45272 | 391_1 | 0.2 | 61 | 4 | 128 | 24 |
| 45272 | 391_1 | 1 | 55 | 14 | 208 | 39 |
| 45560 | 392_1 | 0.2 | 86 | 22 | 97 | 26 |
| 45560 | 392_1 | 1 | 71 | 19 | 125 | 18 |
| 45627 | 393_1 | 0.2 | 48 | 14 | 150 | 64 |
| 45627 | 393_1 | 1 | 39 | 1 | 209 | 35 |
| 45628 | 394_1 | 0.2 | 51 | 4 | 174 | 34 |
| 45628 | 394_1 | 1 | 44 | 8 | 309 | 30 |
| 45629 | 395_1 | 0.2 | 60 | 5 | 151 | 24 |
| 45629 | 395_1 | 1 | 48 | 7 | 297 | 43 |
| 45629 | 396_1 | 0.2 | 86 | 24 | 139 | 55 |
| 45629 | 396_1 | 1 | 64 | 13 | 203 | 38 |
| 45635 | 397_1 | 0.2 | 50 | 10 | 289 | 61 |
| 45635 | 397_1 | 1 | 46 | 2 | 401 | 56 |
| 45709 | 398_1 | 0.2 | 47 | 6 | 207 | 61 |
| 45709 | 398_1 | 1 | 49 | 6 | 233 | NA |
| 45709 | 399_1 | 0.2 | 56 | 6 | 206 | 13 |
| 45709 | 399_1 | 1 | 45 | 4 | 287 | 93 |
| 46215 | 400_1 | 0.2 | 78 | 14 | 122 | 13 |
| 46215 | 400_1 | 1 | 60 | 9 | 114 | 19 |
| 46256 | 401_1 | 0.2 | 62 | 7 | 164 | 56 |
| 46256 | 401_1 | 1 | 45 | 5 | 213 | 20 |
| 46257 | 404_1 | 0.2 | 44 | 4 | 207 | 44 |
| 46257 | 404_1 | 1 | 41 | 3 | 288 | 45 |
| 46257 | 402_1 | 0.2 | 48 | 5 | 197 | 57 |
| 46257 | 402_1 | 1 | 41 | 1 | 300 | 11 |
| 46257 | 403_1 | 0.2 | 51 | 4 | 265 | 50 |
| 46257 | 403_1 | 1 | 44 | 5 | 382 | NA |
| 46259 | 405_1 | 0.2 | 46 | 4 | NA | NA |
| 46259 | 405_1 | 1 | 39 | 10 | 359 | 10 |
| 46260 | 406_1 | 0.2 | 52 | 9 | 153 | 63 |
| 46260 | 406_1 | 1 | 48 | 7 | 262 | 71 |
| 46263 | 407_1 | 0.2 | 52 | 9 | 148 | 9 |
| 46263 | 407_1 | 1 | 41 | 5 | 262 | 45 |
| 46264 | 408_1 | 0.2 | 5 | 17 | 269 | 72 |
| 46264 | 408_1 | 1 | 42 | 8 | 280 | 55 |
| 46392 | 409_1 | 0.2 | 38 | 10 | 359 | 91 |
| 46392 | 409_1 | 1 | 38 | 8 | NA | NA |
| 46393 | 410_1 | 0.2 | 39 | 12 | 295 | 30 |
| 46393 | 410_1 | 1 | 32 | 12 | NA | NA |
| 46420 | 411_1 | 0.2 | 75 | 10 | 69 | 3 |
| 46420 | 411_1 | 1 | 86 | 3 | 101 | 21 |
| 46505 | 412_1 | 0.2 | 65 | 11 | 97 | 7 |
| 46505 | 412_1 | 1 | 53 | 5 | 226 | 59 |
| 46505 | 413_1 | 0.2 | 74 | 16 | 124 | 19 |
| 46505 | 413_1 | 1 | 69 | 13 | 117 | 11 |
| 46506 | 414_1 | 0.2 | 75 | 7 | 149 | 17 |
| 46506 | 414_1 | 1 | 71 | 10 | 169 | 118 |
| 46507 | 415_1 | 0.2 | 86 | 31 | 119 | 36 |
| 46507 | 415_1 | 1 | 66 | 17 | 129 | 28 |
| 46508 | 416_1 | 0.2 | 86 | 22 | 87 | 22 |
| 46508 | 416_1 | 1 | 67 | 10 | 142 | 16 |
| 47364 | 417_1 | 0.2 | 49 | 2 | 166 | 22 |
| 47364 | 417_1 | 1 | 47 | 13 | 295 | NA |
| 47365 | 418_1 | 0.2 | 54 | 3 | 131 | 29 |
| 47365 | 418_1 | 1 | 41 | 3 | 230 | 42 |
| 48110 | 419_1 | 0.2 | 77 | 9 | 101 | 45 |
| 48110 | 419_1 | 1 | 58 | 8 | 178 | 68 |
| 48111 | 420_1 | 0.2 | 63 | 7 | 121 | 32 |
| 48111 | 420_1 | 1 | 51 | 2 | 238 | 59 |

TABLE 6-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 48186 | 421_1 | 0.2 | 69 | 5 | 176 | 52 |
| 48186 | 421_1 | 1 | 44 | 12 | 307 | 62 |
| 48221 | 422_1 | 0.2 | 58 | 15 | 149 | 63 |
| 48221 | 422_1 | 1 | 39 | 6 | 235 | 50 |
| 48222 | 423_1 | 0.2 | 60 | 12 | 143 | 9 |
| 48222 | 423_1 | 1 | 43 | 10 | 209 | 57 |
| 49345 | 85_2 | 0.2 | 43 | 14 | 242 | 38 |
| 49345 | 85_2 | 1 | 37 | 5 | 275 | NA |
| 50282 | 424_1 | 0.2 | 75 | 20 | 138 | 19 |
| 50282 | 424_1 | 1 | 56 | 9 | 226 | 62 |
| 51241 | 426_1 | 0.2 | 61 | 6 | 144 | NA |
| 51241 | 426_1 | 1 | 46 | 9 | 264 | 44 |
| 51241 | 425_1 | 0.2 | 46 | 8 | 164 | 22 |
| 51241 | 425_1 | 1 | 44 | 4 | 244 | 35 |
| 51242 | 428_1 | 0.2 | 57 | 6 | 138 | 30 |
| 51242 | 428_1 | 1 | 48 | 7 | 290 | 39 |
| 51242 | 427_1 | 0.2 | 40 | 15 | 341 | NA |
| 51242 | 427_1 | 1 | 30 | 8 | 286 | 63 |
| 51244 | 429_1 | 0.2 | 46 | 5 | 184 | 25 |
| 51244 | 429_1 | 1 | 44 | 6 | 283 | 4 |
| 51245 | 430_1 | 0.2 | 47 | 7 | 203 | 9 |
| 51245 | 430_1 | 1 | 37 | 5 | 271 | 29 |
| 51358 | 431_1 | 0.2 | 51 | 7 | 265 | 10 |
| 51358 | 431_1 | 1 | 40 | 4 | 363 | 70 |
| 51358 | 432_1 | 0.2 | 60 | 4 | 202 | 51 |
| 51358 | 432_1 | 1 | 37 | 7 | 275 | NA |
| 51359 | 433_1 | 0.2 | 40 | 3 | 238 | 20 |
| 51359 | 433_1 | 1 | 32 | 3 | NA | NA |
| 51359 | 434_1 | 0.2 | 39 | 6 | 424 | 83 |
| 51359 | 434_1 | 1 | 35 | 6 | 360 | NA |
| 51438 | 435_1 | 0.2 | 78 | 15 | 144 | 62 |
| 51438 | 435_1 | 1 | 60 | 14 | 201 | 27 |
| 51438 | 436_1 | 0.2 | 71 | 4 | 125 | 32 |
| 51438 | 436_1 | 1 | 54 | 6 | 205 | 71 |
| 51953 | 437_1 | 0.2 | 46 | 6 | 217 | 35 |
| 51953 | 437_1 | 1 | 37 | 4 | 277 | 52 |
| 52150 | 438_1 | 0.2 | 67 | 6 | 131 | 39 |
| 52150 | 438_1 | 1 | 53 | 13 | 177 | NA |
| 52549 | 439_1 | 0.2 | 56 | 5 | 162 | 31 |
| 52549 | 439_1 | 1 | 50 | 10 | 215 | 39 |
| 52550 | 440_1 | 0.2 | 69 | 13 | 137 | 40 |
| 52550 | 440_1 | 1 | 50 | 5 | 156 | 53 |
| 52551 | 441_1 | 0.2 | 66 | 3 | 132 | 8 |
| 52551 | 441_1 | 1 | 49 | 5 | 169 | 27 |
| 52579 | 442_1 | 0.2 | 38 | 7 | 280 | 60 |
| 52579 | 442_1 | 1 | 37 | 5 | 257 | 51 |
| 53012 | 443_1 | 0.2 | 79 | 10 | 197 | 61 |
| 53012 | 443_1 | 1 | 65 | 7 | 212 | 36 |
| 53013 | 445_1 | 0.2 | 64 | 6 | 211 | 13 |
| 53013 | 445_1 | 1 | 56 | 4 | 264 | 42 |
| 53013 | 444_1 | 0.2 | 68 | 11 | 137 | 33 |
| 53013 | 444_1 | 1 | 58 | 9 | 198 | 35 |
| 53014 | 446_1 | 0.2 | 59 | 6 | 125 | NA |
| 53014 | 446_1 | 1 | 47 | 3 | 216 | 22 |
| 53014 | 447_1 | 0.2 | 53 | 2 | 188 | 94 |
| 53014 | 447_1 | 1 | 51 | 10 | 192 | 47 |
| 54198 | 448_1 | 0.2 | 54 | 15 | 161 | 66 |
| 54198 | 448_1 | 1 | 48 | 11 | 243 | NA |
| 54199 | 449_1 | 0.2 | 63 | 12 | 166 | 20 |
| 54199 | 449_1 | 1 | 45 | 8 | 185 | 41 |
| 54232 | 450_1 | 0.2 | 84 | 17 | 112 | 67 |
| 54232 | 450_1 | 1 | 83 | 8 | 157 | 15 |
| 54233 | 451_1 | 0.2 | 67 | 14 | 118 | 44 |
| 54233 | 451_1 | 1 | 51 | 8 | 192 | 34 |
| 54235 | 452_1 | 0.2 | 50 | 3 | 162 | NA |
| 54235 | 452_1 | 1 | 42 | 7 | 190 | NA |
| 54236 | 453_1 | 0.2 | 47 | 21 | 234 | 17 |
| 54236 | 453_1 | 1 | 42 | 5 | 295 | NA |
| 54238 | 454_1 | 0.2 | 76 | 14 | 85 | NA |
| 54238 | 454_1 | 1 | 48 | 12 | 162 | NA |
| 54239 | 455_1 | 0.2 | 62 | 6 | 132 | 69 |

TABLE 6-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 54239 | 455_1 | 1 | 46 | 7 | 149 | 57 |
| 54609 | 456_1 | 0.2 | 66 | 10 | 130 | 57 |
| 54609 | 456_1 | 1 | 56 | 11 | 141 | 60 |
| 54924 | 457_1 | 0.2 | 78 | 3 | 137 | 29 |
| 54924 | 457_1 | 1 | 61 | 4 | 178 | 25 |

Example 4—Activity of Oligonucleotides Targeting the SNHG14 Transcript in the Region Antisense to to the UBE3A Pre-mRNA Oligonucleotides targeting position 55337-136214 of SEQ ID NO: 1 were tested in patient derived human neuronal cell cultures (see protocol in "Materials and methods" section). The oligonucleotides ability to reduce the SNHG14 transcript in the region downstream of SNORD109B (also termed UBE3A suppressor or UBE3A-SUP in the data table). Furthermore, the ability to induce UBE3A mRNA re-expression was analyzed.

The oligonucleotides were screened according to the protocol for screening oligonucleotides in human neuronal cell cultures described in the section "Materials and methods"—"Screening oligonucleotides in human neuronal cell cultures—96 well system".

The results are shown in table 7.

TABLE 7

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 55337 | 458_1 | 0.2 | 64 | 0 | 177 | 6 |
| 55337 | 458_1 | 1 | 50 | 10 | 233 | 9 |
| 55338 | 459_1 | 0.2 | 48 | 1 | 186 | 6 |
| 55338 | 459_1 | 1 | 44 | 9 | 213 | NA |
| 59565 | 460_1 | 0.2 | 66 | 4 | 110 | 24 |
| 59565 | 460_1 | 1 | 66 | 9 | 131 | 23 |
| 59574 | 461_1 | 0.2 | 56 | 5 | 162 | 19 |
| 59574 | 461_1 | 1 | 45 | 13 | 149 | 6 |
| 59575 | 462_1 | 0.2 | 56 | 7 | 114 | 84 |
| 59575 | 462_1 | 1 | 39 | 11 | 101 | 13 |
| 59576 | 463_1 | 0.2 | 82 | 19 | 52 | NA |
| 59576 | 463_1 | 1 | 65 | 5 | 95 | 18 |
| 60012 | 464_1 | 0.2 | 47 | 5 | 129 | 71 |
| 60012 | 464_1 | 1 | 41 | 3 | 160 | 64 |
| 60298 | 465_1 | 0.2 | 49 | 7 | 206 | 95 |
| 60298 | 465_1 | 1 | 37 | 9 | 222 | 44 |
| 60448 | 466_1 | 0.2 | 47 | 7 | 130 | NA |
| 60448 | 466_1 | 1 | 33 | 8 | 167 | 31 |
| 60821 | 467_1 | 0.2 | 87 | 1 | 73 | NA |
| 60821 | 467_1 | 1 | 62 | 8 | 101 | 3 |
| 61925 | 468_1 | 0.2 | 108 | 19 | 105 | 19 |
| 61925 | 468_1 | 1 | 95 | 17 | 101 | 19 |
| 62287 | 469_1 | 0.2 | 62 | 8 | 180 | 57 |
| 62287 | 469_1 | 1 | 48 | 5 | 196 | 38 |
| 62422 | 470_1 | 0.2 | 71 | 2 | 130 | 20 |
| 62422 | 470_1 | 1 | 57 | 9 | 116 | 18 |
| 62443 | 471_1 | 0.2 | 51 | 2 | NA | NA |
| 62443 | 471_1 | 1 | 43 | 2 | 160 | 34 |
| 64113 | 472_1 | 0.2 | 95 | 4 | 83 | 22 |
| 64113 | 472_1 | 1 | 76 | 14 | 74 | 36 |
| 64461 | 473_1 | 0.2 | 79 | 23 | 141 | 22 |
| 64461 | 473_1 | 1 | 59 | 12 | 279 | 53 |
| 64462 | 474_1 | 0.2 | 80 | 12 | 138 | 3 |
| 64462 | 474_1 | 1 | 84 | 15 | 202 | 3 |
| 65272 | 475_1 | 0.2 | 77 | 3 | 104 | 2 |
| 65272 | 475_1 | 1 | 75 | 23 | 113 | 10 |
| 66840 | 476_1 | 0.2 | 67 | 5 | 86 | 5 |
| 66840 | 476_1 | 1 | 72 | 10 | 100 | 12 |
| 67426 | 477_1 | 0.2 | 62 | 15 | 101 | 8 |
| 67426 | 477_1 | 1 | 65 | 13 | 170 | 52 |
| 68194 | 478_1 | 0.2 | 53 | 10 | 109 | 6 |
| 68194 | 478_1 | 1 | 59 | 4 | 178 | 7 |
| 68328 | 479_1 | 0.2 | 74 | 6 | 94 | 2 |
| 68328 | 479_1 | 1 | 79 | 6 | 111 | 38 |
| 68805 | 480_1 | 0.2 | 58 | 15 | 157 | 63 |
| 68805 | 480_1 | 1 | 49 | 2 | 190 | 26 |
| 68921 | 481_1 | 0.2 | 58 | 7 | 210 | 58 |
| 68921 | 481_1 | 1 | 55 | 10 | 281 | NA |

TABLE 7-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 70133 | 482_1 | 0.2 | 50 | 9 | 149 | 6 |
| 70133 | 482_1 | 1 | 54 | 8 | 247 | 41 |
| 72377 | 483_1 | 0.2 | 44 | 2 | 143 | NA |
| 72377 | 483_1 | 1 | 52 | 6 | 195 | 37 |
| 72378 | 484_1 | 0.2 | 47 | 12 | 111 | 8 |
| 72378 | 484_1 | 1 | 56 | 3 | 201 | NA |
| 72826 | 485_1 | 0.2 | 54 | 2 | 116 | 0 |
| 72826 | 485_1 | 1 | 64 | 13 | 172 | 1 |
| 72861 | 486_1 | 0.2 | 52 | 9 | 93 | 6 |
| 72861 | 486_1 | 1 | 54 | 6 | 167 | 16 |
| 72887 | 487_1 | 0.2 | 55 | 3 | 128 | 5 |
| 72887 | 487_1 | 1 | 59 | 4 | 193 | 24 |
| 73474 | 488_1 | 0.2 | 55 | 10 | 132 | 20 |
| 73474 | 488_1 | 1 | 55 | 5 | 202 | 56 |
| 73992 | 489_1 | 0.2 | 60 | 7 | 146 | 17 |
| 73992 | 489_1 | 1 | 67 | 7 | 197 | 31 |
| 74791 | 490_1 | 0.2 | 42 | 5 | 167 | 65 |
| 74791 | 490_1 | 1 | 46 | 6 | 277 | 19 |
| 74851 | 491_1 | 0.2 | 69 | 14 | 78 | 1 |
| 74851 | 491_1 | 1 | 73 | 6 | 114 | 11 |
| 74853 | 492_1 | 0.2 | 64 | 6 | 84 | 1 |
| 74853 | 492_1 | 1 | 68 | 5 | 136 | 25 |
| 75840 | 493_1 | 0.2 | 40 | 10 | 90 | 6 |
| 75840 | 493_1 | 1 | 61 | 8 | 155 | 32 |
| 75841 | 494_1 | 0.2 | 65 | 10 | 131 | 30 |
| 75841 | 494_1 | 1 | 57 | 4 | 119 | 16 |
| 76238 | 495_1 | 0.2 | 70 | 9 | 109 | 41 |
| 76238 | 495_1 | 1 | 50 | 8 | 156 | 22 |
| 76254 | 496_1 | 0.2 | 67 | 13 | 134 | 34 |
| 76254 | 496_1 | 1 | 55 | 7 | 201 | NA |
| 76811 | 497_1 | 0.2 | 83 | 7 | 134 | 41 |
| 76811 | 497_1 | 1 | 77 | 8 | 148 | 32 |
| 77114 | 498_1 | 0.2 | 59 | 2 | 128 | 13 |
| 77114 | 498_1 | 1 | 64 | 10 | 206 | NA |
| 80468 | 499_1 | 0.2 | 55 | 2 | 105 | 34 |
| 80468 | 499_1 | 1 | 61 | 6 | 151 | 42 |
| 81047 | 500_1 | 0.2 | 103 | 17 | 80 | 6 |
| 81047 | 500_1 | 1 | 143 | 25 | 122 | 7 |
| 82233 | 501_1 | 0.2 | 57 | NA | 104 | NA |
| 82233 | 501_1 | 1 | 6 | 3 | 199 | 39 |
| 84166 | 502_1 | 0.2 | 49 | 6 | 89 | 0 |
| 84166 | 502_1 | 1 | 57 | 5 | 115 | NA |
| 85392 | 503_1 | 0.2 | 61 | 6 | 90 | 14 |
| 85392 | 503_1 | 1 | 62 | 8 | 118 | 15 |
| 86974 | 504_1 | 0.2 | 73 | 7 | 82 | 4 |
| 86974 | 504_1 | 1 | 79 | 3 | 104 | 19 |
| 87728 | 505_1 | 0.2 | 79 | 14 | 76 | 2 |
| 87728 | 505_1 | 1 | 80 | 19 | 97 | 35 |
| 87810 | 506_1 | 0.2 | 69 | 9 | 101 | 20 |
| 87810 | 506_1 | 1 | 73 | 6 | 155 | 2 |
| 88417 | 507_1 | 0.2 | 45 | NA | 116 | 3 |
| 88417 | 507_1 | 1 | 61 | 14 | 168 | 6 |
| 88991 | 508_1 | 0.2 | 51 | 6 | 113 | 20 |
| 88991 | 508_1 | 1 | 59 | 2 | 154 | 31 |
| 90228 | 509_1 | 0.2 | 65 | 6 | 76 | 10 |
| 90228 | 509_1 | 1 | 62 | 7 | 118 | 4 |
| 90474 | 510_1 | 0.2 | 71 | 7 | 83 | 14 |
| 90474 | 510_1 | 1 | 81 | 3 | 125 | NA |
| 91625 | 511_1 | 0.2 | 57 | 17 | 105 | 3 |
| 91625 | 511_1 | 1 | 65 | 11 | 150 | NA |
| 91885 | 512_1 | 0.2 | 57 | 5 | 105 | 1 |
| 91885 | 512_1 | 1 | 66 | 7 | 155 | 30 |
| 92976 | 513_1 | 0.2 | 67 | 6 | 136 | 44 |
| 92976 | 513_1 | 1 | 68 | 11 | 138 | 38 |
| 94304 | 514_1 | 0.2 | 81 | 11 | 110 | 7 |
| 94304 | 514_1 | 1 | 87 | 6 | 153 | 28 |
| 94528 | 515_1 | 0.2 | 48 | 5 | 128 | 6 |
| 94528 | 515_1 | 1 | 55 | 3 | 191 | 25 |
| 95653 | 516_1 | 0.2 | 57 | 3 | 108 | 7 |
| 95653 | 516_1 | 1 | 62 | 3 | 131 | 16 |
| 96751 | 517_1 | 0.2 | 63 | 9 | 90 | 19 |
| 96751 | 517_1 | 1 | 62 | 4 | 106 | NA |
| 97636 | 518_1 | 0.2 | 49 | 5 | 107 | 14 |
| 97636 | 518_1 | 1 | 44 | 9 | 137 | NA |
| 98480 | 519_1 | 0.2 | 55 | 1 | 106 | NA |

TABLE 7-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 98480 | 519_1 | 1 | 5 | 5 | 112 | 23 |
| 98481 | 520_1 | 0.2 | 55 | 2 | 116 | 6 |
| 98481 | 520_1 | 1 | 62 | 4 | 129 | 6 |
| 99646 | 521_1 | 0.2 | 74 | 10 | 105 | 1 |
| 99646 | 521_1 | 1 | 87 | 13 | 119 | 27 |
| 100334 | 522_1 | 0.2 | 49 | 7 | 157 | 28 |
| 100334 | 522_1 | 1 | 57 | 2 | 120 | 37 |
| 101110 | 523_1 | 0.2 | 51 | 10 | 96 | 10 |
| 101110 | 523_1 | 1 | 72 | 14 | 114 | 25 |
| 101898 | 524_1 | 0.2 | 85 | 11 | 79 | 3 |
| 101898 | 524_1 | 1 | 93 | 21 | 92 | 46 |
| 102558 | 525_1 | 0.2 | 82 | 9 | 104 | 8 |
| 102558 | 525_1 | 1 | 86 | 18 | 104 | 30 |
| 103589 | 526_1 | 0.2 | 85 | 17 | 114 | 14 |
| 103589 | 526_1 | 1 | 94 | 39 | 126 | 6 |
| 104309 | 527_1 | 0.2 | 63 | 11 | 148 | 2 |
| 104309 | 527_1 | 1 | 70 | 26 | 155 | NA |
| 105686 | 528_1 | 0.2 | 66 | 11 | 91 | 24 |
| 105686 | 528_1 | 1 | 66 | 14 | 140 | 36 |
| 107972 | 529_1 | 0.2 | 84 | 15 | 109 | 15 |
| 107972 | 529_1 | 1 | 94 | 14 | 127 | 24 |
| 108257 | 530_1 | 0.2 | 63 | 7 | 114 | 19 |
| 108257 | 530_1 | 1 | 67 | 12 | 141 | 40 |
| 109407 | 531_1 | 0.2 | 84 | 24 | 87 | 16 |
| 109407 | 531_1 | 1 | 82 | 11 | 127 | 26 |
| 110210 | 532_1 | 0.2 | 72 | 12 | 91 | 14 |
| 110210 | 532_1 | 1 | 80 | 14 | 122 | 40 |
| 110768 | 533_1 | 0.2 | 67 | 8 | 126 | 16 |
| 110768 | 533_1 | 1 | 87 | 21 | 176 | 45 |
| 111811 | 534_1 | 0.2 | 77 | 2 | 98 | 17 |
| 111811 | 534_1 | 1 | 74 | 6 | 143 | 14 |
| 111812 | 535_1 | 0.2 | 64 | 4 | 97 | 0 |
| 111812 | 535_1 | 1 | 77 | 3 | 136 | 37 |
| 112149 | 536_1 | 0.2 | 73 | 2 | 63 | 2 |
| 112149 | 536_1 | 1 | 77 | 18 | 127 | 36 |
| 112150 | 537_1 | 0.2 | 76 | 6 | 78 | 8 |
| 112150 | 537_1 | 1 | 90 | 29 | 91 | 11 |
| 112945 | 538_1 | 0.2 | 69 | 4 | 121 | 2 |
| 112945 | 538_1 | 1 | 83 | 14 | 102 | 39 |
| 113533 | 539_1 | 0.2 | 95 | 17 | 85 | 2 |
| 113533 | 539_1 | 1 | 91 | 27 | 87 | 17 |
| 114274 | 540_1 | 0.2 | 89 | 11 | 103 | 17 |
| 114274 | 540_1 | 1 | 87 | 26 | 132 | 20 |
| 114495 | 541_1 | 0.2 | 76 | 5 | 88 | 1 |
| 114495 | 541_1 | 1 | 83 | 15 | 120 | 6 |
| 114831 | 542_1 | 0.2 | 59 | 3 | 76 | 4 |
| 114831 | 542_1 | 1 | 74 | 3 | 104 | 4 |
| 115355 | 543_1 | 0.2 | 66 | 8 | 91 | 9 |
| 115355 | 543_1 | 1 | 74 | 16 | 110 | NA |
| 116105 | 544_1 | 0.2 | 55 | 12 | 77 | NA |
| 116105 | 544_1 | 1 | 74 | 6 | 110 | 8 |
| 116106 | 545_1 | 0.2 | 58 | 18 | 96 | 9 |
| 116106 | 545_1 | 1 | 66 | 8 | 130 | 10 |
| 117096 | 546_1 | 0.2 | 69 | 9 | 118 | 20 |
| 117096 | 546_1 | 1 | 65 | 4 | 146 | NA |
| 117189 | 547_1 | 0.2 | 69 | 6 | 98 | 9 |
| 117189 | 547_1 | 1 | 74 | 11 | 146 | 25 |
| 117476 | 548_1 | 0.2 | 59 | 4 | 8 | 5 |
| 117476 | 548_1 | 1 | 65 | 3 | 104 | 10 |
| 118293 | 549_1 | 0.2 | 55 | 8 | 92 | 3 |
| 118293 | 549_1 | 1 | 66 | 10 | 105 | 24 |
| 118294 | 550_1 | 0.2 | 55 | 18 | 90 | 4 |
| 118294 | 550_1 | 1 | 72 | 2 | 119 | 5 |
| 118756 | 551_1 | 0.2 | 60 | 13 | 86 | 18 |
| 118756 | 551_1 | 1 | 88 | 24 | 120 | 26 |
| 119621 | 552_1 | 0.2 | 77 | 21 | 117 | 4 |
| 119621 | 552_1 | 1 | 102 | 19 | 146 | NA |
| 120655 | 553_1 | 0.2 | 55 | 9 | 124 | 19 |
| 120655 | 553_1 | 1 | 57 | 7 | 185 | 14 |
| 123733 | 554_1 | 0.2 | 74 | 6 | 87 | 14 |
| 123733 | 554_1 | 1 | 77 | 4 | 127 | 4 |
| 124163 | 555_1 | 0.2 | 89 | 12 | 117 | 46 |
| 124163 | 555_1 | 1 | 67 | 20 | 152 | 13 |
| 125512 | 556_1 | 0.2 | 70 | 5 | 114 | 26 |
| 125512 | 556_1 | 1 | 69 | 11 | 119 | 47 |

TABLE 7-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 126882 | 557_1 | 0.2 | 78 | 15 | 106 | 8 |
| 126882 | 557_1 | 1 | 84 | 10 | 113 | 33 |
| 127105 | 558_1 | 0.2 | 71 | 7 | 91 | 13 |
| 127105 | 558_1 | 1 | 68 | 5 | 108 | 28 |
| 127809 | 559_1 | 0.2 | 59 | 4 | 74 | NA |
| 127809 | 559_1 | 1 | 58 | 7 | 101 | 26 |
| 129020 | 560_1 | 0.2 | 82 | 11 | 103 | 39 |
| 129020 | 560_1 | 1 | 77 | 9 | 103 | 27 |
| 129205 | 561_1 | 0.2 | 75 | 24 | 78 | 16 |
| 129205 | 561_1 | 1 | 89 | 1 | 102 | 23 |
| 129928 | 562_1 | 0.2 | 57 | 0 | 98 | 21 |
| 129928 | 562_1 | 1 | 63 | 9 | 107 | 18 |
| 130020 | 563_1 | 0.2 | 65 | 5 | 85 | 9 |
| 130020 | 563_1 | 1 | 65 | 3 | 145 | 12 |
| 130884 | 564_1 | 0.2 | 81 | 24 | 117 | 31 |
| 130884 | 564_1 | 1 | 83 | 4 | 139 | 17 |
| 130886 | 565_1 | 0.2 | 80 | 8 | 103 | 13 |
| 130886 | 565_1 | 1 | 69 | 7 | 122 | 11 |
| 131404 | 566_1 | 0.2 | 79 | 4 | 85 | 3 |
| 131404 | 566_1 | 1 | 80 | 7 | 116 | 24 |
| 132514 | 567_1 | 0.2 | 71 | 8 | 98 | 28 |
| 132514 | 567_1 | 1 | 69 | 9 | 97 | 29 |
| 133367 | 568_1 | 0.2 | 78 | 9 | 88 | 16 |
| 133367 | 568_1 | 1 | 91 | 17 | 88 | 32 |
| 136198 | 569_1 | 0.2 | 88 | 5 | 87 | 2 |
| 136198 | 569_1 | 1 | 81 | 6 | 109 | 35 |

Example 5—Activity of Oligonucleotides Targeting the SNHG14 Transcript in the Region Downstream of SNORD109B and Upstream of the Region Antisense to to the UBE3A Pre-mRNA Oligonucleotides targeting position 5224-51257 of SEQ ID NO: 1 were tested in patient derived human neuronal cell cultures (see protocol in "Materials and methods" section). The oligonucleotides ability to reduce the SNHG14 transcript in the region downstream of SNORD109B (also termed UBE3A suppressor or UBE3A-SUP in the data table. Furthermore, the ability to induce UBE3A mRNA re-expression was analyzed.

The oligonucleotides were screened according to the protocol for screening oligonucleotides in human neuronal cell cultures described in the section "Materials and methods" "Screening oligonucleotides in human neuronal cell cultures—96 well system" with the following modifications:

UBE3a-Sense Primer

Using commercially available primers and probe from ThermoFisher: Hs00166580_m1 amplifying a 94 bp sequence in position 838 of refseq ID NM_000462.3.

Each plate include PBS controls (instead on a non-targeting ologinucleotide) and a positive control oligonucleotide CMP ID NO: 2711, resulting in up-regulation of UBE3A mRNA. The additional control oligonucleotides were not included.

Data are presented as average % expression relative to PBS controls across all plates and normalized to the positive control oligonucleotide to manage plate to plate variation in efficacy levels. The results are shown in table 8.

TABLE 8

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 5224 | 169_2 | 7.5 μM | 49 | 4 | 209 | 9 |
| 5224 | 169_3 | 7.5 μM | 47 | 5 | 282 | 5 |
| 5224 | 169_4 | 7.5 μM | 57 | 14 | 202 | 12 |
| 5224 | 169_5 | 7.5 μM | 84 | 36 | 148 | 4 |
| 5224 | 169_6 | 7.5 μM | 42 | 1 | 285 | 16 |
| 5224 | 169_7 | 7.5 μM | 52 | 6 | 233 | 27 |
| 5224 | 169_8 | 7.5 μM | 51 | 7 | 278 | 11 |
| 5224 | 169_9 | 7.5 μM | 51 | 4 | 228 | 20 |
| 5224 | 169_10 | 7.5 μM | 78 | 17 | 143 | 5 |
| 5224 | 169_11 | 7.5 μM | 74 | 15 | 146 | 2 |
| 5224 | 169_12 | 7.5 μM | 47 | 1 | 277 | 26 |
| 5224 | 169_13 | 7.5 μM | 56 | 23 | 244 | 42 |
| 5224 | 169_14 | 7.5 μM | 74 | 16 | 141 | 1 |
| 5224 | 169_15 | 7.5 μM | 95 | 32 | 122 | 13 |
| 5224 | 169_16 | 7.5 μM | 44 | 4 | 276 | 23 |
| 5224 | 169_17 | 7.5 μM | 85 | 5 | 118 | 5 |
| 5224 | 169_18 | 7.5 μM | 75 | 18 | 131 | 4 |
| 5224 | 169_19 | 7.5 μM | 95 | 18 | 126 | 11 |
| 5224 | 169_20 | 7.5 μM | 61 | 12 | 169 | 20 |
| 5224 | 169_21 | 7.5 μM | 79 | 18 | 156 | 3 |
| 5224 | 169_22 | 7.5 μM | 63 | 14 | 173 | 16 |
| 5224 | 169_23 | 7.5 μM | 43 | 2 | 233 | 27 |
| 5224 | 169_24 | 7.5 μM | 56 | 1 | 183 | 9 |
| 5224 | 169_25 | 7.5 μM | 48 | 0 | 220 | 24 |
| 5224 | 169_26 | 7.5 μM | 41 | 1 | 244 | 39 |
| 5224 | 169_27 | 7.5 μM | 55 | 16 | 260 | 42 |
| 5224 | 169_28 | 7.5 μM | 48 | 1 | 265 | 65 |
| 5224 | 169_29 | 7.5 μM | 56 | 2 | 197 | 18 |
| 5224 | 169_30 | 7.5 μM | 57 | 12 | 189 | 12 |
| 5224 | 169_31 | 7.5 μM | 53 | 4 | 196 | 9 |
| 5224 | 169_32 | 7.5 μM | 50 | 1 | 220 | 3 |
| 5224 | 169_33 | 7.5 μM | 64 | 19 | 227 | 8 |
| 5224 | 169_34 | 7.5 μM | 58 | 4 | 193 | 10 |
| 5224 | 169_35 | 7.5 μM | 45 | 2 | 229 | 3 |
| 5224 | 169_36 | 7.5 μM | 44 | 6 | 262 | 14 |
| 5224 | 169_37 | 7.5 μM | 55 | 2 | 180 | 21 |
| 5224 | 169_38 | 7.5 μM | 75 | 22 | 158 | 13 |
| 5224 | 169_39 | 7.5 μM | 76 | 15 | 159 | 17 |

TABLE 8-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 5224 | 169_40 | 7.5 μM | 60 | 18 | 232 | 31 |
| 5224 | 169_41 | 7.5 μM | 46 | 3 | 230 | 10 |
| 5224 | 169_42 | 7.5 μM | 47 | 3 | 240 | 11 |
| 5224 | 169_43 | 7.5 μM | 48 | 9 | 273 | 30 |
| 5224 | 169_44 | 7.5 μM | 83 | 32 | 196 | 11 |
| 5224 | 169_45 | 7.5 μM | 69 | 4 | 185 | 20 |
| 5224 | 169_46 | 7.5 μM | 45 | 9 | 256 | 3 |
| 5224 | 169_47 | 7.5 μM | 41 | 2 | 304 | 4 |
| 5224 | 169_48 | 7.5 μM | 44 | 1 | 260 | 16 |
| 5224 | 169_49 | 7.5 μM | 38 | 1 | 245 | 32 |
| 5224 | 169_50 | 7.5 μM | 35 | 2 | 314 | 28 |
| 5224 | 169_51 | 7.5 μM | 41 | 5 | 281 | 5 |
| 5224 | 169_52 | 7.5 μM | 36 | 1 | 282 | 1 |
| 5224 | 169_53 | 7.5 μM | 38 | 7 | 301 | 7 |
| 5224 | 169_54 | 7.5 μM | 36 | 3 | 304 | 6 |
| 5224 | 169_55 | 7.5 μM | 52 | 5 | 246 | 23 |
| 5224 | 169_56 | 7.5 μM | 33 | 15 | 302 | 15 |
| 5224 | 169_57 | 7.5 μM | 34 | 16 | 273 | 16 |
| 5784 | 570_1 | 7.5 μM | 47 | 0 | 274 | 7 |
| 5784 | 570_2 | 7.5 μM | 47 | 8 | 232 | 8 |
| 5784 | 570_3 | 7.5 μM | 55 | 25 | 280 | 54 |
| 5784 | 570_4 | 7.5 μM | 61 | 1 | 235 | 54 |
| 5784 | 570_5 | 7.5 μM | 72 | 10 | 198 | 30 |
| 5784 | 570_6 | 7.5 μM | 66 | 8 | 244 | 50 |
| 5784 | 570_7 | 7.5 μM | 42 | 1 | 284 | 13 |
| 5784 | 570_8 | 7.5 μM | 43 | 6 | 257 | 11 |
| 5784 | 570_9 | 7.5 μM | 32 | 9 | 242 | 30 |
| 5785 | 571_1 | 7.5 μM | 40 | 1 | 269 | 35 |
| 5785 | 571_2 | 7.5 μM | 42 | 3 | 187 | 6 |
| 5785 | 571_3 | 7.5 μM | 46 | 6 | 242 | 8 |
| 5785 | 571_4 | 7.5 μM | 37 | 4 | 282 | 19 |
| 5785 | 571_5 | 7.5 μM | 48 | 16 | 296 | 2 |
| 5785 | 571_6 | 7.5 μM | 37 | 6 | 274 | 10 |
| 5785 | 571_7 | 7.5 μM | 39 | 1 | 260 | 8 |
| 5785 | 571_8 | 7.5 μM | 35 | 1 | 252 | 3 |
| 5785 | 571_9 | 7.5 μM | 30 | 5 | 297 | 10 |
| 5786 | 572_1 | 7.5 μM | 34 | 4 | 279 | 29 |
| 5786 | 572_2 | 7.5 μM | 63 | 10 | 152 | 4 |
| 5786 | 572_3 | 7.5 μM | 39 | 0 | 280 | 42 |
| 5786 | 572_4 | 7.5 μM | 40 | 1 | 283 | 14 |
| 5786 | 572_5 | 7.5 μM | 38 | 6 | 310 | 11 |
| 5786 | 572_6 | 7.5 μM | 33 | 1 | 316 | 18 |
| 5786 | 572_7 | 7.5 μM | 35 | 1 | 318 | 11 |
| 5786 | 572_8 | 7.5 μM | 47 | 9 | 310 | 19 |
| 5786 | 572_9 | 7.5 μM | 31 | 7 | 321 | 12 |
| 8116 | 573_1 | 7.5 μM | 39 | 8 | 316 | 28 |
| 8116 | 573_2 | 7.5 μM | 49 | 15 | 305 | 41 |
| 8116 | 573_3 | 7.5 μM | 46 | 13 | 308 | 3 |
| 8116 | 573_4 | 7.5 μM | 39 | 3 | 332 | 6 |
| 8116 | 573_5 | 7.5 μM | 34 | 6 | 278 | 12 |
| 8116 | 573_6 | 7.5 μM | 42 | 1 | 285 | 10 |
| 8116 | 573_7 | 7.5 μM | 38 | 0 | 289 | 33 |
| 8116 | 573_8 | 7.5 μM | 40 | 4 | 311 | 20 |
| 8116 | 573_9 | 7.5 μM | 57 | 9 | 315 | 5 |
| 8117 | 574_1 | 7.5 μM | 40 | 2 | 291 | 35 |
| 8117 | 574_2 | 7.5 μM | 42 | 3 | 343 | 18 |
| 8117 | 574_3 | 7.5 μM | 36 | 6 | 325 | 8 |
| 8117 | 574_4 | 7.5 μM | 38 | 1 | 279 | 15 |
| 8117 | 574_5 | 7.5 μM | 42 | 6 | 308 | 10 |
| 8117 | 574_6 | 7.5 μM | 47 | 8 | 340 | 11 |
| 8117 | 574_7 | 7.5 μM | 43 | 0 | 308 | 42 |
| 8117 | 574_8 | 7.5 μM | 44 | 6 | 268 | 10 |
| 8117 | 574_9 | 7.5 μM | 41 | 8 | 241 | 22 |
| 8118 | 575_1 | 7.5 μM | 47 | 0 | 198 | 28 |
| 8118 | 575_2 | 7.5 μM | 83 | 26 | 253 | 31 |
| 8118 | 575_3 | 7.5 μM | 48 | 4 | 348 | 5 |
| 8118 | 575_4 | 7.5 μM | 37 | 2 | 269 | 7 |
| 8118 | 575_5 | 7.5 μM | 43 | 6 | 258 | 17 |
| 8118 | 575_6 | 7.5 μM | 50 | 6 | 286 | 3 |
| 8118 | 575_7 | 7.5 μM | 37 | 2 | 331 | 30 |
| 8118 | 575_8 | 7.5 μM | 47 | 7 | 264 | 1 |
| 8118 | 575_9 | 7.5 μM | 64 | 23 | 243 | 3 |
| 8119 | 576_1 | 7.5 μM | 47 | 1 | 272 | 14 |
| 8119 | 576_2 | 7.5 μM | 109 | 31 | 119 | 3 |
| 8119 | 576_3 | 7.5 μM | 36 | 3 | 287 | 6 |
| 8119 | 576_4 | 7.5 μM | 35 | 3 | 285 | 23 |
| 8119 | 576_5 | 7.5 μM | 49 | 10 | 222 | 1 |
| 8119 | 576_6 | 7.5 μM | 79 | 12 | 132 | 10 |
| 8119 | 576_7 | 7.5 μM | 76 | 4 | 132 | 3 |
| 8119 | 576_8 | 7.5 μM | 62 | 1 | 147 | 5 |
| 8119 | 576_9 | 7.5 μM | 43 | 3 | 230 | 5 |
| 8120 | 577_1 | 7.5 μM | 57 | 3 | 158 | 15 |
| 8120 | 577_2 | 7.5 μM | 39 | 4 | 279 | 60 |
| 8120 | 577_3 | 7.5 μM | 38 | 1 | 290 | 68 |
| 8120 | 577_4 | 7.5 μM | 77 | 11 | 148 | 11 |
| 8120 | 577_5 | 7.5 μM | 31 | 6 | 272 | 36 |
| 8120 | 577_6 | 7.5 μM | 38 | 8 | 228 | 32 |
| 8120 | 577_7 | 7.5 μM | 40 | 8 | 246 | 39 |
| 8120 | 577_8 | 7.5 μM | 43 | 11 | 256 | 26 |
| 8120 | 577_9 | 7.5 μM | 85 | 32 | 109 | 6 |
| 8584 | 578_1 | 7.5 μM | 57 | 7 | 199 | 7 |
| 8584 | 578_2 | 7.5 μM | 40 | 5 | 263 | 3 |
| 8584 | 578_3 | 7.5 μM | 40 | 2 | 289 | 23 |
| 8584 | 578_4 | 7.5 μM | 43 | 8 | 199 | 16 |
| 8584 | 578_5 | 7.5 μM | 42 | 1 | 256 | 15 |
| 8584 | 578_6 | 7.5 μM | 42 | 6 | 241 | 10 |
| 8584 | 578_7 | 7.5 μM | 42 | 5 | 329 | 20 |
| 8584 | 578_8 | 7.5 μM | 49 | 7 | 271 | 13 |
| 8584 | 578_9 | 7.5 μM | 45 | 3 | 222 | 3 |
| 8585 | 579_1 | 7.5 μM | 45 | 0 | 208 | 8 |
| 8585 | 579_2 | 7.5 μM | 51 | 4 | 226 | 6 |
| 8585 | 579_3 | 7.5 μM | 54 | 5 | 178 | 8 |
| 8585 | 579_4 | 7.5 μM | 41 | 4 | 328 | 13 |
| 8585 | 579_5 | 7.5 μM | 50 | 5 | 272 | 3 |
| 8585 | 579_6 | 7.5 μM | 86 | 12 | 161 | 0 |
| 8585 | 579_7 | 7.5 μM | 72 | 5 | 155 | 15 |
| 8585 | 579_8 | 7.5 μM | 57 | 3 | 230 | 14 |
| 8585 | 579_9 | 7.5 μM | 83 | 0 | 123 | 1 |
| 8586 | 580_1 | 7.5 μM | 37 | 2 | 313 | 13 |
| 8586 | 580_2 | 7.5 μM | 43 | 1 | 266 | 3 |
| 8586 | 580_3 | 7.5 μM | 42 | 5 | 303 | 5 |
| 8586 | 580_4 | 7.5 μM | 57 | 4 | 225 | 26 |
| 8586 | 580_5 | 7.5 μM | 51 | 4 | 228 | 35 |
| 8586 | 580_6 | 7.5 μM | 44 | 4 | 253 | 15 |
| 8586 | 580_7 | 7.5 μM | 50 | 1 | 241 | 10 |
| 8586 | 580_8 | 7.5 μM | 44 | 0 | 227 | 26 |
| 8586 | 580_9 | 7.5 μM | 31 | 5 | 323 | 31 |
| 8587 | 581_1 | 7.5 μM | 50 | 6 | 223 | 30 |
| 8587 | 581_2 | 7.5 μM | 66 | 7 | 199 | 19 |
| 8587 | 581_3 | 7.5 μM | 56 | 8 | 197 | 9 |
| 8587 | 581_4 | 7.5 μM | 57 | 12 | 270 | 24 |
| 8587 | 581_5 | 7.5 μM | 51 | 12 | 259 | 12 |
| 8587 | 581_6 | 7.5 μM | 39 | 4 | 282 | 2 |
| 8587 | 581_7 | 7.5 μM | 38 | 11 | 263 | 5 |
| 8587 | 581_8 | 7.5 μM | 45 | 10 | 203 | 19 |
| 8587 | 581_9 | 7.5 μM | 43 | 2 | 234 | 10 |
| 9209 | 582_1 | 7.5 μM | 61 | 7 | 225 | 7 |
| 9209 | 582_2 | 7.5 μM | 46 | 9 | 341 | 36 |
| 9209 | 582_3 | 7.5 μM | 44 | 9 | 306 | 38 |
| 9209 | 582_4 | 7.5 μM | 43 | 1 | 249 | 5 |
| 9209 | 582_5 | 7.5 μM | 33 | 16 | 306 | 6 |
| 9209 | 582_6 | 7.5 μM | 37 | 8 | 329 | 19 |
| 9209 | 582_7 | 7.5 μM | 44 | 9 | 289 | 4 |
| 9209 | 582_8 | 7.5 μM | 39 | 3 | 314 | 20 |
| 9209 | 582_9 | 7.5 μM | 41 | 4 | 299 | 25 |
| 9210 | 583_1 | 7.5 μM | 43 | 5 | 319 | 25 |
| 9210 | 583_2 | 7.5 μM | 53 | 9 | 352 | 5 |
| 9210 | 583_3 | 7.5 μM | 42 | 2 | 362 | 42 |
| 9210 | 583_4 | 7.5 μM | 46 | 5 | 225 | 13 |
| 9210 | 583_5 | 7.5 μM | 39 | 6 | 343 | 21 |
| 9210 | 583_6 | 7.5 μM | 44 | 9 | 298 | 8 |
| 9210 | 583_7 | 7.5 μM | 37 | 5 | 332 | 9 |
| 9210 | 583_8 | 7.5 μM | 42 | 6 | 343 | 25 |
| 9210 | 583_9 | 7.5 μM | 36 | 2 | 341 | 9 |
| 9211 | 584_1 | 7.5 μM | 45 | 5 | 343 | 39 |
| 9211 | 584_2 | 7.5 μM | 42 | 2 | 298 | 22 |
| 9211 | 584_3 | 7.5 μM | 44 | 10 | 321 | 2 |
| 9211 | 584_4 | 7.5 μM | 50 | 1 | 299 | 5 |
| 9211 | 584_5 | 7.5 μM | 44 | 1 | 319 | 25 |
| 9211 | 584_6 | 7.5 μM | 50 | 6 | 323 | 13 |

TABLE 8-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 9211 | 584_7 | 7.5 µM | 42 | 4 | 316 | 27 |
| 9211 | 584_8 | 7.5 µM | 53 | 3 | 217 | 11 |
| 9212 | 208_2 | 7.5 µM | 44 | 7 | 312 | 26 |
| 9212 | 208_3 | 7.5 µM | 38 | 2 | 331 | 21 |
| 9212 | 208_4 | 7.5 µM | 47 | 3 | 353 | 11 |
| 9212 | 208_5 | 7.5 µM | 54 | 11 | 348 | 14 |
| 9212 | 208_6 | 7.5 µM | 51 | 12 | 310 | 8 |
| 9212 | 208_7 | 7.5 µM | 60 | 9 | 224 | 11 |
| 9213 | 209_2 | 7.5 µM | 44 | 12 | 242 | 21 |
| 9213 | 209_3 | 7.5 µM | 37 | 12 | 335 | 12 |
| 9213 | 209_4 | 7.5 µM | 55 | 7 | 350 | 2 |
| 9213 | 209_5 | 7.5 µM | 47 | 7 | 337 | 19 |
| 9213 | 209_6 | 7.5 µM | 51 | 8 | 300 | 19 |
| 9213 | 209_7 | 7.5 µM | 47 | 15 | 342 | 23 |
| 9213 | 209_8 | 7.5 µM | 45 | 12 | 289 | 5 |
| 9213 | 209_9 | 7.5 µM | 41 | 1 | 368 | 37 |
| 9213 | 209_10 | 7.5 µM | 40 | 4 | 315 | 1 |
| 11511 | 585_1 | 7.5 µM | 41 | 7 | 350 | 12 |
| 11511 | 585_2 | 7.5 µM | 44 | 4 | 233 | 7 |
| 11511 | 585_3 | 7.5 µM | 40 | 8 | 310 | 31 |
| 11511 | 585_4 | 7.5 µM | 33 | 8 | 324 | 41 |
| 11511 | 585_5 | 7.5 µM | 29 | 3 | 314 | 23 |
| 11511 | 585_6 | 7.5 µM | 38 | 4 | 332 | 15 |
| 11511 | 585_7 | 7.5 µM | 30 | 2 | 315 | 15 |
| 11511 | 585_8 | 7.5 µM | 36 | 11 | 328 | 37 |
| 11511 | 585_9 | 7.5 µM | 39 | 5 | 303 | 49 |
| 11512 | 586_1 | 7.5 µM | 60 | 3 | 236 | 5 |
| 11512 | 586_2 | 7.5 µM | 40 | 9 | 282 | 53 |
| 11512 | 586_3 | 7.5 µM | 36 | 1 | 279 | 11 |
| 11512 | 586_4 | 7.5 µM | 34 | 3 | 288 | 21 |
| 11512 | 586_5 | 7.5 µM | 30 | 1 | 270 | 4 |
| 11512 | 586_6 | 7.5 µM | 29 | 5 | 269 | 24 |
| 11512 | 586_7 | 7.5 µM | 33 | 4 | 263 | 6 |
| 11512 | 586_8 | 7.5 µM | 32 | 4 | 270 | 4 |
| 11512 | 586_9 | 7.5 µM | 33 | 5 | 310 | 48 |
| 11513 | 587_1 | 7.5 µM | 45 | 2 | 237 | 34 |
| 11513 | 587_2 | 7.5 µM | 44 | 3 | 307 | 4 |
| 11513 | 587_3 | 7.5 µM | 37 | 1 | 285 | 24 |
| 11513 | 587_4 | 7.5 µM | 44 | 1 | 252 | 41 |
| 11513 | 587_5 | 7.5 µM | 51 | 7 | 220 | 29 |
| 11513 | 587_6 | 7.5 µM | 41 | 2 | 262 | 35 |
| 11513 | 587_7 | 7.5 µM | 39 | 7 | 280 | 21 |
| 11513 | 587_8 | 7.5 µM | 48 | 9 | 230 | 11 |
| 11513 | 587_9 | 7.5 µM | 41 | 5 | 270 | 9 |
| 11514 | 588_1 | 7.5 µM | 54 | 9 | 204 | 25 |
| 11514 | 588_2 | 7.5 µM | 98 | 5 | 143 | 4 |
| 11514 | 588_3 | 7.5 µM | 55 | 9 | 180 | 1 |
| 11514 | 588_4 | 7.5 µM | 113 | 24 | 109 | 17 |
| 11514 | 588_5 | 7.5 µM | 66 | 26 | 150 | 5 |
| 11514 | 588_6 | 7.5 µM | 74 | 1 | 131 | 1 |
| 11514 | 588_7 | 7.5 µM | 79 | 4 | 140 | 9 |
| 11514 | 588_8 | 7.5 µM | 49 | 2 | 235 | 2 |
| 11514 | 588_9 | 7.5 µM | 51 | 10 | 281 | 2 |
| 11515 | 589_1 | 7.5 µM | 61 | 2 | 154 | 9 |
| 11515 | 589_2 | 7.5 µM | 70 | 9 | 126 | 12 |
| 11515 | 589_3 | 7.5 µM | 53 | 3 | 212 | 32 |
| 11515 | 589_4 | 7.5 µM | 93 | 14 | 108 | 14 |
| 11515 | 589_5 | 7.5 µM | 69 | 11 | 191 | 7 |
| 11515 | 589_6 | 7.5 µM | 53 | 9 | 183 | 20 |
| 11515 | 589_7 | 7.5 µM | 45 | 8 | 257 | 4 |
| 11515 | 589_8 | 7.5 µM | 35 | 5 | 213 | 5 |
| 11515 | 589_9 | 7.5 µM | 41 | 2 | 290 | 22 |
| 13223 | 236_2 | 7.5 µM | 39 | 6 | 286 | 21 |
| 13223 | 236_3 | 7.5 µM | 32 | 10 | 256 | 29 |
| 13223 | 236_4 | 7.5 µM | 37 | 5 | 285 | 12 |
| 13223 | 236_5 | 7.5 µM | 33 | 8 | 280 | 19 |
| 13223 | 236_6 | 7.5 µM | 40 | 16 | 295 | 7 |
| 13223 | 236_7 | 7.5 µM | 45 | 10 | 254 | 50 |
| 13223 | 236_8 | 7.5 µM | 41 | 22 | 306 | 50 |
| 13223 | 236_9 | 7.5 µM | 32 | 11 | 292 | 47 |
| 13223 | 236_10 | 7.5 µM | 31 | 10 | 307 | 3 |
| 13223 | 236_11 | 7.5 µM | 52 | 32 | 198 | 29 |
| 13223 | 236_12 | 7.5 µM | 31 | 7 | 261 | 18 |
| 13223 | 236_13 | 7.5 µM | 34 | 3 | 279 | 32 |
| 13223 | 236_14 | 7.5 µM | 38 | 0 | 285 | 75 |
| 13223 | 236_15 | 7.5 µM | 40 | 17 | 307 | 53 |
| 13223 | 236_16 | 7.5 µM | 41 | 6 | 321 | 30 |
| 13224 | 237_2 | 7.5 µM | 49 | 18 | 251 | 38 |
| 13224 | 237_3 | 7.5 µM | 53 | 14 | 236 | 33 |
| 13224 | 237_4 | 7.5 µM | 39 | 0 | 283 | 26 |
| 13224 | 237_5 | 7.5 µM | 43 | 2 | 243 | 2 |
| 13224 | 237_6 | 7.5 µM | 39 | 10 | 265 | 48 |
| 13224 | 237_7 | 7.5 µM | 50 | 3 | 302 | 19 |
| 13224 | 237_8 | 7.5 µM | 46 | 7 | 327 | 43 |
| 13224 | 237_9 | 7.5 µM | 38 | 9 | 287 | 12 |
| 13224 | 237_10 | 7.5 µM | 35 | 6 | 248 | 35 |
| 13224 | 237_11 | 7.5 µM | 41 | 1 | 259 | 24 |
| 13224 | 237_12 | 7.5 µM | 33 | 6 | 303 | 35 |
| 13224 | 237_13 | 7.5 µM | 26 | 4 | 265 | 53 |
| 13224 | 237_14 | 7.5 µM | 30 | 8 | 321 | 15 |
| 13224 | 237_15 | 7.5 µM | 33 | 11 | 315 | 24 |
| 13224 | 237_16 | 7.5 µM | 36 | 11 | 292 | 19 |
| 13225 | 239_2 | 7.5 µM | 35 | 16 | 291 | 30 |
| 13225 | 239_3 | 7.5 µM | 40 | 15 | 311 | 42 |
| 13225 | 239_4 | 7.5 µM | 81 | 6 | 144 | 16 |
| 13225 | 239_5 | 7.5 µM | 90 | 16 | 127 | 11 |
| 13225 | 239_6 | 7.5 µM | 49 | 29 | 282 | 3 |
| 13225 | 239_7 | 7.5 µM | 35 | 4 | 296 | 23 |
| 13225 | 239_8 | 7.5 µM | 40 | 1 | 292 | 48 |
| 13225 | 239_9 | 7.5 µM | 36 | 1 | 318 | 44 |
| 13225 | 239_10 | 7.5 µM | 49 | NA | 304 | NA |
| 13225 | 239_11 | 7.5 µM | 45 | NA | 258 | NA |
| 13225 | 239_12 | 7.5 µM | 43 | 1 | 285 | 1 |
| 13225 | 239_13 | 7.5 µM | 31 | 1 | 308 | 31 |
| 13225 | 239_14 | 7.5 µM | 41 | 8 | 253 | 6 |
| 13225 | 239_15 | 7.5 µM | 28 | 3 | 291 | 16 |
| 13225 | 239_16 | 7.5 µM | 29 | 3 | 314 | 14 |
| 13226 | 590_1 | 7.5 µM | 34 | 1 | 283 | 18 |
| 13226 | 590_2 | 7.5 µM | 49 | 7 | 213 | 17 |
| 13226 | 590_3 | 7.5 µM | 40 | 1 | 274 | 51 |
| 13226 | 590_4 | 7.5 µM | 36 | 1 | 300 | 2 |
| 13226 | 590_5 | 7.5 µM | 37 | 3 | 280 | 36 |
| 13226 | 590_6 | 7.5 µM | 38 | 2 | 204 | 17 |
| 13226 | 590_7 | 7.5 µM | 38 | 5 | 245 | 16 |
| 13226 | 590_8 | 7.5 µM | 30 | 6 | 219 | 34 |
| 13226 | 590_9 | 7.5 µM | 33 | 1 | 269 | 2 |
| 13226 | 590_10 | 7.5 µM | 33 | 2 | 258 | 49 |
| 13226 | 590_11 | 7.5 µM | 48 | 17 | 297 | 31 |
| 13226 | 590_12 | 7.5 µM | 33 | 4 | 317 | 65 |
| 13226 | 590_13 | 7.5 µM | 35 | 7 | 337 | 43 |
| 13226 | 590_14 | 7.5 µM | 25 | 1 | 306 | 22 |
| 13226 | 590_15 | 7.5 µM | 30 | 5 | 299 | 2 |
| 15113 | 591_1 | 7.5 µM | 43 | 3 | 313 | 14 |
| 15113 | 591_2 | 7.5 µM | 52 | 2 | 295 | 24 |
| 15114 | 592_1 | 7.5 µM | 53 | 2 | 232 | 17 |
| 15114 | 592_2 | 7.5 µM | 39 | 1 | 309 | 23 |
| 15114 | 592_3 | 7.5 µM | 46 | 1 | 278 | 12 |
| 15114 | 592_4 | 7.5 µM | 36 | 1 | 328 | 13 |
| 15114 | 592_5 | 7.5 µM | 49 | 9 | 295 | 40 |
| 15114 | 592_6 | 7.5 µM | 46 | 3 | 297 | 10 |
| 15114 | 592_7 | 7.5 µM | 75 | 21 | 160 | 23 |
| 15114 | 592_8 | 7.5 µM | 41 | 10 | 325 | 23 |
| 15114 | 592_9 | 7.5 µM | 55 | 15 | 265 | 3 |
| 15115 | 241_2 | 7.5 µM | 66 | 18 | 168 | 2 |
| 15115 | 241_3 | 7.5 µM | 51 | 15 | 265 | 11 |
| 15115 | 241_4 | 7.5 µM | 49 | 4 | 239 | 7 |
| 15115 | 241_5 | 7.5 µM | 52 | 11 | 314 | 20 |
| 15115 | 241_6 | 7.5 µM | 41 | 13 | 307 | 7 |
| 15115 | 241_7 | 7.5 µM | 38 | 6 | 344 | 33 |
| 15115 | 241_8 | 7.5 µM | 39 | 10 | 329 | 9 |
| 15115 | 241_9 | 7.5 µM | 50 | 11 | 321 | 32 |
| 15115 | 241_10 | 7.5 µM | 48 | 9 | 316 | 1 |
| 15563 | 593_1 | 7.5 µM | 38 | 10 | 282 | 14 |
| 15563 | 593_2 | 7.5 µM | 31 | 5 | 279 | 16 |
| 15563 | 593_3 | 7.5 µM | 34 | 7 | 281 | 16 |
| 15563 | 593_4 | 7.5 µM | 32 | 16 | 318 | 2 |
| 15563 | 594_1 | 7.5 µM | 40 | 2 | 320 | 21 |
| 15563 | 594_2 | 7.5 µM | 54 | 7 | 237 | 14 |
| 15563 | 594_3 | 7.5 µM | 35 | 6 | 300 | 45 |
| 15563 | 594_4 | 7.5 µM | 37 | 7 | 254 | 6 |

TABLE 8-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 15564 | 596_1 | 7.5 µM | 47 | 7 | 225 | 35 |
| 15564 | 596_2 | 7.5 µM | 49 | 2 | 184 | 14 |
| 15564 | 596_3 | 7.5 µM | 34 | 8 | 271 | 18 |
| 15564 | 596_4 | 7.5 µM | 45 | 8 | 277 | 29 |
| 15564 | 595_1 | 7.5 µM | 42 | 4 | 254 | 6 |
| 15564 | 595_2 | 7.5 µM | 36 | 9 | 277 | 35 |
| 15564 | 595_3 | 7.5 µM | 40 | 8 | 295 | 31 |
| 15564 | 595_4 | 7.5 µM | 45 | 5 | 173 | 20 |
| 15566 | 597_1 | 7.5 µM | 48 | 6 | 296 | 22 |
| 15566 | 597_2 | 7.5 µM | 44 | 12 | 293 | 8 |
| 15566 | 597_3 | 7.5 µM | 41 | 6 | 318 | 23 |
| 15566 | 597_4 | 7.5 µM | 60 | 9 | 340 | 72 |
| 15567 | 38_3 | 7.5 µM | 41 | 3 | 306 | 14 |
| 15567 | 38_4 | 7.5 µM | 45 | 1 | 303 | 48 |
| 15567 | 38_5 | 7.5 µM | 39 | 15 | 292 | 28 |
| 15567 | 38_6 | 7.5 µM | 46 | 12 | 261 | 40 |
| 15567 | 598_1 | 7.5 µM | 42 | 2 | 257 | 31 |
| 15567 | 598_2 | 7.5 µM | 41 | 12 | 272 | 46 |
| 15567 | 598_3 | 7.5 µM | 54 | 9 | 281 | 29 |
| 15567 | 598_4 | 7.5 µM | 45 | 8 | 307 | 6 |
| 15568 | 599_1 | 7.5 µM | 47 | 3 | 326 | 68 |
| 15568 | 599_2 | 7.5 µM | 60 | 14 | 307 | 30 |
| 15568 | 599_3 | 7.5 µM | 50 | 8 | 274 | 24 |
| 15568 | 599_4 | 7.5 µM | 45 | 6 | 250 | 12 |
| 15568 | 600_1 | 7.5 µM | 37 | 6 | 251 | 1 |
| 15568 | 600_2 | 7.5 µM | 45 | 11 | 267 | 15 |
| 15568 | 600_3 | 7.5 µM | 44 | 5 | 278 | 1 |
| 15568 | 600_4 | 7.5 µM | 41 | 10 | 265 | 5 |
| 15569 | 601_1 | 7.5 µM | 42 | 12 | 271 | 18 |
| 15569 | 601_2 | 7.5 µM | 38 | 6 | 269 | 24 |
| 15569 | 601_3 | 7.5 µM | 39 | 4 | 260 | 34 |
| 15569 | 601_4 | 7.5 µM | 56 | 8 | 146 | 1 |
| 15570 | 244_2 | 7.5 µM | 46 | 1 | 338 | 6 |
| 15570 | 244_3 | 7.5 µM | 47 | 0 | 275 | 47 |
| 15570 | 244_4 | 7.5 µM | 47 | 8 | 281 | 67 |
| 15570 | 244_5 | 7.5 µM | 41 | 8 | 258 | 52 |
| 15570 | 39_2 | 7.5 µM | 53 | 4 | 339 | 25 |
| 15570 | 39_3 | 7.5 µM | 65 | 5 | 200 | 17 |
| 15570 | 39_4 | 7.5 µM | 47 | 7 | 321 | 6 |
| 15570 | 39_5 | 7.5 µM | 46 | 3 | 289 | 20 |
| 15571 | 602_1 | 7.5 µM | 34 | 5 | 278 | 29 |
| 15571 | 602_2 | 7.5 µM | 39 | 8 | 254 | 37 |
| 15571 | 602_3 | 7.5 µM | 41 | 10 | 266 | 23 |
| 15571 | 602_4 | 7.5 µM | 42 | 8 | 256 | 40 |
| 15571 | 40_2 | 7.5 µM | 58 | 0 | 325 | 4 |
| 15571 | 40_3 | 7.5 µM | 58 | 2 | 326 | 35 |
| 15571 | 40_4 | 7.5 µM | 54 | 1 | 306 | 3 |
| 15571 | 40_5 | 7.5 µM | 44 | 2 | 322 | 4 |
| 15571 | 40_6 | 7.5 µM | 43 | 4 | 293 | 17 |
| 15571 | 40_7 | 7.5 µM | 53 | 7 | 343 | 20 |
| 15571 | 40_8 | 7.5 µM | 52 | 1 | 337 | 17 |
| 15572 | 604_1 | 7.5 µM | 58 | 1 | 289 | 3 |
| 15572 | 604_2 | 7.5 µM | 63 | 12 | 230 | 5 |
| 15572 | 604_3 | 7.5 µM | 57 | 3 | 306 | 23 |
| 15572 | 604_4 | 7.5 µM | 46 | 6 | 324 | 4 |
| 15572 | 603_1 | 7.5 µM | 60 | 7 | 339 | 31 |
| 15572 | 603_2 | 7.5 µM | 70 | 0 | 279 | 19 |
| 15572 | 603_3 | 7.5 µM | 59 | 9 | 290 | 48 |
| 15572 | 603_4 | 7.5 µM | 85 | 11 | 123 | 24 |
| 15573 | 605_1 | 7.5 µM | 56 | 5 | 288 | 3 |
| 15573 | 605_2 | 7.5 µM | 58 | 4 | 286 | 6 |
| 15573 | 605_3 | 7.5 µM | 59 | 3 | 261 | 9 |
| 15573 | 605_4 | 7.5 µM | 69 | 24 | 328 | 17 |
| 15573 | 606_1 | 7.5 µM | 50 | 4 | 282 | 19 |
| 15573 | 606_2 | 7.5 µM | 112 | NA | 133 | NA |
| 15573 | 606_3 | 7.5 µM | 55 | 22 | 254 | 43 |
| 15573 | 606_4 | 7.5 µM | 107 | 59 | 116 | 2 |
| 15574 | 607_1 | 7.5 µM | 56 | 2 | 337 | 31 |
| 15574 | 607_2 | 7.5 µM | 59 | 1 | 254 | 10 |
| 15574 | 607_3 | 7.5 µM | 53 | 0 | 295 | 26 |
| 15574 | 607_4 | 7.5 µM | 48 | 3 | 268 | 15 |
| 25248 | 608_1 | 7.5 µM | 86 | 7 | 189 | 5 |
| 25248 | 608_2 | 7.5 µM | 102 | 13 | 136 | 3 |
| 25248 | 608_3 | 7.5 µM | 54 | 17 | 280 | 12 |
| 25248 | 608_4 | 7.5 µM | 71 | 8 | 219 | 31 |
| 25248 | 608_5 | 7.5 µM | 59 | 20 | 179 | 16 |
| 25248 | 608_6 | 7.5 µM | 71 | 2 | 198 | 0 |
| 25248 | 608_7 | 7.5 µM | 47 | 3 | 230 | 21 |
| 25248 | 608_8 | 7.5 µM | 55 | 12 | 287 | 13 |
| 25248 | 608_9 | 7.5 µM | 66 | 19 | 297 | 18 |
| 25249 | 609_1 | 7.5 µM | 58 | 19 | 264 | 7 |
| 25249 | 609_2 | 7.5 µM | 88 | 6 | 156 | 5 |
| 25249 | 609_3 | 7.5 µM | 76 | 19 | 140 | 13 |
| 25249 | 609_4 | 7.5 µM | 50 | 15 | 185 | 6 |
| 25249 | 609_5 | 7.5 µM | 95 | 29 | 139 | 1 |
| 25249 | 609_6 | 7.5 µM | 86 | 15 | 126 | 7 |
| 25249 | 609_7 | 7.5 µM | 72 | 9 | 174 | 1 |
| 25249 | 609_8 | 7.5 µM | 64 | 3 | 189 | 18 |
| 25249 | 609_9 | 7.5 µM | 77 | 12 | 223 | 35 |
| 25250 | 610_1 | 7.5 µM | 55 | 17 | 233 | 7 |
| 25250 | 610_2 | 7.5 µM | 52 | 15 | 233 | 9 |
| 25250 | 610_3 | 7.5 µM | 77 | 5 | 151 | 11 |
| 25250 | 610_4 | 7.5 µM | 48 | 0 | 242 | 21 |
| 25250 | 610_5 | 7.5 µM | 59 | 8 | 234 | 0 |
| 25250 | 610_6 | 7.5 µM | 59 | 12 | 208 | 23 |
| 25250 | 610_7 | 7.5 µM | 69 | 7 | 216 | 5 |
| 25250 | 610_8 | 7.5 µM | 70 | 16 | 211 | 2 |
| 25250 | 610_9 | 7.5 µM | 77 | 22 | 157 | 19 |
| 25251 | 611_1 | 7.5 µM | 43 | 4 | 306 | 10 |
| 25251 | 611_2 | 7.5 µM | 43 | 1 | 300 | 36 |
| 25251 | 611_3 | 7.5 µM | 43 | 17 | 306 | 6 |
| 25251 | 611_4 | 7.5 µM | 40 | 1 | 320 | 37 |
| 25251 | 611_5 | 7.5 µM | 48 | 9 | 273 | 7 |
| 25251 | 611_6 | 7.5 µM | 51 | 2 | 302 | 26 |
| 25251 | 611_7 | 7.5 µM | 40 | 8 | 326 | 8 |
| 25251 | 611_8 | 7.5 µM | 55 | 10 | 330 | 17 |
| 25251 | 611_9 | 7.5 µM | 40 | 3 | 297 | 11 |
| 25252 | 612_1 | 7.5 µM | 58 | 9 | 219 | 5 |
| 25252 | 612_2 | 7.5 µM | 54 | 9 | 282 | 4 |
| 25252 | 612_3 | 7.5 µM | 56 | 13 | 265 | 35 |
| 25252 | 612_4 | 7.5 µM | 81 | 16 | 239 | 51 |
| 25252 | 612_5 | 7.5 µM | 57 | 2 | 234 | 25 |
| 25252 | 612_6 | 7.5 µM | 76 | 18 | 221 | 8 |
| 25252 | 612_7 | 7.5 µM | 45 | 7 | 285 | 11 |
| 25252 | 612_8 | 7.5 µM | 50 | 8 | 231 | 4 |
| 25252 | 612_9 | 7.5 µM | 51 | 3 | 305 | 17 |
| 29636 | 271_1 | 7.5 µM | 35 | 4 | 345 | 29 |
| 29636 | 271_1 | 7.5 µM | 32 | 6 | 383 | 31 |
| 29636 | 271_1 | 7.5 µM | 42 | 7 | 292 | 13 |
| 29636 | 271_1 | 7.5 µM | 40 | 1 | 309 | 41 |
| 29636 | 271_1 | 7.5 µM | 41 | 10 | 339 | 17 |
| 29636 | 271_1 | 7.5 µM | 35 | 8 | 306 | 40 |
| 29636 | 271_1 | 7.5 µM | 33 | 1 | 320 | 12 |
| 29636 | 271_1 | 7.5 µM | 43 | 1 | 347 | 7 |
| 29636 | 271_1 | 7.5 µM | 36 | 2 | 339 | 19 |
| 29636 | 271_1 | 7.5 µM | 36 | 1 | 315 | 5 |
| 29636 | 271_1 | 7.5 µM | 41 | 1 | 326 | 16 |
| 29636 | 271_1 | 7.5 µM | 38 | 2 | 344 | 1 |
| 29636 | 271_1 | 7.5 µM | 34 | 6 | 341 | 8 |
| 29636 | 271_1 | 7.5 µM | 42 | 9 | 320 | 1 |
| 29636 | 271_1 | 7.5 µM | 31 | 8 | 344 | 37 |
| 29636 | 271_1 | 7.5 µM | 44 | 2 | 335 | 11 |
| 29636 | 271_1 | 7.5 µM | 32 | 0 | 316 | 17 |
| 29636 | 271_1 | 7.5 µM | 43 | 11 | 323 | 2 |
| 29636 | 271_1 | 7.5 µM | 35 | 7 | 340 | 2 |
| 29636 | 271_1 | 7.5 µM | 43 | 1 | 340 | 8 |
| 29636 | 271_1 | 7.5 µM | 33 | 4 | 296 | 27 |
| 29636 | 271_1 | 7.5 µM | 38 | 5 | 334 | 4 |
| 29636 | 271_1 | 7.5 µM | 36 | 4 | 341 | 22 |
| 29636 | 271_1 | 7.5 µM | 48 | 4 | 334 | 3 |
| 29636 | 271_1 | 7.5 µM | 36 | 8 | 303 | 13 |
| 29636 | 271_1 | 7.5 µM | 36 | 0 | 343 | 7 |
| 29636 | 271_1 | 7.5 µM | 39 | 1 | 326 | 1 |
| 29636 | 271_1 | 7.5 µM | 38 | 2 | 346 | 14 |
| 29636 | 271_1 | 7.5 µM | 32 | 0 | 332 | 11 |
| 29636 | 271_1 | 7.5 µM | 39 | 4 | 330 | 23 |
| 29636 | 271_1 | 7.5 µM | 39 | 7 | 346 | 33 |
| 29636 | 271_1 | 7.5 µM | 40 | 1 | 329 | 14 |
| 29636 | 271_1 | 7.5 µM | 34 | 6 | 316 | 38 |
| 29636 | 271_1 | 7.5 µM | 33 | 4 | 317 | 14 |

TABLE 8-continued

Oligonucleotide activity in patient derived human neuronal cell cultures.

| Start SEQ ID NO 1 | CMP ID NO | Conc µM | % of Mock UBE3A-SUP | sd | % of Mock UBE3A | sd |
|---|---|---|---|---|---|---|
| 29636 | 271_1 | 7.5 µM | 41 | 6 | 328 | 11 |
| 29636 | 271_1 | 7.5 µM | 45 | 2 | 345 | 3 |
| 29636 | 271_1 | 7.5 µM | 37 | 1 | 330 | 3 |
| 29636 | 271_1 | 7.5 µM | 45 | 7 | 322 | 18 |
| 29636 | 271_1 | 7.5 µM | 36 | 3 | 334 | 13 |
| 29636 | 271_1 | 7.5 µM | 33 | 8 | 333 | 3 |
| 29636 | 271_1 | 7.5 µM | 35 | 10 | 321 | 43 |
| 29636 | 271_1 | 7.5 µM | 41 | 3 | 323 | 18 |
| 29636 | 271_1 | 7.5 µM | 39 | 8 | 354 | 39 |
| 29636 | 271_1 | 7.5 µM | 35 | 2 | 327 | 23 |
| 30599 | 613_1 | 7.5 µM | 73 | 29 | 172 | 22 |
| 30599 | 613_2 | 7.5 µM | 87 | 40 | 114 | 9 |
| 30599 | 613_3 | 7.5 µM | 59 | 23 | 168 | 23 |
| 30599 | 613_4 | 7.5 µM | 43 | 15 | 281 | 31 |
| 30599 | 613_5 | 7.5 µM | 51 | 3 | 271 | 28 |
| 30600 | 614_1 | 7.5 µM | 56 | 11 | 179 | 22 |
| 30600 | 614_2 | 7.5 µM | 96 | 40 | 100 | 7 |
| 30600 | 614_3 | 7.5 µM | 41 | 7 | 246 | 27 |
| 30600 | 614_4 | 7.5 µM | 47 | 19 | 283 | 14 |
| 30600 | 614_5 | 7.5 µM | 52 | 21 | 209 | 16 |
| 30600 | 615_1 | 7.5 µM | 61 | 19 | 197 | 12 |
| 30600 | 615_2 | 7.5 µM | 45 | 11 | 287 | 25 |
| 30600 | 615_3 | 7.5 µM | 102 | NA | 115 | NA |
| 30600 | 615_4 | 7.5 µM | 72 | NA | 170 | NA |
| 30600 | 615_5 | 7.5 µM | 95 | NA | 138 | NA |
| 30601 | 285_2 | 7.5 µM | 83 | NA | 165 | NA |
| 30601 | 285_3 | 7.5 µM | 124 | NA | 111 | NA |
| 30601 | 285_4 | 7.5 µM | 69 | NA | 183 | NA |
| 30601 | 285_5 | 7.5 µM | 47 | 23 | 211 | 7 |
| 30601 | 285_6 | 7.5 µM | 46 | 12 | 183 | 6 |
| 30601 | 617_1 | 7.5 µM | 67 | 26 | 190 | 19 |
| 30601 | 617_2 | 7.5 µM | 74 | 35 | 137 | 6 |
| 30601 | 617_3 | 7.5 µM | 51 | 16 | 211 | 4 |
| 30601 | 617_4 | 7.5 µM | 65 | 22 | 142 | 11 |
| 30601 | 617_5 | 7.5 µM | 43 | 8 | 298 | 26 |
| 30601 | 616_1 | 7.5 µM | 50 | 22 | 181 | 12 |
| 30601 | 616_2 | 7.5 µM | 37 | 13 | 276 | 33 |
| 30601 | 616_3 | 7.5 µM | 38 | 16 | 264 | 9 |
| 30601 | 616_4 | 7.5 µM | 43 | NA | 304 | NA |
| 30601 | 616_5 | 7.5 µM | 50 | NA | 229 | NA |
| 30602 | 619_1 | 7.5 µM | 90 | 43 | 131 | 22 |
| 30602 | 619_2 | 7.5 µM | 78 | 40 | 138 | 2 |
| 30602 | 619_3 | 7.5 µM | 66 | 22 | 123 | 8 |
| 30602 | 619_4 | 7.5 µM | 100 | 43 | 96 | 5 |
| 30602 | 619_5 | 7.5 µM | 75 | 17 | 157 | 5 |
| 30602 | 618_1 | 7.5 µM | 46 | 1 | 226 | 12 |
| 30602 | 618_2 | 7.5 µM | 68 | NA | 151 | NA |
| 30602 | 618_3 | 7.5 µM | 52 | 4 | 207 | 18 |
| 30602 | 618_4 | 7.5 µM | 57 | 12 | 223 | 2 |
| 30602 | 618_5 | 7.5 µM | 54 | 2 | 211 | 3 |
| 30603 | 620_1 | 7.5 µM | 106 | 23 | 110 | 16 |
| 30603 | 620_2 | 7.5 µM | 48 | 10 | 243 | 18 |
| 30603 | 620_3 | 7.5 µM | 53 | 1 | 174 | 32 |
| 30603 | 620_4 | 7.5 µM | 81 | 0 | 138 | 15 |
| 30603 | 620_5 | 7.5 µM | 56 | 5 | 218 | 9 |
| 30604 | 621_1 | 7.5 µM | 39 | 4 | 304 | 10 |
| 30604 | 621_2 | 7.5 µM | 35 | 7 | 311 | 3 |
| 30604 | 621_3 | 7.5 µM | 67 | 18 | 142 | 8 |
| 30604 | 621_4 | 7.5 µM | 34 | 6 | 273 | 21 |
| 30604 | 621_5 | 7.5 µM | 36 | 5 | 266 | 18 |
| 30605 | 622_1 | 7.5 µM | 42 | 1 | 242 | 28 |
| 30605 | 622_2 | 7.5 µM | 31 | 10 | 300 | 8 |
| 30605 | 622_3 | 7.5 µM | 35 | 3 | 319 | 11 |
| 30605 | 622_4 | 7.5 µM | 37 | 4 | 281 | 5 |
| 30605 | 622_5 | 7.5 µM | 39 | 5 | 306 | 11 |
| 30606 | 623_1 | 7.5 µM | 47 | 3 | 287 | 1 |
| 30606 | 623_2 | 7.5 µM | 74 | 23 | 166 | 7 |
| 30606 | 623_3 | 7.5 µM | 82 | 1 | 149 | 8 |
| 30606 | 623_4 | 7.5 µM | 66 | 9 | 135 | 8 |
| 30606 | 623_5 | 7.5 µM | 78 | 7 | 128 | 12 |
| 30608 | 624_1 | 7.5 µM | 84 | 13 | 185 | 25 |
| 30608 | 624_2 | 7.5 µM | 35 | 2 | 245 | 9 |
| 30608 | 624_3 | 7.5 µM | 31 | 3 | 267 | 9 |
| 30608 | 624_4 | 7.5 µM | 39 | 16 | 257 | 13 |
| 30608 | 624_5 | 7.5 µM | 34 | 3 | 283 | 4 |
| 30666 | 625_1 | 7.5 µM | 45 | 5 | 286 | 39 |
| 30666 | 625_2 | 7.5 µM | 39 | 3 | 280 | 13 |
| 30666 | 625_3 | 7.5 µM | 40 | 10 | 258 | 9 |
| 30666 | 625_4 | 7.5 µM | 41 | 14 | 234 | 39 |
| 30666 | 625_5 | 7.5 µM | 42 | 5 | 293 | 26 |
| 30666 | 625_6 | 7.5 µM | 44 | 0 | 284 | 25 |
| 30666 | 625_7 | 7.5 µM | 46 | 3 | 271 | 4 |
| 30666 | 625_8 | 7.5 µM | 47 | 5 | 256 | 17 |
| 30666 | 625_9 | 7.5 µM | 40 | 7 | 302 | 2 |
| 30667 | 626_1 | 7.5 µM | 38 | 1 | 279 | 10 |
| 30667 | 626_2 | 7.5 µM | 39 | 21 | 329 | 22 |
| 30667 | 626_3 | 7.5 µM | 59 | 12 | 265 | 65 |
| 30667 | 626_4 | 7.5 µM | 39 | 5 | 318 | 25 |
| 30667 | 626_5 | 7.5 µM | 36 | 2 | 302 | 33 |
| 30667 | 626_6 | 7.5 µM | 36 | 6 | 273 | 34 |
| 30667 | 626_7 | 7.5 µM | 30 | 0 | 299 | 29 |
| 30667 | 626_8 | 7.5 µM | 35 | 4 | 277 | 43 |
| 30667 | 626_9 | 7.5 µM | 32 | 3 | 275 | 22 |
| 30668 | 627_1 | 7.5 µM | 71 | 3 | 131 | 11 |
| 30668 | 627_2 | 7.5 µM | 49 | 4 | 226 | 30 |
| 30668 | 627_3 | 7.5 µM | 64 | 5 | 147 | 8 |
| 30668 | 627_4 | 7.5 µM | 52 | 6 | 176 | 9 |
| 30668 | 627_5 | 7.5 µM | 78 | 14 | 108 | 3 |
| 30668 | 627_6 | 7.5 µM | 40 | 1 | 183 | 23 |
| 30668 | 627_7 | 7.5 µM | 85 | 8 | 116 | 2 |
| 30668 | 627_8 | 7.5 µM | 45 | 1 | 128 | 7 |
| 30668 | 627_9 | 7.5 µM | 42 | 5 | 215 | 36 |
| 30669 | 628_1 | 7.5 µM | 90 | 11 | 120 | 15 |
| 30669 | 628_2 | 7.5 µM | 73 | 12 | 124 | 4 |
| 30669 | 628_3 | 7.5 µM | 88 | 2 | 115 | 4 |
| 30669 | 628_4 | 7.5 µM | 54 | 4 | 190 | 18 |
| 30669 | 628_5 | 7.5 µM | 64 | 1 | 138 | 3 |
| 30669 | 628_6 | 7.5 µM | 62 | 4 | 138 | 11 |
| 30669 | 628_7 | 7.5 µM | 55 | 1 | 138 | 13 |
| 30669 | 628_8 | 7.5 µM | 62 | 1 | 140 | 5 |
| 30669 | 628_9 | 7.5 µM | 79 | 10 | 134 | 22 |
| 30711 | 629_1 | 7.5 µM | 42 | 1 | 252 | 47 |
| 30711 | 629_2 | 7.5 µM | 40 | 2 | 295 | 30 |
| 30711 | 629_3 | 7.5 µM | 46 | 1 | 302 | 78 |
| 30711 | 629_4 | 7.5 µM | 41 | 3 | 260 | 16 |
| 30711 | 629_5 | 7.5 µM | 41 | 1 | 284 | 3 |
| 30711 | 629_6 | 7.5 µM | 43 | 0 | 262 | 1 |
| 30711 | 629_7 | 7.5 µM | 43 | 3 | 278 | 65 |
| 30711 | 629_8 | 7.5 µM | 53 | 5 | 234 | 24 |
| 30711 | 629_9 | 7.5 µM | 37 | 4 | 289 | 1 |
| 30711 | 629_10 | 7.5 µM | 47 | 6 | 292 | 6 |
| 30711 | 629_11 | 7.5 µM | 50 | 5 | 224 | 20 |
| 30712 | 630_1 | 7.5 µM | 44 | 2 | 282 | 22 |
| 30712 | 630_2 | 7.5 µM | 45 | 6 | 297 | 23 |
| 30712 | 630_3 | 7.5 µM | 46 | 2 | 272 | 10 |
| 30713 | 631_1 | 7.5 µM | 45 | 2 | 294 | 10 |
| 30713 | 631_2 | 7.5 µM | 42 | 0 | 285 | 14 |
| 30713 | 631_3 | 7.5 µM | 38 | 3 | 319 | 21 |
| 30713 | 631_4 | 7.5 µM | 43 | 3 | 282 | 4 |
| 30713 | 631_5 | 7.5 µM | 54 | 2 | 173 | 17 |
| 30713 | 631_6 | 7.5 µM | 37 | 0 | 315 | 10 |
| 30713 | 631_7 | 7.5 µM | 40 | 4 | 317 | 2 |
| 30713 | 631_8 | 7.5 µM | 44 | 1 | 275 | 5 |
| 30713 | 631_9 | 7.5 µM | 47 | 2 | 233 | 8 |
| 30713 | 631_10 | 7.5 µM | 108 | 18 | 101 | 3 |
| 30714 | 632_1 | 7.5 µM | 48 | 4 | 210 | 4 |
| 30714 | 632_2 | 7.5 µM | 53 | 5 | 256 | 5 |
| 30714 | 632_3 | 7.5 µM | 60 | 5 | 224 | 19 |
| 30714 | 632_4 | 7.5 µM | 89 | 12 | 117 | 11 |
| 30714 | 632_5 | 7.5 µM | 39 | 6 | 312 | 6 |
| 30714 | 632_6 | 7.5 µM | 40 | 2 | 278 | 31 |
| 30714 | 632_7 | 7.5 µM | 86 | 1 | 160 | 21 |
| 30714 | 632_8 | 7.5 µM | 57 | 17 | 278 | 40 |
| 30714 | 632_9 | 7.5 µM | 51 | 7 | 236 | 13 |
| 30715 | 304_2 | 7.5 µM | 53 | 5 | 206 | 18 |
| 30715 | 304_3 | 7.5 µM | 70 | 11 | 142 | 24 |
| 30715 | 304_4 | 7.5 µM | 88 | 1 | 120 | 10 |
| 30715 | 304_5 | 7.5 µM | 82 | 15 | 123 | 7 |
| 30715 | 304_6 | 7.5 µM | 43 | 4 | 264 | 12 |
| 30715 | 304_7 | 7.5 µM | 41 | 5 | 266 | 49 |

TABLE 8-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 30715 | 304_8 | 7.5 μM | 43 | 1 | 291 | 12 |
| 30715 | 304_9 | 7.5 μM | 36 | 3 | 285 | 18 |
| 30715 | 304_10 | 7.5 μM | 42 | 1 | 280 | 40 |
| 33376 | 633_1 | 7.5 μM | 53 | 1 | 234 | 50 |
| 33376 | 633_2 | 7.5 μM | 45 | 5 | 301 | 7 |
| 33376 | 633_3 | 7.5 μM | 53 | 7 | 263 | 17 |
| 33376 | 633_4 | 7.5 μM | 53 | 4 | 229 | 22 |
| 33376 | 633_5 | 7.5 μM | 43 | 3 | 264 | 36 |
| 33376 | 633_6 | 7.5 μM | 53 | 5 | 247 | 12 |
| 33376 | 633_7 | 7.5 μM | 49 | 6 | 289 | 6 |
| 33376 | 633_8 | 7.5 μM | 64 | 1 | 238 | 24 |
| 33376 | 633_9 | 7.5 μM | 63 | 2 | 249 | 28 |
| 33377 | 634_1 | 7.5 μM | 57 | 9 | 250 | 14 |
| 33377 | 634_2 | 7.5 μM | 53 | 10 | 265 | 3 |
| 33377 | 634_3 | 7.5 μM | 48 | 2 | 275 | 10 |
| 33377 | 634_4 | 7.5 μM | 39 | 6 | 287 | 12 |
| 33377 | 634_5 | 7.5 μM | 49 | 1 | 255 | 22 |
| 33377 | 634_6 | 7.5 μM | 51 | 2 | 291 | 15 |
| 33377 | 634_7 | 7.5 μM | 47 | 5 | 297 | 16 |
| 33377 | 634_8 | 7.5 μM | 42 | 9 | 311 | 14 |
| 33377 | 634_9 | 7.5 μM | 47 | 5 | 271 | 23 |
| 33378 | 635_1 | 7.5 μM | 56 | 11 | 257 | 3 |
| 33378 | 635_2 | 7.5 μM | 56 | 5 | 213 | 23 |
| 33378 | 635_3 | 7.5 μM | 61 | 8 | 215 | 8 |
| 33378 | 635_4 | 7.5 μM | 58 | 15 | 232 | 16 |
| 33378 | 635_5 | 7.5 μM | 48 | 3 | 316 | 20 |
| 33378 | 635_6 | 7.5 μM | 59 | 5 | 262 | 30 |
| 33378 | 635_7 | 7.5 μM | 55 | 7 | 287 | 15 |
| 33378 | 635_8 | 7.5 μM | 42 | 1 | 284 | 3 |
| 33378 | 635_9 | 7.5 μM | 40 | 0 | 277 | 23 |
| 33379 | 636_1 | 7.5 μM | 50 | 2 | 239 | 7 |
| 33379 | 636_2 | 7.5 μM | 74 | 16 | 204 | 10 |
| 33379 | 636_3 | 7.5 μM | 55 | 4 | 201 | 3 |
| 33379 | 636_4 | 7.5 μM | 54 | 2 | 238 | 7 |
| 33379 | 636_5 | 7.5 μM | 52 | 5 | 207 | 43 |
| 33379 | 636_6 | 7.5 μM | 47 | 3 | 249 | 6 |
| 33379 | 636_7 | 7.5 μM | 48 | 5 | 241 | 1 |
| 33379 | 636_8 | 7.5 μM | 37 | 7 | 304 | 12 |
| 33379 | 636_9 | 7.5 μM | 62 | 9 | 245 | 5 |
| 33380 | 637_1 | 7.5 μM | 39 | 1 | 219 | 25 |
| 33380 | 637_2 | 7.5 μM | 59 | 1 | 197 | 11 |
| 33380 | 637_3 | 7.5 μM | 56 | 1 | 250 | 19 |
| 33380 | 637_4 | 7.5 μM | 53 | 7 | 244 | 36 |
| 33380 | 637_5 | 7.5 μM | 73 | 13 | 297 | 34 |
| 33380 | 637_6 | 7.5 μM | 65 | 1 | 124 | 17 |
| 33380 | 637_7 | 7.5 μM | 74 | 5 | 133 | 5 |
| 33380 | 637_8 | 7.5 μM | 53 | 2 | 207 | 7 |
| 33380 | 637_9 | 7.5 μM | 54 | 15 | 226 | 26 |
| 39806 | 638_1 | 7.5 μM | 37 | 7 | 283 | 31 |
| 39806 | 638_2 | 7.5 μM | 49 | 11 | 291 | 30 |
| 39806 | 638_3 | 7.5 μM | 41 | 1 | 270 | 20 |
| 39806 | 638_4 | 7.5 μM | 42 | 13 | 267 | 9 |
| 39806 | 638_5 | 7.5 μM | 50 | 1 | 184 | 5 |
| 39806 | 638_6 | 7.5 μM | 38 | 1 | 276 | 15 |
| 39806 | 638_7 | 7.5 μM | 56 | 1 | 292 | 4 |
| 39806 | 638_8 | 7.5 μM | 41 | 4 | 267 | 11 |
| 39806 | 638_9 | 7.5 μM | 41 | 4 | 218 | 33 |
| 39807 | 639_1 | 7.5 μM | 48 | 15 | 293 | 30 |
| 39807 | 639_2 | 7.5 μM | 38 | 3 | 269 | 2 |
| 39807 | 639_3 | 7.5 μM | 72 | 5 | 167 | 3 |
| 39807 | 639_4 | 7.5 μM | 69 | 38 | 242 | 36 |
| 39807 | 639_5 | 7.5 μM | 47 | 6 | 303 | 36 |
| 39807 | 639_6 | 7.5 μM | 53 | 6 | 179 | 5 |
| 39807 | 639_7 | 7.5 μM | 51 | 3 | 189 | 8 |
| 39807 | 639_8 | 7.5 μM | 42 | 3 | 185 | 19 |
| 39807 | 639_9 | 7.5 μM | 45 | 3 | 202 | 15 |
| 39808 | 640_1 | 7.5 μM | 39 | 5 | 265 | 7 |
| 39808 | 640_2 | 7.5 μM | 37 | 4 | 272 | 56 |
| 39808 | 640_3 | 7.5 μM | 38 | 3 | 260 | 17 |
| 39808 | 640_4 | 7.5 μM | 33 | 4 | 255 | 2 |
| 39808 | 640_5 | 7.5 μM | 38 | 3 | 253 | 3 |
| 39808 | 640_6 | 7.5 μM | 40 | 8 | 216 | 10 |
| 39808 | 640_7 | 7.5 μM | 39 | 8 | 310 | 7 |
| 39808 | 640_8 | 7.5 μM | 41 | 6 | 282 | 21 |
| 39808 | 640_9 | 7.5 μM | 40 | 5 | 269 | 12 |
| 44439 | 641_1 | 7.5 μM | 35 | 6 | 336 | 32 |
| 44439 | 641_2 | 7.5 μM | 67 | 20 | 161 | 6 |
| 44439 | 641_3 | 7.5 μM | 34 | 9 | 317 | 30 |
| 44439 | 641_4 | 7.5 μM | 62 | 18 | 193 | 9 |
| 44439 | 641_5 | 7.5 μM | 34 | 4 | 280 | 3 |
| 44439 | 641_6 | 7.5 μM | 43 | 1 | 315 | 45 |
| 44439 | 641_7 | 7.5 μM | 45 | 17 | 307 | 53 |
| 44439 | 641_8 | 7.5 μM | 41 | 0 | 294 | 41 |
| 44439 | 641_9 | 7.5 μM | 37 | 2 | 334 | 43 |
| 44440 | 361_2 | 7.5 μM | 36 | 1 | 303 | 15 |
| 44440 | 361_3 | 7.5 μM | 32 | 3 | 315 | 12 |
| 44440 | 361_4 | 7.5 μM | 41 | 1 | 299 | 7 |
| 44440 | 361_5 | 7.5 μM | 40 | 5 | 295 | 6 |
| 44440 | 361_6 | 7.5 μM | 40 | 2 | 296 | 30 |
| 44440 | 361_7 | 7.5 μM | 39 | 1 | 300 | 55 |
| 44440 | 361_8 | 7.5 μM | 45 | 6 | 285 | 45 |
| 44440 | 361_9 | 7.5 μM | 44 | 6 | 321 | 26 |
| 44440 | 361_10 | 7.5 μM | 46 | 7 | 290 | 18 |
| 44441 | 362_2 | 7.5 μM | 50 | 4 | 277 | 4 |
| 44441 | 362_3 | 7.5 μM | 40 | 6 | 296 | 8 |
| 44441 | 362_4 | 7.5 μM | 37 | 5 | 340 | 18 |
| 44441 | 362_5 | 7.5 μM | 45 | 2 | 266 | 21 |
| 44441 | 362_6 | 7.5 μM | 39 | 7 | 263 | 0 |
| 44441 | 362_7 | 7.5 μM | 41 | 12 | 262 | 36 |
| 44441 | 362_8 | 7.5 μM | 35 | 13 | 313 | 6 |
| 44441 | 362_9 | 7.5 μM | 36 | 8 | 300 | 20 |
| 44441 | 362_10 | 7.5 μM | 48 | 10 | 293 | 1 |
| 46391 | 642_1 | 7.5 μM | 51 | 25 | 278 | 6 |
| 46391 | 642_2 | 7.5 μM | 46 | 2 | 303 | 4 |
| 46391 | 642_3 | 7.5 μM | 48 | 3 | 297 | 11 |
| 46391 | 642_4 | 7.5 μM | 45 | 11 | 320 | 37 |
| 46391 | 642_5 | 7.5 μM | 71 | 32 | 303 | 40 |
| 46391 | 642_6 | 7.5 μM | 47 | 15 | 298 | 16 |
| 46391 | 642_7 | 7.5 μM | 38 | 6 | 277 | 5 |
| 46391 | 642_8 | 7.5 μM | 38 | 3 | 280 | 20 |
| 46391 | 642_9 | 7.5 μM | 51 | 20 | 285 | 16 |
| 46391 | 642_10 | 7.5 μM | 32 | 7 | 293 | 20 |
| 46391 | 642_11 | 7.5 μM | 42 | 2 | 291 | 2 |
| 46391 | 642_12 | 7.5 μM | 40 | 3 | 317 | 19 |
| 46391 | 642_13 | 7.5 μM | 39 | 11 | 295 | 5 |
| 46391 | 642_14 | 7.5 μM | 52 | 20 | 295 | 16 |
| 46391 | 642_15 | 7.5 μM | 39 | 8 | 316 | 38 |
| 46391 | 642_16 | 7.5 μM | 35 | 2 | 294 | 30 |
| 46391 | 642_17 | 7.5 μM | 51 | 5 | 292 | 8 |
| 46391 | 643_1 | 7.5 μM | 39 | 4 | 276 | 16 |
| 46392 | 644_1 | 7.5 μM | 39 | 0 | 321 | 7 |
| 46392 | 644_2 | 7.5 μM | 46 | 4 | 308 | 4 |
| 46392 | 644_3 | 7.5 μM | 44 | 1 | 317 | 3 |
| 46392 | 644_4 | 7.5 μM | 38 | 6 | 315 | 11 |
| 46392 | 645_1 | 7.5 μM | 46 | 5 | 342 | 42 |
| 46392 | 645_2 | 7.5 μM | 37 | 5 | 292 | 25 |
| 46392 | 645_3 | 7.5 μM | 46 | 16 | 317 | 30 |
| 46392 | 645_4 | 7.5 μM | 47 | 8 | 381 | 102 |
| 46392 | 645_5 | 7.5 μM | 42 | 2 | 269 | 4 |
| 46393 | 646_1 | 7.5 μM | 49 | 4 | 295 | 2 |
| 46393 | 646_2 | 7.5 μM | 49 | 9 | 304 | 38 |
| 46393 | 646_3 | 7.5 μM | 44 | 6 | 298 | 50 |
| 46393 | 646_4 | 7.5 μM | 43 | 1 | 296 | 41 |
| 46393 | 646_5 | 7.5 μM | 35 | 1 | 260 | 3 |
| 46393 | 646_6 | 7.5 μM | 40 | 2 | 281 | 67 |
| 46393 | 646_7 | 7.5 μM | 38 | 1 | 278 | 44 |
| 46393 | 646_8 | 7.5 μM | 42 | 6 | 262 | 49 |
| 46393 | 646_9 | 7.5 μM | 38 | 3 | 289 | 24 |
| 46393 | 646_10 | 7.5 μM | 38 | 1 | 317 | 4 |
| 46393 | 646_11 | 7.5 μM | 42 | 1 | 320 | 34 |
| 46393 | 646_12 | 7.5 μM | 36 | 5 | 323 | 8 |
| 46393 | 646_13 | 7.5 μM | 41 | 3 | 262 | 27 |
| 46393 | 646_14 | 7.5 μM | 46 | 13 | 315 | 18 |
| 46393 | 646_15 | 7.5 μM | 42 | 4 | 340 | 27 |
| 46393 | 646_16 | 7.5 μM | 45 | 8 | 360 | 14 |
| 46393 | 646_17 | 7.5 μM | 44 | 1 | 303 | 3 |
| 46393 | 646_18 | 7.5 μM | 50 | 2 | 304 | 28 |
| 46393 | 646_19 | 7.5 μM | 54 | 10 | 217 | 25 |
| 51241 | 425_2 | 7.5 μM | 49 | 12 | 296 | 3 |
| 51241 | 425_3 | 7.5 μM | 48 | 6 | 297 | 10 |

TABLE 8-continued

Oligonucleotide activity in patient derived human neuronal cell cultures.

| Start SEQ ID NO 1 | CMP ID NO | Conc μM | % of Mock UBE3A-SUP | sd | % of Mock UBE3A | sd |
|---|---|---|---|---|---|---|
| 51241 | 425_4 | 7.5 μM | 52 | 5 | 275 | 25 |
| 51241 | 425_5 | 7.5 μM | 40 | 6 | 284 | 29 |
| 51241 | 425_6 | 7.5 μM | 39 | 5 | 301 | 22 |
| 51241 | 425_7 | 7.5 μM | 39 | 4 | 263 | 13 |
| 51241 | 425_8 | 7.5 μM | 32 | 5 | 188 | 13 |
| 51241 | 425_9 | 7.5 μM | 42 | 5 | 286 | 2 |
| 51241 | 425_10 | 7.5 μM | 34 | 3 | 165 | 17 |

Example 6—Activity of Exon-Exon Spanning Oligonucleotides

Oligonucleotides designed to be complemnentary across exon-exon junctions of SNHG14-023 (ENST00000554726) were tested for their ability to reduce the SNHG14 transcript in the region downstream of SNORD109B (also termed UBE3A suppressor or UBE3A-SUP in the data table). Furthermore, the ability to induce UBE3A mRNA re-expression was analyzed. The oligonucleotides primarily span exon2 and exon3 (i.e. are complementary to a region in exon2 and a region in exon 3).

The oligonucleotides were screened according to the protocol for screening oligonucleotides in human neuronal cell cultures described in the section Example 5.

The results are shown in table 9.

TABLE 9

Oligonucleotide activity in patient derived human neuronal cell cultures.

| CMP ID NO | Conc μM | % of Mock UBE3A-SUP | sd | % of Mock UBE3A | sd |
|---|---|---|---|---|---|
| 674_1 | 7.5 μM | 47 | 2 | 214 | 12 |
| 675_1 | 7.5 μM | 44 | 6 | 265 | 10 |
| 676_1 | 7.5 μM | 44 | 3 | 284 | 16 |
| 677_1 | 7.5 μM | 55 | 19 | 351 | 18 |
| 678_1 | 7.5 μM | 41 | 11 | 257 | 1 |
| 656_1 | 7.5 μM | 46 | 3 | 140 | 19 |
| 657_1 | 7.5 μM | 35 | 7 | 218 | 27 |
| 658_1 | 7.5 μM | 38 | 12 | 253 | 43 |
| 659_1 | 7.5 μM | 39 | 7 | 274 | 6 |
| 660_1 | 7.5 μM | 38 | 8 | 275 | 29 |
| 661_1 | 7.5 μM | 43 | 13 | 246 | 21 |
| 662_1 | 7.5 μM | 27 | 10 | 290 | 5 |
| 663_1 | 7.5 μM | 28 | 0 | 287 | 23 |
| 664_1 | 7.5 μM | 27 | 2 | 288 | 14 |
| 665_1 | 7.5 μM | 37 | 9 | 321 | 47 |
| 666_1 | 7.5 μM | 54 | 1 | 259 | 10 |
| 667_1 | 7.5 μM | 47 | 8 | 236 | 2 |
| 647_1 | 7.5 μM | 19 | 3 | 300 | 25 |
| 648_1 | 7.5 μM | 22 | 7 | 320 | 3 |
| 649_1 | 7.5 μM | 34 | 8 | 326 | 2 |
| 650_1 | 7.5 μM | 44 | 4 | 292 | 7 |
| 651_1 | 7.5 μM | 36 | 5 | 254 | 9 |
| 652_1 | 7.5 μM | 21 | 2 | 314 | 18 |
| 653_1 | 7.5 μM | 24 | 5 | 299 | 41 |
| 654_1 | 7.5 μM | 31 | 2 | 344 | 41 |
| 655_1 | 7.5 μM | 60 | 9 | 301 | 3 |
| 668_1 | 7.5 μM | 21 | 3 | 297 | 11 |
| 669_1 | 7.5 μM | 24 | 5 | 296 | 27 |
| 670_1 | 7.5 μM | 30 | 3 | 274 | 55 |
| 671_1 | 7.5 μM | 27 | 6 | 263 | 35 |
| 672_1 | 7.5 μM | 27 | 6 | 280 | 50 |
| 673_1 | 7.5 μM | 33 | 2 | 290 | 19 |

Example 7—Testing in vitro efficacy and potency of selected oligonucleotides

Based on the screenings in examples 2 to 5 above 52 oligonucleotides were selected for potency and efficacy testing.

The oligonucleotides were screened in human AS patient derived cells as described in the Materials and Method section "Screening oligonucleotides in human neuronal cell cultures—96 well system" with the following modifications:

For UBE3a-Sense primer commercially available primers and probe from ThermoFisher: Hs00166580_m1 amplifying a 94 bp sequence in position 838 of refseq ID NM_000462.3 were used.

Each plate include PBS controls (instead on a non-targeting oligonucleotide) and the positive control oligonucleotides CMP ID NO: 186_1 and 39_1 identified in previous screens were included. The additional control oligonucleotides described in the materials and method section were not included. Oligonucleotide test concentrations were from 31.6 μM to 1 nM using a 10 point half-log dilution. All oligonucleotides were tested in 5 independent experiments in 5 different weeks. In the data QC process some plates were removed from the analysis if these were obvious outliers e.g. no PCR product detected. After this filtration there is a minimum of three independent experiments behind each the reported values.

The EC50 (UBE3A mRNA re-expression) and IC50 (reduction of the SNHG14 transcript in the region downstream of SNORD109B, also termed UBE3A suppressor or UBE3A-SUP in the data table) were determined after curve fitting using a 4 parameter sigmoidal dose-response model. Fitting was executed using the fit engine available inside the Biobook software by IDBS (XLfit). From the curve-fitting the maximum obtainable up-regulation of UBE3A (UBE3A Max Up) and the maximum obtainable knockdown of UBE3A-SUP (UB3E3A-SUP max $K_d$) were determined. Both are shown as % of control (PBS treated cells). The results are shown in table 10, values are reported as geometric means of each biological replicate.

TABLE 10

Oligonucleotide EC50 and IC 50 values and maximum UBE3A upregulation and UBE3A suppressor knock down.

| CMP ID NO | EC50 ↑ UBE3A | Sd | IC50 ↓ UBE3A-SUP | Sd | UBE3A Max Kd | Sd | UBE3A-SUP max Kd | Sd |
|---|---|---|---|---|---|---|---|---|
| 586_9 | 0.02 | 0.02 | 0.01 | 0.00 | 329.4 | 25.5 | 33.5 | 3.8 |
| 585_1 | 0.03 | 0.01 | 0.03 | 0.02 | 301.6 | 18.3 | 31.0 | 5.3 |
| 572_7 | 0.03 | 0.00 | 0.01 | 0.03 | 294.1 | 30.4 | 31.3 | 3.5 |
| 591_1 | 0.03 | 0.02 | 0.01 | 0.00 | 387.3 | 46.0 | 41.4 | 2.8 |
| 585_8 | 0.04 | 0.02 | 0.02 | 0.01 | 312.3 | 23.1 | 35.2 | 3.3 |
| 626_7 | 0.04 | 0.02 | 0.02 | 0.00 | 362.5 | 44.6 | 38.7 | 3.3 |
| 621_2 | 0.04 | 0.03 | 0.02 | 0.01 | 264.5 | 19.6 | 24.7 | 3.9 |
| 624_3 | 0.04 | 0.03 | 0.04 | 0.03 | 288.1 | 19.2 | 29.7 | 5.2 |
| 169_52 | 0.04 | 0.04 | 0.02 | 0.01 | 303.4 | 23.1 | 27.3 | 1.8 |
| 624_5 | 0.04 | 0.07 | 0.01 | 0.01 | 249.2 | 16.3 | 16.4 | 1.4 |
| 586_5 | 0.04 | 0.01 | 0.01 | 0.00 | 364.4 | 43.9 | 30.4 | 3.3 |
| 626_8 | 0.04 | 0.03 | 0.01 | 0.01 | 338.7 | 24.0 | 39.1 | 2.6 |
| 169_50 | 0.05 | 0.02 | 0.02 | 0.02 | 280.3 | 23.0 | 28.3 | 2.4 |
| 572_6 | 0.05 | 0.01 | 0.01 | 0.02 | 298.5 | 22.4 | 36.3 | 4.0 |
| 639_5 | 0.05 | 0.03 | 0.01 | 0.00 | 327.7 | 22.0 | 38.2 | 3.6 |
| 592_2 | 0.05 | 0.03 | 0.02 | 0.05 | 364.9 | 27.1 | 36.4 | 3.3 |
| 586_8 | 0.05 | 0.03 | 0.02 | 0.01 | 366.6 | 35.1 | 38.0 | 3.9 |
| 625_6 | 0.06 | 0.03 | 0.01 | 0.00 | 335.5 | 34.7 | 32.5 | 1.9 |
| 644_3 | 0.06 | 0.04 | 0.01 | 0.02 | 298.5 | 22.0 | 25.3 | 1.6 |
| 586_4 | 0.06 | 0.03 | 0.01 | 0.01 | 354.3 | 31.5 | 33.0 | 2.3 |
| 642_12 | 0.06 | 0.05 | 0.02 | 0.01 | 289.2 | 14.8 | 24.7 | 3.0 |

TABLE 10-continued

Oligonucleotide EC50 and IC 50 values and maximum UBE3A upregulation and UBE3A suppressor knock down.

| CMP ID NO | EC50 ↑ UBE3A | Sd | IC50 ↓ UBE3A-SUP | Sd | UBE3A Max Kd | Sd | UBE3A-SUP max Kd | Sd |
|---|---|---|---|---|---|---|---|---|
| 572_5 | 0.07 | 0.09 | 0.02 | 0.00 | 312.7 | 25.9 | 31.5 | 3.0 |
| 592_4 | 0.07 | 0.06 | 0.03 | 0.01 | 341.1 | 31.9 | 35.7 | 1.8 |
| 622_3 | 0.07 | 0.04 | 0.02 | 0.01 | 300.9 | 21.0 | 27.6 | 3.6 |
| 622_5 | 0.07 | 0.01 | 0.02 | 0.01 | 306.2 | 13.5 | 24.4 | 4.0 |
| 616_4 | 0.07 | 0.04 | 0.03 | 0.02 | 293.8 | 17.9 | 29.1 | 5.0 |
| 304_6 | 0.08 | 0.08 | 0.02 | 0.00 | 318.1 | 39.2 | 43.8 | 3.9 |
| 638_8 | 0.08 | 0.01 | 0.01 | 0.01 | 354.8 | 30.6 | 42.4 | 4.1 |
| 622_4 | 0.08 | 0.07 | 0.02 | 0.01 | 330.3 | 24.8 | 29.5 | 2.4 |
| 642_13 | 0.08 | 0.07 | 0.04 | 0.03 | 268.4 | 21.0 | 26.8 | 2.5 |
| 573_8 | 0.08 | 0.01 | 0.04 | 0.02 | 320.1 | 34.4 | 34.3 | 3.4 |
| 241_9 | 0.09 | 0.04 | 0.04 | 0.03 | 352.6 | 26.4 | 34.1 | 2.3 |
| 304_10 | 0.09 | 0.07 | 0.03 | 0.01 | 289.5 | 19.9 | 28.3 | 2.8 |
| 636_8 | 0.10 | 0.08 | 0.03 | 0.04 | 330.8 | 34.1 | 53.9 | 13.4 |
| 598_4 | 0.11 | 0.06 | 0.03 | 0.04 | 295.0 | 15.1 | 41.3 | 2.2 |
| 586_6 | 0.11 | 0.10 | 0.02 | 0.02 | 316.2 | 21.2 | 23.8 | 3.5 |
| 621_1 | 0.11 | 0.21 | 0.02 | 0.01 | 311.9 | 19.2 | 27.5 | 5.2 |
| 331_1 | 0.12 | 0.02 | 0.03 | 0.02 | 293.6 | 49.0 | 25.1 | 5.4 |
| 626_9 | 0.13 | 0.12 | 0.02 | 0.03 | 302.2 | 32.6 | 34.4 | 2.2 |
| 169_56 | 0.14 | 0.18 | 0.02 | 0.01 | 356.5 | 22.3 | 26.8 | 2.2 |
| 631_6 | 0.14 | 0.30 | 0.04 | 0.00 | 292.9 | 25.1 | 33.5 | 4.9 |
| 186_1 | 0.16 | 0.02 | 0.04 | 0.05 | 371.7 | 70.1 | 32.5 | 5.5 |
| 611_7 | 0.16 | 0.15 | 0.02 | 0.01 | 369.2 | 29.3 | 37.2 | 3.9 |
| 165_1 | 0.17 | 0.02 | 0.07 | 0.12 | 266.3 | NA | 26.7 | NA |
| 646_16 | 0.18 | 0.15 | 0.03 | 0.02 | 306.0 | 9.0 | 30.6 | 2.9 |
| 640_4 | 0.20 | 0.10 | 0.02 | 0.01 | 328.4 | 31.0 | 40.4 | 7.0 |
| 631_1 | 0.22 | 0.07 | 0.07 | 0.02 | 324.6 | 1.6 | 47.5 | 8.1 |
| 590_13 | 0.23 | 0.59 | 0.02 | 0.02 | 353.4 | 22.3 | 31.8 | 2.2 |
| 172_1 | 0.24 | 0.10 | 0.11 | 0.14 | 254.2 | NA | 34.2 | NA |
| 35_2 | 0.26 | 0.02 | 0.06 | 0.09 | 257.9 | NA | 22.3 | NA |
| 425_5 | 0.26 | 0.14 | 0.08 | 0.08 | 317.3 | 33.9 | 32.9 | 2.4 |
| 359_1 | 0.27 | 0.03 | 0.03 | 0.08 | 260.5 | NA | 31.3 | NA |
| 209_1 | 0.28 | 0.08 | 0.03 | 0.03 | 339.9 | 30.6 | 48.2 | 11.6 |
| 123_1 | 0.28 | 0.13 | 0.26 | 0.08 | 235.9 | NA | 51.8 | NA |
| 361_1 | 0.29 | 0.10 | 0.06 | 0.02 | 331.9 | 17.2 | 30.7 | 6.3 |
| 602_1 | 0.31 | 0.33 | 0.15 | 0.20 | 340.3 | 21.7 | 42.2 | 5.0 |
| NA | 0.44 | 0.12 | 0.15 | 0.18 | 251.3 | NA | 24.6 | NA |
| 287_1 | 0.45 | 0.09 | 0.04 | 0.02 | 318.1 | 45.2 | 28.8 | 9.3 |
| 303_1 | 0.46 | 0.05 | 0.09 | 0.15 | 259.9 | NA | 30.9 | NA |
| 379_1 | 0.47 | 0.02 | 0.08 | 0.16 | 247.2 | NA | 22.5 | NA |
| 405_1 | 0.48 | 0.42 | 0.04 | 0.01 | 323.0 | 56.2 | 32.5 | 11.9 |
| 39_1 | 0.51 | 0.20 | 0.06 | 0.06 | 341.2 | 30.3 | 40.4 | 4.7 |
| 206_1 | 0.52 | 0.07 | 0.14 | 0.31 | 262.9 | NA | 30.5 | NA |
| 155_1 | 0.53 | 0.10 | NA | 0.53 | 260.8 | NA | 26.7 | NA |
| 362_1 | 0.57 | 0.25 | 0.09 | 0.02 | 328.1 | 57.3 | 27.4 | 8.6 |
| 178_1 | 0.58 | 0.35 | 0.11 | 0.04 | 334.3 | 50.8 | 26.6 | 8.0 |
| 48_1 | 0.59 | 0.02 | 0.07 | 0.56 | 262.7 | NA | 27.2 | NA |
| 200_1 | 0.62 | 0.51 | 0.15 | 0.06 | 331.0 | 54.3 | 33.1 | 6.2 |
| 361_5 | 0.67 | 0.18 | 0.07 | 0.00 | 307.1 | 22.9 | 32.1 | 4.5 |
| 597_4 | 0.67 | 0.51 | 0.10 | 0.06 | 325.3 | 17.3 | 35.3 | 2.7 |
| 85_1 | 0.68 | 0.06 | 0.28 | 0.41 | 255.5 | NA | 35.1 | NA |
| 278_1 | 0.69 | 0.67 | 0.08 | 0.09 | 313.8 | 33.4 | 27.2 | 4.6 |
| 271_1 | 0.69 | 0.00 | 0.03 | 0.65 | 247.3 | NA | 24.0 | NA |
| 403_1 | 0.77 | 0.57 | 0.11 | 0.09 | 296.4 | 55.0 | 28.8 | 7.0 |
| 204_1 | 0.78 | 0.59 | 0.05 | 0.05 | 316.1 | 35.5 | 36.3 | 7.9 |
| 116_1 | 0.91 | 0.05 | 0.09 | 0.43 | 240.6 | NA | 31.6 | NA |
| 124_1 | 0.92 | 0.29 | 0.55 | 0.94 | 190.0 | NA | 43.9 | NA |
| 237_8 | 0.93 | 0.66 | 0.05 | 0.03 | 376.2 | 32.8 | 33.6 | 3.7 |
| 378_1 | 0.95 | 0.64 | 0.13 | 0.09 | 317.7 | 30.1 | 48.5 | 6.1 |
| 126_2 | 0.95 | 0.05 | 0.12 | 0.70 | 219.7 | NA | 45.0 | NA |
| 373_1 | 1.03 | 0.63 | 0.13 | 0.08 | 321.7 | 38.6 | 27.5 | 4.8 |
| 641_5 | 1.16 | 1.36 | 0.07 | 0.06 | 335.1 | 28.9 | 26.6 | 5.1 |
| 207_1 | 1.18 | 0.58 | 0.18 | 0.06 | 318.5 | 42.9 | 44.0 | 7.2 |
| 19_1 | 1.50 | 0.19 | 0.24 | 1.07 | 261.7 | NA | 28.4 | NA |
| 175_1 | 1.51 | 0.42 | 0.17 | 0.11 | 333.5 | 23.8 | 29.2 | 5.2 |
| 304_1 | 1.55 | 0.09 | 0.08 | 0.11 | 297.8 | 26.2 | 32.5 | 5.7 |
| 399_1 | 1.86 | 2.50 | 0.44 | 0.26 | 340.1 | 52.2 | 39.6 | 4.3 |
| 38_1 | 2.12 | 0.10 | 0.34 | 0.43 | 257.3 | NA | 45.1 | NA |
| 222_1 | 2.29 | 0.75 | 0.28 | 0.12 | 298.2 | 34.9 | 26.8 | 5.6 |
| 187_1 | 2.30 | 1.39 | 1.00 | 0.91 | 315.3 | 38.4 | 28.6 | 6.2 |
| 272_1 | 2.32 | 1.39 | 0.24 | 0.16 | 330.4 | 41.2 | 37.1 | 6.1 |
| 18_1 | 2.42 | 0.21 | 0.24 | 2.00 | 271.0 | NA | 29.3 | NA |
| 118_1 | 2.78 | 0.30 | 0.31 | 0.07 | 205.4 | NA | 40.4 | NA |
| 35_1 | 2.93 | 4.94 | 3.61 | 1.52 | 258.4 | NA | 48.2 | NA |
| 233_1 | 3.14 | 1.68 | 0.35 | 0.16 | 330.3 | 20.1 | 29.3 | 5.2 |
| 220_1 | 3.47 | 0.99 | 1.02 | 0.48 | 315.5 | 27.4 | 29.6 | 7.6 |
| 33_1 | 3.97 | 0.41 | 1.07 | NA | 265.7 | NA | 32.2 | NA |
| 109_1 | 4.06 | 1.45 | 1.33 | 0.67 | 231.7 | 44.7 | 39.6 | 3.9 |
| 40_1 | 4.17 | 0.05 | 0.12 | 3.74 | 263.6 | NA | 38.3 | NA |
| 115_1 | 4.98 | 0.15 | 0.25 | NA | 184.2 | NA | 47.0 | NA |
| 161_1 | 6.55 | 3.20 | 1.25 | 1.24 | 294.0 | 24.8 | 32.1 | 7.4 |
| 105_4 | 6.61 | 1.62 | 1.38 | 4.20 | NA | NA | 50.6 | NA |
| 19_2 | 6.66 | 1.17 | 3.17 | 1.52 | 201.7 | NA | 57.7 | NA |
| 104_1 | 7.75 | 6.77 | 1.67 | 1.05 | 267.9 | 25.5 | 42.5 | 4.1 |
| 18_2 | 20.00 | 1.67 | 3.50 | NA | 245.9 | NA | 46.4 | NA |
| 108_1 | 20.00 | 0.61 | 1.27 | NA | 219.6 | NA | 51.2 | NA |
| 129_2 | 20.00 | 0.08 | 1.10 | NA | 165.8 | NA | 56.5 | NA |
| 141_1 | 20.00 | 0.03 | 0.15 | NA | 159.0 | NA | 64.1 | NA |
| 142_1 | 20.00 | 1.04 | 1.12 | NA | 133.1 | NA | 57.6 | NA |
| 145_1 | 20.00 | 1.30 | 1.81 | NA | 139.0 | NA | 56.9 | NA |

SEQUENCE LISTING

The patent contains a lengthy sequence listing. A copy of the sequence listing is available in electronic form from the USPTO web site (https://seqdata.uspto.gov/?pageRequest=docDetail&DocID=US12259380B2). An electronic copy of the sequence listing will also be available from the USPTO upon request and payment of the fee set forth in 37 CFR 1.19(b)(3).

The invention claimed is:

1. An antisense oligonucleotide for inducing human paternal ubiquitin-protein ligase E3A (UBE3A) expression, wherein the antisense oligonucleotide comprises a contiguous nucleotide sequence of 10 to 30 nucleotides in length with at least 98% complementarity to position 25278410 to 25419462 on human chromosome 15, wherein the oligonucleotide comprises one or more modified nucleosides.

2. The oligonucleotide of claim 1, wherein the contiguous nucleotide sequence is complementary to a region of a target nucleic acid of SEQ ID NO: 1 and/or 2.

3. The oligonucleotide of claim 1, wherein the contiguous nucleotide sequence is 100% complementary to a region of a target nucleic acid of position 1 to 55318 of SEQ ID NO: 1.

4. The oligonucleotide of claim 2, wherein the contiguous nucleotide sequence is complementary to a sub-sequence of SEQ ID NO: 1, the sub-sequence is selected from the group consisting of positions 10 to 75, 77 to 91, 93 to 108, 168 to 213, 217 to 282, 284 to 299, 301 to 328, 330 to 344, 361 to 400, 415 to 447, 449 to 470, 472 to 487, 489 to 521, 523 to 540, 551 to 570, 590 to 638, 652 to 670, 672 to 733, 735 to 756, 758 to 773, 781 to 829, 831 to 870, 882 to 903, 918 to 949, 961 to 990, 1007 to 1021, 1019 to 1050, 1052 to 1090, 1092 to 1139, 1147 to 1179, 1175 to 1212, 1220 to 1242, 1245 to 1259, 1265 to 1278, 1285 to 1323, 1317 to 1330, 1337 to 1355, 1357 to 1403, 1405 to 1421, 1423 to 1481, 1486 to 1515, 1521 to 1581, 1611 to 1633, 1631 to 1644, 1635 to 1663, 1669 to 1684, 1685 to 1709, 1711 to 1724, 1726 to 1746, 1754 to 1808, 1819 to 1860, 1862 to 1878, 1896 to 1910, 1923 to 1944, 1946 to 1987, 1985 to 2051, 2053 to 2082, 2088 to 2104, 2106 to 2125, 2132 to 2207, 2209 to 2234, 2247 to 2261, 2263 to 2286, 2290 to 2306, 2308 to 2329, 2347 to 2391, 2398 to 2431, 2447 to 2468, 2470 to 2555, 2565 to 2579, 2579 to 2592, 2589 to 2605, 2594 to 2657, 2672 to 2687, 2692 to 2705, 2703 to 2721, 2770 to 2824, 2826 to 2841, 2838 to 2851, 2843 to 2889, 2896 to 2930, 2930 to 2967, 2965 to 2988, 2984 to 3028, 3024 to 3080, 3081 to 3135, 3140 to 3176, 3168 to 3189, 3197 to 3222, 3212 to 3226, 3221 to 3248, 3243 to 3256, 3250 to 3264, 3266 to 3292, 3326 to 3343, 3345 to 3391, 3400 to 3422, 3424 to 3441, 3434 to 3447, 3443 to 3503, 3495 to 3508, 3505 to 3558, 3589 to 3609, 3611 to 3641, 3662 to 3696, 3698 to 3719, 3723 to 3790, 3810 to 3854, 3858 to 3873, 3902 to 3968, 3971 to 4009, 4005 to 4018, 4011 to 4030, 4032 to 4077, 4082 to 4114, 4123 to 4140, 4150 to 4164, 4166 to 4183, 4185 to 4243, 4248 to 4268, 4284 to 4313, 4317 to 4348, 4364 to 4471, 4473 to 4491, 4494 to 4519, 4521 to 4535, 4545 to 4560, 4567 to 4606, 4616 to 4714, 4725 to 4755, 4757 to 4786, 4788 to 4852, 4856 to 4910, 4912 to 4935, 4937 to 4970, 4972 to 5010, 5058 to 5078, 5080 to 5116, 5110 to 5124, 5135 to 5166, 5168 to 5201, 5203 to 5247, 5261 to 5276, 5278 to 5293, 5314 to 5330, 5332 to 5382, 5398 to 5414, 5427 to 5456, 5458 to 5471, 5487 to 5500, 5506 to 5545, 5561 to 5577, 5580 to 5617, 5607 to 5620, 5619 to 5642, 5644 to 5683, 5685 to 5698, 5713 to 5759, 5756 to 5769, 5784 to 5803, 5801 to 5865, 5873 to 5905, 5907 to 5937, 5939 to 5985, 5987 to 6017, 6016 to 6039, 6028 to 6092, 6102 to 6127, 6127 to 6152, 6151 to 6171, 6178 to 6206, 6217 to 6234, 6224 to 6270, 6272 to 6289, 6291 to 6310, 6312 to 6357, 6367 to 6389, 6396 to 6422, 6440 to 6454, 6456 to 6482, 6484 to 6513, 6505 to 6519, 6518 to 6553, 6552 to 6565, 6557 to 6590, 6596 to 6628, 6640 to 6675, 6686 to 6711, 6714 to 6746, 6781 to 6818, 6832 to 6885, 6889 to 6912, 6920 to 6938, 6940 to 6960, 6954 to 6976, 6998 to 7033, 7035 to 7061, 7071 to 7143, 7159 to 7214, 7253 to 7266, 7268 to 7281, 7283 to 7328, 7329 to 7343, 7338 to 7355, 7345 to 7374, 7374 to 7387, 7383 to 7396, 7389 to 7405, 7399 to 7413, 7420 to 7437, 7427 to 7448, 7450 to 7503, 7495 to 7565, 7561 to 7616, 7618 to 7703, 7717 to 7772, 7776 to 7838, 7852 to 7869, 7882 to 7910, 7919 to 7942, 7944 to 7957, 7959 to 7977, 7979 to 7996, 7998 to 8014, 8030 to 8046, 8059 to 8092, 8100 to 8113, 8115 to 8141, 8143 to 8175, 8179 to 8192, 8187 to 8208, 8205 to 8219, 8210 to 8229, 8231 to 8252, 8254 to 8298, 8302 to 8316, 8306 to 8329, 8331 to 8357, 8400 to 8443, 8443 to 8456, 8445 to 8460, 8472 to 8505, 8494 to 8507, 8554 to 8569, 8571 to 8653, 8659 to 8673, 8675 to 8694, 8696 to 8713, 8736 to 8844, 8847 to 8909, 8915 to 8959, 8961 to 8975, 8993 to 9009, 9024 to 9048, 9050 to 9063, 9089 to 9120, 9127 to 9166, 9191 to 9249, 9257 to 9285, 9288 to 9302, 9331 to 9397, 9399 to 9438, 9437 to 9455, 9483 to 9505, 9507 to 9526, 9583 to 9598, 9600 to 9613, 9628 to 9641, 9653 to 9674, 9676 to 9690, 9745 to 9758, 9752 to 9780, 9796 to 9809, 9811 to 9825, 9832 to 9853, 9877 to 9899, 9901 to 9932, 10000 to 10016, 10029 to 10049, 10051 to 10071, 10089 to 10120, 10111 to 10127, 10122 to 10203, 10211 to 10237, 10239 to 10256, 10258 to 10285, 10287 to 10304, 10306 to 10350, 10352 to 10375, 10381 to 10402, 10412 to 10470, 10474 to 10488, 10508 to 10557, 10565 to 10630, 10632 to 10674, 10698 to 10711, 10701 to 10714, 10704 to 10718, 10720 to 10740, 10742 to 10785, 10786 to 10809, 10811 to 10829, 10832 to 10867, 10869 to 10930, 10932 to 10950, 10959 to 10996, 10998 to 11028, 11037 to 11077, 11079 to 11105, 11115 to 11132, 11134 to 11154, 11156 to 11196, 11206 to 11239, 11241 to 11255, 11266 to 11287, 11299 to 11329, 11331 to 11352, 11358 to 11403, 11405 to 11432, 11434 to 11480, 11482 to 11535, 11539 to 11573, 11584 to 11732, 11731 to 11763, 11765 to 11782, 11784 to 11813, 11815 to 11829, 11831 to 11852, 11854 to 11871, 11866 to 11895, 11930 to 11943, 11975 to 12007, 11996 to 12012, 12017 to 12040, 12050 to 12083, 12088 to 12111, 12133 to 12151, 12161 to 12174, 12179 to 12225, 12238 to 12256, 12265 to 12278, 12296 to 12360, 12362 to 12381, 12384 to 12399, 12400 to 12475, 12487 to 12502, 12504 to 12531, 12533 to 12562, 12564 to 12602, 12627 to 12646, 12655 to 12679, 12681 to 12698, 12700 to 12812, 12828 to 12876, 12877 to 12913, 12932 to 12945, 12936 to 12967, 12988 to 13002, 12996 to 13009, 13018 to 13035, 13031 to 13049, 13056 to 13093, 13096 to 13126, 13128 to 13142, 13144 to 13193, 13201 to 13221, 13223 to 13280, 13282 to 13298, 13300 to 13315, 13307 to 13320, 13315 to 13331, 13351 to 13411, 13422 to 13437, 13439 to 13456, 13461 to 13483, 13485 to 13541, 13543 to 13560, 13574 to 13606, 13618 to 13646, 13778 to 13801, 13994 to 14009, 14508 to 14521, 15049 to 15067, 15069 to 15090, 15102 to 15139, 15142 to 15180, 15182 to 15205, 15238 to 15252, 15254 to 15277, 15292 to 15320, 15322 to 15348, 15343 to 15358, 15362 to 15387, 15399 to 15414, 15416 to 15445, 15459 to 15528, 15537 to 15592, 15610 to 15638, 15640 to 15653, 15655 to 15717, 15719 to 15738, 15757 to 15778, 15783 to 15801, 15818 to 15838, 15835 to 15849, 15840 to 15857, 15856 to 15898, 15900 to 15916, 15931 to 15972, 15988 to 16028, 16030 to 16075, 16103 to 16164, 16207 to 16243, 16233 to 16246, 16255 to 16329, 16349 to 16376, 16378 to 16404, 16399 to 16419, 16421 to 16461, 16463 to 16479, 16481 to 16503, 16506 to 16579, 16582 to 16620, 16622 to 16698, 16700 to 16716, 16723 to 16771, 16786 to 16816, 16835 to 16864, 16865 to 16878, 16872 to 16888, 16890 to 16906, 16904 to 16938, 16965 to 17052, 17054 to 17069, 17071 to 17085, 17083 to 17098, 17088 to 17111, 17124 to 17138, 17140 to 17159, 17181 to 17202, 17202 to 17218, 17229 to 17248, 17250 to 17268, 17332 to 17349, 17363 to 17387, 17389 to 17429, 17450 to 17464, 17482 to 17497, 18104 to 18117, 18418 to 18431, 18613 to 18626, 18620 to 18634, 18707 to 18721, 18841 to 18855, 18875 to 18889, 19282 to 19295, 19310 to 19323, 19454 to 19467, 19774 to 19792, 19794 to 19864, 19862 to 19890, 19892 to 19918, 19907 to 19931, 19927 to 19942, 19932 to 19971, 19973 to 20011, 20022 to 20063, 20080 to 20093, 20131 to 20144, 20240 to 20253, 20448 to 20463, 20495 to 20508, 20532 to 20545, 20600 to 20613, 20617 to 20630, 20960 to 20977, 21412 to 21428, 21465 to 21479, 21489 to 21508, 21797 to 21812, 22015 to 22030, 22144 to 22157, 22153 to 22167, 22265 to 22278, 23110 to 23123, 23114 to 23133, 23286 to 23303, 23364 to 23379, 23478 to 23498, 23544 to 23587, 23589 to 23630, 23658 to 23676, 23678 to 23702, 23704 to 23729, 23731 to 23748, 23740 to 23755, 23744 to 23757, 23750 to 23764, 23767 to 23795, 23802 to 23816, 23818 to 23831, 23855 to 23869, 23906 to 23926, 23928 to 23942, 23994 to 24007, 24005 to 24018, 24023 to 24056, 24074 to 24088, 24088 to 24104, 24112 to 24163, 24199 to 24212, 24231 to 24244, 24237 to 24252, 24254 to 24267, 24281 to 24325, 24327 to 24353, 24355 to 24374, 24376 to 24399, 24401 to 24416, 24442 to 24489, 24492 to 24506, 24498 to 24511, 24538 to 24556, 24546 to 24562, 24591 to 24618, 24620 to 24633, 24635 to 24650, 24665 to 24681, 24687 to 24706, 24709 to 24729, 24731 to 24752, 24756 to 24771, 24773 to 24788, 24793 to 24821, 24823 to 24854, 24856 to 24870, 24873 to 24922, 24933 to 24954, 24965 to 24984, 25019 to 25052, 25054 to 25099, 25112 to 25125, 25133 to 25169, 25171 to 25184, 25186 to 25221, 25236 to 25253, 25246 to 25296, 25298 to 25336, 25332 to 25348, 25349 to 25363, 25388 to 25432, 25439 to 25462, 25509 to 25523, 25525 to 25547, 25578 to 25593, 25587 to 25601, 25604 to 25617, 25633 to 25655, 25672 to 25716, 25725 to 25738, 25764 to 25800, 25802 to 25828, 25831 to 25846, 25851 to 25872, 25877 to 25904, 25921 to 25946, 25943 to 25970, 25972 to 25986, 26051 to 26064, 26068 to 26086, 26113 to 26137, 26139 to 26159, 26182 to 26197, 26243 to 26296, 26298 to 26313, 26327 to 26350, 26366 to 26385, 26387 to 26404, 26397 to 26415, 26416 to 26453, 26447 to 26461, 26457 to 26471, 26481 to 26498, 26502 to 26525, 26528 to 26562, 26564 to 26590, 26590 to 26622, 26624 to 26638, 26687 to 26702, 26706 to 26719, 26717 to 26730, 26729 to 26743, 26767 to 26797, 26796 to 26816, 26831 to 26847, 26837 to 26850, 26877 to 26890, 26900 to 26922, 26911 to 26933, 26933 to 26946, 26938 to 26977, 26979 to 26992, 26981 to 27017, 27023 to 27041, 27039 to 27055, 27075 to 27121, 27138 to 27153, 27163 to 27266, 27270 to 27293, 27325 to 27358, 27363 to 27408, 27419 to 27448, 27450 to 27469, 27471 to 27498, 27510 to 27523, 27535 to 27562, 28098 to 28119, 28136 to 28155, 28169 to 28197, 28199 to 28212, 28221 to 28244, 28271 to 28285, 28400 to 28414, 28441 to 28476, 28490 to 28533, 28535 to 28562, 28575 to 28600, 28621 to 28634, 28650 to 28663, 28674 to 28687, 28681 to 28699, 28713 to 28730, 28736 to 28761, 28763 to 28811, 28821 to 28854, 28856 to 28881, 28883 to 28920, 28922 to 28947, 28979 to 29006, 29008 to 29056, 29078 to 29095, 29098 to 29129, 29122 to 29135, 29131 to 29144, 29144 to 29158, 29160 to 29207, 29209 to 29230, 29234 to 29266, 29268 to 29286, 29301 to 29315, 29304 to 29323, 29330 to 29352, 29344 to 29358, 29347 to 29365, 29377 to 29402, 29402 to 29422, 29424 to 29445, 29443 to 29457, 29447 to 29460, 29462 to 29475, 29491 to 29512, 29514 to 29551, 29547 to 29560, 29553 to 29620, 29625 to 29700, 29714 to 29745, 29774 to 29805, 29816 to 29847, 29875 to 29892, 29894 to 29908, 29897 to 29910, 29917 to 29938, 29939 to 29952, 29961 to 29976, 29974 to 29987, 29978 to 30001, 30006 to 30023, 30025 to 30039, 30043 to 30107, 30145 to 30158, 30149 to 30166, 30173 to 30228, 30230 to 30250, 30251 to 30309, 30321 to 30358, 30359 to 30380, 30382 to 30422, 30428 to 30442, 30455 to 30482, 30484 to 30498, 30516 to 30531, 30533 to 30646, 30654 to 30745, 30745 to 30760, 30752 to 30766, 30788 to 30843, 30845 to 30867, 30869 to 30912, 30906 to 30920, 30934 to 30951, 30962 to 30984, 30989 to 31002, 31010 to 31033, 31036 to 31062, 31092 to 31106, 31128 to 31166, 31168 to 31182, 31189 to 31203, 31205 to 31218, 31224 to 31253, 31256 to 31272, 31274 to 31292, 31294 to 31322, 31324 to 31353, 31357 to 31370, 31373 to 31399, 31403 to 31426, 31445 to 31460, 31463 to 31483, 31485 to 31501, 31494 to 31508, 31507 to 31529, 31531 to 31565, 31567 to 31615, 31630 to 31665, 31675 to 31691, 31703 to 31721, 31729 to 31769, 31770 to 31790, 31795 to 31813, 31815 to 31835, 31837 to 31865, 31876 to 31889, 31920 to 31945, 31962 to 31978, 31983 to 32014, 32029 to 32050, 32058 to 32110, 32129 to 32147, 32166 to 32242, 32244 to 32279, 32296 to 32315, 32334 to 32396, 32398 to 32425, 32427 to 32453, 32459 to 32481, 32475 to 32498, 32490 to 32523, 32519 to 32534, 32525 to 32547, 32542 to 32555, 32559 to 32572, 32574 to 32587, 32595 to 32618, 32613 to 32626, 32627 to 32649, 32651 to 32664, 32655 to 32689, 32693 to 32719, 32721 to 32750, 32752 to 32778, 32780 to 32795, 32797 to 32847, 32881 to 32894, 32891 to 32904, 32896 to 32911, 32927 to 32972, 32986 to 33017, 33019 to 33036, 33038 to 33096, 33102 to 33123, 33132 to 33145, 33150 to 33163, 33166 to 33199, 33214 to 33260, 33262 to 33292, 33294 to 33307, 33316 to 33351, 33360 to 33402, 33412 to 33425, 33427 to 33442, 33439 to 33452, 33443 to 33456, 33460 to 33501, 33503 to 33535, 33542 to 33557, 34168 to 34181, 34370 to 34385, 35422 to 35435, 35627 to 35641, 35685 to 35700, 35837 to 35851, 35849 to 35864, 35866 to 35879, 35974 to 35987, 36009 to 36042, 36044 to 36079, 36081 to 36097, 36099 to 36120, 36119 to 36133, 36147 to 36163, 36171 to 36200, 36216 to 36241, 36245 to 36274, 36265 to 36283, 36295 to 36348, 36352 to 36389, 36383 to 36400, 36402 to 36419, 36475 to 36520, 36522 to 36539, 36541 to 36626, 36652 to 36672, 36675 to 36705, 36707 to 36746, 36780 to 36808, 36810 to 36823, 36825 to 36901, 36903 to 36922, 36924 to 36982, 36999 to 37030, 37056 to 37083, 37091 to 37135, 37194 to 37221, 37238 to 37277, 37280 to 37294, 37298 to 37315, 37325 to 37350, 37363 to 37383, 37377 to 37394, 37384 to 37397, 37390 to 37438, 37456 to 37481, 37478 to 37491, 37481 to 37503, 37506 to 37524, 37526 to 37545, 37540 to 37572, 37574 to 37590, 37601 to 37616, 37621 to 37658, 37673 to 37690, 37703 to 37738, 37740 to 37753, 37764 to 37790, 37800 to 37818, 37820 to 37850, 37888 to 37909, 37911 to 37972, 37986 to 38014, 38016 to 38032, 38034 to 38053, 38055 to 38073, 38075 to 38090, 38092 to 38128, 38141 to 38167, 38171 to 38194, 38213 to 38240, 38264 to 38286, 38288 to 38370, 38394 to 38420, 38452 to 38467, 38471 to 38487, 38477 to 38490, 38494 to 38507, 38536 to 38556, 38580 to 38593, 38602 to 38618, 38628 to 38654, 38693 to 38709, 38709 to 38722, 38711 to 38725, 38740 to 38756, 38749 to 38769, 38772 to 38797, 38827 to 38846, 38860 to 38883, 38885 to 38905, 38911 to 38931, 38933 to 38949, 38962 to 39032, 39034 to 39047, 39049 to 39070, 39075 to 39115, 39127 to 39143, 39148 to 39162, 39164 to 39222, 39218 to 39231, 39224 to 39256, 39265 to 39306, 39297 to 39311, 39308 to 39343, 39345 to 39359, 39361 to 39381, 39370 to 39383, 39383 to 39399, 39417 to 39469, 39490 to 39503, 39500 to 39522, 39535 to 39549, 39551 to 39611, 39628 to 39647, 39649 to 39690, 39707 to 39759, 39773 to 39797, 39799 to 39858, 39872 to 39928, 39930 to 39969, 39973 to 39997, 39998 to 40013, 40015 to 40064, 40067 to 40108, 40110 to 40140, 40147 to 40163, 40154 to 40179, 40181 to 40196, 40232 to 40282, 40284 to 40307, 40309 to 40368, 40381 to 40399, 40431 to 40471, 40479 to 40493, 40484 to 40522, 40524 to 40544, 40547 to 40561, 40577 to 40594, 40586 to 40599, 40616 to 40631, 40634 to 40647, 40674 to 40727, 40738 to 40755, 40749 to 40771, 40780 to 40802, 40811 to 40834, 40847 to 40865, 40861 to 40875, 40869 to 40897, 40899 to 40919, 40921 to 40939, 40942 to 40962, 40967 to 40980, 41008 to 41097, 41099 to 41131, 41133 to 41200, 41202 to 41223, 41225 to 41242, 41266 to 41279, 41275 to 41298, 41300 to 41321, 41325 to 41360, 41367 to 41388, 41403 to 41421, 41439 to 41462, 41481 to 41496, 41508 to 41523, 41531 to 41550, 41552 to 41590, 41590 to 41603, 41612 to 41662, 41664 to 41688, 41685 to 41698, 41691 to 41716, 41718 to 41764, 41761 to 41776, 41778 to 41809, 41798 to 41811, 41838 to 41866, 41872 to 41893, 41885 to 41898, 41912 to 41925, 41914 to 41930, 41923 to 41942, 41933 to 41956, 41962 to 41978, 41997 to 42012, 42026 to 42042, 42035 to 42048, 42037 to 42050, 42048 to 42064, 42056 to 42079, 42081 to 42095, 42096 to 42139, 42141 to 42187, 42190 to 42226, 42232 to 42253, 42255 to 42305, 42307 to 42320, 42347 to 42375, 42389 to 42425, 42427 to 42442, 42452 to 42474, 42482 to 42496, 42495 to 42509, 42536 to 42550, 42566 to 42580, 42590 to 42612, 42646 to 42678, 42683 to 42723, 42735 to 42750, 42752 to 42817, 42843 to 42873, 42890 to 42939, 42938 to 42989, 42991 to 43005, 43007 to 43020, 43036 to 43055, 43057 to 43102, 43113 to 43145, 43147 to 43180, 43204 to 43221, 43221 to 43265, 43267 to 43296, 43311 to 43334, 43336 to 43361, 43371 to 43395, 43399 to 43423, 43425 to 43453, 43452 to 43468, 43470 to 43488, 43495 to 43522, 43525 to 43559, 43561 to 43584, 43590 to 43611, 43618 to 43650, 43670 to 43685, 43722 to 43774, 43776 to 43791, 43808 to 43835, 43835 to 43851, 43853 to 43868, 43923 to 43937, 43952 to 43987, 44011 to 44029, 44028 to 44070, 44072 to 44094, 44101 to 44130, 44137 to 44205, 44224 to 44244, 44246 to 44265, 44267 to 44318, 44316 to 44336, 44338 to 44359, 44361 to 44424, 44439 to 44474, 44476 to 44500, 44502 to 44519, 44539 to 44553, 44563 to 44578, 44585 to 44599, 44601 to 44617, 44640 to 44701, 44704 to 44723, 44741 to 44763, 44766 to 44846, 44870 to 44889, 44887 to 44905, 44920 to 44947, 44949 to 44966, 44994 to 45022, 45042 to 45059, 45061 to 45087, 45116 to 45154, 45156 to 45182, 45183 to 45198, 45210 to 45243, 45245 to 45320, 45331 to 45367, 45380 to 45399, 45415 to 45428, 45421 to 45486, 45488 to 45545, 45556 to 45576, 45578 to 45597, 45603 to 45650, 45652 to 45665, 45675 to 45715, 45749 to 45763, 45804 to 45826, 45839 to 45861, 45878 to 45910, 45926 to 45954, 45956 to 45975, 45977 to 45997, 45999 to 46020, 46046 to 46063, 46065 to 46088, 46097 to 46118, 46120 to 46142, 46144 to 46160, 46162 to 46185, 46204 to 46280, 46302 to 46326, 46328 to 46355, 46358 to 46377, 46379 to 46436, 46457 to 46471, 46473 to 46492, 46501 to 46541, 46543 to 46572, 46584 to 46626, 46655 to 46683, 46685 to 46702, 46704 to 46722, 46724 to 46763, 46784 to 46800, 46802 to 46827, 46830 to 46867, 46869 to 46887, 46889 to 46920, 46922 to 46947, 46976 to 47009, 47011 to 47030, 47032 to 47064, 47066 to 47092, 47108 to 47130, 47132 to 47168, 47170 to 47199, 47201 to 47222, 47238 to 47277, 47296 to 47350, 47352 to 47391, 47416 to 47440, 47452 to 47466, 47468 to 47523, 47522 to 47546, 47548 to 47567, 47569 to 47595, 47597 to 47634, 47657 to 47693, 47712 to 47731, 47749 to 47762, 47771 to 47825, 47827 to 47846, 47848 to 47872, 47874 to 47888, 47890 to 47909, 47911 to 47925, 47927 to 47952, 47961 to 47993, 48001 to 48016, 48051 to 48083, 48096 to 48158, 48158 to 48176, 48186 to 48201, 48213 to 48239, 48241 to 48256, 48258 to 48278, 48280 to 48339, 48341 to 48357, 48359 to 48377, 48379 to 48393, 48395 to 48488, 48492 to 48510, 48528 to 48549, 48550 to 48589, 48636 to 48658, 48683 to 48697, 48699 to 48762, 48762 to 48775, 48773 to 48832, 48873 to 48886, 48888 to 48914, 48916 to 48944, 48969 to 49008, 49010 to 49024, 49051 to 49110, 49116 to 49150, 49151 to 49184, 49187 to 49200, 49213 to 49230, 49233 to 49247, 49267 to 49284, 49297 to 49310, 49317 to 49369, 49371 to 49435, 49444 to 49458, 49467 to 49500, 49510 to 49538, 49540 to 49559, 49561 to 49584, 49591 to 49626, 49628 to 49646, 49653 to 49737, 49787 to 49802, 49817 to 49835, 49841 to 49860, 49862 to 49883, 49885 to 49905, 49921 to 49950, 49961 to 49979, 49995 to 50051, 50053 to 50071, 50073 to 50088, 50132 to 50158, 50167 to 50183, 50201 to 50226, 50226 to 50239, 50259 to 50313, 50323 to 50341, 50343 to 50396, 50390 to 50403, 50398 to 50448, 50451 to 50483, 50489 to 50507, 50526 to 50548, 50550 to 50569, 50575 to 50602, 50606 to 50621, 50617 to 50630, 50623 to 50641, 50634 to 50647, 50644 to 50663, 50665 to 50684, 50705 to 50730, 50732 to 50763, 50766 to 50799, 50797 to 50823, 50838 to 50864, 50870 to 50884, 50885 to 50911, 50924 to 50937, 50939 to 50974, 50980 to 51008, 51015 to 51030, 51034 to 51047, 51075 to 51089, 51109 to 51123, 51135 to 51172, 51189 to 51216, 51241 to 51260, 51273 to 51294, 51296 to 51312, 51337 to 51357, 51356 to 51381, 51393 to 51465, 51476 to 51494, 51496 to 51515, 51530 to 51544, 51546 to 51572, 51586 to 51600, 51602 to 51617, 51619 to 51677, 51679 to 51700, 51727 to 51741, 51743 to 51821, 51826 to 51859, 51884 to 51912, 51918 to 51936, 51947 to 51979, 52004 to 52017, 52023 to 52048, 52141 to 52167, 52169 to 52188, 52204 to 52225, 52246 to 52262, 52289 to 52306, 52321 to 52339, 52341 to 52360, 52360 to 52428, 52430 to 52504, 52506 to 52567, 52579 to 52594, 52591 to 52610, 52612 to 52642, 52644 to 52667, 52672 to 52686, 52688 to 52702, 52715 to 52753, 52770 to 52783, 52779 to 52792, 52814 to 52845, 52834 to 52857, 52858 to 52885, 52887 to 52943, 52945 to 52962, 52971 to 53019, 53011 to 53036, 53053 to 53066, 53092 to 53112, 53124 to 53151, 53161 to 53175, 53184 to 53220, 53222 to 53243, 53245 to 53260, 53278 to 53304, 53311 to 53346, 53364 to 53386, 53388 to 53404, 53417 to 53431, 53449 to 53463, 53465 to 53484, 53514 to 53527, 53552 to 53567, 53570 to 53591, 53618 to 53644, 53645 to 53667, 53669 to 53684, 53714 to 53742, 53744 to 53764, 53818 to 53843, 53845 to 53860, 53875 to 53889, 53961 to 53991, 53991 to 54013, 54015 to 54055, 54057 to 54081, 54114 to 54135, 54163 to 54178, 54180 to 54193, 54195 to 54254, 54261 to 54290, 54292 to 54307, 54309 to 54327, 54357 to 54372, 54404 to 54420, 54418 to 54439, 54441 to 54466, 54468 to 54512, 54519 to 54532, 54555 to 54572, 54588 to 54601, 54609 to 54633, 54644 to 54688, 54690 to 54721, 54723 to 54761, 54786 to 54802, 54819 to 54835, 54837 to 54912, 54924 to 54941, 54999 to 55017, 55019 to 55035, 55060 to 55073, 55075 to 55100, 55129 to 55171, 55173 to 55188, 55190 to 55203, 55210 to 55230, 55233 to 55281, 55276 to 55289, 55283 to 55320, 55330 to 55379, 55381 to 55423, 55420 to 55441, 55486 to 55502, 55515 to 55533, 55535 to 55553, 55555 to 55569, 55569 to 55588, 55590 to 55611, 55615 to 55663, 55665 to 55678, 55696 to 55713, 55715 to 55738, 55744 to 55774, 55776 to 55794, 55801 to 55823, 55862 to 55906, 55920 to 55933, 55922 to 55947, 55974 to 55993, 55990 to 56031, 56045 to 56073, 56082 to 56114, 56117 to 56140, 56183 to 56214, 56218 to 56236, 56261 to 56282, 56311 to 56336, 56331 to 56345, 56338 to 56358, 56369 to 56390, 56391 to 56431, 56433 to 56451, 56453 to 56473, 56475 to 56498, 56500 to 56546, 56558 to 56581, 56584 to 56597, 56611 to 56647, 56643 to 56657, 56667 to 56691, 56732 to 56759, 56788 to 56805, 56821 to 56845, 56850 to 56882, 56885 to 56906, 56928 to 56942, 56944 to 56959, 56961 to 56975, 56984 to 57002, 57004 to 57041, 57057 to 57082, 57084 to 57122, 57162 to 57222, 57224 to 57246, 57259 to 57284, 57317 to 57332, 57346 to 57369, 57388 to 57423, 57425 to 57440, 57442 to 57455, 57475 to 57492, 57508 to 57522, 57522 to 57546, 57548 to 57576, 57593 to 57634, 57658 to 57675, 57687 to 57771, 57786 to 57803, 57801 to 57819, 57830 to 57858, 57889 to 57911, 57926 to 57945, 57947 to 57972, 58009 to 58028, 58030 to 58060, 58063 to 58091, 58124 to 58146, 58147 to 58162, 58163 to 58198, 58214 to 58292, 58292 to 58309, 58336 to 58429, 58436 to 58457, 58453 to 58501, 58525 to 58553, 58566 to 58579, 58571 to 58584, 58586 to 58601, 58604 to 58630, 58656 to 58682, 58696 to 58713, 58722 to 58744, 58757 to 58771, 58805 to 58979, 58987 to 59073, 59072 to 59123, 59124 to 59150, 59154 to 59234, 59231 to 59276, 59291 to 59413, 59413 to 59458, 59466 to 59511, 59513 to 59533, 59549 to 59764, 59762 to 59825, 59824 to 59907, 59916 to 60004, 60006 to 60030, 60027 to 60040, 60032 to 60100, 60119 to 60188, 60191 to 60227, 60220 to 60287, 60289 to 60314, 60316 to 60554, 60556 to 60575, 60579 to 60593, 60595 to 60638, 60651 to 60690, 60692 to 60724, 60716 to 60799, 60801 to 60872, 60868 to 60881, 60885 to 60912, 60961 to 61009, 61014 to 61042, 61046 to 61059, 61053 to 61066, 61061 to 61084, 61134 to 61164, 61178 to 61199, 61201 to 61229, 61258 to 61284, 61286 to 61304, 61316 to 61332, 61341 to 61354, 61356 to 61383, 61407 to 61440, 61451 to 61468, 61470 to 61497, 61493 to 61506, 61499 to 61529, 61531 to 61558, 61590 to 61615, 61623 to 61640, 61673 to 61877, 61879 to 61898, 61900 to 61941, 61943 to 61962, 61964 to 61983, 62003 to 62017, 62015 to 62080, 62100 to 62124, 62133 to 62146, 62139 to 62175, 62191 to 62237, 62250 to 62270, 62283 to 62316, 62310 to 62358, 62357 to 62397, 62399 to 62413, 62415 to 62470, 62472 to 62501, 62503 to 62541, 62553 to 62609, 62611 to 62656, 62663 to 62690, 62703 to 62735, 62737 to 62759, 62765 to 62789, 62802 to 62816, 62810 to 62824, 62853 to 62868, 62864 to 62878, 62878 to 62907, 62905 to 62937, 62937 to 62951, 62943 to 62956, 62946 to 62960, 62961 to 62988, 62993 to 63006, 63005 to 63019, 63030 to 63049, 63057 to 63076, 63073 to 63088, 63078 to 63125, 63128 to 63152, 63154 to 63170, 63172 to 63196, 63185 to 63223, 63225 to 63245, 63236 to 63254, 63245 to 63261, 63263 to 63276, 63280 to 63295, 63292 to 63336, 63344 to 63368, 63369 to 63396, 63385 to 63398, 63395 to 63417, 63433 to 63451, 63440 to 63453, 63454 to 63470, 63472 to 63511, 63513 to 63539, 63547 to 63603, 63625 to 63651, 63676 to 63692, 63730 to 63746, 63759 to 63775, 63779 to 63833, 63844 to 63883, 63889 to 63907, 63910 to 63938, 63943 to 63962, 64004 to 64033, 64056 to 64087, 64112 to 64132, 64142 to 64158, 64160 to 64191, 64193 to 64209, 64214 to 64227, 64228 to 64241, 64254 to 64278, 64280 to 64298, 64300 to 64338, 64340 to 64355, 64357 to 64380, 64412 to 64434, 64438 to 64456, 64458 to 64488, 64490 to 64517, 64519 to 64538, 64552 to 64572, 64585 to 64608, 64625 to 64642, 64631 to 64644, 64644 to 64683, 64703 to 64716, 64736 to 64751, 64759 to 64773, 64775 to 64806, 64815 to 64831, 64845 to 64878, 64880 to 64904, 64915 to 64937, 64948 to 64971, 64973 to 64994, 64996 to 65017, 65019 to 65055, 65062 to 65109, 65111 to 65138, 65140 to 65179, 65181 to 65195, 65210 to 65230, 65232 to 65248, 65271 to 65296, 65298 to 65319, 65321 to 65371, 65391 to 65413, 65415 to 65436, 65436 to 65454, 65477 to 65490, 65492 to 65520, 65522 to 65552, 65554 to 65579, 65581 to 65594, 65591 to 65606, 65595 to 65616, 65618 to 65632, 65634 to 65657, 65661 to 65716, 65730 to 65747, 65748 to 65807, 65809 to 65829, 65831 to 65844, 65846 to 65859, 65861 to 65891, 65898 to 65920, 65930 to 65963, 65980 to 66060, 66069 to 66085, 66095 to 66108, 66110 to 66126, 66139 to 66173, 66175 to 66191, 66204 to 66226, 66224 to 66263, 66265 to 66278, 66280 to 66320, 66322 to 66345, 66355 to 66371, 66375 to 66407, 66411 to 66424, 66421 to 66441, 66440 to 66460, 66463 to 66482, 66484 to 66501, 66509 to 66527, 66534 to 66548, 66556 to 66569, 66562 to 66593, 66606 to 66637, 66639 to 66665, 66674 to 66690, 66692 to 66720, 66722 to 66742, 66758 to 66786, 66787 to 66802, 66812 to 66862, 66864 to 66885, 66940 to 66953, 66982 to 66997, 67024 to 67084, 67103 to 67118, 67156 to 67185, 67181 to 67195, 67193 to 67206, 67215 to 67229, 67231 to 67271, 67288 to 67301, 67294 to 67345, 67362 to 67379, 67381 to 67397, 67409 to 67448, 67468 to 67481, 67483 to 67510, 67540 to 67561, 67620 to 67640, 67656 to 67672, 67674 to 67749, 67751 to 67764, 67783 to 67801, 67803 to 67828, 67830 to 67848, 67850 to 67868, 67877 to 67918, 67933 to 67961, 67963 to 67978, 67998 to 68026, 68028 to 68046, 68048 to 68082, 68084 to 68112, 68114 to 68130, 68129 to 68155, 68170 to 68192, 68194 to 68237, 68239 to 68261, 68272 to 68286, 68290 to 68373, 68375 to 68419, 68442 to 68487, 68489 to 68547, 68549 to 68592, 68599 to 68614, 68617 to 68657, 68659 to 68686, 68688 to 68735, 68732 to 68747, 68749 to 68786, 68788 to 68830, 68837 to 68879, 68882 to 68899, 68918 to 68942, 68944 to 68968, 68983 to 69007, 69012 to 69027, 69020 to 69064, 69064 to 69077, 69079 to 69114, 69116 to 69196, 69185 to 69198, 69202 to 69219, 69228 to 69246, 69240 to 69282, 69294 to 69317, 69306 to 69324, 69333 to 69346, 69352 to 69366, 69387 to 69431, 69433 to 69447, 69452 to 69480, 69482 to 69497, 69491 to 69504, 69511 to 69564, 69566 to 69628, 69628 to 69642, 69659 to 69681, 69684 to 69697, 69719 to 69744, 69746 to 69763, 69765 to 69792, 69801 to 69828, 69853 to 69901, 69933 to 69949, 69951 to 69966, 69968 to 69983, 69988 to 70061, 70083 to 70100, 70110 to 70154, 70161 to 70199, 70202 to 70225, 70231 to 70246, 70269 to 70295, 70292 to 70327, 70331 to 70349, 70351 to 70371, 70381 to 70403, 70405 to 70420, 70422 to 70483, 70496 to 70533, 70535 to 70578, 70577 to 70639, 70653 to 70667, 70661 to 70674, 70669 to 70695, 70687 to 70705, 70708 to 70744, 70746 to 70764, 70766 to 70779, 70781 to 70832, 70834 to 70851, 70858 to 70887, 70889 to 70902, 70920 to 70933, 70935 to 70964, 70974 to 70987, 71008 to 71028, 71030 to 71046, 71048 to 71073, 71075 to 71106, 71108 to 71133, 71137 to 71152, 71153 to 71170, 71179 to 71192, 71197 to 71224, 71235 to 71251, 71253 to 71311, 71310 to 71329, 71330 to 71364, 71366 to 71386, 71388 to 71410, 71412 to 71433, 71448 to 71472, 71475 to 71491, 71491 to 71553, 71555 to 71581, 71583 to 71624, 71634 to 71700, 71706 to 71725, 71732 to 71747, 71789 to 71804, 71810 to 71824, 71819 to 71834, 71839 to 71872, 71876 to 71889, 71886 to 71908, 71910 to 71924, 71985 to 71999, 72000 to 72021, 72023 to 72047, 72071 to 72158, 72165 to 72192, 72194 to 72234, 72236 to 72255, 72257 to 72281, 72283 to 72299, 72312 to 72329, 72323 to 72336, 72348 to 72395, 72398 to 72411, 72413 to 72455, 72470 to 72503, 72506 to 72541, 72545 to 72558, 72560 to 72586, 72583 to 72597, 72588 to 72602, 72611 to 72636, 72638 to 72688, 72696 to 72736, 72738 to 72761, 72774 to 72799, 72801 to 72886, 72888 to 72903, 72928 to 72958, 72962 to 72990, 73001 to 73014, 73017 to 73053, 73055 to 73078, 73077 to 73090, 73088 to 73121, 73124 to 73153, 73147 to 73172, 73164 to 73203, 73218 to 73257, 73260 to 73273, 73268 to 73281, 73278 to 73291, 73298 to 73313, 73451 to 73465, 73459 to 73472, 73512 to 73567, 73569 to 73611, 73614 to 73645, 73661 to 73713, 73712 to 73727, 73716 to 73731, 73735 to 73748, 73741 to 73760, 73764 to 73782, 73783 to 73801, 73795 to 73829, 73860 to 73873, 73885 to 73904, 73906 to 73919, 73916 to 73945, 73947 to 73961, 73978 to 74018, 74020 to 74046, 74061 to 74082, 74092 to 74158, 74160 to 74177, 74179 to 74209, 74216 to 74245, 74270 to 74287, 74289 to 74305, 74307 to 74368, 74369 to 74411, 74416 to 74461, 74463 to 74479, 74506 to 74541, 74543 to 74636, 74647 to 74704, 74745 to 74770, 74789 to 74813, 74815 to 74838, 74850 to 74877, 74891 to 74923, 74925 to 74940, 74952 to 74969, 74979 to 75001, 75037 to 75066, 75068 to 75088, 75097 to 75123, 75131 to 75149, 75152 to 75189, 75210 to 75252, 75254 to 75276, 75288 to 75310, 75338 to 75357, 75359 to 75372, 75376 to 75397, 75405 to 75432, 75440 to 75470, 75482 to 75501, 75503 to 75540, 75544 to 75560, 75562 to 75576, 75589 to 75610, 75633 to 75646, 75648 to 75679, 75691 to 75709, 75711 to 75724, 75740 to 75764, 75763 to 75776, 75767 to 75790, 75780 to 75794, 75792 to 75808, 75810 to 75829, 75831 to 75863, 75865 to 75880, 75882 to 75922, 75932 to 75998, 76000 to 76026, 76028 to 76045, 76046 to 76082, 76098 to 76413, 76420 to 76442, 76456 to 76477, 76484 to 76558, 76573 to 76592, 76608 to 76622, 76627 to 76663, 76665 to 76683, 76685 to 76698, 76702 to 76716, 76725 to 76744, 76745 to 76761, 76780 to 76796, 76798 to 76812, 76814 to 76832, 76834 to 76859, 76871 to 76934, 77012 to 77034, 77039 to 77055, 77081 to 77094, 77121 to 77184, 77186 to 77200, 77202 to 77225, 77227 to 77247, 77261 to 77317, 77327 to 77340, 77342 to 77366, 77377 to 77394, 77396 to 77439, 77453 to 77468, 77462 to 77593, 77586 to 77599, 77595 to 77641, 77643 to 77728, 77730 to 77768, 77778 to 77816, 77818 to 77835, 77837 to 77855, 77861 to 77876, 77882 to 77898, 77900 to 77924, 77923 to 77936, 77957 to 77970, 77962 to 77985, 77994 to 78022, 78024 to 78056, 78079 to 78128, 78132 to 78158, 78173 to 78213, 78224 to 78265, 78275 to 78332, 78334 to 78440, 78442 to 78489, 78491 to 78505, 78501 to 78514, 78507 to 78537, 78557 to 78570, 78562 to 78623, 78625 to 78665, 78668 to 78684, 78686 to 78759, 78761 to 78787, 78793 to 78814, 78816 to 78854, 78847 to 78860, 78874 to 78909, 78917 to 78944, 78956 to 78978, 78991 to 79008, 79003 to 79032, 79026 to 79040, 79044 to 79072, 79098 to 79158, 79162 to 79182, 79184 to 79228, 79221 to 79235, 79230 to 79262, 79287 to 79333, 79356 to 79392, 79441 to 79476, 79488 to 79522, 79522 to 79539, 79568 to 79583, 79574 to 79601, 79603 to 79618, 79617 to 79639, 79651 to 79683, 79685 to 79724, 79721 to 79736, 79727 to 79782, 79784 to 79812, 79809 to 79834, 79841 to 79861, 79873 to 79923, 79928 to 79948, 79950 to 79986, 79993 to 80019, 80019 to 80063, 80071 to 80088, 80114 to 80160, 80154 to 80183, 80185 to 80212, 80214 to 80232, 80240 to 80266, 80293 to 80312, 80344 to 80380, 80382 to 80420, 80410 to 80423, 80417 to 80438, 80440 to 80456, 80467 to 80499, 80501 to 80527, 80532 to 80561, 80563 to 80599, 80604 to 80692, 80702 to 80737, 80739 to 80795, 80796 to 80871, 80873 to 80891, 80925 to 80961, 80963 to 80992, 81009 to 81068, 81070 to 81150, 81156 to 81199, 81201 to 81225, 81237 to 81253, 81255 to 81271, 81292 to 81351, 81353 to 81371, 81392 to 81422, 81438 to 81483, 81485 to 81503, 81512 to 81526, 81532 to 81554, 81556 to 81593, 81606 to 81664, 81666 to 81698, 81701 to 81720, 81728 to 81776, 81781 to 81810, 81812 to 81847, 81849 to 81893, 81908 to 81934, 81943 to 81964, 81967 to 82034, 82036 to 82134, 82136 to 82154, 82176 to 82197, 82199 to 82250, 82252 to 82269, 82271 to 82293, 82300 to 82314, 82329 to 82343, 82344 to 82357, 82378 to 82407, 82406 to 82422, 82421 to 82443, 82446 to 82469, 82490 to 82507, 82502 to 82523, 82547 to 82576, 82590 to 82603, 82628 to 82647, 82650 to 82666, 82669 to 82683, 82685 to 82716, 82715 to 82736, 82760 to 82785, 82778 to 82791, 82780 to 82818, 82811 to 82825, 82821 to 82864, 82883 to 82915, 82919 to 82935, 82930 to 82946, 82937 to 82957, 82959 to 82972, 82974 to 83000, 83020 to 83036, 83038 to 83088, 83090 to 83115, 83120 to 83140, 83142 to 83155, 83160 to 83186, 83198 to 83215, 83227 to 83246, 83273 to 83339, 83341 to 83385, 83387 to 83400, 83413 to 83426, 83417 to 83449, 83486 to 83520, 83522 to 83565, 83567 to 83581, 83576 to 83670, 83681 to 83701, 83703 to 83716, 83733 to 83817, 83817 to 83830, 83832 to 83853, 83855 to 83871, 83886 to 83926, 83958 to 83974, 83976 to 83991, 83993 to 84031, 84033 to 84067, 84069 to 84102, 84104 to 84121, 84143 to 84233, 84249 to 84281, 84283 to 84403, 84404 to 84432, 84431 to 84444, 84434 to 84490, 84503 to 84520, 84522 to 84555, 84557 to 84572, 84574 to 84597, 84607 to 84626, 84650 to 84675, 84677 to 84700, 84721 to 84753, 84755 to 84807, 84809 to 84826, 84831 to 84849, 84879 to 84893, 84895 to 84915, 84917 to 84961, 85234 to 85247, 85253 to 85267, 85256 to 85351, 85359 to 85374, 85363 to 85376, 85365 to 85381, 85380 to 85414, 85416 to 85454, 85456 to 85484, 85509 to 85545, 85535 to 85550, 85566 to 85584, 85586 to 85610, 85604 to 85627, 85628 to 85665, 85698 to 85723, 85713 to 85728, 85722 to 85735, 85770 to 85785, 85800 to 85813, 85875 to 85888, 85950 to 85963, 86097 to 86125, 86127 to 86142, 86175 to 86198, 86226 to 86242, 86237 to 86302, 86308 to 86327, 86321 to 86334, 86329 to 86382, 86384 to 86400, 86403 to 86417, 86414 to 86437, 86439 to 86455, 86461 to 86478, 86473 to 86487, 86480 to 86517, 86517 to 86531, 86565 to 86583, 86600 to 86632, 86634 to 86651, 86653 to 86678, 86697 to 86756, 86782 to 86796, 86786 to 86809, 86811 to 86855, 86857 to 86891, 86894 to 86908, 86916 to 86933, 86945 to 86959, 86951 to 86965, 86969 to 86990, 87017 to 87057, 87059 to 87073, 87062 to 87076, 87066 to 87089, 87097 to 87121, 87110 to 87134, 87130 to 87155, 87160 to 87194, 87185 to 87198, 87209 to 87260, 87257 to 87270, 87274 to 87287, 87276 to 87294, 87294 to 87328, 87317 to 87333, 87336 to 87360, 87368 to 87418, 87441 to 87460, 87462 to 87487, 87489 to 87518, 87520 to 87539, 87542 to 87570, 87572 to 87601, 87603 to 87644, 87642 to 87750, 87756 to 87776, 87778 to 87803, 87803 to 87837, 87872 to 87888, 87890 to 87917, 87949 to 87964, 87963 to 88008, 88010 to 88027, 88029 to 88046, 88048 to 88089, 88091 to 88108, 88110 to 88177, 88179 to 88192, 88194 to 88229, 88234 to 88259, 88261 to 88291, 88303 to 88328, 88328 to 88341, 88340 to 88354, 88356 to 88372, 88411 to 88446, 88448 to 88465, 88469 to 88511, 88518 to 88533, 88531 to 88557, 88547 to 88560, 88573 to 88593, 88597 to 88618, 88620 to 88690, 88692 to 88745, 88954 to 88973, 88988 to 89047, 89066 to 89091, 89098 to 89119, 89135 to 89149, 89151 to 89181, 89177 to 89193, 89223 to 89273, 89285 to 89300, 89315 to 89383, 89404 to 89442, 89444 to 89541, 89579 to 89639, 89660 to 89692, 89694 to 89741, 89773 to 89787, 89789 to 89817, 89826 to 89888, 89904 to 89922, 89937 to 89950, 89945 to 89958, 89956 to 89974, 89971 to 89985, 89979 to 89992, 89984 to 90000, 89999 to 90014, 90017 to 90041, 90036 to 90049, 90077 to 90093, 90099 to 90128, 90130 to 90155, 90157 to 90200, 90225 to 90256, 90258 to 90293, 90305 to 90318, 90320 to 90352, 90356 to 90370, 90400 to 90421, 90423 to 90461, 90464 to 90507, 90509 to 90530, 90529 to 90542, 90531 to 90567, 90569 to 90612, 90614 to 90730, 90732 to 90758, 90760 to 90885, 90887 to 90918, 90920 to 90946, 90938 to 90955, 90960 to 90973, 90965 to 90981, 90973 to 91000, 90997 to 91011, 91002 to 91019, 91059 to 91140, 91142 to 91157, 91157 to 91194, 91196 to 91231, 91233 to 91251, 91253 to 91274, 91296 to 91310, 91335 to 91367, 91406 to 91442, 91447 to 91477, 91489 to 91509, 91520 to 91621, 91623 to 91674, 91680 to 91703, 91715 to 91731, 91733 to 91771, 91773 to 91788, 91790 to 91805, 91807 to 91823, 91825 to 91859, 91861 to 91900, 91907 to 91926, 91928 to 91943, 91950 to 91980, 91982 to 91996, 91998 to 92011, 92010 to 92027, 92027 to 92067, 92069 to 92126, 92128 to 92321, 92323 to 92540, 92542 to 92558, 92566 to 92684, 92686 to 92726, 92728 to 92837, 92839 to 93032, 93034 to 93094, 93100 to 93209, 93211 to 93254, 93256 to 93323, 93325 to 93448, 93459 to 93477, 93475 to 93497, 93509 to 93530, 93532 to 93566, 93568 to 93601, 93606 to 93646, 93668 to 93716, 93718 to 93742, 93744 to 93788, 93790 to 93808, 93811 to 93832, 93874 to 93901, 93904 to 93986, 94021 to 94036, 94038 to 94079, 94073 to 94086, 94097 to 94116, 94118 to 94141, 94140 to 94219, 94242 to 94257, 94264 to 94335, 94337 to 94356, 94358 to 94378, 94373 to 94386, 94384 to 94403, 94405 to 94422, 94453 to 94497, 94497 to 94558, 94560 to 94605, 94630 to 94724, 94739 to 94752, 94755 to 94786, 94800 to 94815, 94872 to 94901, 94903 to 94953, 94955 to 95060, 95070 to 95085, 95093 to 95110, 95135 to 95149, 95154 to 95168, 95170 to 95210, 95227 to 95257, 95302 to 95318, 95311 to 95356, 95359 to 95401, 95403 to 95453, 95450 to 95463, 95475 to 95491, 95503 to 95553, 95555 to 95569, 95583 to 95609, 95634 to 95668, 95718 to 95738, 95727 to 95740, 95836 to 95849, 95851 to 95872, 95874 to 95888, 95890 to 95910, 95912 to 95925, 95938 to 95969, 95973 to 95990, 95992 to 96066, 96073 to 96087, 96103 to 96120, 96122 to 96167, 96169 to 96182, 96183 to 96211, 96213 to 96234, 96246 to 96279, 96300 to 96334, 96358 to 96375, 96377 to 96398, 96424 to 96467, 96496 to 96518, 96520 to 96535, 96540 to 96566, 96572 to 96592, 96604 to 96646, 96642 to 96655, 96648 to 96667, 96681 to 96728, 96730 to 96781, 96804 to 96829, 96831 to 96879, 96887 to 96916, 96928 to 96944, 96946 to 96959, 96970 to 96990, 96992 to 97021, 97023 to 97037, 97039 to 97073, 97075 to 97366, 97368 to 97393, 97420 to 97466, 97469 to 97507, 97513 to 97529, 97531 to 97583, 97585 to 97600, 97602 to 97631, 97633 to 97683, 97685 to 97703, 97705 to 97742, 97787 to 97803, 97805 to 97822, 97824 to 97876, 97878 to 97921, 97923 to 97943, 97945 to 97963, 97965 to 97994, 97995 to 98011, 98014 to 98044, 98039 to 98061, 98055 to 98076, 98077 to 98090, 98079 to 98092, 98085 to 98098, 98100 to 98115, 98113 to 98145, 98142 to 98160, 98162 to 98180, 98188 to 98219, 98215 to 98237, 98227 to 98240, 98232 to 98255, 98255 to 98268, 98264 to 98287, 98292 to 98326, 98373 to 98397, 98399 to 98428, 98442 to 98461, 98480 to 98501, 98499 to 98520, 98524 to 98538, 98537 to 98550, 98545 to 98585, 98595 to 98610, 98599 to 98624, 98644 to 98668, 98678 to 98704, 98703 to 98718, 98736 to 98754, 98778 to 98794, 98802 to 98821, 98845 to 98876, 98878 to 98900, 98900 to 98972, 98961 to 98976, 98974 to 98998, 99011 to 99029, 99033 to 99065, 99067 to 99107, 99151 to 99186, 99188 to 99219, 99222 to 99245, 99254 to 99276, 99288 to 99312, 99314 to 99338, 99367 to 99430, 99444 to 99491, 99496 to 99554, 99570 to 99585, 99587 to 99618, 99620 to 99669, 99679 to 99710, 99720 to 99748, 99750 to 99763, 99768 to 99805, 99818 to 99841, 99855 to 99879, 99881 to 99900, 99902 to 99932, 99934 to 99954, 99959 to 100011, 100011 to 100037, 100057 to 100071, 100073 to 100102, 100104 to 100118, 100131 to 100186, 100188 to 100201, 100194 to 100212, 100214 to 100277, 100279 to 100303, 100309 to 100355, 100349 to 100386, 100379 to 100393, 100388 to 100401, 100403 to 100423, 100452 to 100473, 100508 to 100542, 100548 to 100580, 100582 to 100612, 100614 to 100652, 100695 to 100714, 100736 to 100749, 100751 to 100790, 100808 to 100842, 100844 to 100860, 100862 to 100930, 100939 to 100953, 100955 to 100971, 100973 to 101003, 101021 to 101048, 101057 to 101093, 101109 to 101148, 101145 to 101189, 101194 to 101208, 101210 to 101244, 101256 to 101271, 101277 to 101300, 101310 to 101327, 101329 to 101345, 101374 to 101397, 101409 to 101426, 101453 to 101466, 101474 to 101487, 101481 to 101515, 101518 to 101541, 101542 to 101560, 101554 to 101591, 101593 to 101609, 101635 to 101695, 101707 to 101746, 101748 to 101763, 101774 to 101810, 101812 to 101828, 101819 to 101835, 101829 to 101842, 101842 to 101855, 101857 to 101878, 101880 to 101943, 101947 to 101988, 101988 to 102009, 102022 to 102066, 102068 to 102084, 102100 to 102113, 102115 to 102130, 102132 to 102145, 102192 to 102241, 102269 to 102285, 102312 to 102327, 102357 to 102392, 102407 to 102428, 102430 to 102444, 102460 to 102485, 102487 to 102508, 102532 to 102573, 102595 to 102642, 102653 to 102694, 102701 to 102718, 102720 to 102734, 102736 to 102757, 102799 to 102836, 102847 to 102882, 102890 to 102927, 102938 to 102971, 102982 to 103019, 103014 to 103027, 103027 to 103054, 103065 to 103088, 103090 to 103108, 103098 to 103112, 103117 to 103138, 103152 to 103170, 103174 to 103204, 103206 to 103234, 103240 to 103268, 103286 to 103325, 103327 to 103347, 103349 to 103384, 103386 to 103405, 103422 to 103449, 103451 to 103493, 103495 to 103509, 103511 to 103560, 103565 to 103582, 103585 to 103607, 103631 to 103645, 103653 to 103684, 103683 to 103696, 103691 to 103733, 103738 to 103762, 103752 to 103765, 103755 to 103768, 103758 to 103771, 103790 to 103814, 103803 to 103816, 103830 to 103865, 103900 to 103923, 103912 to 103933, 103945 to 103964, 103990 to 104005, 104024 to 104055, 104058 to 104077, 104086 to 104099, 104095 to 104122, 104124 to 104146, 104148 to 104168, 104162 to 104176, 104173 to 104187, 104201 to 104241, 104234 to 104266, 104268 to 104286, 104288 to 104302, 104304 to 104335, 104340 to 104354, 104356 to 104373, 104375 to 104391, 104393 to 104417, 104426 to 104439, 104448 to 104478, 104480 to 104504, 104519 to 104546, 104549 to 104580, 104604 to 104620, 104620 to 104646, 104654 to 104673, 104675 to 104691, 104689 to 104776, 104829 to 104842, 104838 to 104852, 104934 to 104952, 104956 to 104987, 104993 to 105045, 105041 to 105055, 105047 to 105078, 105090 to 105107, 105101 to 105115, 105109 to 105137, 105149 to 105167, 105163 to 105176, 105185 to 105237, 105230 to 105243, 105233 to 105250, 105260 to 105286, 105288 to 105340, 105345 to 105370, 105372 to 105402, 105441 to 105458, 105460 to 105521, 105526 to 105541, 105543 to 105560, 105562 to 105575, 105582 to 105606, 105616 to 105671, 105677 to 105704, 105703 to 105725, 105746 to 105759, 105750 to 105765, 105776 to 105796, 105798 to 105824, 105827 to 105907, 105924 to 105939, 105941 to 105963, 105990 to 106014, 106017 to 106048, 106039 to 106072, 106061 to 106074, 106073 to 106102, 106092 to 106107, 106114 to 106159, 106161 to 106180, 106197 to 106243, 106237 to 106250, 106243 to 106256, 106247 to 106267, 106273 to 106333, 106335 to 106367, 106369 to 106417, 106419 to 106471, 106486 to 106523, 106525 to 106538, 106552 to 106572, 106584 to 106598, 106609 to 106696, 106698 to 106723, 106725 to 106740, 106743 to 106781, 106783 to 106811, 106826 to 106866, 106875 to 106902, 106916 to 106935, 106942 to 106960, 106991 to 107010, 107019 to 107038, 107040 to 107072, 107079 to 107094, 107087 to 107101, 107090 to 107109, 107113 to 107127, 107129 to 107143, 107154 to 107172, 107174 to 107198, 107210 to 107226, 107226 to 107239, 107237 to 107274, 107296 to 107356, 107358 to 107381, 107383 to 107415, 107417 to 107433, 107435 to 107455, 107457 to 107508, 107510 to 107525, 107527 to 107546, 107559 to 107573, 107586 to 107617, 107643 to 107689, 107694 to 107716, 107744 to 107792, 107790 to 107832, 107834 to 107860, 107864 to 107896, 107898 to 107912, 107914 to 107953, 107967 to 107992, 107994 to 108008, 108010 to 108038, 108065 to 108084, 108113 to 108215, 108220 to 108249, 108253 to 108281, 108283 to 108304, 108317 to 108359, 108361 to 108375, 108386 to 108402, 108421 to 108440, 108538 to 108551, 108561 to 108575, 108577 to 108616, 108618 to 108665, 108677 to 108707, 108735 to 108768, 108762 to 108777, 108780 to 108824, 108842 to 108885, 108907 to 108970, 108983 to 109019, 109021 to 109053, 109055 to 109068, 109070 to 109099, 109097 to 109122, 109113 to 109132, 109125 to 109165, 109167 to 109181, 109183 to 109200, 109214 to 109248, 109256 to 109277, 109281 to 109298, 109298 to 109311, 109300 to 109318, 109324 to 109374, 109377 to 109397, 109399 to 109437, 109446 to 109461, 109463 to 109476, 109472 to 109485, 109478 to 109514, 109516 to 109540, 109556 to 109588, 109601 to 109644, 109661 to 109681, 109683 to 109709, 109707 to 109737, 109739 to 109754, 109754 to 109768, 109770 to 109798, 109810 to 109829, 109859 to 109877, 109879 to 109934, 109955 to 109975, 109975 to 109988, 109994 to 110096, 110103 to 110129, 110131 to 110152, 110153 to 110173, 110175 to 110195, 110192 to 110226, 110297 to 110312, 110301 to 110314, 110308 to 110333, 110335 to 110351, 110353 to 110368, 110376 to 110401, 110418 to 110462, 110464 to 110481, 110531 to 110558, 110571 to 110590, 110599 to 110639, 110630 to 110643, 110641 to 110661, 110668 to 110681, 110683 to 110709, 110717 to 110798, 110804 to 110849, 110853 to 110890, 110928 to 110966, 110971 to 111003, 111000 to 111013, 111015 to 111033, 111035 to 111050, 111062 to 111094, 111092 to 111105, 111107 to 111140, 111161 to 111203, 111209 to 111223, 111224 to 111280, 111275 to 111290, 111283 to 111303, 111305 to 111320, 111311 to 111347, 111355 to 111368, 111357 to 111371, 111360 to 111381, 111373 to 111421, 111412 to 111426, 111451 to 111468, 111467 to 111480, 111482 to 111496, 111486 to 111500, 111497 to 111510, 111531 to 111564, 111580 to 111606, 111616 to 111637, 111658 to 111671, 111674 to 111688, 111692 to 111710, 111712 to 111725, 111727 to 111761, 111781 to 111804, 111811 to 111828, 111831 to 111849, 111856 to 111871, 111901 to 111917, 111919 to 111940, 111942 to 111987, 111984 to 112002, 112004 to 112069, 112070 to 112091, 112093 to 112116, 112118 to 112132, 112139 to 112170, 112180 to 112196, 112204 to 112223, 112236 to 112283, 112329 to 112343, 112345 to 112383, 112385 to 112401, 112404 to 112423, 112463 to 112477, 112485 to 112547, 112563 to 112581, 112583 to 112597, 112607 to 112638, 112640 to 112664, 112683 to 112721, 112730 to 112759, 112773 to 112811, 112811 to 112825, 112828 to 112862, 112882 to 112912, 112914 to 112967, 112968 to 112982, 112984 to 113016, 113044 to 113064, 113074 to 113097, 113111 to 113153, 113169 to 113194, 113198 to 113212, 113214 to 113230, 113232 to 113263, 113265 to 113284, 113306 to 113328, 113330 to 113355, 113357 to 113371, 113404 to 113422, 113421 to 113489, 113533 to 113559, 113561 to 113574, 113595 to 113616, 113648 to 113700, 113702 to 113739, 113762 to 113823, 113825 to 113960, 113962 to 114015, 114017 to 114048, 114045 to 114124, 114151 to 114170, 114182 to 114218, 114230 to 114270, 114272 to 114292, 114296 to 114339, 114354 to 114433, 114440 to 114457, 114459 to 114484, 114478 to 114536, 114538 to 114559, 114567 to 114592, 114594 to 114610, 114612 to 114652, 114681 to 114752, 114775 to 114805, 114803 to 114816, 114807 to 114821, 114823 to 114847, 114868 to 114912, 114947 to 114961, 114974 to 114997, 115001 to 115015, 115004 to 115017, 115019 to 115069, 115060 to 115073, 115072 to 115085, 115087 to 115100, 115102 to 115124, 115132 to 115151, 115154 to 115168, 115188 to 115208, 115219 to 115256, 115258 to 115283, 115285 to 115300, 115331 to 115353, 115355 to 115372, 115380 to 115397, 115399 to 115412, 115426 to 115475, 115496 to 115510, 115521 to 115545, 115555 to 115580, 115582 to 115600, 115602 to 115621, 115653 to 115677, 115692 to 115720, 115722 to 115738, 115769 to 115783, 115792 to 115808, 115819 to 115837, 115846 to 115878, 115888 to 115901, 115916 to 115932, 115943 to 115956, 115967 to 115993, 115996 to 116014, 116027 to 116045, 116105 to 116127, 116126 to 116139, 116141 to 116158, 116171 to 116186, 116194 to 116208, 116257 to 116279, 116318 to 116373, 116375 to 116437, 116439 to 116454, 116456 to 116496, 116500 to 116532, 116534 to 116554, 116556 to 116573, 116575 to 116592, 116596 to 116615, 116617 to 116650, 116650 to 116664, 116666 to 116694, 116775 to 116792, 116794 to 116811, 116813 to 116838, 116840 to 116872, 116890 to 116911, 116921 to 116948, 116952 to 116988, 116990 to 117006, 117008 to 117036, 117059 to 117133, 117187 to 117207, 117204 to 117217, 117209 to 117237, 117239 to 117252, 117255 to 117275, 117277 to 117300, 117337 to 117371, 117373 to 117416, 117418 to 117450, 117456 to 117507, 117518 to 117532, 117534 to 117590, 117582 to 117604, 117593 to 117617, 117621 to 117648, 117640 to 117662, 117664 to 117688, 117690 to 117711, 117728 to 117743, 117747 to 117781, 117784 to 117801, 117792 to 117822, 117824 to 117842, 117850 to 117869, 117890 to 117940, 117936 to 117968, 117970 to 117990, 117989 to 118034, 118034 to 118057, 118061 to 118083, 118086 to 118122, 118122 to 118182, 118172 to 118186, 118197 to 118211, 118216 to 118275, 118291 to 118316, 118318 to 118354, 118373 to 118388, 118391 to 118405, 118407 to 118423, 118425 to 118456, 118465 to 118492, 118498 to 118521, 118533 to 118551, 118553 to 118581, 118587 to 118617, 118620 to 118679, 118687 to 118716, 118731 to 118771, 118779 to 118805, 118816 to 118830, 118832 to 118895, 118910 to 119065, 119067 to 119081, 119095 to 119140, 119170 to 119205, 119210 to 119232, 119230 to 119246, 119236 to 119252, 119255 to 119274, 119271 to 119284, 119290 to 119307, 119320 to 119335, 119357 to 119463, 119465 to 119483, 119485 to 119535, 119550 to 119571, 119577 to 119608, 119610 to 119646, 119648 to 119688, 119713 to 119752, 119743 to 119784, 119786 to 119800, 119822 to 119836, 119830 to 119847, 119849 to 119900, 119912 to 119925, 119960 to 119982, 119984 to 120013, 120038 to 120054, 120057 to 120090, 120092 to 120134, 120138 to 120154, 120157 to 120189, 120187 to 120200, 120191 to 120211, 120225 to 120239, 120242 to 120267, 120271 to 120301, 120320 to 120340, 120363 to 120406, 120406 to 120421, 120414 to 120468, 120457 to 120470, 120487 to 120518, 120545 to 120563, 120567 to 120587, 120589 to 120625, 120619 to 120633, 120650 to 120663, 120676 to 120694, 120703 to 120717, 120721 to 120737, 120755 to 120802, 120816 to 120838, 120843 to 120871, 120873 to 120899, 120903 to 120922, 120933 to 120946, 120936 to 120981, 120983 to 121004, 121006 to 121021, 121023 to 121036, 121035 to 121061, 121063 to 121079, 121081 to 121097, 121105 to 121134, 121138 to 121156, 121155 to 121168, 121158 to 121174, 121166 to 121189, 121194 to 121208, 121201 to 121218, 121213 to 121237, 121246 to 121271, 121298 to 121314, 121311 to 121324, 121327 to 121351, 121359 to 121388, 121390 to 121419, 121446 to 121462, 121468 to 121487, 121499 to 121515, 121517 to 121543, 121545 to 121564, 121575 to 121597, 121599 to 121617, 121619 to 121662, 121664 to 121681, 121683 to 121700, 121702 to 121751, 121773 to 121788, 121790 to 121805, 121807 to 121834, 121836 to 121857, 121859 to 121874, 121877 to 121925, 121923 to 121936, 121928 to 121943, 121962 to 121976, 121978 to 121992, 122004 to 122028, 122030 to 122056, 122046 to 122059, 122052 to 122072, 122080 to 122095, 122099 to 122122, 122143 to 122163, 122169 to 122189, 122258 to 122274, 122289 to 122309, 122311 to 122346, 122357 to 122395, 122446 to 122468, 122471 to 122489, 122491 to 122512, 122526 to 122541, 122543 to 122557, 122579 to 122592, 122606 to 122653, 122663 to 122690, 122728 to 122742, 122757 to 122770, 122779 to 122840, 122842 to 122857, 122900 to 122923, 122933 to 122955, 122968 to 123042, 123055 to 123076, 123094 to 123108, 123114 to 123134, 123143 to 123160, 123162 to 123180, 123184 to 123198, 123200 to 123235, 123237 to 123321, 123314 to 123329, 123342 to 123360, 123356 to 123389, 123391 to 123410, 123412 to 123453, 123455 to 123485, 123488 to 123503, 123506 to 123524, 123526 to 123543, 123545 to 123578, 123598 to 123634, 123654 to 123683, 123685 to 123706, 123710 to 123774, 123803 to 123816, 123818 to 123831, 123896 to 123939, 123941 to 123974, 123976 to 124021, 124026 to 124040, 124042 to 124079, 124091 to 124109, 124158 to 124185, 124238 to 124274, 124319 to 124332, 124335 to 124373, 124394 to 124412, 124419 to 124445, 124450 to 124470, 124472 to 124493, 124499 to 124520, 124522 to 124561, 124564 to 124595, 124607 to 124649, 124662 to 124729, 124750 to 124767, 124769 to 124793, 124812 to 124828, 124853 to 124906, 124923 to 124948, 124958 to 124986, 125023 to 125042, 125032 to 125046, 125065 to 125083, 125073 to 125091, 125093 to 125107, 125132 to 125149, 125139 to 125154, 125151 to 125200, 125201 to 125274, 125314 to 125329, 125331 to 125370, 125372 to 125386, 125411 to 125431, 125433 to 125462, 125475 to 125562, 125564 to 125589, 125605 to 125639, 125641 to 125699, 125719 to 125732, 125737 to 125769, 125815 to 125829, 125834 to 125848, 125850 to 125884, 125899 to 125966, 125967 to 125999, 126026 to 126080, 126097 to 126115, 126130 to 126149, 126151 to 126179, 126186 to 126238, 126241 to 126279, 126275 to 126295, 126297 to 126312, 126320 to 126363, 126376 to 126395, 126406 to 126419, 126420 to 126442, 126467 to 126501, 126503 to 126538, 126566 to 126580, 126584 to 126597, 126620 to 126653, 126654 to 126694, 126697 to 126715, 126764 to 126777, 126792 to 126828, 126842 to 126862, 126866 to 126879, 126881 to 126897, 126906 to 126925, 126956 to 126987, 126989 to 127023, 127026 to 127135, 127142 to 127174, 127176 to 127191, 127193 to 127217, 127229 to 127253, 127255 to 127280, 127294 to 127394, 127396 to 127415, 127417 to 127478, 127491 to 127504, 127506 to 127530, 127542 to 127566, 127582 to 127628, 127654 to 127675, 127681 to 127706, 127706 to 127739, 127769 to 127792, 127808 to 127829, 127839 to 127888, 127900 to 127932, 127943 to 127975, 127988 to 128046, 128048 to 128069, 128068 to 128106, 128105 to 128118, 128121 to 128157, 128159 to 128188, 128190 to 128268, 128279 to 128317, 128321 to 128335, 128342 to 128368, 128374 to 128446, 128444 to 128540, 128546 to 128586, 128588 to 128640, 128642 to 128674, 128675 to 128879, 128881 to 128936, 128934 to 129000, 129002 to 129060, 129074 to 129100, 129107 to 129123, 129125 to 129163, 129168 to 129230, 129264 to 129277, 129284 to 129318, 129320 to 129346, 129357 to 129391, 129393 to 129420, 129447 to 129485, 129489 to 129504, 129514 to 129540, 129550 to 129563, 129559 to 129595, 129606 to 129627, 129633 to 129681, 129683 to 129697, 129699 to 129716, 129706 to 129738, 129757 to 129790, 129792 to 129820, 129812 to 129846, 129851 to 129867, 129869 to 129883, 129885 to 129915, 129917 to 129955, 129957 to 130046, 130042 to 130070, 130110 to 130156, 130158 to 130309, 130311 to 130373, 130375 to 130391, 130407 to 130429, 130439 to 130461, 130475 to 130507, 130512 to 130550, 130552 to 130582, 130584 to 130614, 130616 to 130764, 130766 to 130869, 130871 to 131021, 131033 to 131051, 131092 to 131105, 131112 to 131188, 131194 to 131237, 131233 to 131247, 131236 to 131287, 131292 to 131307, 131314 to 131333, 131373 to 131386, 131396 to 131417, 131419 to 131439, 131429 to 131458, 131481 to 131499, 131676 to 131689, 131729 to 131743, 131745 to 131764, 131785 to 131807, 131809 to 131875, 131877 to 131953, 131955 to 131980, 132020 to 132068, 132086 to 132108, 132118 to 132138, 132152 to 132183, 132185 to 132205, 132219 to 132232, 132234 to 132252, 132261 to 132291, 132319 to 132337, 132345 to 132363, 132365 to 132378, 132414 to 132483, 132504 to 132547, 132549 to 132582, 132584 to 132602, 132616 to 132642, 132643 to 132681, 132685 to 132714, 132736 to 132769, 132771 to 132793, 132809 to 132825, 132827 to 132841, 132861 to 132884, 132882 to 132900, 132899 to 132915, 132917 to 132951, 132940 to 132954, 132958 to 132983, 132985 to 133031, 133032 to 133051, 133042 to 133060, 133051 to 133071, 133073 to 133087, 133083 to 133104, 133097 to 133110, 133131 to 133199, 133198 to 133222, 133233 to 133249, 133251 to 133284, 133327 to 133429, 133431 to 133596, 133588 to 133602, 133598 to 133611, 133613 to 133628, 133628 to 133646, 133651 to 133670, 133666 to 133707, 133718 to 133742, 133743 to 133777, 133779 to 133794, 133821 to 133851, 133859 to 133880, 133890 to 133921, 133923 to 133974, 133982 to 133998, 134000 to 134036, 134065 to 134107, 134120 to 134173, 134165 to 134179, 134187 to 134200, 134207 to 134242, 134244 to 134258, 134260 to 134273, 134275 to 134299, 134314 to 134346, 134356 to 134371, 134365 to 134380, 134374 to 134420, 134445 to 134477, 134508 to 134523, 134531 to 134548, 134542 to 134555, 134568 to 134621, 134647 to 134667, 134679 to 134719, 134721 to 134824, 134826 to 134849, 134856 to 134869, 134877 to 134910, 134912 to 134966, 134960 to 134980, 134989 to 135012, 135014 to 135066, 135074 to 135093, 135108 to 135125, 135151 to 135260, 135264 to 135277, 135273 to 135310, 135321 to 135337, 135340 to 135365, 135360 to 135374, 135364 to 135386, 135388 to 135430, 135432 to 135447, 135498 to 135521, 135519 to 135545, 135559 to 135622, 135624 to 135647, 135656 to 135673, 135675 to 135704, 135721 to 135742, 135753 to 135796, 135815 to 135858, 135860 to 135880, 135883 to 135915, 135922 to 135965, 135979 to 135993, 135995 to 136036, 136051 to 136065, 136108 to 136165, 136173 to 136190, 136192 to 136287, 136289 to 136303, 136317 to 136346, 136375 to 136415, 136429 to 136470, 136472 to 136496, 136498 to 136532, 136542 to 136565, 136643 to 136657, 136674 to 136701, 136704 to 136719, 136715 to 136728, 136721 to 136737, 136737 to 136750, 136783 to 136810, 136824 to 136849, 136859 to 136896, 136898 to 136927, 136949 to 136983, 136985 to 137000, 137053 to 137071, 137077 to 137097, 137108 to 137164, 137166 to 137196, 137198 to 137221, 137223 to 137267, 137276 to 137359, 137360 to 137385, 137393 to 137440, 137438 to 137496, 137498 to 137518, 137523 to 137536, 137539 to 137572, 137584 to 137612, 137614 to 137628, 137630 to 137644, 137646 to 137669, 137702 to 137727, 137731 to 137745, 137759 to 137772, 137784 to 137819, 137832 to 137858, 137861 to 137876, 137878 to 137900, 137909 to 137925, 137924 to 137961, 137968 to 137981, 138011 to 138033, 138035 to 138077, 138079 to 138097, 138224 to 138238, 138232 to 138252, 138242 to 138256, 138255 to 138284, 138295 to 138326, 138328 to 138357, 138359 to 138389, 138403 to 138449, 138451 to 138492, 138500 to 138515, 138524 to 138548, 138555 to 138568, 138571 to 138589, 138589 to 138629, 138644 to 138680, 138697 to 138710, 138712 to 138729, 138744 to 138761, 138776 to 138801, 138860 to 138896, 138898 to 138923, 138925 to 138965, 138967 to 139008, 139010 to 139031, 139029 to 139043, 139034 to 139048, 139041 to 139056, 139055 to 139074, 139078 to 139094, 139084 to 139098, 139092 to 139116, 139133 to 139147, 139154 to 139173, 139175 to 139192, 139204 to 139229, 139231 to 139255, 139257 to 139270, 139272 to 139303, 139315 to 139335, 139337 to 139372, 139383 to 139397, 139399 to 139419, 139423 to 139437, 139435 to 139492, 139501 to 139518, 139508 to 139521, 139571 to 139586, 139588 to 139622, 139636 to 139655, 139657 to 139673, 139685 to 139699, 139724 to 139795, 139796 to 139811, 139818 to 139834, 139836 to 139857, 139856 to 139869, 139859 to 139882, 139891 to 139920, 139930 to 139952, 139965 to 139980, 139982 to 140011, 140013 to 140031, 140047 to 140072, 140074 to 140099, 140101 to 140119, 140121 to 140135, 140144 to 140158, 140157 to 140183, 140185 to 140210, 140231 to 140262, 140258 to 140272, 140264 to 140288, 140290 to 140325, 140339 to 140364, 140369 to 140402, 140428 to 140451, 140453 to 140510, 140512 to 140541, 140556 to 140621, 140626 to 140651, 140653 to 140724, 140726 to 140789, 140802 to 140825, 140837 to 140861, 140863 to 140896, 140903 to 140927, 140958 to 140993, 141001 to 141014, 141022 to 141053, 225 to 238, 1163-1178, 2526-2539, 2805-2820, 3027-3040, 3208-3222, 3212-3225, 3228-3241, 3243-3256, 3810-3854, 4664-4680, 5516-5529, 5657-5671, 5661-5676, 5964-5977, 6217-6234, 6224-6237, 6408-6422, 7300-7313, 7399-7412, 7541-7564, 7626-7640, 7662-7694, 7791-7806, 7853-7868, 8206-8219, 8443-8456, 8739-8752, 9197-9212, 10189-10203, 10754-10768, 10758-10771, 11790-11803, 11870-11883, 11993-12007, B11996-12011, 12017-12040, 12095-12108, 12345-12358, 12721-12734, 13372-13386, 13489-13505, 15576-15590, 15617-15632, 15840-15853, 16041-16054, 16207-16222, 16308-16321, 16349-16362, 16463-16479, 16528-16542, 16543-16556, 20495-20508, 20617-20630, 20960-20977, 21465-21479, 21491-21508, 23479-23496, 23741-23755, 25236-25249, 25323-25336, 25447-25462, 25588-25601, 25853-25867, 25885-25898, 26280-26293, 26388-26404, 26416-26450, 26687-26702, 26706-26719, 26783-26796, 27039-27052, 27251-27265, 28683-28698, 29302-29315, 29304-29317, 29308-29321, 29532-29545, 29974-29987, 30054-30068, 30267-30281, 30623-30638, 30628-30641, 30814-30827, 30881-30894, 32459-32478, 37299-37315, 39083-39096, 39370-39383, 39659-39672, 40814-40831, 40851-40864, 41782-41795, 41873-41886, 42037-42050, 42048-42063, 42096-42116, 42959-42973, 43165-43178, 45926-45939, 48163-48176, 52732-52745, 52984-53015, 54404-54420, 55294-55320, 55337-55350, 55420-55434, 55487-55501, 55623-55638, 56195-56214, 56584-56597, 57267-57282, 58126-58139, 58170-58183, 58295-58309, 58658-58671, 58906-58921, 58988-59005, 59024-59045, 59191-59207, 59236-59251, 59298-59312, 59358-59378, 59400-59413, 59434-59447, 59589-59602, 59620-59642, 59718-59743, 59826-59841, 59843-59864, 59882-59906, 59930-59958, 59959-60004, 60006-60029, 60033-60071, 60139-60171, 60193-60215, 60212-60225, 60231-60244, 60246-60265, 60267-60282, 60292-60309, 60348-60361, 60358-60429, 60427-60517, 60519-60545, 60557-60575, 60580-60593, 60595-60622, 60675-60690, 60697-60713, 60727-60754, 60756-60799, 60801-60817, 60819-60855, 61423-61436, 61592-61605, 61624-61637, 61673-61713, 61715-61731, 61733-61752, 61769-61794, 61805-61825, 62101-62114, 62302-62315, 62436-62449, 62664-62679, 62993-63006, 63098-63111, 63347-63367, 63371-63396, 63385-63398, 63526-63539, 65032-65045, 66556-66569, 67158-67183, 67181-67194, 68007-68021, 68644-68657, 69294-69317, 69306-69323, 69353-69366, 70497-70511, 71600-71613, 71887-71905, 72259-72272, 72589-72602, 72783-72796, 73528-73541, 73783-73800, 74907-74920, 75965-75981, 75983-75998, 76004-76020, 76110-76166, 76186-76205, 76234-76253, 76261-76280, 76369-76382, 77139-77152, 77409-77422, 77478-77524, 77526-77590, 77628-77641, 77688-77701, 78275-78308, 78310-78332, 78340-78356, 78358-78371, 78373-78395, 78397-78440, 78442-78455, 78475-78489, 78696-78709, 78847-78860, 79493-79516, 79705-79718, 81009-81054, 81353-81367, 81970-81986, 81991-82006, 82042-82106, 82278-82291, 82716-82735, 84314-84328, 85628-85665, 86226-86239, 86237-86253, 86566-86579, 86945-86959, 87337-87358, 87662-87675, 89424-89439, 89972-89985, 90782-90795, 90939-90953, 90942-90955, 90965-90981, 91101-91115, 92083-92096, 92164-92177, 92179-92192, 92194-92210, 92212-92236, 92245-92260, 92262-92302, 92304-92321, 92323-92366, 92375-92389, 92392-92405, 92407-92426, 92442-92459, 92497-92516, 92578-92591, 92599-92612, 92614-92651, 92659-92684, 92686-92699, 92704-92726, 92731-92750, 92752-92774, 92780-92795, 92800-92813, 92839-92858, 92860-92891, 92893-92906, 92908-92921, 92923-92941, 92965-92986, 92988-93002, 93044-93059, 93061-93076, 93105-93122, 93142-93209, 93227-93241, 93288-93305, 93325-93344, 93398-93412, 93572-93586, 94509-94522, 95720-95738, 97050-97065, 97079-97098, 97127-97194, 97208-97230, 97232-97284, 97286-97311, 97313-97362, 97368-97383, 97426-97439, 98077-98090, 98227-98240, 98232-98255, 99151-99164, 99405-99418, 99570-99583, 99733-99748, 101829-101842, 101882-101895, 101955-101968, 102202-102215, 103310-103325, 103653-103666, 103908-103923, 103912-103928, 103917-103933, 104971-104984, 105217-105230, 105233-105250, 105443-105457, 105544-105559, 106047-106071, 106061-106074, 106093-106107, 106114-106130, 106243-106256, 106251-106264, 106840-106855, 108113-108130, 108325-108338, 108856-108869, 109109-109122, 109113-109127, 109116-109132, 110301-110314, 110315-110328, 110317-110330, 112528-112546, 112607-112620, 114775-114788, 116322-116335, 116968-116981, 117788-117801, 118034-118057, 118230-118246, 118235-118248, 118870-118883, 119755-119784, 119786-119800, 120363-120406, 120504-120517, 121161-121174, 121330-121347, 121338-121351, 123417-123430, 123464-123481, 125026-125042, 127046-127071, 127090-127103, 127311-127324, 127354-127367, 127363-127379, 127399-127412, 127863-127876, 128134-128148, 128280-128310, 128343-128368, 128444-128457, 128446-128469, 128498-128511, 128511-128524, 129892-129905, 130261-130283, 130375-130388, 130415-130428, 130634-130650, 130667-130717, 130719-130764, 130783-130796, 130798-130820, 130840-130861, 130975-130994, 131112-131132, 131142-131161, 131233-131246, 131729-131743, 132754-132767, 132924-132937, 133174-133190, 133198-133212, 133207-133222, 133476-133489, 133479-133492, 133491-133531, 133533-133550, 133555-133594, 134160-134173, 134165-134178, 134533-134546, 136724-136737, 137438-137463, 137878-137891, 138082-138097, 138233-138252, 138930-138943, 138947-138960, 138950-138963, 139502-139518, 139508-139521, and 140978-140991 of SEQ ID NO: 1.

5. The oligonucleotide of claim 1, wherein the oligonucleotide comprises or consists of either 17 to 22 nucleotides in length or 15 to 20 nucleotides in length.

6. The oligonucleotide of claim 1, wherein the oligonucleotide consists of 20 nucleotides in length.

7. The oligonucleotide of claim 1, wherein 5-methyl cytosine is used in place of cytosine in the oligonucleotide.

8. The oligonucleotide of claim 1, wherein the one or more modified nucleosides is a 2' sugar modified nucleoside.

9. The oligonucleotide of claim 8, wherein each of the one or more 2' sugar modified nucleoside is a 2'-O-alkyl-RNA nucleoside, a 2'-O-methyl-RNA nucleoside, a 2'-alkoxy-RNA nucleoside, a 2'-O-methoxyethyl-RNA nucleoside, a 2'-amino-DNA nucleoside, a 2'-fluoro-DNA nucleoside, an arabino nucleic acid (ANA) nucleoside, a 2'-fluoro-ANA nucleoside, or a LNA nucleoside.

10. The oligonucleotide of claim 1, wherein the one or more modified nucleoside is a 2'-O-methoxyethyl-RNA nucleoside.

11. The oligonucleotide of claim 1, wherein the oligonucleotide comprises at least one modified internucleoside linkage.

12. The oligonucleotide of claim 11, wherein the modified internucleoside linkage is a phosphorothioate internucleoside linkage.

13. The oligonucleotide of claim 12, wherein at least 60% of the internucleoside linkages in the oligonucleotide are phosphorothioate internucleoside linkages.

14. The oligonucleotide of claim 1, wherein the oligonucleotide is capable of recruiting RNase H.

15. The oligonucleotide of claim 14, wherein the oligonucleotide is a gapmer.

16. The oligonucleotide of claim 14, wherein the oligonucleotide is a gapmer of formula 5'-F-G-F'-3', where region F and F' independently comprise 1 to 7 modified nucleosides and G is a region comprising between 6 and 16 nucleosides which are capable of recruiting RNaseH.

17. The oligonucleotide of claim 16, wherein the modified nucleosides are 2' sugar modified nucleosides, wherein each of the 2' sugar modified nucleosides is a 2'-O-alkyl-RNA nucleoside, a 2'-O-methyl-RNA nucleoside, a 2'-alkoxy-RNA nucleoside, a 2'-O-methoxyethyl-RNA nucleoside, a 2'-amino-DNA nucleoside, a 2'-fluoro-DNA nucleoside, an arabino nucleic acid (ANA) nucleoside, a 2'-fluoro-ANA nucleoside, or a LNA nucleoside.

18. The oligonucleotide of claim 1, wherein the oligonucleotide is a gapmer of the formula F-G-F' wherein each of regions F and F' independently consists of 2, 3, 4, or 5 modified nucleoside units and region G consists of 9, 10, 11, 12, 13, 14, or 15 nucleoside units.

19. The oligonucleotide of claim 1, wherein the oligonucleotide is a gapmer of the formula F-G-F' wherein each of regions F and F' independently consists of 2, 3, 4, or 5 2'—O-methoxyethyl-ribose sugar (2'-MOE) units, and region G consists of 9, 10, 11, 12, 13, 14, or 15 DNA units.

20. The oligonucleotide of claim 16, wherein each of regions F and F' independently consists of 5 2'—O-methoxyethyl-ribose sugar (2'-MOE) nucleoside units and region G consists of 10 DNA nucleoside units.

21. An antisense oligonucleotide for inducing human paternal ubiquitin-protein ligase E3A (UBE3A) expression, wherein the antisense oligonucleotide comprises a contiguous nucleotide sequence that is 100% complementary to a region of the target nucleic acid of position 1 to 55318 of SEQ ID NO: 1, wherein the oligonucleotide is either 15 to 20 nucleotides in length or 17 to 22 nucleotides in length, wherein the oligonucleotide comprises one or more modified nucleosides, wherein the one or more modified nucleosides is a 2' sugar modified nucleoside, wherein each of the 2' sugar modified nucleosides is a 2'-O-alkyl-RNA nucleoside, a 2'-O-methyl-RNA nucleoside, a 2'-alkoxy-RNA nucleoside, a 2'-O-methoxyethyl-RNA nucleoside, a 2'-amino-DNA nucleoside, a 2'-fluoro-DNA nucleoside, an arabino A nucleic acid (ANA) nucleoside, a 2'-fluoro-ANA nucleoside, or a LNA nucleoside, wherein the oligonucleotide comprises at least one modified internucleoside linkage, wherein the modified internucleoside linkage is a phosphorothioate linkage, wherein the oligonucleotide is a gapmer of the formula F-G-F', wherein each of regions F and F' independently consists of 2, 3, 4, or 5 modified nucleoside units and region G consists of 9, 10, 11, 12, 13, 14, or 15 nucleoside units.

22. The oligonucleotide of claim 1, wherein the oligonucleotide is in the form of a pharmaceutically acceptable salt.

23. The oligonucleotide of claim 22, wherein the oligonucleotide is in the form of a pharmaceutically acceptable sodium salt.

24. The oligonucleotide of claim 22, wherein the oligonucleotide is in the form of a pharmaceutically acceptable potassium salt.

25. A conjugate comprising the oligonucleotide of claim 1 and at least one conjugate moiety covalently attached to the oligonucleotide.

26. A pharmaceutical composition comprising the oligonucleotide of claim 1, and a pharmaceutically acceptable diluent, solvent, carrier, salt, and/or adjuvant.

* * * * *

UNITED STATES PATENT AND TRADEMARK OFFICE
CERTIFICATE OF CORRECTION

PATENT NO. : 12,259,380 B2
APPLICATION NO. : 18/172707
DATED : March 25, 2025
INVENTOR(S) : Veronica Costa et al.

It is certified that error appears in the above-identified patent and that said Letters Patent is hereby corrected as shown below:

In the Claims

Column 353, Claim 4, Line 3, replace, "the sub-sequence" with --wherein the sub-sequence--;

Column 372, Claim 21, Line 18, replace, "an arabino A nucleic acid" with --an arabino nucleic acid--.

Signed and Sealed this
Sixth Day of January, 2026

John A. Squires
*Director of the United States Patent and Trademark Office*